(12) United States Patent
Hagel et al.

(10) Patent No.: US 11,998,557 B2
(45) Date of Patent: *Jun. 4, 2024

(54) HALOGENATED PSILOCYBIN DERIVATIVES AND METHODS OF USING

(71) Applicant: Enveric Biosciences Canada Inc., Calgary (CA)

(72) Inventors: Jillian M. Hagel, Calgary (CA); Peter J. Facchini, Calgary (CA)

(73) Assignee: Enveric Biosciences Canada Inc., Calgary (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/903,080

(22) Filed: Sep. 6, 2022

(65) Prior Publication Data

US 2023/0293558 A1 Sep. 21, 2023

Related U.S. Application Data

(63) Continuation of application No. PCT/CA2021/051209, filed on Sep. 1, 2021.
(Continued)

(51) Int. Cl.
*A61K 31/675* (2006.01)
*A61K 31/4045* (2006.01)
*C12N 9/02* (2006.01)
*C12N 9/10* (2006.01)
*C12N 9/12* (2006.01)
(Continued)

(52) U.S. Cl.
CPC ........ *A61K 31/675* (2013.01); *A61K 31/4045* (2013.01); *C12N 9/0083* (2013.01); *C12N 9/1007* (2013.01); *C12N 9/1205* (2013.01); *C12N 15/52* (2013.01); *C12P 17/10* (2013.01)

(58) Field of Classification Search
CPC .............. A61K 31/4045; A61K 31/675; C07D 209/16; C07F 9/5728; C07K 2319/21; C07K 2319/40; C07K 2319/41; C07K 2319/42; C07K 2319/43; C12N 15/52; C12N 9/0071; C12N 9/0083;
(Continued)

(56) References Cited

U.S. PATENT DOCUMENTS 5,688,807 A 11/1997 Audia et al.
2008/0171779 A1 7/2008 De Bruin et al.
(Continued)

FOREIGN PATENT DOCUMENTS

WO 2004000845 A1 12/2003
WO 2018064465 A1 4/2018
(Continued)

OTHER PUBLICATIONS

Winkelblech et al.(Organic and Biomolecular Chemistry, 2016, 14, 9883-9895) (Year: 2016).*
(Continued)

*Primary Examiner* — Savitha M Rao
(74) *Attorney, Agent, or Firm* — BERESKIN & PARR LLP/ S.E.N.C.R.L., s.r.l.; Michael Fenwick

(57) ABSTRACT

Disclosed are novel halogenated psilocybin derivative compounds and pharmaceutical and recreational drug formulations containing the same. The compounds may be produced using a biosynthetic system which comprises cells comprising a psilocybin biosynthetic enzyme complement.

22 Claims, 36 Drawing Sheets

Specification includes a Sequence Listing.

Related U.S. Application Data

(60) Provisional application No. 63/073,104, filed on Sep. 1, 2020.

(51) Int. Cl.
*C12N 15/52* (2006.01)
*C12P 17/10* (2006.01)

(58) Field of Classification Search
CPC .. C12N 9/1007; C12N 9/1029; C12N 9/1205; C12N 9/88; C12P 17/10; C12Y 402/0102
See application file for complete search history.

(56) References Cited

U.S. PATENT DOCUMENTS

| | | |
|---|---|---|
| 2009/0093513 A1 | 4/2009 | Hamann et al. |
| 2020/0397752 A1 | 12/2020 | Perez Castillo et al. |

FOREIGN PATENT DOCUMENTS

| | | |
|---|---|---|
| WO | 2019173797 A1 | 9/2019 |
| WO | 2021011913 A1 | 1/2021 |
| WO | 2021108911 A1 | 6/2021 |
| WO | 2021168082 A1 | 8/2021 |
| WO | 2022051670 A1 | 3/2022 |

OTHER PUBLICATIONS

Williams et al. (Foye's Principles of Medicinal chemistry, fifth edition, 2002) (Year: 2002).*
Patani et al. (Chem. Rev.1996, 96, 3147-3176) (Year: 1996).*
Pratuangdejkul et al (Current Medicinal Chemistry, 2005, 12, 2393-2410 (Year: 2005).*
Daniel, J. et al. Clinical potential of psilocybin as a treatment for mental health conditions. Mental Health Clin/, 2017;7(1): 24-28.
Grob, C. et al. Pilot study of psilocybin treatment for anxiety in patients with advanced-stage cancerArch. Gen. Psychiatry, 2011, 68(1) 71-78.
Cathart-Harris, R.L. et al. Psilocybin with psychological support for treatment-resistant depression: an open-label feasibility study. Lancet Psychiatry, 2016, 3: 619-627.
Needleman and Wunsch. A general method applicable to the search for similarities in the amino acid sequence of two proteins J. Mol. Biol., 1970, 48: 443.
Smith and Waterman. Adv. Appl. Math., 1981, 2: 482.
Carillo and Lipton. Siam J. Applied Math., 1988, 48:1073.
Romeo, B. et al. Clinical and biological predictors of psychedelic response in the treatment of psychiatric and addictive disorders: A systematic review. J Psychiatr Res 137: 273, 2021.
Devereux et al., A comprehensive set of sequence analysis programs for the VAX. Nucleic Acids Res., 1984, 12: 387.
Altschul et al., J. Mol. Biol., 1990:215:403.
Thompson, J D, Higgines, D G and Gibson T J, 1994, Nucleic Acid Res 22(22): 4673-4680.
S. Kawai et al., Transformation of *Saccharomyces cerevisiae* and other fungi: methods and possible underlying mechanism. Bioeng Bugs. Nov.-Dec. 2010;1(6):395-403.
Henikoff S & Henikoff, J G, 1992, Proc. Natl. Acad. Sci. USA 89: 10915-10919.
Roy A.D. et al. Development of fluorescent aryltryptophans by Pd mediated cross-coupling of unprotected halotryptophans in water. Chem Commun (Camb). Oct. 21, 2008;(39):4831-3.
Corr M.J. et al. Sonogashira diversification of unprotected halotryptophans, halotryptophan containing tripeptides; and generation of a new to nature bromo-natural product and its diversification in water Chem Sci. Mar. 1, 2017;8(3):2039-2046.
Finnin, B. and Morgan, T.M., Transdermal penetration enhancers: applications, limitations, and potential J Pharm Sci. Oct. 1999;88(10):955-8.
Ross, S. et al. Acute and Sustained Reductions in Loss of Meaning and Suicidal Ideation Following Psilocybin-Assisted Psychotherapy for Psychiatric and Existential Distress in Life-Threatening Cancer. ACS Pharmacol Transl Sci. Apr. 9, 2021; 4(2): 553-562.
Schnepel C. et al. Enzymatic Halogenation: A Timely Strategy for Regioselective C-H Activation. Chemistry. Sep. 7, 2017;23(50):12064-12086.
Durak L.J. et al. Late-Stage Diversification of Biologically Active Molecules via Chemoenzymatic C-H Functionalization ACS Catal. Mar. 4, 2016; 6(3): 1451-1454.
Runguphan W. et al. Diversification of monoterpene indole alkaloid analogs through cross-coupling. Org Lett. Jun. 7, 2013;15(11):2850-3.
Ding, L. et al. Discovery and Structure-Based Optimization of 6-Bromotryptamine Derivatives as Potential 5-HT2A Receptor Antagonists. Molecules, 2015, 20:17675-17683.
Shoubhye, J. et al. Hybrid molecules inhibiting myeloperoxidase activity and serotonin reuptake: a possible new approach of major depressive disorders with inflammatory syndrome. Royal Pharmaceutical Society, Journal of Pharmacy and Pharmacology, 2014, 66, pp. 1122-1132.
Cregg et al., Recombinant protein expression in Pichia pastoris. Mol Biotechnol. (2000) 16(1): 23-52.
Mattanovich et al., Recombinant protein production in yeasts. Methods Mol. Biol., 2012, 824:329-58.
Romanos et al., Foreign gene expression in yeast: a review. Yeast. Jun. 1992;8(6):423-88.
Andorfer M.C., et al. Directed Evolution of RebH for Catalyst-Controlled Halogenation of Indole C-H Bonds. (2016) Chem. Sci. 7: 3720.
Glenn W.S., et al. Reengineering a tryptophan halogenase to preferentially chlorinate a direct alkaloid precursor (2011) J. Am. Chem. Soc. 133: 19346.
Campos et al. A general synthesis of substituted indoles from cyclic enol ethers and enol lactones 2004, Org. Lett 6: 79-82.
Dastmalchi et al., 2019, Nat. Chem Biol. 15: 384-390.
Chen et al., A pathogenesis-related 10 protein catalyzes the final step in thebaine biosynthesis Nat. Chem Biol. 14: 738-743, 2018.
Chang, L. et al. Isolation and Characterization of O-methyltransferases Involved in the Biosynthesis of Glaucine in Glaucium flavum1. Plant Physiology, Oct. 2015, vol. 169, pp. 1127-1140.
Jones et al. ePathOptimize: A Combinatorial Approach for Transcriptional Balancing of Metabolic Pathways. 2015, Sci Rep. 5: 11301.
Pyrgiotakis G. et al., 2009, Ann. Biomed. Eng. 37: 1464-1473.
Rickli A. et al., 2016, Europ. Neuropsychopharmacol., 26: 1326-1337.
Lombardo et al. A tandem isomerization/prins strategy: iridium(III)/ Brønsted acid cooperative catalysis 2013, Angew. Chem. Int. Ed. 52: 12910-12914.
Go et al. Amino derivatives of indole as potent inhibitors of isoprenylcysteine carboxyl methyltransferase 2010, J. Med. Chem. 53: 6838-6850.

* cited by examiner

HALOGENATED PSILOCYBIN DERIVATIVES AND METHODS OF USING

RELATED APPLICATION

This application is a continuation of PCT Application No. PCT/CA2021/051209 filed Sep. 1, 2021, which claims the benefit of U.S. Provisional Application No. 63/073,104 filed Sep. 1, 2020; the entire contents of Patent Application No. 63/073,104 are hereby incorporated by reference.

INCORPORATION OF SEQUENCE LISTING

A computer readable form of the Sequence Listing "29664-P62051US02_SequenceListing.xml" (217,220_bytes), submitted via EFS-WEB and created on Apr. 19, 2023, is herein incorporated by reference.

FIELD OF THE DISCLOSURE

The compositions and methods disclosed herein relate to a chemical compound known as psilocybin. Furthermore, the compositions and methods disclosed herein relate in particular to halogenated forms of psilocybin.

BACKGROUND OF THE DISCLOSURE

The following paragraphs are provided by way of background to the present disclosure. They are not however an admission that anything discussed therein is prior art or part of the knowledge of a person of skill in the art.

The biochemical pathways in the cells of living organisms may be classified as being part of primary metabolism, or as being part of secondary metabolism. Pathways that are part of a cell's primary metabolism are involved in catabolism for energy production or in anabolism for building block production for the cell. Secondary metabolites, on the other hand, are produced by the cell without having an obvious anabolic or catabolic function. It has long been recognized that secondary metabolites can be useful in many respects, including as therapeutic compounds.

Psilocybin, for example, is a secondary metabolite that is naturally produced by certain mushrooms which taxonomically can be classified as belonging the Basidiomycota division of the fungi kingdom. Mushroom species which can produce psilocybin include species belonging to the genus *Psilocybe*, such as *Psilocybe azurescens, Psilocybe semilanceata, Psilocybe serbica, Psilocybe mexicana*, and *Psilocybe cyanescens*, for example. The interest of the art in psilocybin is well established. Thus, for example, psilocybin is a psychoactive compound and is therefore used as a recreational drug. Furthermore, psilocybin is used as a research tool in behavioral and neuro-imaging studies in psychotic disorders, and has been evaluated for its clinical potential in the treatment of mental health conditions (Daniel, J. et al. Mental Health Clin/, 2017; 7(1): 24-28), including to treat anxiety in terminal cancer patients (Grob, C. et al. Arch. Gen. Psychiatry, 2011, 68(1) 71-78) and to alleviate symptoms of treatment-resistant depression (Cathart-Harris, R. L. et al. Lancet Psychiatry, 2016, 3: 619-627).

Although the toxicity of psilocybin is low, adverse side effects, including, for example, panic attacks, paranoia and psychotic states, sometimes together or individually referred to as "a bad trip", are not infrequently experienced by recreational psilocybin users.

There exists therefore a need in the art for improved psilocybin compounds.

SUMMARY OF THE DISCLOSURE

The following paragraphs are intended to introduce the reader to the more detailed description, not to define or limit the claimed subject matter of the present disclosure.

In one aspect, the present disclosure relates to psilocybin and derivative compounds.

In another aspect, the present disclosure relates to halogenated psilocybin derivative compounds and methods of making and using these compounds.

Accordingly, in one aspect, the present disclosure provides, in accordance with the teachings herein, in at least one embodiment, a chemical compound or salts thereof having the formula (I):

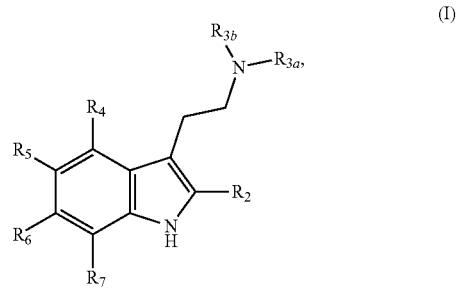

wherein, at least one of $R_2$, $R_4$, $R_5$, $R_6$ or $R_7$ is a halogen atom, wherein each non-halogenated $R_2$, $R_5$, $R_6$, or $R_7$ is a hydrogen atom or an alkyl group or O-alkyl group, wherein $R_4$ when it is not halogenated is a phosphate group, hydrogen atom or an alkyl or O-alkyl group, and wherein $R_{3A}$ and $R_{3B}$ are a hydrogen atom, an alkyl group, an aryl group, or an acyl group.

In at least one embodiment, in an aspect, the halogen atom can be a bromine atom.

In at least one embodiment, in an aspect, the halogen atom can be a chlorine atom.

In at least one embodiment, in an aspect, the halogen atom can be a fluorine atom.

In at least one embodiment, in an aspect, the halogen atom can be an iodine atom.

In at least one embodiment, in an aspect, $R_2$ can be a halogen atom and $R_5$, $R_6$ and $R_7$ can each be a hydrogen atom or an alkyl group or O-alkyl group, and $R_4$ can be a phosphate group, a hydrogen atom or an alkyl group or O-alkyl group.

In at least one embodiment, in an aspect, $R_4$ can be a halogen atom and $R_2$, $R_5$, $R_6$ and $R_7$ can each be a hydrogen atom or an alkyl group or O-alkyl group.

In at least one embodiment, in an aspect, $R_5$ can be a halogen atom and $R_2$, $R_6$ and $R_7$ can each be a hydrogen atom or an alkyl group or O-alkyl group, and $R_4$ can be a phosphate group, a hydrogen atom or an alkyl group or O-alkyl group.

In at least one embodiment, in an aspect, $R_6$ can be a halogen atom and $R_2$, $R_5$ and $R_7$ can each be a hydrogen atom or an alkyl group or O-alkyl group, and $R_4$ can be a phosphate group, a hydrogen atom or an alkyl group or O-alkyl group.

In at least one embodiment, in an aspect, $R_7$ can be a halogen atom and $R_2$, $R_5$ and $R_6$ can each be a hydrogen atom or an alkyl group or O-alkyl group, and $R_4$ can be a phosphate group, a hydrogen atom or an alkyl group or O-alkyl group.

In at least one embodiment, in an aspect, at least two of $R_2$, $R_4$, $R_5$, $R_6$ or $R_7$ can be a halogen atom.

In at least one embodiment, in an aspect, the at least of two of $R_2$, $R_4$, $R_5$, $R_6$ or $R_7$ that are halogen atoms can be at least two identical halogen atoms.

In at least one embodiment, in an aspect, the at least of two of $R_2$, $R_4$, $R_5$, $R_6$ or $R_7$ that are halogen atoms can at least two non-identical halogen atoms.

In at least one embodiment, in an aspect, $R_2$ and $R_4$ can be a halogen atom, and $R_5$, $R_6$ and $R_7$ can be a hydrogen atom or an alkyl group or O-alkyl group.

In at least one embodiment, in an aspect, $R_2$ and $R_5$ can be a halogen atom, $R_6$ and $R_7$ can be a hydrogen atom or an alkyl group or O-alkyl group, and $R_4$ can be a hydrogen atom, a phosphate group or an alkyl group or O-alkyl group.

In at least one embodiment, in an aspect, $R_2$ and $R_6$ can be a halogen atom, $R_5$ and $R_7$ can be a hydrogen atom or an alkyl group or O-alkyl group, and $R_4$ can be a hydrogen atom, a phosphate group or an alkyl group or O-alkyl group.

In at least one embodiment, in an aspect, $R_2$ and $R_7$ can be a halogen atom, $R_5$ and $R_6$ can be a hydrogen atom or an alkyl group or O-alkyl group, and $R_4$ can be a hydrogen atom, a phosphate group or an alkyl group or O-alkyl group.

In at least one embodiment, in an aspect, $R_4$ and $R_5$ can be a halogen atom, and $R_2$, $R_6$ and $R_7$ can be a hydrogen atom or an alkyl group or O-alkyl group.

In at least one embodiment, in an aspect, $R_4$ and $R_6$ can be a halogen atom, and $R_2$, $R_5$ and $R_7$ can be a hydrogen atom or an alkyl group or O-alkyl group.

In at least one embodiment, in an aspect, $R_4$ and $R_7$ can be a halogen atom, and $R_2$, $R_5$ and $R_6$ can be a hydrogen atom or an alkyl group or O-alkyl group.

In at least one embodiment, in an aspect, $R_5$ and $R_6$ can be a halogen atom, $R_2$ and $R_7$ can be a hydrogen atom or an alkyl group or O-alkyl group, and $R_4$ can be a hydrogen atom, a phosphate group or an alkyl group or O-alkyl group.

In at least one embodiment, in an aspect, $R_5$ and $R_7$ can be a halogen atom, $R_2$ and $R_6$ can be a hydrogen atom or an alkyl group or O-alkyl group, and $R_4$ can be a hydrogen atom, a phosphate group or an alkyl group or O-alkyl group.

In at least one embodiment, in an aspect, $R_6$ and $R_7$ can be a halogen atom, $R_2$ and $R_5$ can be a hydrogen atom or an alkyl group or O-alkyl group, and $R_4$ can be a hydrogen atom, a phosphate group or an alkyl group or O-alkyl group.

In at least one embodiment, in an aspect, $R_4$ when it is not halogenated can be a hydrogen atom.

In at least one embodiment, in an aspect, $R_4$ when it is not halogenated can be an alkyl group.

In at least one embodiment, in an aspect, $R_4$ when it is not halogenated can be an O-alkyl group.

In at least one embodiment, in an aspect, $R_4$ when it is not halogenated can be a phosphate group.

In at least one embodiment, in an aspect, three, four or all five of $R_2$, $R_4$, $R_5$, $R_6$ or $R_7$ can be a halogen atom.

In at least one embodiment, in an aspect, the three, four, or five of $R_2$, $R_4$, $R_5$, $R_6$ or $R_7$ that are halogen atoms can all be identical halogen atoms.

In at least one embodiment, in an aspect, the three, four or five of $R_2$, $R_4$, $R_5$, $R_6$ or $R_7$ that are halogen atoms, can include at least two non-identical halogen atoms.

In at least one embodiment, in an aspect, the chemical compound can be selected from the group consisting of compounds having formulas (II); (III); (IV); (V); (VI); (VII): (VIII); (IX); (X); (XI), (XII); (XIII); (XIV); (XV); (XVI); and (XVII):

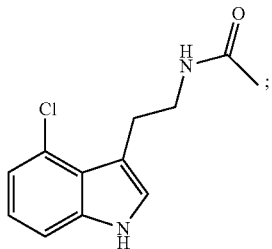

(II)

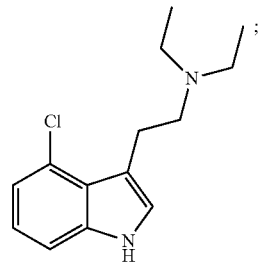

(III)

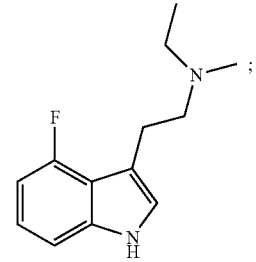

(IV)

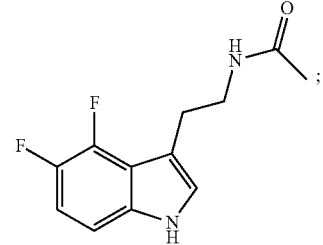

(V)

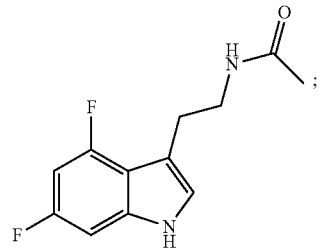

(VI)

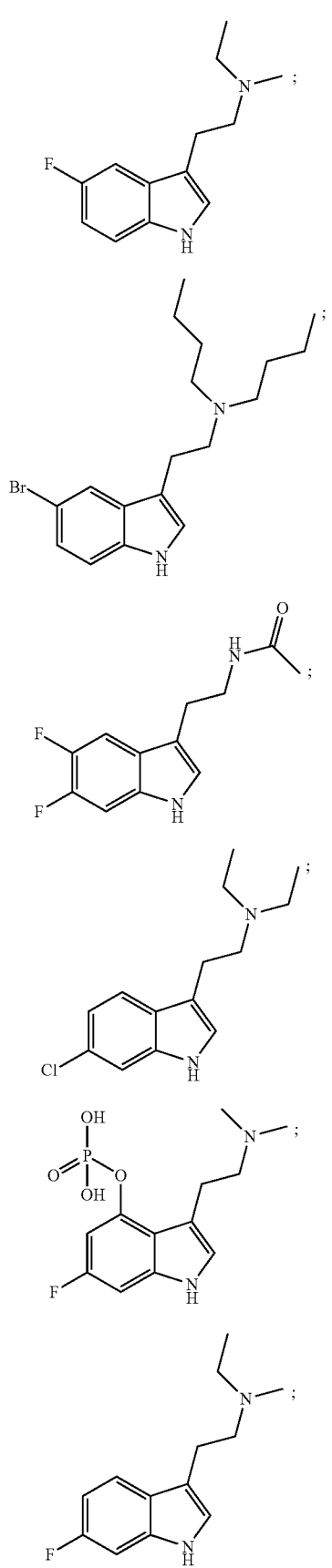
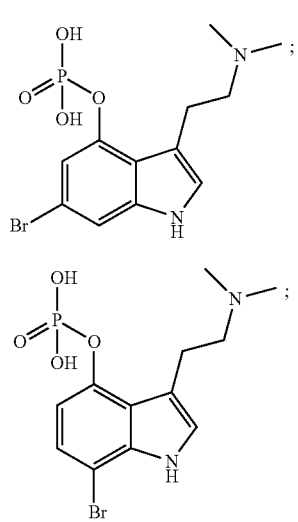
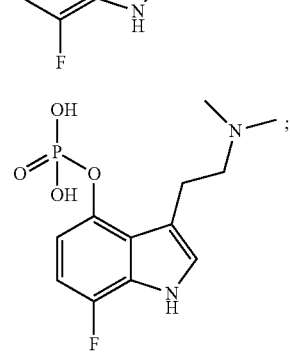
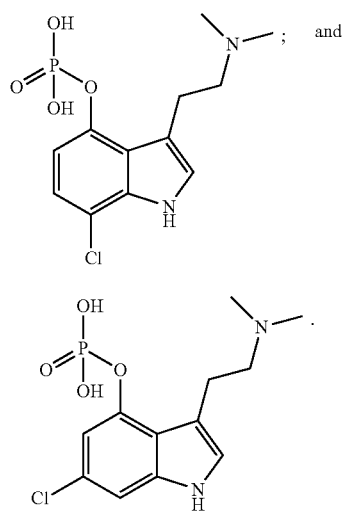
In at least one embodiment, the chemical compound is at least about 95% (w/w) pure.

In another aspect, the present disclosure relates to pharmaceutical and recreational drug formulations comprising halogenated psilocybin derivatives. Accordingly, in one aspect, the present disclosure provides in at least one aspect, a pharmaceutical or recreational drug formulation comprising an effective amount of a chemical compound or salts thereof having the formula (I):

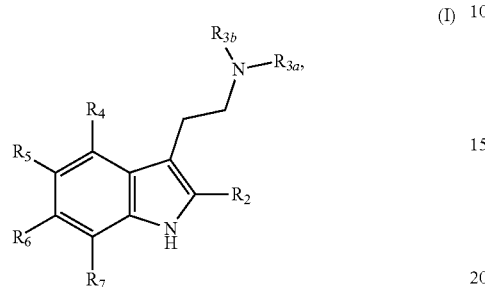

wherein, at least one of $R_2$, $R_4$, $R_5$, $R_6$ or $R_7$ is a halogen atom, wherein each non-halogenated $R_2$, $R_5$, $R_6$, or $R_7$ is a hydrogen atom or an alkyl group or O-alkyl group, wherein $R_4$ when it is not halogenated is a phosphate group, a hydrogen atom or an alkyl group or O-alkyl group, and wherein $R_{3A}$ and $R_{3B}$ are a hydrogen atom, an alkyl group, an aryl group, or an acyl group, together with a pharmaceutically acceptable excipient, diluent or carrier.

In another aspect, the present disclosure relates to methods of treatment of psychiatric disorders. Accordingly, the present disclosure further provide a method for treating a psychiatric disorder, the method comprising administering to a subject in need thereof a pharmaceutical formulation comprising a chemical compound or salts thereof having the formula (I):

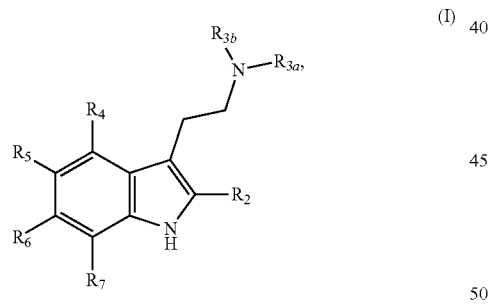

wherein, at least one of $R_2$, $R_4$, $R_5$, $R_6$ or $R_7$ is a halogen atom, wherein each non-halogenated $R_2$, $R_5$, $R_6$, or $R_7$ is a hydrogen atom or an alkyl group or O-alkyl group, wherein $R_4$ when it is not halogenated is a phosphate group, a hydrogen atom or an alkyl group or O-alkyl group, and wherein $R_{3A}$ and $R_{3B}$ are a hydrogen atom, an alkyl group, an aryl group, or an acyl group, wherein the pharmaceutical formulation is administered in an effective amount to treat the psychiatric disorder in the subject.

In at least one embodiment, in an aspect the disorder can be a 5-$HT_{2A}$ receptor mediated disorder.

In at least one embodiment, in an aspect, a dose can be administered of about 0.001 mg to about 5,000 mg.

In another aspect, the present disclosure relates to methods of making halogenated psilocybin derivatives. Accordingly, in one aspect, the present disclosure provides in at least one aspect, a method of making a halogenated psilocybin derivative the method comprising:
(a) contacting a halogenated psilocybin precursor compound with a host cell comprising a psilocybin biosynthetic enzyme complement; and
(b) growing the host cell to produce a halogenated psilocybin derivative or salts thereof having the formula (I):

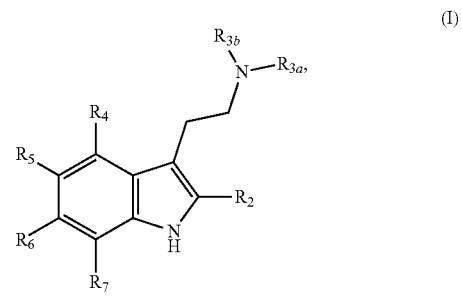

wherein, at least one of $R_2$, $R_4$, $R_5$, $R_6$ or $R_7$ is a halogen atom, wherein each non-halogenated $R_2$, $R_5$, $R_6$, or $R_7$ is a hydrogen atom or an alkyl group or O-alkyl group, wherein $R_4$ when it is not halogenated is a phosphate group, a hydrogen atom or an alkyl group or O-alkyl group, and wherein $R_{3A}$ and $R_{3B}$ are a hydrogen atom, an alkyl group, an aryl group, or an acyl group.

In at least one embodiment, in an aspect, the halogenated psilocybin precursor compound can be contacted with the host cell by including the psilocybin precursor compound in a growth medium for the host cell.

In at least one embodiment, in an aspect, the halogenated psilocybin precursor compound can be formed by contacting the host cell with a non-halogenated psilocybin precursor compound and a halogen, the host cell further comprising a halogenase capable of halogenating the non-halogenated psilocybin compound and forming the halogenated psilocybin precursor compound.

In at least one embodiment, in an aspect, $R_2$ can be a halogen atom and $R_5$, $R_6$ and $R_7$ can each be a hydrogen atom, and $R_4$ can be a phosphate group, a hydrogen atom or an alkyl group or O-alkyl group.

In at least one embodiment, in an aspect, $R_4$ can be a halogen atom and $R_2$, $R_5$, $R_6$ and $R_7$ can each be a hydrogen atom or an alkyl group or O-alkyl group.

In at least one embodiment, in an aspect, $R_5$ can be a halogen atom and $R_2$, $R_6$ and $R_7$ can each be a hydrogen atom or an alkyl group or O-alkyl group, and $R_4$ can be a phosphate group, a hydrogen atom or an alkyl group or O-alkyl group.

In at least one embodiment, in an aspect, $R_6$ can be a halogen atom and $R_2$, $R_5$ and $R_7$ can each be a hydrogen atom or an alkyl group or O-alkyl group, and $R_4$ can be a phosphate group, a hydrogen atom or an alkyl group or O-alkyl group.

In at least one embodiment, in an aspect, $R_7$ can be a halogen atom and $R_2$, $R_5$ and $R_6$ can each be a hydrogen atom or an alkyl group or O-alkyl group, and $R_4$ can be a phosphate group, a hydrogen atom or an alkyl group or O-alkyl group.

In at least one embodiment, in an aspect, at least two of $R_2$, $R_4$, $R_5$, $R_6$ or $R_7$ can be a halogen atom.

In at least one embodiment, in an aspect, the at least of two of $R_2$, $R_4$, $R_5$, $R_6$ or $R_7$ that are halogen atoms can be two identical halogen atoms.

In at least one embodiment, in an aspect, the at least of two of $R_2$, $R_4$, $R_5$, $R_6$ or $R_7$ that are halogen atoms can be two non-identical halogen atoms.

In at least one embodiment, in an aspect, $R_2$ and $R_4$ can be a halogen atom, and $R_5$, $R_6$ and $R_7$ can be a hydrogen atom or an alkyl group or O-alkyl group.

In at least one embodiment, in an aspect, $R_2$ and $R_5$ can be a halogen atom, $R_6$ and $R_7$ can be a hydrogen atom or an alkyl group or O-alkyl group, and $R_4$ can be a hydrogen atom, an alkyl group or O-alkyl group or a phosphate group.

In at least one embodiment, in an aspect, $R_2$ and $R_6$ can be a halogen atom, $R_5$ and $R_7$ can be a hydrogen atom or an alkyl group or O-alkyl group, and $R_4$ can be a hydrogen atom, an alkyl group or O-alkyl group or a phosphate group.

In at least one embodiment, in an aspect, $R_2$ and $R_7$ can be a halogen atom, $R_5$ and $R_6$ can be a hydrogen atom or an alkyl group or O-alkyl group, and $R_4$ can be a hydrogen atom, an alkyl group or O-alkyl group or a phosphate group.

In at least one embodiment, in an aspect, $R_4$ and $R_5$ can be a halogen atom, and $R_2$, $R_6$ and $R_7$ can be a hydrogen atom or an alkyl group or O-alkyl group.

In at least one embodiment, in an aspect, $R_4$ and $R_6$ can be a halogen atom, and $R_2$, $R_5$ and $R_7$ can be a hydrogen atom or an alkyl group or O-alkyl group.

In at least one embodiment, in an aspect, $R_4$ and $R_7$ can be a halogen atom, and $R_2$, $R_5$ and $R_6$ can be a hydrogen atom or an alkyl group or O-alkyl group.

In at least one embodiment, in an aspect, $R_5$ and $R_6$ can be a halogen atom, $R_2$ and $R_7$ can be a hydrogen atom or an alkyl group or O-alkyl group, and $R_4$ can be a hydrogen atom, an alkyl group or O-alkyl group or a phosphate group.

In at least one embodiment, in an aspect, $R_5$ and $R_7$ can be a halogen atom, $R_2$ and $R_6$ can be a hydrogen atom or an alkyl group or O-alkyl group, and $R_4$ can be a hydrogen atom, an alkyl group or O-alkyl group or a phosphate group.

In at least one embodiment, in an aspect, $R_6$ and $R_7$ can be a halogen atom, $R_2$ and $R_5$ can be a hydrogen atom or an alkyl group or O-alkyl group, and $R_4$ can be a hydrogen atom, an alkyl group or O-alkyl group or a phosphate group.

In at least one embodiment, in an aspect, $R_4$ when it is not halogenated can be a hydrogen atom.

In at least one embodiment, in an aspect, $R_4$ when it is not halogenated can be an alkyl group.

In at least one embodiment, in an aspect, $R_4$ when it is not halogenated can be an O-alkyl group.

In at least one embodiment, in an aspect, $R_4$ when it is not halogenated can be a phosphate group.

In at least one embodiment, in an aspect, the halogenated psilocybin derivative can be a derivative selected from the group consisting of derivatives having formulas (II); (III); (IV); (V); (VI); (VII): (VIII); (IX); (X); (XI), (XII); (XIII); (XIV); (XV); (XVI); and (XVII):

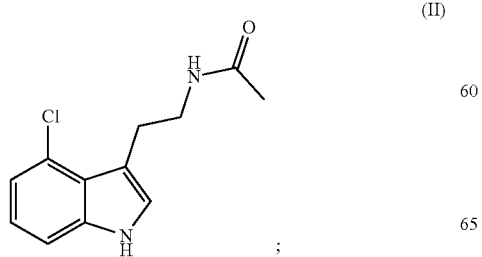

(II)

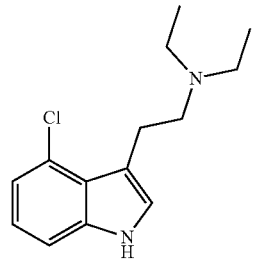

(III)

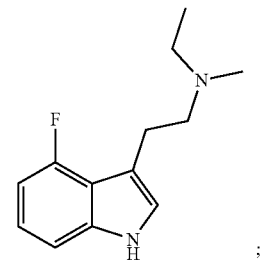

(IV)

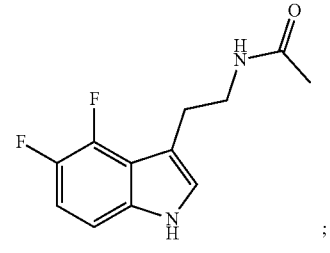

(V)

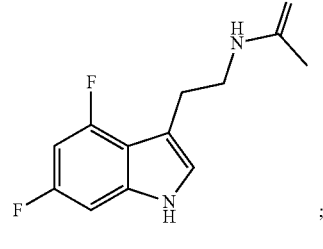

(VI)

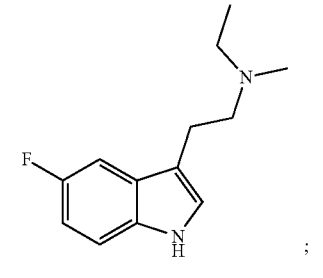

(VII)

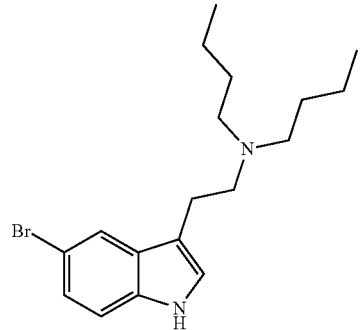

(VIII)

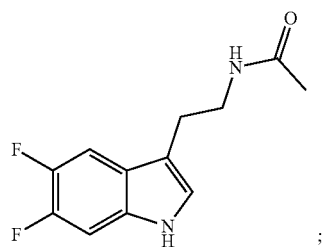 (IX);

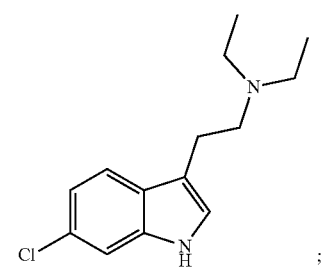 (X);

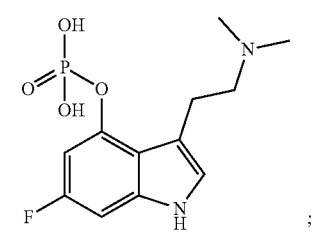 (XI);

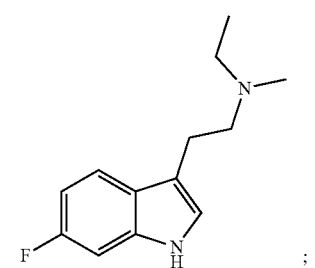 (XII);

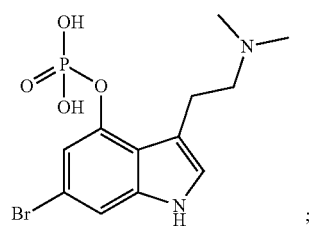 (XIII);

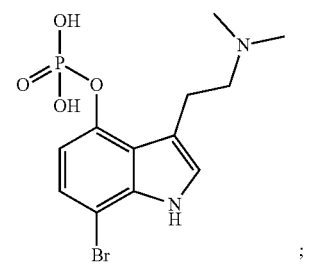 (XIV);

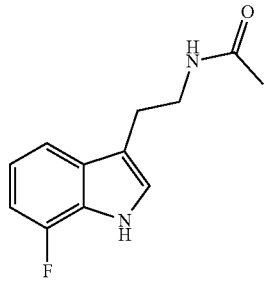 (XV);

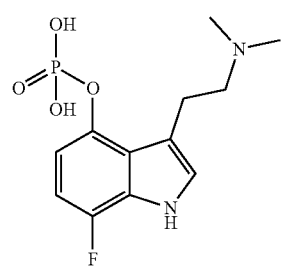 (XVI);

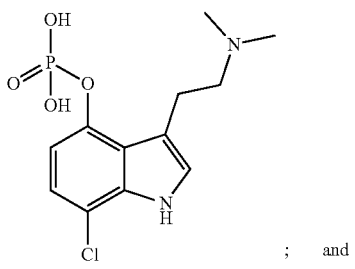 (XVII); and

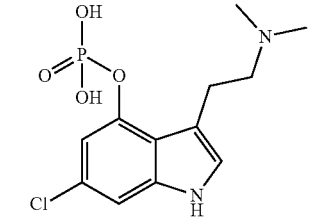 (XVIII).

In at least one embodiment, in an aspect, the halogenated psilocybin precursor compound can be selected from the group of halogenated compounds consisting of halogenated tryptophan, halogenated tryptamine, halogenated 4-hydroxytryptamine, halogenated 4-hydroxy-indole, halogenated 4-hydroxytryptophan, halogenated norbaeocystin, and halogenated baeocystin.

In at least one embodiment, in an aspect, the psilocybin biosynthetic enzyme complement can comprise at least one enzyme encoded by a nucleic acid selected from:
(a) SEQ. ID NO: 1, SEQ. ID NO: 3, SEQ. ID NO: 5, SEQ. ID NO: 7, SEQ. ID NO: 9, SEQ. ID NO 11, SEQ. ID NO: 36, SEQ. ID NO: 38, SEQ. ID NO: 40, SEQ. ID NO: 42, SEQ. ID NO: 44, SEQ. ID NO: 46, SEQ. ID NO: 48, SEQ. ID NO: 50, SEQ. ID NO: 52, SEQ. ID NO: 54, SEQ. ID NO: 56, SEQ. ID NO: 58, SEQ. ID NO: 60, SEQ. ID NO: 64, SEQ. ID NO: 66, SEQ. ID NO: 68, SEQ. ID NO: 70, and SEQ. ID NO: 72;
(b) a nucleic acid sequence that is substantially identical to any one of the nucleic acid sequences of (a);
(c) a nucleic acid sequence that is substantially identical to any one of the nucleic acid sequences of (a) but for the degeneration of the genetic code;

(d) a nucleic acid sequence that is complementary to any one of the nucleic acid sequences of (a);

(e) a nucleic acid sequence encoding a polypeptide having any one of the amino acid sequences set forth in SEQ. ID NO: 2, SEQ. ID NO: 4, SEQ. ID NO: 6, SEQ. ID NO: 8, SEQ. ID NO: 10, SEQ. ID NO 12, SEQ. ID NO: 37, SEQ. ID NO: 39, SEQ. ID NO: 41, SEQ. ID NO: 43, SEQ. ID NO: 45, SEQ. ID NO: 47, SEQ. ID NO: 49, SEQ. ID NO: 51, SEQ. ID NO: 53, SEQ. ID NO: 55, SEQ. ID NO: 57, SEQ. ID NO: 59, SEQ. ID NO: 61, SEQ. ID NO: 65, SEQ. ID NO: 67, SEQ. ID NO: 69, SEQ. ID NO: 71, and SEQ. ID NO: 73;

(f) a nucleic acid sequence that encodes a functional variant of any one of the amino acid sequences set forth in SEQ. ID NO: 2, SEQ. ID NO: 4, SEQ. ID NO: 6, SEQ. ID NO: 8, SEQ. ID NO: 10, SEQ. ID NO 12, SEQ. ID NO: 37, SEQ. ID NO: 39, SEQ. ID NO: 41, SEQ. ID NO: 43, SEQ. ID NO: 45, SEQ. ID NO: 47, SEQ. ID NO: 49, SEQ. ID NO: 51, SEQ. ID NO: 53, SEQ. ID NO: 55, SEQ. ID NO: 57, SEQ. ID NO: 59, SEQ. ID NO: 61, SEQ. ID NO: 65, SEQ. ID NO: 67, SEQ. ID NO: 69, SEQ. ID NO: 71, and SEQ. ID NO: 73; and (g) a nucleic acid sequence that hybridizes under stringent conditions to any one of the nucleic acid sequences set forth in (a), (b), (c), (d), (e) or (f).

In at least one embodiment, in an aspect, the halogenase can be encoded by a nucleic acid selected from:

(a) SEQ. ID NO: 13, SEQ. ID NO: 15, SEQ. ID NO: 17, SEQ. ID NO: 19, SEQ. ID NO: 21, SEQ. ID NO: 23, SEQ. ID NO: 25, and SEQ. ID NO: 27;

(b) a nucleic acid sequence that is substantially identical to any one of the nucleic acid sequences of (a);

(c) a nucleic acid sequence that is substantially identical to any one of the nucleic acid sequences of (a) but for the degeneration of the genetic code;

(d) a nucleic acid sequence that is complementary to any one of the nucleic acid sequences of (a);

(e) a nucleic acid sequence encoding a polypeptide having any one of the amino acid sequences set forth in SEQ. ID NO: 14, SEQ. ID NO: 16, SEQ. ID NO: 18, SEQ. ID NO: 20, SEQ. ID NO: 22, SEQ. ID NO: 24, SEQ. ID NO: 26, SEQ. ID NO: 28, SEQ. ID NO: 29, SEQ. ID NO: 30, SEQ. ID NO: 31, SEQ. ID NO: 32. SEQ. ID NO: 33, SEQ. ID NO: 34, and SEQ. ID NO: 35;

(f) a nucleic acid sequence that encodes a functional variant of any one of the amino acid sequences set forth in SEQ. ID NO: 14, SEQ. ID NO: 16, SEQ. ID NO: 18, SEQ. ID NO: 20, SEQ. ID NO: 22, SEQ. ID NO: 24, SEQ. ID NO: 26, SEQ. ID NO: 28, SEQ. ID NO: 29, SEQ. ID NO: 30, SEQ. ID NO: 31, SEQ. ID NO: 32. SEQ. ID NO: 33, SEQ. ID NO: 34, and SEQ. ID NO: 35; and (g) a nucleic acid sequence that hybridizes under stringent conditions to any one of the nucleic acid sequences set forth in (a), (b), (c), (d), (e) or (f).

In at least one embodiment, in an aspect, the host cell can further comprise an acetyl transferase capable of acetylating $R_{3a}$ or $R_{3b}$, wherein the cell comprises a compound having chemical formula (I):

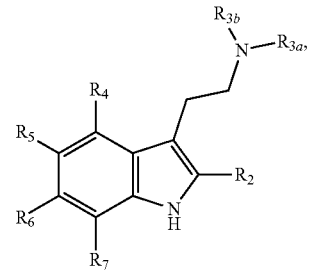

(I)

wherein, at least one of $R_2$, $R_4$, $R_5$, $R_6$ or $R_7$ is a halogen atom, wherein each non-halogenated $R_2$, $R_5$, $R_6$, or $R_7$ is a hydrogen atom or an alkyl group or O-alkyl group, wherein $R_4$ when it is not halogenated is a phosphate group, a hydrogen atom or an alkyl group or O-alkyl group, and wherein at least one of $R_{3A}$ and $R_{3B}$ is a hydrogen atom, to form a compound having the chemical formula (XIX):

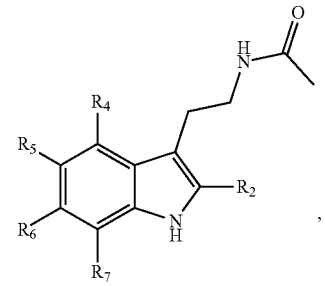

(XIX)

wherein, at least one of $R_2$, $R_4$, $R_5$, $R_6$ or $R_7$ is a halogen atom, wherein each non-halogenated $R_2$, $R_5$, $R_6$, or $R_7$ is a hydrogen atom or an alkyl group or O-alkyl group, wherein $R_4$ when it is not halogenated is a phosphate group, a hydrogen atom or an alkyl group or O-alkyl group.

In at least one embodiment, the acetylase can be encoded by a nucleic acid selected from:

(a) SEQ. ID NO: 62;

(b) a nucleic acid sequence that is substantially identical the nucleic acid sequence of (a);

(c) a nucleic acid sequence that is substantially identical to the nucleic acid sequence of (a) but for the degeneration of the genetic code;

(d) a nucleic acid sequence that is complementary to the nucleic acid sequence of (a);

(e) a nucleic acid sequence encoding a polypeptide having an amino acid sequences set forth in SEQ. ID NO: 63;

(f) a nucleic acid sequence that encodes a functional variant of the amino acid sequence set forth in SEQ. ID NO: 63; and (g) a nucleic acid sequence that hybridizes under stringent conditions to any one of the nucleic acid sequences set forth in (a), (b), (c), (d), (e) or (f).

In at least one embodiment, in an aspect, (a) the halogenated psilocybin precursor compound can be a halogenated indole, and the a psilocybin biosynthetic enzyme complement can comprise (i) a nucleic acid encoding TrpB selected from SEQ. ID NO: 12, SEQ. ID NO: 65, SEQ. ID NO: 67, SEQ. ID NO: 69, SEQ. ID NO: 71, and SEQ. ID NO: 73, or a nucleic acid sequence encoding a polypeptide sequence substantially similar thereto; (ii) a nucleic acid encoding PsiD selected from SEQ. ID NO: 2, SEQ. ID NO: 10, SEQ. ID NO: 37, SEQ. ID NO: 39, SEQ. ID NO: 41, SEQ. ID NO: 43, SEQ. ID NO: 45, SEQ. ID NO: 47, SEQ. ID NO: 49, SEQ. ID NO: 51, SEQ. ID NO: 53, SEQ. ID NO: 55, and SEQ. ID NO: 57, or a nucleic acid sequence encoding a polypeptide sequence substantially similar thereto; (iii) a nucleic acid encoding PsiK encoded by SEQ. ID NO: 6, or a nucleic acid sequence encoding a polypeptide sequence substantially similar thereto; and (iv) a nucleic acid encoding PsiM selected from SEQ. ID NO: 8, SEQ. ID NO: 59 and SEQ. ID NO: 61 or a nucleic acid sequence encoding a polypeptide sequence substantially similar thereto; or (b) the halogenated psilocybin precursor compound can be a halogenated tryptophan, and the psilocybin biosynthetic enzyme complement can comprise (i) a nucleic acid encoding PsiD selected from SEQ. ID NO: 2, SEQ. ID NO: 10, SEQ. ID NO: 37, SEQ. ID NO: 39, SEQ. ID NO: 41, SEQ. ID NO: 43, SEQ. ID NO: 45, SEQ. ID NO: 47, SEQ. ID NO: 49, SEQ. ID NO: 51, SEQ. ID NO: 53, SEQ. ID NO: 55, and SEQ. ID NO: 57, or a nucleic acid sequence encoding a polypeptide sequence substantially similar thereto; (ii) a nucleic acid encoding PsiK encoded by SEQ. ID NO: 6, or a nucleic acid sequence encoding a polypeptide sequence substantially similar thereto; and (iii) a nucleic acid encoding PsiM selected from SEQ. ID NO: 8, SEQ. ID NO: 59 and SEQ. ID NO: 61 or a nucleic acid sequence encoding a polypeptide sequence substantially similar thereto; or (c) the halogenated psilocybin precursor compound can be a halogenated tryptamine, and the psilocybin biosynthetic enzyme complement can comprise (i) a nucleic acid encoding PsiK encoded by SEQ. ID NO: 6, or a nucleic acid sequence encoding a polypeptide sequence substantially similar thereto; and (ii) and a nucleic acid encoding PsiM selected from SEQ. ID NO: 8, SEQ. ID NO: 59 and SEQ. ID NO: 61 or a nucleic acid sequence encoding a polypeptide sequence substantially similar thereto; or (d) the halogenated psilocybin precursor compound can be a halogenated norbaeocystin or a halogenated baeocystin and the psilocybin biosynthetic enzyme complement can comprise a nucleic acid encoding PsiM selected from SEQ. ID NO: 8, SEQ. ID NO: 59 and SEQ. ID NO: 61 or a nucleic acid sequence encoding a polypeptide sequence substantially similar thereto; or (e) the halogenated psilocybin precursor compound can be a halogenated tryptophan, and the psilocybin biosynthetic enzyme complement can comprise (i) a nucleic acid encoding PsiD selected from SEQ. ID NO: 2, SEQ. ID NO: 10, SEQ. ID NO: 37, SEQ. ID NO: 39, SEQ. ID NO: 41, SEQ. ID NO: 43, SEQ. ID NO: 45, SEQ. ID NO: 47, SEQ. ID NO: 49, SEQ. ID NO: 51, SEQ. ID NO: 53, SEQ. ID NO: 55, and SEQ. ID NO: 57, or a nucleic acid sequence encoding a polypeptide sequence substantially similar thereto; (ii) a nucleic acid encoding PsiH encoded by SEQ. ID NO: 4, or a nucleic acid sequence encoding a polypeptide sequence substantially similar thereto; (iii) a nucleic acid encoding PsiK encoded by SEQ. ID NO: 6, or a nucleic acid sequence encoding a polypeptide sequence substantially similar thereto; and (iv) and a nucleic acid encoding PsiM selected from SEQ. ID NO: 8, SEQ. ID NO: 59 and SEQ. ID NO: 61 or a nucleic acid sequence encoding a polypeptide sequence substantially similar thereto; or (f) the halogenated psilocybin precursor compound can be, a halogenated tryptamine, and psilocybin biosynthetic enzyme complement can comprise (i) a nucleic acid encoding PsiH encoded by SEQ. ID NO: 4, or a nucleic acid sequence encoding a polypeptide sequence substantially similar thereto; (ii) a nucleic acid encoding PsiK encoded by SEQ. ID NO: 6, or a nucleic acid sequence encoding a polypeptide sequence substantially similar thereto; and (iii) and a nucleic acid encoding PsiM selected from SEQ. ID NO: 8, SEQ. ID NO: 59 and SEQ. ID NO: 61 or a nucleic acid sequence encoding a polypeptide sequence substantially similar thereto.

In at least one embodiment, in an aspect, the method can further include a step comprising isolating the halogenated psilocybin derivative.

In at least one embodiment, in an aspect, the host cell can be a microbial cell.

In at least one embodiment, in an aspect, the host cell can be a bacterial cell or a yeast cell.

In another aspect, the present disclosure provides, in at least one embodiment, a method for modulating a $5\text{-}HT_{2A}$ receptor, the method comprising contacting a $5\text{-}HT_{2A}$ receptor with a chemical compound or salts thereof having the formula (I):

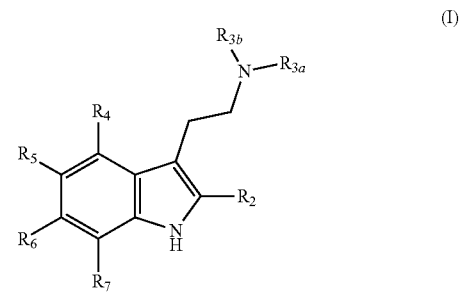

wherein, at least one of $R_2$, $R_4$, $R_5$, $R_6$ or $R_7$ is a halogen atom, wherein each non-halogenated $R_2$, $R_5$, $R_6$, or $R_7$ is a hydrogen atom or an alkyl group or O-alkyl group, wherein $R_4$ when it is not halogenated is a phosphate group, a hydrogen atom or an alkyl group or O-alkyl group, and wherein $R_{3A}$ and $R_{3B}$ are a hydrogen atom, an alkyl group, an aryl group, or an acyl group under reaction conditions sufficient to thereby modulate receptor activity.

In at least one embodiment, in an aspect, the reaction conditions can be in vitro reaction conditions.

In at least one embodiment, in an aspect, the reaction conditions can be in vivo reaction conditions.

In another aspect, the present disclosure provides, in at least one embodiment, a use of a chemical compound or salts thereof having the formula (I):

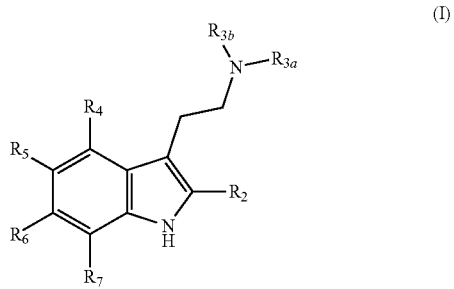

(I)

wherein, at least one of $R_2$, $R_4$, $R_5$, $R_6$ or $R_7$ is a halogen atom, wherein each non-halogenated $R_2$, $R_5$, $R_6$, or $R_7$ is a hydrogen atom or an alkyl group or O-alkyl group, wherein $R_4$ when it is not halogenated is a phosphate group, a hydrogen atom or an alkyl group or O-alkyl group, and wherein $R_{3A}$ and $R_{3B}$ are a hydrogen atom, an alkyl group, an aryl group, or an acyl group in the manufacture of a pharmaceutical or recreational drug formulation.

In at least one embodiment, in an aspect, the manufacture of a pharmaceutical or recreational drug formulation can comprise formulating the chemical compound with an excipient, diluent or carrier.

In at least one embodiment, the manufacture of a pharmaceutical or recreational drug formulation can comprise derivatizing the chemical compound having the formula (I) by substituting the halogen atom with another atom or chemical group.

In another aspect, the present disclosure provides, in at least one embodiment, a use of a chemical compound or salts thereof having the formula

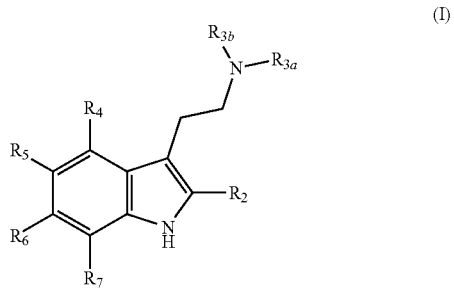

(I)

wherein, at least one of $R_2$, $R_4$, $R_5$, $R_6$ or $R_7$ is a halogen atom, wherein each non-halogenated $R_2$, $R_5$, $R_6$, or $R_7$ is a hydrogen atom or an alkyl group or O-alkyl group, wherein $R_4$ when it is not halogenated is a phosphate group, a hydrogen atom or an alkyl group or O-alkyl group, and wherein $R_{3A}$ and $R_{3B}$ are a hydrogen atom, an alkyl group, an aryl group, or an acyl group together with a diluent, carrier or excipient, as a pharmaceutical or recreational drug formulation.

Other features and advantages will become apparent from the following detailed description. It should be understood, however, that the detailed description, while indicating preferred implementations of the disclosure, are given by way of illustration only, since various changes and modifications within the spirit and scope of the disclosure will become apparent to those of skill in the art from the detailed description.

BRIEF DESCRIPTION OF THE DRAWINGS

The disclosure is in the hereinafter provided paragraphs described, by way of example, in relation to the attached figures. The figures provided herein are provided for a better understanding of the example embodiments and to show more clearly how the various embodiments may be carried into effect. The figures are not intended to limit the present disclosure.

Figure 1:
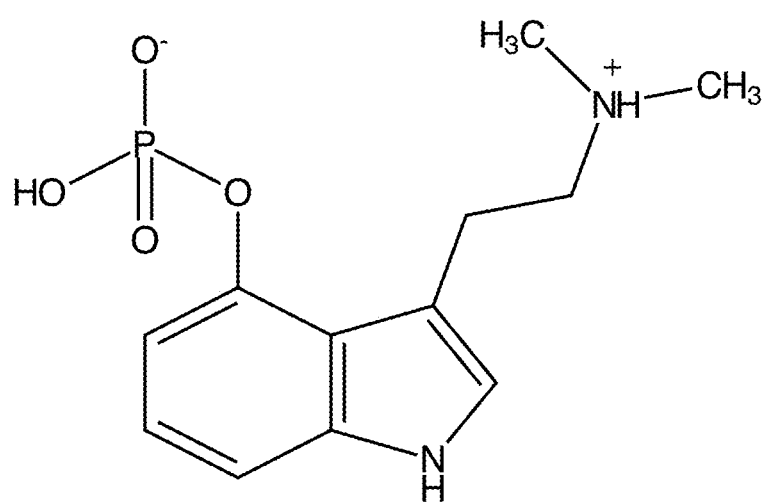
FIG. 1 depicts the chemical structure of psilocybin.

The figures together with the following detailed description make apparent to those skilled in the art how the disclosure may be implemented in practice.

DETAILED DESCRIPTION

Various compositions, systems or processes will be described below to provide an example of an embodiment of each claimed subject matter. No embodiment described below limits any claimed subject matter and any claimed subject matter may cover processes, compositions or systems that differ from those described below. The claimed subject matter is not limited to compositions, processes or systems having all of the features of any one composition, system or process described below or to features common to multiple or all of the compositions, systems or processes described below. It is possible that a composition, system or process described below is not an embodiment of any claimed subject matter. Any subject matter disclosed in a composition, system or process described below that is not claimed in this document may be the subject matter of another protective instrument, for example, a continuing patent application, and the applicant(s), inventor(s) or owner(s) do not intend to abandon, disclaim or dedicate to the public any such subject matter by its disclosure in this document.

As used herein and in the claims, the singular forms, such "a", "an" and "the" include the plural reference and vice versa unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers.

Various compositions, systems or processes will be described below to provide an example of an embodiment of each claimed subject matter. No embodiment described below limits any claimed subject matter and any claimed subject matter may cover processes, compositions or systems that differ from those described below. The claimed subject matter is not limited to compositions, processes or systems having all of the features of any one composition, system or process described below or to features common to multiple or all of the compositions, systems or processes described below. It is possible that a composition, system or process described below is not an embodiment of any claimed subject matter. Any subject matter disclosed in a composition, system or process described below that is not claimed in this document may be the subject matter of another protective instrument, for example, a continuing patent application, and the applicant(s), inventor(s) or owner(s) do not intend to abandon, disclaim or dedicate to the public any such subject matter by its disclosure in this document.

When ranges are used herein for physical properties, such as molecular weight, or chemical properties, such as chemical formulae, all combinations and sub-combinations of ranges and specific embodiments therein are intended to be included. Other than in the operating examples, or where otherwise indicated, all numbers expressing quantities of ingredients or reaction conditions used herein should be understood as modified in all instances by the term "about." The term "about" when referring to a number or a numerical range means that the number or numerical range referred to is an approximation within experimental variability (or within statistical experimental error), and thus the number or numerical range may vary between 1% and 15% of the stated number or numerical range, as will be readily recognized by context. Furthermore any range of values described herein is intended to specifically include the limiting values of the range, and any intermediate value or sub-range within the given range, and all such intermediate values and sub-ranges are individually and specifically disclosed (e.g. a range of 1 to 5 includes 1, 1.5, 2, 2.75, 3, 3.90, 4, and 5). Similarly, other terms of degree such as "substantially" and "approximately" as used herein mean a reasonable amount of deviation of the modified term such that the end result is not significantly changed. These terms of degree should be construed as including a deviation of the modified term if this deviation would not negate the meaning of the term it modifies.

Unless otherwise defined, scientific and technical terms used in connection with the formulations described herein shall have the meanings that are commonly understood by those of ordinary skill in the art. The terminology used herein is for the purpose of describing particular embodiments only, and is not intended to limit the scope of the present invention, which is defined solely by the claims.

All publications, patents and patent applications are herein incorporated by reference in their entirety to the same extent as if each individual publication, patent or patent application was specifically and individually indicated to be incorporated by reference in its entirety.

Terms and Definitions

The term "psilocybin", as used herein, refers to a chemical compound having the structure set forth in FIG. 1, and further includes salts, thereof, such as a sodium salt, a potassium salt, etc.

The term "psilocybin precursor compound", as used herein, refers to a chemical compound that may serve as a precursor compound in the synthesis or biosynthesis of psilocybin, and includes compounds comprising an indole prototype structure, including, for example, tryptophan, tryptamine, 4-hydroxyindole, 4-hydroxytryptophan, 4-hydroxytryptamine, norbaeocystin, and baeocystin, and further includes halogenated derivatives and salts of any of the foregoing.

Figure 2:
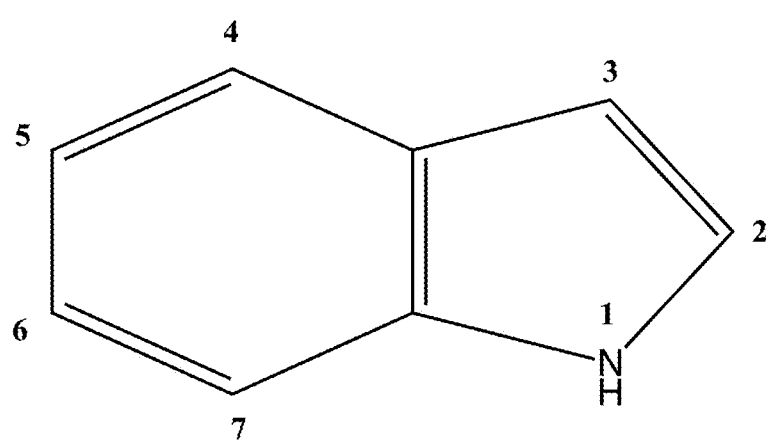
FIG. 2 depicts a certain prototype structure of a psilocybin precursor compound, namely an indole. Certain carbon and nitrogen atoms may be referred herein by reference to their position within the indole structure, i.e. $N_1$, $C_2$, $C_3$ etc. The pertinent atom numbering is shown.

The term "indole prototype structure", as used herein, refers to the chemical structure shown in FIG. 2. It is noted that specific carbon atoms and a nitrogen atom in the indole prototype structure are numbered. Reference may be made to these carbon and nitrogen numbers herein, for example $C_2$, $C_4$, $N_1$, and so forth. Furthermore, reference may be made to chemical groups attached to the indole prototype structure in accordance with the same numbering, for example $R_4$ and $R_6$ reference chemical groups attached to the $C_4$ and $C_6$ atom, respectively. In addition, $R_{3A}$ and $R_{3B}$, in this respect, reference chemical groups extending from the ethyl-amino group extending in turn from the $C_3$ atom of the prototype indole structure.

Figure 3A:
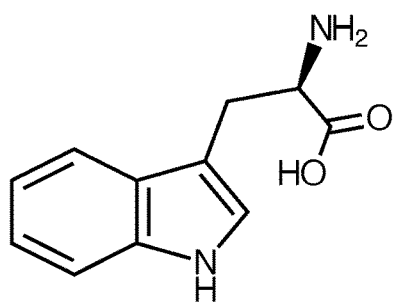
FIGS. 3A, 3B, 3C, 3D, 3E, 3F and 3G depict the chemical structures of example psilocybin precursor compounds, notably L-tryptophan (FIG. 3A), tryptamine (FIG. 3B), 4-hydroxytryptamine (FIG. 3C), L-4-hydroxytryptophan (FIG. 3D), 4-hydroxyindole (FIG. 3E), norbaeocystin (FIG. 3F), and baeocystin (FIG. 3G).

The term "tryptophan", as used herein, refers to a chemical compound having the structure set forth in FIG. 3A and further includes its D-enantiomeric form (not shown).

Figure 3B:
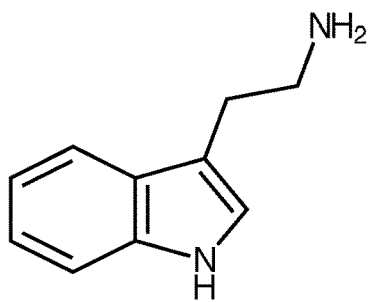

The term "tryptamine", as used herein, refers to a chemical compound having the structure set forth in FIG. 3B.

Figure 3C:
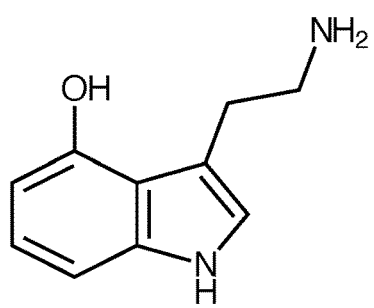

The term "4-hydroxytryptamine", as used herein, refers to a chemical compound having the structure set forth in FIG. 3C.

Figure 3D:
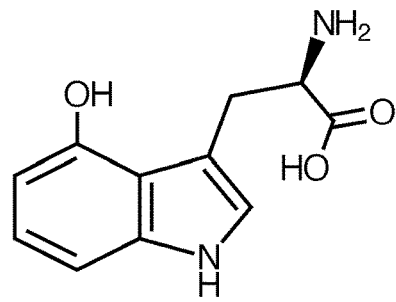

The term "4-hydroxytryptophan", as used herein, refers to a chemical compound having the structure set forth in FIG. 3D and further includes its D-enantiomeric form (not shown).

Figure 3E:
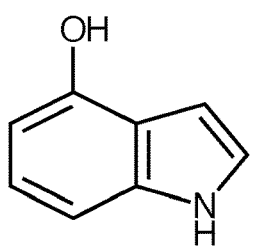

The term "4-hydroxyindole", as used herein, refers to a chemical compound having the structure set forth in FIG. 3E.

Figure 3F:
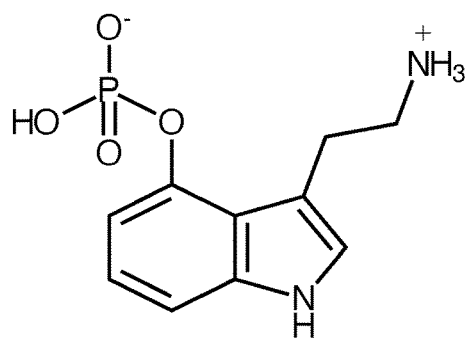

The term "norbaeocystin", as used herein, refers to a chemical compound having the structure set forth in FIG. 3F.

Figure 3G:
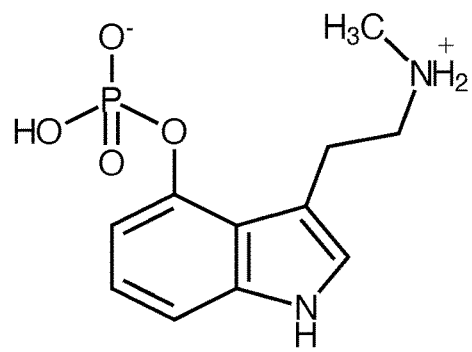

The term "baeocystin", as used herein, refers to a chemical compound having the structure set forth in FIG. 3G.

The term "phosphate group", as used herein, is a molecule containing one atom of phosphorus, covalently bound to four oxygen atoms (three single bonds and one double bond). Of the four oxygen atoms one oxygen atom may be a hydroxy group, and one of the non-hydroxylated oxygen atom may be chemically bonded to another entity.

The terms "hydroxy group", and "hydroxy", as used herein, refers to a molecule containing one atom of oxygen bonded to one atom of hydrogen, and having the formula —OH. A hydroxy group through its oxygen atom may be chemically bonded to another entity.

The terms "halogen", "halogenated" and "halo-", as used herein, refer to the class of chemical elements consisting of fluorine (F), chlorine (Cl), bromine (Br), and iodine (I). Accordingly, halogenated compounds can refer to "fluorinated", "chlorinated", "brominated", or "iodinated" compounds.

The term "halogenated psilocybin derivative", as used herein, refers to a psilocybin derivative in which a halogen been bonded to psilocybin, or a derivative thereof. Reference may be made to specific carbon atoms of the psilocybin derivative which may be halogenated, for example, 7-halo-psilocybin refers to a halogenated psilocybin in which carbon atom number 7 (as identified in the indole prototype structure) is halogenated, or, similarly, 2-bromo-psilocybin refers to a brominated psilocybin in which carbon atom number 2 (as identified in the indole prototype structure) is brominated, and so on. The term further includes salts of halogenated psilocybin derivatives, such as sodium salt, potassium salt, or a chlorine salt, for example. Salts may be formed by virtue of a charged atom or group included in the psilocybin derivative, notably a charged nitrogen atom, and/or a charged phosphate group.

The term "halogenated psilocybin precursor compound", as used herein, refers to a psilocybin precursor compound possessing a halogen. Reference may be made to specific carbon atoms of the psilocybin precursor compound which may be halogenated, for example, 6-halo-baeocystin refers to a halogenated baeocystin in which carbon atom number 6 (as identified in the indole prototype structure) is halogenated, or, similarly, 2-chloro-4-hydroxytryptamine refers to a chlorinated 4-hydroxytryptamine in which carbon atom number 2 (as identified in the indole prototype structure) is chlorinated. Furthermore, halogenated psilocybin precursor compounds include, without limitation, halogenated tryptophan, e.g. 7-bromo tryptophan, 6-chloro tryptophan, 5,6-difluoro tryptophan, halogenated 4-hydroxy indole e.g. 4-hydroxy-7-bromo indole, 4-hydroxy-5-chloro indole, 6,7-di-fluoro-indole The term "alkyl", as used herein, refers to a straight and/or branched chain, saturated alkyl radical containing from one to "p" carbon atoms ("$C_1$-$C_p$-alkyl") and includes, depending on the identity of "p", methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like, where the variable p is an integer representing the largest number of carbon atoms in the alkyl radical. Alkyl groups further include hydrocarbon groups arranged in a chain having the chemical formula —$C_nH_{2n+1}$, including, without limitation, methyl groups (—$CH_3$), ethyl groups (—$C_2H_5$), propyl groups (—$C_3H_7$), and butyl groups (—$C_4H_9$).

The term "O-alkyl", as used herein, refers to a hydrocarbon group arranged in a chain having the chemical formula —O—$C_nH_{2n+1}$. O-alkyl groups include, without limitation, O-methyl groups (—O—$CH_3$), O-ethyl groups (—O—$C_2H_5$), O-propyl groups (—O—$C_3H_7$) and O-butyl groups (—O—$C_4H_9$).

The term "acyl", as used herein, refers to a carbon atom double bonded to an oxygen and single bonded to an alkyl group. The carbon atom further can be bonded to another entity. An acyl group can be described by the chemical formula: —C(=O)—$C_nH_{2n+1}$.

The term "aryl", as used herein, refers to a monocyclic, bicyclic or tricyclic aromatic ring system containing, depending on the number of atoms in the rings, for example, from 6 to 14 carbon atoms ($C_6$-$C_{14}$-aryl) or from 6 to 10 carbons ($C_6$-$C_{10}$-aryl), and at least 1 aromatic ring and includes phenyl, naphthyl, anthracenyl, 1,2-dihydronaphthyl, 1,2,3,4-tetrahydronaphthyl, fluorenyl, phenanthrenyl, biphenylenyl, indanyl, indenyl and the like.

The term "5-$HT_{2A}$ receptor", as used herein, refers to a subclass of a family of receptors for the neurotransmitter and peripheral signal mediator serotonin. 5-$HT_{2A}$ receptors can mediate a plurality of central and peripheral physiologic functions of serotonin. Central nervous system effects can include mediation of hallucinogenic effects of hallucinogenic compounds.

The term "modulating 5-$HT_{2A}$ receptors", as used herein, refers to the ability of a compound disclosed herein to alter the function of 5-$HT_{2A}$ receptors. A 5-$HT_{2A}$ receptor modulator may activate the activity of a 5-$HT_{2A}$ receptor, may activate or inhibit the activity of a 5-$HT_{2A}$ receptor depending on the concentration of the compound exposed to the 5-$HT_{2A}$ receptor, or may inhibit the activity of a 5-$HT_{2A}$ receptor. Such activation or inhibition may be contingent on the occurrence of a specific event, such as activation of a signal transduction pathway, and/or maybe manifest only in particular cell types. The term "modulating 5-HT$_{2A}$ receptors," also refers to altering the function of a 5-HT$_{2A}$ receptor by increasing or decreasing the probability that a complex forms between a 5-HT$_{2A}$ receptor and a natural binding partner to form a multimer. A 5-HT$_{2A}$ receptor modulator may increase the probability that such a complex forms between the 5-HT$_{2A}$ receptor and the natural binding partner, may increase or decrease the probability that a complex forms between the 5-HT$_{2A}$ receptor and the natural binding partner depending on the concentration of the compound exposed to the 5-HT$_{2A}$ receptor, and or may decrease the probability that a complex forms between the 5-HT$_{2A}$ receptor and the natural binding partner. Furthermore, the term includes allosteric modulation of the receptor 5-HT$_{2A}$, i.e. modulation of the 5-HT$_{2A}$ receptor through interaction with the 5-HT$_{2A}$ receptor that is topographically different than the orthosteric site recognized by the cell's endogenous agonist, such modulation further including positive allosteric modulation (PAM), negative allosteric modulation (NAM) and silent allosteric modulation (SAM).

The term "5-HT$_{2A}$ receptor-mediated disorder", as used herein, refers to a disorder that is characterized by abnormal 5-HT$_{2A}$ receptor activity. A 5-HT$_{2A}$ receptor-mediated disorder may be completely or partially mediated by modulating 5-HT$_{2A}$ receptors. In particular, a 5-HT$_{2A}$ receptor-mediated disorder is one in which modulation of 5-HT$_{2A}$ receptors results in some effect on the underlying disorder e.g., administration of a 5-HT$_{2A}$ receptor modulator results in some improvement in at least some of the subjects being treated.

The term "pharmaceutical formulation", as used herein, refers to a preparation in a form which allows an active ingredient, including a psychoactive ingredient; contained therein to provide effective treatment; and which does not contain any other ingredients which cause excessive toxicity, an allergic response, irritation, or other adverse response commensurate with a reasonable risk/benefit ratio. The pharmaceutical formulation may contain other pharmaceutical ingredients such as excipients, carriers, diluents, or auxiliary agents.

The term "recreational drug formulation", as used herein, refers to a preparation in a form which allows a psychoactive ingredient contained therein to be effective for administration as a recreational drug, and which does not contain any other ingredients which cause excessive toxicity, an allergic response, irritation, or other adverse response commensurate with a reasonable risk/benefit ratio. The recreational drug formulation may contain other ingredients such as excipients, carriers, diluents, or auxiliary agents.

The term "effective for administration as a recreational drug", as used herein, refers to a preparation in a form which allows a subject to voluntarily induce a psychoactive effect for non-medical purposes upon administration, generally in the form of self-administration. The effect may include an altered state of consciousness, satisfaction, pleasure, euphoria, perceptual distortion, or hallucination.

The term "effective amount", as used herein, refers to an amount of an active agent, pharmaceutical formulation or recreational drug formulation, sufficient to induce a desired biological or therapeutic effect, including a prophylactic effect, and further including a psychoactive effect. Such effect can include an effect with respect to the signs, symptoms or causes of a disorder, or disease or any other desired alteration of a biological system. The effective amount can vary depending, for example, on the health condition, injury stage, disorder stage, or disease stage, weight, or sex of a subject being treated, timing of the administration, manner of the administration, age of the subject, and the like, all of which can be determined by those of skill in the art.

The terms "treating" and "treatment", and the like, as used herein, are intended to mean obtaining a desirable physiological, pharmacological, or biological effect, and includes prophylactic and therapeutic treatment. The effect may result in the inhibition, attenuation, amelioration, or reversal of a sign, symptom or cause of a disorder, or disease, attributable to the disorder, or disease, which includes mental and psychiatric diseases and disorders. Clinical evidence of the prevention or treatment may vary with the disorder, or disease, the subject and the selected treatment.

The term "pharmaceutically acceptable", as used herein, refers to materials, including excipients, carriers, diluents, or auxiliary agents, that are compatible with other materials in a pharmaceutical or recreational drug formulation and within the scope of reasonable medical judgement suitable for use in contact with a subject without excessive toxicity, allergic response, irritation, or other adverse response commensurate with a reasonable risk/benefit ratio.

The term "psilocybin biosynthetic enzyme complement", as used herein, refers to one or more polypeptides which alone or together are capable of facilitating the chemical conversion of a psilocybin precursor compound and form another psilocybin precursor compound or psilocybin or a halogenated form thereof. A psilocybin biosynthetic enzyme complement can include, for example, PsiD, PsiH, PsiK, PsiM, Psi-ncAAAD and TrpB.

The term "PsiD" as used herein, refers to any and all enzymes comprising a sequence of amino acid residues which is (i) substantially identical to the amino acid sequences constituting any PsiD polypeptide set forth herein, including, for example, SEQ. ID NO: 2, SEQ. ID NO: 37, SEQ. ID NO: 39, SEQ. ID NO: 41, SEQ. ID NO: 43, SEQ. ID NO: 45, SEQ. ID NO: 47, SEQ. ID NO: 49, SEQ. ID NO: 51, SEQ. ID NO: 53, SEQ. ID NO: 55, and SEQ. ID NO: 57 or (ii) encoded by a nucleic acid sequence capable of hybridizing under at least moderately stringent conditions to any nucleic acid sequence encoding any PsiD set forth herein, but for the use of synonymous codons.

The term "PsiH" as used herein, refers to any and all enzymes comprising a sequence of amino acid residues which is (i) substantially identical to the amino acid sequences constituting any PsiH polypeptide set forth herein, including, for example, SEQ. ID NO: 4, or (ii) encoded by a nucleic acid sequence capable of hybridizing under at least moderately stringent conditions to any nucleic acid sequence encoding any PsiH set forth herein, but for the use of synonymous codons.

The term "PsiK" as used herein, refers to any and all enzymes comprising a sequence of amino acid residues which is (i) substantially identical to the amino acid sequences constituting any PsiK polypeptide set forth herein, including, for example, SEQ. ID NO: 6, or (ii) encoded by a nucleic acid sequence capable of hybridizing under at least moderately stringent conditions to any nucleic acid sequence encoding any PsiK set forth herein, but for the use of synonymous codons.

The term "PsiM" as used herein, refers to any and all enzymes comprising a sequence of amino acid residues which is (i) substantially identical to the amino acid sequences constituting any PsiM polypeptide set forth herein, including, for example, SEQ. ID NO: 8, and SEQ. ID NO: 59 or (ii) encoded by a nucleic acid sequence capable of hybridizing under at least moderately stringent conditions to any nucleic acid sequence encoding any PsiM set forth herein, but for the use of synonymous codons.

The term "Psi-ncAAAD" as used herein, refers to any and all enzymes comprising a sequence of amino acid residues which is (i) substantially identical to the amino acid sequences constituting any Psi-ncAAAD polypeptide set forth herein, including, for example, SEQ. ID NO: 10, or (ii) encoded by a nucleic acid sequence capable of hybridizing under at least moderately stringent conditions to any nucleic acid sequence encoding any Psi-ncAAAD set forth herein, but for the use of synonymous codons.

The term "TrpB" as used herein, refers to any and all enzymes comprising a sequence of amino acid residues which is (i) substantially identical to the amino acid sequences constituting any TrpB polypeptide set forth herein, including, for example, SEQ. ID NO: 12, SEQ. ID NO: 65, SEQ. ID NO: 67, SEQ. ID NO: 69, SEQ. ID NO: 71, and SEQ. ID NO: 73, or (ii) encoded by a nucleic acid sequence capable of hybridizing under at least moderately stringent conditions to any nucleic acid sequence encoding any TrpB set forth herein, but for the use of synonymous codons.

The term "halogenase", as used herein, refers to any and all enzymes comprising a sequence of amino acid residues which is (i) substantially identical to the amino acid sequences constituting any halogenase polypeptide set forth herein, including, for example, SEQ. ID NO: 14, or (ii) encoded by a nucleic acid sequence capable of hybridizing under at least moderately stringent conditions to any nucleic acid sequence encoding any halogenase set forth herein, but for the use of synonymous codons.

The term "acetyl transferase", as used herein, refers to any and all enzymes comprising a sequence of amino acid residues which is (i) substantially identical to the amino acid sequences constituting any acetyl transferase polypeptide set forth herein, including, for example, SEQ. ID NO: 63, or (ii) encoded by a nucleic acid sequence capable of hybridizing under at least moderately stringent conditions to any nucleic acid sequence encoding any acetyl transferase set forth herein, but for the use of synonymous codons.

The terms "nucleic acid sequence encoding PsiD", and "nucleic acid sequence encoding a PsiD polypeptide", as may be used interchangeably herein, refer to any and all nucleic acid sequences encoding a PsiD polypeptide, including, for example, SEQ. ID NO: 1, SEQ. ID NO: 36, SEQ. ID NO: 38, SEQ. ID NO: 40, SEQ. ID NO: 42, SEQ. ID NO: 44, SEQ. ID NO: 46, SEQ. ID NO: 48, SEQ. ID NO: 50, SEQ. ID NO: 52, SEQ. ID NO: 54, and SEQ. ID NO: 56. Nucleic acid sequences encoding a PsiD polypeptide further include any and all nucleic acid sequences which (i) encode polypeptides that are substantially identical to the PsiD polypeptide sequences set forth herein; or (ii) hybridize to any PsiD nucleic acid sequences set forth herein under at least moderately stringent hybridization conditions or which would hybridize thereto under at least moderately stringent conditions but for the use of synonymous codons.

The terms "nucleic acid sequence encoding PsiH", and "nucleic acid sequence encoding a PsiH polypeptide", as may be used interchangeably herein, refer to any and all nucleic acid sequences encoding a PsiH polypeptide, including, for example, SEQ. ID NO: 3. Nucleic acid sequences encoding a PsiH polypeptide further include any and all nucleic acid sequences which (i) encode polypeptides that are substantially identical to the PsiH polypeptide sequences set forth herein; or (ii) hybridize to any PsiH nucleic acid sequences set forth herein under at least moderately stringent hybridization conditions or which would hybridize thereto under at least moderately stringent conditions but for the use of synonymous codons.

The terms "nucleic acid sequence encoding PsiK", and "nucleic acid sequence encoding a PsiK polypeptide", as may be used interchangeably herein, refer to any and all nucleic acid sequences encoding a PsiK polypeptide, including, for example, SEQ. ID NO: 5. Nucleic acid sequences encoding a PsiK polypeptide further include any and all nucleic acid sequences which (i) encode polypeptides that are substantially identical to the PsiK polypeptide sequences set forth herein; or (ii) hybridize to any PsiK nucleic acid sequences set forth herein under at least moderately stringent hybridization conditions or which would hybridize thereto under at least moderately stringent conditions but for the use of synonymous codons.

The terms "nucleic acid sequence encoding PsiM", and "nucleic acid sequence encoding a PsiM polypeptide", as may be used interchangeably herein, refer to any and all nucleic acid sequences encoding a PsiD polypeptide, including, for example, SEQ. ID NO: 7 SEQ. ID NO: 58 and SEQ. ID NO: 61. Nucleic acid sequences encoding a PsiM polypeptide further include any and all nucleic acid sequences which (i) encode polypeptides that are substantially identical to the PsiM polypeptide sequences set forth herein; or (ii) hybridize to any PsiM nucleic acid sequences set forth herein under at least moderately stringent hybridization conditions or which would hybridize thereto under at least moderately stringent conditions but for the use of synonymous codons.

The terms "nucleic acid sequence encoding Psi-ncAAAD", and "nucleic acid sequence encoding a Psi-ncAAAD polypeptide", as may be used interchangeably herein, refer to any and all nucleic acid sequences encoding a PsiD polypeptide, including, for example, SEQ. ID NO: 9. Nucleic acid sequences encoding a Psi-ncAAAD polypeptide further include any and all nucleic acid sequences which (i) encode polypeptides that are substantially identical to the Psi-ncAAAD polypeptide sequences set forth herein; or (ii) hybridize to any Psi-ncAAAD nucleic acid sequences set forth herein under at least moderately stringent hybridization conditions or which would hybridize thereto under at least moderately stringent conditions but for the use of synonymous codons.

The terms "nucleic acid sequence encoding TrpB", and "nucleic acid sequence encoding a TrpB polypeptide", as may be used interchangeably herein, refer to any and all nucleic acid sequences encoding a TrpB polypeptide, including, for example, SEQ. ID NO: 11, SEQ. ID NO: 64, SEQ. ID NO: 66, SEQ. ID NO: 68, SEQ. ID NO: 70, and SEQ. ID NO: 72. Nucleic acid sequences encoding a TrpB polypeptide further include any and all nucleic acid sequences which (i) encode polypeptides that are substantially identical to the TrpB polypeptide sequences set forth herein; or (ii) hybridize to any TrpB nucleic acid sequences set forth herein under at least moderately stringent hybridization conditions or which would hybridize thereto under at least moderately stringent conditions but for the use of synonymous codons.

The terms "nucleic acid sequence encoding a halogenase", and "nucleic acid sequence encoding a halogenase polypeptide", as may be used interchangeably herein, refer to any and all nucleic acid sequences encoding a halogenase polypeptide, including, for example, SEQ. ID NO: 13. Nucleic acid sequences encoding a halogenase polypeptide further include any and all nucleic acid sequences which (i) encode polypeptides that are substantially identical to the halogenase polypeptide sequences set forth herein; or (ii) hybridize to any halogenase nucleic acid sequences set forth herein under at least moderately stringent hybridization conditions or which would hybridize thereto under at least moderately stringent conditions but for the use of synonymous codons.

The terms "nucleic acid sequence encoding an acetyl transferase", and "nucleic acid sequence encoding an acetyl transferase polypeptide", as may be used interchangeably herein, refer to any and all nucleic acid sequences encoding an acetyl transferase polypeptide, including, for example, SEQ. ID NO: 62. Nucleic acid sequences encoding an acetyl transferase polypeptide further include any and all nucleic acid sequences which (i) encode polypeptides that are substantially identical to the acetyl transferase polypeptide sequences set forth herein; or (ii) hybridize to any acetyl transferase nucleic acid sequences set forth herein under at least moderately stringent hybridization conditions or which would hybridize thereto under at least moderately stringent conditions but for the use of synonymous codons.

The terms "nucleic acid", or "nucleic acid sequence", as used herein, refer to a sequence of nucleoside or nucleotide monomers, consisting of naturally occurring bases, sugars and intersugar (backbone) linkages. The term also includes modified or substituted sequences comprising non-naturally occurring monomers or portions thereof. The nucleic acids of the present disclosure may be deoxyribonucleic nucleic acids (DNA) or ribonucleic acids (RNA) and may include naturally occurring bases including adenine, guanine, cytosine, thymidine and uracil. The nucleic acids may also contain modified bases. Examples of such modified bases include aza and deaza adenine, guanine, cytosine, thymidine and uracil, and xanthine and hypoxanthine. A sequence of nucleotide or nucleoside monomers may be referred to as a polynucleotide sequence, nucleic acid sequence, a nucleotide sequence or a nucleoside sequence.

The term "polypeptide", as used herein in conjunction with a reference SEQ. ID NO, refers to any and all polypeptides comprising a sequence of amino acid residues which is (i) substantially identical to the amino acid sequence constituting the polypeptide having such reference SEQ. ID NO, or (ii) encoded by a nucleic acid sequence capable of hybridizing under at least moderately stringent conditions to any nucleic acid sequence encoding the polypeptide having such reference SEQ. ID NO, but for the use of synonymous codons. A sequence of amino acid residues may be referred to as an amino acid sequence, or polypeptide sequence.

The term "nucleic acid sequence encoding a polypeptide", as used herein in conjunction with a reference SEQ. ID NO, refers to any and all nucleic acid sequences encoding a polypeptide having such reference SEQ. ID NO. Nucleic acid sequences encoding a polypeptide, in conjunction with a reference SEQ. ID NO, further include any and all nucleic acid sequences which (i) encode polypeptides that are substantially identical to the polypeptide having such reference SEQ. ID NO; or (ii) hybridize to any nucleic acid sequences encoding polypeptides having such reference SEQ. ID NO under at least moderately stringent hybridization conditions or which would hybridize thereto under at least moderately stringent conditions but for the use of synonymous codons.

By the term "substantially identical" it is meant that two amino acid sequences preferably are at least 70% identical, and more preferably are at least 85% identical and most preferably at least 95% identical, for example 96%, 97%, 98% or 99% identical. In order to determine the percentage of identity between two amino acid sequences the amino acid sequences of such two sequences are aligned, using for example the alignment method of Needleman and Wunsch (J. Mol. Biol., 1970, 48: 443), as revised by Smith and Waterman (Adv. Appl. Math., 1981, 2: 482) so that the highest order match is obtained between the two sequences and the number of identical amino acids is determined between the two sequences. Methods to calculate the percentage identity between two amino acid sequences are generally art recognized and include, for example, those described by Carillo and Lipton (SIAM J. Applied Math., 1988, 48:1073) and those described in Computational Molecular Biology, Lesk, e.d. Oxford University Press, New York, 1988, Biocomputing: Informatics and Genomics Projects. Generally, computer programs will be employed for such calculations. Computer programs that may be used in this regard include, but are not limited to, GCG (Devereux et al., Nucleic Acids Res., 1984, 12: 387) BLASTP, BLASTN and FASTA (Altschul et al., J. Mol. Biol., 1990: 215:403). A particularly preferred method for determining the percentage identity between two polypeptides involves the Clustal W algorithm (Thompson, J D, Higgines, D G and Gibson T J, 1994, Nucleic Acid Res 22(22): 4673-4680 together with the BLOSUM 62 scoring matrix (Henikoff S & Henikoff, J G, 1992, Proc. Natl. Acad. Sci. USA 89: 10915-10919 using a gap opening penalty of 10 and a gap extension penalty of 0.1, so that the highest order match obtained between two sequences wherein at least 50% of the total length of one of the two sequences is involved in the alignment.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na$^+$])+0.41(% (G+C)− 600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5×sodium chloride/sodium citrate (SSC)/5×Denhardt's solution/1.0% SDS at Tm (based on the above equation) −5° C., followed by a wash of 0.2×SSC/ 0.1% SDS at 60° C. Moderately stringent hybridization conditions include a washing step in 3×SSC at 42° C. It is understood however that equivalent stringencies may be achieved using alternative buffers, salts and temperatures. Additional guidance regarding hybridization conditions may be found in: Current Protocols in Molecular Biology, John Wiley & Sons, N.Y., 1989, 6.3.1.-6.3.6 and in: Sambrook et al., Molecular Cloning, a Laboratory Manual, Cold Spring Harbor Laboratory Press, 1989, Vol. 3.

The term "functional variant", as used herein in reference to polynucleotides or polypeptides, refers to polynucleotides or polypeptides capable of performing the same function as a noted reference polynucleotide or polypeptide. Thus, for example, a functional variant of the polypeptide set forth in SEQ. ID NO: 2, refers to a polypeptide capable of performing the same function as the polypeptide set forth in SEQ. ID NO: 2. Functional variants include modified a polypeptide wherein, relative to a noted reference polypeptide, the modification includes a substitution, deletion or addition of one or more amino acids. In some embodiments, substitutions are those that result in a replacement of one amino acid with an amino acid having similar characteristics. Such substitutions include, without limitation (i) glutamic acid and aspartic acid; (i) alanine, serine, and threonine; (iii) isoleucine, leucine and valine, (iv) asparagine and glutamine, and (v) tryptophan, tyrosine and phenylalanine. Functional variants further include polypeptides having retained or exhibiting an enhanced psilocybin biosynthetic bioactivity.

The term "chimeric", as used herein in the context of nucleic acids, refers to at least two linked nucleic acids which are not naturally linked. Chimeric nucleic acids include linked nucleic acids of different natural origins. For example, a nucleic acid constituting a microbial promoter linked to a nucleic acid encoding a plant polypeptide is considered chimeric. Chimeric nucleic acids also may comprise nucleic acids of the same natural origin, provided they are not naturally linked. For example a nucleic acid constituting a promoter obtained from a particular cell-type may be linked to a nucleic acid encoding a polypeptide obtained from that same cell-type, but not normally linked to the nucleic acid constituting the promoter. Chimeric nucleic acids also include nucleic acids comprising any naturally occurring nucleic acids linked to any non-naturally occurring nucleic acids.

The terms "substantially pure" and "isolated", as used herein, as may be used interchangeably herein describe a compound, e.g., a secondary metabolite, psilocybin or a psilocybin derivative, polynucleotide or a polypeptide, which has been separated from components that naturally accompany it. Typically, a compound is substantially pure when at least 60%, more preferably at least 75%, more preferably at least 90%, 95%, 96%, 97%, or 98%, and most preferably at least 99% of the total material (by volume, by wet or dry weight, or by mole percent or mole fraction) in a sample is the compound of interest. Purity can be measured by any appropriate method, e.g., in the case of polypeptides, by chromatography, gel electrophoresis or HPLC analysis.

The term "recovered" as used herein in association with an enzyme, protein, a secondary metabolite or a chemical compound, refers to a more or less pure form of the enzyme, protein, secondary metabolite, or chemical compound.

General Implementation

As hereinbefore mentioned, the present disclosure relates to psilocybin derivatives. In particular, the present disclosure provides novel halogenated psilocybin derivatives. In general, the herein provided compositions exhibit functional properties which deviate from the functional properties of psilocybin. Thus, for example, the psilocybin derivatives, can exhibit pharmacological properties which deviate from psilocybin. The halogenated psilocybin derivatives in this respect are useful in the formulation of pharmaceutical and recreation drug formulations. Furthermore, the halogenated psilocybin derivatives of the present disclosure may be used as a feedstock material for deriving further psilocybin derivatives. In one embodiment, the halogenated psilocybin derivatives of the present disclosure can conveniently be biosynthetically produced. The practice of this method avoids the extraction of psilocybin from mushrooms and the performance of subsequent chemical reactions to achieve halogenation. Furthermore, the growth of mushrooms can be avoided thus limiting the dependence on climate and weather, and potential legal and social challenges associated with the cultivation of mushrooms containing psychoactive compounds. The method can efficiently yield substantial quantities of halogenated psilocybin derivatives.

In what follows selected embodiments are described with reference to the drawings.

Initially various halogenated psilocybin derivatives will be described. Thereafter methods example methods of using and making the halogenated psilocybin derivatives will be described In at least one aspect, and in at least one example embodiment, the present disclosure provides a chemical compound or salts thereof having the formula (I):

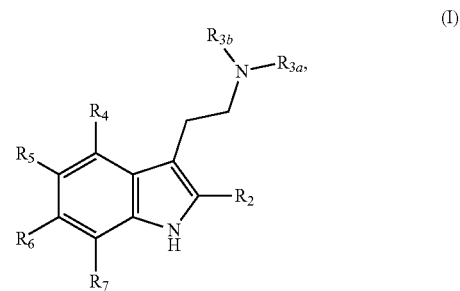

wherein, at least one of $R_2$, $R_4$, $R_5$, $R_6$ or $R_7$ is a halogen atom, wherein each non-halogenated $R_2$, $R_5$, $R_6$, or $R_7$ is a hydrogen atom, wherein $R_4$ when it is not halogenated is a phosphate group or a hydrogen atom, and wherein $R_{3A}$ and $R_{3B}$ are a hydrogen atom, an alkyl group, an aryl group or an acyl group.

It is noted that in reference to the indole prototype structure shown in FIG. 2 carbon atoms $C_2$, $C_4$, $C_5$, $C_6$ and $C_7$ are bonded to $R_2$, $R_4$, $R_5$, $R_6$ and $R_7$, respectively. Furthermore, $R_{3A}$ and $R_{3B}$ reference chemical groups extending from the ethyl-amino group extending in turn from carbon atom $C_3$ of the prototype indole structure.

Figure 4A:
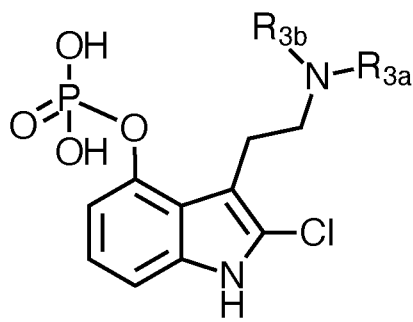
FIGS. 4A, 4B, 4C, 4D, 4E, 4F, 4G, 4H, 4I, 4J, 4K, 4L, 4M, 4N, 4O, 4P, 4Q and 4R depict the chemical structures of certain example halogenated psilocybin derivative compounds, notably a 2-chloro-4-phospho psilocybin derivative (FIG. 4A); a 2-bromo psilocybin derivative (FIG. 4B); a 4-iodo psilocybin derivative (FIG. 4C); a 4-fluoro psilocybin derivative (FIG. 4D); a 4-phospho-5-fluoro psilocybin derivative (FIG. 4E); a 5-chloro psilocybin derivative (FIG. 4F); a 4-phospho-6-bromo psilocybin derivative (FIG. 4G); a 6-chloro psilocybin derivative (FIG. 4H) a 4-phospho-7-fluoro psilocybin derivative (FIG. 4I); a 7-iodo psilocybin derivative (FIG. 4J); a 2-chloro-4-methyl psilocybin derivative (FIG. 4K); a 4-ethyl-5-bromo psilocybin derivative (FIG. 4L); a 4-methyl-6-fluoro psilocybin derivative (FIG. 4M); a 4-propyl-7-iodo psilocybin derivative (FIG. 4N); a 2-chloro-4-O-methyl psilocybin derivative (FIG. 4K); a 4-O-ethyl-5-bromo psilocybin derivative (FIG. 4L); a 4-O-methyl-6-fluoro psilocybin derivative (FIG. 4M); and a 4-O-propyl-7-iodo psilocybin derivative (FIG. 4N). It is noted that in each of FIGS. 4A, 4B, 4C, 4D, 4E, 4F, 4G, 4H, 4I, 4J, 4K, 4L, 4M, 4N, 4O, 4P, 4Q and 4R $R_{3a}$ and $R_{3b}$ can be a hydrogen atom, an alkyl group, an aryl group, or an acyl group.
Figure 4B:
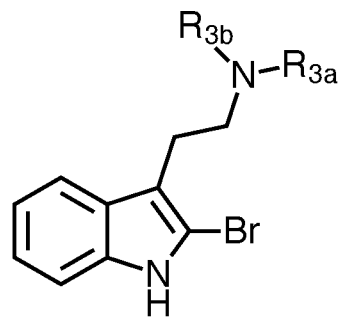

Referring to the chemical compound having formula (I), in one embodiment, one of $R_2$, $R_4$, $R_5$, $R_6$ and $R_7$ can be a halogen atom. Thus, in one embodiment, $R_2$ can be a bromine, chlorine, fluorine or iodine atom, each of $R_5$, $R_6$ and $R_7$ can be a hydrogen atom or an alkyl group or O-alkyl group, and $R_4$, when it is not a halogen atom, can be a phosphate group, a hydrogen atom or an alkyl group or O-alkyl group (see: the example halogenated psilocybin derivatives shown in FIG. 4A ($R_2$ is chlorine; $R_4$ is a phosphate group; $R_5$, $R_6$ and $R_7$ are each a hydrogen atom; $R_{3a}$ and $R_{3b}$ are a hydrogen atom, an alkyl group, an aryl group, or an acyl group); FIG. 4B ($R_2$ is bromine; $R_4$, $R_5$, $R_6$ and $R_7$ are each a hydrogen atom; $R_{3a}$ and $R_{3b}$ are a hydrogen atom, an alkyl group, an aryl group, or an acyl group; FIG. 4K ($R_2$ is chlorine; $R_4$ is a methyl group; $R_5$, $R_6$ and $R_7$ are each a hydrogen atom; $R_{3a}$ and $R_{3b}$ are a hydrogen atom, an alkyl group, an aryl group, or an acyl group); and FIG. 4O ($R_2$ is chlorine; $R_4$ is an O-methyl group; $R_5$, $R_6$ and $R_7$ are each a hydrogen atom; $R_{3a}$ and $R_{3b}$ are a hydrogen atom, an alkyl group, an aryl group, or an acyl group)).

Figure 4C:
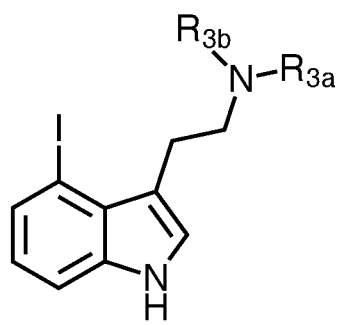
Figure 4D:
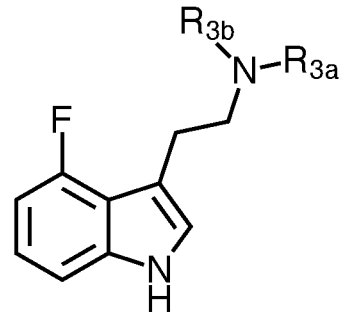

Continuing to refer to the chemical compound having formula (I), in one embodiment, $R_4$ can be a bromine, chlorine, fluorine or iodine atom, and each of $R_2$, $R_5$, $R_6$ and $R_7$ can be a hydrogen atom or an alkyl group or O-alkyl group (see: the example halogenated psilocybin derivatives shown in FIG. 4C ($R_4$ is iodine; $R_2$, $R_5$, $R_6$ and $R_7$ are each a hydrogen atom; $R_{3a}$ and $R_{3b}$ are a hydrogen atom, an alkyl group, an aryl group, or an acyl group); FIG. 4D ($R_4$ is fluorine; $R_2$, $R_5$, $R_6$ and $R_7$ are each a hydrogen atom; $R_{3a}$ and $R_{3b}$ are a hydrogen atom, an alkyl group, an aryl group, or an acyl group))

Figure 4E:
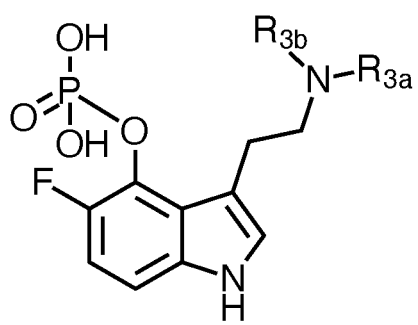
Figure 4F:
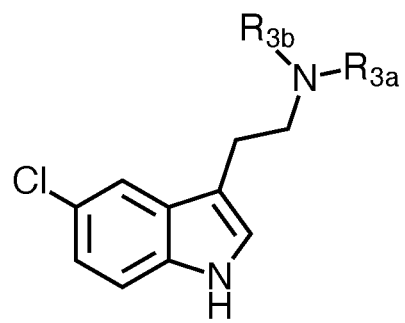

Continuing to refer to the chemical compound having formula (I), in one embodiment, $R_5$ can be a bromine, chlorine, fluorine or iodine atom, and each of $R_2$, $R_6$ and $R_7$ can be a hydrogen atom or an alkyl group or O-alkyl group, and $R_4$ can be a phosphate group, a hydrogen atom or an alkyl group or O-alkyl group (see: the example halogenated psilocybin derivatives shown in FIG. 4E ($R_5$ is fluorine; $R_4$ is a phosphate group; $R_2$, $R_6$ and $R_7$ are each a hydrogen atom; $R_{3a}$ and $R_{3b}$ are a hydrogen atom, an alkyl group, an aryl group, or an acyl group); FIG. 4F ($R_5$ is chlorine; $R_2$, $R_4$, $R_6$ and $R_7$ are each a hydrogen atom; $R_{3a}$ and $R_{3b}$ are a hydrogen atom, an alkyl group, an aryl group, or an acyl group); FIG. 4L ($R_5$ is bromine; $R_4$ is an ethyl group; $R_2$, $R_6$ and $R_7$ are each a hydrogen atom; $R_{3a}$ and $R_{3b}$ are a hydrogen atom, an alkyl group, an aryl group, or an acyl group); and FIG. 4P ($R_5$ is bromine; $R_2$, $R_6$ and $R_7$ are each a hydrogen atom; $R_4$ is an O-ethyl group; $R_{3a}$ and $R_{3b}$ are a hydrogen atom, an alkyl group, an aryl group, or an acyl group)).

Figure 4G:
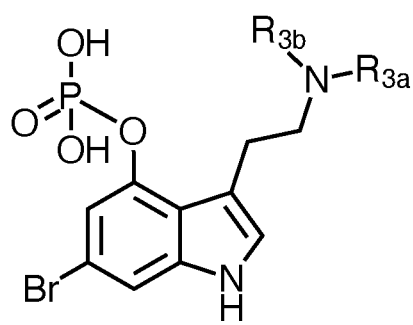
Figure 4H:
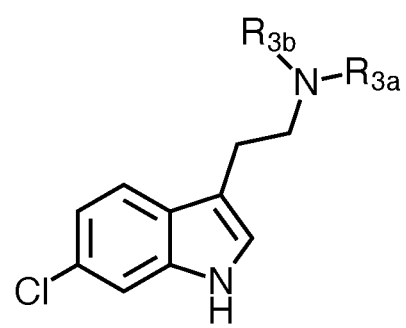

Continuing to refer to the chemical compound having formula (I), in one embodiment, $R_6$ can be a bromine, chlorine, fluorine or iodine atom, and each of $R_2$, $R_5$ and $R_7$ can be a hydrogen atom or an alkyl group or O-alkyl group, and $R_4$ can be a phosphate group, a hydrogen atom or an alkyl group or O-alkyl group (see: the example halogenated psilocybin derivatives shown in FIG. 4G ($R_6$ is bromine; $R_4$ is a phosphate group; $R_2$, $R_5$ and $R_7$ are each a hydrogen atom; $R_{3a}$ and $R_{3b}$ are a hydrogen atom, an alkyl group, an aryl group, or an acyl group); FIG. 4H ($R_6$ is chlorine; $R_2$, $R_4$, $R_5$ and $R_7$ are each a hydrogen atom; $R_{3a}$ and $R_{3b}$ are a hydrogen atom, an alkyl group, an aryl group, or an acyl group); FIG. 4M ($R_6$ is fluorine; $R_4$ is a methyl group; $R_2$, $R_5$ and $R_7$ are each a hydrogen atom; $R_{3a}$ and $R_{3b}$ are a hydrogen atom, an alkyl group, an aryl group, or an acyl group); and FIG. 4Q ($R_6$ is fluorine; $R_2$, $R_5$ and $R_7$ are each a hydrogen atom; $R_4$ is an O-methyl group; $R_{3a}$ and $R_{3b}$ are a hydrogen atom, an alkyl group, an aryl group, or an acyl group)).

Figure 4I:
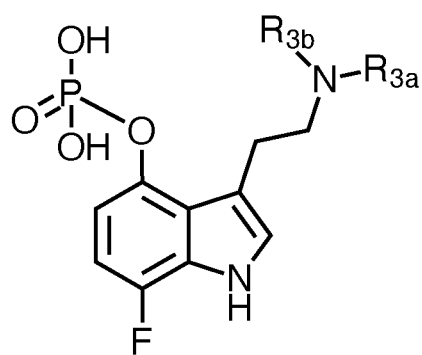
Figure 4J:
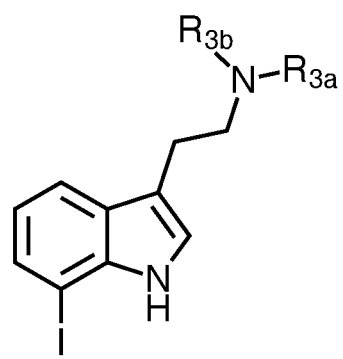
Figure 4K:
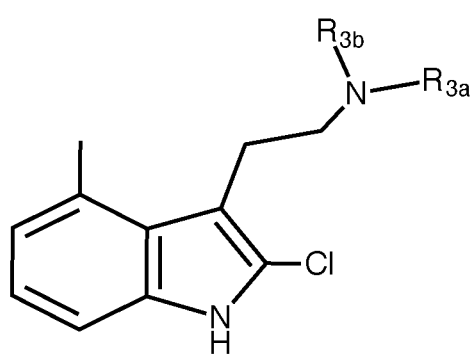
Figure 4L:
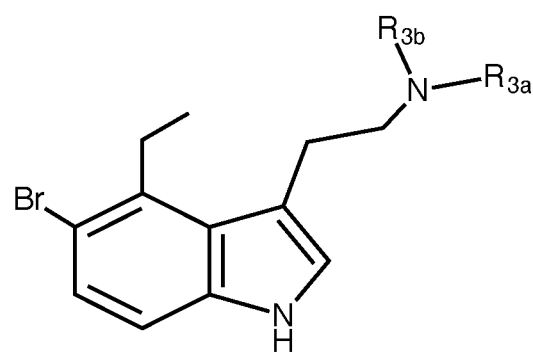
Figure 4M:
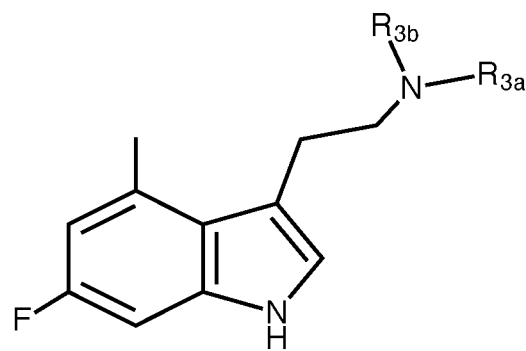
Figure 4N:
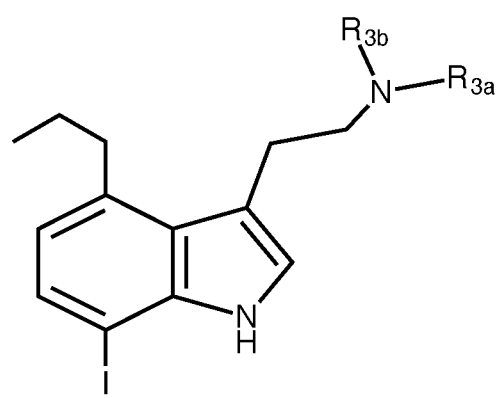
Figure 4O:
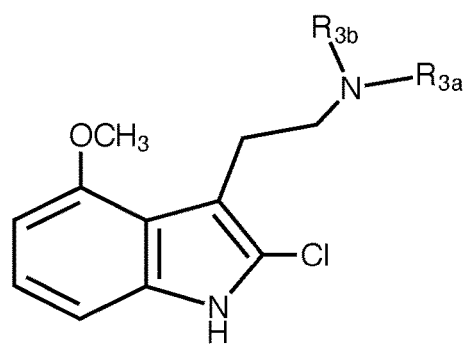
Figure 4P:
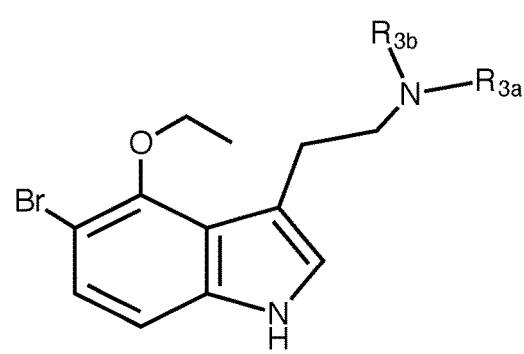
Figure 4Q:
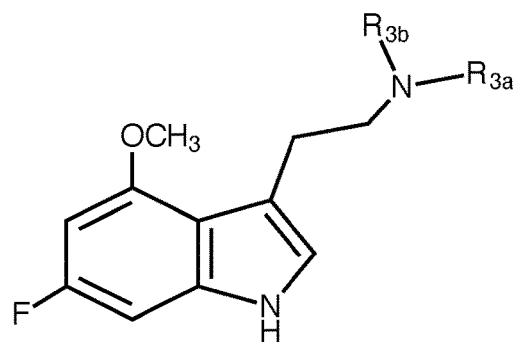
Figure 4R:
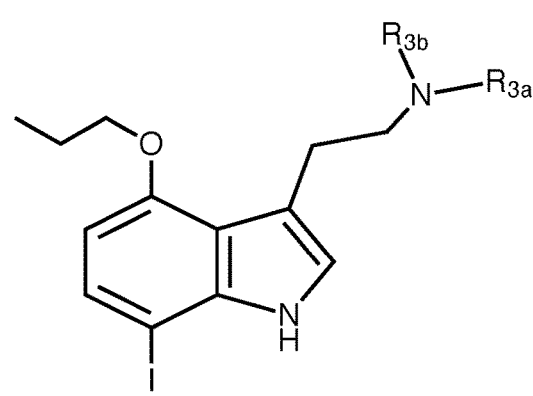

Continuing to refer to the chemical compound having formula (I), in one embodiment, $R_7$ can be a bromine, chlorine, fluorine or iodine atom, and each of $R_2$, $R_5$ and $R_6$ can be a hydrogen atom or an alkyl group or O-alkyl group, and $R_4$ can be a phosphate group, a hydrogen atom or an alkyl group or O-alkyl group (see: the example halogenated psilocybin derivatives shown in FIG. 4I ($R_7$ is fluorine; $R_4$ is a phosphate group; $R_2$, $R_5$ and $R_6$ are each a hydrogen atom $R_{3a}$ and $R_{3b}$ are a hydrogen atom, an alkyl group, an aryl group, or an acyl group); FIG. 4J ($R_7$ is iodine; $R_2$, $R_4$, $R_5$ and $R_6$ are each a hydrogen atom; $R_{3a}$ and $R_{3b}$ are a hydrogen atom, an alkyl group, an aryl group, or an acyl group); FIG. 4N ($R_7$ is iodine; $R_4$ is a propyl group; $R_2$, $R_5$ and $R_6$ are each a hydrogen atom $R_{3a}$ and $R_{3b}$ are a hydrogen atom, an alkyl group, an aryl group, or an acyl group); and FIG. 4R ($R_7$ is iodine; $R_2$, $R_5$ and $R_6$ are each a hydrogen atom; $R_4$ is an O-propyl group; $R_{3a}$ and $R_{3b}$ are a hydrogen atom, an alkyl group, an aryl group, or an acyl group)).

Still, continuing to refer to the chemical compound having formula (I), in one embodiment, two of $R_2$, $R_4$, $R_5$, $R_6$ and $R_7$ can be a halogen atom, wherein the halogen atoms are independently selected from a bromine, chlorine fluorine or iodine atom, and wherein each non-halogenated $R_2$, $R_5$, $R_6$ and $R_7$ is a hydrogen atom or an alkyl group or O-alkyl group, and wherein $R_4$, when it is not a halogen atom, is a phosphate group, a hydrogen atom or an alkyl group or O-alkyl group.

Figure 5A:
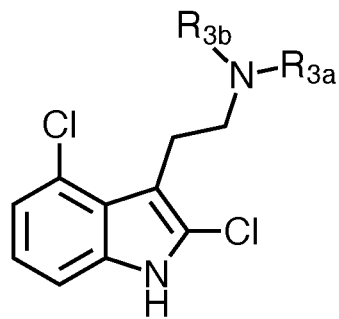
FIGS. 5A, 5B, 5C, 5D, 5E, 5F, 5G, 5H, 5I and 5J depict the chemical structures of certain example halogenated psilocybin derivative compounds, notably a 2,4-di-chloro psilocybin derivative (FIG. 5A); a 2-bromo-5-fluoro-7-methyl psilocybin derivative (FIG. 5B); a 2-chloro-O-methyl-6-bromo psilocybin derivative (FIG. 5C); a 2-fluoro-4-phospho-7-iodo psilocybin derivative (FIG. 5D); a 4,5-di-bromo psilocybin derivative (FIG. 5E); a 4,6-di-chloro psilocybin derivative (FIG. 5F); a 4-chloro-5-fluoro psilocybin derivative (FIG. 5G); a 4-phospho-5-fluoro-6-bromo psilocybin derivative (FIG. 5H) a 4-phospho-5,7-di-fluoro psilocybin derivative (FIG. 5I); and a 6,7-di-iodo psilocybin derivative (FIG. 5J). It is noted that in each of FIGS. 5A, 5B, 5C, 5D, 5E, 5F, 5G, 5H, 5I and 5J $R_{3a}$ and $R_{3b}$ can be a hydrogen atom, an alkyl group, an aryl group, or an acyl group.

Thus, continuing to refer to the chemical compound having formula (I), in one embodiment, $R_2$ and $R_4$ can be halogen atoms, wherein the halogen atoms are independently selected from a bromine, chlorine fluorine or iodine atom, and $R_5$, $R_6$ and $R_7$ can be a hydrogen atom or an alkyl group or O-alkyl group (see: the example halogenated psilocybin derivative shown in FIG. 5A ($R_2$ is a chlorine atom; $R_4$ is a chlorine atom; $R_5$, $R_6$ and $R_7$ are each a hydrogen atom; and $R_{3a}$ and $R_{3b}$ are a hydrogen atom, an alkyl group, an aryl group, or an acyl group)).

Figure 5B:
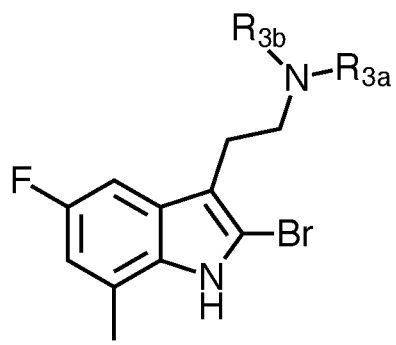

Continuing to refer to the chemical compound having formula (I), in one embodiment, $R_2$ and $R_5$ can be halogen atoms, wherein the halogen atoms are independently selected from a bromine, chlorine fluorine or iodine atom, and $R_6$ and $R_7$ can be a hydrogen atom or an alkyl group or O-alkyl group and $R_4$ can be a phosphate group, a hydrogen atom or an alkyl group or O-alkyl group (see: the example halogenated psilocybin derivative shown in FIG. 5B ($R_2$ is a bromine atom; $R_5$ is a fluorine atom; $R_4$, and $R_6$ are each a hydrogen atom and $R_7$ is a methyl group; and $R_{3a}$ and $R_{3b}$ are a hydrogen atom, an alkyl group, an aryl group, or an acyl group)).

Figure 5C:
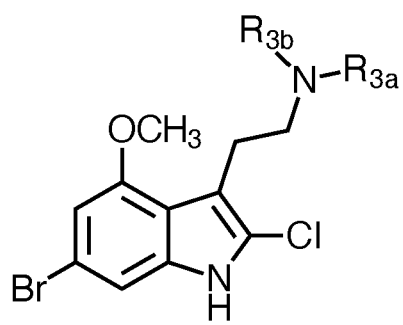

Continuing to refer to the chemical compound having formula (I), in one embodiment, $R_2$ and $R_6$ can be halogen atoms, wherein the halogen atoms are independently selected from a bromine, chlorine fluorine or iodine atom, and $R_5$ and $R_7$ can be a hydrogen atom or an alkyl group or O-alkyl group, and $R_4$ can be a phosphate group, a hydrogen atom or an alkyl group or O-alkyl group (see: the example halogenated psilocybin derivative shown in FIG. 5C ($R_2$ is a chlorine atom; $R_6$ is a bromine atom; $R_5$ and $R_7$ are each a hydrogen atom; $R_4$ is an O-methyl group; and $R_{3a}$ and $R_{3b}$ are a hydrogen atom, an alkyl group, an aryl group, or an acyl group)).

Figure 5D:
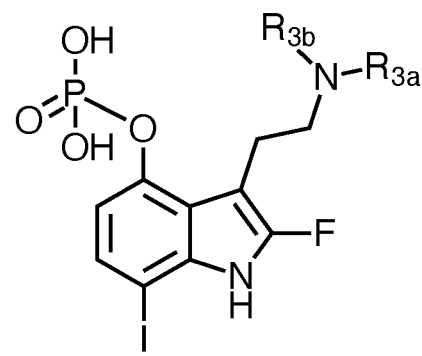

Continuing to refer to the chemical compound having formula (I), in one embodiment, $R_2$ and $R_7$ can be halogen atoms, wherein the halogen atoms are independently selected from a bromine, chlorine fluorine or iodine atom, and $R_5$ and $R_6$ can be a hydrogen atom or an alkyl group or O-alkyl group and $R_4$ can be a phosphate group, a hydrogen atom or an alkyl group or O-alkyl group (see: the example halogenated psilocybin derivative shown in FIG. 5D ($R_2$ is a fluorine atom; $R_7$ is an iodine atom; $R_4$ is a phosphate, $R_5$ and $R_6$ are each a hydrogen atom; and $R_{3a}$ and $R_{3b}$ are a hydrogen atom, an alkyl group, an aryl group, or an acyl group)).

Figure 5E:
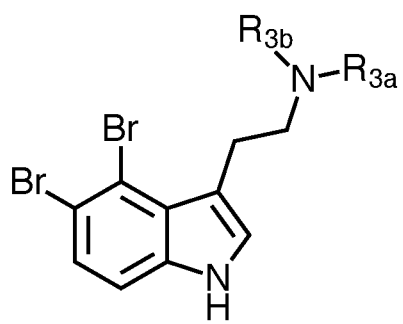

Continuing to refer to the chemical compound having formula (I), in one embodiment, $R_4$ and $R_5$ can be halogen atoms, wherein the halogen atoms are independently selected from a bromine, chlorine fluorine or iodine atom, and $R_2$, $R_6$ and $R_7$ can be a hydrogen atom or an alkyl group or O-alkyl group (see: the example halogenated psilocybin derivative shown in FIG. 5E ($R_4$ and $R_5$ are each bromine atoms; $R_2$, $R_6$ and $R_7$ are each a hydrogen atom; and $R_{3a}$ and $R_{3b}$ are a hydrogen atom, an alkyl group, an aryl group, or an acyl group)).

Figure 5F:
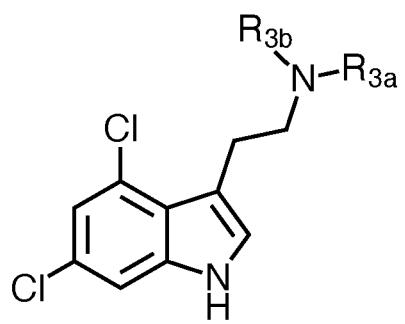

Continuing to refer to the chemical compound having formula (I), in one embodiment, $R_4$ and $R_6$ can be halogen atoms, wherein the halogen atoms are independently selected from a bromine, chlorine fluorine or iodine atom, and $R_2$, $R_5$ and $R_7$ can be a hydrogen atom or an alkyl group or O-alkyl group (see: the example halogenated psilocybin derivative shown in FIG. 5F ($R_4$ and $R_6$ are each chlorine atoms; $R_2$, $R_5$ and $R_7$ are each a hydrogen atom; and $R_{3a}$ and $R_{3b}$ are a hydrogen atom, an alkyl group, an aryl group, or an acyl group)).

Figure 5G:
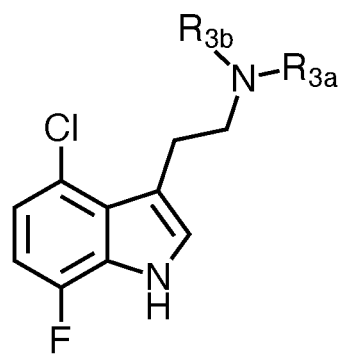

Continuing to refer to the chemical compound having formula (I), in one embodiment, $R_4$ and $R_7$ can be halogen atoms, wherein the halogen atoms are independently selected from a bromine, chlorine fluorine or iodine atom, and $R_2$, $R_5$ and $R_6$ can be a hydrogen atom or an alkyl group or O-alkyl group (see: the example halogenated psilocybin derivative shown in FIG. 5G ($R_4$ is a chlorine atom; $R_7$ is a fluorine atom; $R_2$, $R_5$ and $R_6$ are each a hydrogen atom; and $R_{3a}$ and $R_{3b}$ are a hydrogen atom, an alkyl group, an aryl group, or an acyl group)).

Figure 5H:
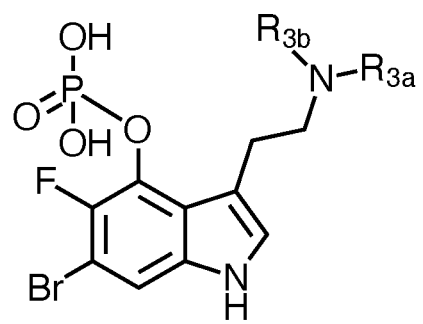

Continuing to refer to the chemical compound having formula (I), in one embodiment, $R_5$ and $R_6$ can be halogen atoms, wherein the halogen atoms are independently selected from a bromine, chlorine fluorine or iodine atom, and $R_2$ and $R_7$ can be a hydrogen atom or an alkyl group or O-alkyl group and $R_4$ can be a phosphate group, a hydrogen atom or an alkyl group or O-alkyl group (see: the example halogenated psilocybin derivative shown in FIG. 5H ($R_5$ is a fluorine atom; $R_6$ is a bromine atom; $R_4$ is a phosphate group, $R_2$ and $R_7$ are each a hydrogen atom; and $R_{3a}$ and $R_{3b}$ are a hydrogen atom, an alkyl group, an aryl group, or an acyl group)).

Figure 5I:
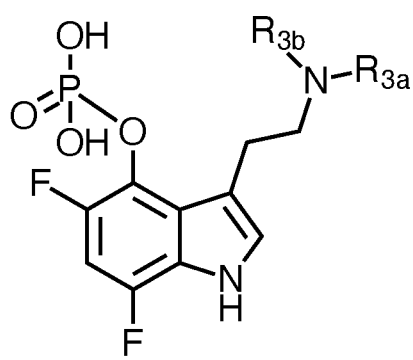

Continuing to refer to the chemical compound having formula (I), in one embodiment, $R_5$ and $R_7$ can be halogen atoms, wherein the halogen atoms are independently selected from a bromine, chlorine fluorine or iodine atom, and $R_2$ and $R_6$ can be a hydrogen atom or an alkyl group or O-alkyl group and $R_4$ can be a phosphate group, a hydrogen atom or an alkyl group or O-alkyl group (see: the example halogenated psilocybin derivative shown in FIG. 5I ($R_5$ and $R_7$ are each fluorine atoms; $R_4$ is a phosphate group, $R_2$ and $R_6$ are each a hydrogen atom; and $R_{3a}$ and $R_{3b}$ are a hydrogen atom, an alkyl group, an aryl group, or an acyl group)).

Figure 5J:
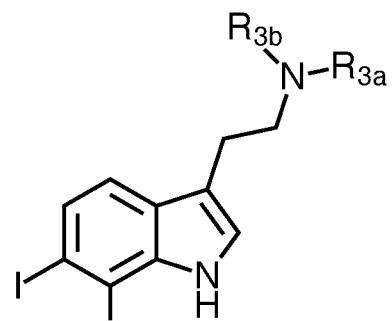

Continuing to refer to the chemical compound having formula (I), in one embodiment, $R_6$ and $R_7$ can be halogen atoms, wherein the halogen atoms are independently selected from a bromine, chlorine fluorine or iodine atom, and $R_2$ and $R_5$ can be a hydrogen atom or an alkyl group or O-alkyl group and $R_4$ can be a phosphate group, a hydrogen atom or an alkyl group or O-alkyl group (see: the example halogenated psilocybin derivative shown in FIG. 5J ($R_6$ and $R_7$ are each iodine atoms; $R_2$, $R_4$ and $R_5$ are each a hydrogen atom; and $R_{3a}$ and $R_{3b}$ are a hydrogen atom, an alkyl group, an aryl group, or an acyl group)).

In one embodiment, two of $R_2$, $R_4$, $R_5$, $R_6$ and $R_7$ can be a halogen atom, and the halogen atoms are identical, the remaining of $R_2$, $R_5$, $R_6$, and $R_7$ being a hydrogen atom or an alkyl group or O-alkyl group, and $R_4$ when it is not a halogen atom, being a phosphate group, a hydrogen atom or an alkyl group or O-alkyl group (see: e.g. the halogenated psilocybin derivatives shown in FIGS. 5A, 5E, 5F, 5I and 5J).

In one embodiment, two of $R_2$, $R_4$, $R_5$, $R_6$ and $R_7$ can be a halogen atom, and the halogen atoms are non-identical, the remaining of $R_2$, $R_5$, $R_6$, and $R_7$ being a hydrogen atom or an alkyl group or O-alkyl group, and $R_4$ when it is not a halogen atom, being a phosphate, a hydrogen atom or an alkyl group or O-alkyl group (see: e.g. the halogenated psilocybin derivatives shown in FIGS. 5B, 5C, 5D, 5G and 5H).

Still continuing to refer to the chemical compound having formula (I). In one further embodiment, three of $R_2$, $R_4$, $R_5$, $R_6$ and $R_7$ can be a halogen atom, wherein the halogen atoms are independently selected from a bromine, chlorine fluorine or iodine atom, and wherein the non-halogenated $R_2$, $R_5$, $R_6$, or $R_7$ is a hydrogen atom or an alkyl group or O-alkyl group, and wherein $R_4$, when it is not a halogen atom, is a phosphate group, a hydrogen atom or an alkyl group or O-alkyl group.

Figure 6A:
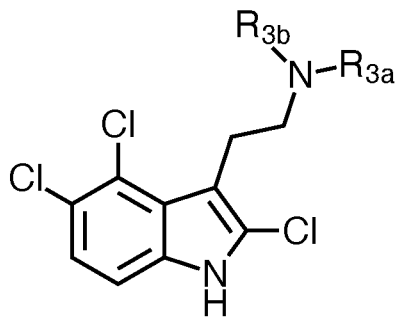
FIGS. 6A, 6B, 6C, 6D, 6E, and 6F depict the chemical structures of certain example halogenated psilocybin derivative compounds, notably a 2,4,5-tri-chloro psilocybin derivative (FIG. 6A); a 2-bromo-5,6-di-fluoro psilocybin derivative (FIG. 6B); a 2-chloro-5-bromo-7-fluoro psilocybin derivative (FIG. 6C); a 4,5-di-bromo-6-chloro psilocybin derivative (FIG. 6D); a 4,5,7-tri-bromo psilocybin derivative (FIG. 6E); and a 4-phospho-5-fluoro-6-chloro-7-iodo psilocybin derivative (FIG. 6F). It is noted that in each of FIGS. 6A, 6B, 6C, 6D, 6E, and 6F $R_{3a}$ and $R_{3b}$ can be a hydrogen atom, an alkyl group, an aryl group, or an acyl group.

Thus, continuing to refer to the chemical compound having formula (I), in one embodiment $R_2$, $R_4$, and $R_5$ can be halogen atom, wherein the halogen atoms are independently selected from a bromine, chlorine fluorine or iodine atom, and $R_6$ and $R_7$ can be a hydrogen atom or an alkyl group or O-alkyl group (see: the example halogenated psilocybin derivative shown in FIG. 6A ($R_2$, $R_4$ and $R_5$ are each chlorine atoms; $R_6$ and $R_7$ are each a hydrogen atom; and $R_{3a}$ and $R_{3b}$ are a hydrogen atom, an alkyl group, an aryl group, or an acyl group)).

Figure 6B:
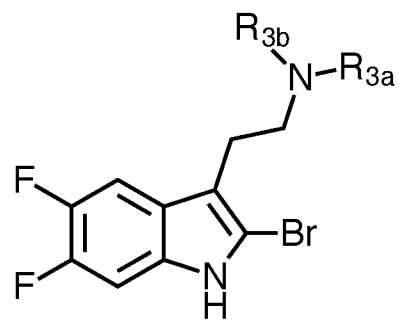

Continuing to refer to the chemical compound having formula (I), in one embodiment $R_2$, $R_5$, and $R_6$ can be halogen atom, wherein the halogen atoms are independently selected from a bromine, chlorine fluorine or iodine atom and $R_7$ can be a hydrogen atom or an alkyl group or O-alkyl group, and $R_4$ can a phosphate group, a hydrogen atom or an alkyl group or O-alkyl group (see: the example halogenated psilocybin derivative shown in FIG. 6B ($R_2$ is a bromine atom, $R_5$ and $R_6$ are each fluorine atoms; $R_4$ and $R_7$ are each a hydrogen atom; and $R_{3a}$ and $R_{3b}$ are a hydrogen atom, an alkyl group, an aryl group, or an acyl group)).

Figure 6C:
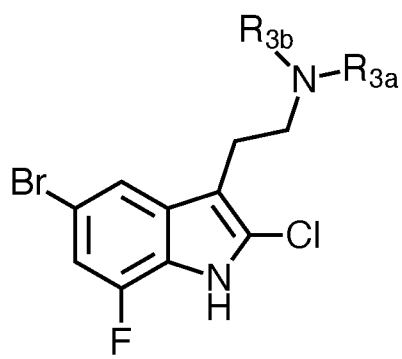

Continuing to refer to the chemical compound having formula (I), in one embodiment $R_2$, $R_5$, and $R_7$ can be halogen atom, wherein the halogen atoms are independently selected from a bromine, chlorine fluorine or iodine atom and $R_6$ can be a hydrogen atom or an alkyl group or O-alkyl group, and $R_4$ can a phosphate group, a hydrogen atom or an alkyl group or O-alkyl group (see: the example halogenated psilocybin derivative shown in FIG. 6C ($R_2$ is a chlorine atom, $R_5$ is a bromine atom, and $R_7$ is a fluorine atoms; $R_4$ and $R_6$ are each a hydrogen atom; and $R_{3a}$ and $R_{3b}$ are a hydrogen atom, an alkyl group, an aryl group, or an acyl group)).

Figure 6D:
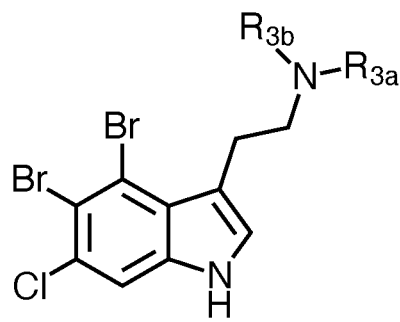

Continuing to refer to the chemical compound having formula (I), in one embodiment $R_4$, $R_5$, and $R_6$ can be halogen atom, wherein the halogen atoms are independently selected from a bromine, chlorine fluorine or iodine atom, and $R_2$ and $R_7$ can be a hydrogen atom or an alkyl group or O-alkyl group (see: the example halogenated psilocybin derivative shown in FIG. 6D ($R_4$ and $R_5$ are each a bromine atom, $R_6$ is a chlorine atom; $R_2$ and $R_7$ are each a hydrogen atom; and $R_{3a}$ and $R_{3b}$ are a hydrogen atom, an alkyl group, an aryl group, or an acyl group)).

Figure 6E:
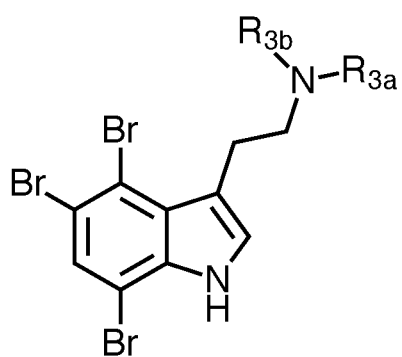

Continuing to refer to the chemical compound having formula (I), in one embodiment $R_4$, $R_5$, and $R_7$ can be halogen atom, wherein the halogen atoms are independently selected from a bromine, chlorine fluorine or iodine atom, and $R_2$ and $R_6$ can be a hydrogen atom or an alkyl group or O-alkyl group (see: the example halogenated psilocybin derivative shown in FIG. 6E ($R_4$, $R_5$ and $R_7$ are each a bromine atom; $R_2$ and $R_6$ are each a hydrogen atom; and $R_{3a}$ and $R_{3b}$ are a hydrogen atom, an alkyl group, an aryl group, or an acyl group)).

Figure 6F:
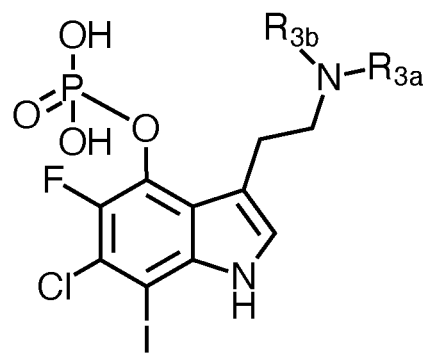

Continuing to refer to the chemical compound having formula (I), in one embodiment $R_5$, $R_6$, and $R_7$ can be halogen atom, wherein the halogen atoms are independently selected from a bromine, chlorine fluorine or iodine atom and $R_2$ can be a hydrogen atom or an alkyl group or O-alkyl group, and $R_4$ can be a phosphate group, a hydrogen atom or an alkyl group or O-alkyl group (see: the example halogenated psilocybin derivative shown in FIG. 6F ($R_5$ is a fluorine atom, $R_6$ is a chlorine atom, and $R_7$ is an iodine atom; $R_4$ is a phosphate group; $R_2$ is a hydrogen atom; and $R_{3a}$ and $R_{3b}$ are a hydrogen atom, an alkyl group, an aryl group, or an acyl group)).

In one embodiment, three of $R_2$, $R_4$, $R_5$, $R_6$ and $R_7$ can be a halogen atom, wherein at least two halogen atoms are identical, the remaining $R_2$, $R_5$, $R_6$, and $R_7$ being a hydrogen atom or an alkyl group or O-alkyl group, and $R_4$ when it is nota halogen atom, being a phosphate group, a hydrogen atom or an alkyl group or O-alkyl group (see: e.g. the halogenated psilocybin derivatives shown in FIGS. 6A, 6B and 6E).

In one embodiment, three of $R_2$, $R_4$, $R_5$, $R_6$ and $R_7$ can be a halogen atom, and at least two halogen atoms are non-identical, the remaining $R_2$, $R_5$, $R_6$, and $R_7$ being a hydrogen atom or an alkyl group or O-alkyl group, and $R_4$ when it is nota halogen atom, being a phosphate group, a hydrogen atom or an alkyl group or O-alkyl group (see: e.g. the halogenated psilocybin derivatives shown in FIGS. 6B, 6C, 6D and 6F).

In one embodiment, three of $R_2$, $R_4$, $R_5$, $R_6$ and $R_7$ can be a halogen atom, and all three halogen atoms are identical, the remaining $R_2$, $R_5$, $R_6$, or $R_7$ being a hydrogen atom or an alkyl group or O-alkyl group, and $R_4$ when it is not a halogen atom, being a phosphate group, a hydrogen atom or an alkyl group or O-alkyl group (see: e.g. the halogenated psilocybin derivatives shown in FIGS. 6A and 6E).

Still continuing to refer to the chemical compound having formula (I), in one embodiment, four of $R_2$, $R_4$, $R_5$, $R_6$ and $R_7$ can be a halogen atom, wherein the halogen atoms are independently selected from a bromine, chlorine fluorine or iodine atom, and wherein the non-halogenated $R_2$, $R_5$, $R_6$, or $R_7$ is a hydrogen atom or an alkyl group or O-alkyl group, and wherein $R_4$, when it is not a halogen, is a phosphate group, a hydrogen atom or an alkyl group or O-alkyl group.

Figure 7A:
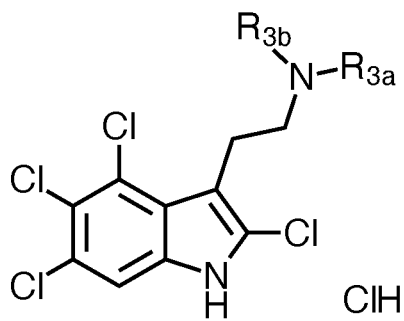
FIGS. 7A, 7B, 7C, 7D, and 7E depict the chemical structures of certain example halogenated psilocybin derivative compounds, notably a 2,4,5,6-tetra-chloro psilocybin derivative (FIG. 7A); a 4,7-di-chloro-5,6-di-fluoro psilocybin derivative (FIG. 7B); a 2-chloro-4-phospho-5-fluoro-6-chloro-7-iodo psilocybin derivative (FIG. 7C); a 2,4,7-tri-bromo-6-chloro psilocybin derivative (FIG. 7D); and a 2-fluoro-4,5,7-tri-bromo psilocybin derivative (FIG. 7E). It is noted that in each of FIGS. 7A, 7B, 7C, 7D, and 7E $R_{3a}$ and $R_{3b}$ can be a hydrogen atom, an alkyl group, an aryl group, or an acyl group.

Thus, continuing to refer to the chemical compound having formula (I), in one embodiment $R_2$, $R_4$, $R_5$ and $R_6$ can be halogen atom, wherein the halogen atoms are independently selected from a bromine, chlorine fluorine or iodine atom, and $R_7$ can be a hydrogen atom or an alkyl group or O-alkyl group (see: the example halogenated psilocybin derivative shown in FIG. 7A ($R_2$, $R_4$, $R_5$ and $R_6$ are each chlorine atoms; $R_7$ is a hydrogen atom; and $R_{3a}$ and $R_{3b}$ are a hydrogen atom, an alkyl group, an aryl group, or an acyl group)).

Figure 7B:
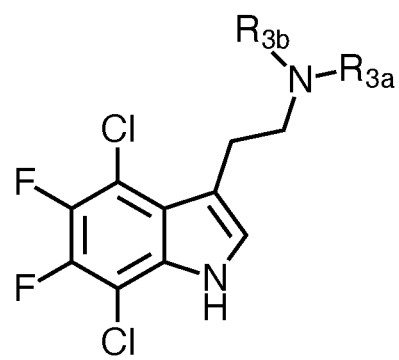

Continuing to refer to the chemical compound having formula (I), in one embodiment $R_4$, $R_5$, $R_6$ and $R_7$ can be halogen atom, wherein the halogen atoms are independently selected from a bromine, chlorine fluorine or iodine atom and $R_2$ can be a hydrogen atom or an alkyl group or O-alkyl group (see: the example halogenated psilocybin derivative shown in FIG. 7B ($R_4$ and $R_7$ are chlorine atoms, $R_5$ and $R_6$ are each fluorine atoms; $R_2$ is a hydrogen atom; and $R_{3a}$ and $R_{3b}$ are a hydrogen atom, an alkyl group, an aryl group, or an acyl group).

Figure 7C:
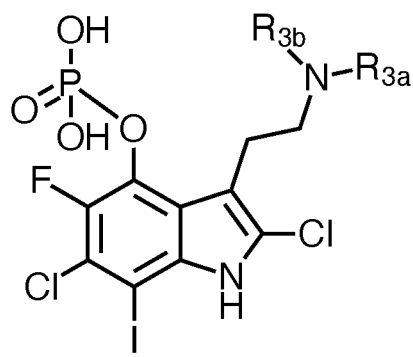

Continuing to refer to the chemical compound having formula (I), in one embodiment $R_2$, $R_5$, $R_6$ and $R_7$ can be halogen atom, wherein the halogen atoms are independently selected from a bromine, chlorine fluorine or iodine atom and $R_4$ can be a phosphate group, a hydrogen atom or an alkyl group or O-alkyl group (see: the example halogenated psilocybin derivative shown in FIG. 7C ($R_2$ and are $R_6$ are each chlorine atoms, $R_5$ is a fluorine atom, $R_7$ is an iodine atoms, $R_4$ is a phosphate group; and $R_{3a}$ and $R_{3b}$ are a hydrogen atom, an alkyl group, an aryl group, or an acyl group)).

Figure 7D:
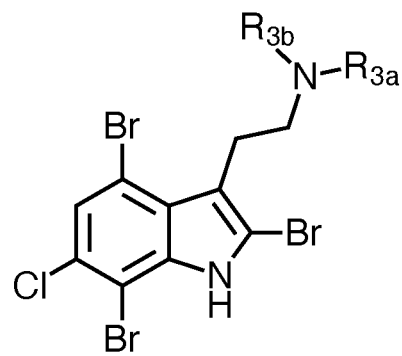

Continuing to refer to the chemical compound having formula (I), in one embodiment $R_2$, $R_4$, $R_6$ and $R_7$ can be halogen atom, wherein the halogen atoms are independently selected from a bromine, chlorine fluorine or iodine atom and $R_5$ can be a hydrogen atom or an alkyl group or O-alkyl group (see: the example halogenated psilocybin derivative shown in FIG. 7D ($R_2$, $R_4$ and are $R_7$ are each bromine atoms, $R_6$ is a chlorine atom, $R_5$ is a hydrogen atom; and $R_{3a}$ and $R_{3b}$ are a hydrogen atom, an alkyl group, an aryl group, or an acyl group)).

Figure 7E:
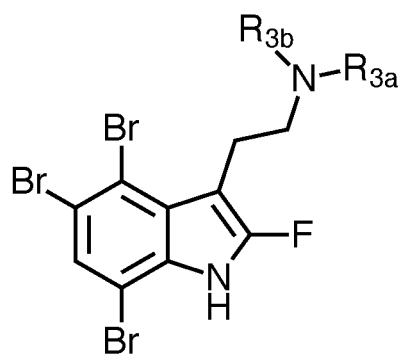

In one embodiment $R_2$, $R_4$, $R_5$ and $R_7$ can be halogen atom, wherein the halogen atoms are independently selected from a bromine, chlorine fluorine or iodine atom and $R_6$ can be a hydrogen atom or an alkyl group or O-alkyl group (see: the example halogenated psilocybin derivative shown in FIG. 7E ($R_4$, $R_5$ and are $R_7$ are each bromine atoms, $R_2$ is a fluorine atom, $R_6$ is a hydrogen atom; and $R_{3a}$ and $R_{3b}$ are a hydrogen atom, an alkyl group, an aryl group, or an acyl group)).

In one embodiment, four of $R_2$, $R_4$, $R_5$, $R_6$ and $R_7$ can be a halogen atom, wherein at least two halogen atoms are identical, the remaining $R_2$, $R_5$, $R_6$, and $R_7$ being a hydrogen atom or an alkyl group or O-alkyl group, and $R_4$ when it is nota halogen atom, being a phosphate group, a hydrogen atom or an alkyl group or O-alkyl group (see: e.g. the halogenated psilocybin derivatives shown in FIGS. 7A, 7B, 7C, 7D and 7E).

In one embodiment, four of $R_2$, $R_4$, $R_5$, $R_6$ and $R_7$ can be a halogen atom, and at least two halogen atoms are non-identical, the remaining $R_2$, $R_5$, $R_6$, and $R_7$ being a hydrogen atom or an alkyl group or O-alkyl group, and $R_4$ when it is nota halogen atom, being a phosphate group, a hydrogen atom or an alkyl group or O-alkyl group (see: e.g. the halogenated psilocybin derivatives shown in FIGS. 7B, 7C, 7D and 7E).

In one embodiment, four of $R_2$, $R_4$, $R_5$, $R_6$ and $R_7$ can be a halogen atom, and all four halogen atoms are identical, the remaining $R_2$, $R_5$, $R_6$, or $R_7$ being a hydrogen atom or an alkyl group or O-alkyl group, and $R_4$ when it is not a halogen atom, being a phosphate group, a hydrogen atom or an alkyl group or O-alkyl group (see: e.g. the halogenated psilocybin derivative shown in FIG. 7A).

Still continuing to refer to the chemical compound having formula (I). In one embodiment, all five of $R_2$, $R_4$, $R_5$, $R_6$ and $R_7$ can be a halogen atom, the halogen selected from bromine, chlorine, fluorine or iodine.

In one embodiment, all five of $R_2$, $R_4$, $R_5$, $R_6$ and $R_7$ can be a halogen atom, and at least two halogen atoms are identical.

In one embodiment, all five of $R_2$, $R_4$, $R_5$, $R_6$ and $R_7$ can be a halogen atom, and at least three halogen atoms are identical.

In one embodiment, all five of $R_2$, $R_4$, $R_5$, $R_6$ and $R_7$ can be a halogen atom, and at least four halogen atoms are identical.

In one embodiment, all five of $R_2$, $R_4$, $R_5$, $R_6$ and $R_7$ can be a halogen atom, and all five halogen atoms are identical.

In one embodiment, all five of $R_2$, $R_4$, $R_5$, $R_6$ and $R_7$ can be a halogen atom, and the chemical compound comprises at least two non-identical halogen atoms.

In one embodiment, all five of $R_2$, $R_4$, $R_5$, $R_6$ and $R_7$ can be a halogen atom, and the chemical compound comprises at least three non-identical halogen atoms.

In one embodiment, all five of $R_2$, $R_4$, $R_5$, $R_6$ and $R_7$ can be a halogen atom, and four halogen atoms are non-identical.

Still continuing to refer to the chemical compound having formula (I), it is noted that, in a further aspect hereof, $R_{3A}$ and $R_{3B}$ can be a hydrogen atom, an alkyl group, an aryl group or an acyl group. Thus, for example, $R_{3A}$ and $R_{3B}$ can each be a hydrogen atom, or $R_{3A}$ and $R_{3B}$ can each be an alkyl group, such as a methyl group, ethyl group, propyl group, or longer chain alkyl group, or $R_{3A}$ and $R_{3B}$ can each be an aryl group, such as a phenyl group or a naphthyl group, or $R_{3A}$ and $R_{3B}$ can each be an acyl group, such as an acetyl group. Furthermore, one of $R_{3A}$ and $R_{3B}$ can be a hydrogen atom, and one of $R_{3A}$ and $R_{3B}$ can be an alkyl group, and aryl group, or an acyl group. Furthermore, $R_{3A}$ and $R_{3B}$ can be an aryl group and an alkyl group, an aryl group and an acyl group, or an alkyl group and an acyl group.

Furthermore, in one embodiment, a psilocybin derivative according to the present disclosure can be a chemical compound having the formula (II):

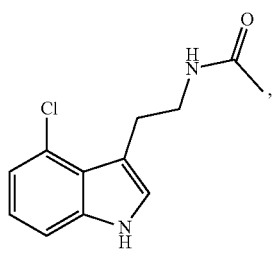

(II)

or, a chemical compound having the formula (II), wherein the chlorine is substituted for a bromine, fluorine or iodine.

Furthermore, in one embodiment, a psilocybin derivative according to the present disclosure can be a chemical compound having the formula (III):

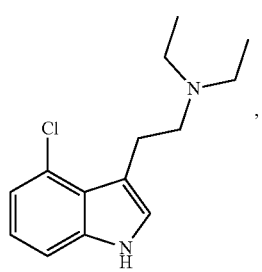

(III)

or, a chemical compound having the formula (III), wherein the chlorine is substituted for a bromine, fluorine or iodine.

Furthermore, in one embodiment, a psilocybin derivative according to the present disclosure can be a chemical compound having the formula (IV):

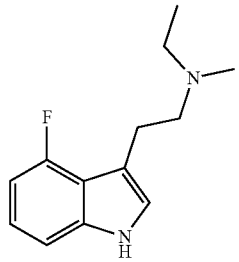

(IV)

or, a chemical compound having the formula (IV), wherein the fluorine is substituted for a bromine, chlorine or iodine.

Furthermore, in one embodiment, a psilocybin derivative according to the present disclosure can be a chemical compound having the formula (V):

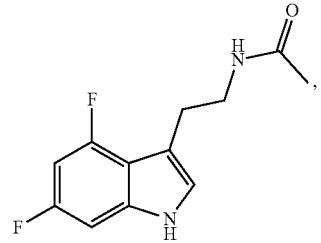

(V)

or, a chemical compound having the formula (V), wherein one or both of the fluorines are substituted for a bromine, chlorine or iodine.

Furthermore, in one embodiment, a psilocybin derivative according to the present disclosure can be a chemical compound having the formula (VI):

(VI)

or, a chemical compound having the formula (VI), wherein one or both of the fluorines are substituted for a bromine, chlorine or iodine.

Furthermore, in one embodiment, a psilocybin derivative according to the present disclosure can be a chemical compound having the formula (VII):

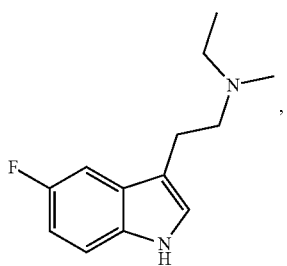

(VII)

or, a chemical compound having the formula (VII), wherein the fluorine is substituted for a bromine, chlorine or iodine.

Furthermore, in one embodiment, a psilocybin derivative according to the present disclosure can be a chemical compound having the formula (VIII):

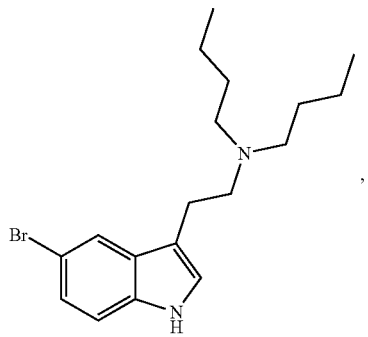

(VIII)

or, a chemical compound having the formula (VIII), wherein the bromine is substituted for a, chlorine, fluorine or iodine.

Furthermore, in one embodiment, a psilocybin derivative according to the present disclosure can be a chemical compound having the formula (IX):

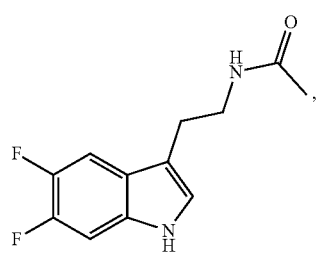

(IX)

or, a chemical compound having the formula (IX), wherein one or both of the fluorines are substituted for a bromine, chlorine or iodine.

Furthermore, in one embodiment, a psilocybin derivative according to the present disclosure can be a chemical compound having the formula (X):

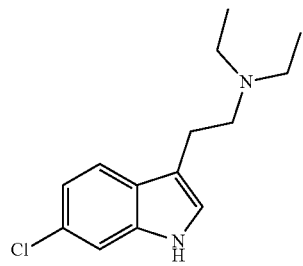

(X)

or, a chemical compound having the formula (X), wherein the chlorine is substituted for a bromine, chlorine or iodine.

Furthermore, in one embodiment, a psilocybin derivative according to the present disclosure can be a chemical compound having the formula (XI):

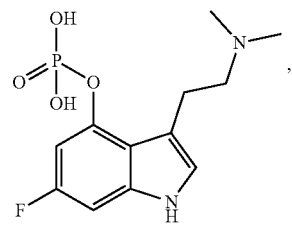

(XI)

or, a chemical compound having the formula (XI), wherein the fluorine is substituted for a bromine, chlorine or iodine.

Furthermore, in one embodiment, a psilocybin derivative according to the present disclosure can be a chemical compound having the formula (XII):

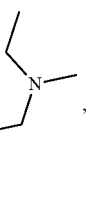

(XII)

or, a chemical compound having the formula (XII), wherein the fluorine is substituted for a bromine, chlorine or iodine.

Furthermore, in one embodiment, a psilocybin derivative according to the present disclosure can be a chemical compound having the formula (XIII):

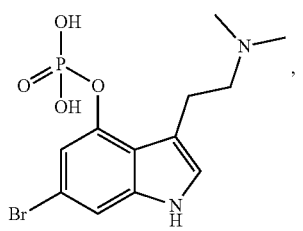

(XIII)

or, a chemical compound having the formula (XIII), wherein the bromine is substituted for a chlorine, fluorine or iodine.

Furthermore, in one embodiment, a psilocybin derivative according to the present disclosure can be a chemical compound having the formula (XIV):

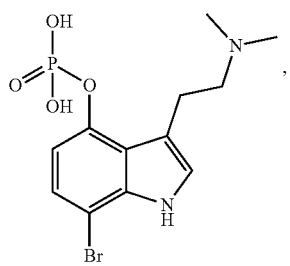

(XIV)

or, a chemical compound having the formula (XIV), wherein the bromine is substituted for a chlorine, fluorine or iodine.

Furthermore, in one embodiment, a psilocybin derivative according to the present disclosure can be a chemical compound having the formula (XV):

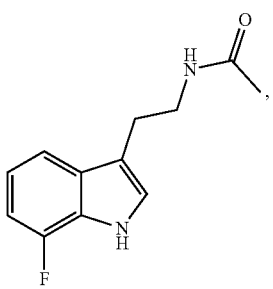

(XV)

or, a chemical compound having the formula (XV), wherein the fluorine is substituted for a bromine, chlorine or iodine.

Furthermore, in one embodiment, a psilocybin derivative according to the present disclosure can be a chemical compound having the formula (XVI):

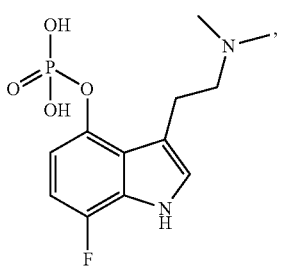

(XVI)

or, a chemical compound having the formula (XV), wherein the fluorine is substituted for a bromine, chlorine or iodine.

Furthermore, in one embodiment, a psilocybin derivative according to the present disclosure can be a chemical compound having the formula (XVII):

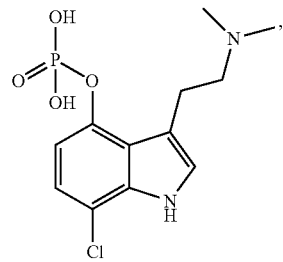

(XVII)

or, a chemical compound having the formula (XVII), wherein the fluorine is substituted for a bromine, chlorine or iodine.

Furthermore, in one embodiment, a psilocybin derivative according to the present disclosure can be a chemical compound having the formula (XVII):

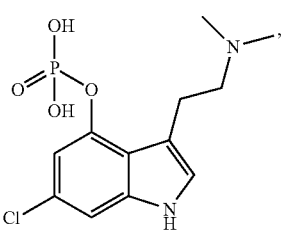

(XVII)

or, a chemical compound having the formula (XVII), wherein the fluorine is substituted for a bromine, chlorine or iodine.

Furthermore, it is noted that the halogenated psilocybin derivatives of the present disclosure include salts thereof. Thus, the nitrogen atom of the ethyl-amino group extending in turn from the O3 atom may be protonated, and the positive charge may be balanced by, for example, chloride or sulfate ions, to thereby form a chloride salt or a sulfate salt. Furthermore, in compounds wherein $R_4$ is a phosphate group, the phosphate group may be de-protonated, and the negative charge may be balanced by, for example, sodium ions or potassium ions, to thereby form a sodium salt or a potassium salt.

Furthermore, it is noted that when $R_4$ is a phosphate group, the term halogenated psilocybin derivative also includes compounds having the formula (XVIII):

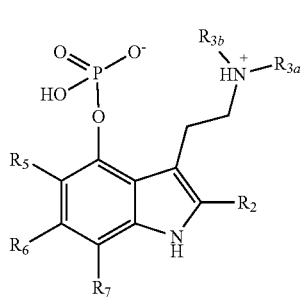

(XVIII)

wherein, at least one of $R_2$, $R_5$, $R_6$, or $R_7$ is a halogen atom or an alkyl group or O-alkyl group, and wherein any $R_2$, $R_5$, $R_6$, or $R_7$ which are not a halogen is a hydrogen atom, and wherein $R_{3A}$ and $R_{3B}$ are a hydrogen atom, an alkyl group, and aryl group or an acyl group. The term further includes salts, including pharmaceutically acceptable salts, of halogenated psilocybins having the formula (XVIII), such as a sodium salt, a potassium salt etc.

Thus, to briefly recap, the present disclosure provides halogenated psilocybin derivatives. The disclosure provides, in particular, a chemical compound or salts thereof having formula (I):

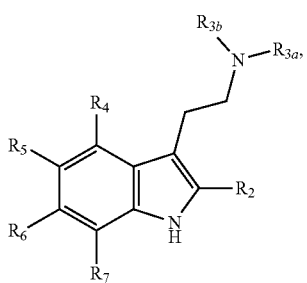

(I)

wherein in an aspect, at least one of $R_2$, $R_4$, $R_5$, $R_6$, or $R_7$ is a halogen atom. In an aspect, in formula (I), each non-halogenated $R_2$, $R_5$, $R_6$, or $R_7$ is a hydrogen atom or an alkyl group or O-alkyl group. In a further aspect, in formula (I), $R_4$ when it is not halogenated is a hydrogen atom, an alkyl group or O-alkyl group, a hydroxy group, or a phosphate group. Yet in a further aspect, $R_{3A}$ and $R_{3B}$ are a hydrogen atom, an alkyl group, an aryl group, or an acyl group.

In one embodiment of the disclosure, a chemical compound or salts thereof having formula (I) is included:

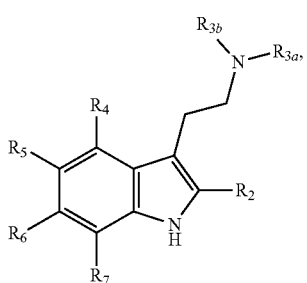

(I)

wherein at least one of $R_2$, $R_4$, $R_5$, $R_6$, or $R_7$ is a halogen atom, and wherein each non-halogenated $R_2$, $R_5$, $R_6$, or $R_7$ is a hydrogen atom or an alkyl group or O-alkyl group, wherein $R_4$ when it is not halogenated is a hydrogen atom, alkyl group or O-alkyl group, a hydroxy group, or a phosphate group, and wherein $R_{3A}$ and $R_{3B}$ are a hydrogen atom, an alkyl group, an aryl group, or an acyl group.

In one embodiment, at least one of $R_2$, $R_4$, $R_5$, $R_6$, or $R_7$ is a halogen atom, and wherein each non-halogenated $R_2$, $R_5$, $R_6$, or $R_7$ is a hydrogen atom or a $(C_1\text{-}C_{20})$-alkyl group or $(C_1\text{-}C_{20})$—O-alkyl group. In another embodiment, each non-halogenated $R_2$, $R_5$, $R_6$, or $R_7$ is a hydrogen atom, a methyl group, ethyl group, a propyl group, an O-methyl group, an O-ethyl group, or an O-propyl group.

In another embodiment, each non-halogenated $R_2$, $R_5$, $R_6$, or $R_7$ is a hydrogen atom or a $(C_1\text{-}C_{10})$-alkyl group or $(C_1\text{-}C_{10})$—O-alkyl group. In another embodiment, each non-halogenated $R_2$, $R_5$, $R_6$, or $R_7$ is a hydrogen atom, a methyl group, ethyl group, a propyl group, an O-methyl group, an O-ethyl group, or an O-propyl group.

In another embodiment, each non-halogenated $R_2$, $R_5$, $R_6$, or $R_7$ is a hydrogen atom or a $(C_1\text{-}C_6)$-alkyl group or $(C_1\text{-}C_6)$—O-alkyl group. In another embodiment, each non-halogenated $R_2$, $R_5$, $R_6$, or $R_7$ is a hydrogen atom, a methyl group, ethyl group, a propyl group, an O-methyl group, an O-ethyl group, or an O-propyl group.

In another embodiment, when $R_4$ is not halogenated, $R_4$ is a hydrogen atom, a $(C_1\text{-}C_{20})$-alkyl group or $(C_1\text{-}C_{20})$—O-alkyl group, a hydroxy group, or a phosphate group. In another embodiment, when $R_4$ is not halogenated, $R_4$ is a hydrogen atom, a $(C_1\text{-}C_{10})$-alkyl group or $(C_1\text{-}C_{10})$—O-alkyl group, a hydroxy group, or a phosphate group. In another embodiment, when $R_4$ is not halogenated, $R_4$ is a hydrogen atom, a $(C_1\text{-}C_6)$-alkyl group or $(C_1\text{-}C_6)$—O-alkyl group, a hydroxy group, or a phosphate group. In another embodiment, when $R_4$ is not halogenated, $R_4$ is a hydrogen atom, a methyl group, an ethyl group, a propyl group, a phosphate group, an O-methyl group, an O-ethyl group, or an O-propyl group.

In another embodiment, $R_{3A}$ and $R_{3B}$ are a hydrogen atom, a $(C_1\text{-}C_{20})$-alkyl group, a $(C_6\text{-}C_{14})$-aryl group, or a —C(=O)($C_1\text{-}C_{20}$)-alkyl group. In another embodiment, $R_{3A}$ and $R_{3B}$ are a hydrogen atom, a $(C_1\text{-}C_{10})$-alkyl group, a $(C_6\text{-}C_{10})$-aryl group, or a —C(=O)($C_1\text{-}C_{10}$)-alkyl group. In another embodiment, $R_{3A}$ and $R_{3B}$ are a hydrogen atom, a $(C_1\text{-}C_6)$-alkyl group, a phenyl group, or a —C(=O)($C_1\text{-}C_6$)-alkyl group. In another embodiment, $R_{3A}$ and $R_{3B}$ are a hydrogen atom, a methyl group, an ethyl group, a propyl group, a phenyl group, —C(=O)—CH$_3$, —C(=O)—CH$_2$CH$_3$, or —C(=O)—CH$_2$CH$_2$CH$_3$.

In one embodiment of the disclosure, a chemical compound or salts thereof having formula (I) is included:

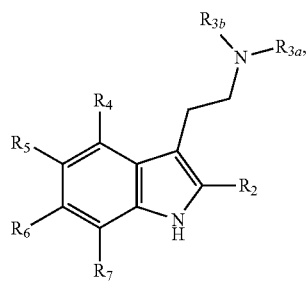

(I)

wherein
$R_2$, $R_5$, $R_6$, and $R_7$ are independently or simultaneously H, an alkyl group or O-alkyl group or a halogen atom, $R_{3A}$ and $R_{3B}$ are a hydrogen atom, an alkyl group, an aryl group, or an acyl group; and $R_4$ is hydrogen atom, alkyl group or O-alkyl group, a halogen, a hydroxy group, or a phosphate group; wherein at least one of $R_2$, $R_4$ $R_5$, $R_6$, and $R_7$ is a halogen.

In one embodiment, $R_2$, $R_5$, $R_6$, and $R_7$ are independently or simultaneously H, $(C_1\text{-}C_{20})$-alkyl group or $(C_1\text{-}C_{20})$—O-alkyl group or a halogen atom. In one embodiment, $R_2$, $R_5$, $R_6$, and $R_7$ are independently or simultaneously H, $(C_1\text{-}C_{10})$-alkyl group or $(C_1\text{-}C_{10})$—O-alkyl group or a halogen atom. In one embodiment, $R_2$, $R_5$, $R_6$, and $R_7$ are independently or simultaneously H, $(C_1\text{-}C_6)$-alkyl group or $(C_1\text{-}C_6)$—O-alkyl group or a halogen atom. In one embodiment, $R_2$, $R_5$, $R_6$, and $R_7$ are independently or simultaneously H, methyl, ethyl, propyl, O-methyl, O-ethyl, O-propyl, or a halogen atom.

In one embodiment, $R_4$ is H, $(C_1-C_{20})$-alkyl group or $(C_1-C_{20})$—O-alkyl group, a halogen atom or a phosphate group. In one embodiment, $R_4$ is H, $(C_1-C_{10})$-alkyl group or $(C_1-C_{10})$—O-alkyl group, a halogen atom or a phosphate group. In one embodiment, $R_4$ is H, $(C_1-C_6)$-alkyl group or $(C_1-C_6)$—O-alkyl group, a halogen atom, a hydroxy group, or a phosphate group. In one embodiment, $R_4$ is H, methyl, ethyl, propyl, O-methyl, O-ethyl, O-propyl, a halogen atom, a hydroxy group, or a phosphate group.

In another embodiment, $R_{3A}$ and $R_{3B}$ are a hydrogen atom independently or simultaneously a $(C_1-C_{20})$-alkyl group, a $(C_6-C_{14})$-aryl group, or a —C(=O)($C_1-C_{20}$)-alkyl group. In another embodiment, $R_{3A}$ and $R_{3B}$ are independently or simultaneously a hydrogen atom, a $(C_1-C_{10})$-alkyl group, a $(C_6-C_{10})$-aryl group, or a —C(=O)($C_1-C_{10}$)-alkyl group or O-alkyl group. In another embodiment, $R_{3A}$ and $R_{3B}$ are independently or simultaneously a hydrogen atom, a $(C_1-C_6)$-alkyl group, a phenyl group, or a —C(=O)($C_1-C_6$)-alkyl group. In another embodiment, $R_{3A}$ and $R_{3B}$ are independently or simultaneously a hydrogen atom, a methyl group, an ethyl group, a propyl group, a butyl group, a phenyl group, —C(=O)—CH$_3$, —C(=O)—CH$_2$CH$_3$, or —C(=O)—CH$_2$CH$_2$CH$_3$.

The halogenated psilocybin derivatives of the present disclosure may be used to prepare a pharmaceutical or recreational drug formulation. Thus in one embodiment, the present disclosure further provides in another aspect, pharmaceutical and recreational drug formulations comprising halogenated psilocybin derivatives. Accordingly, in one aspect, the present disclosure provides in a further embodiment a pharmaceutical or recreational drug formulation comprising a chemical compound or salts thereof having the formula (I):

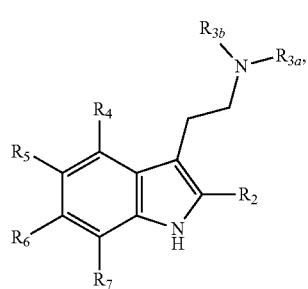

wherein, at least one of $R_2$, $R_4$, $R_5$, $R_6$ or $R_7$ is a halogen atom, wherein each non-halogenated $R_2$, $R_5$, $R_6$, or $R_7$ is a hydrogen atom or an alkyl group or O-alkyl group, wherein $R_4$ when it is not halogenated is a phosphate group, a hydrogen atom or an alkyl group or O-alkyl group, and wherein $R_{3A}$ and $R_{3B}$ are a hydrogen atom, an alkyl group, an aryl group, or an acyl group, together with a diluent, carrier or excipient. The pharmaceutical or recreational drug formulations may be prepared as liquids, tablets, capsules, microcapsules, nanocapsules, trans-dermal patches, gels, foams, oils, aerosols, nanoparticulates, powders, creams, emulsions, micellar systems, films, sprays, ovules, infusions, teas, decoctions, suppositories, etc. and include a pharmaceutically acceptable salt or solvate of the halogenated psilocybin compound together with an excipient. The term "excipient" as used herein means any ingredient other than the chemical compound of the disclosure. As will readily be appreciated by those of skill in art, the selection of excipient may depend on factors such as the particular mode of administration, the effect of the excipient on solubility of the chemical compounds of the present disclosure and methods for their preparation will be readily apparent to those skilled in the art. Such compositions and methods for their preparation may be found, for example, in "Remington's Pharmaceutical Sciences", 22nd Edition (Pharmaceutical Press and Philadelphia College of Pharmacy at the University of the Sciences, 2012).

The dose when using the compounds of the present disclosure can vary within wide limits, and as is customary and is known to those of skill in the art, the dose can be tailored to the individual conditions in each individual case. The dose depends, for example, on the nature and severity of the illness to be treated, on the condition of the patient, on the compound employed or on whether an acute or chronic disease state is treated or prophylaxis is conducted, on the mode of delivery of the compound, or on whether further active compounds are administered in addition to the compounds of the present disclosure. Representative doses of the present disclosure include, but are not limited to, about 0.001 mg to about 5000 mg, about 0.001 mg to about 2500 mg, about 0.001 mg to about 1000 mg, about 0.001 mg to about 500 mg, about 0.001 mg to about 250 mg, about 0.001 mg to about 100 mg, about 0.001 mg to about 50 mg, and about 0.001 mg to about 25 mg. Representative doses of the present disclosure include, but are not limited to, about 0.0001 to about 1,000 mg, about 10 to about 160 mg, about 10 mg, about 20 mg, about 40 mg, about 80 mg, or about 160 mg. Multiple doses may be administered during the day, especially when relatively large amounts are deemed to be needed, for example 2, 3 or 4, doses. Depending on the subject and as deemed appropriate from the patient's physician or care giver it may be necessary to deviate upward or downward from the doses described herein.

The pharmaceutical and drug formulations comprising the halogenated psilocybin derivatives of the present disclosure may be administered orally. Oral administration may involve swallowing, so that the compound enters the gastrointestinal tract, or buccal or sublingual administration may be employed by which the compound enters the blood stream directly from the mouth. Formulations suitable for oral administration include both solid and liquid formulations.

Solid formulations include tablets, capsules (containing particulates, liquids, microcapsules, or powders), lozenges (including liquid-filled lozenges), chews, multi- and nanoparticulates, gels, solid solutions, liposomal preparations, microencapsulated preparations, creams, films, ovules, suppositories and sprays.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose.

Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80. When present, surface active agents may comprise from 0.2% (w/w) to 5% (w/w) of the tablet.

Tablets may further contain lubricants such as magnesium stearate, calcium stearate, zinc stearate, sodium stearyl fumarate, and mixtures of magnesium stearate with sodium lauryl sulphate. Lubricants generally comprise from 0.25% (w/w) to 10% (w/w), from 0.5% (w/w) to 3% (w/w) of the tablet.

In addition to the halogenated psilocybin derivative, tablets may contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1% (w/w) to 25% (w/w) or from 5% (w/w) to 20% (w/w) of the dosage form.

Other possible auxiliary ingredients include anti-oxidants, colourants, flavouring agents, preservatives and taste-masking agents.

For tablet dosage forms, depending on the desired effective amount of the chemical compound, the chemical compound of the present disclosure may make up from 1% (w/w) to 80% (w/w) of the dosage form, more typically from 5% (w/w) to 60% (w/w) of the dosage form.

Exemplary tablets contain up to about 80% (w/w) of the chemical compound, from about 10% (w/w) to about 90% (w/w) binder, from about 0% (w/w) to about 85% (w/w) diluent, from about 2% (w/w) to about 10% (w/w) disintegrant, and from about 0.25% (w/w) to about 10% (w/w) lubricant.

The formulation of tablets is discussed in "Pharmaceutical Dosage Forms: Tablets", Vol. 1-Vol. 3, by CRC Press (2008).

The pharmaceutical and recreational drug formulations comprising the halogenated psilocybin derivatives of the present disclosure may also be administered directly into the blood stream, into muscle, or into an internal organ. Thus, the pharmaceutical and recreational drug formulations can be administered parenterally (for example, by subcutaneous, intravenous, intraarterial, intrathecal, intraventricular, intracranial, intramuscular, or intraperitoneal injection). Parenteral formulations are typically aqueous solutions which may contain excipients such as salts, carbohydrates and buffering agents (in one embodiment, to a pH of from 3 to 9), but, for some applications, they may be more suitably formulated as a sterile non-aqueous solution or as a dried form to be used in conjunction with a suitable vehicle such as sterile water.

Formulations comprising the halogenated psilocybin derivatives of the present disclosure for parenteral administration may be formulated to be immediate and/or modified release. Modified release formulations include delayed-, sustained-, pulsed-, controlled-, targeted and programmed release. Thus the chemical compounds of the disclosure may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The pharmaceutical or recreational drug formulations of the present disclosure also may be administered topically to the skin or mucosa, i.e. dermally or transdermally. Example pharmaceutical and recreational drug formulations for this purpose include gels, hydrogels, lotions, solutions, creams, ointments, dusting powders, cosmetics, oils, eye drops, dressings, foams, films, skin patches, wafers, implants, sponges, fibres, bandages and microemulsions. Liposomes may also be used. Example carriers include alcohol, water, mineral oil, liquid petrolatum, white petrolatum, glycerin, polyethylene glycol and propylene glycol. Penetration enhancers may be incorporate (see: for example, Finnin, B. and Morgan, T. M., 1999 J. Pharm. Sci, 88 (10), 955-958).

Other means of topical administration include delivery by electroporation, iontophoresis, phonophoresis, sonophoresis and microneedle or needle-free (e.g., Powderject™, Bioject™, etc.) injection.

Pharmaceutical and recreational drug formulations for inhalation or insufflation include solutions and suspensions in pharmaceutically acceptable, aqueous or organic solvents, or mixtures thereof, and powders. The liquid or solid pharmaceutical compositions can contain suitable pharmaceutically acceptable excipients. In some embodiments, the pharmaceutical compositions are administered by the oral or nasal respiratory route for local or systemic effect.

Pharmaceutical compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder pharmaceutical compositions can be administered, e.g., orally or nasally, from devices that deliver the formulation in an appropriate manner.

In further embodiments, in which the halogenated psilocybin compounds of present disclosure are used as a recreational drug, the compounds may be included in compositions such as food or food product, a beverage, a food seasoning, a personal care product, such as a cosmetic, perfume or bath oil, or oils (both for topical administration as massage oil, or to be burned or aerosolized). The chemical compounds of the present disclosure may also be included in a "vape" product, which may also include other drugs, such as nicotine, and flavorings.

The pharmaceutical formulations comprising the chemical compounds of the present disclosure may be used to treat a subject, and in particular to treat a psychiatric disorder in a subject. Accordingly, the present disclosure includes in a further embodiment, a method for treating a psychiatric disorder, the method comprising administering to a subject in need thereof a pharmaceutical formulation comprising a chemical compound or salts thereof having the formula (I):

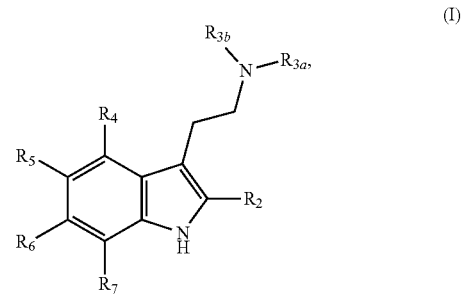

wherein, at least one of $R_2$, $R_4$, $R_5$, $R_6$ or $R_7$ is a halogen atom, wherein each non-halogenated $R_2$, $R_5$, $R_6$, or $R_7$ is a hydrogen atom or an alkyl group or O-alkyl group, wherein $R_4$ when it is not halogenated is a phosphate group, a hydrogen atom or an alkyl group or O-alkyl group, and wherein $R_{3A}$ and $R_{3B}$ are a hydrogen atom, or an alkyl group, an aryl group, or an acyl group, wherein the pharmaceutical formulation is administered in an effective amount to treat the psychiatric disorder in the subject.

Psychiatric disorders that may be treated include, for example, neurodevelopmental disorders such as intellectual disability, global development delay, communication disorders, autism spectrum disorder, and attention-deficit hyperactivity disorder (ADHD); bipolar and related disorders, such as mania, and depressive episodes; anxiety disorder, such as generalized anxiety disorder (GAD), agoraphobia, social anxiety disorder, specific phobias (natural events, medical, animal, situational, for example), panic disorder, and separation anxiety disorder; stress disorders, such as acute stress disorder, adjustment disorders, post-traumatic stress disorder (PTSD), and reactive attachment disorder; dissociative disorders, such as dissociative amnesia, dissociative identity disorder, and depersonalization/derealization disorder; somatoform disorders, such as somatic symptom disorders, illness anxiety disorder, conversion disorder, and factitious disorder; eating disorders, such as anorexia nervosa, bulimia nervosa, rumination disorder, pica, and binge-eating disorder; sleep disorders, such as narcolepsy, insomnia disorder, hypersomnolence, breathing-related sleep disorders, parasomnias, and restless legs syndrome; disruptive disorders, such as kleptomania, pyromania, intermittent explosive disorder, conduct disorder, and oppositional defiant disorder; depressive disorders, such as disruptive mood dysregulation disorder, major depressive disorder, persistent depressive disorder (dysthymia), premenstrual dysphoric disorder, substance/medication-induced depressive disorder, postpartum depression, and depressive disorder caused by another medical condition, for example, psychiatric and existential distress within life-threatening cancer situations (ACS Pharmacol Transl Sci 4: 553-562; J Psychiatr Res 137: 273); substance-related disorders, such as alcohol-related disorders, *Cannabis* related disorders, inhalant-use related disorders, stimulant use disorders, and tobacco use disorders; neurocognitive disorders, such as delirium; schizophrenia; compulsive disorders, such as obsessive compulsive disorders (OCD), body dysmorphic disorder, hoarding disorder, trichotillomania disorder, excoriation disorder, substance/medication induced obsessive-compulsive disorder, and obsessive-compulsive disorder related to another medical condition; and personality disorders, such as antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, schizotypal personality disorder.

In an aspect, the compounds of the present disclosure may be used to be contacted with a 5-$HT_{2A}$ receptor to thereby modulate the 5-$HT_{2A}$ receptor. Such contacting includes bringing a compound of the present disclosure and 5-$HT_{2A}$ receptor together under in vitro conditions, for example, by introducing the compounds in a sample containing a 5-$HT_{2A}$ receptor, for example, a sample containing purified 5-$HT_{2A}$ receptors, or a sample containing cells comprising 5-$HT_{2A}$ receptors. In vitro conditions further include the conditions described in Example 3 hereof. Contacting further includes bringing a compound of the present disclosure and 5-$HT_{2A}$ receptor together under in vivo conditions. Such in vivo conditions include the administration to an animal or human subject, for example, of a pharmaceutically effective amount of the compound of the present disclosure, when the compound is formulated together with a pharmaceutically active carrier, diluent or excipient, as hereinbefore described, to thereby treat the subject. Upon having contacted the 5-$HT_{2A}$ receptor, the compound may activate the 5-$HT_{2A}$ receptor or inhibit the 5-$HT_{2A}$ receptor.

Thus, in a further aspect, the condition that may be treated in accordance herewith can be any 5-$HT_{2A}$ receptor mediated disorder. Such disorders include, but are not limited to schizophrenia, psychotic disorder, attention deficit hyperactivity disorder, autism, and bipolar disorder.

The chemical compounds of the present disclosure may also be used as a feedstock material for other psilocybin derivatives. Thus in one embodiment, the chemical compounds of the present disclosure may be in used manufacture of a pharmaceutical or recreational drug formulation, wherein the manufacture may comprise derivatizing a chemical compound or salts thereof having the formula (I):

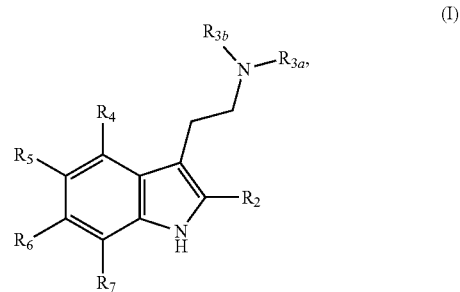

(I)

wherein, at least one of $R_2$, $R_4$, $R_5$, $R_6$ or $R_7$ is a halogen atom, wherein each non-halogenated $R_2$, $R_5$, $R_6$, or $R_7$ is a hydrogen atom or an alkyl group or O-alkyl group, wherein $R_4$ when it is not halogenated is a phosphate group, a hydrogen atom or an alkyl group or O-alkyl group, and wherein $R_{3A}$ and $R_{3B}$ are a hydrogen atom, an alkyl group, an aryl group, or an acyl group.

In order to use the compound having formula (I) as a feedstock, one or more halogen atoms may be replaced by any atoms or groups, for example hydrocarbon groups. Those of skill in the art will be generally familiar with methods that may be used to substitute halogen groups. In this respect, guidance may be found in Schnepel C. et al. (2017) Chem. Eur. J. 23:12064-12086; Durak L. J. et al. (2016) ACS Catal. 6: 1451; Runguphan W. et al. (2013) Org Lett 15: 2850; Corr M. J. et al. (2017) Chem. Sci. 8: 2039; and Roy A. D. et al. Chem. Comm. 4831.

Turning now to methods of making the halogenated psilocybin derivatives, it is noted that the psilocybin compounds of the present disclosure may be prepared in any suitable manner, including any organic chemical synthesis methods, biosynthetic methods, or a combination thereof. Synthesis generally may involve selecting a psilocybin precursor compound, and modifying the psilocybin precursor compound to form a halogenated psilocybin derivative. In this respect, it is noted that a non-halogenated psilocybin derivative may be selected and modified to form psilocybin, which subsequently may be halogenated, or, alternatively, a halogenated psilocybin derivative may be selected to subsequently form a halogenated psilocybin. Suitable psilocybin precursor compounds include compounds comprising an indole prototype structure (see: FIG. 2), including, for example tryptophan, tryptamine, 4-hydroxyindole, 4-hydroxytryptophan, 4-hydroxytryptamine, norbaeocystin and baeocystin, and halogenated forms thereof, notably, with respect to the indole prototype structure, 2-, 5-, 6-, 7-halogenated forms thereof. The halogenated psilocybin precursor compounds may be provided in a more or less chemically pure form, for example, in the form of a psilocybin precursor preparation having a purity of at least about 95%, at least about 96%, at least about 97%, at least about 98%, at least about 99%, or at least 99.9%. The psilocybin precursor compounds may be chemically synthesized, or obtained from a fine chemical manufacturer.

In one embodiment of the present disclosure the halogenated psilocybin derivatives may be formed biosynthetically. Accordingly, the present disclosure further includes in one embodiment, a method of making a halogenated psilocybin derivative the method comprising:
(a) contacting a halogenated psilocybin precursor compound with a host cell comprising a psilocybin biosynthetic enzyme complement; and
(b) growing the host cell to produce a halogenated psilocybin compound or salts thereof having the formula (I):

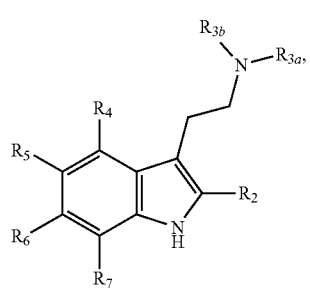

wherein, at least one of $R_2$, $R_4$, $R_5$, $R_6$ or $R_7$ is a halogen atom, wherein each non-halogenated $R_2$, $R_5$, $R_6$, or $R_7$ is a hydrogen atom or an alkyl group or O-alkyl group, wherein $R_4$ when it is not halogenated is a phosphate group, hydrogen atom or an alkyl group or O-alkyl group, and wherein $R_{3A}$ and $R_{3B}$ are a hydrogen atom, or an alkyl group, an aryl group, or an acyl group of the chemical compound.

Implementation of the foregoing example embodiment initially involves providing halogenated psilocybin precursor compounds and host cells having a psilocybin biosynthetic enzyme complement. Accordingly, next, exemplary halogenated psilocybin precursor compounds and example host cells that may be selected and used in accordance with the present disclosure will be described. Thereafter, example methodologies and techniques will be described to contact and use the halogenated psilocybin precursor compounds and cells to produce example halogenated psilocybin compounds.

A variety of halogenated psilocybin precursor compounds may be selected, prepared and used. In some embodiments, for example, the halogenated psilocybin precursor compound is a compound comprising a halogenated indole prototype structure. Examples of such compounds are halogenated tryptophan, halogenated tryptamine, halogenated 4-hydroxyindole, halogenated 4-hydroxytryptophan, halogenated 4-hydroxytryptamine, halogenated norbaeocystin, and halogenated baeocystin, and in particular the 2-halogenated, 5-halogenated, 6-halogenated and 7-halogenated forms (with respect to the indole prototype structure) of any of the foregoing.

Turning now to the host cells that can be used in accordance with the present disclosure, it is initially noted that a variety of host cells may be selected in accordance with the present disclosure, including microorganism host cells, plant host cells, and animal host cells.

In accordance herewith the host cell includes a psilocybin biosynthetic enzyme complement. Such cells can be obtained in at least two ways. First, in some embodiments, host cells may be selected in which a psilocybin biosynthetic enzyme complement is naturally present. Generally cells naturally producing psilocybin for example, cells of fungal species belonging to the genus *Psilocybe*, are suitable in this respect. Second, in some embodiments, a host cell that not naturally produces psilocybin may be modulated to produce a psilocybin biosynthetic enzyme complement. Thus, for example, a nucleic acid sequence encoding a psilocybin biosynthetic enzyme complement may be introduced into a host cell, and upon cell growth the host cells can make the psilocybin biosynthetic enzyme complement.

Typically a nucleic acid sequence encoding one or more enzymes constituting a psilocybin biosynthetic enzyme complement further includes one or more additional nucleic acid sequences, for example, a nucleic acid sequences controlling expression of the one or more enzymes, and these one or more additional nucleic acid sequences together with the nucleic acid sequence encoding the one or more enzymes can be said to form a chimeric nucleic acid sequence.

A host cell which upon cultivation expresses the chimeric nucleic acid can be selected and used in accordance with the present disclosure. Suitable host cells in this respect include, for example, microbial cells, such as bacterial cells, yeast cells, for example, and algal cells or plant cells. A variety of techniques and methodologies to manipulate host cells to introduce nucleic acid sequences in cells and attain expression exists and are well known to the skilled artisan. These methods include, for example, cation based methods, for example, lithium ion or calcium ion based methods, electroporation, biolistics, and glass beads based methods. As will be known to those of skill in the art, depending on the host cell selected, the methodology to introduce nucleic acid material in the host cell may vary, and, furthermore, methodologies may be optimized for uptake of nucleic acid material by the host cell, for example, by comparing uptake of nucleic acid material using different conditions. Detailed guidance can be found, for example, in Sambrook et al., Molecular Cloning, a Laboratory Manual, Cold Spring Harbor Laboratory Press, 2012, Fourth Ed. It is noted that the chimeric nucleic acid is a non-naturally occurring chimeric nucleic acid sequence and can be said to be heterologous to the host cell.

In some embodiments, the one or more enzymes constituting a psilocybin enzyme complement can be selected from by a nucleic acid sequence selected from the nucleic acid sequences consisting of:
(a) SEQ. ID NO: 1, SEQ. ID NO: 3, SEQ. ID NO: 5, SEQ. ID NO: 7, SEQ. ID NO: 9, SEQ. ID NO 11, SEQ. ID NO: 36, SEQ. ID NO: 38, SEQ. ID NO: 40, SEQ. ID NO: 42, SEQ. ID NO: 44, SEQ. ID NO: 46, SEQ. ID NO: 48, SEQ. ID NO: 50, SEQ. ID NO: 52, SEQ. ID NO: 54, SEQ. ID NO: 56, SEQ. ID NO: 58, SEQ. ID NO: 60, SEQ. ID NO: 64, SEQ. ID NO: 66, SEQ. ID NO: 68, SEQ. ID NO: 70, and SEQ. ID NO: 72;

(b) a nucleic acid sequence that is substantially identical to any one of the nucleic acid sequences of (a);
(c) a nucleic acid sequence that is substantially identical to any one of the nucleic acid sequences of (a) but for the degeneration of the genetic code;
(d) a nucleic acid sequence that is complementary to any one of the nucleic acid sequences of (a);
(e) a nucleic acid sequence encoding a polypeptide having any one of the amino acid sequences set forth in SEQ. ID NO: 2, SEQ. ID NO: 4, SEQ. ID NO: 6, SEQ. ID NO: 8, SEQ. ID NO: 10, SEQ. ID NO 12, SEQ. ID NO: 37, SEQ. ID NO: 39, SEQ. ID NO: 41, SEQ. ID NO: 43, SEQ. ID NO: 45, SEQ. ID NO: 47, SEQ. ID NO: 49, SEQ. ID NO: 51, SEQ. ID NO: 53, SEQ. ID NO: 55, SEQ. ID NO: 57, SEQ. ID NO: 59, SEQ. ID NO: 61, SEQ. ID NO: 63, SEQ. ID NO: 65, SEQ. ID NO: 67, SEQ. ID NO: 69, SEQ. ID NO: 71, and SEQ. ID NO: 73;
(f) a nucleic acid sequence that encodes a functional variant of any one of the amino acid sequences set forth in SEQ. ID NO: 2, SEQ. ID NO: 4, SEQ. ID NO: 6, SEQ. ID NO: 8, SEQ. ID NO: 10, SEQ. ID NO 12, SEQ. ID NO: 37, SEQ. ID NO: 39, SEQ. ID NO: 41, SEQ. ID NO: 43, SEQ. ID NO: 45, SEQ. ID NO: 47, SEQ. ID NO: 49, SEQ. ID NO: 51, SEQ. ID NO: 53, SEQ. ID NO: 55, SEQ. ID NO: 57, SEQ. ID NO: 59, SEQ. ID NO: 61, SEQ. ID NO: 63, SEQ. ID NO: 65, SEQ. ID NO: 67, SEQ. ID NO: 69, SEQ. ID NO: 71, and SEQ. ID NO: 73; and
(g) a nucleic acid sequence that hybridizes under stringent conditions to any one of the nucleic acid sequences set forth in (a), (b), (c), (d), (e) or (f).

Thus any of the nucleic acid sequence set forth in (a), (b), (c), (d), (e), (f) or (g) may be selected and introduced into a host cell. In general, however the nucleic acid sequence is selected in conjunction with the selected psilocybin precursor compound, as hereinafter further discussed in reference to FIGS. 8A and 8B.

One example host cell that conveniently may be used is *Escherichia coli*. The preparation of the *E. coli* vectors may be accomplished using commonly known techniques such as restriction digestion, ligation, gel electrophoresis, DNA sequencing, the polymerase chain reaction (PCR) and other methodologies. A wide variety of cloning vectors is available to perform the necessary steps required to prepare a recombinant expression vector. Among the vectors with a replication system functional in *E. coli*, are vectors such as pBR322, the pUC series of vectors, the M13 mp series of vectors, pBluescript etc. Suitable promoter sequences for use in *E. coli* include; for example, the T7 promoter, the T5 promoter, tryptophan (trp) promoter, lactose (lac) promoter, tryptophan/lactose (tac) promoter, lipoprotein (lpp) promoter, and A phage PL promoter. Typically, cloning vectors contain a marker, for example, an antibiotic resistance marker, such as ampicillin or kanamycin resistance marker, allowing selection of transformed cells. Nucleic acid sequences may be introduced in these vectors, and the vectors may be introduced in *E. coli* by preparing competent cells, electroporation or using other well known methodologies to a person of skill in the art. *E. coli* may be grown in an appropriate medium, such as Luria-Broth medium and harvested. Recombinant expression vectors may readily be recovered from cells upon harvesting and lysing of the cells.

Another example host cell that may be conveniently used is a yeast cell. Example yeast host cells that can be used are yeast cells belonging to the genus *Candida, Kluyveromyces, Saccharomyces, Schizosaccharomyces, Pichia, Hansenula,* and *Yarrowia*. In specific example embodiments, the yeast cell can be a *Saccharomyces cerevisiae* cell, a *Yarrowia lipolytica* cell, or *Pichia pastoris* cell.

A number of vectors exist for the expression of recombinant proteins in yeast host cells. Examples of vectors that may be used in yeast host cells include, for example, Yip type vectors. YEp type vectors, YRp type vectors, YCp type vectors, pGPD-2, pA0815, pGAPZ, pGAPZα, pHIL-D2, pHIL-S1, pPIC3.5K, pPIC9K, pPICZ, pPICZα, pPIC3K, pHWO10, pPUZZLE and 2 μm plasmids. Such vectors are known to the art and are, for example, described in Cregg et al, Mol Biotechnol. (2000) 16(1): 23-52. Suitable promoter sequences for use in yeast host cells are also known and described, for example, in Mattanovich et al., Methods Mol. Biol., 2012, 824:329-58, and in Romanos et al., 1992, Yeast 8: 423-488. Examples of suitable promoters for use in yeast host cells include promoters of glycolytic enzymes, like triosephosphate isomerase (TPI), phosphoglycerate kinase (PGK), glyceraldehyde-3-phosphate dehydrogenase (GAPDH or GAP) and variants thereof, lactase (LAC) and galactosidase (GAL), *P. pastoris* glucose-6-phosphate isomerase promoter (PPGI), the 3-phosphoglycerate kinase promoter (PPGK), the glycerol aldehyde phosphate dehydrogenase promoter (PGAP), translation elongation factor promoter (PTEF), *S. cerevisiae* enolase (ENO-1), *S. cerevisiae* galactokinase (GAL1), *S. cerevisiae* alcohol dehydrogenase/glyceraldehyde-3-phosphate dehydrogenase (ADH1, ADH2/GAP), *S. cerevisiae* triose phosphate isomerase (TPI), *S. cerevisiae* metallothionein (CUP1), and *S. cerevisiae* 3-phosphoglycerate kinase (PGK), and the maltase gene promoter (MAL). Marker genes suitable for use in yeast host cells are also known to the art. Thus, antibiotic resistance markers, such as ampicillin resistance markers, can be used in yeast, as well as marker genes providing genetic functions for essential nutrients, for example, leucine (LEU2), tryptophan (TRP1 and TRP2), uracil (URA3, URA5, URA6), histidine (HIS3), and the like. Methods for introducing vectors into yeast host cells can, for example, be found in S. Kawai et al, 2010, Bioeng. Bugs 1(6): 395-403.

Further, guidance with respect to the preparation of expression vectors and introduction thereof into host cells, including in *E. coli* cells, yeast cells, and other host cells, may be found in, for example: Sambrook et al., Molecular Cloning, a Laboratory Manual, Cold Spring Harbor Laboratory Press, 2012, Fourth Ed.

Thus, to briefly recap, a host cell comprising a chimeric nucleic acid comprising (i) a nucleic acid sequence controlling expression in a host cell and (ii) a nucleic acid sequence encoding a psilocybin biosynthetic enzyme complement, can be prepared in accordance with the present disclosure.

In accordance herewith, host cells are grown to multiply and to express a chimeric nucleic acid. Expression of the chimeric nucleic acid results in the biosynthetic production in the host cell of a psilocybin biosynthetic enzyme complement. Growth media and growth conditions can vary depending on the host cell that is selected, as will be readily appreciated to those of ordinary skill in the art. Growth media typically contain a carbon source, one or several nitrogen sources, essential salts including salts of potassium, sodium, magnesium, phosphate and sulphate, trace metals, water soluble vitamins, and process aids including but not limited to antifoam agents, protease inhibitors, stabilizers, ligands and inducers. Example carbon sources are e.g. mono- or disaccharides. Example nitrogen sources are, e.g. ammonia, urea, amino acids, yeast extract, corn steep liquor and fully or partially hydrolyzed proteins. Example trace metals are e.g. Fe. Zn, Mn, Cu, Mo and $H_3BO_3$. Example water soluble vitamins are e.g. biotin, pantothenate, niacin, thiamine, p-aminobenzoic acid, choline, pyridoxine, folic acid, riboflavin and ascorbic acid. Further, specific example media include liquid culture media for the growth of yeast cells and bacterial cells including, Luria-Bertani (LB) broth for bacterial cell cultivation, and yeast extract peptone dextrose (YEPD or YPD), for yeast cell cultivation. Further media and growth conditions can be found in Sambrook et al., Molecular Cloning, a Laboratory Manual, Cold Spring Harbor Laboratory Press, 2012, Fourth Ed.

In order for the host cells to produce the halogenated psilocybin compound, the cells are provided with a psilocybin precursor compound. Thus in accordance herewith, host cells may be contacted with a psilocybin precursor compound. In some embodiments, a psilocybin precursor compound can be exogenously supplied, for example, by including a psilocybin precursor compound in the growth medium of the host cells, and growing the host cells in a medium including the psilocybin precursor compound.

Figure 8A:
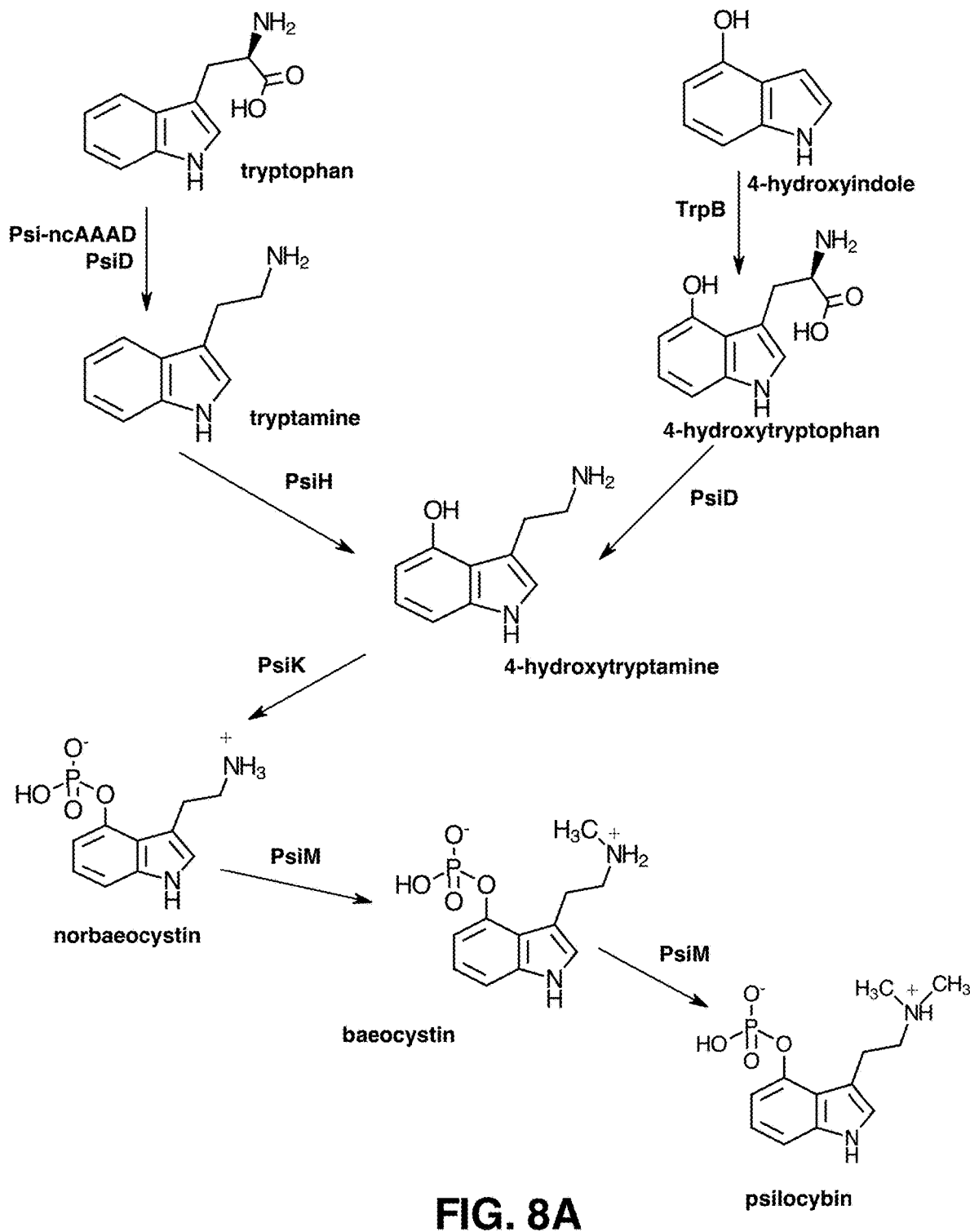
FIGS. 8A and 8B depict example biosynthesis pathway relating to the synthesis of a halogenated psilocybin derivatives.
Figure 8B:
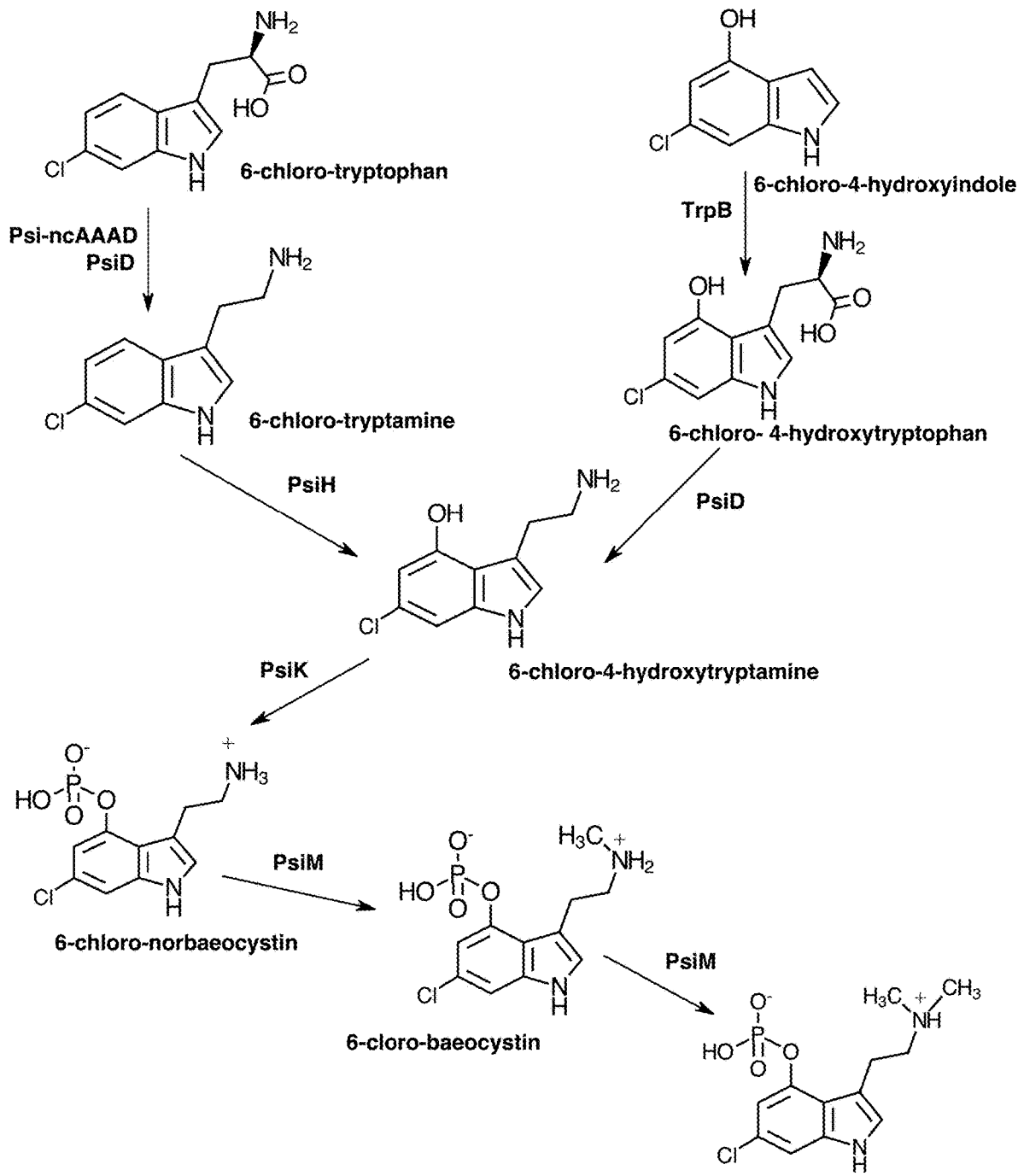

Referring next to FIGS. 8A and 8B, shown therein is an example natural biosynthetic pathway showing the conversion of example psilocybin precursor compounds to form psilocybin (FIG. 8A). Thus, as can be appreciated from FIG. 8A, various psilocybin precursor compounds may be selected and prepared in halogenated form, in conjunction with a psilocybin biosynthetic enzyme complement.

Thus, by way of example, referring to FIG. 8B, a chlorinated psilocybin precursor compound, for example, 6-chloro-4-hydroxy indole may be selected and contacted with a host cell comprising a psilocybin biosynthetic enzyme complement comprising PsiD, (e.g. SEQ. ID NO: 2) PsiH (e.g. SEQ. ID NO: 4), PsiK (e.g. SEQ. ID NO; 6) and PsiM (e.g. SEQ. ID NO: 8), and upon growth of the cells 6-chloro-psilocybin can be formed. Or by way of another example, 6-chloro-tryptophan may be selected and contacted with a host cell comprising a psilocybin biosynthetic enzyme complement comprising TrpB (SEQ. ID NO: 12) PsiD, (e.g. SEQ. ID NO: 2), PsiK (e.g. SEQ. ID NO; 6) and PsiM (e.g. SEQ. ID NO: 8), and upon growth of the cells 6-chloro-psilocybin can be formed. It will be clear to those of skill in the art that by referring to FIGS. 8A and 8B, other halogenated psilocybin precursors may be selected (e.g. 2-chloro tryptophan, 4-chloro-tryptophan, 5-chloro-tryptophan, 7-chlorotryptophan; 6-bromo-tryptophan, 6-fluorotryptophan, 6-iodotryptophan; and 6-chlorotryptamine, 6-chloro-4-hydroxytryptophan, 6-hydroxy-4-chloro-tryptamine, 6-chloro-norbaeocystin or 6-chloro-baeocystin), and contacted with a host cell comprising an appropriate psilocybin biosynthetic enzyme complement to produce a halogenated psilocybin derivative.

Thus, in one further example embodiment, a halogenated indole, such as 6-chloro-4-hydroxy indole, for example (see: FIG. 8B), may be selected and contacted with a host cell comprising a psilocybin biosynthetic enzyme complement comprising (i) a nucleic acid encoding TrpB selected from SEQ. ID NO: 12, SEQ. ID NO: 65, SEQ. ID NO: 67, SEQ. ID NO: 69, SEQ. ID NO: 71, and SEQ. ID NO: 73, or a nucleic acid sequence encoding a polypeptide sequence substantially similar to any of the aforementioned sequences; (ii) a nucleic acid encoding PsiD selected from SEQ. ID NO: 2, SEQ. ID NO: 10, SEQ. ID NO: 37, SEQ. ID NO: 39, SEQ. ID NO: 41, SEQ. ID NO: 43, SEQ. ID NO: 45, SEQ. ID NO: 47, SEQ. ID NO: 49, SEQ. ID NO: 51, SEQ. ID NO: 53, SEQ. ID NO: 55, and SEQ. ID NO: 57, or a nucleic acid sequence encoding a polypeptide sequence substantially similar to any of the aforementioned sequences; (iii) a nucleic acid encoding PsiK encoded by SEQ. ID NO: 6, or a nucleic acid sequence encoding a polypeptide sequence substantially similar thereto; and (iv) a nucleic acid encoding PsiM selected from SEQ. ID NO: 8, SEQ. ID NO: 59 and SEQ. ID NO: 61 or a nucleic acid sequence encoding a polypeptide sequence substantially similar to any of the aforementioned sequences to produce a halogenated psilocybin derivative.

Thus, in one further example embodiment, a halogenated tryptophan, such as 6-chloro-4-hydroxy tryptophan, for example (see: FIG. 8B), may be selected and contacted with a host cell comprising a psilocybin biosynthetic enzyme complement comprising (i) a nucleic acid encoding PsiD selected from SEQ. ID NO: 2, SEQ. ID NO: 10, SEQ. ID NO: 37, SEQ. ID NO: 39, SEQ. ID NO: 41, SEQ. ID NO: 43, SEQ. ID NO: 45, SEQ. ID NO: 47, SEQ. ID NO: 49, SEQ. ID NO: 51, SEQ. ID NO: 53, SEQ. ID NO: 55, and SEQ. ID NO: 57, or a nucleic acid sequence encoding a polypeptide sequence substantially similar to any of the aforementioned sequences; (ii) a nucleic acid encoding PsiK encoded by SEQ. ID NO: 6, or a nucleic acid sequence encoding a polypeptide sequence substantially similar thereto; and (iii) a nucleic acid encoding PsiM selected from SEQ. ID NO: 8, SEQ. ID NO: 59 and SEQ. ID NO: 61 or a nucleic acid sequence encoding a polypeptide sequence substantially similar to any of the aforementioned sequences to produce a halogenated psilocybin derivative.

Thus, in one further example embodiment, a halogenated tryptamine, such as 6-chloro-4-hydroxy tryptamine, for example (see: FIG. 8B), may be selected and contacted with a host cell comprising a psilocybin biosynthetic enzyme complement comprising (i) a nucleic acid encoding PsiK encoded by SEQ. ID NO: 6, or a nucleic acid sequence encoding a polypeptide sequence substantially similar thereto; and (ii) and a nucleic acid encoding PsiM selected from SEQ. ID NO: 8, SEQ. ID NO: 59 and SEQ. ID NO: 61 or a nucleic acid sequence encoding a polypeptide sequence substantially similar to any of the aforementioned sequences to produce a halogenated psilocybin derivative.

Thus, in one further example embodiment, a halogenated norbaeocystin, such as 6-chloro-norbaeocystin, or a halogenated baeocystin may, such as 6-chlorobaeocystin, for example (see: FIG. 8B), may be selected and contacted with a host cell comprising a psilocybin biosynthetic enzyme complement comprising a nucleic acid encoding PsiM selected from SEQ. ID NO: 8, SEQ. ID NO: 59 and SEQ. ID NO: 61 or a nucleic acid sequence encoding a polypeptide sequence substantially similar to any of the aforementioned sequences to produce a halogenated psilocybin derivative.

Thus, in one further example embodiment, a halogenated tryptophan, such as 6-chloro-4-hydroxy tryptophan, for example (see: FIG. 8B), may be selected and contacted with a host cell comprising a psilocybin biosynthetic enzyme complement comprising (i) a nucleic acid encoding PsiD selected from SEQ. ID NO: 2, SEQ. ID NO: 10, SEQ. ID NO: 37, SEQ. ID NO: 39, SEQ. ID NO: 41, SEQ. ID NO: 43, SEQ. ID NO: 45, SEQ. ID NO: 47, SEQ. ID NO: 49, SEQ. ID NO: 51, SEQ. ID NO: 53, SEQ. ID NO: 55, and SEQ. ID NO: 57, or a nucleic acid sequence encoding a polypeptide sequence substantially similar to any of the aforementioned sequences; (ii) a nucleic acid encoding PsiH encoded by SEQ. ID NO: 4, or a nucleic acid sequence encoding a polypeptide sequence substantially similar thereto; (iii) a nucleic acid encoding PsiK encoded by SEQ. ID NO: 6, or a nucleic acid sequence encoding a polypeptide sequence substantially similar thereto; and (iv) and a nucleic acid encoding PsiM selected from SEQ. ID NO: 8, SEQ. ID NO: 59 and SEQ. ID NO: 61 or a nucleic acid sequence encoding a polypeptide sequence substantially similar to any of the aforementioned sequences to produce a halogenated psilocybin derivative.

Thus, in one further example embodiment, a halogenated tryptamine, such as 6-chloro-tryptamine, for example (see: FIG. 8B), may be selected and contacted with a host cell comprising a psilocybin biosynthetic enzyme complement comprising (i) a nucleic acid encoding PsiH encoded by SEQ. ID NO: 4, or a nucleic acid sequence encoding a polypeptide sequence substantially similar thereto; (ii) a nucleic acid encoding PsiK encoded by SEQ. ID NO: 6, or a nucleic acid sequence encoding a polypeptide sequence substantially similar thereto; and (iii) and a nucleic acid encoding PsiM selected from SEQ. ID NO: 8, SEQ. ID NO: 59 and SEQ. ID NO: 61 or a nucleic acid sequence encoding a polypeptide sequence substantially similar to any of the aforementioned sequences to produce a halogenated psilocybin derivative.

In some embodiments, the psilocybin can be a halogenated psilocybin precursor compound which is exogenously supplied to a host cell, for example by inclusion in the host cell's growth medium. Thus, for example, referring to FIG. 8, it will be understood that in accordance herewith, for example, 6-chloro-tryptophan or 6-chloro-4-hydroxy indole, may be included in the growth medium of a host cell comprising a psilocybin biosynthetic enzyme complement.

It is noted that in some embodiments, the host cells may in addition to the psilocybin biosynthetic enzyme complement include a halogenase. In such embodiments the cell may be contacted with a non-halogenated psilocybin precursor compound, and halogenation may occur in vivo in the host cells. Thus, referring again to FIG. 8, by way of example, non-halogenated tryptophan may be selected and contacted with a host cell comprising a psilocybin biosynthetic enzyme complement comprising PsiD, (e.g. SEQ. ID NO: 2) PsiH (e.g. SEQ. ID NO: 4). PsiK (e.g. SEQ. ID NO; 6) and PsiM (e.g. SEQ. ID NO: 8), the host cells further including a halogenase, and upon growth of the host cells in the presence of a halogen, for example in the form of a halogen salt, sodium chloride (NaCl) or sodium bromide (NaBr) halogenated psilocybin derivatives can be formed.

Suitable halogenases that may be used in accordance herewith include, for example, a PyrH halogenase of *Streptomyces rugosporus* (SEQ. ID NO: 13; SEQ. ID NO: 14), which may, for example, be contacted with non-halogenated tryptophan to form 5-halo-tryptophan; a KtZR halogenase of *Kutzneria* sp. 744 (SEQ. ID NO: 15; SEQ. ID NO: 16), which may be contacted with non-halogenated tryptophan to form 6-halo-tryptophan; a SstH halogenase of *Streptomyces toxytrinici* (SEQ. ID NO: 17; SEQ. ID NO: 18), which may be contacted with non-halogenated tryptophan to form 6-halo-tryptophan; a ThaI halogenase of *Streptomyces albogriseolus* (SEQ. ID NO: 19; SEQ. ID NO: 20), which may be contacted with non-halogenated tryptophan to form 6-halo-tryptophan; a BorH halogenase (see: SEQ. ID NO: 21; SEQ. ID NO: 22), which may be contacted with non-halogenated tryptophan to form 6-halo-tryptophan; a KtzQ halogenase of *Kutzneria* sp. 744 (SEQ. ID NO: 23; SEQ. ID NO: 24), which may be contacted with non-halogenated tryptophan to form 7-halo-tryptophan; a PrnA halogenase of *Pseudomonas fluorescens* (SEQ. ID NO: 25; SEQ. ID NO: 26), which may be contacted with non-halogenated tryptophan and other psilocybin precursor compounds to form 7-halo-tryptophan or 2-halo-tryptophan and other 7-halo or 2-halo psilocybin precursor compounds; a RebH halogenase of *Lentzea aerocolonigenes* (SEQ. ID NO: 27; SEQ. ID NO: 28), which may be contacted with non-halogenated tryptophan to form 7-halo-tryptophan; and a SatH halogenase of *Streptomyces albus* (SEQ. ID NO: 29), which may be contacted with non-halogenated tryptophan to form 6-halo-tryptophan.

It is noted that halogenases comprising amino acid sequences substantially similar to any of the aforementioned halogenase sequences may be prepared and used to modulate the substrate specificity and/or the enzyme's catalytic efficiency. Thus, for example, halogenases comprising amino acid sequences substantially similar to SEQ. ID NO: 14; SEQ. ID NO: 16; SEQ. ID NO: 18; SEQ. ID NO: 20; SEQ. ID NO: 22; SEQ. ID NO: 24; SEQ. ID NO: 26; SEQ. ID NO: 28, and SEQ. ID NO: 29, may be prepared and used to obtain 2-halo, 5-halo, 6-halo or 7-halo tryptophan, or halogenases comprising amino acid sequences substantially similar to SEQ. ID NO: 14; SEQ. ID NO: 16; SEQ. ID NO: 18; SEQ. ID NO: 20; SEQ. ID NO: 22; SEQ. ID NO: 24; SEQ. ID NO: 26; SEQ. ID NO: 28, and SEQ. ID NO: 29 may be prepared and used to halogenate other non-halogenated psilocybin precursor compounds, such as tryptamine, 4-hydroxyindole, 4-hydroxytryptophan, 4-hydroxytryptamine, norbaeocystin, and baeocystin, for example, to form halogenated forms thereof.

Thus, for example, the native polypeptide sequence of a RebH halogenase *Lentzea aerocolonigenes* (SEQ. ID NO: 27; SEQ. ID NO: 28) may be modulated to thereby modulate the substrate specificity. Thus, for example, a modulated *Lentzea aerocolonigenes* RebH halogenase, which may be referred to as a RebH-Y455W mutant, set forth in SEQ. ID NO: 30 prefers tryptamine over tryptophan as a substrate and when contacted with tryptamine forms 7-halo-tryptamine.

By way of a further example, a modulated *Lentzea aerocolonigenes* RebH halogenase, which may be referred to as a RebH-N470S mutant, set forth in SEQ. ID NO: 31 prefers tryptamine over tryptophan as a substrate and when contacted with tryptamine forms 7-halo-tryptamine.

By way of a further example, a modulated *Lentzea aerocolonigenes* RebH halogenase, which may be referred to as a RebH-8F mutant, set forth in SEQ. ID NO: 32 prefers tryptamine over tryptophan as a substrate and when contacted with tryptamine forms 6-halo-tryptamine.

By way of a further example, a modulated *Lentzea aerocolonigenes* RebH halogenase, which may be referred to as a RebH-10F mutant, set forth in SEQ. ID NO: 33 prefers tryptamine over tryptophan as a substrate and when contacted with tryptamine forms 5-halo-tryptamine.

By way of a further example, a modulated *Lentzea aerocolonigenes* RebH halogenase, which may be referred to as a RebH-3SS mutant, set forth in SEQ. ID NO: 34 has an altered substrate acceptance profile and converts tricyclic tryptoline derivatives.

By way of yet a further example, a modulated *Lentzea aerocolonigenes* RebH halogenase, which may be referred to as a RebH-3SS mutant set forth in SEQ. ID NO: 35 has an altered substrate acceptance profile and converts a broad range of large indoles and carbazoles.

The foregoing examples of halogenases exhibiting modulated substrate specificity and/or catalytic efficiency are known to the art and are documented in, for example, Andorfer M. C., et al. (2016) Chem. Sci. 7: 3720; Andorfer M. C. et al. (2017) Catalysis 7: 1897; Glenn W. S., et al. (2011) J. Am. Chem. Soc. 133: 19346; and Payne J. T. et al. (2015) Angew. Chem. Int. Ed. 54: 4226.

Accordingly, in one embodiment the halogenase can be encoded by a nucleic acid selected from:

(a) SEQ. ID NO: 13, SEQ. ID NO: 15, SEQ. ID NO: 17, SEQ. ID NO: 19, SEQ. ID NO: 21, SEQ. ID NO: 23, SEQ. ID NO: 25, and SEQ. ID NO: 27;

(b) a nucleic acid sequence that is substantially identical to any one of the nucleic acid sequences of (a);

(c) a nucleic acid sequence that is substantially identical to any one of the nucleic acid sequences of (a) but for the degeneration of the genetic code;

(d) a nucleic acid sequence that is complementary to any one of the nucleic acid sequences of (a);

(e) a nucleic acid sequence encoding a polypeptide having any one of the amino acid sequences set forth in SEQ. ID NO: 14, SEQ. ID NO: 16, SEQ. ID NO: 18, SEQ. ID NO: 20, SEQ. ID NO: 22, SEQ. ID NO: 24, SEQ. ID NO: 26, SEQ. ID NO: 28, SEQ. ID NO: 29, SEQ. ID NO: 30, SEQ. ID NO: 31, SEQ. ID NO: 32. SEQ. ID NO: 33, SEQ. ID NO: 34, and SEQ. ID NO: 35;

(f) a nucleic acid sequence that encodes a functional variant of any one of the amino acid sequences set forth in SEQ. ID NO: 14, SEQ. ID NO: 16, SEQ. ID NO: 18, SEQ. ID NO: 20, SEQ. ID NO: 22, SEQ. ID NO: 24, SEQ. ID NO: 26, SEQ. ID NO: 28, SEQ. ID NO: 29, SEQ. ID NO: 30, SEQ. ID NO: 31, SEQ. ID NO: 32. SEQ. ID NO: 33, SEQ. ID NO: 34, and SEQ. ID NO: 35; and (g) a nucleic acid sequence that hybridizes under stringent conditions to any one of the nucleic acid sequences set forth in (a), (b), (c), (d), (e) or (f).

In one further embodiment, the host cell can comprise an acetyl transferase capable of acetylating $R_{3a}$ or $R_{3b}$, wherein the cell comprises a compound having chemical formula (I):

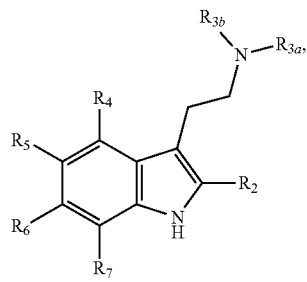
(I)

wherein, at least one of $R_2$, $R_4$, $R_5$, $R_6$ or $R_7$ is a halogen atom, wherein each non-halogenated $R_2$, $R_5$, $R_6$, or $R_7$ is a hydrogen atom or an alkyl group or O-alkyl group, wherein $R_4$ when it is not halogenated is a phosphate group, a hydrogen atom or an alkyl group or O-alkyl group, and wherein at least one of $R_{3A}$ and $R_{3B}$ is a hydrogen atom, to form a compound having the chemical formula (XIX):

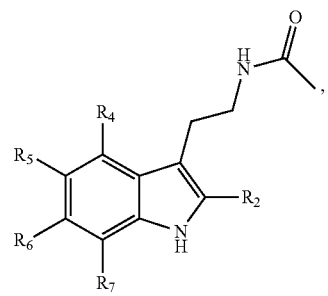
(XIX)

wherein, at least one of $R_2$, $R_4$, $R_5$, $R_6$ or $R_7$ is a halogen atom, wherein each non-halogenated $R_2$, $R_5$, $R_6$, or $R_7$ is a hydrogen atom or an alkyl group or O-alkyl group, wherein $R_4$ when it is not halogenated is a phosphate group, a hydrogen atom or an alkyl group or O-alkyl group.

In some embodiments, $R_{3a}$ and $R_{3b}$ are each a hydrogen atom.

Suitable acyl transferases that may be used in accordance herewith include a PsmF acetyl transferase obtained from Streptomyces griseofuscus, including a PsmF N-acetyltransferase comprising polypeptide sequence SEQ. ID NO: 63 set forth herein, and further including a PsmF polypeptide encoded by a nucleic acid selected from:

(a) SEQ. ID NO: 62;

(b) a nucleic acid sequence that is substantially identical the nucleic acid sequence of (a);

(c) a nucleic acid sequence that is substantially identical to the nucleic acid sequence of (a) but for the degeneration of the genetic code;

(d) a nucleic acid sequence that is complementary to the nucleic acid sequence of (a);

(e) a nucleic acid sequence encoding a polypeptide having an amino acid sequences set forth in SEQ. ID NO: 63;

(f) a nucleic acid sequence that encodes a functional variant of the amino acid sequence set forth in SEQ. ID NO: 63; and (g) a nucleic acid sequence that hybridizes under stringent conditions to any one of the nucleic acid sequences set forth in (a), (b), (c), (d), (e) or (f).

It will be clear to those of skill in the art that a significant variety of different halogenated and non-halogenated psilocybin precursor compounds may be selected. FIGS. 8A and 8B in this respect provide guidance and allow a person of skill in the art to select appropriate psilocybin precursor compounds and a matching a psilocybin biosynthetic enzyme complement.

Upon production by the host cells of the halogenated psilocybin compounds in accordance with the methods of the present disclosure, the halogenated psilocybin compounds may be extracted from the host cell suspension, and separated from other constituents within the host cell suspension, such as media constituents and cellular debris. Separation techniques will be known to those of skill in the art and include, for example, solvent extraction (e.g. butane, chloroform, ethanol), column chromatography based techniques, high-performance liquid chromatography (HPLC), for example, and/or countercurrent separation (CCS) based systems. The recovered halogenated psilocybin compounds may be obtained in a more or less pure form, for example, a preparation of halogenated psilocybin compounds of at least about 60% (w/w), about 70% (w/w), about 80% (w/w), about 90% (w/w), about 95% (w/w), about 96% (w/w), about 97% (w/w), about 98% (w/w) or about 99% (w/w) purity may be obtained. Thus, in this manner, halogenated psilocybin derivatives in more or less pure form may be prepared.

Similarly, other methods of making the halogenated psilocybin compounds that may be used in accordance herewith may yield preparations of halogenated compounds of at least about 60% (w/w), about 70% (w/w), about 80% (w/w), about 90% (w/w), about 95% (w/w), about 96% (w/w), about 97% (w/w), about 98% (w/w), or about 99% (w/w) purity.

It will now be clear form the foregoing that novel halogenated psilocybin derivatives are disclosed herein. The halogenated psilocybin compounds may be formulated for use as a pharmaceutical drug or recreational drug. The halogenated psilocybin compounds may also be used as a feedstock to produce other psilocybin derivatives.

SUMMARY OF SEQUENCES

SEQ. ID NO: 1 sets forth a *Psilocybe cubensis* nucleic acid sequence encoding a PsiD polypeptide.

SEQ. ID NO: 2 sets forth a deduced amino acid sequence of a *Psilocybe cubensis* PsiD polypeptide.

SEQ. ID NO: 3 sets forth a *Psilocybe cubensis* nucleic acid sequence encoding a PsiH polypeptide.

SEQ. ID NO: 4 sets forth a deduced amino acid sequence of a *Psilocybe cubensis* PsiH polypeptide.

SEQ. ID NO: 5 sets forth a *Psilocybe cubensis* nucleic acid sequence encoding a PsiK polypeptide.

SEQ. ID NO: 6 sets forth a deduced amino acid sequence of a *Psilocybe cubensis* PsiK polypeptide.

SEQ. ID NO: 7 sets forth a *Psilocybe cubensis* nucleic acid sequence encoding a PsiM polypeptide.

SEQ. ID NO: 8 sets forth a deduced amino acid sequence of a *Psilocybe cubensis* PsiM polypeptide.

SEQ. ID NO: 9 sets forth a *Psilocybe cubensis* nucleic acid sequence encoding a Psi-ncAAAD polypeptide.

SEQ. ID NO: 10 sets forth a deduced amino acid sequence of a *Psilocybe cubensis* Psi-ncAAAD polypeptide.

SEQ. ID NO: 11 sets forth a *Psilocybe cubensis* nucleic acid sequence encoding a TrpB polypeptide.

SEQ. ID NO: 12 sets forth a deduced amino acid sequence of a *Psilocybe cubensis* TrpB polypeptide.

SEQ. ID NO: 13 sets forth a *Streptomyces rugosporus* nucleic acid sequence encoding a PyrH halogenase polypeptide.

SEQ. ID NO: 14 sets forth a deduced amino acid sequence of a *Streptomyces rugosporus* PyrH halogenase polypeptide.

SEQ. ID NO: 15 sets forth a *Kutzneria* sp. 744 nucleic acid sequence encoding a KtzR halogenase polypeptide.

SEQ. ID NO: 16 sets forth a deduced amino acid sequence of a *Kutzneria* sp. 744 KtzR halogenase polypeptide.

SEQ. ID NO: 17 sets forth a *Streptomyces toxytrinici* nucleic acid sequence encoding a SttH halogenase polypeptide.

SEQ. ID NO: 18 sets forth a deduced amino acid sequence of a *Streptomyces toxytrinici* SttH halogenase polypeptide.

SEQ. ID NO: 19 sets forth a *Streptomyces albogriseolus* nucleic acid sequence encoding a Thal halogenase polypeptide.

SEQ. ID NO: 20 sets forth a deduced amino acid sequence of a *Streptomyces albogriseolus* Thal halogenase polypeptide.

SEQ. ID NO: 21 sets forth a nucleic acid sequence encoding a BorH halogenase polypeptide of an unidentified soil bacterium.

SEQ. ID NO: 22 sets forth a deduced amino acid sequence of a BorH halogenase polypeptide of an unidentified soil bacterium.

SEQ. ID NO: 23 sets forth a *Kutzneria* sp. 744 nucleic acid sequence encoding a KtzQ halogenase polypeptide.

SEQ. ID NO: 24 sets forth a deduced amino acid sequence of a *Kutzneria* sp. 744 KtzQ halogenase polypeptide.

SEQ. ID NO: 25 sets forth a *Pseudomonas fluorescens* nucleic acid sequence encoding a PrnA halogenase polypeptide.

SEQ. ID NO: 26 sets forth a deduced amino acid sequence of a *Pseudomonas fluorescens* PrnA halogenase polypeptide.

SEQ. ID NO: 27 sets forth a nucleic acid sequence encoding a *Lentzea areocolonigenes* RebH halogenase polypeptide.

SEQ. ID NO: 28 sets forth a deduced amino acid sequence of a *Lentzea aerocologinenes* RebH halogenase polypeptide.

SEQ. ID NO: 29 sets forth a deduced amino acid sequence of a *Streptomyces albus* SatH halogenase polypeptide.

SEQ. ID NO: 30 sets forth a deduced amino acid sequence of a mutated *Lentzea aerocologinenes* RebH halogenase polypeptide.

SEQ. ID NO: 31 sets forth a deduced amino acid sequence of another mutated *Lentzea aerocologinenes* RebH halogenase polypeptide.

SEQ. ID NO: 32 sets forth a deduced amino acid sequence of another mutated *Lentzea aerocologinenes* RebH halogenase polypeptide.

SEQ. ID NO: 33 sets forth a deduced amino acid sequence of another mutated *Lentzea aerocologinenes* RebH halogenase polypeptide.

SEQ. ID NO: 34 sets forth a deduced amino acid sequence of another mutated *Lentzea aerocologinenes* RebH halogenase polypeptide.

SEQ. ID NO: 35 sets forth a deduced amino acid sequence of another mutated *Lentzea aerocologinenes* RebH halogenase polypeptide.

SEQ. ID NO: 36 sets forth a nucleic acid sequence encoding a *Bacillus atrophaeus* BaTDC tryptophan decarboxylase polypeptide.

SEQ. ID NO: 37 sets forth a deduced amino acid sequence of a *Bacillus atrophaeus* BaTDC tryptophan decarboxylase polypeptide.

SEQ. ID NO: 38 sets forth a nucleic acid sequence encoding a *Ruminococcus gnavus* RgnTDC tryptophan decarboxylase polypeptide.

SEQ. ID NO: 39 sets forth a deduced amino acid sequence of a *Ruminococcus gnavus* RgnTDC tryptophan decarboxylase polypeptide.

SEQ. ID NO: 40 sets forth a nucleic acid sequence encoding a *Streptomyces griseofuscus* SgTDC tryptophan decarboxylase polypeptide.

SEQ. ID NO: 41 sets forth a deduced amino acid sequence of a *Streptomyces griseofuscus* SgTDC tryptophan decarboxylase polypeptide.

SEQ. ID NO: 42 sets forth a nucleic acid sequence encoding a *Ceriporiopsis subvermispora* CsTDC tryptophan decarboxylase polypeptide.

SEQ. ID NO: 43 sets forth a deduced amino acid sequence of a *Ceriporiopsis subvermispora* CsTDC tryptophan decarboxylase polypeptide.

SEQ. ID NO: 44 sets forth a nucleic acid sequence encoding a *Clostridium sporogenes* ClostSporTDC tryptophan decarboxylase polypeptide.

SEQ. ID NO: 45 sets forth a deduced amino acid sequence of a *Clostridium sporogenes* ClostSporTDC tryptophan decarboxylase polypeptide.

SEQ. ID NO: 46 sets forth a nucleic acid sequence encoding a *Homo sapiens* HsDDC DOPA decarboxylase polypeptide.

SEQ. ID NO: 47 sets forth a deduced amino acid sequence of a *Homo sapiens* HsDDC DOPA decarboxylase polypeptide.

SEQ. ID NO: 48 sets forth a nucleic acid sequence encoding an *Ophiorrhiza pumila* OpTDC tryptophan decarboxylase polypeptide.

SEQ. ID NO: 49 sets forth a deduced amino acid sequence of an *Ophiorrhiza pumila* OpTDC tryptophan decarboxylase polypeptide.

SEQ. ID NO: 50 sets forth a nucleic acid sequence encoding an *Oryza sativa* OsTDC1 tryptophan decarboxylase polypeptide.

SEQ. ID NO: 51 sets forth a deduced amino acid sequence of an *Oryza sativa* OsTDC1 tryptophan decarboxylase polypeptide.

SEQ. ID NO: 52 sets forth a nucleic acid sequence encoding another *Oryza sativa* OsTDC2 tryptophan decarboxylase polypeptide.

SEQ. ID NO: 53 sets forth a deduced amino acid sequence of another *Oryza sativa* OsTDC2 tryptophan decarboxylase polypeptide.

SEQ. ID NO: 54 sets forth a nucleic acid sequence encoding a *Xenorhabdus doucetiae* XdTDC decarboxylase polypeptide.

SEQ. ID NO: 55 sets forth a deduced amino acid sequence of a *Xenorhabdus doucetiae* XdTDC decarboxylase polypeptide.

SEQ. ID NO: 56 sets forth a nucleic acid sequence encoding a *Camptotheca acuminata* CaTDC tryptophan decarboxylase polypeptide.

SEQ. ID NO: 57 sets forth a deduced amino acid sequence of a *Camptotheca acuminata* CaTDC tryptophan decarboxylase polypeptide.

SEQ. ID NO: 58 sets forth a nucleic acid sequence encoding an Oryctolagus *cuniculus* OcINMT indolethylamine N-methyltransferase polypeptide.

SEQ. ID NO: 59 sets forth a deduced amino acid sequence of an *Oryctolagus cuniculus* OcINMT indolethylamine N-methyltransferase polypeptide.

SEQ. ID NO: 60 sets forth a nucleic acid sequence encoding a *Hordeum vulgare* HvNMT N-methyltransferase polypeptide.

SEQ. ID NO: 61 sets forth a deduced amino acid sequence of a *Hordeum vulgare* HvNMT N-methyltransferase polypeptide.

SEQ. ID NO: 62 sets forth a nucleic acid sequence encoding a *Streptomyces griseofuscus* PsmF N-acetyltransferase polypeptide.

SEQ. ID NO: 63 sets forth a deduced amino acid sequence of a *Streptomyces griseofuscus* PsmF N-acetyltransferase polypeptide.

SEQ. ID NO: 64 sets forth a nucleic acid sequence encoding a mutated *Thermotoga maritima* TmTrpB-2F3 tryptophan synthase subunit B polypeptide.

SEQ. ID NO: 65 sets forth a deduced amino acid sequence of a mutated *Thermotoga maritima* TmTrpB-2F3 tryptophan synthase subunit B polypeptide.

SEQ. ID NO: 66 sets forth a nucleic acid sequence encoding a mutated *Pyrococcus furiosus* PfTrpB-0A9 tryptophan synthase subunit B polypeptide.

SEQ. ID NO: 67 sets forth a deduced amino acid sequence of a mutated *Pyrococcus furiosus* PfTrpB-0A9 tryptophan synthase subunit B polypeptide.

SEQ. ID NO: 68 sets forth a nucleic acid sequence encoding another mutated *Pyrococcus furiosus* PfTrpB-2A6 tryptophan synthase subunit B polypeptide.

SEQ. ID NO: 69 sets forth a deduced amino acid sequence of a mutated *Pyrococcus furiosus* PfTrpB-2A6 tryptophan synthase subunit B polypeptide.

SEQ. ID NO: 70 sets forth a nucleic acid sequence encoding another mutated *Pyrococcus furiosus* PfTrpB-7E6 tryptophan synthase subunit B polypeptide.

SEQ. ID NO: 71 sets forth a deduced amino acid sequence of a mutated *Pyrococcus furiosus* PfTrpB-7E6 tryptophan synthase subunit B polypeptide.

SEQ. ID NO: 72 sets forth a nucleic acid sequence encoding another mutated *Pyrococcus furiosus* PfTrpB-Quat tryptophan synthase subunit B polypeptide.

SEQ. ID NO: 73 sets forth a deduced amino acid sequence of a mutated *Pyrococcus furiosus* PfTrpB-Quat tryptophan synthase subunit B polypeptide.

SEQ. ID NO: 74 sets forth a nucleic acid sequence used as integration cassette XII-4::TADH1-PsiH-HA-PPGK1-PTDH3-CPR-c-myc-TCYC1 for homologous recombination-based genome editing of *Saccharomyces cerevisiae* strain Sc-1.

SEQ. ID NO: 75 sets forth a nucleic acid sequence used as integration cassette XII-5::TADH1-PsiK-V5-PPGK1-PTDH3-PsiM-FLAG-TCYC1 for homologous recombination-based genome editing of *Saccharomyces cerevisiae* strain Sc-1.

SEQ. ID NO: 76 sets forth a nucleic acid sequence of modified pMM1 vector pMM1-PTDH3-ClostSporTDC-His-TCYC1 for engineering of *Saccharomyces cerevisiae* strain Sc-1.

SEQ. ID NO: 77 sets forth a nucleic acid sequence for *Saccharomyces cerevisiae* promoter PGK1.

SEQ. ID NO: 78 sets forth a nucleic acid sequence for *Saccharomyces cerevisiae* promoter TDH3.

SEQ. ID NO: 79 sets forth a nucleic acid sequence for *Saccharomyces cerevisiae* promoter CLN1.

SEQ. ID NO: 80 sets forth a nucleic acid sequence for *Saccharomyces cerevisiae* promoter UGA1.

SEQ. ID NO: 81 sets forth a nucleic acid sequence encoding a synthetic HA epitope tag polypeptide SEQ. ID NO: 82 sets forth deduced amino acid sequence of a synthetic HA epitope tag polypeptide SEQ. ID NO: 83 sets forth a nucleic acid sequence encoding a synthetic c-MYC epitope tag polypeptide SEQ. ID NO: 84 sets forth deduced amino acid sequence of a synthetic c-MYC epitope tag polypeptide SEQ. ID NO: 85 sets forth a nucleic acid sequence encoding a synthetic FLAG epitope tag polypeptide SEQ. ID NO: 86 sets forth deduced amino acid sequence of a synthetic FLAG epitope tag polypeptide SEQ. ID NO: 87 sets forth a nucleic acid sequence encoding a synthetic V5 epitope tag polypeptide SEQ. ID NO: 88 sets forth deduced amino acid sequence of a synthetic V5 epitope tag polypeptide SEQ. ID NO: 89 sets forth a nucleic acid sequence encoding a synthetic HIS epitope tag polypeptide SEQ. ID NO: 90 sets forth deduced amino acid sequence of a synthetic HIS epitope tag polypeptide SEQ. ID NO: 91 sets forth a nucleic acid sequence of pMM1 vector SEQ. ID NO: 92 sets forth a nucleic acid sequence of pCDM4 vector SEQ. ID NO: 93 sets forth a nucleic acid sequence of pETM6 vector SEQ. ID NO: 94 sets forth a nucleic acid sequence of pET28a(+) vector SEQ. ID NO: 95 sets forth a nucleic acid sequence encoding a *Psilocybe cubensis* PcCPR cytochrome P450 reductase polypeptide.

SEQ. ID NO: 96 sets forth a deduced amino acid sequence of a *Psilocybe cubensis* PcCPR cytochrome P450 reductase polypeptide.

SEQ. ID NO: 97 sets forth a nucleic acid sequence of pETM6-H10 vector.

SEQ. ID NO: 98 sets forth a nucleic acid sequence of pRSM3 vector.

SEQUENCE LISTING

SEQ.ID NO: 1
ATGCAGGTGATACCCGCGTGCAACTCGGCAGCAATAAGATCACTATGT
CCTACTCCCGAGTCTTTTAGAAACATGGGATGGCTCTCTGTCAGCGAT
GCGGTCTACAGCGAGTTCATAGGAGAGTTGGCTACCCGCGCTTCCAAT
CGAAATTACTCCAACGAGTTCGGCCTCATGCAACCTATCCAGGAATTC
AAGGCTTTCATTGAAAGCGACCCGGTGGTGCACCAAGAATTTATTGAC
ATGTTCGAGGGCATTCAGGACTCTCCAAGGAATTATCAGGAACTATGT
AATATGTTCAACGATATCTTTCGCAAAGCTCCCGTCTACGGAGACCTT
GGCCCTCCCGTTTATATGATTATGGCCAAATTAATGAACACCCGAGCG
GGCTTCTCTGCATTCACGAGACAAAGGTTGAACCTTCACTTCAAAAAA
CTTTTCGATACCTGGGGATTGTTCCTGTCTTCGAAAGATTCTCGAAAT
GTTCTTGTGGCCGACCAGTTCGACGACAGACATTGCGGCTGGTTGAAC
GAGCGGGCCTTGTCTGCTATGGTTAAACATTACAATGGACGCGCATTT
GATGAAGTCTTCCTCTGCGATAAAAATGCCCCATACTACGGCTTCAAC
TCTTACGACGACTTCTTTAATCGCAGATTTCGAAACCGAGATATCGAC
CGACCTGTAGTCGGTGGAGTTAACAACACCACCCTCATTTCTGCTGCT
TGCGAATCACTTTCCTACAACGTCTCTTATGACGTCCAGTCTCTCGAC
ACTTTAGTTTTCAAAGGAGAGACTTATTCGCTTAAGCATTTGCTGAAT
AATGACCCTTTCACCCCACAATTCGAGCATGGGAGTATTCTACAAGGA
TTCTTGAACGTCACCGCTTACCACCGATGGCACGCACCCGTCAATGGG
ACAATCGTCAAAATCATCAACGTTCCAGGTACCTACTTTGCGCAAGCC
CCGAGCACGATTGGCGACCCTATCCCGGATAACGATTACGACCCACCT
CCTTACCTTAAGTCTCTTGTCTACTTCTCTAATATTGCCGCAAGGCAA
ATTATGTTTATTGAAGCCGACAACAAGGAAATTGGCCTCATTTTCCTT
GTGTTCATCGGCATGACCGAAATCTCGACATGTGAAGCCACGGTGTCC
GAAGGTCAACACGTCAATCGTGGCGATGACTTGGGAATGTTCCATTTC
GGTGGTTCTTCGTTCGCGCTTGGTCTGAGGAAGGATTGCAGGGCAGAG
ATCGTTGAAAAGTTCACCGAACCCGGAACAGTGATCAGAATCAACGAA
GTCGTCGCTGCTCTAAAGGCTTAG

SEQ.ID NO: 2
MQVIPACNSAAIRSLCPTPESFRNMGWLSVSDAVYSEFIGELATRASN
RNYSNEFGLMQPIQEFKAFIESDPVVHQEFIDMFEGIQDSPRNYQELC
NMFNDIFRKAPVYGDLGPPVYMIMAKLMNTRAGFSAFTRQRLNLHFKK
LFDTWGLFLSSKDSRNVLVADQFDDRHCGWLNERALSAMVKHYNGRAF
DEVFLCDKNAPYYGFNSYDDFFNRRFRNRDIDRPVVGGVNNTTLISAA
CESLSYNVSYDVQSLDTLVFKGETYSLKHLLNNDPFTPQFEHGSILQG
FLNVTAYHRWHAPVNGTIVKIINVPGTYFAQAPSTIGDPIPDNDYDPP
PYLKSLVYFSNIAARQIMFIEADNKEIGLIFLVFIGMTEISTCEATVS
EGQHVNRGDDLGMFHFGGSSFALGLRKDCRAEIVEKFTEPGTVIRINE
VVAALKA

SEQ.ID NO: 3
ATGATCGCTGTACTATTCTCCTTCGTCATTGCAGGATGCATATACTAC
ATCGTTTCTCGTAGAGTGAGGCGGTCGCGCTTGCCACCAGGGCCGCCT
GGCATTCCTATTCCCTTCATTGGGAACATGTTTGATATGCCTGAAGAA
TCTCCATGGTTAACATTTCTACAATGGGGACGGGATTACAGTCTGTCT
TGCCGCGTTGACTTCTAATATATGAACAGCTAATATATTGTCAGACAC
CGATATTCTCTACGTGGATGCTGGAGGGACAGAAATGGTTATTCTTAA
CACGTTGGAGACCATTACCGATCTATTAGAAAAGCGAGGGTCCATTTA
TTCTGGCCGGTGAGCTGATGTTGAGTTTTTTGCAATTGAATTTGTGGT
CACACGTTTCCAGACTTGAGAGTACAATGGTCAACGAACTTATGGGGT
GGGAGTTTGACTTAGGGTTCATCACATACGGCGACAGGTGGCGCGAAG
AAAGGCGCATGTTCGCCAAGGAGTTCAGTGAGAAGGGCATCAAGCAAT
TTCGCCATGCTCAAGTGAAAGCTGCCCATCAGCTTGTCCAACAGCTTA
CCAAAACGCCAGACCGCTGGGCACAACATATTCGCCAGTAAGTACTAC
TTGAGGAAAATAGCGTACGCTTCGCTGACCGGTCCGTACATCAAAGTC
AGATAGCGGCAATGTCACTGGATATTGGTTATGGAATTGATCTTGCAG
AAGACGACCCTTGGCTGGAAGCGACCCATTTGGCTAATGAAGGCCTCG
CCATAGCATCAGTGCCGGGCAAATTTTGGGTCGATTCGTTCCCTTCTC
GTGAGCATCCTTCTTCTATGTAGGAAGGGAAGGAGTCTAACAAGTGTT
AGTAAAATACCTTCCTGCTTGGTTCCCAGGTGCTGTCTTCAAGCGCAA
AGCGAAGGTCTGGCGAGAAGCCGCCGACCATATGGTTGACATGCCTTA
TGAAACTATGAGGAAATTAGCAGTTAGTCAAATGCGTTCTCCCCGTAT
TTTTTCAATACTCTAACTTCAGCTCACAGCCTCAAGGATTGACTCGTC
CGTCGTATGCTTCAGCTCGTCTGCAAGCCATGGATCTCAACGGTGACC
TTGAGCATCAAGAACACGTAATCAAGAACACAGCCGCAGAGGTTAATG
TCGGTAAGTCAAAAGCGTCCGTCGGCAATTCAAAATTCAGGCGCTAAA
GTGGGTCTTCTCACCAAGGTGGAGGCGATACTGTAAGGATTTCTCAAT
CGTTAGAGTATAAGTGTTCTAATGCAGTACATACTCCACCAACCAGAC
TGTCTCTGCTATGTCTGCGTTCATCTTGGCCATGGTGAAGTACCCTGA
GGTCCAGCGAAAGGTTCAAGCGGAGCTTGATGCTCTGACCAATAACGG
CCAAATTCCTGACTATGACGAAGAAGATGACTCCTTGCCATACCTCAC
CGCATGTATCAAGGAGCTTTTCCGGTGGAATCAAATCGCACCCCTCGC
TATACCGCACAAATTAATGAAGGACGACGTGTACCGCGGGTATCTGAT

-continued

TCCCAAGAACACTCTAGTCTTCGCAAACACCTGGTGAGGCTGTCCATT

CATTCCTAGTACATCCGTTGCCCCACTAATAGCATCTTGATAACAGGG

CAGTATTAAACGATCCAGAAGTCTATCCAGATCCCTCTGTGTTCCGCC

CAGAAAGATATCTTGGTCCTGACGGGAAGCCTGATAACACTGTACGCG

ACCCACGTAAAGCGGCATTTGGCTATGGACGACGAAATTGGTAAGTGC

GCTTTCAGAACCCCCCCTTCCGTTGACTAGTGCCATGCGCGCATACAA

TATCGCTATTGATCTGATATAACTTCCCTGCGGCATTTATTTTGGCAT

TCCTTTAGTCCCGGAATTCATCTAGCGCAGTCGACGGTTTGGATTGCA

GGGGCAACCCTCTTATCAGCGTTCAATATCGAGCGACCTGTCGATCAG

AATGGGAAGCCCATTGACATACCGGCTGATTTTACTACAGGATTCTTC

AGGTAGCTAATTTCCGTCTTTGTGTGCATAATACCCCTAACGACGCAC

GTTTACCTTTTTGTAAAGACACCCAGTGCCTTTCCAGTGCAGGTTTGT

TCCTCGAACAGAGCAAGTCTCACAGTCGGTATCCGGACCCTGA

SEQ.ID NO: 4
MIAVLFSFVIAGCIYYIVSRRVRRSRLPPGPPGIPIPFIGNMFDMPEE

SPWLTFLQWGRDYNTDILYVDAGGTEMVILNTLETITDLLEKRGSIYS

GRLESTMVNELMGWEFDLGFITYGDRWREERRMFAKEFSEKGIKQFRH

AQVKAAHQLVQQLTKTPDRWAQHIRHQIAAMSLDIGYGIDLAEDDPWL

EATHLANEGLAIASVPGKFWVDSFPSLKYLPAWFPGAVFKRKAKVWRE

AADHMVDMPYETMRKLAPQGLTRPSYASARLQAMDLNGDLEHQEHVIK

NTAAEVNVGGGDTTVSAMSAFILAMVKYPEVQRKVQAELDALTNNGQI

PDYDEEDDSLPYLTACIKELFRWNQIAPLAIPHKLMKDDVYRGYLIPK

NTLVFANTWAVLNDPEVYPDPSVFRPERYLGPDGKPDNTVRDPRKAAF

GYGRRNCPGIHLAQSTVWIAGATLLSAFNIERPVDQNGKPIDIPADFT

TGFFRHPVPFQCRFVPRTEQVSQSVSGP

SEQ.ID NO: 5
ATGGCGTTCGATCTCAAGACTGAAGACGGCCTCATCACATATCTCACT

AAACATCTTTCTTTGGACGTCGACACGAGCGGAGTGAAGCGCCTTAGC

GGAGGCTTTGTCAATGTAACCTGGCGCATTAAGCTCAATGCTCCTTAT

CAAGGTCATACGAGCATCATCCTGAAGCATGCTCAGCCGCACATGTCT

ACGGATGAGGATTTTAAGATAGGTGTAGAACGTTCGGTTTACGAATAC

CAGGCTATCAAGCTCATGATGGCCAATCGGGAGGTTCTGGGAGGCGTG

GATGGCATAGTTTCTGTGCCAGAAGGCCTGAACTACGACTTAGAGAAT

AATGCATTGATCATGCAAGATGTCGGGAAGATGAAGACCCTTTTAGAT

TATGTCACCGCCAAACCGCCACTTGCGACGGATATAGCCCGCCTTGTT

GGGACAGAAATTGGGGGGTTCGTTGCCAGACTCCATAACATAGGCCGC

GAGAGGCGAGACGATCCTGAGTTCAAATTCTTCTCTGGAAATATTGTC

GGAAGGACGACTTCAGACCAGCTGTATCAAACCATCATACCCAACGCA

GCGAAATATGGCGTCGATGACCCCTTGCTGCCTACTGTGGTTAAGGAC

CTTGTGGACGATGTCATGCACAGCGAAGAGACCCTTGTCATGGCGGAC

CTGTGGAGTGGAAATATTCTTCTCCAGTTGGAGGAGGGGAAACCCATCG

AAGCTGCAGAAGATATATATCCTGGATTGGGAACTTTGCAAGTACGGC

CCAGCGTCGTTGGACCTGGGCTATTTCTTGGGTGACTGCTATTTGATA

TCCCGCTTTCAAGACGAGCAGGTCGGTACGACGATGCGGCAAGCCTAC

TTGCAAAGCTATGCGCGTACGAGCAAGCATTCGATCAACTACGCCAAA

GTCACTGCAGGTATTGCTGCTCATATTGTGATGTGGACCGACTTTATG

CAGTGGGGGAGCGAGGAAGAAAGGATAAATTTTGTGAAAAAGGGGGTA

GCTGCCTTTCACGACGCCAGGGGCAACAACGACAATGGGGAAATTACG

TCTACCTTACTGAAGGAATCATCCACTGCGTAA

SEQ.ID NO: 6
MHIRNPYRTPIDYQALSEAFPPLKPFVSVNADGTSSVDLTIPEAQRAF

TAALLHRDFGLTMTIPEDRLCPTVPNRLNYVLWIEDIFNYTNKTLGLS

DDRPIKGVDIGTGASAIYPMLACARFKAWSMVGTEVERKCIDTARLNV

VANNLQDRLSILETSIDGPILVPIFEATEEYEYEFTMCNPPFYDGAAD

MQTSDAAKGFGFGVGAPHSGTVIEMSTEGGESAFVAQMVRESLKLRTR

CRWYTSNLGKLKSLKEIVGLLKELEISNYAINEYVQGSTRRYAVAWSF

TDIQLPEELSRPSNPELSSLF

SEQ.ID NO: 7
ATGCATATCAGAAATCCTTACCGTACACCAATTGACTATCAAGCACTT

TCAGAGGCCTTCCCTCCCCTCAAGCCATTTGTGTCTGTCAATGCAGAT

GGTACCAGTTCTGTTGACCTCACTATCCCAGAAGCCCAGAGGGCGTTC

ACGGCCGCTCTTCTTCATCGTGACTTCGGGCTCACCATGACCATACCA

GAAGACCGTCTGTGCCCAACAGTCCCCAATAGGTTGAACTACGTTCTG

TGGATTGAAGATATTTTCAACTACACGAACAAAACCCTCGGCCTGTCG

GATGACCGTCCTATTAAAGGCGTTGATATTGGTACAGGAGCCTCCGCA

ATTTATCCTATGCTTGCCTGTGCTCGGTTCAAGGCATGGTCTATGGTT

GGAACAGAGGTCGAGAGGAAGTGCATTGACACGGCCCGCCTCAATGTC

GTCGCGAACAATCTCCAAGACCGTCTCTCGATATTAGAGACATCCATT

GATGGTCCTATTCTCGTCCCCATTTTCGAGGCGACTGAAGAATACGAA

TACGAGTTTACTATGTGTAACCCTCCATTCTACGACGGTGCTGCCGAT

ATGCAGACTTCGGATGCTGCCAAAGGATTTGGATTTGGCGTGGGCGCT

CCCCATTCTGGAACAGTCATCGAAATGTCGACTGAGGGAGGTGAATCG

GCTTTCGTCGCTCAGATGGTCCGTGAGAGCTTGAAGCTTCGAACACGA

TGCAGATGGTACACGAGTAACTTGGGAAAGCTGAAATCCTTGAAAGAA

ATAGTGGGCTGCTGAAAGAACTTGAGATAAGCAACTATGCCATTAAC

GAATACGTTCAGGGGTCCACACGTCGTTATGCCGTTGCGTGGTCTTTC

ACTGATATTCAACTGCCTGAGGAGCTTTCTCGTCCCTCTAACCCCGAG

CTCAGCTCTCTTTTCTAG

SEQ.ID NO: 8
MHIRNPYRTPIDYQALSEAFPPLKPFVSVNADGTSSVDLTIPEAQRAF

TAALLHRDFGLTMTIPEDRLCPTVPNRLNYVLWIEDIFNYTNKTLGLS

DDRPIKGVDIGTGASAIYPMLACARFKAWSMVGTEVERKCIDTARLNV

VANNLQDRLSILETSIDGPILVPIFEATEEYEYEFTMCNPPFYDGAAD

MQTSDAAKGFGFGVGAPHSGTVIEMSTEGGESAFVAQMVRESLKLRTR
CRWYTSNLGKLKSLKEIVGLLKELEISNYAINEYVQGSTRRYAVAWSF
TDIQLPEELSRPSNPELSSLF

SEQ.ID NO: 9
ATGCCTTCCAGTCACCCTCACATTACTCATCGCTATCGGTTCCTTCG
AGTGACGACCATGAACGTATATCTGCTCTGTTCTTGGGTCCCAAAGCA
GAAAATGCCGCATTTCTCCAGCAATGGTTGACCACGGTCGTCGCACAG
CAAAAGGCTGCCCGCGATGCATACTTCCCGGATGACAATGCTTTTATT
ACTACAGACATGCAAACTTCCCCCGCCTTTGCTCAGACTACTAAAGTA
ATCGCCTCCAATCTCACCGAATTATTGACTGCACTCGGTGAAAGGTCG
ATTCCTTTCTTCTCACCTCGGTACAGCGGCCATATGTCTGTGGACCAA
AGTCTACCTGCCATTCTCGGATTCTTATCGACCACATTTTATAATCCT
AACAATGTTGCCTTCGAGGCTAGTCCATTCACGACCCTCATCGAGGAA
GAAGTTGGCTTGCAACTCTCTGAAATGCTGGGTTATAATCGGCTAAAT
AACACCGAGAAACCTCTCGCCTGGGGACATATTGCATCAGGTGGAACT
GTTGCAAACTTGGAAGCGATGTGGGCGGCGCGAAACCTCAAGTTTTAC
CCTCTCTCACTCCGTGATGCTTCAGCCGAAGGCGCAGAGATGGAATTC
ATTCGTGACACATTCTCCGTCAAAACCTGTGTTGGTGACAAAAAATTA
TTAAAGGATTGCAGCCCATGGGAACTCCTCAATTTGCATGTTTCTACT
ATCTTAGACATGCCCGACCGTCTGCACGACGAGTACAATATTTCACCT
CAGTTCCTCGAAAAGGTTATGCGAAAGTATATCATCCAGTCTACCAAC
AAAGACACGTTGATGCAGCGTTGGGGACTTACCCAACAACCTGTCGTT
TTATCCCCGAGCACAAACCATTATTCCTGGCCAAAGGCTGCAGCTGTG
CTCGGTATTGGCTCAGACAACCTTCGCAACGTCCCAGTAGACATCCAA
GCCCACATGGACATAAACGAACTCGATCGTATGTTAAAAATTTGCTTG
GACGAGGAGACGCCAGTATATCAAGTAGTTGCTGTTATCGGTACCACC
GAAGAGGGCGGTGTCGATCGCATTACGGAGATCCTGAAGCTGCGCCAA
AAGTATGAAGCTTTGGGGCTGTCTTTTGCCATCCATGCAGATGCTGCT
TGGGGAGGCTATTTTGCAACCATGCTACCCAAAGATACATTGGGTCGA
AACCGGACTAGGCTTCCCAAAGAGGACACTACCTCGGGCTTTGTCCCT
CACGTCGGTCTGCGCGAGGAGAGCGCGTTACAACTCAGCCATATAAAG
TATGCCGATTCTATTACTATCGACCCGCACAAGGCAGGCTATGTTCCT
TACCCCGCTGGGGCACTCTGTTATCGCGACGGAAGAATGAGGTACCTG
CTTACATGGTCCGCGCCCTACCTTGCCCAAGGCAACGAGGGCCAAAGT
ATCGGAATATACGGGATCGAAGGAAGCAAACCTGGTGCAGCAGCATCC
GCGGTATTCATGGCGCACGAAACCATTGGCCTGACTCCTTCTGGATAC
GGGAACCTTCTTGGCCAGGCAATGTTTACATGTCGCCGATACGCTGCT
CACTGGTCTGCAATGTCAACGGATACTACCAGTTTCACTGTCACCCCG
TTCAATCCTATCCCTGCTGACATCGACCCCAACGCTGACCCCGCAAAG
GTCGAAGAGCAAAAACAGTTCATCAGAGATCGTATCTTGTTCAAATCG
AACGAGGAAATATACAACGATTCTGAGGCTATGGAACTCTTGCACCAA

CTTGGGTCCGATCTCAATATCAACGTTTTCGCATGCAACTTCCGCGAC
CGCGATAATAATCTCAACACCGACGTCGAGGAAGCCAACTGGCTCAAT
AACCGTATTTTCCAACGCTTTTCTGTTACAAGTGCTGAGGAGAACCCA
TTGGAAACGCCATTCTTCCTCAGCTCAACTACATTGAAACAATCCGAA
TACGGCGTCTGCGCAACCGAAGTAAAGAGACGCATGGGACTTGTTGGT
GACCAGGATGTTATAGTCCTGAGGAACGTCGTTATGTCTCCATTTACT
ACAACGAACGACTTTGTGGGAACTCTGGCAAACACCTTCCAAAAGATC
GTTGAGGAGGAGGTCGAGTATGCACGGATCCGCAACGATATGAAACCT
AGCATTCACACCTTCCTTCTTCATGGTTCAGGAGAGCAATACTATCTT
GTCCACACCCCAACGATCCATATGGCCAGCGGCCGTCGCCAAATCATC
CTTTCAGTAAATGTTGAAGGCCAAGTTCGGCAGGCGATACATGCCCAT
GAAAGAGTTGAAGCAGTGATTGTACATAACACTGTGCCCCTCCGCCTT
GACGAAATCGTTGACGGAGGATCATTTGACGGCATACTCACCATCGGA
AAGAGGAAAACTAGTTTCAAAGTGAAGATTTCAAACATTAAAGTAGTC
AAGAAGCGCTCTCTGATGACTGAGGACCTGGAATCTGCGTACCCATCG
TTGATGCCATTCTATTTCTACGGGACTCAAGGACACGCTCATCTCGAC
CATGTCATTACTGTCGTTCCTAACATCCATCTGAGTGCTGGCGAAATA
CAGTACAAATTCGACGACGAGGTGTCAAGCGAGGACCTCGCCAAGGGC
CTCATTGTTGTTGCTGAGAACGTACACGAGGCATCCATGCAGCCCTTC
CCGCTCATGAAAGATTTCAAGATCACCAACCAATTCTTCTTCAGCTCC
GGGCAAATACTCCGCGTCAAAGTGTACAGAGATCCATACCCGGCATCG
ACAATGGATCCCATCCCTCTCCACGACATCAAGAACCAGCCCGTCGTG
ACACAAGGCACCATCACGCTCGTCGGAAATATTTACGTCGATTCTGAT
GCGCTCAACGTCGCTTCCGAGCCTACTGCCGACGAAGACGCGGCGCAT
GTTCCTCACGCTCGCAACATGTACGGCGAGATGACCGCTGGAACGATC
AAAGGCTGGCAAAACGCTGTTCGTCATTTCCACAACAAATTGGAGACT
GTTGCTCCGACGAAGTAG

SEQ.ID NO: 10
MPSSHPHITHRYRVPSSDDHERISALFLGPKAENAAFLQQWLTTVVAQ
QKAARDAYFPDDNAFITTDMQTSPAFAQTTKVIASNLTELLTALGERS
IPFFSPRYSGHMSVDQSLPAILGFLSTTFYNPNNVAFEASPFTTLIEE
EVGLQLSEMLGYNRLNNTEKPLAWGHIASGGTVANLEAMWAARNLKFY
PLSLRDASAEGAEMEFIRDTFSVKTCVGDKKLLKDCSPWELLNLHVST
ILDMPDRLHDEYNISPQFLEKVMRKYIIQSTNKDTLMQRWGLTQQPVV
LSPSTNHYSWPKAAAVLGIGSDNLRNVPVDIQAHMDINELDRMLKICL
DEETPVYQVVAVIGTTEEGGVDRITEILKLRQKYEALGLSFAIHADAA
WGGYFATMLPKDTLGRNRTRLPKEDTTSGFVPHVGLREESALQLSHIK
YADSITIDPHKAGYVPYPAGALCYRDGRMRYLLTWSAPYLAQGNEGQS
IGIYGIEGSKPGAAASAVFMAHETIGLTPSGYGNLLGQAMFTCRRYAA
HWSAMSTDTTSFTVTPFNPIPADIDPNADPAKVEEQKQFIRDRILFKS
NEEIYNDSEAMELLHQLGSDLNINVFACNFRDRDNNLNTDVEEANWLN

```
-continued
NRIFQRFSVTSAEENPLETPFFLSSTTLKQSEYGVCATEVKRRMGLVG
DQDVIVLRNVVMSPFTTTNDFVGTLANTFQKIVEEEVEYARIRNDMKP
SIHTFLLHGSGEQYYLVHTPTIHMASGRRQIILSVNVEGQVRQAIHAH
ERVEAVIVHNTVPLRLDEIVDGGSFDGILTIGKRKTSFKVKISNIKVV
KKRSLMTEDLESAYPSLMPFYFYGTQGHAHLDHVITVVPNIHLSAGEI
QYKFDDEVSSEDLAKGLIVVAENVHEASMQPFPLMKDFKITNQFFFSS
GQILRVKVYRDPYPASTMDPIPLHDIKNQPVVTQGTITLVGNIYVDSD
ALNVASEPTADEDAAHVPHARNMYGEMTAGTIKGWQNAVRHFHNKLET
VAPTK
```

SEQ.ID NO: 11
```
ATGGAGGCTATCAAAAAGGTTTTTGAGAACAAAAAGGCGGAGGGCATT
CCTGTGTTGGTGACCTTTGTTACTGCAGGATATCCTCGTCCCGAAGAT
ACTGTTCCCATCTTGCTGGCCATGGAGGCCGGTGGTGCTGATATCATC
GAGCTTGGTATGCCATTTTCAGACCCAATTGCAGATGGTCCTGTCATC
CAGGAAACGAACACAATCGCCGTTGCAAACCAGGTAGATTATACCACT
GTTCTCGGACAACTTCGGGAAGCCCGCAAACAAGGGCTCAAGGCACCC
GTTCTTCTGATGGGATATTATAACCCCATATTGGCTTACGGAGAAGAC
AGATCTATTCAAGATGCGGCTGAAGCTGGAGCCAATGGGTTTATTATG
GTCGACCTTCCACCCGAGGAGGCTGTCGCTTTTCGAGAGAAATGTATC
AAATCCAACCTCTCATATGTTCCTCTAATTGCACCCTCAACGACTCTG
TCGCGTATAAAGTTCCTCTCAACAATTGCAGACACGTTCATCTATGTC
GTGTCTAAAATGGGAACCACCGGATCCTCAGAGAAGGTTGCCATGAAT
AACGCCCTTCCCACCATCATCGATCGTATTCGCGAGTACGCTGAAGTT
CCTTTAGCAGTCGGATTTGGAGTCGCCACTCGGGCTCACTTCAACTAC
GTCGCCGATTCCGGTGCTGATGGTGTCGTTATTGGCACCAAACTCGTT
AACGTTATTAAAGAGTCACCGCAAGGGGAAGCACCCAAAAATGTTGAG
GCATACTGCCGTGAGATGAGCCAAAAGGGAGAAACAAATCGCGTCAAA
TCTCCACCAACTGCCCGTGCTGCCAGCTCCGAATCAATTCCTGTTGTT
GTTCCTTCTGTTCTCCCCGCACGTTTCGGAGAATTCGGAGGACAATAC
GTTCCCGAAGCTCTTGTCGATTGTCTGGTTGAACTAGAAGAAGCTCAC
AAATCTGCCATGGCTGATCCTGAATTCCAGAAGGAACTACAATCGCAT
GCCGGATATGCAAATCGTCCTTCACAAATATACCTCGCCGAAAATCTC
ACCAAGGATGCTGGGGGTGCAAATATTTGGTTGAAACGTGAAGATTTG
AACCACACAGGTTCCCACAAAATCAATAACGCTTTGGGACAAATTCTG
CTTGCCCGGAGAATCGGAAAGACCAGAATTATCGCAGAAACAGGTGCC
GGCCAGCATGGTGTTGCAACAGCGACTGTTTGCGCTAAGTTTGGAATG
GAATGTGTTATCTACATGGGCGCAGAAGATGTGCGACGGCAAGCTCTA
AATGTATTCAGGATTGAGATGCTAGGAGCAAAAGTTGTTCCTGTTACT
TCAGGATCATGCACATTGAAGGACGCTGTAAACGAGGCCTTCCGTGAC
TGGGTGACAAACCTTTCTACGACGCATTATTTGGTTGGCTCTGTAATT
GGACCTCATCCCTTCCCCACCATTGTCCGAGATTTCCAAAAGGTCATT
```

```
-continued
GGTCAAGAGATCAAGGCTCAGATGTTGGCCGCCCGCGGCAAACTTCCT
GATGTCGTCGTCGCTTGTGTTGGTGGAGGAAGCAATGCTATCGGTACG
TTCTATGATTTTATTGGCGACAAGAGTGTACGTCTAGTTGGGGTGGAA
GCAGGAGGAGAAGGTATTGACGGAGACCGACATAGCGCCACACTTTCG
ATGGGGCAACCGGGAGTACTTCACGGTGTTAGAACATATATTCTACAA
GACAAGGCCGGTCAAATCATCGAGACGCACTCAATCAGCGCTGGATTG
GATTATCCCGGCGTTGGACCAGAACATGCTTGGCTAAAGGACTCTAAA
AGAGCAGAATATGTTGTCGCCACAGACGAAGAAGCACTTCGCGGTTTC
CGTATGCTAACACAAAGGGAGGGAATTATTCCTGCCCTTGAATCTTCC
CATGCGATCTGGGAGGCTGTCAGGATTGCCCGCACCATGTCGAAGGAC
CAGGATCTTGTTGTGTGTTTGTCTGGCCGAGGTGATAAAGACGTTGAG
CAAATTTCTCAACTTCTTCCCAAGTGGGCGGATATTCTAGACTGGCAT
GTTTCTTCCCATGCCGTTGGACACACAACAAAATTCTAA
```

SEQ.ID NO: 12
```
MEAIKKVFENKKAEGIPVLVTFVTAGYPRPEDTVPILLAMEAGGADII
ELGMPFSDPIADGPVIQETNTIAVANQVDYTTVLGQLREARKQGLKAP
VLLMGYYNPILAYGEDRSIQDAAEAGANGFIMVDLPPEEAVAFREKCI
KSNLSYVPLIAPSTTLSRIKFLSTIADTFIYVVSKMGTTGSSEKVAMN
NALPTIIDRIREYAEVPLAVGFGVATRAHFNYVADSGADGVVIGTKLV
NVIKESPQGEAPKNVEAYCREMSQKGETNRVKSPPTARAASSESIPVV
VPSVLPARFGEFGGQYVPEALVDCLVELEEAHKSAMADPEFQKELQSH
AGYANRPSQIYLAENLTKDAGGANIWLKREDLNHTGSHKINNALGQIL
LARRIGKTRIIAETGAGQHGVATATVCAKFGMECVIYMGAEDVRRQAL
NVFRIEMLGAKVVPVTSGSCTLKDAVNEAFRDWVTNLSTTHYLVGSVI
GPHPFPTIVRDFQKVIGQEIKAQMLAARGKLPDVVVACVGGGSNAIGT
FYDFIGDKSVRLVGVEAGGEGIDGDRHSATLSMGQPGVLHGVRTYILQ
DKAGQIIETHSISAGLDYPGVGPEHAWLKDSKRAEYVVATDEEALRGF
RMLTQREGIIPALESSHAIWEAVRIARTMSKDQDLVVCLSGRGDKDVE
QISQLLPKWADILDWHVSSHAVGHTTKF
```

SEQ.ID NO: 13
```
ATGGAAAGGCGGAAGCGTGAGCGTCTTGGCTCACTCGGCCGACCGACC
AAAAAGGAGCTCCGCATGATCCGATCTGTGGTGATCGTGGGTGGTGGC
ACGGCGGGCTGGATGACCGCCTCCTACCTCAAGGCCGCCTTCGACGAC
CGCATCGACGTAACGCTCGTGGAGTCAGGGAACGTCAGGCGGATCGGG
GTCGGCGAAGCGACCTTCAGCACGGTCCGCCACTTCTTCGACTACCTG
GGCCTCGACGAGCGCGAGTGGCTGCCCCGCTGCGCCGGCGGCTACAAG
CTCGGCATCCGCTTCGAGAACTGGAGCGAGCGGGCGAGTACTTCTAC
CACCCGTTCGAGCGCCTGCGCGTCGTCGACGGCTTCAACATGGCCGAG
TGGTGGCTCGCGGTCGGCGACCGCAGGACGTCCTCAGCGAGGCCTGC
TATCTCACGCACCGGCTGTGCGAGGCCAAGCGGGCGCCCCGCATGCTC
GACGGCTCGCTCTTCGCCTCCCAGGTGGACGAGTCGCTCGGCCGCTCG
ACCCTGGCCGAGCAGCGCGCCCAGTTCCCGTACGCCTACCACTTCGAC
```

```
GCCGACGAGGTCGCCCGCTACCTGTCGGAGTACGCCATCGCCCGCGGC

GTCCGCCACGTGGTCGACGACGTGCAGCACGTCGGCCAGGACGAGCGC

GGCTGGATCAGCGGCGTCCACACCAAGCAGCACGGCGAGATCAGCGGC

GACCTGTTCGTCGACTGCACCGGCTTCCGCGGCCTGCTCATCAACCAG

ACGCTGGGCGGCAGGTTCCAGTCCTTCTCCGACGTGCTGCCCAACAAC

CGGGCGGTCGCGCTGCGCGTCCCGCGGGAGAACGACGAGGACATGCGG

CCGTACACGACGGCGACCGCGATGAGCGCCGGCTGGATGTGGACGATC

CCGCTGTTCAAGCGCGACGGCAACGGCTACGTCTACTCCGACGAGTTC

ATCTCGCCGGAGGAGGCCGAGCGCGAGCTGCGGTCCACCGTCGCCCCC

GGCCGCGACGACCTGGAGGCCAACCACATCCAGATGCGGATCGGCAGG

AACGAGCGCACCTGGATCAACAACTGCGTCGCCGTCGGCCTGTCCGCC

GCCTTCGTCGAGCCGCTGGAGTCGACCGGCATCTTCTTCATCCAGCAC

GCCATCGAGCAGCTCGTGAAGCACTTCCCCGGCGAGCGCTGGGACCCG

GTGCTGATCAGCGCGTACAACGAGCGCATGGCGCACATGGTCGACGGG

GTCAAGGAGTTCCTCGTCCTCCACTACAAGGGCGCCCAGCGCGAGGAC

ACCCCCTACTGGAAGGCCGCCAAGACCAGGGCCATGCCCGACGGCCTC

GCCCGCAAGCTGGAGCTGTCCGCCTCCCACCTGCTGGACGAGCAGACG

ATCTACCCCTACTACCACGGCTTCGAGACCTATTCGTGGATCACCATG

AACCTCGGTCTCGGCATCGTGCCCGAGCGGCCGCGTCCCGCGCTCCTG

CACATGGACCCGGCGCCCGCGCTGGCCGAGTTCGAACGGCTCAGGCGC

GAGGGCGACGAGCTGATCGCCGCCCTGCCCAGCTGCTACGAGTACCTC

GCCAGCATCCAATGA
                                          SEQ.ID NO: 14
MERRKRERLGSLGRPTKKELRMIRSVVIVGGGTAGWMTASYLKAAFDD

RIDVTLVESGNVRRIGVGEATFSTVRHFFDYLGLDEREWLPRCAGGYK

LGIRFENWSEPGEYFYHPFERLRVVDGFNMAEWWLAVGDRRTSFSEAC

YLTHRLCEAKRAPRMLDGSLFASQVDESLGRSTLAEQRAQFPYAYHFD

ADEVARYLSEYAIARGVRHVVDDVQHVGQDERGWISGVHTKQHGEISG

DLFVDCTGFRGLLINQTLGGRFQSFSDVLPNNRAVALRVPRENDEDMR

PYTTATAMSAGWMWTIPLFKRDGNGYVYSDEFISPEEAERELRSTVAP

GRDDLEANHIQMRIGRNERTWINNCVAVGLSAAFVEPLESTGIFFIQH

AIEQLVKHFPGERWDPVLISAYNERMAHMVDGVKEFLVLHYKGAQRED

TPYWKAAKTRAMPDGLARKLELSASHLLDEQTTYPYYHGFETYSWITM

NLGLGIVPERPRPALLHMDPAPALAEFERLRREGDELIAALPSCYEYL

ASIQ
                                          SEQ.ID NO: 15
ATGACCGCCGCCTACCTGAAGACCGCGTTCGGCGACCGGCTTTCGATC

ACCGTCGTGGAATCGAGCAGAATCGGGACCATCGGCGTCGGTGAGGCG

ACCTTCAGCGACATCCAGCACTTCTTCCAGTTCCTCAACCTCCGGGAA

CAGGACTGGATGCCGGCCTGCAACGCCACCTACAAGCTGGGCATCCGC

TTCGAGAACTGGCGGCATGTCGGCCATCATTTCTACCAGCCGTTCGAG

CAGATCCGCCCGGTCTACGGCTTTCCGCTGACCGACTGGTGGCTGCAC

GACGCGCCGACCGACCGCTTCGACACCGACTGCTTCGTCATGCCCAAC

CTGTGCGAGGCCGGGCGCAGCCCGCGCCACCTCGACGGCACGCTGGCC

GACGAGGACTTCGTGGAGGAGGGCGACGAGCTCGCCAACCGCACCATG

TCCGAGCACCAGGGCAAGTCGCAGTTCCCGTACGCCTACCACTTCGAG

GCGGCGCTGCTGGCCAAGTTCCTCACCGGGTACGCGGTGGACCGCGGC

GTCGAGCACGTCGTCGACGACGTCCTGGACGTGCGGCTGGACCAGCGC

GGGTGGATCGAGCACGTGGTCACCGCCGAGCACGGCGAGATCCACGGC

GACCTGTTCGTCGACTGCACCGGTTTCCGGGGACTGCTGCTGAACAAG

GCGCTCGGTGTGCCGTTCGTGTCCTATCAGGACACTCTGCCCAACGAC

AGCGCGGTCGCCCTCCAGGTCCCGCTGGACATGCAGCGGCGCGGCATC

GTGCCGAACACCACGGCCACCGCGCGGGAGGCCGGCTGGATCTGGACC

ATCCCGCTGTTCGGTCGGGTCGGCACCGGGTACGTCTACGCCAAGGAC

TACCTCTCGCCCGAGGAGGCCGAGCGCACGCTGCGCGAGTTCGTCGGC

CCGGCGGCCGCGGACGTGGAGGCCAACCACATCCGCATGCGGATCGGC

CGCAGCCAGGAGTCCTGGCGGAACAACTGCGTGGCCATCGGCCTGTCC

AGCGGCTTCGTCGAGCCGCTGGAGTCGACCGGGATCTTCTTCATCCAC

CACGCCATCGAGCAGCTGGTGAAGCACTTCCCGGCGGCCGACTGGAAC

CCGAAGTCCCGGGACATGTACAACTCCGCGGTCGCGCACGTGATGGAC

GGCATCCGCGAGTTCCTGGTGATCCACTACCGGGGCGCGGCGCGGGCC

GACAACCAGTACTGGCGCGACACCAAGACCCGCCCGCTGCCGGACGGC

CTGGCCGAGCGCATCGAGTGCTGGCAGACGCAGCTGCCGGACACCGAG

ACGATCTACCCGTACTACCACGGGCTGCCGCCCTACTCCTACATGTGC

ATCCTGATGGGCGGCGGGGCCATCCGGACGCCGGCCTCGGCCGCGTTG

GCCCTGACCGACCAGGGGCCGCGCAGAAGGAGTTCGCCGCCGTCCGG

GACCGGGCCGCGCAGCTGCGCGACACGCTGCCCAGCCACTACGAGTAC

CTCGCGCGGATGCGTGGTCTGGATGTCTGA
                                          SEQ.ID NO: 16
MTAAYLKTAFGDRLSITVVESSRIGTIGVGEATFSDIQHFFQFLNLRE

QDWMPACNATYKLGIRFENWRHVGHHFYQPFEQIRPVYGFPLTDWWLH

DAPTDRFDTDCFVMPNLCEAGRSPRHLDGTLADEDFVEEGDELANRTM

SEHQGKSQFPYAYHFEAALLAKFLTGYAVDRGVEHVVDDVLDVRLDQR

GWIEHVVTAEHGEIHGDLFVDCTGFRGLLLNKALGVPFVSYQDTLPND

SAVALQVPLDMQRRGIVPNTTATAREAGWIWTIPLFGRVGTGYVYAKD

YLSPEEAERTLREFVGPAAADVEANHIRMRIGRSQESWRNNCVAIGLS

SGFVEPLESTGIFFIHHAIEQLVKHFPAADWNPKSRDMYNSAVAHVMD

GIREFLVIHYRGAARADNQYWRDTKTRPLQKEFAAVRDRAAQLRDTLP

SHYEYLARMRGLDV
                                          SEQ.ID NO: 17
ATGAACACGAGAAATCCGGACAAGGTCGTCATCGTCGGCGGCGGCACG

GCGGGATGGATGACCGCCTCGTACCTGAAGAAGGCGTTCGGCGAGCGC

GTGTCCGTGACCCTCGTCGAATCGGGCACCATCGGCACCGTCGGCGTC
```

-continued

GGCGAGGCGACCTTCAGCGACATCCGGCACTTCTTCGAATTCCTCGAC
CTGCGGGAGGAGGAATGGATGCCGGCCTGCAACGCCACGTACAAGCTG
GCCGTCCGCTTCCAGGACTGGCAGCGCCCCGGCCACCACTTCTACCAC
CCGTTCGAGCAGATGCGCTCCGTAGACGGGTTCCCCCTGACCGACTGG
TGGCTGCAGAACGGGCCGACCGACCGGTTCGACAGGGACTGCTTCGTG
ATGGCGTCGCTGTGCGACGCGGGGCGCAGCCCGCGCTATCTCAACGGT
TCCCTGCTGCAGCAGGAGTTCGACGAGCGCGCGGAGGAGCCGGCGGGG
CTCACCATGTCCGAGCACCAGGGCAAGACGCAGTTCCCCTACGCCTAC
CACTTCGAGGCGGCCCTGCTCGCCGAATTCCTTTCTGGGTACTCCAAG
GACCGCGGCGTGAAGCACGTGGTCGACGAGGTGCTGGAGGTGAAGCTC
GACGACCGCGGATGGATCAGCCACGTTGTCACCAAGGAGCACGGCGAC
ATCGGCGGCGACCTGTTCGTCGACTGCACCGGTTTCCGCGGCGTACTG
CTGAACCAGGCGCTGGGTGTGCCCTTCGTCTCCTACCAGGACACCCTG
CCCAATGACAGCGCGGTCGCCCTCCAGGTGCCGCTCGACATGGAGGCG
CGGGGCATCCCGCCGTACACCCGGGCCACCGCCAAGGAGGCCGGGTGG
ATCTGGACGATCCCGCTGATCGGCCGGATCGGCACCGGGTACGTGTAC
GCCAAGGACTACTGCTCGCCGGAGGAGGCCGAGCGCACCCTGCGCGAG
TTCGTCGGTCCGGAGGCCGCCGACGTCGAGGCCAACCACATCCGCATG
CGGATCGGGCGCAGCGAGCAGTCCTGGAAGAACAACTGCGTCGCGATC
GGGCTCTCCAGTGGCTTCGTCGAACCCCTCGAGTCGACCGGCATCTTC
TTCATCCACCACGCCATCGAGCAGTTGGTGAAGCACTTCCCGGCGGGC
GACTGGCACCCGCAGCTGCGCGCCGGCTACAACTCGGCCGTCGCCAAC
GTCATGGACGGGGTCCGGGAGTTCCTCGTCCTGCACTACCTGGGCGCC
GCGCGCAACGACACCCGGTACTGGAAGGACACCAAGACCCGGGCGGTT
CCGGATGCCCTGGCGGAGCGCATCGAGCGCTGGAAGGTGCAGCTGCCC
GACTCCGAGAACGTCTTCCCCTACTACCACGGCCTGCCGCCGTACTCG
TACATGGCCATCCTGCTCGGGACCGGCGCGATCGGGCTGCGACCGTCG
CCGGCGCTCGCACTGGCCGACCCGGCGGCGGCGGAGAAGGAGTTCACC
GCGATCCGGGACAGGGCGCGGTTCCTGGTCGACACCCTGCCGAGCCAG
TACGAGTACTTCGCCGCGATGGGGCAGCGTGTCTGA

SEQ ID NO: 18

MNTRNPDKVVIVGGGTAGWMTASYLKKAFGERVSVTLVESGTIGTVGV
GEATFSDIRHFFEFLDLREEEWMPACNATYKLAVRFQDWQRPGHHFYH
PFEQMRSVDGFPLTDWWLQNGPTDRFDRDCFVMASLCDAGRSPRYLNG
SLLQQEFDERAEEPAGLTMSEHQGKTQFPYAYHFEAALLAEFLSGYSK
DRGVKHVVDEVLEVKLDDRGWISHVVTKEHGDIGGDLFVDCTGFRGVL
LNQALGVPFVSYQDTLPNDSAVALQVPLDMEARGIPPYTRATAKEAGW
IWTIPLIGRIGTGYVYAKDYCSPEEAERTLREFVGPEAADVEANHIRM
RIGRSEQSWKNNCVAIGLSSGFVEPLESTGIFFIHHAIEQLVKHFPAG
DWHPQLRAGYNSAVANVMDGVREFLVLHYLGAARNDTRYWKDTKTRAV

PDALAERIERWKVQLPDSENVFPYYHGLPPYSYMAILLGTGAIGLRPS
PALALADPAAAEKEFTAIRDRARFLVDTLPSQYEYFAAMGQRV

SEQ ID NO: 19

ATGGACAATCG
AATCAAGACAGTCGTGATCCTGGGCGGCGGCACCGCCGGCTGGATGAC
TGCGGCGTATCTCGGCAAGGCGCTGCAGAACACGGTGAAGATCGTGGT
CCTGGAGGCGCCCACCATCCCGCGGATCGGTGTGGGCGAAGCCACCGT
CCCCAACCTGCAGCGCGCGTTCTTCGACTACCTCGGCATCCCCGAGGA
GGAGTGGATGCGCGAGTGCAACGCCAGTTACAAGATGGCGGTGAAGTT
CATCAACTGGCGCACACCGGGGAGGGCAGCCCGGATCCCCGGACGCT
CGACGACGGTCACACCGACACCTTCCACCACCCCTTCGGACTGCTGCC
GTCCGCCGACCAGATACCGCTCTCCCACTACTGGGCGGCCAAGCGGCT
CCAGGGCGAGACCGACGAGAACTTCGACGAGGCGTGTTTCGCCGACAC
CGCGATCATGAACGCCAAGAAGGCGCCCCGCTTCCTCGACATGCGGCG
GGCGACCAACTACGCCTGGCACTTCGACGCCAGCAAGGTCGCCGCGTT
CCTGCGCAACTTCGCCGTCACCAAGCAGGCGGTCGAGCACGTCGAGGA
CGAGATGACCGAGGTCCTCACCGACGAACGGGGCTTCATCACCGCCCT
GCGCACCAAGTCGGGACGGATCCTGCAGGGTGACCTCTTCGTCGACTG
CTCCGGCTTCCGCGGGCTGCTGATCAACAAGGCCATGGAGGAGCCGTT
CATCGACATGAGCGACCACCTCCTGTGCAACAGCGCGGTCGCCACGGC
CGTACCGCACGACGACGAGAAGAACGGTGTCGAGCCGTACACCTCCTC
GATCGCCATGGAGGCCGGCTGGACCTGGAAGATTCCCATGCTGGGCCG
GTTCGGCAGCGGTCACGTCTACTCCGACCACTTCGCCACCCAGGACGA
GGCCACCCTGGCCTTCTCGAAGCTGTGGGGCCTCGACCCGGACAACAC
CGAGTTCAACCACGTCCGCTTCCGGGTCGGCCGCAACCGCAGGGCCTG
GGTGCGCAACTGCGTCAGCGTCGGCCTCGCGTCGTGCTTCGTGGAGCC
GCTGGAGTCCAGCGGCATCTACTTCATCTACGCGGCCATCCACATGCT
GGCCAAGCACTTCCCCGACAAGACCTTCGACAAGGTGCTCGTCGACCG
GTTCAACCGGGAGATCGAGGAGATGTTCGACGACACCCGGGACTTCCT
CCAGGCGCACTACTACTTCTCGCCGCGCGTCGACACGCCGTTCTGGCG
GGCGAACAAGGAACTGAAGCTGGCCGACTCCATCAAGGACAAGGTCGA
GACGTACCGGGCCGGGCTGCCGGTCAACCTGCCGGTCACCGACGAGGG
GACCTACTACGGCAACTTCGAGGCCGAGTTCCGGAACTTCTGGACCAA
CGGCAGCTACTACTGCATCTTCGCCGCCTCGGCCTGATGCCGCGCAA
CCCGCTGCCCGCGCTCGCCTACAAGCCGCAGTCGATCGCGGAGGCCGA
GCTGCTGTTCGCCGACGTCAAGCGCAAGGGGGACACCCTGGTCGAGTC
GCTGCCGTCGACCTATGACCTGCTGCGTCAGTTGCACGGTGCGTCGTG
A

SEQ ID NO: 20

MDNRIKTVVILGGGTAGWMTAAYLGKALQNTVKIVVLEAPTIPRIGVG
EATVPNLQRAFFDYLGIPEEEWMRECNASYKMAVKFINWRTPGEGSPD

```
PRTLDDGHTDTFHHPFGLLPSADQIPLSHYWAAKRLQGETDENFDEAC
FADTAIMNAKKAPRFLDMRRATNYAWHFDASKVAAFLRNFAVTKQAVE
HVEDEMTEVLTDERGFITALRTKSGRILQGDLFVDCSGFRGLLINKAM
EEPFIDMSDHLLCNSAVATAVPHDDEKNGVEPYTSSIAMEAGWTWKIP
MLGRFGSGHVYSDHFATQDEATLAFSKLWGLDPDNTEFNHVRFRVGRN
RRAWVRNCVSVGLASCFVEPLESSGIYFIYAAIHMLAKHFPDKTFDKV
LVDRFNREIEEMFDDTRDFLQAHYYFSPRVDTPFWRANKELKLADSIK
DKVETYRAGLPVNLPVTDEGTYYGNFEAEFRNFWTNGSYYCIFAGLGL
MPRNPLPALAYKPQSIAEAELLFADVKRKGDTLVESLPSTYDLLRQLH
GAS
                                        SEQ.ID NO: 21
ATGGACAACCGCATCAACCGGATCGTCATCCTCGGCGGCGGGACCGCG
GGATGGATGACCGCCTCCTACCTGGCGAAGGCGCTCGGTGACACCGTC
ACGATCACCCTGCTGGAAGCACCGGCGATCGGCCGGATCGGGGTCGGC
GAGGCCACCGTGCCCAACCTGCAGCGCGTGTTCTTCGACTTCCTCGGC
CTCCGCGAGGAGGAGTGGATGCCGGAGTGCAACGCCGCGTTCAAGACG
GCCGTGAAGTTCATCAACTGGCGTACCCCCGGGCCCGGCGAGGCCAAG
GCCCGCACGATCGACGGCCGGCCGGACCACTTCTACCACCCGTTCGGG
CTGCTGCCCGAGCACGGCCAGGTGCCGCTGTCGCACTACTGGGCCTAC
AACCGGGCGGCCGGCACCACCGACGAGCCGTTCGACTACGCCTGTTTC
GCCGAGACCGCCGCCATGGACGCGGTCCGCGCGCCCAAGTGGCTCGAC
GGGCGGCCCGCCACCCGGTATGCCTGGCACTTCGACGCCCACCTGGTC
GCCGAGTTCCTGCGCCGGCACGCCACCGAGCGGCTCAACGTGGAGCAC
GTGCAGGGTGAGATGCAGCAGGTGCTGCGCGACGAGCGGGGCTTCATC
ACCGCCCTGCGCACGGTCGAGGGCCGGGACCTCGAGGGTGACCTGTTC
ATCGACTGCTCCGGCTTCCGCGGCCTGCTGATCAACAAGGCCATGGAG
GAGCCCTTCATCGACATGAACGACCAGCTGCTGTGCAACCGCGCGGTG
GCCACGGCGATCAAGCACGACGACGACGCGCACGGGGTCGAGCCGTAC
ACCTCGGCGATCGCCATGCGGTCCGGCTGGAGCTGGAAGATCCCGATG
CTGGGCCGCTTCGGGACCGGCTACGTCTACTCCAGCCGGTTCGCCGAG
AAGGACGAGGCCACCCTCGACTTCTGCCGGATGTGGGGCCTGGACCCG
GAGAACACCCCGCTCAACCAGGTGGCCTTCCGGGTCGGCCGCAACCGC
CGGGCCTGGGTGAAGAACTGCGTGAGCATCGGCCTGGCGTCGTGCTTC
CTGGAGCCACTGGAGTCCACCGGCATCTACTTCATCACCGCGGCCATC
TACCAGCTGACTCAGCACTTCCCGGACCGCACCTTCGCGCTCGCGTTG
AGCGACGCGTTCAACCACGAGATCGAAGCCATGTTCGACGACACCCGG
GACTTCATCCAGGCGCACTTCTACGTGTCGCCGCGCACCGACACGCCC
TTCTGGAAGGCGAACAAGGACCTGCACCTGCCCGAGCAGATGCGCGAG
AAGATCGCGATGTACAAGGCCGGCCTGCCGATCAACGCGCCGGTCACC
GACGAGTCGACCTACTACGGCAGGTTCGAGGCCGAGTTCCGCAACTTC
TGGACCAACGGCAGCTACTACTGCATCTTCGCGGGCCTCGGGCTGCGC
```

```
CCGGACAACCCGCTGCCGATGCTGCGACACCGTCCGGAGCAGGTCCGC
GAGGCGCAGGCGCTGTTCGCCGGGGTGAAGGACAAGCAGCGGGAGTTG
GTGGAGACGCTGCCGAGCAACCTGGAGTTCCTGCGCAGCCTGCACGGC
AAGTAG
                                        SEQ.ID NO: 22
MDNRINRIVILGGGTAGWMTASYLAKALGDTVTITLLEAPAIGRIGVG
EATVPNLQRVFFDFLGLREEEWMPECNAAFKTAVKFINWRTPGPGEAK
ARTIDGRPDHFYHPFGLLPEHGQVPLSHYWAYNRAAGTTDEPFDYACF
AETAAMDAVRAPKWLDGRPATRYAWHFDAHLVAEFLRRHATERLNVEH
VQGEMQQVLRDERGFITALRTVEGRDLEGDLFIDCSGFRGLLINKAME
EPFIDMNDQLLCNRAVATAIKHDDDAHGVEPYTSAIAMRSGWSWKIPM
LGRFGTGYVYSSRFAEKDEATLDFCRMWGLDPENTPLNQVAFRVGRNR
RAWVKNCVSIGLASCFLEPLESTGIYFITAAIYQLTQHFPDRTFALAL
SDAFNHEIEAMFDDTRDFIQAHFYVSPRTDTPFWKANKDLHLPEQMRE
KIAMYKAGLPINAPVTDESTYYGRFEAEFRNFWINGSYYCIFAGLGLR
PDNPLPMLRHRPEQVREAQALFAGVKDKQRELVETLPSNLEFLRSLHG
K
                                        SEQ.ID NO: 23
ATGGATGACAATCGAATTCGGAGCATCCTTGTCCTTGGCGGCGGCACG
GCCGGCTGGATGTCCGCCTGCTACCTGAGCAAGGCGCTCGGGCCCGGC
GTCGAGGTCACCGTGCTCGAGGCGCCCTCCATCTCGCGCATCCGGGTC
GGCGAGGCCACCATTCCCAACCTGCACAAGGTCTTCTTCGACTTCCTG
GGCATCGCCGAGGACGAGTGGATGCGGGAGTGCAACGCCAGCTACAAG
GCCGCGGTCCGGTTCGTCAACTGGCGGACGCCGGGCGACGGCCAGGCC
ACGCCGCGGCGGCGTCCGGACGGCCGCCCCGACCACTTCGACCACCTG
TTCGGCCAGCTGCCCGAGCACGAGAACCTGCCGCTGTCGCAGTACTGG
GCGCACCGGCGCCTCAACGGCCTGACCGACGAACCCTTCGACCGCTCC
TGCTACGTGCAGCCCGAGCTGCTGGACCGCAAGCTCTCGCCGAGGTTG
ATGGACGGCACGAAACTGGCCAGCTACGCCTGGCACTTCGACGCCGAC
CTGGTGGCCGACTTCCTCTGCCGGTTCGCCGTGCAGAAGCTGAACGTG
ACCCACGTCCAGGACGTGTTCACGCATGCCGACCTCGACCAGCGCGGC
CACATCACGGCCGTCAACACCGAGTCCGGCCGCACGCTGGCCGCCGAC
CTGTTCATCGACTGCAGCGGCTTCCGCAGCGTGCTCATGGGCAAGGTC
ATGCAGGAGCCGTTCCTGGACATGAGCAAGCACCTGCTCAACGACCGC
GCGGTGGCGCTGATGCTCCCGCACGACGACGAGAAGGTGGGCATCGAG
CCGTACACCTCGTCGCTGGCCATGCGGTCGGGCTGGTCGTGGAAGATC
CCGCTGCTCGGCCGGTTCGGCTCCGGCTACGTCTACTCCAGCCAGTTC
ACCTCCCAGGACGAGGCGGCCGAGGAGCTCTGCCGCATGTGGGACGTC
GACCCGGCGGAGCAGACGTTCAACAACGTCCGGTTCCGGGTCGGCCGC
AGCCGCCGGGCCTGGGTGCGCAACTGCGTCGCCATCGGCGTGTCCGCC
ATGTTCGTGGAGCCGCTGGAGTCGACCGGCCTGTACTTCAGTTACGCC
TCGCTCTACCAGCTGGTGAAGCACTTCCCGGACAAGCGGTTCCGGCCG
```

ATCCTGGCCGACCGGTTCAACCGCGAGGTGGCGACCATGTACGACGAC

ACCCGCGACTTCCTCCAGGCGCACTTCAGCCTGTCGCCGCGTGACGAC

TCCGAGTTCTGGCGGGCCTGCAAGGAGCTGCCGTTCGCGGACGGGTTC

GCCGAGAAGGTCGAGATGTACAGGGCCGGGCTGCCGGTCGAACTGCCG

GTCACCATCGACGACGGGCACTACTACGGCAATTTCGAGGCCGAGTTC

CGCAACTTCTGGACCAACTCGAACTACTACTGCATCTTCGCCGGGCTC

GGTTTCCTGCCCGAGCATCCGCTGCCGGTGCTCGAATTCCGCCCGGAG

GCCGTCGATCGCGCGGAGCCGGTGTTCGCCGCGGTGCGCCGGCGCACG

GAGGAGCTGGTCGCCACCGCCCCGACCATGCAGGCCTACCTGCGGCGC

CTGCACCAGGGCACGTAG

SEQ.ID NO: 24
MDDNRIRSILVLGGGTAGWMSACYLSKALGPGVEVTVLEAPSISRIRV

GEATIPNLHKVFFDFLGIAEDEWMRECNASYKAAVRFVNWRTPGDGQA

TPRRRPDGRPDHFDHLFGQLPEHENLPLSQYWAHRRLNGLTDEPFDRS

CYVQPELLDRKLSPRLMDGTKLASYAWHFDADLVADFLCRFAVQKLNV

THVQDVFTHADLDQRGHITAVNTESGRTLAADLFIDCSGFRSVLMGKV

MQEPFLDMSKHLLNDRAVALMLPHDDEKVGIEPYTSSLAMRSGWSWKI

PLLGRFGSGYVYSSQFTSQDEAAEELCRMWDVDPAEQTFNNVRFRVGR

SRRAWVRNCVAIGVSAMFVEPLESTGLYFSYASLYQLVKHFPDKRFRP

ILADRFNREVATMYDDTRDFLQAHFSLSPRDDSEFWRACKELPFADGF

AEKVEMYRAGLPVELPVTIDDGHYYGNFEAEFRNFWTNSNYYCIFAGL

GFLPEHPLPVLEFRPEAVDRAEPVFAAVRRRTEELVATAPTMQAYLRR

LHQGT

SEQ.ID NO: 25
ATGAACAAGCCGATCAAGAATATCGTCATCGTGGGCGGCGGTACTGCG

GGCTGGATGGCCGCCTCGTACCTCGTCCGGGCCCTCCAACAGCAGGCG

AACATTACGCTCATCGAATCTGCGGCGATCCCTCGGATCGGCGTGGGC

GAAGCGACCATCCCAAGTTTGCAGAAGGTGTTCTTCGATTTCCTCGGG

ATACCGGAGCGGGAATGGATGCCCCAAGTGAACGGCGCGTTCAAGGCC

GCGATCAAGTTCGTGAATTGGAGAAAGTCTCCCGACCCCTCGCGCGAC

GATCACTTCTACCATTTGTTCGGCAACGTGCCGAACTGCGACGGCGTG

CCGCTTACCCACTACTGGCTGCGCAAGCGCGAACAGGGCTTCCAGCAG

CCGATGGAGTACGCGTGCTACCCGCAGCCCGGGGCACTCGACGGCAAG

CTGGCACCGTGCCTGTCCGACGGCACCCGCCAGATGTCCCACGCGTGG

CACTTCGACGCGCACCTGGTGGCCGACTTCTTGAAGCGCTGGGCCGTC

GAGCGCGGGGTGAACCGCGTGGTCGATGAGGTGGTGGACGTTCGCCTG

AACAACCGCGGCTACATCTCCAACCTGCTCACCAAGGAGGGGCGGACG

CTGGAGGCGGACCTGTTCATCGACTGCTCCGGCATGCGGGGGCTCCTG

ATCAATCAGGCGCTGAAGGAACCCTTCATCGACATGTCCGACTACCTG

CTGTGCGACAGCGCGGTCGCCAGCGCCGTGCCCAACGACGACGCGCGC

GATGGGGTCGAGCCGTACACCTCCTCGATCGCCATGAACTCGGGATGG

ACCTGGAAGATTCCGATGCTGGGCCGGTTCGGCAGCGGCTACGTCTTC

TCGAGCCATTTCACCTCGCGCGACCAGGCCACCGCCGACTTCCTCAAA

CTCTGGGGCCTCTCGGACAATCAGCCGCTCAACCAGATCAAGTTCCGG

GTCGGGCGCAACAAGCGGGCGTGGGTCAACAACTGCGTCTCGATCGGG

CTGTCGTCGTGCTTTCTGGAGCCCCTGGAATCGACGGGGATCTACTTC

ATCTACGCGGCGCTTTACCAGCTCGTGAAGCACTTCCCCGACACCTCG

TTCGACCCGCGGCTGAGCGACGCTTTCAACGCCGAGATCGTCCACATG

TTCGACGACTGCCGGGATTTCGTCCAAGCGCACTATTTCACCACGTCG

CGCGATGACACGCCGTTCTGGCTCGCGAACCGGCACGACCTGCGGCTC

TCGGACGCCATCAAAGAGAAGGTTCAGCGCTACAAGGCGGGGCTGCCG

CTGACCACCACGTCGTTCGACGATTCCACGTACTACGAGACCTTCGAC

TACGAATTCAAGAATTTCTGGTTGAACGGCAACTACTACTGCATCTTT

GCCGGCTTGGGCATGCTGCCCGACCGGTCGCTGCCGCTGTTGCAGCAC

CGACCGGAGTCGATCGAGAAGCCGAGGCGATGTTCGCCAGCATCCGG

CGCGAGGCCGAGCGTCTGCGCACCAGCCTGCCGACAAACTACGACTAC

CTGCGGTCGCTGCGTGACGGCGACGCGGGGCTGTCGCGCGGCCAGCGT

GGGCCGAAGCTCGCAGCGCAGGAAAGCCTGTAG

SEQ.ID NO: 26
MNKPIKNIVIVGGGTAGWMAASYLVRALQQQANITLIESAAIPRIGVG

EATIPSLQKVFFDFLGIPEREWMPQVNGAFKAAIKFVNWRKSPDPSRD

DHFYHLFGNVPNCDGVPLTHYWLRKREQGFQQPMEYACYPQPGALDGK

LAPCLSDGTRQMSHAWHFDAHLVADFLKRWAVERGVNRVVDEVVDVRL

NNRGYISNLLTKEGRTLEADLFIDCSGMRGLLINQALKEPFIDMSDYL

LCDSAVASAVPNDDARDGVEPYTSSIAMNSGWTWKIPMLGRFGSGYVF

SSHFTSRDQATADFLKLWGLSDNQPLNQIKFRVGRNKRAWVNNCVSIG

LSSCFLEPLESTGIYFIYAALYQLVKHFPDTSFDPRLSDAFNAEIVHM

FDDCRDFVQAHYFTTSRDDTPFWLANRHDLRLSDAIKEKVQRYKAGLP

LTTTSFDDSTYYETFDYEFKNFWLNGNYYCIFAGLGMLPDRSLPLLQH

RPESIEKAEAMFASIRREAERLRTSLPTNYDYLRSLRDGDAGLSRGQR

GPKLAAQESL

SEQ.ID NO: 27
ATGTCCGGCAAGATTGACAAGATCCTCATCGTCGGCGGCGGCACCGCC

GGATGGATGGCCGCGTCCTATCTCGGCAAGGCCCTGCAGGGCACCGCG

GACATCACACTGCTGCAGGCACCCGACATCCCGACGCTCGGGGTCGGC

GAGGCCACGATCCCCAATCTGCAGACGGCGTTCTTCGACTTCCTCGGA

ATCCCCGAGGACGAGTGGATGCGGGAGTGCAACGCGAGCTACAAGGTC

GCCATCAAGTTCATCAACTGGCGCACCGCGGGCGAGGGGACGTCCGAG

GCCCGCGAGCTCGACGGAGGGCCCGACCACTTCTACCACTCCTTCGGT

CTGCTCAAGTACCACGAGCAGATTCCGCTGTCGCACTACTGGTTCGAC

CGTTCGTACCGGGGGAAGACCGTCGAGCCGTTCGACTACGCCTGCTAC

AAGGAACCCGTCATCCTCGACGCCAACAGGTCACCGCGCAGGCTCGAC

GGTTCCAAGGTGACGAACTACGCGTGGCACTTCGACGCGCACCTCGTC

-continued
```
GCCGACTTCCTGCGCCGGTTCGCCACCGAGAAGCTCGGCGTGCGCCAC

GTCGAGGACCGCGTCGAGCACGTCCAGCGCGACGCCAACGGCAACATC

GAGTCGGTTCGCACGGCAACGGGGCGTGTCTTCGATGCCGACCTCTTC

GTCGACTGCTCGGGCTTCCGCGGGCTGCTGATCAACAAGGCGATGGAG

GAGCCCTTCCTCGACATGAGCGATCACCTGCTCAACGACAGCGCCGTC

GCCACCCAGGTGCCGCACGACGACGACGCGAACGGTGTGGAACCGTTC

ACCTCGGCGATCGCCATGAAGTCGGGCTGGACGTGGAAGATCCCGATG

CTCGGCAGGTTCGGCACCGGGTACGTCTACTCGAGCCGGTTCGCCACC

GAGGACGAGGCGGTGCGCGAGTTCTGCGAGATGTGGCACCTCGACCCG

GAGACCCAGCCCCTCAACAGGATCCGGTTCCGGGTCGGCCGCAACCGG

CGCGCGTGGGTCGGCAACTGCGTCAGCATCGGCACGTCGTCGTGCTTC

GTGGAACCACTGGAGTCGACGGGCATCTACTTCGTCTACGCCGCGCTG

TACCAGCTGGTGAAGCACTTCCCCGACAAGAGCCTCAACCCCGTGCTG

ACCGCCAGGTTCAACCGCGAGATCGAGACGATGTTCGACGACACGCGC

GACTTCATCCAGGCGCACTTCTACTTCTCGCCGCGCACGGACACCCCG

TTCTGGAGGGCCAACAAGGAGCTGCGCCTGGCGGACGGCATGCAGGAG

AAGATCGACATGTACCGCGCGGGCATGGCGATCAACGCGCCCGCGTCC

GACGACGCCCAGCTCTACTACGGCAACTTCGAGGAGGAGTTCCGCAAC

TTCTGGAACAACAGCAACTACTACTGCGTGCTGGCCGGCCTCGGTCTG

GTGCCCGACGCACCCTCACCACGCCTGGCGCACATGCCACAGGCGACG

GAGTCGGTGGACGAGGTCTTCGGCGCCGTCAAGGACCGGCAGCGGAAC

CTGCTCGAGACCCTGCCGAGCCTCCACGAGTTCCTGAGGCAACAGCAC

GGCCGCTGA
```

SEQ.ID NO: 28
```
MSGKIDKILIVGGGTAGWMAASYLGKALQGTADITLLQAPDIPTLGVG
EATIPNLQTAFFDFLGIPEDEWMRECNASYKVAIKFINWRTAGEGTSE
ARELDGGPDHFYHSFGLLKYHEQIPLSHYWFDRSYRGKTVEPFDYACY
KEPVILDANRSPRRLDGSKVTNYAWHFDAHLVAKAMEEPFLDMSDHLL
NDSAVATQVPHDDDANGVEPFTSAIAMKSGWTWKIPMLGRFGTGYVYS
SRFATEDEAVREFCEMWHLDPETQPLNRIRFRVGRNRRAWVGNCVSIG
TSSCFVEPLESTGIYFVYAALYQLVKHFPDKSLNPVLTARFNREIETM
FDDTRDFIQAHFYFSPRTDTPFWRANKELRLADGMQEKIDMYRAGMAI
NAPASDDAQLYYGNFEEEFRNFWNNSNYYCVLAGLGLVPDAPSPRLAH
MPQATESVDEVFGAVKDRQRNLLETLPSLHEFLRQQHGR
```

SEQ.ID NO: 29
```
MLNNVVIVGGGTAGWMTASYFKAAFGERINITLVESGNIGAVGVGEAT
FSDIRHFFDFLGLKEKDWMPACNATYKLAVRFENWREEGHYFYHPFEQ
MRSVNGFPLADWWLREKPTDRFDKDCFVMPSIIDAGLSPRHLDGSLID
QPFVEGAEEMQGLTMSEHQGKTQFPYAYQFEAALLAKYLTTYSVERGV
KHIVDDVQQVNLDERGWIRNVTTAEHGEIGGDLFIDCTGFRGLLLNKA
LEEPFISFQDTLPNDSAVALQVPMDMERRGILPCTTATAQDAGWIWTI
PLMGRVGTGYVYAKDYISPEEAERTLREFVGPAAADAEANHIKMRVGR
SENSWVKNCVAIGLSSGFVEPLESTGIFFIHHAIEQLAKNFPGEDWNP
VQRNLYNDSVAHVMDGVREFLVLHYVAAKRSDTQYWRDTKTRKIPDAL
AERIEKWKTQLPDTETVFPYYHGLPPYSYHCVLLGMGGIDVKPSPALA
LGDSAAAEREFAEIREKTRHLTSVLPKAYDYFSRMR
```

SEQ.ID NO: 30
```
MSGKIDKILIVGGGTAGWMAASYLGKALQGTADITLLQAPDIPTLGVG
EATIPNLQTAFFDFLGIPEDEWMRECNASYKVAIKFINWRTAGEGTSE
ARELDGGPDHFYHSFGLLKYHEQIPLSHYWFDRSYRGKTVEPFDYACY
KEPVILDANRSPRRLDGSKVTNYAWHFDAHLVAKAMEEPFLDMSDHLL
NDSAVATQVPHDDDANGVEPFTSAIMKSGWTWKIPMLGRFGTGYVYS
SRFATEDEAVREFCEMWHLDPETQPLNRIRFRVGRNRRAWVGNCVSIG
TSSCFVEPLESTGIYFVYAALYQLVKHFPDKSLNPVLTARFNREIETM
FDDTRDFIQAHFYFSPRTDTPFWRANKELRLADGMQEKIDMYRAGMAI
NAPASDDAQLYWGNFEEEFRNFWNNSNYYCVLAGLGLVPDAPSPRLAH
MPQATESVDEVFGAVKDRQRNLLETLPSLHEFLRQQHGR
```

SEQ.ID NO: 31
```
MSGKIDKILIVGGGTAGWMAASYLGKALQGTADITLLQAPDIPTLGVG
EATIPNLQTAFFDFLGIPEDEWMRECNASYKVAIKFINWRTAGEGTSE
ARELDGGPDHFYHSFGLLKYHEQIPLSHYWFDRSYRGKTVEPFDYACY
KEPVILDANRSPRRLDGSKVTNYAWHFDAHLVADFLRRFATEKLGVRH
VEDRVEHVQRDANGNIESVRTATGRVFDADLFVDCSGFRGLLINKAME
EPFLDMSDHLLNDSAVATQVPHDDDANGVEPFTSAIAMKSGWTWKIPM
LGRFGTGYVYSSRFATEDEAVREFCEMWHLDPETQPLNRIRFRVGRNR
RAWVGNCVSIGTSSCFVEPLESTGIYFVYAALYQLVKHFPDKSLNPVL
TARFNREIETMFDDTRDFIQAHFYFSPRTDTPFWRANKELRLADGMQE
KIDMYRAGMAINAPASDDAQLYYGNFEEEFRNFWNNSSYYCVLAGLGL
VPDAPSPRLAHMPQATESVDEVFGAVKDRQRNLLETLPSLHEFLRQQH
GR
```

SEQ.ID NO: 32
```
MSGKIDKILIVGGGTAGWMAASYLGKALQGTADITLLQAPDIPTLGVG
EATMPNLQTAFFDFLGIPEDEWMRECNASYKVAIKFINWRTAGEGTSE
ARELDGGPDHFYHPFGLLKYHEQIPLSHYWFDRLYRGKTVEPFDYACY
KEPVILDANRSPRRLDGSKVTSYAWHFDAHLVAKAMEEPFLDMSDHLL
NDSAVATQVPHDDDANGVEPFTSAIAMKSGWTWKIPMLGRFGTGYVYS
SRFATEDEAVREFCEMWHLDPETQPLNRIRFRVGRNRRAWVGNCVSIG
TSSCFVEPLESTGIYFVYAALYQLVKHFPDKSFNPVLTARFNREIETM
FDDTRDFIQAHFYFSPRTDTPFWRANKELRLADGMQEKIDMYRAGMAI
NAPAPDDAQLYWGNFEEEFRNLWNNSSYYCVLAGLGLVPDAPSPRLAH
MPRATESVDEVFGAVKDQQRNLLETLPSLHEFLRQQHGR
```

SEQ.ID NO: 33
```
MSGKIDKILIVGGGTAGWMAASYLGKALQGTADITLLQAPDIPTLGVG
EATHPNLQTAFFDFLGIPEDEWMRECNASYKVAIKFINWRTAGEGTSE
```

ARELDGGPDHFYHSFGLLKYHEQIPLSHYWFDRSYRGKTVEPFDYACY
KEPVILDANRSPRRLDGSKVTNYAWHFDAHLVAKAMEEPFLDMSDHLL
NDSAVATQVPHDDDANGVEPFTSAIAMKSGWTWKIPMLGRFGTGYVYS
SRFATEDEAVREFCEMWHLDPETQPLNRIRFRVGRNRRAWVGNCVSIG
TSSCFVEPLESTGIYFVYAALYQLVKHFPDKSFNPVLTARFNREIETM
FDDTRDFIQAHFYFSPRTDTPFWRANKELRLADGMQEKIDMYRAGMAI
NAPASDDAQLYYGNFEEEFRNCWNNSSYYCVLAGLGLVPDAPSPRLAH
MPRATESVDEVFGAVKDQQRNLLETLPSLHEFLRQQHGR

SEQ.ID NO: 34
MSGKIDKILIVGGGTAGWMAASYLGKALQGTADITLLQAPDIPTLGVG
EATIPNLQTAFFDFLGIPEDEWMRECNASYKVAIKFINWRTAGEGTSE
ARELDGGPDHFYHSFSLLKYHEQIPLSHYWFDRSYRGKTVEPFDYACY
KEPVILDANRSPRRLDGSKVTNYAWHFDAHLVAKAMEEPFLDMSDHLL
NDSAVATQVPHDDDANGVEPFTSAIAMKSGWTWKIPMLGRFGTGYVYS
SRFATEDEAVREFCEMWHLDPETQPLNRIRFRVGRNRRAWVGNCVSIG
TSSCFVEPLESTGIYFVYAALYQLVKHFPDKSLNPVLTARFNREIETM
FDDTRDFIQAHFYFSPRTDTPFWRANKELRLADGMQEKIDMYRAGMAI
NAPASDDAQLYYGNFEEEFRNFWNNSSYYCVLAGLGLVPDAPSPRLAH
MPQATESVDEVFGAVKDRQRNLLETLPSLHEFLRQQHGR

SEQ.ID NO: 35
MSGKIDKILIVGGGTAGWMAASYLGKALQGTADITLLQAPDIPTLGVG
EATIPNLQTAFFDFLGIPEDEWMRECNASYKVAIKFINWRTAGEGTSE
ARELDGGPDHFYHSFGLLKYHEQIPLSHYWFDRSYRGKTVEPFDYACY
KEPVILDANRSPRRLDGSKVTNYAWHFDAHLVADFLRRFATEKLGVRH
VEDRVEHVQRDANGNIESVRTATGRVFDADLFVDCSGFRGLLINKAME
EPFLDMSDHLLNDSAVATQVPHDDDANGVEPFTSAIAMKSGWTWKIPM
LGRFGTGYVYSSRFATEDEAVREFCEMWHLDPETQPLNRIRFRVGRNR
RAWVGNCVSIGTSSCFVEPLESTGIYFVYAALYQLVKHFPDKSLNPVL
TARFNREIETMFDDTRDFIQAHFYFSPRTDTPFWRANKELRLADGMQE
KIDMYRAGMVINAPASDDAQLYYGNFEEEFRNFWNNSNYYCVLAGLGL
VPDAPSPRLAHMPQATESVDEVFGAVKDRQRNLLETLPSLHEFLRQQH
GR

SEQ.ID NO: 36
ATGATGTCTGAAAATTTGCAATTGTCAGCTGAAGAAATGAGACAATTG
GGTTACCAAGCAGTTGATTTGATCATCGATCACATGAACCATTTGAAG
TCTAAGCCAGTTTCAGAAACAATCGATTCTGATATCTTGAGAAATAAG
TTGACTGAATCTATCCCAGAAAATGGTTCAGATCCAAAGGAATTGTTG
CATTTCTTGAACAGAAACGTTTTTAATCAAATTACACATGTTGATCAT
CCACATTTCTTGGCTTTTGTTCCAGGTCCAAATAATTACGTTGGTGTT
GTTGCAGATTTCTTGGCTTCTGGTTTTAATGTTTTTCCAACTGCATGG
ATTGCTGGTGCAGGTGCTGAACAAATCGAATTGACTACAATTAATTGG
TTGAAATCTATGTTGGGTTTTCCAGATTCAGCTGAAGGTTTATTTGTT
TCTGGTGGTTCAATGGCAAATTTGACAGCTTTGACTGTTGCAAGACAG
GCTAAGTTGAACAACGATATCGAAAATGCTGTTGTTTACTTCTCTGAT
CAAACACATTTCTCAGTTGATAGAGCATTGAAGGTTTTAGGTTTTAAA
CATCATCAAATCTGTAGAATCGAAACAGATGAACATTTGAGAATCTCT
GTTTCAGCTTTGAAGAAACAAATTAAAGAAGATAGAACTAAGGGTAAA
AAGCCATTCTGTGTTATTGCAAATGCTGGTACTACAAATTGTGGTGCT
GTTGATTCTTTGAACGAATTAGCAGATTTGTGTAACGATGAAGATGTT
TGGTTGCATGCTGATGGTTCTTATGGTGCTCCAGCTATCTTGTCTGAA
AAGGGTTCAGCTATGTTGCAAGGTATTCATAGAGCAGATTCTTTGACT
TTAGATCCACATAAGTGGTTGTTCCAACCATACGATGTTGGTTGTGTT
TTGATCAGAAACTCTCAATATTTGTCAAAGACTTTTAGAATGATGCCA
GAATACATCAAGGATTCAGAAACTAACGTTGAAGGTGAAATTAATTTC
GGTGAATGTGGTATCGAATTGTCAAGAAGATTCAGAGCTTTGAAGGTT
TGGTTGTCTTTTAAAGTTTTCGGTGTTGCTGCTTTTAGACAAGCAATC
GATCATGGTATCATGTTAGCAGAACAAGTTGAAGCATTTTTGGGTAAA
GCAAAAGATTGGGAAGTTGTTACACCAGCTCAATTGGGTATCGTTACT
TTTAGATACATTCCATCTGAATTGGCATCAACAGATACTATTAATGAA
ATTAATAAGAAATTGGTTAAGGAAATCACACATAGAGGTTTCGCTATG
TTATCTACTACAGAATTGAAGGAAAAGGTTGTTATTAGATTGTGTTCA
ATTAATCCAAGAACTACAACTGAAGAAATGTTGCAAATCATGATGAAG
ATTAAAGCATTGGCTGAAGAAGTTTCTATTTCATACCCATGTGTTGCT
GAATAA

SEQ.ID NO: 37
MMSENLQLSAEEMRQLGYQAVDLIIDHMNHLKSKPVSETIDSDILRNK
LTESIPENGSDPKELLHFLNRNVFNQITHVDHPHFLAFVPGPNNYVGV
VADFLASGFNVFPTAWIAGAGAEQIELTTINWLKSMLGFPDSAEGLFV
SGGSMANLTALTVARQAKLNNDIENAVVYFSDQTHFSVDRALKVLGFK
HHQICRIETDEHLRISVSALKKQIKEDRTKGKKPFCVIANAGTTFQPY
DVGCVLIRNSQYLSKTFRMMPEYIKDSETNVEGEINFGECGIELSRRF
RALKVWLSFKVFGVAAFRQAIDHGIMLAEQVEAFLGKAKDWEVVTPAQ
LGIVTFRYIPSELASTDTINEINKKLVKEITHRGFAMLSTTELKEKVV
IRLCSINPRTTTEEMLQIMMKIKALAEEVSISYPCVAE

SEQ.ID NO: 38
ATGTCTCAAGTGATCAAAAAAAGAGAAACACTTTCATGATCGGTACCG
AATATATATTGAACTCTACCCAATTAGAAGAGGCTATTAAATCTTTCG
TCCATGATTTCTGTGCCGAAAAGCACGAAATTCACGACCAACCAGTTG
TCGTTGAAGCTAAGGAACACCAAGAAGATAAGATTAAGCAAATCAAAA
TTCCAGAAAAGGGTCGTCCAGTCAATGAAGTTGTTTCTGAAATGATGA
ACGAAGTCTACAGATACAGAGGTGATGCCAACCATCCAAGATTCTTCT
CTTTCGTTCCAGGTCCAGCTTCCTCTGTCTCCTGGTTGGGTGACATCA
TGACTTCTGCTTACAACATCCACGCTGGTGGTTCTAAATTGGCCCCAA

```
TGGTTAACTGTATCGAACAAGAAGTCTTGAAATGGCTCGCAAAGCAAG
TTGGTTTCACCGAAAACCCTGGTGGTGTTTTCGTTTCCGGTGGTTCTA
TGGCTAACATTACTGCTTTGACAGCCGCTAGAGACAACAAGCTTACCG
ATATTAACTTGCACTTGGGTACTGCTTACATTTCCGACCAAACCCACT
CTTCAGTTGCTAAGGGTTTACGTATCATTGGTATCACTGACTCCAGAA
TCAGAAGAATTCCAACTAACTCCCACTTCCAAATGGACACCACTAAGT
TGGAAGAAGCTATCGAAACCGACAAGAAGTCCGGTTACATCCCATTTG
TTGTTATCGGTACTGCCGGTACCACCAACACTGGTTCCATTGACCCAT
TGACTGAAATTTCCGCTTTGTGTAAGAAGCATGACATGTGGTTCCACA
TTGATGGTGCCTACGGTGCTTCAGTTTTGTTGTCTCCAAAGTACAAGT
CTTTGTTAACAGGTACCGGTTTGGCTGACTCTATCTCTTGGGATGCTC
ACAAGTGGTTATTTCAAACTTACGGTTGTGCTATGGTTTTGGTCAAGG
ATATTAGAAACTTGTTTCATTCCTTCCACGTCAATCCAGAATACTTGA
AGGATCTGGAAAACGACATCGATAACGTTAACACCTGGGACATCGGCA
TGGAATTGACCAGACCAGCCAGAGGTTTGAAGTTGTGGTTGACTTTGC
AAGTTCTAGGTTCTGATCTTATTGGTTCTGCCATTGAACACGGTTTCC
AATTGGCTGTCTGGGCTGAAGAAGCCTTGAATCCAAAGAAGGACTGGG
AAATTGTCTCTCCTGCTCAAATGGCTATGATCAACTTCAGATATGCTC
CAAAGGACTTGACCAAGGAAGAACAAGATATCTTGAACGAAAAGATCT
CTCACCGTATTTTGGAATCCGGTTACGCTGCTATCTTCACTACCGTCC
TAAACGGTAAGACTGTCTTGAGAATCTGCGCTATTCACCCAGAAGCTA
CTCAAGAAGACATGCAACACACCATTGATTTGTTGGACCAATACGGTA
GAGAAATCTACACTGAAATGAAGAAGGCTTAG
                                                SEQ.ID NO: 39
MSQVIKKKRNTFMIGTEYILNSTQLEEAIKSFVHDFCAEKHEIHDQPV
VVEAKEHQEDKIKQIKIPEKGRPVNEVVSEMMNEVYRYRGDANHPRFF
SFVPGPASSVSWLGDIMTSAYNIHAGGSKLAPMVNCIEQEVLKWLAKQ
VGFTENPGGVFVSGGSMANITALTAARDNKLTDINLHLGTAYISDQTH
SSVAKGLRIIGITDSRIRRIPTNSHFQMDTTKLEEAIETDKKSGYIPF
VVIGTAGTTNTGSIDPLTEISALCKKHDMWFHIDGAYGASVLLSPKYK
SLLTGTGLADSISWDAHKWLFQTYGCAMVLVKDIRNLFHSFHVNPEYL
KDLENDIDNVNTWDIGMELTRPARGLKLWLTLQVLGSDLIGSAIEHGF
QLAVWAEEALNPKKDWEIVSPAQMAMINFRYAPKDLTKEEQDILNEKI
SHRILESGYAAIFTTVLNGKTVLRICAIHPEATQEDMQHTIDLLDQYG
REIYTEMKKA
                                                SEQ.ID NO: 40
ATGAAGCCAGCTGAAGCTAAACCACCTCACATGGACCATGATACTTTC
AGATCCTTGGGTCACCAAGCTATTGACTGGATTGCTGATTACTGGCAA
CACTTGGCTGACAGACCAGTTGCTCCATTGGTTGAACCAGGTACTGTT
AGAGCCCAATTGCCTACCACTCCACCAGAGTACGGTGAAGACTTCCCA
GCTTTGTTATCTGACTTGGAAAGAATTGTCTTGCCAGGCTTGTTGCAC
TGGCAACACCCAAGATTCTTCGGTTACTTCCCAGCTAACGCTTCCGGT
CCAGCCGTTTTAGCTGAATTATTATCTGCTGGTCTAGGTGTCCAAGGT
ATGAACTGGAACACTTCTCCAGCTTGTACCGAAGTTGAACAACAAATG
TTGGACTGGTTCGTTCATTTGTTAGGGTTGCCAGAACACTTCAGAGGT
GGTGGTGTTATCCAAGACACTGCCTCCTCCGCCGTTTTGGTCGCTCTA
TTGACTGCTTTGCACAGAGCTTCTGCTGGTAGAACCAGAGATCACGGT
ACTGGTGAATGTGGTTACAGGGTTTACCTAACCGCTGAAACTCACTCC
GCTGCTAGAAAGGCTGCCGTCATCACCGGTTTGGGTTTGCGTGCTGTT
TGTGAAGTCGCAACTGATGCTGACGGTGCTATGGATGCCGCTGACTTG
GCCGCTCGTATTCAAGCCGATTTGGCTGCCGGTTTGACCCCATTGATG
GTTGTTGCTACCCGTGGTACCACCTCTGATTTGTCCTTCGATCCATTG
GAAGACATCGGTCCAGTCTGTAGAAGACATGGTGTCTGGTTACACGTT
GACGCTGCTTATGCTGGTGTTGCTGCAGTGTGCGATGAATTGCATTGG
GTTAATGATGGTGTTAGATACGCTGATTCTTACTGTACTAACCCACAC
AAGTGGTTGTTGACCAACTTCGACTGTGATTTATTATGGGTTGCCGAC
CCAGAAGCTTTGGTCAACGCTTTGTCCGTTTTGCCTGCTTACTTGAGA
AACCCAGCTTCTGAATCAGGTAGAGTTACTGACTACAGACACTGGCAA
GTTCCATTGGGCAGAAGATTCAGAGCCTTGAAGTTGTGGTCTGTCTTA
AGATGGTACGGTGCCGAAGGTTTGAGATCTCACATCAGAACTGGTGTC
AGACACGCCAGATTGTTCGCTGACCTGGTCAGAGAAGATGACCGTTTC
ACCTTGTTGGCGCCAGCTACTTTGGGTTTGGTCACTTTCCGTCACGCT
GGTTCTGACACCGACAACAGAAACTTGTTGCACGCTATCAACGCCGAA
GGTACAACTTTTTTAACTCATAGTGAAAAGAACGGTACCTTTTTCTTG
AGATTTGCTACCGGTGGTACCCACACTGAAGACCATCACGTCCACGAA
GCTTGGAGAGCTGTCCAAAATGCCGTCCAAAACGCCGTCCCAAGAGCC
CAACATGCCACCGATGGTACTGCCGATGCTTTGAACGGTTAA
                                                SEQ.ID NO: 41
MKPAEAKPPHMDHDTFRSLGHQAIDWIADYWQHLADRPVAPLVEPGTV
RAQLPTTPPEYGEDFPALLSDLERIVLPGLLHWQHPRFFGYFPANASG
PAVLAELLSAGLGVQGMNWNTSPACTEVEQQMLDWFVHLLGLPEHFRG
GGVIQDTASSAVLVALLTALHRASAGRTRDHGTGECGYRVYLTAETHS
AARKAAVITGLGLRAVCEVATDADGAMDAADLAARIQADLAAGLTPLM
VVATRGTTSDLSFDPLEDIGPVCRRHGVWLHVDAAYAGVAAVCDELHW
VNDGVRYADSYCTNPHKWLLTNFDCDLLWVADPEALVNALSVLPAYLR
NPASESGRVTDYRHWQVPLGRRFRALKLWSVLRWYGAEGLRSHIRTGV
RHARLFADLVREDDRFTLLAPATLGLVTFRHAGSDTDNRNLLHAINAE
GTTFLTHSEKNGTFFLRFATGGTHTEDHHVHEAWRAVQNAVQNAVPRA
QHATDGTADALNG
                                                SEQ.ID NO: 42
ATGGATATTGAAGCTTTTAGAAAAGCAGGTTACCAAGCTATCGATAGA
ATTTGTGACTACTACTACTCTTTGCAAAATAGACCAGTTGTTCCATCA
GTTCAACCAGGTTATTGTTAGATGCATTACCAGATTCTCCACCAGAA
```

-continued

CAAGGTGAAGATTTCACTGTTATTGCTGATGATTACCAAAAGTACATC
TTGCCAGGTTTGACACATTGGCAACATCCATCTTTCTTTGCATACTTT
CCAACAGCTTGTACTTTTGAAGGTATTTTGGGTGACTTGTATTCTACA
TCAACTGCAAATCCAGGTTTTAATTGGTTGGCTTCTCCAGCATGTACT
GAATTAGAAATGGTTGTTATGGATTGGTCTGCTAAGTTGTTAGGTTTG
TCAGAACATTTCTTGCATTCTTCAGGTAAAGGTGGTGGTGTTATTCAA
ACTACAGCATCAGAATTGGCTTTAGTTGTTGTTGTTGCTGCAAGAGAA
AGATACTTGAGAATTCATCCAGATGCTAAGGCAGATGAATTGGTTATA
TATACTACAACTCAAACACATTCTTTGGGTGTTAAAGCTGGTTTAGTT
TTTGGTATGGAATGTAGAGCATTGGAAGTTAAAGCTGAAGATGCTTAC
GCATTAAGAGGTGCAACTTTGAAGTCAGCTTTAGAAGAAGATGAAAAG
AGAGGTAAAAGACCTTTTATTTTGGTTGCAACAGTTGGTACAACTTCT
TCAGGTGCTATTGATAGATTGGATGAAATTGGTCAAGTTTCTGAAGAT
TATCCATCATTATGGATTCATGTTGATGCTGCATGGGCAGGTGTTACT
TTGGCTTGTCCAGAATACAGAGGTACAGCTCAATTAGAAAACATCAAC
GCTTATGCAACATCTTTCGGTACTAACTTCCATAAGTGGGGTTTGGTT
AACTTTGATGCTGCATTGTTGTGGGTTAAGGATAGAAAGGATTTGACA
GATGCTTTAGATGTTACTCCAGAATTCTTGAGAACAAAACAAGGTGAC
GCTGGTGCAGTTGTTGATTTTAGAAATTGGCATTTGGGTTTGGGTAGA
AGATTCAGATCTTTGAAGGTTTGGTTCGTTTTGAGATCATACGGTGTT
GAAGGTTTTAGAAACTACATCAGACAAGGTATTAAATTGAATGAACAT
TTTACTTCTTTAATTAGAGCTTCTTTGGATTTTTCATTAGTTACAGCA
CCATCATTCGCTTTGACAGTTTTTAGATTGACTCCAGCTGGTGCATCT
TTGACTGGTTCAGAATTGAACGAATTAAACAGAGCTTTCTACGCAAGA
TTATCTTCAAGACATGATATCATGTTGACACAAACTGTTTTGAACGGT
GTTTTCTGTATCAGATTTGCAGTTGGTGCTGCAAGAACTCAACAAGAA
CATATTGATACAGCTTGGGATTTGTTACAACAAGAAGGTGCTGTTGCA
GTTCAAGAATACATGCAAAAGATTTCTAAGGATGTTCAATAA

SEQ.ID NO: 43

MDIEAFRKAGYQAIDRICDYYYSLQNRPVVPSVQPGYLLDALPDSPPE
QGEDFTVIADDYQKYILPGLTHWQHPSFFAYFPTACTFEGILGDLYST
STANPGFNWLASPACTELEMVVMDWSAKLLGLSEHFLHSSGKGGGVIQ
TTASELALVVVAARERYLRIHPDAKADELVIYTTTQTHSLGVKAGLV
FGMECRALEVKAEDAYALRGATLKSALEEDEKRGKRPFILVATVGTTS
SGAIDRLDEIGQVSEDYPSLWIHVDAAWAGVTLACPEYRGTAQLENIN
AYATSFGTNFHKWGLVNFDAALLWVKDRKDLTDALDVTPEFLRTKQGD
AGAVVDFRNWHLGLGRRFRSLKVWFVLRSYGVEGFRNYIRQGIKLNEH
FTSLIRASLDFSLVTAPSFALTVFRLTPAGASLTGSELNELNRAFYAR
LSSRHDIMLTQTVLNGVFCIRFAVGAARTQQEHIDTAWDLLQQEGAVA
VQEYMQKISKDVQ

SEQ.ID NO: 44

ATGAAGTTCTGGAGAAAGTACACACAACAAGAAATGGATGAAAAGATT
ACTGAATCTTTGGAAAAGACTTTGAACTACGATAACACTAAGACAATC
GGTATTCCAGGTACTAAGTTGGATGATACAGTTTTCTATGATGATCAT
TCTTTCGTTAAGCATTCACCATACTTGAGAACTTTTATTCAAAACCCA
AACCATATCGGTTGTCATACTTATGATAAGGCTGATATCTTGTTCGGT
GGTACATTCGATATCGAAAGAGAATTAATCCAATTGTTAGCAATCGAT
GTTTTGAACGGTAACGATGAAGAATTTGATGGTTACGTTACTCAAGGT
GGTACAGAAGCTAACATCCAAGCAATGTGGGTTTACAGAAACTACTTC
AAGAAAGAAAGAAAGGCTAAGCATGAAGAAATCGCTATCATCACTTCA
GCAGATACACATTACTCTGCATACAAAGGTTCAGATTTGTTGAACATC
GATATTATTAAGGTTCCAGTTGATTTTTATTCAAGAAAAATTCAAGAA
AATACATTGGATTCAATTGTTAAAGAAGCTAAAGAAATTGGTAAAAAG
TACTTCATCGTTATCTCTAACATGGGTACTACAATGTTTGGTTCAGTT
GATGATCCAGATTTGTACGCTAACATCTTCGATAAGTACAATTTGGAA
TACAAAATTCATGTTGATGGTGCATTTGGTGGTTTTATATATCCAATT
GATAATAAGGAATGTAAAACTGATTTCTCTAATAAGAACGTTTCTTCA
ATCACATTAGATGGTCATAAGATGTTGCAAGCTCCATACGGTACTGGT
ATCTTCGTTTCAAGAAAGAATTTGATCCATAACACTTTGACAAAGGAA
GCAACTTACATCGAAAATTTGGATGTTACATTGTCTGGTTCAAGATCT
GGTTCAAATGCTGTTGCAATTTGGATGGTTTTAGCTTCTTATGGTCCA
TACGGTTGGATGGAAAAGATTAATAAGTTGAGAAATAGAACTAAATGG
TTGTGTAAGCAATTGAACGATATGAGAATTAAATATTACAAAGAAGAT
TCAATGAATATTGTTACAATTGAAGAACAATATGTTAATAAGGAAATC
GCTGAAAAGTACTTTTTAGTTCCAGAAGTTCATAACCCAACTAACAAC
TGGTACAAGATCGTTGTTATGGAACATGTTGAATTGGATATCTTGAAC
TCTTTGGTTTACGATTTGAGAAAGTTTAATAAGGAACATTTGAAGGCA
ATGTAA

SEQ.ID NO: 45

MKFWRKYTQQEMDEKITESLEKTLNYDNTKTIGIPGTKLDDTVFYDDH
SFVKHSPYLRTFIQNPNHIGCHTYDKADILFGGTFDIERELIQLLAID
VLNGNDEEFDGYVTQGGTEANIQAMWVYRNYFKKERKAKHEEIAIITS
ADTHYSAYKGSDLLNIDIIKVPVDFYSRKIQENTLDSIVKEAKEIGKK
YFIVISNMGTTMFGSVDDPDLYANIFDKYNLEYKIHVDGAFGGFIYPI
DNKECKTDFSNKNVSSITLDGHKMLQAPYGTGIFVSRKNLIHNTLTKE
ATYIENLDVTLSGSRSGSNAVAIWMVLASYGPYGWMEKINKLRNRTKW
LCKQLNDMRIKYYKEDSMNIVTIEEQYVNKEIAEKYFLVPEVHNPTNN
WYKIVVMEHVELDILNSLVYDLRKFNKEHLKAM

SEQ.ID NO: 46

ATGAATGCATCTGAATTCAGAAGAAGAGGTAAAGAAATGGTTGATTAC
ATGGCTAACTACATGGAAGGTATTGAAGGTAGACAAGTTTATCCAGAT
GTTGAACCAGGTTACTTGAGACCATTAATTCCAGCTGCAGCTCCACAA

-continued

GAACCAGATACATTTGAAGATATTATTAACGATGTTGAAAAGATTATC

ATGCCAGGTGTTACACATTGGCATTCACCATATTTCTTTGCATACTTT

CCAACTGCTTCTTCATATCCAGCAATGTTGGCTGATATGTTATGTGGT

GCAATTGGTTGTATTGGTTTTTCTTGGGCAGCTTCACCAGCTTGTACA

GAATTGGAAACTGTTATGATGGATTGGTTAGGTAAAATGTTGGAATTA

CCAAAGGCATTTTTGAACGAAAAGGCTGGTGAAGGTGGTGGTGTTATT

CAAGGTTCTGCATCAGAAGCTACATTAGTTGCTTTGTTAGCAGCTAGA

ACTAAAGTTATTCATAGATTGCAAGCAGCTTCTCCAGAATTAACACAA

GCAGCTATCATGGAAAAATTGGTTGCATATTCTTCAGATCAAGCTCAT

TCTTCAGTTGAAAGAGCTGGTTTGATCGGTGGTGTTAAGTTGAAGGCA

ATCCCATCTGATGGTAATTTTGCTATGAGAGCATCAGCTTTGCAAGAA

GCATTAGAAAGAGATAAAGCAGCTGGTTTGATTCCATTTTTCATGGTT

GCTACTTTAGGTACTACAACTTGTTGTTCTTTCGATAATTTGTTAGAA

GTTGGTCCAATTTGTAATAAGGAAGATATTTGGTTGCATGTTGATGCA

GCTTACGCAGGTTCAGCTTTTATTTGTCCAGAATTCAGACATTTGTTG

AACGGTGTTGAATTCGCTGATTCTTTTAATTTCAATCCACATAAATGG

TTGTTAGTTAACTTCGATTGTTCAGCAATGTGGGTTAAGAAAAGAACA

GATTTGACTGGTGCTTTTAGATTAGATCCAACATATTTGAAGCATTCT

CATCAAGATTCAGGTTTGATCACTGATTACAGACATTGGCAAATTCCA

TTGGGTAGAAGATTCAGATCTTTGAAGATGTGGTTCGTTTTTAGAATG

TACGGTGTTAAGGGTTTGCAAGCTTACATCAGAAAGCATGTTCAATTG

TCTCATGAATTCGAATCATTAGTTAGACAAGATCCAAGATTCGAAATC

TGTGTTGAAGTTATTTTGGGTTTAGTTTGTTTCAGATTGAAGGGTTCT

AATAAGGTTAACGAAGCATTGTTGCAAAGAATTAATTCAGCTAAGAAA

ATTCATTTGGTTCCATGTCATTTGCGTGATAAGTTCGTTTTGAGATTC

GCTATTTGTTCAAGAACTGTTGAATCAGCACATGTTCAAAGAGCTTGG

GAACATATCAAGGAATTGGCAGCTGATGTTTTGAGAGCTGAAAGAGAA

TAA

SEQ.ID NO: 47

MNASEFRRRGKEMVDYMANYMEGIEGRQVYPDVEPGYLRPLIPAAAPQ
EPDTFEDIINDVEKIIMPGVTHWHSPYFFAYFPTASSYPAMLADMLCG
AIGCIGFSWAASPACTELETVMMDWLGKMLELPKAFLNEKAGEGGGVI
QGSASEATLVALLAARTKVIHRLQAASPELTQAAIMEKLVAYSSDQAH
SSVERAGLIGGVKLKAIPSDGNFAMRASALQEALERDKAAGLIPFFMV
ATLGTTTCCSFDNLLEVGPICNKEDIWLHVDAAYAGSAFICPEFRHLL
NGVEFADSFNFNPHKWLLVNFDCSAMWVKKRTDLTGAFRLDPTYLKHS
HQDSGLITDYRHWQIPLGRRFRSLKMWFVFRMYGVKGLQAYIRKHVQL
SHEFESLVRQDPRFEICVEVILGLVCFRLKGSNKVNEALLQRINSAKK
IHLVPCHLRDKFVLRFAICSRTVESAHVQRAWEHIKELAADVLRAERE

SEQ.ID NO: 48

ATGGGTTCTATCTCAGAAAACTGTGATGATTCTATTTCATTAGCTGCA

CCTTTTAGACCATTGGAACCAGAAGAATTCAGAAAGCAAGCTCATGTT

ATGGTTGATTTCATCGCAGATTACTACAAGAACATTGAAAATTATCCA

GTTTTGTCACAAGTTGAACCAGGTTATTTGAAAAATAGATTGCCAGAA

ACTGCTCCACATTTGCCAGAATCTTTCGAAACAATCTTGAAGGATATT

AAGAAAGATATCGTTCCTGGTATGACTAATTGGTTGTCACCAAATTTC

TTTGCTTATTTTCCAGCAACTGTTTCTTCAGCTGCATTTGTTGGTGAA

ATGTTGTGTACAGGTTTTAATTCTGTTGGTTTTAATTGGTTAGCTTCA

CCAGCATCTACAGAATTGGAAATGGTTGTTATTGATTGGTTAGCTAAC

ATGTTGAAGTTGCCAAAGTCTTTTATGTTTCATGGTACTGGTGGTGGT

GTTATTCAAGGTACTACATCTGAAGCTATCTTGTGTACATTGATTGCT

GCAAGAGATGGTGCTTTGGAAAAGATTGGTATGGAAAACGTTGGTAAA

TTAGTTGTTTACGGTTCAGATCAAACTCATTCTTTCTTTCAAAAGACT

TGTAAGGTTGCTGGTATCTTCCCATGTAACATCAAGTTGATCCCAACT

ACAAGAGAAGATAACTTCTCTATGTCACCAATCGCATTGAGAGAACAA

ATTGAAGCTGATGTTGCAGATGGTTTAGTTCCAATTTTCTTGTGTACT

ACAGTTGGTACTACATCAACTGCTGCAATTGATCCAGTTTCTGAAGTT

GCTAAGGTTGCAAACGATTTCAATATTTGGGTTCATGTTGATGCTGCT

TATGCTGGTTCTGCATGTATTTGTCCAGAATTCAGACAATACTTAGAT

GGTATCGAATTGGTTGATTCTTTTCATTGTCTCCACATAAGTGGTTG

TTGTGTTTCTTGGATTGTTGTTGTTTGTGGTTGAAGAAACCACATTTG

ATGGTTAAGGCTTTGTCAACTAACCCAGAATATTTGAGAAATAAGAGA

TCTGAATTCGATGGTGTTGTTGATTTCAAGGATTGGCAAATCGGTACA

GGTAGAAGATTCAAAGCTTTGAGATTATGGTTGGTTATGAGATCATAC

GGTGTTGAAAATTTGAAGAGACATATCTTGTCTGATGTTCAAATGGCT

AAGATGTTCGAAGGTTTAGTTAAATCTGATCCAAGATTCGAAATCATC

GTTCCAAGAGCTTTCGCATTAGTTTGTTTCAGATTGAACCCTGGTAAA

GGTTATGATGATGAAATCGATAAGGAAATCTTGAATAAGGAATTGTTA

GATTTGATTAATTCAACAGGTAGAGCTTACATGACTCATACAAAAGCA

GGTGGTATCTATATGTTGAGATTTGCTGTTGGTACTACATTGACTGAA

GAACATCATGTTTACGCTGCATGGGAATTGATTAAAGAATGTACAGAT

GCATCTTTGACTAAAACAAATATTATTGAATAA

SEQ.ID NO: 49

MGSISENCDDSISLAAPFRPLEPEEFRKQAHVMVDFIADYYKNIENYP
VLSQVEPGYLKNRLPETAPHLPESFETILKDIKKDIVPGMTNWLSPNF
FAYFPATVSSAAFVGEMLCTGFNSVGFNWLASPASTELEMVVIDWLAN
MLKLPKSFMFHGTGGGVIQGTTSEAILCTLIAARDGALEKIGMENVGK
LVVYGSDQTHSFFQKTCKVAGIFPCNIKLIPTTREDNFSMSPIALREQ
IEADVADGLVPIFLCTTVGTTSTAAIDPVSEVAKVANDFNIWVHVDAA
YAGSACICPEFRQYLDGIELVDSFSLSPHKWLLCFLDCCCLWLKKPHL

MVKALSTNPEYLRNKRSEFDGVVDFKDWQIGTGRRFKALRLWLVMRSY
GVENLKRHILSDVQMAKMFEGLVKSDPRFEIIVPRAFALVCFRLNPGK
GYDDEIDKEILNKELLDLINSTGRAYMTHTKAGGIYMLRFAVGTTLTE
EHHVYAAWELIKECTDASLTKTNIIE

SEQ.ID NO: 50
ATGGGTTCATTAGATACAAATCCAACTGCTTTTTCTGCATTTCCAGCT
GGTGAAGGTGAAACTTTTCAACCATTGAACGCAGATGATGTTAGATCA
TATTTGCATAAGGCTGTTGATTTCATCTCTGATTACTACAAATCAGTT
GAATCTATGCCAGTTTTGCCAAACGTTAAGCCAGGTTATTTGCAAGAT
GAATTAAGAGCATCACCACCAACTTACTCTGCTCCATTCGATGTTACA
ATGAAGGAATTGAGATCTTCAGTTGTTCCTGGTATGACTCATTGGGCA
TCTCCAAATTTCTTTGCTTTCTTTCCATCAACAAATTCTGCTGCAGCT
ATTGCTGGTGACTTGATTGCATCAGCTATGAATACAGTTGGTTTTACT
TGGCAAGCTTCTCCAGCAGCTACTGAAATGGAAGTTTTGGCATTAGAT
TGGTTGGCTCAAATGTTGAATTTGCCAACTTCTTTTATGAACAGAACT
GGTGAAGGTAGAGGTACTGGTGGTGGTGTTATTTTGGGTACTACATCT
GAAGCTATGTTGGTTACATTAGTTGCAGCTAGAGATGCAGCTTTGAGA
AGATCTGGTTCAGATGGTGTTGCAGGTTTGCATAGATTAGCTGTTTAT
GCAGCTGATCAAACACATTCAACTTTCTTTAAGGCATGTAGATTGGCT
GGTTTTGATCCAGCAAATATTAGATCTATTCCAACAGGTGCTGAAACT
GATTATGGTTTAGATCCAGCAAGATTGTTAGAAGCTATGCAAGCAGAT
GCTGATGCAGGTTTAGTTCCAACATACGTTTGTGCAACTGTTGGTACT
ACATCTTCAAATGCTGTTGATCCAGTTGGTGCTGTTGCAGATGTTGCA
GCTAGATTTGCAGCTTGGGTTCATGTTGATGCAGCTTACGCAGGTTCA
GCTTGTATTTGTCCAGAATTCAGACATCATTTGGATGGTGTTGAAAGA
GTTGATTCTATCTCAATGTCTCCACATAAGTGGTTGATGACATGTTTA
GATTGTACTTGTTTGTACGTTAGAGATACACATAGATTGACTGGTTCT
TTAGAAACTAACCCAGAATACTTGAAAAATCATGCTTCAGATTCTGGT
GAAGTTACAGATTTGAAAGATATGCAAGTTGGTGTTGGTAGAAGATTC
AGAGGTTTGAAGTTGTGGATGGTTATGAGAACTTATGGTGTTGCTAAG
TTGCAAGAACATATCAGATCAGATGTTGCTATGGCAAAAGTTTTTGAA
GATTTGGTTAGAGGTGACGATAGATTCGAAGTTGTTGTTCCAAGAAAC
TTCGCTTTGGTTTGTTTCAGAATTAGAGCTGGTGCAGGTGCAGCTGCA
GCTACAGAAGAAGATGCAGATGAAGCTAACAGAGAATTGATGGAAAGA
TTGAATAAGACTGGTAAAGCATACGTTGCTCATACAGTTGTTGGTGGT
AGATTTGTTTTGAGATTTGCAGTTGGTTCTTCATTACAAGAAGAACAT
CATGTTAGATCTGCTTGGGAATTGATTAAGAAAACTACAACTGAAATG
ATGAACTAA

SEQ.ID NO: 51
MGSLDTNPTAFSAFPAGEGETFQPLNADDVRSYLHKAVDFISDYYKSV
ESMPVLPNVKPGYLQDELRASPPTYSAPFDVTMKELRSSVVPGMTHWA
SPNFFAFFPSTNSAAAIAGDLIASAMNTVGFTWQASPAATEMEVLALD
WLAQMLNLPTSFMNRTGEGRGTGGGVILGTTSEAMLVTLVAARDAALR
RSGSDGVAGLHRLAVYAADQTHSTFFKACRLAGFDPANIRSIPTGAET
DYGLDPARLLEAMQADADAGLVPTYVCATVGTTSSNAVDPVGAVADVA
ARFAAWVHVDAAYAGSACICPEFRHHLDGVERVDSISMSPHKWLMTCL
DCTCLYVRDTHRLTGSLETNPEYLKNHASDSGEVTDLKDMQVGVGRRF
RGLKLWMVMRTYGVAKLQEHIRSDVAMAKVFEDLVRGDDRFEVVVPRN
FALVCFRIRAGAGAAAATEEDADEANRELMERLNKTGKAYVAHTVVGG
RFVLRFAVGSSLQEEHHVRSAWELIKKTTTEMMN

SEQ.ID NO: 52
ATGGAAGGTGTTGGTGGTGGTGGTGGTGGTGAAGAATGGTTGAGACCA
ATGGATGCAGAACAATTAAGAGAATGTGGTCATAGAATGGTTGATTTC
GTTGCAGATTACTACAAGTCAATCGAAGCTTTTCCAGTTTTGTCTCAA
GTTCAACCAGGTTATTTGAAAGAAGTTTTGCCAGATTCAGCTCCAAGA
CAACCAGATACTTTAGATTCTTTGTTCGATGATATCCAACAAAAGATT
ATCCCAGGTGTTACACATTGGCAATCACCAAACTACTTCGCATACTAC
CCATCTAATTCTTCTACTGCTGGTTTCTTGGGTGAAATGTTGTCTGCT
GCTTTTAATATCGTTGGTTTTCATGGATCACTTCTCCAGCTGCAACA
GAATTGGAAGTTATTGTTTAGATTGGTTCGCAAAGATGTTGCAATTG
CCATCACAATTCTTATCTACTGCTTTGGGTGGTGGTGTTATTCAAGGT
ACAGCTTCAGAAGCAGTTTTGGTTGCATTGTTAGCTGCAAGAGATAGA
GCTTTGAAGAAACATGGTAAACATTCTTTAGAAAAATTGGTTGTTTAC
GCATCAGATCAAACTCATTCTGCTTTACAAAAAGCATGTCAAATCGCT
GGTATTTTCTCTGAAAACGTTAGAGTTGTTATTGCTGATTGTAATAAG
AACTACGCTGTTGCACCAGAAGCAGTTTCAGAAGCTTTGTCTATCGAT
TTGTCTTCAGGTTTGATCCCATTTTTCATTTGTGCAACAGTTGGTACT
ACATCTTCATCTGCTGTTGATCCATTACCAGAATTGGGTCAAATCGCT
AAGTCAAACGATATGTGGTTCCATATCGATGCTGCTTATGCTGGTTCT
GCATGTATTTGTCCAGAATACAGACATCATTTGAATGGTGTTGAAGAA
GCAGATTCTTTTAATATGAATGCTCATAAGTGGTTCTTGACTAACTTC
GATTGTTCATTGTTGTGGGTTAAGGATAGATCATTTTTGATCCAATCA
TTATCTACAAATCCAGAATTCTTGAAAAATAAGGCTTCACAAGCAAAC
TCTGTTGTTGATTTCAAGGATTGGCAAATCCCATTGGGTAGAAGATTC
AGATCATTGAAGTTGTGGATGGTTTTGAGATTGTACGGTGTTGATAAT
TTGCAATCTTACATCAGAAAGCATATCCATTTGGCTGAACATTTCGAA
CAATTGTTGTTCAGATTCAAGATTCGAAGTTGTTACTCCAAGAACA
TTTTCATTGGTTTGTTTCAGATTAGTTCCACCAACTTCTGATCATGAA
AACGGTAGAAAGTTGAACTACGATATGATGGATGGTGTTAATTCATCT
GGTAAAATTTTCTTGTCACATACAGTTTTGTCTGGTAAATTCGTTTTG
AGATTTGCTGTTGGTGCACCATTAACTGAAGAAAGACATGTTGATGCT
GCATGGAAGTTGTTGAGAGATGAAGCTACAAAGGTTTTAGGTAAAATG
GTTTAA

SEQ.ID NO: 53
MEGVGGGGGGEEWLRPMDAEQLRECGHRMVDFVADYYKSIEAFPVLSQ
VQPGYLKEVLPDSAPRQPDTLDSLFDDIQQKIIPGVTHWQSPNYFAYY
PSNSSTAGFLGEMLSAAFNIVGFSWITSPAATELEVIVLDWFAKMLQL
PSQFLSTALGGGVIQGTASEAVLVALLAARDRALKKHGKHSLEKLVVY
ASDQTHSALQKACQIAGIFSENVRVVIADCNKNYAVAPEAVSEALSID
LSSGLIPFFICATVGTTSSSAVDPLPELGQIAKSNDMWFHIDAAYAGS
ACICPEYRHHLNGVEEADSFNMNAHKWFLTNFDCSLLWVKDRSFLIQS
LSTNPEFLKNKASQANSVVDFKDWQIPLGRRFRSLKLWMVLRLYGVDN
LQSYIRKHIHLAEHFEQLLLSDSRFEVVTPRTFSLVCFRLVPPTSDHE
NGRKLNYDMMDGVNSSGKIFLSHTVLSGKFVLRFAVGAPLTEERHVDA
AWKLLRDEATKVLGKMV

SEQ.ID NO: 54
ATGACAAAGCCATTCCATCCAAATTTGAACGTTGATGCATTGTTTTTA
GGTCCAAAGTCTGAAAACGCTGTTTTCTTTAGAGAAATGATGGATTAT
GCAGTTTCTGAACACATGCATTGGAGATCAGGTTTTCATCCAGAAGAT
TCTACATTGGTTACTTCAGTTGATAGATACGAACATAACTACAGAGAA
ACATTGTACAGAACTGAAGGTATTTTGAATCAATTATCTGCTAAGTTG
AAAAATTCTTCAATCCCATTTTTCTCTCCAAGATACTTAGGTCATATT
TCTTCAGATACTTTGATGGTTTCTAATTTGGCTTATGTTATGGCTATG
ATGTACAACCCAAACAACTGTTCTTATGAAGCTTCACCAACTACAACT
GAATTGGAATTAGAATCTGGTTTGGATTTGTGTAGAATGTTCGGTTAC
AATCCACAACAATCTTGGGGTCATATTACATCAGGTGGTACTGTTGCA
AATTACGAAGGTTTGTGGGTTGCTAGAAATTTGAAGACATTGTCTTTC
GCAATCTCACAACATCCAAAGGCTAAGGATTTGATCGAACATAAGACT
CCAAAGCAATTGAAAAATATGCCAACATCTGAATTGTTAGATTTGATC
ACTGAATTACAAAAGAGAGGTTTGTTCGAAGAAATCAGAGATATGACA
TGTAGAGGTACTGGTGTTAAGGCTCAAATTTTAGGTAAATTGTTAGTT
CCACAATCTAAGCATTATTCATGGATGAAAGCTGCAGATATCTTCGGT
ATCGGTCAAGAAAACATCATCCCATTGCCAGTTAATGATCATTACCAA
ACAGATGTTGCTCAAATGAGAAAGATCACTTTCGGTTTGATTGAACAA
GGTGAACCAATTTTAGCAATGATTGCTGTTGTTGGTACAACTGAAGTT
GGTGCAATCGATAGAATCGATGAAGTTATTGCTTTAAGAAAAGAATGT
GAAGAAAGATACGGTGAATCTTTCTACATCCATGTTGATGCTGCTTAT
GCTGGTTACGCTTGTTCAATGTTGTTGAACGAACAGGGTGAATTCGTT
GAATACGATGAATTGGCAAACTACCATAGATCTGCTGGTATTATGCCA
GAAAATATTTCATGGCCAAAACCAGAAGTTTACCAATCTTTTAAAGCT
TTGAAAGATGTTGATTCAATTACAGTTGATCCACATAAGGTTGGTTTT
ATTCAATATGCTGCAGGTGCAATTTGTATGAAGGATAAGAGAATTTTG
GAATTAATTTCTTCACATGCTGCATACGTTTTTGAAGGTCATGCTGAT
AAGACATCTACTAAAAATAGAGGTATTTTGGGTTCTTCAATTATGGAA
GGTTCTAAATCAGGTGCAACAGCTGCAGCTTTGTGGGCAGCTCATAGA
TTGTTACCATTGAACATCAACGGTTACGGTAAAGTTATTGCAGCTGGT
ATCGTTACTGCACAATCTTTGTTGAATAAGTTGGCTAATTTGCCACCA
ATCGAAATCGGTAAACATAGATTCGAAGTTCATATTTTTCCATCACCA
GATTTCCACATGATCAACTTCACTTTTAAAGAAGTTGGTAACGAATCT
TTGTCAAACCATAACGCTTTGAATAAGAGATTGTATGAATTATGTTCT
TACTCAGCAGGTAGAGCTTACACAAATGATTTCTTGACATCTTCAACT
ATTTTAGATTACAAGGAATACGGTGACACTCCTTGGCATCATGCTCAA
AAATGTGGTTTTTCAAGATCAGAATGGGAAAAAGTTAGAAACATCTAT
GTTTTGAGAGCAGCTGTTATGACATACTGTTTGAGAGATGAAGAACAT
TTCGAAGAATTCTGGGAACAATTGCAAGCTATCTTCGTTAAGAAATTG
ACTCAAATCGTTGATGAAGAAGATAAGAAAGCAAGATTGAGATTAGAA
CCAGATGTTCCTTTTATTGGTTAA

SEQ.ID NO: 55
MTKPFHPNLNVDALFLGPKSENAVFFREMMDYAVSEHMHWRSGFHPED
STLVTSVDRYEHNYRETLYRTEGILNQLSAKLKNSSIPFFSPRYLGHI
SSDTLMVSNLAYVMAMMYNPNNCSYEASPTTTELELESGLDLCRMFGY
NPQQSWGHITSGGTVANYEGLWVARNLKTLSFAISQHPKAKDLIEHKT
PKQLKNMPTSELLDLITELQKRGLFEEIRDMTCRGTGVKAQILGKLLV
PQSKHYSWMKAADIFGIGQENIIPLPVNDHYQTDVAQMRKITFGLIEQ
GEPILAMIAVVGTTEVGAIDRIDEVIALRKECEERYGESFYIHVDAAY
AGYACSMLLNEQGEFVEYDELANYHRSAGIMPENISWPKPEVYQSFKA
LKDVDSITVDPHKVGFIQYAAGAICMKDKRILELISSHAAYVFEGHAD
KTSTKNRGILGSSIMEGSKSGATAAALWAAHRLLPLNINGYGKVIAAG
IVTAQSLLNKLANLPPIEIGKHRFEVHIFPSPDFHMINFTFKEVGNES
LSNHNALNKRLYELCSYSAGRAYTNDFLTSSTILDYKEYGDTPWHHAQ
KCGFSRSEWEKVRNIYVLRAAVMTYCLRDEEHFEEFWEQLQAIFVKKL
TQIVDEEDKKARLRLEPDVPFIG

SEQ.ID NO: 56
ATGGGTTCTTTGGATTCAAACTACGATACTGAATCTCCAGCTTCAGTT
GGTCAATTCAATCCATTAGATCCAGAAGAATTCAGAAAGCAAGCTCAT
TGTATCGTTGATTCATCGCAGATTACTACAAGAACATTGAATCTTAT
CCAGTTTTGTCACAAGTTGATCCAGGTTACAGACATTCAAGATTGGGT
AAAAATGCTCCATACAGATCTGAACCATTCGAATCAATCTTGAAGGAT
GTTCAAAGGATATCATCCCTGGTATGACTCATTGGATGTCTCCAAAT
TTCTTTGCTCATTTTCCAGCAACTGTTTCTTCAGCTGCATTTGTTGGT
GAAATGTTGTGTACATGTTCAACTCTGTTGGTTTTAATTGGTTAGCA
TCACCAGCTGCAACAGAATTGGAAATGGTTGTTATTGATTGGTTAGCT
AACATGTTGAAGTTGCCAAAGTCTTTTATGTTTTCAGGTACTGGTGGT
GGTGTTTTGCAAGGTACTACATCTGAAGCTATCTTGTGTACATTGATT
GCTGCATCACCAATGCATTTCGAAATCGTTGGTGTTAAGACTTCTACA
TCATTCGTTGTTTATGGTTCTGATCAAACTCATTCAACATACGCTAAA

-continued

GCATGTAAATTAGCAGGTATTTTGCCATGTAACATCAGATCTATTCCA
ACTACAGCTGATTCAAACTTCTCTGTTTCACCATTGTTGTTGAGAAGA
GCTATTGAAGCAGATAAAGCTGCAGGTATGGTTCCATTGTATATTTGT
GCTACAGTTGGTACTACATCTACTACAGCAATTGATCCATTATCTTCA
TTGGCTGATGTTGCAAATGATTATGGTGTTTGGTTTCATGTTGATGCT
GCATACGCTGGTTCTGCATGTATTTGTCCAGAATTCAGACATTATTTG
GATGGTATCGAAAGAGCAGATTCTTTGTCATTGTCTCCACATAAGTGG
TTGTTGTCTTACTTAGATTGTTGTTGTTTGTGGGTTAAGTCACCATCT
TTATTGGTTAAGGCTTTATCAACTGATCCAGAATATTTGAAAAATCAA
CCATCAGAATCTAAGTCAGTTGTTGATTACAAGGATTGGCAAGTTGGT
ACAGGTAGAAGATTCAAAGCTTTGAGATTGTGGTTCGTTATGAGATCT
TATGGTGTTGCAAATTTGCAATCACATATCAGAACTGATGTTCAAATG
GCTAAGATGTTCGAAGGTTTCGTTAAGTCTGATCCAAGATTCGAAATT
TTGGTTCCAAGAGTTTTCTCTTTGGTTTGTTTCAGATTGAACCCAATC
TCTGGTTCAGATCCAACTGGTACAGAAGCTTTGAACAGAAAGTTATTG
GATTGGGTTAATTCTACAGGTAGAGTTTATATGACTCATACAAAAGTT
GGTGGTATCTATATGTTGAGATTTGCTGTTGGTGCAACTTTAACAGAA
AAGAGACATGTTTCTTCAGCTTGGAAGTTGATTAAAGAAGGTGCAGAT
GTTTTGTTGAAGGAAGATTAA

SEQ.ID NO: 57
MGSLDSNYDTESPASVGQFNPLDPEEFRKQAHCIVDFIADYYKNIESY
PVLSQVDPGYRHSRLGKNAPYRSEPFESILKDVQKDIIPGMTHWMSPN
FFAHFPATVSSAAFVGEMLCTCFNSVGFNWLASPAATELEMVVIDWLA
NMLKLPKSFMFSGTGGGVLQGTTSEAILCTLIAASPMHFEIVGVKTST
SFVVYGSDQTHSTYAKACKLAGILPCNIRSIPTTADSNFSVSPLLLRR
AIEADKAAGMVPLYICATVGTTSTTAIDPLSSLADVANDYGVWFHVDA
AYAGSACICPEFRHYLDGIERADSLSLSPHKWLLSYLDCCCLWVKSPS
LLVKALSTDPEYLKNQPSESKSVVDYKDWQVGTGRRFKALRLWFVMRS
YGVANLQSHIRTDVQMAKMFEGFVKSDPRFEILVPRVFSLVCFRLNPI
SGSDPTGTEALNRKLLDWVNSTGRVYMTHTKVGGIYMLRFAVGATLTE
KRHVSSAWKLIKEGADVLLKED

SEQ.ID NO: 58
ATGGAAGGTGGTTTTACTGGTGGTGACGAATACCAAAAGCATTTCTTG
CCAAGAGATTACTTAAACACATACTACTCATTCCAATCTGGTCCATCA
CCAGAAGCTGAAATGTTGAAGTTTAATTTGGAATGTTTGCATAAGACT
TTCGGTCCAGGTGGTTTGCAAGGTGACACTTTAATTGATATTGGTTCT
GGTCCAACAATCTATCAAGTTTTGGCTGCATGTGAATCTTTTAAAGAT
ATCACTTTGTCAGATTTTACAGATAGAAATAGAGAAGAATTGGCTAAA
TGGTTGAAGAAAGAACCAGGTGCATACGATTGGACTCCAGCTTTGAAG
TTCGCATGTGAATTAGAAGGCAACTCTGGTAGATGGCAAGAAAAAGCT
GAAAAGTTGAGAGCAACAGTTAAGAGAGTTTTGAAGTGTGATGCTAAT

-continued

TTGTCAAATCCATTAACTCCAGTTGTTTTGCCACCAGCAGATTGTGTT
TTGACATTGTTAGCTATGGAATGTGCATGTTGTTCTTTGGATGCTTAT
AGAGCTGCATTGAGAAATTTGGCATCATTGTTAAAACCAGGTGGTCAT
TTGGTTACTACAGTTACTTTGCAATTATCTTCATACATGGTTGGTGAA
AGAGAATTTTCTTGTGTTGCTTTGGAAAAAGAAGAAGTTGAACAAGCT
GTTTTAGATGCAGGTTTCGATATCGAACAATTGTTGTACTCTCCACAA
TCTTACTCAGCTTCTACAGCACCAAATAGAGGTGTTTGTTTCTTGGTT
GCTAGAAAGAAACCAGGTTCATAA

SEQ.ID NO: 59
MEGGFTGGDEYQKHFLPRDYLNTYYSFQSGPSPEAEMLKFNLECLHKT
FGPGGLQGDTLIDIGSGPTIYQVLAACESFKDITLSDFTDRNREELAK
WLKKEPGAYDWTPALKFACELEGNSGRWQEKAEKLRATVKRVLKCDAN
LSNPLTPVVLPPADCVLTLLAMECACCSLDAYRAALRNLASLLKPGGH
LVTTVTLQLSSYMVGEREFSCVALEKEEVEQAVLDAGFDIEQLLYSPQ
SYSASTAPNRGVCFLVARKKPGS

SEQ.ID NO: 60
ATGGATAAGATCTCTGCACCATTTTTCTCTGGTACTTCACCAGCTGCA
GCTTCAGTTGCTGGTGTTGATGAAGATGATAGATTGTGTTTCCAAGCT
CAAGAATTGATGTTCGCATACAACATCTCTATGGTTTTGAGAGCAGCT
ATTCAATTAGGTTTGTTAGATGCTTTGTCAGCAGCTGGTGGTAAAGCA
TTGACTCCAAACGAATTAGTTGAAAACGTTGAAACATCTTCAAATAAG
GCTGAAGCAGCTGCAGCTGTTGATAGAATTTTGAGATATTGTCTTGT
TTCAACGTTGTTACTTGTTCTTCAGAAGCAGCTGGTCCAGATGGTACA
TTAGTTAGAAGATACACTACAGGTCCATTGTGTAGATGGTTAACTAAA
GATAGAGGTGACGGTACATTATCTCCATTTGCTGTTTTTGTTGTTGAT
CCAGATCATTTGTTTCCTTGGCATCATATTGCAGAAGCTGTTACTGCT
GGTGGTCCATCAGCATTCGAAAGAACACAAAAGTGGCCATACTACGAA
TACATGGGTAAAAATCAAAGATTGGGTACTTTGTTCGATAACGCAATG
GCTCAACATTCTGTTATTTTGGTTACAAAGATGTTAGAAAGATTCAAA
GGTTTTGATGGTGTTCAAAGATTAGTTGATGTTGGTGGTGGTACTGGT
TCTACATTGGGTATGATCACTTCAAAGTACAAGCACATGACAGGTATT
AATTACGATTTGCCACATGTTATTGCTCAAGGTTTGCCATTACCAGGT
GTTGAACATGTTGCAGGTGACATGTACGAATCTATTCCAACTGGTGAC
GCTGTTTTGTTACAATGGATTACATTGATGTTGAACGATGATGAATTC
GTTAAGATCTTGTCAAATTGTCATAATGCTTTGCCAAAAGATGGTAAA
GTTATTGTTGTTGATGGTATTTTACCAGAAAACCCAGATTCTTCATTG
ACTGCAAGAGATGCTTTTACATTAGATATCATCATGTTCGTTTTGTTT
AAAGGTGCAAAGCAAAGAACTGAAAAGGAATTCGCAAGATTAGCTAAG
CAAGCAGGTTTTACTGGTGGTATTAAGAAAACTTATATTTTCTTTAAT
TTTTACGCTTTGGAATTCACTAAATAA

SEQ.ID NO: 61
MDKISAPFFSGTSPAAASVAGVDEDDRLCFQAQELMFAYNISMVLRAA
IQLGLLDALSAAGGKALTPNELVENVETSSNKAEAAAAVDRILRYLSC
FNVVTCSSEAAGPDGTLVRRYTTGPLCRWLTKDRGDGTLSPFAVFVVD
PDHLFPWHHIAEAVTAGGPSAFERTQKWPYYEYMGKNQRLGTLFDNAM
AQHSVILVTKMLERFKGFDGVQRLVDVGGGTGSTLGMITSKYKHMTGI
NYDLPHVIAQGLPLPGVEHVAGDMYESIPTGDAVLLQWITLMLNDDEF
VKILSNCHNALPKDGKVIVVDGILPENPDSSLTARDAFTLDIIMFVLF
KGAKQRTEKEFARLAKQAGFTGGIKKTYIFFNFYALEFTK

SEQ.ID NO: 62
ATGAACACCTTCAGAACAGCCACTGCCAGAGACATACCTGATGTAGCA
GCAACTCTTACGGAAGCCTTCGCAACTGATCCACCCACGCAGTGGGTG
TTCCCCGACGGTACTGCCGCCGTCAGCAGGTTCTTTACACATGTTGCA
GATAGGGTTCACACGGCCGGTGGTATTGTTGAGCTACTACCAGACAGA
GCCGCCATGATTGCATTGCCACCACACGTGAGGCTGCCAGGAGAAGCT
GCCGACGGAAGGCAGGCGGAAATTCAGAGAAGGCTGGCAGACAGGCAC
CCGCTGACACCTCACTACTACCTGCTGTTTTACGGAGTTAGAACGGCA
CACCAGGGTTCGGGATTGGCGGAAGAATGCTGGCCAGATTAACTAGC
AGAGCTGATAGGGACAGGGTGGGTACATATACTGAGGCATCCACCTGG
CGTGGCGCTAGACTGATGCTGAGACATGGATTCCATGCTACAAGGCCA
CTAAGATTGCCAGATGGACCCAGCATGTTTCCACTTTGGAGAGATCCA
ATCCATGATCATTCTGATTAG

SEQ.ID NO: 63
MNTFRTATARDIPDVAATLTEAFATDPPTQWVFPDGTAAVSRFFTHVA
DRVHTAGGIVELLPDRAAMIALPPHVRLPGEAADGRQAEIQRRLADRH
PLTPHYYLLFYGVRTAHQGSGLGGRMLARLTSRADRDRVGTYTEASTW
RGARLMLRHGFHATRPLRLPDGPSMFPLWRDPIHDHSD

SEQ.ID NO: 64
ATGAAAGGATATTTCGGACCATACGGTGGCCAGTACGTACCAGAAATA
TTAATGGGTGCCTTAGAGGAGTTAGAGGCAGCATACGAGGAGATTATG
AAGGATGAGAGCTTCTGGAAGGAGTTCAACGATCTACTGAGGGATTAC
GCAGGCAGACCAACGCCATTGTACTTTGCCAGGAGATTGTCTGAGAAG
TACGGCGCCCGTGTTTACTTGAAGCGTGAGGATCTGCTGCACACTGGA
GCACACAAGATAAATAACGCTATCGGACAGGTTTTATTGGCCAAATTA
ATGGGGAAGACACGTATCATAGCCGAGACGGGAGCTGGGCAGCATGGA
GTCGCTACTGCTACCGCTGCTGCCCTGTTCGGAATGGAATGTGTGATC
TACATGGGTGAAGAGGACACAATCAGACAGAAGTTGAACGTGGAGCGT
ATGAAATTATTAGGGGCTAAAGTTGTCCCTGTTAAGTCTGGCAGTAGG
ACCTTGAAGGATGCGATAGACGAGGCTTTGAGAGACTGGATTACTAAT
TTACAGACAACATATTATGTTATCGGATCTGTTGTTGGTCCCCACCCT
TACCCAATTATCGTAAGGAATTTCCAGAAAGGTTATCGGTGAGGAGACC
AAGAAGCAAATACCAGAAAAGGAAGGTCGTTTGCCAGACTATATAGTT

GCCTGCGTAGGCGGCGGTAGCAATGCCGCAGGTATATTTTACCCATTC
ATAGACTCTGGAGTAAAGCTGATAGGTGTTGAGGCAGGTGGCGAGGGA
TTGGAGACAGGTAAACACGCAGCCTCGTTATTAAAGGGTAAAATTGGC
TATTTACATGGATCGAAGACCTTTGTTCTACAAGATGACTGGGGTCAA
GTCCAAGTGAGCCATTCGGTGTCAGCTGGTCTTGACTATTCAGGAGTA
GGACCTGAGCATGCTTATTGGAGAGAGACAGGGAAGGTTCTGTACGAC
GCAGTGACTGACGAAGAGGCTTTGGACGCATTTATAGAGTTATCAAGA
CTAGAGGGCATTATACCCGCTTTAGAGTCATCGCATGCTCTAGCATAT
TTGAAGAAGATAAATATAAAAGGTAAGGTTGTGGTGGTCAACCTATCA
GGGAGAGGGGATAAAGACCTGGAGTCAGTCTTAAACCATCCATACGTG
AGAGAAAGAATTAGATGA

SEQ.ID NO: 65
MKGYFGPYGGQYVPEILMGALEELEAAYEEIMKDESFWKEFNDLLRDY
AGRPTPLYFARRLSEKYGARVYLKREDLLHTGAHKINNAIGQVLLAKL
MGKTRIIAETGAGQHGVATATAAALFGMECVIYMGEEDTIRQKLNVER
MKLLGAKVVPVKSGSRTLKDAIDEALRDWITNLQTTYYVIGSVVGPHP
YPIIVRNFQKVIGEETKKQIPEKEGRLPDYIVACVGGGSNAAGIFYPF
IDSGVKLIGVEAGGEGLETGKHAASLLKGKIGYLHGSKTFVLQDDWGQ
VQVSHSVSAGLDYSGVGPEHAYWRETGKVLYDAVTDEEALDAFIELSR
LEGIIPALESSHALAYLKKINIKGKVVVVNLSGRGDKDLESVLNHPYV
RERIR

SEQ.ID NO: 66
ATGTGGTTCGGTGAGTTTGGTGGACAATATGTGCCAGAGACTTTAGTG
GGTCCTCTTAAGGAATTGGAAAAGGCATATAAAAGGTTCAAGGACGAT
GAGGAGTTCAACAGGCAACTAAACTATTATTTGAAGACATGGGCCGGT
AGACCAACGCCCTTGTATTATGCTAAGAGGTTAACTGAAAAGATTGGC
GGCGCGAAAGTGTATCTGAAAAGAGAAGACCTAGTTCATGGTGGAGCA
CACAAGACAAATAATGCCATTGGACAAGCACTATTGGCAAAGCTAATG
GGTAAAACTAGATTGATAGCTGAGACAGGAGCGGGTCAACATGGGGTC
GCGACAGCGATGGCTGGTGCACTACTGGGGATGAAGGTAGATATTTAC
ATGGGTGCTGAGGACGTTGAGCGTCAGAAACTAAATGTCTTCAGGATG
AAGCTATTAGGTGCCAATGTTATACCTGTAAATTCTGGCTCAAGAACA
CTAAAGGACGCCTTCGACGAGGCTCTTAGAGACTGGGTTGCCACTTTC
GAGTATACTCATTACTTGATCGGTTCAGTGGTTGGACCACATCCATAC
CCAACCATCGTTAGGGACTTTCAGAGCGTGATTGGTAGAGAGGCTAAG
GCACAGATCTTAGAAGCAGAGGGACAGCTACCTGACGTCATAGTTGCC
TGCGTCGGCGGTGGCTCTAACGCAATGGGTATATTCTATCCATTCGTT
AATGACAAGAAGGTTAAATTAGTAGGAGTCGAAGCTGGCGGAAAGGGG
TTAGAGTCGGGTAAACACTCAGCAAGCTTAAATGCAGGACAGGTAGGG
GTGTCCCACGCATGTTGTCGTATTTCTTGCAAGACGAGGAAGGTCAG
ATAAAGCCAAGTCATTCAATTGCTCCAGGCCTTGACCACCCCGGTGTT
GGTCCAGAGCACGCTTACTTAAAGAAGATTCAAAGGGCCGAGTACGTC

-continued

GCTGTAACAGACGAAGAGGCATTGAAAGCTTTCCATGAGCTATCCAGA

ACTGAGGGGATTATACCCGCCCTTGAGTCTGCCCATGCTGTGGCGTAC

GCCATGAAGTTAGCTAAAGAGATGTCCCGTGACGAAATCATCATTGTA

AATCTATCAGGGAGAGGAGACAAGGATTTGGACATTGTATTGAAGGCA

AGCGGAAATGTTTGA

SEQ.ID NO: 67
MWFGEFGGQYVPETLVGPLKELEKAYKRFKDDEEFNRQLNYYLKTWAG

RPTPLYYAKRLTEKIGGAKVYLKREDLVHGGAHKTNNAIGQALLAKLM

GKTRLIAETGAGQHGVATAMAGALLGMKVDIYMGAEDVERQKLNVFRM

KLLGANVIPVNSGSRTLKDAFDEALRDWVATFEYTHYLIGSVVGPHPY

PTIVRDFQSVIGREAKAQILEAEGQLPDVIVACVGGGSNAMGIFYPFV

NDKKVKLVGVEAGGKGLESGKHSASLNAGQVGVSHGMLSYFLQDEEGQ

IKPSHSIAPGLDHPGVGPEHAYLKKIQRAEYVAVTDEEALKAFHELSR

TEGIIPALESAHAVAYAMKLAKEMSRDEIIIVNLSGRGDKDLDIVLKA

SGNV

SEQ.ID NO: 68
ATGTGGTTTGGGGAATTCGGTGGTCAATACGTGCCAGAAACCTTAGTT

GGGCCTTTAAAGGAGCTTGAGAAAGCTTACAAAAGATTTAAGGACGAC

GAGGAGTTTAATAGGCAATTAAACTATTACTTGAAGACTTGGGCAGGT

AGACCAACACCACTTTATTACGCGAAGAGACTTACAGAGAAGATCGGT

GGCGCTAAGGTTTATTTGAAGCGTGAGGATTTGGTTCATGGTGGAGCA

CATAAGACAAACAATGCCATCGGGCAAGCCTTGTTGGCCAAATTGATG

GGTAAGACTAGGTTGATAGCTGGCACAGGTGCCGGCCAGCATGGCGTT

GCAACAGCAATGGCTGGTGCTCTTTTAGGGATGAAGGTGGATATCTAT

ATGGGCGCCGAGGACGTTGAAAGACAAAAGCTTAACGTATTCAGAATG

AAGTTATTAGGTGCGAATGTTATTCCAGTGAATTCAGGTTCCAGGACG

CTGAAGGACGCAATAGACGAAGCCTTGAGAGACTGGGTTGCTACTTTT

GAGTACACACATTATTTGATTGGTTCCGTGGTTGGACCCCACCCGTAC

CCTACAATAGTTAGAGATTTTCAATCTGTTATCGGTAGAGAGGCGAAG

GCTCAAATTCCAGAGGCCGAGGACAGCTACCCGATGTTATAGTCGCC

TGCGTTGGAGGAGGATCAAATGCGATGGGAATCTTCTACCCTTTTGTA

AATGATAAGAAAGTTAAGTTAGTCGGAGTTGAGGCCGGTGGTAAGGGG

CTAGAAAGCGGCAAACACTCGGCATCTCTTAATGCCGGTCAAGTAGGA

GTAAGTCACGGGATGTTATCTTACTTCTTGCAGGATGAGGAAGGTCAA

ATTAAGCCATCTCATTCTATAGCCCCAGGATTAGACTATCCCGGTGTT

GGGCCTGAGCACGCTTATCTGAAGAAGATACAGCGTGCTGAGTACGTT

GCAGTAACTGATGAAGAGGCTTTGAAGGCTTTTCACGAGTTATCAAGA

ACTGAGGGAATAATTCCTGCCTTGGAATCGGCACATGCGGTTGCCTAC

GCCATGAAGCTTGCTAAGGAAATGTCAAGAGACGAAATCATTATAGTG

AATTTATCGGAAGGGGCGATAAGGACTTGGACATTGTTTTAAAAGCA

AGTGGCAATGTATAA

SEQ.ID NO: 69
MWFGEFGGQYVPETLVGPLKELEKAYKRFKDDEEFNRQLNYYLKTWAG

RPTPLYYAKRLTEKIGGAKVYLKREDLVHGGAHKTNNAIGQALLAKLM

GKTRLIAGTGAGQHGVATAMAGALLGMKVDIYMGAEDVERQKLNVFRM

KLLGANVIPVNSGSRTLKDAIDEALRDWVATFEYTHYLIGSVVGPHPY

PTIVRDFQSVIGREAKAQIPEAEGQLPDVIVACVGGGSNAMGIFYPFV

NDKKVKLVGVEAGGKGLESGKHSASLNAGQVGVSHGMLSYFLQDEEGQ

IKPSHSIAPGLDYPGVGPEHAYLKKIQRAEYVAVTDEEALKAFHELSR

TEGIIPALESAHAVAYAMKLAKEMSRDEIIIVNLSGRGDKDLDIVLKA

SGNV

SEQ.ID NO: 70
ATGTGGTTTGGTGAGTTTGGTGGTCAGTATGTGCCTGAGACGCTAGTT

GGGCCACTGAAGGAGTTAGAGAAAGCGTACAAGAGATTCAAAGATGAC

GAGGAGTTTAACCGTCAGTTGAATTATTATCTTAAGACGTGGGCTGGT

AGGCCGACCCCTCTATACTACGCTAAGCGTTTAACCGAAAAGATAGGT

GGCGCCAAGATCTATCTGAAGAGAGAGGACCTAGTCCACGGCGGGGCT

CACAAAACTAACAACGCAATTGGTCAGGCACCATTAGCAAAGTTAATG

GGCAAAACACGTCTAATTGCCGAAACTGGTGCTGGTCAACATGGAGTT

GCTACGGCAATGGCGGGCGCACTGTTAGGTATGAAAGTGGATATCTAT

ATGGGAGCAGAAGACGTGGAGAGACAGAAGATGAACGTGTTCCGTATG

AAACTATTGGGAGCTAATGTTATCCCGGTTAACTCTGGCTCAAGAACT

GCAAAGGACGCCATAAACGAAGCTTTGAGGGATTGGGAAGCCACATTC

GAGTACACACACTACCTTATAGGCTCAGTCGTAGGCCCGCATCCCTAC

CCCACCATAGTTCGTGACTTCCAGAGTGTTATTGGCCGTGAGGCCAAG

GCACAGATCTTGGAAGCTGAAGGTCAATTGCCTGACGTAATAGTTGCA

TGTGTGGGTGGCGGTTCTAACGCTATGGGTATATTCTACCCCCTTCGTG

AACGATAAGAAAGTAAAGCTAGTTGGAGTGGAAGCAGGTGGCAAAGGG

TTGGAGTCGGGCAAGCACTCAGCCTCATTAAACGCAGGTCAGGTAGGC

GTTCTGCACGGTATGTTATCCTATTTCTTACAGGACGAGGAAGGCCAA

ATCAAACCATCGCACTCAATCGCACCTGGTTTAGATTACCCAGGAGTC

GGTCCCGAGCACGCATATTTAAAGAAAATCCAGAGAGCAGAGTACGTC

ACGGTGACGGATGAGGAAGCCCTTAAAGCGTTTCACGAGCTGTCGAGG

ACCGAGGGCATAATACCTGCTCTTGAAAGTGCCCACGCAGTTGCCTAT

GCTATGAAGTTGGCCAAGGAGATGAGTAGAGACGAGATTATCATAGTA

AATCTGTCAGGCAGAGGTGACAAGGATCTTGACATAGTCCTTAAGGCG

AGCGGTAATGTTTTGGAGTAA

SEQ.ID NO: 71
MWFGEFGGQYVPETLVGPLKELEKAYKRFKDDEEFNRQLNYYLKTWAG

RPTPLYYAKRLTEKIGGAKIYLKREDLVHGGAHKTNNAIGQAPLAKLM

GKTRLIAETGAGQHGVATAMAGALLGMKVDIYMGAEDVERQKMNVFRM

KLLGANVIPVNSGSRTAKDAINEALRDWEATFEYTHYLIGSVVGPHPY

PTIVRDFQSVIGREAKAQILEAEGQLPDVIVACVGGGSNAMGIFYPFV

-continued

NDKKVKLVGVEAGGKGLESGKHSASLNAGQVGVLHGMLSYFLQDEEGQ
IKPSHSIAPGLDYPGVGPEHAYLKKIQRAEYVTVTDEEALKAFHELSR
TEGIIPALESAHAVAYAMKLAKEMSRDEIIIVNLSGRGDKDLDIVLKA
SGNVLE

SEQ. ID NO: 72
ATGTGGTTCGGAGAGTTCGGCGGGCAGTACGTCCCAGAAACGCTAGTC
GGCCCACTGAAGGAGCTGGAGAAAGCATACAAAAGATTCAAGGATGAC
GAGGAGTTCAACAGGCAATTAAACTATTACCTAAAGACCTGGGCTGGT
AGGCCCACCCCTTTATACTATGCAAAACGTTTAACGGAGAAAATCGGT
GGCGCAAAAGTGTACTTGAAGAGAGAAGACTTAGTCCACGGTGGTGCT
CATAAAACTAACAACGCTATAGGGCAGGCACTTTTAGCTAAGTTGATG
GGTAAAACGAGGTTGATTGCGGGTACCGGTGCCGGTCAACATGGCGTT
GCTACGGCAATGGCGGGAGCCCTATTGGGCATGAAGGTTGACATTTAT
ATGGGCGCTGAGGACGTGGAACGTCAGAAACTGAACGTCTATCGTATG
AAATTGCTTGGTGCCAACGTTATACCAGTCAATTCCGGCTCGCGTACG
GTTAAAGACGCTTTCGATGAGGCACTATGTGATAGAGTTGCCACTTTC
GAATACACCCACTATCTTATTGGTACTGTCTGGGGTCCACATCCGTAT
CCAACTATTGTAAGGGACTTCCAGACTGTTATCGGAAGAGAGGCAAAG
GCCCAAATATTAGAGGCTGAGGGAAGGTTACCCGACGCCATTGTTGCA
TGCGTAGGCGGTGGTAGTAACGCAATGGGTATTTTCTATCCCTTCGTT
AACGATAAGAAGGTTAAGTTAGTGGGTGTCGAGGCCGGTGGTAAGGGG
CTTGAGTCCGGTAAACATTCCGCATCTTTGAATGCTGGGCAAGTAGGT
GTCAGTCATGGAATGTTATCATACTTTCTACAGGACGAGGAAGGACAG
ATAAAACCTTCTCATTCTATAGCGCCAGGTCTTGACCACCCTGGCGTT
GGACCAGAGCATGCTTATTTGAAGAAGATCCAGAGAGCTGAATATGTA
GCTGTTACGGATGAGGAAGCTCTAAAGGCGTTCCACGAGTTAAGTAGG
ACTGAGGGAATTATACCGGCATTAGAGTCTGCCCACGCTGTAGCTTAC
GCAATGAAGCTGGCCAAAGAGATGAGCCGTGACGAGATCATCATCGTA
AACTTGTCTGGCAGAGGCGATAAGGACCTAGACATCGTATTAAAGGCC
TCGGGGAACGTCCTAGAGTAG

SEQ. ID NO: 73
MWFGEFGGQYVPETLVGPLKELEKAYKRFKDDEEFNRQLNYYLKTWAG
RPTPLYYAKRLTEKIGGAKVYLKREDLVHGGAHKTNNAIGQALLAKLM
GKTRLIAGTGAGQHGVATAMAGALLGMKVDIYMGAEDVERQKLNVYRM
KLLGANVIPVNSGSRTVKDAFDEALCDRVATFEYTHYLIGTVWGPHPY
PTIVRDFQTVIGREAKAQILEAEGRLPDAIVACVGGGSNAMGIFYPFV
NDKKVKLVGVEAGGKGLESGKHSASLNAGQVGVSHGMLSYFLQDEEGQ
IKPSHSIAPGLDHPGVGPEHAYLKKIQRAEYVAVTDEEALKAFHELSR
TEGIIPALESAHAVAYAMKLAKEMSRDEIIIVNLSGRGDKDLDIVLKA
SGNVLE

SEQ. ID NO: 74
GTATCCGGCTGTTCCTTCATAGCCCTTTCAATGAACGTTGCAGCCCTT
TGAAGATTGGCCATTTTGTCAGGACTCGAGCCTGACAGTTGGACCAAC
GCAACTTTAATTTTTTGTGAAAGAATCTTCGAAGCACTCATACTGGCG
ATCTTCACGCCCTCCTGCTATTACAAAAGCTGTGTTTTTACAAGAATC
AAATTAAGTTAGCAAGATATTATACAACATTATTGATAATTTCAATAT
CGTGTTCGTACCTGATGACGTATCTGTGCATTGATAAGGCCCGCATGG
TTTCAGAAAGCAGAGCGGAACGATTCCAAATTAGTGGCCTTGTGCTTT
GCATGTCAATTGTGTTACCTTCAGCTCGTGGATTTGTTTTATCAATAC
ACAGTCTACAGTCAAGAATTTTTTTTATCAAATTTTGCGTTCGAGCGT
ATAAAATAGCCGCTGTAGCTACTTAAGTTCCTGTTCAGCGATAGTTTT
TTTCCATCACACGTACTATGGCAATTAAGTCCTCAGCGAGCTCGCATG
GAATGCGTGCGATGAGCGACCTCATGCTATACCTGAGAAAGCAACCTG
ACCTACAGGAAAGAGTTACTCAAGAATAAGAATTTTCGTTTTAAAACC
TAAGAGTCACTTTAAAATTTGTATACACTTATTTTTTTTATAACTTAT
TTAATAATAAAAATCATAAATCATAAGAAATTCGCTTATTTAGAAGTG
TCAACAACGTATCTACCAACGGAATGCGTGCGATTCAGGCGTAGTCTG
GAACGTCGTATGGGTATGGACCAGAGACGGATTGAGAAACTTGTTCGG
TTCTTGGGACGAATCTACATTGGAATGGAACTGGGTGCCTGAAGAAAC
CAGTGGTGAAATCAGCTGGGATGTCAATTGGCTTACCGTTTTGGTCAA
CTGGTCTTTCAATGTTGAAAGCAGACAACAAAGTAGCACCGGCAATCC
AAACAGTAGATTGAGCTAGGTGAATACCTGGGCAGTTTCTTCTACCGT
AACCGAAAGCAGCCTTTCTTGGGTCTCTAACAGTGTTGTCTGGTTTAC
CATCAGGACCCAAGTATCTTTCTGGACGGAAAACGGATGGATCTGGAT
AGACTTCTGGGTCATTCAAAACTGCCCAGGTGTTAGCAAAAACCAATG
TGTTCTTTGGAATCAAATAACCTCTGTAAACATCATCCTTCATCAATT
TATGAGGGATGGCTAATGGAGCAATTTGGTTCCATCTGAATAATTCCT
TGATACAAGCGGTCAAATATGGGAGTGAGTCGTCTTCCTCATCGTAGT
CAGGGATTTGACCGTTGTTGGTCAAAGCATCCAATTCAGCTTGAACCT
TTCTTTGCACTTCTGGGTATTTAACCATGGCCAATATGAAAGCGGACA
TAGCAGAGACGGTAGTGTCGCCACCACCAACGTTAACTTCAGCAGCAG
TGTTCTTGATAACATGTTCTTGGTGTTCTAAATCACCGTTCAAGTCCA
TAGCTTGTAATCTAGCAGAAGCGTAAGATGGTCTGGTTAGACCTTGTG
GAGCCAACTTTCTCATAGTTTCGTATGGCATGTCAACCATGTGGTCAG
CGGCTTCTCTCCAGACCTTGGCCTTACGCTTGAAGACGGCACCTGGGA
ACCAAGCTGGCAAGTACTTCAAAGATGGGAAGGAGTCAACCCAGAACT
TACCTGGAACACTAGCAATGGCCAAACCTTCGTTGGCTAAGTGGGTAG
CTTCTAACCATGGGTCATCTTCGGCTAGATCGATACCGTAACCAATGT
CCAAAGACATAGCAGCGATTTGATGTCTGATGTGTTGAGCCCACCGGT
CCGGAGTCTTGGTCAATTGTTGAACCAATTGGTGAGCAGCCTTGACTT
GAGCGTGTCTGAATTGCTTGATACCCTTTTCAGAGAATTCCTTAGCAA

```
ACATTCTTCTTTCTTCTCTCCAACGGTCACCGTAAGTGATAAAACCCA
GATCAAATTCCCAACCCATCAATTCATTGACCATAGTGGATTCCAATC
TACCGGAGTAGATGGAACCACGTTTTTCCAAGAGATCCGTGATAGTTT
CCAAGGTGTTTAAAATGACCATTTCGGTACCACCAGCATCTACGTACA
AGATATCAGTGTTGTAGTCACGACCCCATTGCAAGAAAGTCAACCATG
GAGATTCTTCTGGCATGTCAACATGTTACCAATAAATGGGATTGGAA
TTCCTGGTGGACCAGGTGGCAATCTGGATCTACGAACTCTTCTGGAGA
CGATGTAGTAAATACAACCAGCAATGACGAAAGAGAACAAGACAGCAA
TCATTGTTTTATATTTGTTGTAAAAGTAGATAATTACTTCCTTGATG
ATCTGTAAAAAGAGAAAAGAAAGCATCTAAGAACTTGAAAAACTAC
GAATTAGAAAAGACCAAATATGTATTTCTTGCATTGACCAATTTATGC
AAGTTTATATATATGTAAATGTAAGTTTCACGAGGTTCTACTAAACTA
AACCACCCCCTTGGTTAGAAGAAAAGAGTGTGTGAGAACAGGCTGTTG
TTGTCACACGATTCGGACAATTCTGTTTGAAAGAGAGAGTAACAGT
ACGATCGAACGAACTTTGCTCTGGAGATCACAGTGGGCATCATAGCAT
GTGGTACTAAACCCTTTCCCGCCATTCCAGAACCTTCGATTGCTTGTT
ACAAAACCTGTGAGCCGTCGCTAGGACCTTGTTGTGTGACGAAATTGG
AAGCTGCAATCAATAGGAAGACAGGAAGTCGAGCGTGTCTGGGTTTTT
TCAGTTTTGTTCTTTTTGCAAACAACAGTTTATTCCTGGCATCCACTA
AATATAATGGAGCCCGCTTTTTAAGCTGGCATCCAGAAAAAAAAAGAA
TCCCAGCACCAAAATATTGTTTTCTTCACCAACCATCAGTTCATAGGT
CCATTCTCTTAGCGCAACTACAGAGAACAGGGGCACAAACAGGCAAAA
AACGGGCACAACCTCAATGGAGTGATGCAACCTGCCTGGAGTAAATGA
TGACACAAGGCAATTGACCCACGCATGTATCTATCTCATTTTCTTACA
CCTTCTATTACCTTCTGCTCTCTCTGATTTGGAAAAAGCTGAAAAAAA
AGGTTGAAACCAGTTCCCTGAAATTATTCCCCTACTTGACTAATAAGT
ATATAAAGACGGTAGGTATTGATTGTAATTCTGTAAATCTATTTCTTA
AACTTCTTAAATTCTACTTTTATAGTTAGTCTTTTTTTTAGTTTTAAA
ACACCAAGAACTTAGTTTCGAATAAACACACATAAACAAACAAAATGG
CTTCTAGTTCTTCCGATGTCTTCGTTTTGGGTCTAGGTGTTGTTTTGG
CTGCCTTGTATATCTTCAGAGACCAATTATTCGCTGCTTCTAAGCCAA
AGGTGGCTCCAGTTTCCACTACGAAGCCTGCCAACGGTTCCGCTAACC
CAAGAGACTTCATCGCCAAGATGAAACAAGGTAAGAAGAGAATCGTAA
TCTTCTACGGTTCTCAAACTGGTACCGCTGAAGAATATGCTATTCGTT
TGGCTAAGGAAGCTAAGCAAAAGTTCGGTCTAGCCTCCTTGGTTTGTG
ATCCAGAAGAATACGATTTTGAAAAGTTGGACCAATTGCCAGAAGATT
CTATTGCTTTCTTCGTCGTTGCTACCTATGGTGAAGGTGAACCTACAG
ACAACGCTGTCCAATTGTTGCAAAACTTGCAAGATGAAAGCTTCGAAT
TCTCCTCTGGTGAGAGAAGTTGTCAGGTTTGAAGTACGTTGTTTTTG
GTCTGGGTAACAAGACCTACGAACATTACAACCTCATTGGGAGAACTG
```

```
TTGACGCTCAATTGGCCAAGATGGGTGCTATCAGAATCGGTGAAAGAG
GTGAAGGTGATGATGACAAGTCCATGGAAGAAGACTACTTGGAATGGA
AGGATGGTATGTGGGAAGCGTTTGCCACTGCTATGGGTGTTGAAGAAG
GTCAAGGTGGTGACTCCGCTGATTTCGTCGTTTCCGAATTGGAATCTC
ACCCACCAGAAAAGGTTTACCAAGGTGAATTTTCTGCTAGAGCTTTAA
CCAAAACCAAGGGTATTCACGACGCTAAGAATCCTTTTGCTGCTCCAA
TTGCGGTTGCTAGAGAATTGTTCCAATCTGTTGTCGATAGAAACTGTG
TCCACGTCGAATTCAACATTGAAGGCTCTGGTATCACCTATCAACACG
GTGACCACGTTGGTTTGTGGCCATTGAATCCAGATGTTGAAGTCGAAC
GGTTGTTGTGTGTTTTAGGTTTAGCTGAAAAGAGAGATGCTGTCATCT
CCATTGAATCCTTAGACCCGGCTTTGGCTAAGGTTCCATTCCCAGTCC
CAACTACTTACGGTGCTGTGTTGAGACACTACATTGACATCTCTGCTG
TCGCCGGTAGACAAATCTTGGGTACTTTGTCCAAATTCGCTCCAACCC
CAGAAGCTGAAGCTTTCTTGAGAAACTTGAACACTAACAAGGAAGAAT
ACCACAACGTCGTCGCTAACGGTTGTTTGAAATTGGGTGAAATTTTGC
AAATCGCTACCGGTAACGACATTACTGTCCCACCAACTACTGCCAACA
CCACCAAATGGCCAATTCCATTCGACATCATTGTTTCTGCCATCCCAA
GATTGCAACCAAGATACTACTCTATCTCTTCTTCCCCAAAAATTCATC
CAAACACCATCCACGCTACCGTTGTTGTGCTCAAATACGAAAACGTTC
CAACCGAACCAATCCCAAGAAAGTGGGTTTACGGTGTCGGTAGTAACT
TCTTGTTGAATTTAAAGTACGCTGTTAACAAGGAACCAGTTCCATACA
TCACTCAAAATGGCGAACAAAGAGTCGGTGTCCCGGAATACTTGATTG
CTGGTCCACGTGGTTCTTACAAGACTGAATCTTTCTACAAGGCTCCAA
TCCATGTTAGACGTTCTACTTTCCGTTTGCCAACCAACCCAAAGTCTC
CAGTCATCATGATTGGTCCAGGTACTGGTGTCGCCCCATTCAGAGGCT
TCGTTCAAGAAAGAGTTGCCTTGGCCAGAAGATCCATCGAAAAGAACG
GTCCTGACTCTTTGGCTGACTGGGGTCGTATTTCCTTGTTCTACGGTT
GTAGAAGATCCGACGAAGACTTCTTGTACAAGGACGAATGGCCACAAT
ACGAAGCTGAGTTGAAGGGTAAGTTCAAGTTGCACTGTGCTTTCTCCA
GACAAAACTACAAGCCAGACGGTTCTAAGATTTACGTCCAAGATTTGA
TCTGGGAAGACAGAGAACACATTGCCGATGCCATCTTAAACGGTAAGG
GTTACGTCTACATCTGCGGTGAAGCTAAGTCCATGTCTAAACAAGTTG
AAGAAGTTCTAGCCAAGATCTTGGGCGAAGCCAAAGGTGGTTCCGGTC
CAGTTGAAGGTGTTGCTGAAGTCAAGTTACTGAAGGAACGGTCCAGAT
TGATGTTGGATGTCTGGTCTGAACAAAAGTTAATTTCTGAAGAAGATT
TGGAATGAATCGCGTGCATTCATCCGCTCTAACCGAAAAGGAAGGAGT
TAGACAACCTGAAGTCTAGGTCCCTATTTATTTTTTATAGTTATGTT
AGTATTAAGAACGTTATTTATATTTCAAATTTTTCTTTTTTTCTGTA
CAGACGCGTGTACGCATGTAACATTATACTGAAAACCTTGCTTGAGAA
GGTTTTGGGACGCTCGAAGATCGCGTCCCAATTCGCCCTATAGTGAGT
CGTATTACGCGCGCTCACTGGCCGTCGTTTTACAACGTCGTGACTGGG
```

```
AAAACCCTGGCGTTACCCCTGCAGGACTAGTGCTGAGGCATTAATAGT

TTACTCAATTCTTGAAGCCAATTTGTACAATTCCCCATTAGAGTCAAA

TAAAAGGATGCCTCACGGAGGTATGTTACCCGCGCTATTTCACATGGC

TCATTGAATTAGAGGTGGAATTTGGTGTACCCTCCCCTCCTCATCTGA

TGAAGTAGTGATCCGACAATTCTTAAAAGTTGTAGACATTACTTTTAC

CACCAACTAAGTTGTATTTATATTGCTACCCTTATCCTTTTATATCTA

ACTAGCGCTCATAAGGTTGGGGCAATACTAAAACTGTGTTCTTATTCA

ACTCATTAAATACGTGGCAGTACGTACCCTATTAGAAACAATAGGAAA

CAGCAGAGTCGGAAGAAGCCAAATGCCAGATTTGAAGTCCAAAACCTT

GTCAAGCCAATCTTTGGGAGCGGCTATTCCTCCAGAAATTGTGTACCA

AATACTTACATACCAGTTTAGGGATTTGTTAAGAAATGACCATCCAGG

TACGGCAGAAA
```

SEQ.ID NO: 75
```
CAATCTGGCGGCTTGAGTTCTCAACATGTTTTATTTTTTACTTATATT

GCTGGTAGGGTAAAAAAATATAACTCCTAGGAATAGGTTGTCTATATG

TTTTTGTCTTGCTTCTATAATTGTAACAAACAAGGAAAGGGAAAATAC

TGGGTGTAAAAGCCATTGAGTCAAGTTAGGTCATCCCTTTTATACAAA

ATTTTTCAATTTTTTTTCCAAGATTCTTGTACGATTAATTATTTTTT

TTTGCGTCCTACAGCGTGATGAAAATTTCGCCTGCTGCAAGATGAGCG

GGAACGGGCGAAATGTGCACGCGCACAACTTACGAAACGCGGATGAGT

CACTGACAGCCACCGCAGAGGTTCTGACTCCTACTGAGCTCTATTGGA

GGTGGCAGAACCGGTACCGGAGGAGGCCGCTATAACCGGTTTGAATTT

ATTGTCACAGTGTCACATCAGCATTAAGTCCTCAGCGAGCTCGCATGG

AATGCGTGCGATGAGCGACCTCATGCTATACCTGAGAAAGCAACCTGA

CCTACAGGAAAGAGTTACTCAAGAATAAGAATTTTCGTTTTAAAACCT

AAGAGTCACTTTAAAATTTGTATACACTTATTTTTTTTATAACTTATT

TAATAATAAAAATCATAAATCATAAGAAATTCGCTTATTTAGAAGTGT

CAACAACGTATCTACCAACGGAATGCGTGCGATTCAGGTGGAGTCCAA

ACCCAACAAAGGATTTGGAATTGGCTTACCGGCAGTGGAGGATTCCTT

TAGCAACGTGGAAGTGATTTCACCGTTGTCGTTGTTACCTCTAGCATC

GTGGAAAGCAGCAACACCCTTCTTAACAAAGTTGATTCTTTCTTCTTC

AGAACCCCATTGCATGAAGTCAGTCCACATAACAATGTGAGCGGCGAT

ACCAGCGGTAACCTTGGCGTAGTTGATGGAATGCTTGGAAGTACGGGC

GTAAGATTGCAAGTAAGCTTGTCTCATGGTTGTACCAACTTGTTCGTC

TTGGAATCTGCTAATCAAGTAACAGTCACCCAAGAAGTAACCCAAATC

CAATGAAGCTGGACCGTACTTACACAATTCCCAGTCTAAGATGTAGAT

CTTTTGCAACTTAGATGGGTTACCTTCTTCAAGTTGCAACAAGATGTT

CCCAGACCACAAGTCAGCCATGACCAAAGTTTCTTCGGAGTGCATAAC

ATCGTCAACTAGATCCTTGACAACAGTTGGCAACAATGGATCATCGAC

GCCGTATTTAGCGGCGTTTGGGATAATAGTTTGGTACAATTGGTCAGA

GGTGGTTCTACCGACAATGTTACCAGAGAAGAACTTGAATTCTGGGTC

GTCTCTTCTTTCTCTACCTATGTTGTGCAATCTGGCGACGAAACCACC

AATCTCGGTACCAACCAATCTAGCAATATCGGTAGCCAAAGGTGGCTT

AGCAGTAACGTAGTCTAATAAGGTCTTCATTTTACCGACATCTTGCAT

AATCAAAGCATTGTTTTCCAAGTCATAGTTGAGACCTTCTGGAACAGA

GACAATACCATCAACACCACCCAAAACTTCTCTGTTAGCCATCATCAA

CTTGATAGCTTGGTATTCGTAGACAGAACGTTCAACACCGATTTTGAA

ATCTTCATCAGTAGACATGTGTGGTTGAGCGTGCTTCAAAATGATAGA

AGTGTGACCTTGGTATGGAGCGTTCAATTTAATACGCCAGGTGACGTT

AACGAAACCACCGGATAATCTCTTGACACCAGAAGTGTCAACATCTAA

AGACAAATGCTTGGTCAAATAGGTGATTAAACCGTCTTCAGTCTTCAA

GTCAAAGGCCATTGTTTTATATTTGTTGTAAAAAGTAGATAATTACTT

CCTTGATGATCTGTAAAAAAGAGAAAAAGAAAGCATCTAAGAACTTGA

AAAACTACGAATTAGAAAAGACCAAATATGTATTTCTTGCATTGACCA

ATTTATGCAAGTTTATATATATGTAAATGTAAGTTTCACGAGGTTCTA

CTAAACTAAACCACCCCCTTGGTTAGAAGAAAAGAGTGTGTGAGAACA

GGCTGTTGTTGTCACACGATTCGGACAATTCTGTTTGAAAGAGAGAGA

GTAACAGTACGATCGAACGAACTTTGCTCTGGAGATCACAGTGGGCAT

CATAGCATGTGGTACTAAACCCTTTCCCGCCATTCCAGAACCTTCGAT

TGCTTGTTACAAAACCTGTGAGCCGTCGCTAGGACCTTGTTGTGTGAC

GAAATTGGAAGCTGCAATCAATAGGAAGACAGGAAGTCGAGCGTGTCT

GGGTTTTTTCAGTTTTGTTCTTTTTGCAAACAACAGTTTATTCCTGGC

ATCCACTAAATATAATGGAGCCCGCTTTTTAAGCTGGCATCCAGAAAA

AAAAAGAATCCCAGCACCAAAATATTGTTTTCTTCACCAACCATCAGT

TCATAGGTCCATTCTCTTAGCGCAACTACAGAGAACAGGGGCACAAAC

AGGCAAAAACGGGCACAACCTCAATGGAGTGATGCAACCTGCCTGGA

GTAAATGATGACAAGGCAATTGACCCACGCATGTATCTATCTCATT

TTCTTACACCTTCTATTACCTTCTGCTCTCTCTGATTTGGAAAAAGCT

GAAAAAAAAGGTTGAAACCAGTTCCCTGAAATTATTCCCCTACTTGAC

TAATAAGTATATAAAGACGGTAGGTATTGATTGTAATTCTGTAAATCT

ATTTCTTAAACTTCTTAAATTCTACTTTTATAGTTAGTCTTTTTTTA

GTTTTAAAACACCAAGAACTTAGTTTCGAATAAACACACATAAACAAA

CAAAATGCATATCAGAAACCCATATAGAACTCCAATTGACTACCAAGC

TTTGTCTGAAGCTTTCCCACCATTGAAGCCATTTGTTTCCGTTAACGC

TGATGGTACCTCCTCAGTTGACTTGACCATTCCAGAAGCCCAAAGAGC

TTTTACCGCTGCCCTTTTGCACAGAGACTTCGGCTTGACTATGACTAT

CCCAGAAGATCGTTTGTGTCCAACCGTTCCAAACAGATTGAACTACGT

TTTGTGGATTGAAGACATTTTCAACTACACCAACAAGACTTTGGGTTT

ATCTGACGACCGTCCAATCAAGGGTGTTGATATCGGTACCGGTGCTTC

TGCCATTTACCCAATGTTGGCTTGCGCCAGATTCAAGGCTTGGTCCAT

GGTTGGTACTGAAGTTGAAAGAAAGTGTATCGACACTGCTAGATTAAA
```

-continued
CGTTGTTGCTAACAACTTGCAAGATCGTCTATCCATCTTGGAAACCTC
TATTGACGGTCCAATTTTAGTCCCAATTTTCGAAGCTACCGAAGAATA
CGAATACGAATTCACCATGTGTAACCCACCTTTCTACGATGGTGCCGC
TGACATGCAAACTAGCGATGCTGCAAAGGGTTTTGGTTTCGGTGTCGG
TGCTCCACACTCTGGTACAGTCATCGAAATGTCTACTGAAGGTGGTGA
ATCCGCTTTCGTGGCTCAAATGGTTAGAGAATCTCTTAAGTTGAGAAC
CAGATGTAGATGGTACACTTCTAACTTAGGTAAGTTGAAATCTTTGAA
GGAAATTGTCGGTTTGTTGAAGGAATTAGAAATCTCTAATTACGCCAT
CAACGAATATGTCCAAGGTTCCACTAGAAGATACGCTGTCGCTTGGAG
TTTCACTGATATCCAATTGCCAGAAGAATTGTCCAGACCATCTAATCC
TGAATTGTCCTCTTTGTTCGACTACAAGGATGACGATGACAAATGAAT
CGCGTGCATTCATCCGCTCTAACCGAAAAGGAAGGAGTTAGACAACCT
GAAGTCTAGGTCCCTATTTATTTTTTATAGTTATGTTAGTATTAAGA
ACGTTATTTATATTTCAAATTTTTCTTTTTTTCTGTACAGACGCGTG
TACGCATGTAACATTATACTGAAAACCTTGCTTGAGAAGGTTTTGGGA
CGCTCGAAGATCGCGTACCCAATTCGCCCTATAGTGAGTCGTATTACG
CGCGCTCACTGGCCGTCGTTTTACAACGTCGTGACTGGGAAAACCCTG
GCGTTACCCCTGCAGGACTAGTGCTGAGGCATTAATGCAACTCAGAAG
TTTGACAGCAAGCAAGTTCATCATTCGAACTAGCCTTATTGTTTAGT
TCAGTGACAGCGAACTGCCGTACTCGATGCTTTATTTCTCACGGTAGA
GCGGAAGAACAGATAGGGGCAGCGTGAGAAGAGTTAGAAAGTAAATTT
TTATCACGTCTGAAGTATTCTTATTCATAGGAAATTTTGCAAGGTTTT
TTAGCTCAATAACGGGCTAAGTTATATAAGGTGTTCACGCGATTTTCT
TGTTATGTATACCTCTTCTCTGAGGAATGGTACTACTGTCCTGATGTA
GGCTCCTTAAATTGGTGGGCAAGAATAACTTATCGATATTTTGTATAT
TGGTCTTGGAGTTCACCACGTAATGCCTGTTTAAGACCATCAGTTAAC
TCTAGTATTATTTGGTCTTGGCTACTGGCCGTTTGCTATTATTCAAGT
CTTTTGTGCCTTCCCGTCGGGTAAGGGAGTTATTTAGGGATACAGAAT
CTAACGAAAACTAAATCTCAATGATTAACTCTATTTAATCCTTTTTG
AAAGGCAAAAGAGGTCCCTTGTTCACTTACAACGTTCTTAGCCAAATT
CGCTTATCACTTACTACTTCACGATATACAGAAGTAAAAACATATAAA
AAGATGTCTGTTTGTTTAGCCATCACAAAAGGTATCGCAG SEQ.ID NO: 76
TGTTTTATATTTGTTGTAAAAAGTAGATAATTACTTCCTTGATGATCT
GTAAAAAGAGAAAAGAAAGCATCTAAGAACTTGAAAAACTACGAAT
TAGAAAAGACCAAATATGTATTTCTTGCATTGACCAATTTATGCAAGT
TTATATATATGTAAATGTAAGTTTCACGAGGTTCTACTAAACTAAACC
ACCCCCTTGGTTAGAAGAAAAGAGTGTGTGAGAACAGGCTGTTGTTGT
CACACGATTCGGACAATTCTGTTTGAAAGAGAGAGAGTAACAGTACGA
TCGAACGAACTTTGCTCTGGAGATCACAGTGGGCATCATAGCATGTGG
TACTAAACCCTTTCCCGCCATTCCAGAACCTTCGATTGCTTGTTACAA -continued
AACCTGTGAGCCGTCGCTAGGACCTTGTTGTGTGACGAAATTGGAAGC
TGCAATCAATAGGAAGACAGGAAGTCGAGCGTGTCTGGGTTTTTTCAG
TTTTGTTCTTTTTGCAAACAACAGTTTATTCCTGGCATCCACTAAATA
TAATGGAGCCCGCTTTTTAAGCTGGCATCCAGAAAAAAAAAGAATCCC
AGCACCAAAATATTGTTTTCTTCACCAACCATCAGTTCATAGGTCCAT
TCTCTTAGCGCAACTACAGAGAACAGGGGCACAAACAGGCAAAAAACG
GGCACAACCTCAATGGAGTGATGCAACCTGCCTGGAGTAAATGATGAC
ACAAGGCAATTGACCCACGCATGTATCTATCTCATTTTCTTACACCTT
CTATTACCTTCTGCTCTCTCTGATTTGGAAAAAGCTGAAAAAAAAGGT
TGAAACCAGTTCCCTGAAATTATTCCCCTACTTGACTAATAAGTATAT
AAAGACGGTAGGTATTGATTGTAATTCTGTAAATCTATTTCTTAAACT
TCTTAAATTCTACTTTTATAGTTAGTCTTTTTTTTAGTTTTAAAACAC
CAAGAACTTAGTTTCGAATAAACACACATAAACAAACAAAGGATCCAT
GATGAAGTTCTGGAGAAAGTACACACAACAAGAAATGGATGAAAAGAT
TACTGAATCTTTGAAAAGACTTTGAACTACGATAACACTAAGACAAT
CGGTATTCCAGGTACTAAGTTGGATGATACAGTTTTCTATGATGATCA
TTCTTTCGTTAAGCATTCACCATACTTGAGAACTTTTATTCAAAACCC
AAACCATATCGGTTGTCATACTTATGATAAGGCTGATATCTTGTTCGG
TGGTACATTCGATATCGAAAGAGAATTAATCCAATTGTTAGCAATCGA
TGTTTTGAACGGTAACGATGAAGAATTTGATGGTTACGTTACTCAAGG
TGGTACAGAAGCTAACATCCAAGCAATGTGGGTTTACAGAAACTACTT
CAAGAAAGAAAGAAAGGCTAAGCATGAAGAAATCGCTATCATCACTTC
AGCAGATACACATTACTCTGCATACAAAGGTTCAGATTTGTTGAACAT
CGATATTATTAAGGTTCCAGTTGATTTTTATTCAAGAAAAATTCAAGA
AAATACATTGGATTCAATTGTTAAAGAAGCTAAAGAATTGGTAAAAA
GTACTTCATCGTTATCTCTAACATGGGTACTACAATGTTTGGTTCAGT
TGATGATCCAGATTTGTACGCTAACATCTTCGATAAGTACAATTTGGA
ATACAAAATTCATGTTGATGGTGCATTTGGTGGTTTTATATATCCAAT
TGATAATAAGGAATGTAAAACTGATTTCTCTAATAAGAACGTTTCTTC
AATCACATTAGATGGTCATAAGATGTTGCAAGCTCCATACGGTACTGG
TATCTTCGTTTCAAGAAGAATTTGATCCATAACACTTTGACAAAGGA
AGCAACTTACATCGAAAATTTGGATGTTACATTGTCTGGTTCAAGATC
TGGTTCAAATGCTGTTGCAATTTGGATGGTTTTAGCTTCTTATGGTCC
ATACGGTTGGATGAAAAGATTAATAAGTTGAGAAATAGAACTAAATG
GTTGTGTAAGCAATTGAACGATATGAGAATTAAATATTACAAAGAAGA
TTCAATGAATATTGTTACAATTGAAGAACAATATGTTAATAAGGAAAT
CGCTGAAAAGTACTTTTTAGTTCCAGAAGTTCATAACCCAACTAACAA
CTGGTACAAGATCGTTGTTATGGAACATGTTGAATTGGATATCTTGAA
CTCTTTGGTTTACGATTTGAGAAAGTTTAATAAGGAACATTTGAAGGC
AATGCATCATCATCATCATCATTAACCGCGGCTAGCTAAGATCCGCTC
TAACCGAAAAGGAAGGAGTTAGACAACCTGAAGTCTAGGTCCCTATTT

```
ATTTTTTTATAGTTATGTTAGTATTAAGAACGTTATTTATATTTCAAA
TTTTTCTTTTTTTTCTGTACAGACGCGTGTACGCATGTAACATTATAC
TGAAAACCTTGCTTGAGAAGGTTTTGGGACGCTCGAAGATCCAGCTGC
ATTAATGAATCGGCCAACGCGCGGGGAGAGGCGGTTTGCGTATTGGGC
GCTCTTCCGCTTCCTCGCTCACTGACTCGCTGCGCTCGGTCGTTCGGC
TGCGGCGAGCGGTATCAGCTCACTCAAAGGCGGTAATACGGTTATCCA
CAGAATCAGGGGATAACGCAGGAAAGAACATGTGAGCAAAAGGCCAGC
AAAAGGCCAGGAACCGTAAAAAGGCCGCGTTGCTGGCGTTTTTCCATA
GGCTCCGCCCCCCTGACGAGCATCACAAAAATCGACGCTCAAGTCAGA
GGTGGCGAAACCCGACAGGACTATAAAGATACCAGGCGTTTCCCCCTG
GAAGCTCCCTCGTGCGCTCTCCTGTTCCGACCCTGCCGCTTACCGGAT
ACCTGTCCGCCTTTCTCCCTTCGGGAAGCGTGGCGCTTTCTCATAGCT
CACGCTGTAGGTATCTCAGTTCGGTGTAGGTCGTTCGCTCCAAGCTGG
GCTGTGTGCACGAACCCCCCGTTCAGCCCGACCGCTGCGCCTTATCCG
GTAACTATCGTCTTGAGTCCAACCCGGTAAGACACGACTTATCGCCAC
TGGCAGCAGCCACTGGTAACAGGATTAGCAGAGCGAGGTATGTAGGCG
GTGCTACAGAGTTCTTGAAGTGGTGGCCTAACTACGGCTACACTAGAA
GAACAGTATTTGGTATCTGCGCTCTGCTGAAGCCAGTTACCTTCGGAA
AAAGAGTTGGTAGCTCTTGATCCGGCAAACAAACCACCGCTGGTAGCG
GTGGTTTTTTTGTTTGCAAGCAGCAGATTACGCGCAGAAAAAAAGGAT
CTCAAGAAGATCCTTTGATCTTTTCTACGGGGTCTGACGCTCAGTGGA
ACGAAAACTCACGTTAAGGGATTTTGGTCATGAGATTATCAAAAGGA
TCTTCACCTAGATCCTTTTAAATTAAAAATGAAGTTTTAAATCAATCT
AAAGTATATATGAGTAAACTTGGTCTGACAGTTACCAATGCTTAATCA
GTGAGGCACCTATCTCAGCGATCTGTCTATTTCGTTCATCCATAGTTG
CCTGACTCCCCGTCGTGTAGATAACTACGATACGGGAGGGCTTACCAT
CTGGCCCCAGTGCTGCAATGATACCGCGAGACCCACGCTCACCGGCTC
CAGATTTATCAGCAATAAACCAGCCAGCCGGAAGGGCCGAGCGCAGAA
GTGGTCCTGCAACTTTATCCGCCTCCATCCAGTCTATTAATTGTTGCC
GGGAAGCTAGAGTAAGTAGTTCGCCAGTTAATAGTTTGCGCAACGTTG
TTGCCATTGCTACAGGCATCGTGGTGTCACGCTCGTCGTTTGGTATGG
CTTCATTCAGCTCCGGTTCCCAACGATCAAGGCGAGTTACATGATCCC
CCATGTTGTGCAAAAAAGCGGTTAGCTCCTTCGGTCCTCCGATCGTTG
TCAGAAGTAAGTTGGCCGCAGTGTTATCACTCATGGTTATGGCAGCAC
TGCATAATTCTCTTACTGTCATGCCATCCGTAAGATGCTTTTCTGTGA
CTGGTGAGTACTCAACCAAGTCATTCTGAGAATAGTGTATGCGGCGAC
CGAGTTGCTCTTGCCCGGCGTCAATACGGGATAATACCGCGCCACATA
GCAGAACTTTAAAAGTGCTCATCATTGGAAAACGTTCTTCGGGGCGAA
AACTCTCAAGGATCTTACCGCTGTTGAGATCCAGTTCGATGTAACCCA
CTCGTGCACCCAACTGATCTTCAGCATCTTTTACTTTCACCAGCGTTT
```

```
CTGGGTGAGCAAAAACAGGAAGGCAAATGCCGCAAAAAAGGGAATAA
GGGCGACACGGAAATGTTGAATACTCATACTCTTCCTTTTTCAATATT
ATTGAAGCATTTATCAGGGTTATTGTCTCATGAGCGGATACATATTTG
AATGTATTTAGAAAAATAAACAAATAGGGGTTCCGCGCACATTTCCCC
GAAAAGTGCCACCTGAACGAAGCATCTGTGCTTCATTTTGTAGAACAA
AAATGCAACGCGAGAGCGCTAATTTTTCAAACAAAGAATCTGAGCTGC
ATTTTTACAGAACAGAAATGCAACGCGAAAGCGCTATTTTACCAACGA
AGAATCTGTGCTTCATTTTTGTAAAACAAAAATGCAACGCGAGAGCGC
TAATTTTTCAAACAAAGAATCTGAGCTGCATTTTTACAGAACAGAAAT
GCAACGCGAGAGCGCTATTTTACCAACAAAGAATCTATACTTCTTTTT
TGTTCTACAAAAATGCATCCCGAGAGCGCTATTTTTCTAACAAAGCAT
CTTAGATTACTTTTTTTCTCCTTTGTGCGCTCTATAATGCAGTCTCTT
GATAACTTTTTGCACTGTAGGTCCGTTAAGGTTAGAAGAAGGCTACTT
TGGTGTCTATTTTCTCTTCCATAAAAAAAGCCTGACTCCACTTCCCGC
GTTTACTGATTACTAGCGAAGCTGCGGGTGCATTTTTTCAAGATAAAG
GCATCCCCGATTATATTCTATACCGATGTGGATTGCGCATACTTTGTG
AACAGAAAGTGATAGCGTTGATGATTCTTCATTGGTCAGAAAATTATG
AACGGTTTCTTCTATTTTGTCTCTATATACTACGTATAGGAAATGTTT
ACATTTCGTATTGTTTTCGATTCACTCTATGAATAGTTCTTACTACA
ATTTTTTGTCTAAAGAGTAATACTAGAGATAAACATAAAAAATGTAG
AGGTCGAGTTTAGATGCAAGTTCAAGGAGCGAAAGGTGGATGGGTAGG
TTATATAGGGATATAGCACAGAGATATATAGCAAAGAGATACTTTTGA
GCAATGTTTGTGGAAGCGGTATTCGCAATATTTTAGTAGCTCGTTACA
GTCCGGTGCGTTTTTGGTTTTTTGAAAGTGCGTCTTCAGAGCGCTTTT
GGTTTTCAAAAGCGCTCTGAAGTTCCTATACTTTCTAGAGAATAGGAA
CTTCGGAATAGGAACTTCAAAGCGTTTCCGAAAACGAGCGCTTCCGAA
AATGCAACGCGAGCTGCGCACATACAGCTCACTGTTCACGTCGCACCT
ATATCTGCGTGTTGCCTGTATATATATATACATGAGAAGAACGGCATA
GTGCGTGTTTATGCTTAAATGCGTACTTATATGCGTCTATTTATGTAG
GATGAAAGGTAGTCTAGTACCTCCTGTGATATTATCCCATTCCATGCG
GGGTATCGTATGCTTCCTTCAGCACTACCCTTTAGCTGTTCTATATGC
TGCCACTCCTCAATTGGATTAGTCTCATCCTTCAATGCTATCATTTCC
TTTGATATTGGATCATACTAAGAAACCATTATTATCATGACATTAACC
TATAAAAATAGGCGTATCACGAGGCCCTTTCGTCTCGCGCGTTTCGGT
GATGACGGTGAAAACCTCTGACACATGCAGCTCCCGGAGACGGTCACA
GCTTGTCTGTAAGCGGATGCCGGGAGCAGACAAGCCCGTCAGGGCGCG
TCAGCGGGTGTTGGCGGGTGTCGGGGCTGGCTTAACTATGCGGCATCA
GAGCAGATTGTACTGAGAGTGCACCATATTTCACACCGCATAGATCCG
TCGAGTTCAAGAGAAAAAAAAGAAAAAGCAAAAGAAAAAAGGAAAG
CGCGCCTCGTTCAGAATGACACGTATAGAATGATGCATTACCTTGTCA
TCTTCAGTATCATACTGTTCGTATACATACTTACTGACATTCATAGGT
```

-continued

ATACATATATACACATGTATATATATCGTATGCTGCAGCTTTAAATAA

TCGGTGTCACTACATAAGAACACCTTTGGTGGAGGGAACATCGTTGGT

ACCATTGGGCGAGGTGGCTTCTCTTATGGCAACCGCAAGAGCCTTGAA

CGCACTCTCACTACGGTGATGATCATTCTTGCCTCGCAGACAATCAAC

GTGGAGGGTAATTCTGCTAGCCTCTGCAAAGCTTTCAAGAAAATGCGG

GATCATCTCGCAAGAGAGATCTCCTACTTTCTCCCTTTGCAAACCAAG

TTCGACAACTGCGTACGGCCTGTTCGAAAGATCTACCACCGCTCTGGA

AAGTGCCTCATCCAAAGGCGCAAATCCTGATCCAAACCTTTTTACTCC

ACGCACGGCCCCTAGGGCCTCTTTAAAAGCTTGACCGAGAGCAATCCC

GCAGTCTTCAGTGGTGTGATGGTCGTCTATGTGTAAGTCACCAATGCA

CTCAACGATTAGCGACCAGCCGGAATGCTTGGCCAGAGCATGTATCAT

ATGGTCCAGAAACCCTATACCTGTGTGGACGTTAATCACTTGCGATTG

TGTGGCCTGTTCTGCTACTGCTTCTGCCTCTTTTTCTGGGAAGATCGA

GTGCTCTATCGCTAGGGGACCACCCTTTAAAGAGATCGCAATCTGAAT

CTTGGTTTCATTTGTAATACGCTTTACTAGGGCTTTCTGCTCTGTCAT

CTTTGCCTTCGTTTATCTTGCCTGCTCATTTTTTAGTATATTCTTCGA

AGAAATCACATTACTTTATATAATGTATAATTCATTATGTGATAATGC

CAATCGCTAAGAAAAAAAAGAGTCATCCGCTAGGTGGAAAAAAAAAA

ATGAAAATCATTACCGAGGCATAAAAAAATATAGAGTGTACTAGAGGA

GGCCAAGAGTAATAGAAAAGAAAATTGCGGGAAAGGACTGTGTTATG

ACTTCCCTGACTAATGCCGTGTTCAAACGATACCTGGCAGTGACTCCT

AGCGCTCACCAAGCTCTTAAAACGGGAATTTATGGTGCACTCTCAGTA

CACGCGCCAGATCTGTTTAGCTTGCCTCGTCCCCGCCGGGTCACCCGG

CCAGCGACATGGAGGCCCAGAATACCCTCCTTGACAGTCTTGACGTGC

GCAGCTCAGGGGCATGATGTGACTGTCGCCCGTACATTTAGCCCATAC

ATCCCCATGTATAATCATTTGCATCCATACATTTTGATGGCCGCACGG

CGCGAAGCAAAAATTACGGCTCCTCGCTGCAGACCTGCGAGCAGGGAA

ACGCTCCCCTCACAGACGCGTTGAATTGTCCCCACGCCGCGCCCCTGT

AGAGAAATATAAAAGGTTAGGATTTGCCACTGAGGTTCTTCTTTCATA

TACTTCCTTTTAAAATCTTGCTAGGATACAGTTCTCACATCACATCCG

AACATAAACAACCATGGGTAAGGAAAAGACTCACGTTTCGAGGCCGCG

ATTAAATTCCAACATGGATGCTGATTTATATGGGTATAAATGGGCTCG

CGATAATGTCGGGCAATCAGGTGCGACAATCTATCGATTGTATGGGAA

GCCCGATGCGCCAGAGTTGTTTCTGAAACATGGCAAAGGTAGCGTTGC

CAATGATGTTACAGATGAGATGGTCAGACTAAACTGGCTGACGGAATT

TATGCCTCTTCCGACCATCAAGCATTTTATCCGTACTCCTGATGATGC

ATGGTTACTCACCACTGCGATCCCCGGCAAAACAGCATTCCAGGTATT

AGAAGAATATCCTGATTCAGGTGAAAATATTGTTGATGCGCTGGCAGT

GTTCCTGCGCCGGTTGCATTCGATTCCTGTTTGTAATTGTCCTTTTAA

CAGCGATCGCGTATTTCGTCTCGCTCAGGCGCAATCACGAATGAATAA

-continued

CGGTTTGGTTGATGCGAGTGATTTTGATGACGAGCGTAATGGCTGGCC

TGTTGAACAAGTCTGGAAAGAAATGCATAAGCTTTTGCCATTCTCACC

GGATTCAGTCGTCACTCATGGTGATTTCTCACTTGATAACCTTATTTT

TGACGAGGGGAAATTAATAGGTTGTATTGATGTTGGACGAGTCGGAAT

CGCAGACCGATACCAGGATCTTGCCATCCTATGGAACTGCCTCGGTGA

GTTTTCTCCTTCATTACAGAAACGGCTTTTTCAAAAATATGGTATTGA

TAATCCTGATATGAATAAATTGCAGTTTCATTTGATGCTCGATGAGTT

TTTCTAATCAGTACTGACAATAAAAAGATTCTTGTTTTCAAGAACTTG

TCATTTGTATAGTTTTTTTATATTGTAGTTGTTCTATTTTAATCAAAT

GTTAGCGTGATTTATATTTTTTTTCGCCTCGACATCATCTGCCCAGAT

GCGAAGTTAAGTGCGCAGAAAGTAATATCATGCGTCAATCGTATGTGA

ATGCTGGTCGCTATACTGCTGTCGATTCGATACTAACGCCGCCATCCA

GTGTCGAATTCGCCATTCAGGCTGCGCAACTGTTGGGAAGGGCGATCG

GTGCGGGCCTCTTCGCTATTACGCCAGCTGAATTGGAGCGACCTCATG

CTATACCTGAGAAAGCAACCTGACCTACAGGAAAGAGTTACTCAAGAA

TAAGAATTTTCGTTTTAAAACCTAAGAGTCACTTTAAAATTTGTATAC

ACTTATTTTTTTATAACTTATTTAATAATAAAAATCATAAATCATAA

GAAATTCGCTTATTTAGAAGTGTCAACAACGTATCTACCAACGATTTG

ACCCTTTTCCATCTTTTCGTAAATTTCTGGCAAGGTAGACAAGCCGAC

AACCTTGATTGGAGACTTGACCAAACCTCTGGCGAAGAATTGTTAATT

AAGAGCTCAGATCTTTTGCGGCCGC

SEQ.ID NO: 77

GTTTGCAAAAAGAACAAAACTGAAAAAACCCAGACACGCTCGACTTCC

TGTCTTCCTATTGATTGCAGCTTCCAATTTCGTCACACAACAAGGTCC

TAGCGACGGCTCACAGGTTTTGTAACAAGCAATCGAAGGTTCTGGAAT

GGCGGGAAAGGGTTTAGTACCACATGCTATGATGCCCACTGTGATCTC

CAGAGCAAAGTTCGTTCGATCGTACTGTTACTCTCTCTCTTTCAAACA

GAATTGTCCGAATCGTGTGACAACAACAGCCTGTTCTCACACACTCTT

TTCTTCTAACCAAGGGGGTGGTTTAGTTTAGTAGAACCTCGTGAAACT

TACATTTACATATATATAAACTTGCATAAATTTGGTCAATGCAAGAAAT

ACATATTTGGTCTTTTCTAATTCGTAGTTTTTCAAGTTCTTAGATGCT

TTCTTTTTCTCTTTTTTACAGATCATCAAGGAAGTAATTATCTACTTT

TTACAACAAATATAAAACA

SEQ.ID NO: 78

ACAGTTTATTCCTGGCATCCACTAAATATAATGGAGCCCGCTTTTTAA

GCTGGCATCCAGAAAAAAAAGAATCCCAGCACCAAAATATTGTTTTC

TTCACCAACCATCAGTTCATAGGTCCATTCTCTTAGCGCAACTACAGA

GAACAGGGGCACAAACAGGCAAAAAACGGGCACAACCTCAATGGAGTG

ATGCAACCTGCCTGGAGTAAATGATGACACAAGGCAATTGACCCACGC

ATGTATCTATCTCATTTCTTACACCTTCTATTACCTTCTGCTCTCTC

TGATTTGGAAAAAGCTGAAAAAAAAGGTTGAAACCAGTTCCCTGAAAT

TATTCCCCTACTTGACTAATAAGTATATAAAGACGGTAGGTATTGATT

GTAATTCTGTAAATCTATTTCTTAAACTTCTTAAATTCTACTTTTATA
GTTAGTCTTTTTTTTAGTTTTAAAACACCAAGAACTTAGTTTCGAATA
AACACACATAAACAAACAAA

SEQ.ID NO: 79
GCTGGATTGAGCTGAATGGTGCCAGGTCGAGGCTGGGAGGGAGACTAA
CTCGAAAGTGACGAAGACTCGAAAATTAAAAAAAAAGATACTGCAGAA
GGCAAGATTGAGAATGGAGTAAAGGCAGCGTGGGTCCCCTGTGGAAAC
CGCAGTTTTCCTGCGCCAAGTGGTACCGGTGCGAGTGCAGCAATTAAT
CTCTCGATATTTTCTTAGTATCTCTTTTTATATAAGAATATATTTTGG
AATTGGTAATGCTTATCTTCAATAGTTTCTTAGTTGAATGCACACTTA
AGAGCAAATTGGCCAAGGAGTTCTTCGTTCGCTTTAATTTATTTCCTG
GTTATTGTCAATTTATTCATCCCATCTCCCCAGGATAGAAGAAATTAG
TGTAATTTTGCTGACAATACATTTTAACGACGATAACAATAATAGCAA
TTAAATAAAATAGCACTACCACCACTCCACTGCTCGTTAGCTATTTCT
GTAAAATAAATAAAAAGATC

SEQ.ID NO: 80
ATTCGCGCTATCTCGATTTCTACCTATATAGTTAATCTCTGTACAAAA
ACAATCTTTCCAACTATCCATTAATCATAGTATATTATCAGCGTCGGC
GATTTTACCACGCTTGACAAAAGCCGCGGGCGGGATTCCTGTGGGTAG
TGGCACCGGCAGTTAATCTAATCAAAGGCGCTTGAAGGAAGAGATAGA
TAATAGAACAAAGCAATCGCCGCTTTGGACGGCAAATATGTTTATCCA
TTGGTGCGGTGATTGGATATGATTTGTCTCCAGTAGTATAAGCAAGCG
CCAGATCTGTTTACTGTAAAATTAAGTGAGTAATCTCGCGGGATGTAA
TGATTTAAGGGAATCTGGTTCAGGTTTTCACATATATTTGTATATAAG
GCCATTTGTAATTTCAATAGTTTTAGGATTTTTCCTTCTCCCAAAATA
CTCACTTACTGTGTTACATTACAGAAAGAACAGACAAGAAACCGTCAA
TAAGAAATATAACTAAGAACA

SEQ.ID NO: 81
TACCCATACGACGTTCCAGACTACGCC

SEQ.ID NO: 82
YPYDVPDYA

SEQ.ID NO: 83
GAACAAAAGTTAATTTCTGAAGAAGATTTGGAA

SEQ.ID NO: 84
EQKLISEEDL

SEQ.ID NO: 85
GACTACAAGGATGACGATGACAAA

SEQ.ID NO: 86
DYKDDDDK

SEQ.ID NO: 87
GGTAAGCCAATTCCAAATCCTTTGTTGGGTTTGGACTCCACC

SEQ.ID NO: 88
GKPIPNPLLGLDST

SEQ.ID NO: 89
CATCATCATCATCATCAT

SEQ.ID NO: 90
HHHHHH

SEQ.ID NO: 91
CAGGTGGCACTTTTCGGGGAAATGTGCGCGGAACCCCTATTTGTTTAT
TTTTCTAAATACATTCAAATATGTATCCGCTCATGAGACAATAACCCT
GATAAATGCTTCAATAATATTGAAAAAGGAAGAGTATGAGTATTCAAC
ATTTCCGTGTCGCCCTTATTCCCTTTTTTGCGGCATTTTGCCTTCCTG
TTTTTGCTCACCCAGAAACGCTGGTGAAAGTAAAAGATGCTGAAGATC
AGTTGGGTGCACGAGTGGGTTACATCGAACTGGATCTCAACAGCGGTA
AGATCCTTGAGAGTTTTCGCCCCGAAGAACGTTTTCCAATGATGAGCA
CTTTTAAAGTTCTGCTATGTGGCGCGGTATTATCCCGTATTGACGCCG
GGCAAGAGCAACTCGGTCGCCGCATACACTATTCTCAGAATGACTTGG
TTGAGTACTCACCAGTCACAGAAAAGCATCTTACGGATGGCATGACAG
TAAGAGAATTATGCAGTGCTGCCATAACCATGAGTGATAACACTGCGG
CCAACTTACTTCTGACAACGATCGGAGGACCGAAGGAGCTAACCGCTT
TTTTGCACAACATGGGGGATCATGTAACTCGCCTTGATCGTTGGGAAC
CGGAGCTGAATGAAGCCATACCAAACGACGAGCGTGACACCACGATGC
CTGTAGCAATGGCAACAACGTTGCGCAAACTATTAACTGGCGAACTAC
TTACTCTAGCTTCCCGGCAACAATTAATAGACTGGATGGAGGCGGATA
AAGTTGCAGGACCACTTCTGCGCTCGGCCCTTCCGGCTGGCTGGTTTA
TTGCTGATAAATCTGGAGCCGGTGAGCGTGGGTCTCGCGGTATCATTG
CAGCACTGGGGCCAGATGGTAAGCCCTCCCGTATCGTAGTTATCTACA
CGACGGGGAGTCAGGCAACTATGGATGAACGAAATAGACAGATCGCTG
AGATAGGTGCCTCACTGATTAAGCATTGGTAACTGTCAGACCAAGTTT
ACTCATATATACTTTAGATTGATTTAAAACTTCATTTTTAATTTAAAA
GGATCTAGGTGAAGATCCTTTTTGATAATCTCATGACCAAAATCCCTT
AACGTGAGTTTTCGTTCCACTGAGCGTCAGACCCCGTAGAAAAGATCA
AAGGATCTTCTTGAGATCCTTTTTTTCTGCGCGTAATCTGCTGCTTGC
AAACAAAAAAACCACCGCTACCAGCGGTGGTTTGTTTGCCGGATCAAG
AGCTACCAACTCTTTTTCCGAAGGTAACTGGCTTCAGCAGAGCGCAGA
TACCAAATACTGTTCTTCTAGTGTAGCCGTAGTTAGGCCACCACTTCA
AGAACTCTGTAGCACCGCCTACATACCTCGCTCTGCTAATCCTGTTAC
CAGTGGCTGCTGCCAGTGGCGATAAGTCGTGTCTTACCGGGTTGGACT
CAAGACGATAGTTACCGGATAAGGCGCAGCGGTCGGGCTGAACGGGGG
GTTCGTGCACACAGCCCAGCTTGGAGCGAACGACCTACACCGAACTGA
GATACCTACAGCGTGAGCTATGAGAAAGCGCCACGCTTCCCGAAGGGA
GAAAGGCGGACAGGTATCCGGTAAGCGGCAGGGTCGGAACAGGAGAGC
GCACGAGGGAGCTTCCAGGGGGAAACGCCTGGTATCTTTATAGTCCTG
TCGGGTTTCGCCACCTCTGACTTGAGCGTCGATTTTTGTGATGCTCGT
CAGGGGGCGGAGCCTATGGAAAAACGCCAGCAACGCGGCCTTTTTAC
GGTTCCTGGCCTTTTGCTGGCCTTTTGCTCACATGTTCTTTCCTGCGT

-continued

```
TATCCCCTGATTCTGTGGATAACCGTATTACCGCCTTTGAGTGAGCTG
ATACCGCTCGCCGCAGCCGAACGACCGAGCGCAGCGAGTCAGTGAGCG
AGGAAGCGGAAGAGCGCCCAATACGCAAACCGCCTCTCCCCGCGCGTT
GGCCGATTCATTAATGCAGCTGGATCTTCGAGCGTCCCAAAACCTTCT
CAAGCAAGGTTTTCAGTATAATGTTACATGCGTACACGCGTCTGTACA
GAAAAAAAGAAAAATTTGAAATATAAATAACGTTCTTAATACTAACA
TAACTATAAAAAATAAATAGGGACCTAGACTTCAGGTTGTCTAACTC
CTTCCTTTTCGGTTAGAGCGGATCTTAGCTAGCCGCGGTACCAAGCTG
GTGGATCCTTTGTTTGTTTATGTGTGTTTATTCGAAACTAAGTTCTTG
GTGTTTTAAAACTAAAAAAAAGACTAACTATAAAAGTAGAATTTAAGA
AGTTTAAGAAATAGATTTACAGAATTACAATCAATACCTACCGTCTTT
ATATACTTATTAGTCAAGTAGGGGAATAATTTCAGGGAACTGGTTTCA
ACCTTTTTTTTCAGCTTTTTCCAAATCAGAGAGAGCAGAAGGTAATAG
AAGGTGTAAGAAAATGAGATAGATACATGCGTGGGTCAATTGCCTTGT
GTCATCATTTACTCCAGGCAGGTTGCATCACTCCATTGAGGTTGTGCC
CGTTTTTTGCCTGTTTGTGCCCCTGTTCTCTGTAGTTGCGCTAAGAGA
ATGGACCTATGAACTGATGGTTGGTGAAGAAAACAATATTTTGGTGCT
GGGATTCTTTTTTTTTCTGGATGCCAGCTTAAAAAGCGGGCTCCATTA
TATTTAGTGGATGCCAGGAATAAACTGTTGTTTGCAAAAAGAACAAAA
CTGAAAAAACCCAGACACGCTCGACTTCCTGTCTTCCTATTGATTGCA
GCTTCCAATTTCGTCACACAACAAGGTCCTAGCGACGGCTCACAGGTT
TTGTAACAAGCAATCGAAGGTTCTGGAATGGCGGGAAAGGGTTTAGTA
CCACATGCTATGATGCCCACTGTGATCTCCAGAGCAAAGTTCGTTCGA
TCGTACTGTTACTCTCTCTTTCAAACAGAATTGTCCGAATCGTGTG
ACAACAACAGCCTGTTCTCACACACTCTTTTCTTCTAACCAAGGGGT
GGTTTAGTTTAGTAGAACCTCGTGAAACTTACATTTACATATATATAA
ACTTGCATAAATTGGTCAATGCAAGAAATACATATTTGGTCTTTTCTA
ATTCGTAGTTTTTCAAGTTCTTAGATGCTTTCTTTTTCTCTTTTTTAC
AGATCATCAAGGAAGTAATTATCTACTTTTTACAACAAATATAAAACA
GCGGCCGCAAAAGATCTGAGCTCTTAATTAACAATTCTTCGCCAGAGG
TTTGGTCAAGTCTCCAATCAAGGTTGTCGGCTTGTCTACCTTGCCAGA
AATTTACGAAAAGATGGAAAAGGGTCAAATCGTTGGTAGATACGTTGT
TGACACTTCTAAATAAGCGAATTTCTTATGATTTATGATTTTTATTAT
TAAATAAGTTATAAAAAAAATAAGTGTATACAAATTTTAAAGTGACTC
TTAGGTTTTAAAACGAAAATTCTTATTCTTGAGTAACTCTTTCCTGTA
GGTCAGGTTGCTTTCTCAGGTATAGCATGAGGTCGCTCCAATTCAGCT
GGCGTAATAGCGAAGAGGCCCGCACCGATCGCCCTTCCCAACAGTTGC
GCAGCCTGAATGGCGAATTCGCACTGGATGGCGGCGTTAGTATCGAA
TCGACAGCAGTATAGCGACCAGCATTCACATACGATTGACGCATGATA
TTACTTTCTGCGCACTTAACTTCGCATCTGGGCAGATGATGTCGAGGC
GAAAAAAATATAAATCACGCTAACATTTGATTAAAATAGAACAACTA
```

-continued

```
CAATATAAAAAAACTATACAAATGACAAGTTCTTGAAAACAAGAATCT
TTTTATTGTCAGTACTGATTAGAAAAACTCATCGAGCATCAAATGAAA
CTGCAATTTATTCATATCAGGATTATCAATACCATATTTTTGAAAAAG
CCGTTTCTGTAATGAAGGAGAAAACTCACCGAGGCAGTTCCATAGGAT
GGCAAGATCCTGGTATCGGTCTGCGATTCCGACTCGTCCAACATCAAT
ACAACCTATTAATTTCCCCTCGTCAAAAATAAGGTTATCAAGTGAGAA
ATCACCATGAGTGACGACTGAATCCGGTGAGAATGGCAAAAGCTTATG
CATTTCTTTCCAGACTTGTTCAACAGGCCAGCCATTACGCTCGTCATC
AAAATCACTCGCATCAACCAAACCGTTATTCATTCGTGATTGCGCCTG
AGCGAGACGAAATACGCGATCGCTGTTAAAAGGACAATTACAAACAGG
AATCGAATGCAACCGGCGCAGGAACACTGCCAGCGCATCAACAATATT
TTCACCTGAATCAGGATATTCTTCTAATACCTGGAATGCTGTTTTGCC
GGGGATCGCAGTGGTGAGTAACCATGCATCATCAGGAGTACGGATAAA
ATGCTTGATGGTCGGAAGAGGCATAAATTCCGTCAGCCAGTTTAGTCT
GACCATCTCATCTGTAACATCATTGGCAACGCTACCTTTGCCATGTTT
CAGAAACAACTCTGGCGCATCGGGCTTCCCATACAATCGATAGATTGT
CGCACCTGATTGCCCGACATTATCGCGAGCCCATTTATACCCATATAA
ATCAGCATCCATGTTGGAATTTAATCGCGGCCTCGAAACGTGAGTCTT
TTCCTTACCCATGGTTGTTTATGTTCGGATGTGATGTGAGAACTGTAT
CCTAGCAAGATTTTAAAAGGAAGTATATGAAAGAAGAACCTCAGTGGC
AAATCCTAACCTTTTATATTTCTACAGGGGCGCGGCGTGGGGACAA
TTCAACGCGTCTGTGAGGGGAGCGTTTCCCTGCTCGCAGGTCTGCAGC
GAGGAGCCGTAATTTTTGCTTCGCGCCGTGCGGCCATCAAAATGTATG
GATGCAAATGATTATACATGGGGATGTATGGGCTAAATGTACGGGCGA
CAGTCACATCATGCCCCTGAGCTGCGCACGTCAAGACTGTCAAGGAGG
GTATTCTGGGCCTCCATGTCGCTGGCCGGGTGACCCGGCGGGGACGAG
GCAAGCTAAACAGATCGGCGCGTGTACTGAGAGTGCACCATAAATTC
CCGTTTTAAGAGCTTGGTGAGCGCTAGGAGTCACTGCCAGGTATCGTT
TGAACACGGCATTAGTCAGGGAAGTCATAACACAGTCCTTTCCCGCAA
TTTTCTTTTTCTATTACTCTTGGCCTCCTCTAGTACACTCTATATTTT
TTTATGCCTCGGTAATGATTTTCATTTTTTTTTTCCACCTAGCGGAT
GACTCTTTTTTTTCTTAGCGATTGGCATTATCACATAATGAATTATA
CATTATATAAAGTAATGTGATTTCTTCGAAGAATATACTAAAAAATGA
GCAGGCAAGATAAACGAAGGCAAAGATGACAGAGCAGAAAGCCCTAGT
AAAGCGTATTACAAATGAAACCAAGATTCAGATTGCGATCTCTTTAAA
GGGTGGTCCCCTAGCGATAGAGCACTCGATCTTCCCAGAAAAGAGGC
AGAAGCAGTAGCAGAACAGGCCACACAATCGCAAGTGATTAACGTCCA
CACAGGTATAGGGTTTCTGGACCATATGATACATGCTCTGGCCAAGCA
TTCCGGCTGGTCGCTAATCGTTGAGTGCATTGGTGACTTACACATAGA
CGACCATCACACCACTGAAGACTGCGGGATTGCTCTCGGTCAAGCTTT
```

```
TAAAGAGGCCCTAGGGGCCGTGCGTGGAGTAAAAAGGTTTGGATCAGG

ATTTGCGCCTTTGGATGAGGCACTTTCCAGAGCGGTGGTAGATCTTTC

GAACAGGCCGTACGCAGTTGTCGAACTTGGTTTGCAAAGGGAGAAAGT

AGGAGATCTCTCTTGCGAGATGATCCCGCATTTTCTTGAAAGCTTTGC

AGAGGCTAGCAGAATTACCCTCCACGTTGATTGTCTGCGAGGCAAGAA

TGATCATCACCGTAGTGAGAGTGCGTTCAAGGCTCTTGCGGTTGCCAT

AAGAGAAGCCACCTCGCCCAATGGTACCAACGATGTTCCCTCCACCAA

AGGTGTTCTTATGTAGTGACACCGATTATTTAAAGCTGCAGCATACGA

TATATATACATGTGTATATATGTATACCTATGAATGTCAGTAAGTATG

TATACGAACAGTATGATACTGAAGATGACAAGGTAATGCATCATTCTA

TACGTGTCATTCTGAACGAGGCGCGCTTTCCTTTTTTCTTTTTGCTTT

TTCTTTTTTTTTCTCTTGAACTCGACGGATCTATGCGGTGTGAAATAT

GGTGCACTCTCAGTACAATCTGCTCTGATGCCGCATAGTTAAGCCAGC

CCCGACACCCGCCAACACCCGCTGACGCGCCCTGACGGGCTTGTCTGC

TCCCGGCATCCGCTTACAGACAAGCTGTGACCGTCTCCGGGAGCTGCA

TGTGTCAGAGGTTTTCACCGTCATCACCGAAACGCGCGAGACGAAAGG

GCCTCGTGATACGCCTATTTTTATAGGTTAATGTCATGATAATAATGG

TTTCTTAGTATGATCCAATATCAAAGGAAATGATAGCATTGAAGGATG

AGACTAATCCAATTGAGGAGTGGCAGCATATAGAACAGCTAAAGGGTA

GTGCTGAAGGAAGCATACGATACCCCGCATGGAATGGGATAATATCAC

AGGAGGTACTAGACTACCTTTCATCCTACATAAATAGACGCATATAAG

TACGCATTTAAGCATAAACACGCACTATGCCGTTCTTCTCATGTATAT

ATATATACAGGCAACACGCAGATATAGGTGCGACGTGAACAGTGAGCT

GTATGTGCGCAGCTCGCGTTGCATTTTCGGAAGCGCTCGTTTTCGGAA

ACGCTTTGAAGTTCCTATTCCGAAGTTCCTATTCTCTAGAAAGTATAG

GAACTTCAGAGCGCTTTTGAAAACCAAAAGCGCTCTGAAGACGCACTT

TCAAAAAACCAAAAACGCACCGGACTGTAACGAGCTACTAAAATATTG

CGAATACCGCTTCCACAAACATTGCTCAAAAGTATCTCTTTGCTATAT

ATCTCTGTGCTATATCCCTATATAACCTACCCATCCACCTTTCGCTCC

TTGAACTTGCATCTAAACTCGACCTCTACATTTTTTATGTTTATCTCT

AGTATTACTCTTTAGACAAAAAATTGTAGTAAGAACTATTCATAGAG

TGAATCGAAAACAATACGAAAATGTAAACATTTCCTATACGTAGTATA

TAGAGACAAAATAGAAGAAACCGTTCATAATTTTCTGACCAATGAAGA

ATCATCAACGCTATCACTTTCTGTTCACAAAGTATGCGCAATCCACAT

CGGTATAGAATATAATCGGGGATGCCTTTATCTTGAAAAAATGCACCC

GCAGCTTCGCTAGTAATCAGTAAACGCGGGAAGTGGAGTCAGGCTTTT

TTTATGGAAGAGAAAATAGACACCAAAGTAGCCTTCTTCTAACCTTAA

CGGACCTACAGTGCAAAAGTTATCAAGAGACTGCATTATAGAGCGCA

CAAAGGAGAAAAAAGTAATCTAAGATGCTTTGTTAGAAAAATAGCGC

TCTCGGGATGCATTTTTGTAGAACAAAAAGAAGTATAGATTCTTTGT

TGGTAAAATAGCGCTCTCGCGTTGCATTTCTGTTCTGTAAAATGCAG

CTCAGATTCTTTGTTTGAAAAATTAGCGCTCTCGCGTTGCATTTTTGT

TTTACAAAAATGAAGCACAGATTCTTCGTTGGTAAAATAGCGCTTTCG

CGTTGCATTTCTGTTCTGTAAAAATGCAGCTCAGATTCTTTGTTTGAA

AAATTAGCGCTCTCGCGTTGCATTTTTGTTCTACAAAATGAAGCACAG

ATGCTTCGTT

SEQ.ID NO: 92

GCTAACAGCGCGATTTGCTGGTGACCCAATGCGACCAGATGCTCCACG

CCCAGTCGCGTACCGTCTTCATGGGAGAAAATAATACTGTTGATGGGT

GTCTGGTCAGAGACATCAAGAAATAACGCCGGAACATTAGTGCAGGCA

GCTTCCACAGCAATGGCATCCTGGTCATCCAGCGGATAGTTAATGATC

AGCCCACTGACGCGTTGCGCGAGAAGATTGTGCACCGCCGCTTTACAG

GCTTCGACGCCGCTTCGTTCTACCATCGACACCACCACGCTGGCACCC

AGTTGATCGGCGCGAGATTTAATCGCCGCGACAATTTGCGACGGCGCG

TGCAGGGCCAGACTGGAGGTGGCAACGCCAATCAGCAACGACTGTTTG

CCCGCCAGTTGTTGTGCCACGCGGTTGGGAATGTAATTCAGCTCCGCC

ATCGCCGCTTCCACTTTTTCCCGCGTTTTCGCAGAAACGTGGCTGGCC

TGGTTCACCACGCGGGAAACGGTCTGATAAGAGACACCGGCATACTCT

GCGACATCGTATAACGTTACTGGTTTCACATTCACCACCCTGAATTGA

CTCTCTTCCGGGCGCTATCATGCCATACCGCGAAAGGTTTTGCGCCAT

TCGATGGTGTCCGGGATCTCGACGCTCTCCCTTATGCGACTCCTGCAT

TAGGAAGCAGCCCAGTAGTAGGTTGAGGCCGTTGAGCACCGCCGCCGC

AAGGAATGGTGCATGCAAGGAGATGGCGCCCAACAGTCCCCGGCCAC

GGGGCCTGCCACCATACCCACGCCGAAACAAGCGCTCATGAGCCCGAA

GTGGCGAGCCCGATCTTCCCCATCGGTGATGTCGGCGATATAGGCGCC

AGCAACCGCACCTGTGGCGCCGGTGATGCCGGCCACGATGCGTCCGGC

GTAGCCTAGGATCGAGATCGATCTCGATCCCGCGAAATTAATACGACT

CACTATAGGGAATTGTGAGCGGATAACAATTCCCCTCTAGAAATAAT

TTTGTTTAACTTTAAGAAGGAGATATACATATGGCAGATCTCAATTGG

ATATCGGCCGGCCACGCGATCGCTGACGTCGGTACCCTCGAGTCTGGT

AAAGAAACCGCTGCTGCGAAATTTGAACGCCAGCACATGGACTCGTCT

ACTAGTCGCAGCTTAATTAACCTAAACTGCTGCCACCGCTGAGCAATA

ACTAGCATAACCCCTTGGGGCCTCTAAACGGGTCTTGAGGGGTTTTTT

GCTAGCGAAAGGAGGAGTCGACACTGCTTCCGGTAGTCAATAAACCGG

TAAACCAGCAATAGACATAAGCGGCTATTTAACGACCCTGCCCTGAAC

CGACGACCGGGTCATCGTGGCCGGATCTTGCGGCCCCTCGGCTTGAAC

GAATTGTTAGACATTATTTGCCGACTACCTTGGTGATCTCGCCTTTCA

CGTAGTGGACAAATTCTTCCAACTGATCTGCGCGCGAGGCCAAGCGAT

CTTCTTCTTGTCCAAGATAAGCCTGTCTAGCTTCAAGTATGACGGGCT

GATACTGGGCCGGCAGGCGCTCCATTGCCCAGTCGGCAGCGACATCCT

TCGGCGCGATTTTGCCGGTTACTGCGCTGTACCAAATGCGGGACAACG

TAAGCACTACATTTCGCTCATCGCCAGCCCAGTCGGGCGGCGAGTTCC
```

```
ATAGCGTTAAGGTTTCATTTAGCGCCTCAAATAGATCCTGTTCAGGAA
CCGGATCAAAGAGTTCCTCCGCCGCTGGACCTACCAAGGCAACGCTAT
GTTCTCTTGCTTTTGTCAGCAAGATAGCCAGATCAATGTCGATCGTGG
CTGGCTCGAAGATACCTGCAAGAATGTCATTGCGCTGCCATTCTCCAA
ATTGCAGTTCGCGCTTAGCTGGATAACGCCACGGAATGATGTCGTCGT
GCACAACAATGGTGACTTCTACAGCGCGGAGAATCTCGCTCTCTCCAG
GGGAAGCCGAAGTTTCCAAAAGGTCGTTGATCAAAGCTCGCCGCGTTG
TTTCATCAAGCCTTACGGTCACCGTAACCAGCAAATCAATATCACTGT
GTGGCTTCAGGCCGCCATCCACTGCGGAGCCGTACAAATGTACGGCCA
GCAACGTCGGTTCGAGATGGCGCTCGATGACGCCAACTACCTCTGATA
GTTGAGTCGATACTTCGGCGATCACCGCTTCCCTCATACTCTTCCTTT
TTCAATATTATTGAAGCATTTATCAGGGTTATTGTCTCATGAGCGGAT
ACATATTTGAATGTATTTAGAAAAATAAACAAATAGCCAGCTCACTCG
GTCGCTACGCTCCGGGCGTGAGACTGCGGCGGGCGCTGCGGACACATA
CAAAGTTACCCACAGATTCCGTGGATAAGCAGGGGACTAACATGTGAG
GCAAAACAGCAGGGCCGCGCCGGTGGCGTTTTTCCATAGGCTCCGCCC
TCCTGCCAGAGTTCACATAAACAGACGCTTTTCCGGTGCATCTGTGGG
AGCCGTGAGGCTCAACCATGAATCTGACAGTACGGGCGAAACCCGACA
GGACTTAAAGATCCCCACCGTTTCCGGCGGGTCGCTCCCTCTTGCGCT
CTCCTGTTCCGACCCTGCCGTTTACCGGATACCTGTTCCGCCTTTCTC
CCTTACGGGAAGTGTGGCGCTTTCTCATAGCTCACACACTGGTATCTC
GGCTCGGTGTAGGTCGTTCGCTCCAAGCTGGGCTGTAAGCAAGAACTC
CCCGTTCAGCCCGACTGCTGCGCCTTATCCGGTAACTGTTCACTTGAG
TCCAACCCGGAAAAGCACGGTAAAACGCCACTGGCAGCAGCCATTGGT
AACTGGGAGTTCGCAGAGGATTTGTTTAGCTAAACACGCGGTTGCTCT
TGAAGTGTGCGCCAAAGTCCGGCTACACTGGAAGGACAGATTTGGTTG
CTGTGCTCTGCGAAAGCCAGTTACCACGGTTAAGCAGTTCCCCAACTG
ACTTAACCTTCGATCAAACCACCTCCCCAGGTGGTTTTTTCGTTTACA
GGGCAAAAGATTACGCGCAGAAAAAAAGGATCTCAAGAAGATCCTTTG
ATCTTTTCTACTGAACCGCTCTAGATTTCAGTGCAATTTATCTCTTCA
AATGTAGCACCTGAAGTCAGCCCCATACGATATAAGTTGTAATTCTCA
TGTTAGTCATGCCCCGCGCCCACCGGAAGGAGCTGACTGGGTTGAAGG
CTCTCAAGGGCATCGGTCGAGATCCCGGTGCCTAATGAGTGAGCTAAC
TTACATTAATTGCGTTGCGCTCACTGCCCGCTTTCCAGTCGGGAAACC
TGTCGTGCCAGCTGCATTAATGAATCGGCCAACGCGCGGGGAGAGGCG
GTTTGCGTATTGGGCGCCAGGGTGGTTTTTCTTTTCACCAGTGAGACG
GGCAACAGCTGATTGCCCTTCACCGCCTGGCCCTGAGAGAGTTGCAGC
AAGCGGTCCACGCTGGTTTGCCCCAGCAGGCGAAAATCCTGTTTGATG
GTGGTTAACGGCGGGATATAACATGAGCTGTCTTCGGTATCGTCGTAT
CCCACTACCGAGATGTCCGCACCAACGCGCAGCCCGGACTCGGTAATG
GCGCGCATTGCGCCCAGCGCCATCTGATCGTTGGCAACCAGCATCGCA
GTGGGAACGATGCCCTCATTCAGCATTTGCATGGTTTGTTGAAAACCG
GACATGGCACTCCAGTCGCCTTCCCGTTCCGCTATCGGCTGAATTTGA
TTGCGAGTGAGATATTTATGCCAGCCAGCCAGACGCAGACGCGCCGAG
ACAGAACTTAATGGGCCC
```
SEQ.ID NO: 93
```
GGGGAATTGTGAGCGGATAACAATTCCCCTCTAGAAATAATTTTGTTT
AACTTTAAGAAGGAGATATACATATGGCAGATCTCAATTGGATATCGG
CCGGCCACGCGATCGCTGACGTCGGTACCCTCGAGTCTGGTAAAGAAA
CCGCTGCTGCGAAATTTGAACGCCAGCACATGGACTCGTCTACTAGTC
GCAGCTTAATTAACCTAAACTGCTGCCACCGCTGAGCAATAACTAGCA
TAACCCCTTGGGGCCTCTAAACGGGTCTTGAGGGGTTTTTTGCTAGCG
AAAGGAGGAGTCGACTATATCCGGATTGGCGAATGGGACGCGCCCTGT
AGCGGCGCATTAAGCGCGGCGGGTGTGGTGGTTACGCGCAGCGTGACC
GCTACACTTGCCAGCGCCCTAGCGCCCGCTCCTTTCGCTTTCTTCCCT
TCCTTTCTCGCCACGTTCGCCGGCTTTCCCCGTCAAGCTCTAAATCGG
GGGCTCCCTTTAGGGTTCCGATTTAGTGCTTTACGGCACCTCGACCCC
AAAAAACTTGATTAGGGTGATGGTTCACGTAGTGGGCCATCGCCCTGA
TAGACGGTTTTTCGCCCTTTGACGTTGGAGTCCACGTTCTTTAATAGT
GGACTCTTGTTCCAAACTGGAACAACACTCAACCCTATCTCGGTCTAT
TCTTTTGATTTATAAGGGATTTTGCCGATTTCGGCCTATTGGTTAAAA
AATGAGCTGATTTAACAAAAATTTAACGCGAATTTTAACAAAATATTA
ACGTTTACAATTTCTGGCGGCACGATGGCATGAGATTATCAAAAAGGA
TCTTCACCTAGATCCTTTTAAATTAAAAATGAAGTTTTAAATCAATCT
AAAGTATATATGAGTAAACTTGGTCTGACAGTTACCAATGCTTAATCA
GTGAGGCACCTATCTCAGCGATCTGTCTATTTCGTTCATCCATAGTTG
CCTGACTCCCCGTCGTGTAGATAACTACGATACGGGAGGGCTTACCAT
CTGGCCCCAGTGCTGCAATGATACCGCGAGACCCACGCTCACCGGCTC
CAGATTTATCAGCAATAAACCAGCCAGCCGGAAGGGCCGAGCGCAGAA
GTGGTCCTGCAACTTTATCCGCCTCCATCCAGTCTATTAATTGTTGCC
GGGAAGCTAGAGTAAGTAGTTCGCCAGTTAATAGTTTGCGCAACGTTG
TTGCCATTGCTACAGGCATCGTGGTGTCACGCTCGTCGTTTGGTATGG
CTTCATTCAGCTCCGGTTCCCAACGATCAAGGCGAGTTACATGATCCC
CCATGTTGTGCAAAAAAGCGGTTAGCTCCTTCGGTCCTCCGATCGTTG
TCAGAAGTAAGTTGGCCGCAGTGTTATCACTCATGGTTATGGCAGCAC
TGCATAATTCTCTTACTGTCATGCCATCCGTAAGATGCTTTTCTGTGA
CTGGTGAGTACTCAACCAAGTCATTCTGAGAATAGTGTATGCGGCGAC
CGAGTTGCTCTTGCCCGGCGTCAATACGGGATAATACCGCGCCACATA
GCAGAACTTTAAAAGTGCTCATCATTGGAAAACGTTCTTCGGGGCGAA
AACTCTCAAGGATCTTACCGCTGTTGAGATCCAGTTCGATGTAACCCA
CTCGTGCACCCAACTGATCTTCAGCATCTTTTACTTTCACCAGCGTTT
```

-continued
CTGGGTGAGCAAAAACAGGAAGGCAAAATGCCGCAAAAAAGGGAATAA
GGGCGACACGGAAATGTTGAATACTCATACTCTTCCTTTTTCAATCAT
GATTGAAGCATTTATCAGGGTTATTGTCTCATGAGCGGATACATATTT
GAATGTATTTAGAAAAATAAACAAATAGGTCATGACCAAAATCCCTTA
ACGTGAGTTTTCGTTCCACTGAGCGTCAGACCCCGTAGAAAAGATCAA
AGGATCTTCTTGAGATCCTTTTTTTCTGCGCGTAATCTGCTGCTTGCA
AACAAAAAAACCACCGCTACCAGCGGTGGTTTGTTTGCCGGATCAAGA
GCTACCAACTCTTTTTCCGAAGGTAACTGGCTTCAGCAGAGCGCAGAT
ACCAAATACTGTCCTTCTAGTGTAGCCGTAGTTAGGCCACCACTTCAA
GAACTCTGTAGCACCGCCTACATACCTCGCTCTGCTAATCCTGTTACC
AGTGGCTGCTGCCAGTGGCGATAAGTCGTGTCTTACCGGGTTGGACTC
AAGACGATAGTTACCGGATAAGGCGCAGCGGTCGGGCTGAACGGGGGG
TTCGTGCACACAGCCCAGCTTGGAGCGAACGACCTACACCGAACTGAG
ATACCTACAGCGTGAGCTATGAGAAAGCGCCACGCTTCCCGAAGGGAG
AAAGGCGGACAGGTATCCGGTAAGCGGCAGGGTCGGAACAGGAGAGCG
CACGAGGGAGCTTCCAGGGGGAAACGCCTGGTATCTTTATAGTCCTGT
CGGGTTTCGCCACCTCTGACTTGAGCGTCGATTTTTGTGATGCTCGTC
AGGGGGGCGGAGCCTATGGAAAAACGCCAGCAACGCGGCCTTTTTACG
GTTCCTGGCCTTTTGCTGGCCTTTTGCTCACATGTTCTTTCCTGCGTT
ATCCCCTGATTCTGTGGATAACCGTATTACCGCCTTTGAGTGAGCTGA
TACCGCTCGCCGCAGCCGAACGACCGAGCGCAGCGAGTCAGTGAGCGA
GGAAGCGGAAGAGCGCCTGATGCGGTATTTTCTCCTTACGCATCTGTG
CGGTATTTCACACCGCATATATGGTGCACTCTCAGTACAATCTGCTCT
GATGCCGCATAGTTAAGCCAGTATACACTCCGCTATCGCTACGTGACT
GGGTCATGGCTGCGCCCCGACACCCGCCAACACCCGCTGACGCGCCCT
GACGGGCTTGTCTGCTCCCGGCATCCGCTTACAGACAAGCTGTGACCG
TCTCCGGGAGCTGCATGTGTCAGAGGTTTTCACCGTCATCACCGAAAC
GCGCGAGGCAGCTGCGGTAAAGCTCATCAGCGTGGTCGTGAAGCGATT
CACAGATGTCTGCCTGTTCATCCGCGTCCAGCTCGTTGAGTTTCTCCA
GAAGCGTTAATGTCTGGCTTCTGATAAAGCGGGCCATGTTAAGGGCGG
TTTTTTCCTGTTTGGTCACTGATGCCTCCGTGTAAGGGGGATTTCTGT
TCATGGGGGTAATGATACCGATGAAACGAGAGAGGATGCTCACGATAC
GGGTTACTGATGATGAACATGCCCGGTTACTGGAACGTTGTGAGGGTA
AACAACTGGCGGTATGGATGCGGCGGGACCAGAGAAAAATCACTCAGG
GTCAATGCCAGCGCTTCGTTAATACAGATGTAGGTGTTCCACAGGGTA
GCCAGCAGCATCCTGCGATGCAGATCCGGAACATAATGGTGCAGGGCG
CTGACTTCCGCGTTTCAGACTTTACGAAACACGGAAACCGAAGACCA
TTCATGTTGTTGCTCAGGTCGCAGACGTTTTGCAGCAGCAGTCGCTTC
ACGTTCGCTCGCGTATCGGTGATTCATTCTGCTAACCAGTAAGGCAAC
CCCGCCAGCCTAGCCGGGTCCTCAACGACAGGAGCACGATCATGCTAG
TCATGCCCCGCGCCCACCGGAAGGAGCTGACTGGGTTGAAGGCTCTCA -continued
AGGGCATCGGTCGAGATCCCGGTGCCTAATGAGTGAGCTAACTTACAT
TAATTGCGTTGCGCTCACTGCCCGCTTTCCAGTCGGGAAACCTGTCGT
GCCAGCTGCATTAATGAATCGGCCAACGCGCGGGGAGAGGCGGTTTGC
GTATTGGGCGCCAGGGTGGTTTTTCTTTTCACCAGTGAGACGGGCAAC
AGCTGATTGCCCTTCACCGCCTGGCCCTGAGAGAGTTGCAGCAAGCGG
TCCACGCTGGTTTGCCCCAGCAGGCGAAAATCCTGTTTGATGGTGGTT
AACGGCGGGATATAACATGAGCTGTCTTCGGTATCGTCGTATCCCACT
ACCGAGATGTCCGCACCAACGCGCAGCCCGGACTCGGTAATGGCGCGC
ATTGCGCCCAGCGCCATCTGATCGTTGGCAACCAGCATCGCAGTGGGA
ACGATGCCCTCATTCAGCATTTGCATGGTTTGTTGAAAACCGGACATG
GCACTCCAGTCGCCTTCCCGTTCCGCTATCGGCTGAATTTGATTGCGA
GTGAGATATTTATGCCAGCCAGCCAGACGCAGACGCGCCGAGACAGAA
CTTAATGGGCCCGCTAACAGCGCGATTTGCTGGTGACCCAATGCGACC
AGATGCTCCACGCCCAGTCGCGTACCGTCTTCATGGGAGAAAATAATA
CTGTTGATGGGTGTCTGGTCAGAGACATCAAGAAATAACGCCGGAACA
TTAGTGCAGGCAGCTTCCACAGCAATGGCATCCTGGTCATCCAGCGGA
TAGTTAATGATCAGCCCACTGACGCGTTGCGCGAGAAGATTGTGCACC
GCCGCTTTACAGGCTTCGACGCCGCTTCGTTCTACCATCGACACCACC
ACGCTGGCACCCAGTTGATCGGCGCGAGATTTAATCGCCGCGACAATT
TGCGACGGCGCGTGCAGGGCCAGACTGGAGGTGGCAACGCCAATCAGC
AACGACTGTTTGCCCGCCAGTTGTTGTGCCACGCGGTTGGGAATGTAA
TTCAGCTCCGCCATCGCCGCTTCCACTTTTTCCCGCGTTTTCGCAGAA
ACGTGGCTGGCCTGGTTCACCACGCGGGAAACGGTCTGATAAGAGACA
CCGGCATACTCTGCGACATCGTATAACGTTACTGGTTTCACATTCACC
ACCCTGAATTGACTCTCTTCCGGGCGCTATCATGCCATACCGCGAAAG
GTTTTGCGCCATTCGATGGTGTCCGGGATCTCGACGCTCTCCCTTATG
CGACTCCTGCATTAGGAAGCAGCCCAGTAGTAGGTTGAGGCCGTTGAG
CACCGCCGCCGCAAGGAATGGTGCATGCAAGGAGATGGCGCCCAACAG
TCCCCCGGCCACGGGCCTGCCACCATACCCACGCCGAAACAAGCGCT
CATGAGCCCGAAGTGGCGAGCCCGATCTTCCCCATCGGTGATGTCGGC
GATATAGGCGCCAGCAACCGCACCTGTGGCGCCGGTGATGCCGGCCAC
GATGCGTCCGGCGTAGCCTAGGATCGAGATCGATCTCGATCCCGCGAA
ATTAATACGACTCACTATA SEQ.ID NO: 94
ATCCGGATATAGTTCCTCCTTTCAGCAAAAAACCCCTCAAGACCCGTT
TAGAGGCCCCAAGGGGTTATGCTAGTTATTGCTCAGCGGTGGCAGCAG
CCAACTCAGCTTCCTTTCGGGCTTTGTTAGCAGCCGGATCTCAGTGGT
GGTGGTGGTGGTGCTCGAGTGCGGCCGCAAGCTTGTCGACGGAGCTCG
AATTCGGATCCGCGACCCATTTGCTGTCCACCAGTCATGCTAGCCATA
TGGCTGCCGCGCGGCACCAGGCCGCTGCTGTGATGATGATGATGATGG
CTGCTGCCCATGGTATATCTCCTTCTTAAAGTTAAACAAAATTATTTC

```
TAGAGGGGAATTGTTATCCGCTCACAATTCCCCTATAGTGAGTCGTAT
TAATTTCGCGGGATCGAGATCTCGATCCTCTACGCCGGACGCATCGTG
GCCGGCATCACCGGCGCCACAGGTGCGGTTGCTGGCGCCTATATCGCC
GACATCACCGATGGGGAAGATCGGGCTCGCCACTTCGGGCTCATGAGC
GCTTGTTTCGGCGTGGGTATGGTGGCAGGCCCCGTGGCCGGGGGACTG
TTGGGCGCCATCTCCTTGCATGCACCATTCCTTGCGCGGCGGTGCTC
AACGGCCTCAACCTACTACTGGGCTGCTTCCTAATGCAGGAGTCGCAT
AAGGGAGAGCGTCGAGATCCCGACACCATCGAATGGCGCAAAACCTT
TCGCGGTATGGCATGATAGCGCCCGGAAGAGAGTCAATTCAGGGTGGT
GAATGTGAAACCAGTAACGTTATACGATGTCGCAGAGTATGCCGGTGT
CTCTTATCAGACCGTTTCCCGCGTGGTGAACCAGGCCAGCCACGTTTC
TGCGAAAACGCGGGAAAAAGTGGAAGCGGCGATGGCGGAGCTGAATTA
CATTCCCAACCGCGTGGCACAACAACTGGCGGGCAAACAGTCGTTGCT
GATTGGCGTTGCCACCTCCAGTCTGGCCCTGCACGCGCCGTCGCAAAT
TGTCGCGGCGATTAAATCTCGCGCCGATCAACTGGGTGCCAGCGTGGT
GGTGTCGATGGTAGAACGAAGCGGCGTCGAAGCCTGTAAAGCGGCGT
GCACAATCTTCTCGCGCAACGCGTCAGTGGGCTGATCATTAACTATCC
GCTGGATGACCAGGATGCCATTGCTGTGGAAGCTGCCTGCACTAATGT
TCCGGCGTTATTTCTTGATGTCTCTGACCAGACACCCATCAACAGTAT
TATTTTCTCCCATGAAGACGGTACGCGACTGGGCGTGGAGCATCTGGT
CGCATTGGGTCACCAGCAAATCGCGCTGTTAGCGGGCCCATTAAGTTC
TGTCTCGGCGCGTCTGCGTCTGGCTGGCTGGCATAAATATCTCACTCG
CAATCAAATTCAGCCGATAGCGGAACGGGAAGGCGACTGGAGTGCCAT
GTCCGGTTTTCAACAAACCATGCAAATGCTGAATGAGGGCATCGTTCC
CACTGCGATGCTGGTTGCCAACGATCAGATGGCGCTGGGCGCAATGCG
CGCCATTACCGAGTCCGGGCTGCGCGTTGGTGCGGATATCTCGGTAGT
GGGATACGACGATACCGAAGACAGCTCATGTTATATCCCGCCGTTAAC
CACCATCAAACAGGATTTTCGCCTGCTGGGGCAAACCAGCGTGGACCG
CTTGCTGCAACTCTCTCAGGGCCAGGCGGTGAAGGGCAATCAGCTGTT
GCCCGTCTCACTGGTGAAAAGAAAAACCACCCTGGCGCCCAATACGCA
AACCGCCTCTCCCCGCGCGTTGGCCGATTCATTAATGCAGCTGGCACG
ACAGGTTTCCCGACTGGAAAGCGGGCAGTGAGCGCAACGCAATTAATG
TAAGTTAGCTCACTCATTAGGCACCGGGATCTCGACCGATGCCCTTGA
GAGCCTTCAACCCAGTCAGCTCCTTCCGGTGGGCGCGGGGCATGACTA
TCGTCGCCGCACTTATGACTGTCTTCTTTATCATGCAACTCGTAGGAC
AGGTGCCGGCAGCGCTCTGGGTCATTTTCGGCGAGGACCGCTTTCGCT
GGAGCGCGACGATGATCGGCCTGTCGCTTGCGGTATTCGGAATCTTGC
ACGCCCTCGCTCAAGCCTTCGTCACTGGTCCCGCCACCAAACGTTTCG
GCGAGAAGCAGGCCATTATCGCCGGCATGGCGGCCCCACGGGTGCGCA
TGATCGTGCTCCTGTCGTTGAGGACCCGGCTAGGCTGGCGGGGTTGCC
```

```
TTACTGGTTAGCAGAATGAATCACCGATACGCGAGCGAACGTGAAGCG
ACTGCTGCTGCAAAACGTCTGCGACCTGAGCAACAACATGAATGGTCT
TCGGTTTCCGTGTTTCGTAAAGTCTGGAAACGCGGAAGTCAGCGCCCT
GCACCATTATGTTCCGGATCTGCATCGCAGGATGCTGCTGGCTACCCT
GTGGAACACCTACATCTGTATTAACGAAGCTTACCCTCACAACGTTCC
AGTAACCGGGCATGTTCATCATCAGTAACCCGTATCGTGAGCATCCTC
TCTCGTTTCATCGGTATCATTACCCCCATGAACAGAAATCCCCCTTAC
ACGGAGGCATCAGTGACCAAACAGGAAAAAACCGCCCTTAACATGGCC
CGCTTTATCAGAAGCCAGACATTAACGCTTCTGGAGAAACTCAACGAG
CTGGACGCGGATGAACAGGCAGACATCTGTGAATCGCTTCACGACCAC
GCTGATGAGCTTTACCGCAGCTGCCTCGCGCGTTTCGGTGATGACGGT
GAAAACCTCTGACACATGCAGCTCCCGGAGACGGTCACAGCTTGTCTG
TAAGCGGATGCCGGGAGCAGACAAGCCCGTCAGGGCGCGTCAGCGGGT
GTTGGGGGGTGTCGGGGCGCAGCCATGACCCAGTCACGTAGCGATAGC
GGAGTGTATACTGGCTTAACTATGCGGCATCAGAGCAGATTGTACTGA
GAGTGCACCATATATGCGGTGTGAAATACCGCACAGATGCGTAAGGAG
AAAATACCGCATCAGGCGCTCTTCCGCTTCCTCGCTCACTGACTCGCT
GCGCTCGGTCGTTCGGCTGCGGCGAGCGGTATCAGCTCACTCAAAGGC
GGTAATACGGTTATCCACAGAATCAGGGGATAACGCAGGAAAGAACAT
GTGAGCAAAAGGCCAGCAAAAGGCCAGGAACCGTAAAAAGGCCGCGTT
GCTGGCGTTTTTCCATAGGCTCCGCCCCCCTGACGAGCATCACAAAAA
TCGACGCTCAAGTCAGAGGTGGCGAAACCCGACAGGACTATAAAGATA
CCAGGCGTTTCCCCCTGGAAGCTCCCTCGTGCGCTCTCCTGTTCCGAC
CCTGCCGCTTACCGGATACCTGTCCGCCTTTCTCCCTTCGGGAAGCGT
GGCGCTTTCTCATAGCTCACGCTGTAGGTATCTCAGTTCGGTGTAGGT
CGTTCGCTCCAAGCTGGGCTGTGTGCACGAACCCCCCGTTCAGCCCGA
CCGCTGCGCCTTATCCGGTAACTATCGTCTTGAGTCCAACCCGGTAAG
ACACGACTTATCGCCACIGGCAGCAGCCACTGGTAACAGGATTAGCAG
AGCGAGGTATGTAGGCGGTGCTACAGAGTTCTTGAAGTGGTGGCCTAA
CTACGGCTAC
ACTAGAAGGACAGTATTTGGTATCTGCGCTCTGCTGAAGCCAGTTACC
TTCGGAAAAAGAGTTGGTAGCTCTTGATCCGGCAAACAAACCACCGCT
GGTAGCGGTGGTTTTTTTGTTTGCAAGCAGCAGATTACGCGCAGAAAA
AAAGGATCTCAAGAAGATCCTTTGATCTTTTCTACGGGGTCTGACGCT
CAGTGGAACGAAAACTCACGTTAAGGGATTTTGGTCATGAACAATAAA
ACTGTCTGCTTACATAAACAGTAATACAAGGGGTGTTATGAGCCATAT
TCAACGGGAAACGTCTTGCTCTAGGCCGCGATTAAATTCCAACATGGA
TGCTGATTTATATGGGTATAAATGGGCTCGCGATAATGTCGGGCAATC
AGGTGCGACAATCTATCGATTGTATGGGAAGCCCGATGCGCCAGAGTT
GTTTCTGAAACATGGCAAAGGTAGCGTTGCCAATGATGTTACAGATGA
GATGGTCAGACTAAACTGGCTGACGGAATTTATGCCTCTTCCGACCAT
```

```
CAAGCATTTTATCCGTACTCCTGATGATGCATGGTTACTCACCACTGC
GATCCCCGGGAAAACAGCATTCCAGGTATTAGAAGAATATCCTGATTC
AGGTGAAAATATTGTTGATGCGCTGGCAGTGTTCCTGCGCCGGTTGCA
TTCGATTCCTGTTTGTAATTGTCCTTTTAACAGCGATCGCGTATTTCG
TCTCGCTCAGGCGCAATCACGAATGAATAACGGTTTGGTTGATGCGAG
TGATTTTGATGACGAGCGTAATGGCTGGCCTGTTGAACAAGTCTGGAA
AGAAATGCATAAACTTTTGCCATTCTCACCGGATTCAGTCGTCACTCA
TGGTGATTTCTCACTTGATAACCTTATTTTTGACGAGGGGAAATTAAT
AGGTTGTATTGATGTTGGACGAGTCGGAATCGCAGACCGATACCAGGA
TCTTGCCATCCTATGGAACTGCCTCGGTGAGTTTTCTCCTTCATTACA
GAAACGGCTTTTTCAAAAATATGGTATTGATAATCCTGATATGAATAA
ATTGCAGTTTCATTTGATGCTCGATGAGTTTTTCTAAGAATTAATTCA
TGAGCGGATACATATTTGAATGTATTTAGAAAAATAAACAAATAGGGG
TTCCGCGCACATTTCCCCGAAAAGTGCCACCTGAAATTGTAAACGTTA
ATATTTTGTTAAAATTCGCGTTAAATTTTTGTTAAATCAGCTCATTTT
TTAACCAATAGGCCGAAATCGGCAAAATCCCTTATAAATCAAAAGAAT
AGACCGAGATAGGGTTGAGTGTTGTTCCAGTTTGGAACAAGAGTCCAC
TATTAAAGAACGTGGACTCCAACGTCAAAGGGCGAAAAACCGTCTATC
AGGGCGATGGCCCACTACGTGAACCATCACCCTAATCAAGTTTTTTGG
GGTCGAGGTGCCGTAAAGCACTAAATCGGAACCCTAAAGGGAGCCCCC
GATTTAGAGCTTGACGGGGAAAGCCGGCGAACGTGGCGAGAAAGGAAG
GGAAGAAAGCGAAAGGAGCGGGCGCTAGGGCGCTGGCAAGTGTAGCGG
TCACGCTGCGCGTAACCACCACACCCGCCGCGCTTAATGCGCCGCTAC
AGGGCGCGTCCCATTCGCCA
          SEQ.ID NO: 95
ATGGCTTCTAGTTCTTCCGATGTCTTCGTTTTGGGTCTAGGTGTTGTT
TTGGCTGCCTTGTATATCTTCAGAGACCAATTATTCGCTGCTTCTAAG
CCAAAGGTGGCTCCAGTTTCCACTACGAAGCCTGCCAACGGTTCCGCT
AACCCAAGAGACTTCATCGCCAAGATGAAACAAGGTAAGAAGAGAATC
GTAATCTTCTACGGTTCTCAAACTGGTACCGCTGAAGAATATGCTATT
CGTTTGGCTAAGGAAGCTAAGCAAAAGTTCGGTCTAGCCTCCTTGGTT
TGTGATCCAGAAGAATACGATTTTGAAAAGTTGGACCAATTGCCAGAA
GATTCTATTGCTTTCTTCGTCGTTGCTACCTATGGTGAAGGTGAACCT
ACAGACAACGCTGTCCAATTGTTGCAAAACTTGCAAGATGAAAGCTTC
GAATTCTCCTCGGTGAGAGAAAGTTGTCAGGTTTGAAGTACGTTGTT
TTTGGTCTGGGTAACAAGACCTACGAACATTACAACCTCATTGGGAGA
ACTGTTGACGCTCAATTGGCCAAGATGGGTGCTATCAGAATCGGTGAA
AGAGGTGAAGGTGATGATGACAAGTCCATGGAAGAAGACTACTTGGAA
TGGAAGGATGGTATGTGGGAAGCGTTTGCCACTGCTATGGGTGTTGAA
GAAGGTCAAGGTGGTGACTCCGCTGATTTCGTCGTTTCCGAATTGGAA
TCTCACCCACCAGAAAAGGTTTACCAAGGTGAATTTTCTGCTAGAGCT
```

```
TTAACCAAAACCAAGGGTATTCACGACGCTAAGAATCCTTTTGCTGCT
CCAATTGCGGTTGCTAGAGAATTGTTCCAATCTGTTGTCGATAGAAAC
TGTGTCCACGTCGAATTCAACATTGAAGGCTCTGGTATCACCTATCAA
CACGGTGACCACGTTGGTTTGTGGCCATTGAATCCAGATGTTGAAGTC
GAACGGTTGTTGTGTGTTTTAGGTTTAGCTGAAAAGAGAGATGCTGTC
ATCTCCATTGAATCCTTAGACCCGGCTTTGGCTAAGGTTCCATTCCCA
GTCCCAACTACTTACGGTGCTGTGTTGAGACACTACATTGACATCTCT
GCTGTCGCCGGTAGACAAATCTTGGGTACTTTGTCCAAATTCGCTCCA
ACCCCAGAAGCTGAAGCTTTCTTGAGAAACTTGAACACTAACAAGGAA
GAATACCACAACGTCGTCGCTAACGGTTGTTTGAAATTGGGTGAAATT
TTGCAAATCGCTACCGGTAACGACATTACTGTCCCACCAACTACTGCC
AACACCACCAAATGGCCAATTCCATTCGACATCATTGTTTCTGCCATC
CCAAGATTGCAACCAAGATACTACTCTATCTCTTCTTCCCCAAAAATT
CATCCAAACACCATCCACGCTACCGTTGTTGTGCTCAAATACGAAAAC
GTTCCAACCGAACCAATCCCAAGAAAGTGGGTTTACGGTGTCGGTAGT
AACTTCTTGTTGAATTTAAAGTACGCTGTTAACAAGGAACCAGTTCCA
TACATCACTCAAAATGGCGAACAAAGAGTCGGTGTCCCGGAATACTTG
ATTGCTGGTCCACGTGGTTCTTACAAGACTGAATCTTTCTACAAGGCT
CCAATCCATGTTAGACGTTCTACTTTCCGTTTGCCAACCAACCCAAAG
TCTCCAGTCATCATGATTGGTCCAGGTACTGGTGTCGCCCCATTCAGA
GGCTTCGTTCAAGAAAGAGTTGCCTTGGCCAGAAGATCCATCGAAAAG
AACGGTCCTGACTCTTTGGCTGACTGGGGTCGTATTTCCTTGTTCTAC
GGTTGTAGAAGATCCGACGAAGACTTCTTGTACAAGGACGAATGGCCA
CAATACGAAGCTGAGTTGAAGGGTAAGTTCAAGTTGCACTGTGCTTTC
TCCAGACAAAACTACAAGCCAGACGGTTCTAAGATTTACGTCCAAGAT
TTGATCTGGGAAGACAGAGAACACATTGCCGATGCCATCTTAAACGGT
AAGGGTTACGTCTACATCTGCGGTGAAGCTAAGTCCATGTCTAAACAA
GTTGAAGAAGTTCTAGCCAAGATCTTGGGCGAAGCCAAAGGTGGTTCC
GGTCCAGTTGAAGGTGTTGCTGAAGTCAAGTTACTGAAGGAACGGTCC
AGATTGATGTTGGATGTCTGGTCTTGA
          SEQ.ID NO: 96
MASSSSDVFVLGLGVVLAALYIFRDQLFAASKPKVAPVSTTKPANGSA
NPRDFIAKMKQGKKRIVIFYGSQTGTAEEYAIRLAKEEAKQKFGLASLV
CDPEEYDFEKLDQLPEDSIAFFVVATYGEGEPTDNAVQLLQNLQDESF
EFSSGERKLSGLKYVVFGLGNKTYEHYNLIGRTVDAQLAKMGAIRIGE
RGEGDDDKSMEEDYLEWKDGMWEAFATAMGVEEGQGGDSADFVVSELE
SHPPEKVYQGEFSARALTKTKGIHDAKNPFAAPIAVARELFQSVVDRN
CVHVEFNIEGSGITYQHGDHVGLWPLNPDVEVERLLCVLGLAEKRDAV
ISIESLDPALAKVPFPVPTTYGAVLRHYIDISAVAGRQILGTLSKFAP
TPEAEAFLRNLNTNKEEYHNVANGCLKLGEILQIATGNDITVPPTTA
NTTKWPIPFDIIVSAIPRLQPRYYSISSSPKIHPNTIHATVVVLKYEN
```

VPTEPIPRKWVYGVGSNFLLNLKYAVNKEPVPYITQNGEQRVGVPEYL
IAGPRGSYKTESFYKAPIHVRRSTFRLPTNPKSPVIMIGPGTGVAPFR
GFVQERVALARRSIEKNGPDSLADWGRISLFYGCRRSDEDFLYKDEWP
QYEAELKGKFKLHCAFSRQNYKPDGSKIYVQDLIWEDREHIADAILNG
KGYVYICGEAKSMSKQVEEVLAKILGEAKGGSGPVEGVAEVKLLKERS
RLMLDVWS

SEQ.ID NO: 97
GAAGAATTGTGAGCGGATAACAATTCCCCTCTAGAAATAATTTTGTTT
AACTTTAAGAAGGAGATATACATATGGCAGATCTCAATTGGATATCGG
CCCGGCCACGCGATCGCTGACGTCGGTACCCTCGAGTCTGGTAAAGAAA
CCGCTGCTGCGAAATTTGAACGCCAGCACATGGACTCGTCTACTAGTC
GCAGCTTAATTAACCTAAACTGCTGCCACCGCTGAGCAATAACTAGCA
TAACCCCTTGGGGCCTCTAAACGGGTCTTGAGGGGTTTTTTGCTAGCG
AAAGGAGGAGTCGACTATATCCGGATTGGCGAATGGGACGCGCCCTGT
AGCGGCGCATTAAGCGCGGCGGGTGTGGTGGTTACGCGCAGCGTGACC
GCTACACTTGCCAGCGCCCTAGCGCCCGCTCCTTTCGCTTTCTTCCCT
TCCTTTCTCGCCACGTTCGCCGGCTTTCCCCGTCAAGCTCTAAATCGG
GGGCTCCCTTTAGGGTTCCGATTTAGTGCTTTACGGCACCTCGACCCC
AAAAAACTTGATTAGGGTGATGGTTCACGTAGTGGGCCATCGCCCTGA
TAGACGGTTTTTCGCCCTTTGACGTTGGAGTCCACGTTCTTTAATAGT
GGACTCTTGTTCCAAACTGGAACAACACTCAACCCTATCTCGGTCTAT
TCTTTTGATTTATAAGGGATTTTGCCGATTTCGGCCTATTGGTTAAAA
AATGAGCTGATTTAACAAAAATTTAACGCGAATTTTAACAAAATATTA
ACGTTTACAATTTCTGGCGGCACGATGGCATGAGATTATCAAAAAGGA
TCTTCACCTAGATCCTTTTAAATTAAAAATGAAGTTTTAAATCAATCT
AAAGTATATATGAGTAAACTTGGTCTGACAGTTACCAATGCTTAATCA
GTGAGGCACCTATCTCAGCGATCTGTCTATTTCGTTCATCCATAGTTG
CCTGACTCCCCGTCGTGTAGATAACTACGATACGGGAGGGCTTACCAT
CTGGCCCCAGTGCTGCAATGATACCGCGAGACCCACGCTCACCGGCTC
CAGATTTATCAGCAATAAACCAGCCAGCCGGAAGGGCCGAGCGCAGAA
GTGGTCCTGCAACTTTATCCGCCTCCATCCAGTCTATTAATTGTTGCC
GGGAAGCTAGAGTAAGTAGTTCGCCAGTTAATAGTTTGCGCAACGTTG
TTGCCATTGCTACAGGCATCGTGGTGTCACGCTCGTCGTTTGGTATGG
CTTCATTCAGCTCCGGTTCCCAACGATCAAGGCGAGTTACATGATCCC
CCATGTTGTGCAAAAAAGCGGTTAGCTCCTTCGGTCCTCCGATCGTTG
TCAGAAGTAAGTTGGCCGCAGTGTTATCACTCATGGTTATGGCAGCAC
TGCATAATTCTCTTACTGTCATGCCATCCGTAAGATGCTTTTCTGTGA
CTGGTGAGTACTCAACCAAGTCATTCTGAGAATAGTGTATGCGGCGAC
CGAGTTGCTCTTGCCCGGCGTCAATACGGGATAATACCGCGCCACATA
GCAGAACTTTAAAAGTGCTCATCATTGGAAAACGTTCTTCGGGGCGAA
AACTCTCAAGGATCTTACCGCTGTTGAGATCCAGTTCGATGTAACCCA

CTCGTGCACCCAACTGATCTTCAGCATCTTTTACTTTCACCAGCGTTT
CTGGGTGAGCAAAAACAGGAAGGCAAATGCCGCAAAAAAGGGAATAA
GGGCGACACGGAAATGTTGAATACTCATACTCTTCCTTTTTCAATCAT
GATTGAAGCATTTATCAGGGTTATTGTCTCATGAGCGGATACATATTT
GAATGTATTTAGAAAAATAAACAAATAGGTCATGACCAAAATCCCTTA
ACGTGAGTTTTCGTTCCACTGAGCGTCAGACCCCGTAGAAAAGATCAA
AGGATCTTCTTGAGATCCTTTTTTTCTGCGCGTAATCTGCTGCTTGCA
AACAAAAAAACCACCGCTACCAGCGGTGGTTTGTTTGCCGGATCAAGA
GCTACCAACTCTTTTTCCGAAGGTAACTGGCTTCAGCAGAGCGCAGAT
ACCAAATACTGTCCTTCTAGTGTAGCCGTAGTTAGGCCACCACTTCAA
GAACTCTGTAGCACCGCCTACATACCTCGCTCTGCTAATCCTGTTACC
AGTGGCTGCTGCCAGTGGCGATAAGTCGTGTCTTACCGGGTTGGACTC
AAGACGATAGTTACCGGATAAGGCGCAGCGGTCGGGCTGAACGGGGGG
TTCGTGCACACAGCCCAGCTTGGAGCGAACGACCTACACCGAACTGAG
ATACCTACAGCGTGAGCTATGAGAAAGCGCCACGCTTCCCGAAGGGAG
AAAGGCGGACAGGTATCCGGTAAGCGGCAGGGTCGGAACAGGAGAGCG
CACGAGGGAGCTTCCAGGGGGAAACGCCTGGTATCTTTATAGTCCTGT
CGGGTTTCGCCACCTCTGACTTGAGCGTCGATTTTTGTGATGCTCGTC
AGGGGGGCGGAGCCTATGGAAAAACGCCAGCAACGCGGCCTTTTTACG
GTTCCTGGCCTTTTGCTGGCCTTTTGCTCACATGTTCTTTCCTGCGTT
ATCCCCTGATTCTGTGGATAACCGTATTACCGCCTTTGAGTGAGCTGA
TACCGCTCGCCGCAGCCGAACGACCGAGCGCAGCGAGTCAGTGAGCGA
GGAAGCGGAAGAGCGCCTGATGCGGTATTTTCTCCTTACGCATCTGTG
CGGTATTTCACACCGCATATATGGTGCACTCTCAGTACAATCTGCTCT
GATGCCGCATAGTTAAGCCAGTATACACTCCGCTATCGCTACGTGACT
GGGTCATGGCTGCGCCCCGACACCCGCCAACACCCGCTGACGCGCCCT
GACGGGCTTGTCTGCTCCCGGCATCCGCTTACAGACAAGCTGTGACCG
TCTCCGGGAGCTGCATGTGTCAGAGGTTTTCACCGTCATCACCGAAAC
GCGCGAGGCAGCTGCGGTAAAGCTCATCAGCGTGGTCGTGAAGCGATT
CACAGATGTCTGCCTGTTCATCCGCGTCCAGCTCGTTGAGTTTCTCCA
GAAGCGTTAATGTCTGGCTTCTGATAAAGCGGGCCATGTTAAGGGCGG
TTTTTTCCTGTTTGGTCACTGATGCCTCCGTGTAAGGGGGATTTCTGT
TCATGGGGGTAATGATACCGATGAAACGAGAGAGGATGCTCACGATAC
GGGTTACTGATGATGAACATGCCCGGTTACTGGAACGTTGTGAGGGTA
AACAACTGGCGGTATGGATGCGGCGGGACCAGAGAAAATCACTCAGG
GTCAATGCCAGCGCTTCGTTAATACAGATGTAGGTGTTCCACAGGGTA
GCCAGCAGCATCCTGCGATGCAGATCCGGAACATAATGGTGCAGGGCG
CTGACTTCCGCGTTTCCAGACTTTACGAAACACGGAAACCGAAGACCA
TTCATGTTGTTGCTCAGGTCGCAGACGTTTTGCAGCAGCAGTCGCTTC
ACGTTCGCTCGCGTATCGGTGATTCATTCTGCTAACCAGTAAGGCAAC

-continued

CCCGCCAGCCTAGCCGGGTCCTCAACGACAGGAGCACGATCATGCTAG

TCATGCCCCGCGCCCACCGGAAGGAGCTGACTGGGTTGAAGGCTCTCA

AGGGCATCGGTCGAGATCCCGGTGCCTAATGAGTGAGCTAACTTACAT

TAATTGCGTTGCGCTCACTGCCCGCTTTCCAGTCGGGAAACCTGTCGT

GCCAGCTGCATTAATGAATCGGCCAACGCGCGGGGAGAGGCGGTTTGC

GTATTGGGCGCCAGGGTGGTTTTTCTTTTCACCAGTGAGACGGGCAAC

AGCTGATTGCCCTTCACCGCCTGGCCCTGAGAGAGTTGCAGCAAGCGG

TCCACGCTGGTTTGCCCCAGCAGGCGAAAATCCTGTTTGATGGTGGTT

AACGGCGGGATATAACATGAGCTGTCTTCGGTATCGTCGTATCCCACT

ACCGAGATGTCCGCACCAACGCGCAGCCCGGACTCGGTAATGGCGCGC

ATTGCGCCCAGCGCCATCTGATCGTTGGCAACCAGCATCGCAGTGGGA

ACGATGCCCTCATTCAGCATTTGCATGGTTTGTTGAAAACCGGACATG

GCACTCCAGTCGCCTTCCCGTTCCGCTATCGGCTGAATTTGATTGCGA

GTGAGATATTTATGCCAGCCAGCCAGACGCAGACGCGCCGAGACAGAA

CTTAATGGGCCCGCTAACAGCGCGATTTGCTGGTGACCCAATGCGACC

AGATGCTCCACGCCCAGTCGCGTACCGTCTTCATGGGAGAAAATAATA

CTGTTGATGGGTGTCTGGTCAGAGACATCAAGAAATAACGCCGGAACA

TTAGTGCAGGCAGCTTCCACAGCAATGGCATCCTGGTCATCCAGCGGA

TAGTTAATGATCAGCCCACTGACGCGTTGCGCGAGAAGATTGTGCACC

GCCGCTTTACAGGCTTCGACGCCGCTTCGTTCTACCATCGACACCACC

ACGCTGGCACCCAGTTGATCGGCGCGAGATTTAATCGCCGCGACAATT

TGCGACGGCGCGTGCAGGGCCAGACTGGAGGTGGCAACGCCAATCAGC

AACGACTGTTTGCCCGCCAGTTGTTGTGCCACGCGGTTGGGAATGTAA

TTCAGCTCCGCCATCGCCGCTTCCACTTTTTCCCGCGTTTTCGCAGAA

ACGTGGCTGGCCTGGTTCACCACGCGGGAAACGGTCTGATAAGAGACA

CCGGCATACTCTGCGACATCGTATAACGTTACTGGTTTCACATTCACC

ACCCTGAATTGACTCTCTTCCGGGCGCTATCATGCCATACCGCGAAAG

GTTTTGCGCCATTCGATGGTGTCCGGGATCTCGACGCTCTCCCTTATG

CGACTCCTGCATTAGGAAGCAGCCCAGTAGTAGGTTGAGGCCGTTGAG

CACCGCCGCCGCAAGGAATGGTGCATGCAAGGAGATGGCGCCCAACAG

TCCCCCGGCCACGGGGCCTGCCACCATACCCACGCCGAAACAAGCGCT

CATGAGCCCGAAGTGGCGAGCCCGATCTTCCCCATCGGTGATGTCGGC

GATATAGGCGCCAGCAACCGCACCTGTGGCGCCGGTGATGCCGGCCAC

GATGCGTCCGGCGTAGCCTAGGATCGAGATCGATCTCGATCCCGCGAA

ATTAATACGACTCACTACG

SEQ.ID NO: 98

CGCTAACAGCGCGATTTGCTGGTGACCCAATGCGACCAGATGCTCCAC

GCCCAGTCGCGTACCGTCTTCATGGGAGAAAATAATACTGTTGATGGG

TGTCTGGTCAGAGACATCAAGAAATAACGCCGGAACATTAGTGCAGGC

AGCTTCCACAGCAATGGCATCCTGGTCATCCAGCGGATAGTTAATGAT

CAGCCCACTGACGCGTTGCGCGAGAAGATTGTGCACCGCCGCTTTACA

-continued

GGCTTCGACGCCGCTTCGTTCTACCATCGACACCACCACGCTGGCACC

CAGTTGATCGGCGCGAGATTTAATCGCCGCGACAATTTGCGACGGCGC

GTGCAGGGCCAGACTGGAGGTGGCAACGCCAATCAGCAACGACTGTTT

GCCCGCCAGTTGTTGTGCCACGCGGTTGGGAATGTAATTCAGCTCCGC

CATCGCCGCTTCCACTTTTTCCCGCGTTTTCGCAGAAACGTGGCTGGC

CTGGTTCACCACGCGGGAAACGGTCTGATAAGAGACACCGGCATACTC

TGCGACATCGTATAACGTTACTGGTTTCACATTCACCACCCTGAATTG

ACTCTCTTCCGGGCGCTATCATGCCATACCGCGAAAGGTTTTGCGCCA

TTCGATGGTGTCCGGGATCTCGACGCTCTCCCTTATGCGACTCCTGCA

TTAGGAAGCAGCCCAGTAGTAGGTTGAGGCCGTTGAGCACCGCCGCCG

CAAGGAATGGTGCATGCAAGGAGATGGCGCCCAACAGTCCCCCGGCCA

CGGGGCCTGCCACCATACCCACGCCGAAACAAGCGCTCATGAGCCCGA

AGTGGCGAGCCCGATCTTCCCCATCGGTGATGTCGGCGATATAGGCGC

CAGCAACCGCACCTGTGGCGCCGGTGATGCCGGCCACGATGCGTCCGG

CGTAGCCTAGGATCGAGATCGATCTCGATCCCGCGAAATTAATACGAC

TCACTATAGGGGAATTGTGAGCGGATAACAATTCCCCTCTAGAAATAA

TTTTGTTTAACTTTAAGAAGGAGATATACATATGGCAGATCTCAATTG

GATATCGGCCGGCCACGCGATCGCTGACGTCGGTACCCTCGAGTCTGG

TAAAGAAACCGCTGCTGCGAAATTTGAACGCCAGCACATGGACTCGTC

TACTAGTCGCAGCTTAATTAACCTAAACTGCTGCCACCGCTGAGCAAT

AACTAGCATAACCCCTTGGGGCCTCTAAACGGGTCTTGAGGGGTTTTT

TGCTAGCGAAAGGAGGAGTCGACAAGCTGACGACCGGGTCTCCGCAAG

TGGCACTTTTCGGGGAAATGTGCGCGGAACCCCTATTTGTTTATTTTT

CTAAATACATTCAAATATGTATCCGCTCATGAATTAATTCTTAGAAAA

ACTCATCGAGCATCAAATGAAACTGCAATTTATTCATATCAGGATTAT

CAATACCATATTTTTGAAAAAGCCGTTTCTGTAATGAAGGAGAAAACT

CACCGAGGCAGTTCCATAGGATGGCAAGATCCTGGTATCGGTCTGCGA

TTCCGACTCGTCCAACATCAATACAACCTATTAATTTCCCCTCGTCAA

AAATAAGGTTATCAAGTGAGAAATCACCATGAGTGACGACTGAATCCG

GTGAGAATGGCAAAAGTTTATGCATTTCTTTCCAGACTTGTTCAACAG

GCCAGCCATTACGCTCGTCATCAAAATCACTCGCATCAACCAAACCGT

TATTCATTCGTGATTGCGCCTGAGCGAGACGAAATACGCGGTCGCTGT

TAAAAGGACAATTACAAACAGGAATCGAATGCAACCGGCGCAGGAACA

CTGCCAGCGCATCAACAATATTTTCACCTGAATCAGGATATTCTTCTA

ATACCTGGAATGCTGTTTTCCCGGGGATCGCAGTGGTGAGTAACCATG

CATCATCAGGAGTACGGATAAAATGCTTGATGGTCGGAAGAGGCATAA

ATTCCGTCAGCCAGTTTAGTCTGACCATCTCATCTGTAACATCATTGG

CAACGCTACCTTTGCCATGTTTCAGAAACAACTCTGGCGCATCGGGCT

TCCCATACAATCGATAGATTGTCGCACCTGATTGCCCGACATTATCGC

GAGCCCATTTATACCCATATAAATCAGCATCCATGTTGGAATTTAATC

GCGGCCTAGAGCAAGACGTTTCCCGTTGAATATGGCTCATACTCTTCC

-continued

```
TTTTTCAATATTATTGAAGCATTTATCAGGGTTATTGTCTCATGAGCG
GATACATATTTGAATGTATTTAGAAAAATAAACAAATAGGCATGCAGC
GCTCTTCCGCTTCCTCGCTCACTGACTCGCTACGCTCGGTCGTTCGAC
TGCGGCGAGCGGTGTCAGCTCACTCAAAAGCGGTAATACGGTTATCCA
CAGAATCAGGGGATAAAGCCGGAAAGAACATGTGAGCAAAAAGCAAAG
CACCGGAAGAAGCCAACGCCGCAGGCGTTTTTCCATAGGCTCCGCCCC
CCTGACGAGCATCACAAAAATCGACGCTCAAGCCAGAGGTGGCGAAAC
CCGACAGGACTATAAAGATACCAGGCGTTTCCCCCTGGAAGCTCCCTC
GTGCGCTCTCCTGTTCCGACCCTGCCGCTTACCGGATACCTGTCCGCC
TTTCTCCCTTCGGGAAGCGTGGCGCTTTCTCATAGCTCACGCTGTTGG
TATCTCAGTTCGGTGTAGGTCGTTCGCTCCAAGCTGGGCTGTGTGCAC
GAACCCCCCGTTCAGCCCGACCGCTGCGCCTTATCCGGTAACTATCGT
CTTGAGTCCAACCCGGTAAGACACGACTTATCGCCACTGGCAGCAGCC
ATTGGTAACTGATTTAGAGGACTTTGTCTTGAAGTTATGCACCTGTTA
AGGCTAAACTGAAAGAACAGATTTTGGTGAGTGCGGTCCTCCAACCCA
CTTACCTTGGTTCAAAGAGTTGGTAGCTCAGCGAACCTTGAGAAAACC
ACCGTTGGTAGCGGTGGTTTTTCTTTATTTATGAGATGATGAATCAAT
CGGTCTATCAAGTCAACGAACAGCTATTCCGTTACTCTAGATTTCAGT
GCAATTTATCTCTTCAAATGTAGCACCTGAAGTCAGCCCCATACGATA
TAAGTTGTAATTCTCATGTTAGTCATGCCCCGCGCCCACCGGAAGGAG
CTGACTGGGTTGAAGGCTCTCAAGGGCATCGGTCGAGATCCCGGTGCC
TAATGAGTGAGCTAACTTACATTAATTGCGTTGCGCTCACTGCCCGCT
TTCCAGTCGGGAAACCTGTCGTGCCAGCTGCATTAATGAATCGGCCAA
CGCGCGGGGAGAGGCGGTTTGCGTATTGGGCGCCAGGGTGGTTTTTCT
TTTCACCAGTGAGACGGGCAACAGCTGATTGCCCTTCACCGCCTGGCC
CTGAGAGAGTTGCAGCAAGCGGTCCACGCTGGTTTGCCCCAGCAGGCG
AAAATCCTGTTTGATGGTGGTTAACGGCGGGATATAACATGAGCTGTC
TTCGGTATCGTCGTATCCCACTACCGAGATGTCCGCACCAACGCGCAG
CCCGGACTCGGTAATGGCGCGCATTGCGCCCAGCGCCATCTGATCGTT
GGCAACCAGCATCGCAGTGGGAACGATGCCCTCATTCAGCATTTGCAT
GGTTTGTTGAAAACCGGACATGGCACTCCAGTCGCCTTCCCGTTCCGC
TATCGGCTGAATTTGATTGCGAGTGAGATATTTATGCCAGCCAGCCAG
ACGCAGACGCGCCGAGACAGAACTTAATGGGCC
```

Hereinafter are provided examples of specific implementations for performing the methods of the present disclosure, as well as implementations representing the compositions of the present disclosure. The examples are provided for illustrative purposes only, and are not intended to limit the scope of the present disclosure in any way.

EXAMPLES

Example 1—Process for Making a First Halogenated Psilocybin Derivative from Halogenated Tryptophan Feedstock Yeast (*Saccharomyces cerevisiae*) was genetically engineered to enable bioconversion of commercially obtained, halogenated, simple indole, tryptophan, or tryptamine feedstock to generate final product. The parent yeast (*Saccharomyces cerevisiae*) strain was CEN.PK with genotype Matα; ura3-52; trp1-289; leu2-3,112; his3 Δ1, MAL2-8C, SUC2. The parent strain was engineered to include three enzymatic steps through chromosomal homologous recombination of integration cassettes as described previously (Dastmalchi et al., 2019, Nat. Chem Biol. 15: 384-390; Chen et al., 2018, Nat. Chem Biol. 14: 738-743). The three steps were comprised of PsiH (SEQ. ID NO: 4), PsiK (SEQ. ID NO: 6) and PsiM (SEQ. ID NO: 8), encoded by SEQ. ID NO: 3, SEQ. ID NO: 5 and SEQ. ID NO: 7, respectively, with addition of in-frame, C-terminal HA (SEQ. ID NO: 81, SEQ. ID NO: 82), V5 (SEQ. ID NO: 87, SEQ. ID NO: 88), and FLAG (SEQ. ID NO: 85, SEQ. ID NO: 86) epitope tags, respectively. DNA (SEQ. ID NO: 95) encoding a fifth enzyme, PcCPR (SEQ. ID NO: 96) was also integrated following PCR-based, C-terminal, in-frame addition of epitope tag c-MYC (SEQ. ID NO: 83, SEQ. ID NO: 84) to support functionality of PsiH. Integration cassettes were built using yeast promoter sequences amplified from *S. cerevisiae* genomic DNA as described (Dastmalchi et al. 2019; Chen et al. 2018) enabling constitutive gene expression. Amplified promoters included PGK1 (SEQ. ID NO: 77), TDH3 (SEQ. ID NO: 78), CLN1 (SEQ. ID NO: 79), and UGA1 (SEQ. ID NO: 80). Two integration cassettes were assembled: the first (SEQ. ID NO: 74) harbored tagged PsiH and PcCPR, and the second (SEQ. ID NO: 75) harbored tagged PsiK and PsiM: Successive genomic integration of these cassettes was performed as described previously (Chen et al. 2018). Following stable integration of these two cassettes, the strain was further manipulated by transformation with a yeast episomal vector encoding a promiscuous decarboxylase, ClostSporTDC (pMM1-pTDH3-ClostSporTDC-His-tCYC1) (SEQ. ID NO: 76) enabling efficient decarboxylation of halogenated tryptophan intermediates and/or feedstocks. For this Example, heterologous expression of a non-native or engineered TrpB gene was not necessary, as endogenous tryptophan synthase activity proved sufficient. The final engineered strain was called Sc-1. For scaled-up production of halogenated product, culturing was performed as follows. Seed cultures were inoculated in SD-drop-out medium overnight. The overnight culture was then divided into two flasks containing 500 ml each of SD-drop-out medium containing 2% (w/v) glucose, 0.3% (w/v) $KH_2PO_4$, 0.05% (w/v) $MgSO_4 \cdot 7H_2O$, 0.5% (w/v) $(NH_4)_2SO_4$ plus 500 μM 6-fluorotryptophan (ThermoFisher Scientific) for conversion by Sc-1. Yeast cultures were grown for 48 h. Cultures were then centrifuged (10,000 g×5 minutes) to remove cellular content, and culture broth containing secreted halogenated product was stored at −80° C. until further processing. To determine successful biosynthesis of 6-fluoro-psilocybin (compound with formula (XI)), culture broth was analyzed using high-resolution LC-HESI-LTQ-Orbitrap-XL MS (Thermo Fisher Scientific), employing a modified version of a method described previously (Chang et al., 2015, Plant Physiol. 169: 1127-1140), with the exception that liquid chromatography was carried out using an UltiMate 3000 HPLC (Thermo Fisher Scientific)

equipped with a Poroshell 120 SB-C18 column (Agilent Technologies) instead of an Accela HPLC system (Thermo Fisher Scientific) equipped with a Zorbax C18 column (Agilent Technologies). Briefly, 10 microliters of sample was injected at a flow rate of 0.5 mL/min and a gradient of solvent A (water with 0.1% of formic Acid) and solvent B (ACN with 0.1% formic Acid) as follows: 100% to 0% (v/v) solvent A over 5 min; isocratic at 0% (v/v) for 1 min; 0% to 100% (v/v) over 0.1 min; and isocratic at 100% (v/v) for 1.9 min. Total run time was 8 minutes. Heated ESI source and interface conditions were operated in positive ion mode as follows: vaporizer temperature, 400° C.; source voltage, 3 kV; sheath gas, 60 au, auxiliary gas, 20 au; capillary temperature, 380° C.; capillary voltage, 6 V; tube lens, 45 V. Instrumentation was performed as a single, HR scan event using Orbitrap detection of m/z in the range of 100-500 m/z. Ion injection time was 300 ms with scan time of 1 s. External and internal calibration procedures ensured <2 ppm error to facilitate elemental formulae predictions. Singly protonated product with exact m/z and expected elemental formula matching 6-fluoro-psilocybin having chemical formula (XI):

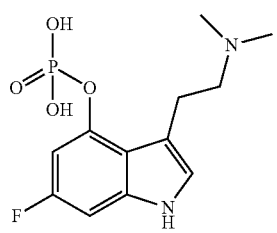

Figure 10:
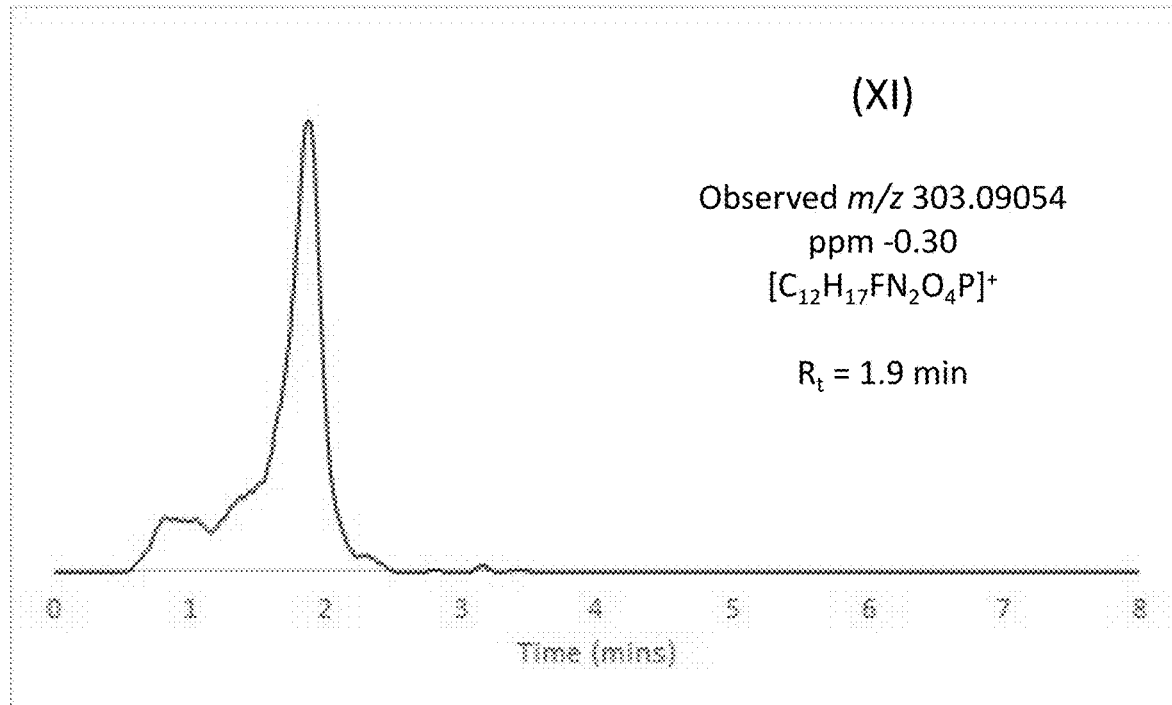
FIG. 10 depicts a representation of mass spectrometry data in the form of a chromatogram, notably a chromatogram obtained in the performance of an experiment to synthesize an example halogenated psilocybin derivative compound having the chemical formula (XI) set forth herein.

(XI)

eluted at 1.9 minutes (DC, see: FIG. 10).

Example 2—Process for Making a Second Halogenated Psilocybin Derivative from Halogenated Tryptophan Feedstock The same yeast strain (Sc-1) and procedures described in Example 1 were used to biosynthesize a halogenated psilocybin derivative with chemical formula (XIV), with the following exception: in place of 6-fluorotryptophan, 500 μM 7-bromotryptophan (Combi-Blocks, www.combi-blocks.com) was supplied as feedstock for bioconversion. Singly protonated product with exact m/z and expected elemental formula matching 7-bromo-psilocybin having chemical formula (XIV).

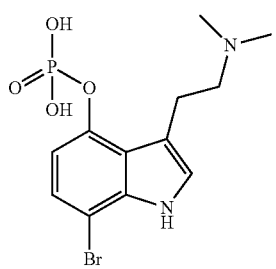

Figure 11:
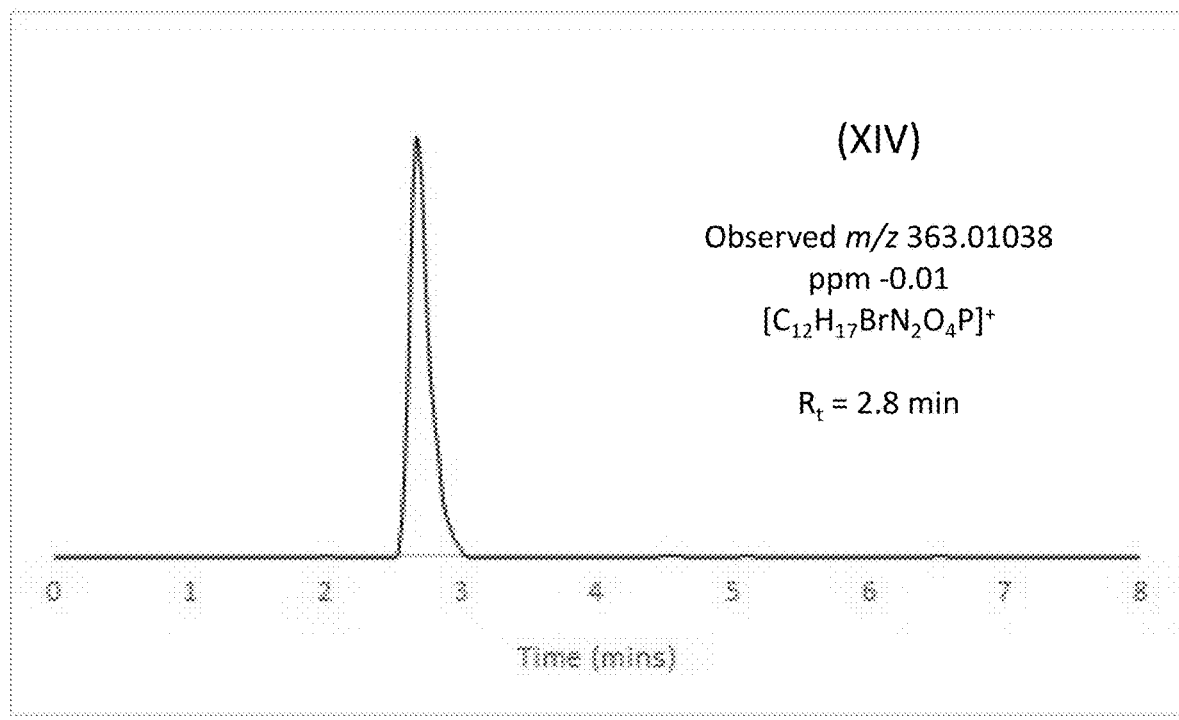
FIG. 11 depicts a representation of mass spectrometry data in the form of a chromatogram, notably a chromatogram obtained in the performance of an experiment to synthesize an example halogenated psilocybin derivative compound having the chemical formula (XIV) set forth herein.

(XIV)

eluted at 2.8 minutes (EC, see: FIG. 11).

Example 3—Process for Making a Third Halogenated Psilocybin Derivative from Halogenated Indole Feedstock The same yeast strain (Sc-1) and procedures described in Example 1 were used to biosynthesize a halogenated psilocybin derivative with chemical formula (XVI), with the following exception: in place of 6-fluorotryptophan, 500 μM 7-fluoroindole (Combi-Blocks, www.combi-blocks.com) was supplied as feedstock for bioconversion. Singly protonated product with exact m/z and expected elemental formula matching 7-fluoro-psilocybin compound having chemical formula (XVI):

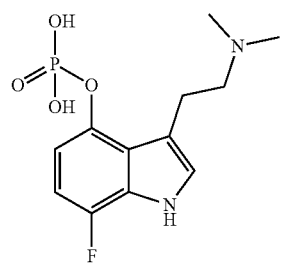

Figure 12:
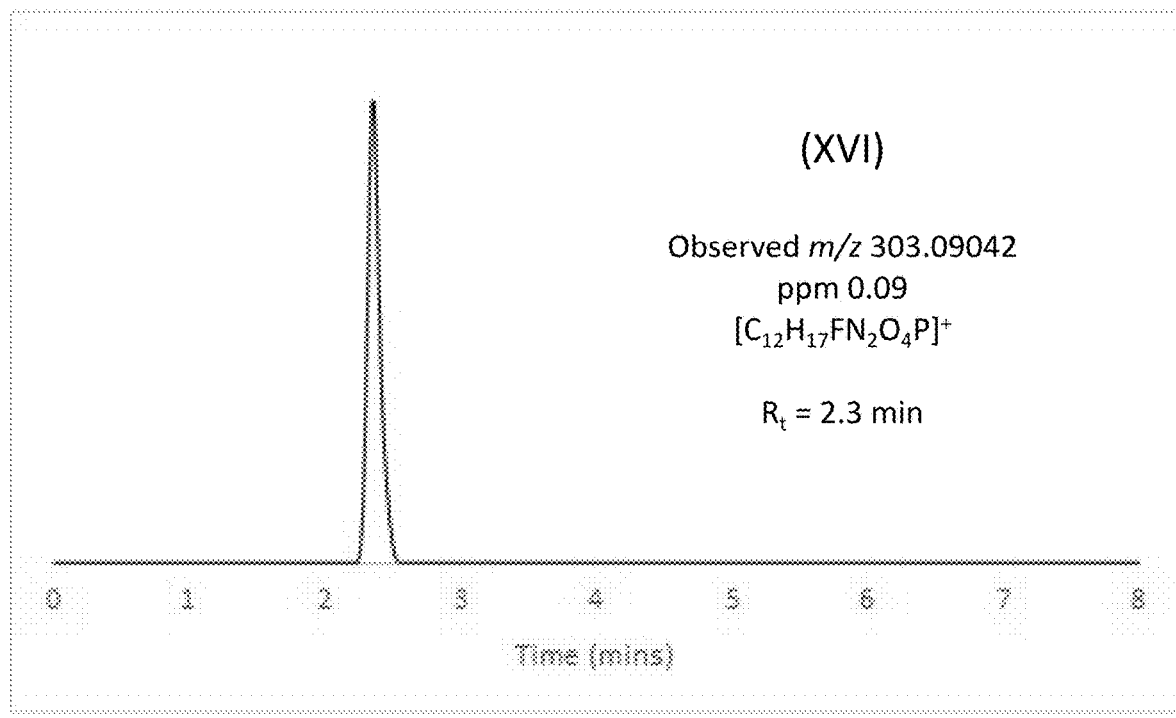
FIG. 12 depicts a representation of mass spectrometry data in the form of a chromatogram, notably a chromatogram obtained in the performance of an experiment to synthesize an example halogenated psilocybin derivative compound having the chemical formula (XVI) set forth herein.

(XVI)

eluted at 2.3 minutes (EIC, see: FIG. 12).

Example 4—Process for Making a Fourth Halogenated Psilocybin Derivative from Halogenated Indole Feedstock The same yeast strain (Sc-1) and procedures described in Example 1 were used to biosynthesize a halogenated psilocybin derivative with formula (XVII), with the following exception: in place of 6-fluorotryptophan, 500 μM 7-chloroindole (Combi-Blocks, www.combi-blocks.com) was supplied as feedstock for bioconversion. Singly protonated product with exact m/z and expected elemental formula matching 7-chloro-psilocybin having formula (XVII):

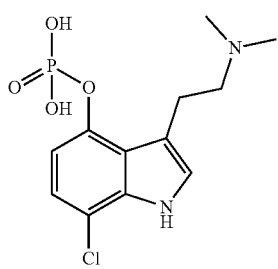

Figure 13:
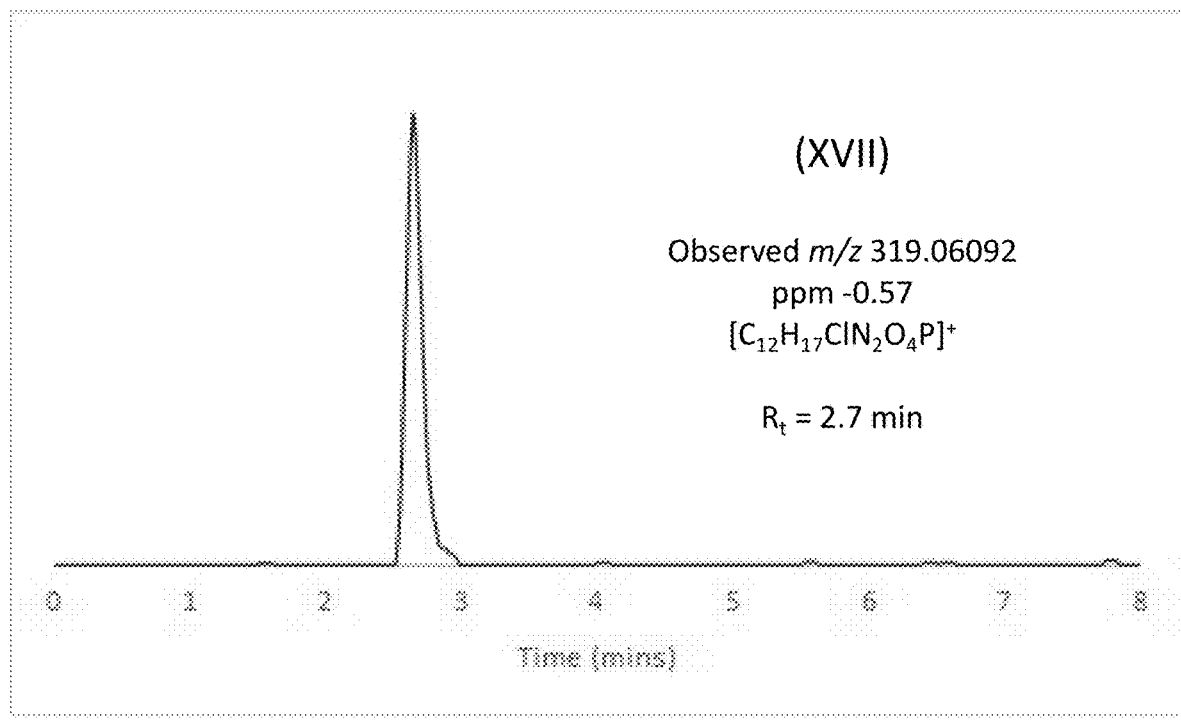
FIG. 13 depicts a representation of mass spectrometry data in the form of a chromatogram, notably a chromatogram obtained in the performance of an experiment to synthesize an example halogenated psilocybin derivative compound having the chemical formula (XVII) set forth herein.

(XVII)

eluted at 2.7 minutes (DC, see: FIG. 13).

Example 5—Process for Making a Fifth Halogenated Psilocybin Derivative from Halogenated Indole Feedstock E. coli strain Ec-1 was constructed as follows. For plasmid cloning, Top10 or XL1-blue strains were used depending on antibiotic markers. Standard LB media was used for culturing. For gene expression and feeding experiments, the parent host strain employed was BL21 (DE3). For this Example, heterologous expression of a non-native or engineered TrpB gene was not necessary, as endogenous tryptophan synthase activity proved sufficient. An in frame, C-terminally His-tagged (SEQ. ID NO: 89, SEQ. ID NO: 90) BaTDC (SEQ. ID NO: 36, SEQ. ID NO: 37) was generated by PCR, followed by cloning into the NdeI and XhoI sites of the plasmid pCDM4 (SEQ. ID NO: 92) where the expression of the gene was driven by a T7 promoter. In a second plasmid, an in-frame, C-terminally His-tagged (SEQ. ID NO: 89, SEQ. ID NO: 90) PsmF (SEQ. ID NO: 62, SEQ. ID NO: 63) was cloned into the NdeI and XhoI sites of pET28a(+) (SEQ. ID NO: 94) where the expression of the gene was also driven by a T7 promoter. The E. coli host strain BL21 (DE3) was transformed with both plasmids and selected for using streptomycin and kanamycin antibiotics. This strain (Ec-1, F– ompT hsdSB (rB–, mB–) gal dcm (DE3), pCDM4-BaTDC-His, pET28a(+)-PsmF-His) enabled production of N-acetylated products from modified indole feedstock. Further, the use of promiscuous BaTDC (SEQ. ID NO: 36, SEQ. ID NO: 37) allowed decarboxylation of a wide variety of halogenated tryptophan intermediates. Scaled-up culturing of engineered E. coli was conducted as follows: seed cultures were inoculated in AMM (Jones et al., 2015, Sci. Rep. 5: 11301) medium overnight. The overnight culture was then divided into two flasks containing 500 mL each of AMM medium additionally containing 0.5% (w/v) serine, 1M IPTG, 50 ug/L kanamycin and streptomycin, and 100 mg/L 7-fluoroindole (Combi-Blocks, www.combi-blocks.com) for conversion by the E. coli strain. Cultures were grown for 24 h. Cultures were then centrifuged (10,000 g×5 minutes) to remove cellular content, and culture broth containing secreted derivative was stored at –80C until further processing. The N-(2-(7-difluoro-1H-indol-3-yl)ethyl)acetamide product having chemical formula (XV):

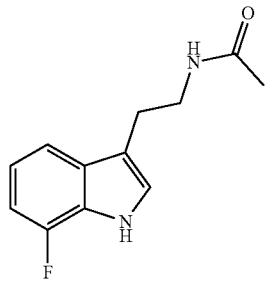

(XV)

contained in 1 L of E. coli culture was extracted by ethyl acetate (3×300 ml). The organic layer was dried over $Na_2SO_4$, followed by concentration under reduced pressure. The residue was purified by column chromatography on silica gel using ethyl acetate-hexane (50→80%) as eluent to give the compound as a light yellow solid (22 mg). Following purification, high-resolution MS (HRMS), $^1$H NMR, and selective $^{13}$C NMR were performed to assess purity, estimate total quantity, and confirm molecular structure. $^1$H NMR (400 MHz, CDCl$_3$): δ=1.96 (s, 3H), 2.97 (t, J=6.8 Hz, 2H,), 3.59 (dt, J=6.7, 6.1 Hz, 2H,), 5.7 (br, s, 1H), 6.91 (dd, J=11.2, 7.8 Hz, 1H), 7.03 (m, 2H), 7.35 (d, J=7.9 Hz, 1H), 8.6 (br, s, 1H). $^{13}$C NMR (100 MHz, CDCl$_3$): δ=23.3, 25.3, 39.8, 106.9 (d, $J_{C,F}$=16.1 Hz), 113.7, 114.4 (d, $J_{C,F}$=3.4 Hz), 119.6 (d, $J_{C,F}$=6.1 Hz), 122.8, 124.7, 131.1 (d, $J_{C,F}$=5.3 Hz), 149.7 (d, $J_{C,F}$=244.2 Hz), 170.3. HRMS (ESI) m/z: calcd. for $C_{12}H_{13}FN_2O$ [M+H]$^+$ 221.1090, found 221.1087. The compound having chemical formula (XV) was 95% (w/w) pure. It is noted that the acetyl group of the compound having chemical formula (XV) is included therein by virtue of the acetyl transferase having SEQ. ID NO: 63 in Escherichia coli strain Ec-1.

Cell lines for pharmacology assays. CHO-K1/Galpha15 (GenScript, M00257) (–5-HT$_{2A}$) and CHO-K1/5-HT$_{2A}$ (GenScript, M00250) (+5-HT$_{2A}$) cells lines were used in both toxicology/growth inhibition (MTT) and calcium release assays. Briefly, CHO-K1/Galpha15 is a control cell line that constitutively expresses Galpha15 which is a promiscuous Gq protein. It is engineered as a host cell, allowing transfected receptor(s) to signal through the Gq signal transduction pathway and mobilize intracellular calcium from the endoplasmic reticulum (ER). These control cells lack any transgene encoding 5-HT$_{2A}$ receptors, thus preventing calcium mobilization in response to 5-HT$_{2A}$ activation. Conversely, CHO-K1/5-HT$_{2A}$ cells stably express 5-HT$_{2A}$ receptor in the CHO-K1 host background. This design enables Gq-11 expressed in CHO-K1 cells to mobilize intracellular calcium changes when 5-HT$_{2A}$ receptors are activated by ligands.

Cell lines were maintained in Ham's F12 media plus 10% FBS in the presence of 100 ug/ml hygromycin for CHO-K1/Ga15 or 400 ug/ml G418 for CHO-K1/5-HT$_{2A}$ unless indicated otherwise for specific assays. Cell maintenance was carried out as recommended by the cell supplier. Briefly, vials with cells were removed from the liquid nitrogen and thawed quickly in 37° C. water bath. Just before cells were completely thawed, vial exteriors were decontaminated with 70% ethanol spray. Cell suspension was then retrieved from the vial and added to warm (37° C.), 'complete' (non-dropout) growth media, and centrifuged at 1,000 rpm for 5 minutes. The supernatant was discarded and the cell pellet was then resuspended in another 10 ml of complete growth media, and added to a 10 cm cell culture dish (Greiner Bio-One #664160). The media was changed every third day until the cells reached ~90% confluence. The ~90% confluent cells were then split 10:1, and used either for maintenance or pharmacological study.

Figure 14:
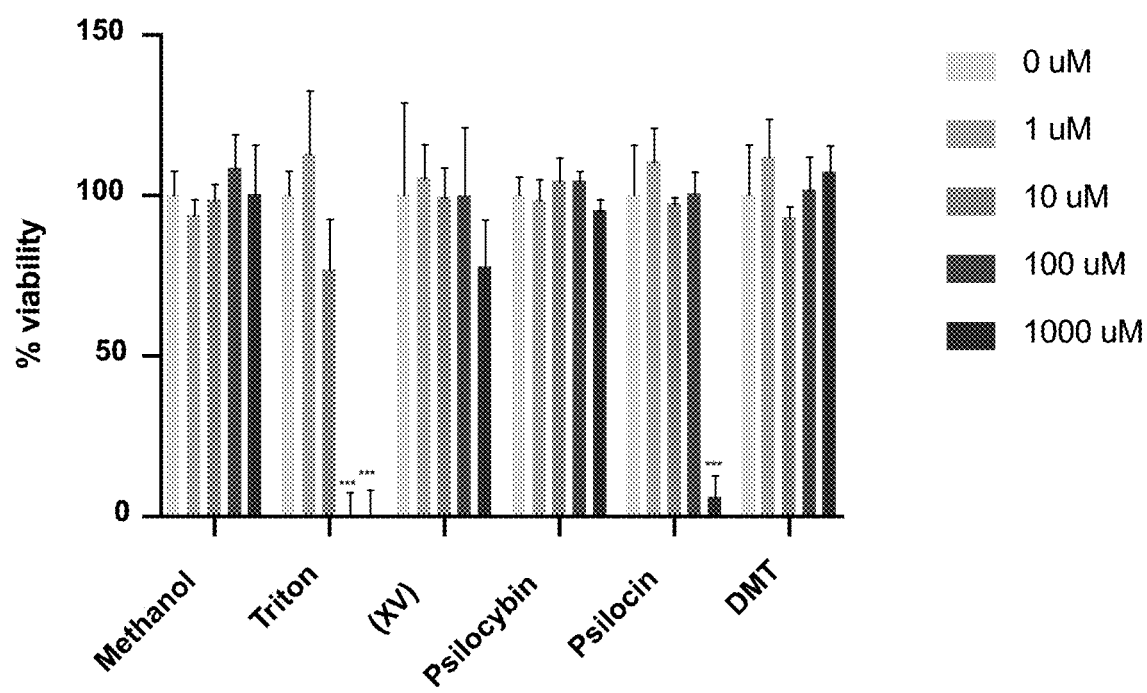
FIG. 14 depicts a graph obtained in the performance of an experimental assay to evaluate the efficacy of an example halogenated psilocybin derivative, notably a cell viability assay involving an example halogenated psilocybin derivative compound having the chemical formula (XV) set forth herein.

Assessment of cell viability upon treatment of glycosylated psilocybin derivatives. To establish suitable ligand concentrations for the calcium release assays, MTT (3-(4, 5-dimethylthiazol-2-yl)-2,5-diphenyltetrazolium) assays were first performed. Results of these assays were conducted using both control ligands (e.g. psilocybin, psilocin, DMT) and novel derivatives, in part as a pre-screen for any remarkable toxic effects on cell cultures up to concentrations of 1 mM. A known cellular toxin (Triton X-100, Pyrgiotakis G. et al., 2009, Ann. Biomed. Eng. 37: 1464-1473) was included as a general marker of toxicity. Modified Chinese Hamster Ovary cells (CHO-K1/Ga15) were cultured using standard procedures using the manufacture's protocols (Genscript, M00257). Briefly, cells were cultured in Ham's F12 medium supplemented with 10% fetal bovine serum and 100 mg/ml Hygromycin B, and grown at 37° C. in the presence of 5% CO2. To test the various compounds with the cell line, cells were seeded in a clear 96-well culture plate at 10,000 cells per well. After allowing cells to attach and grow for 24 hours, assay compounds were added at 1 µM, 10 µM, 100 µM, and 1 mM final concentrations. Methanol concentrations used are 0.001, 0.01, 0.1, and 1%. Triton concentrations used are 0.0001, 0.001, 0.01 and 0.1%. Cells were incubated with compounds for 48 hours before accessing cell viability with the MTT assay following the manufacture's protocol (MTT Cell Growth Assay Kit; Millipore Sigma, CT02). MTT reagent was added to cells and allowed to incubate for 4 hours before solubilization with isopropanol plus 0.04 N HCl. Absorbance readings were performed at 570 nm with the reference at 630 nm on a SpectraMax iD3 plate reader. Non-treated cells were assigned 100% viability. Results of the cell viability assays are shown in FIG. 14. Bar graphs show the mean+/−SD (n=3). Significance (P<0.0001), as indicated by (***) was determined using 2-way ANOVA with Dunnett's multiple comparisons test. The results using compound with formula (XV) are indicated as "(XV)" on the x-axis.

Figure 15A:
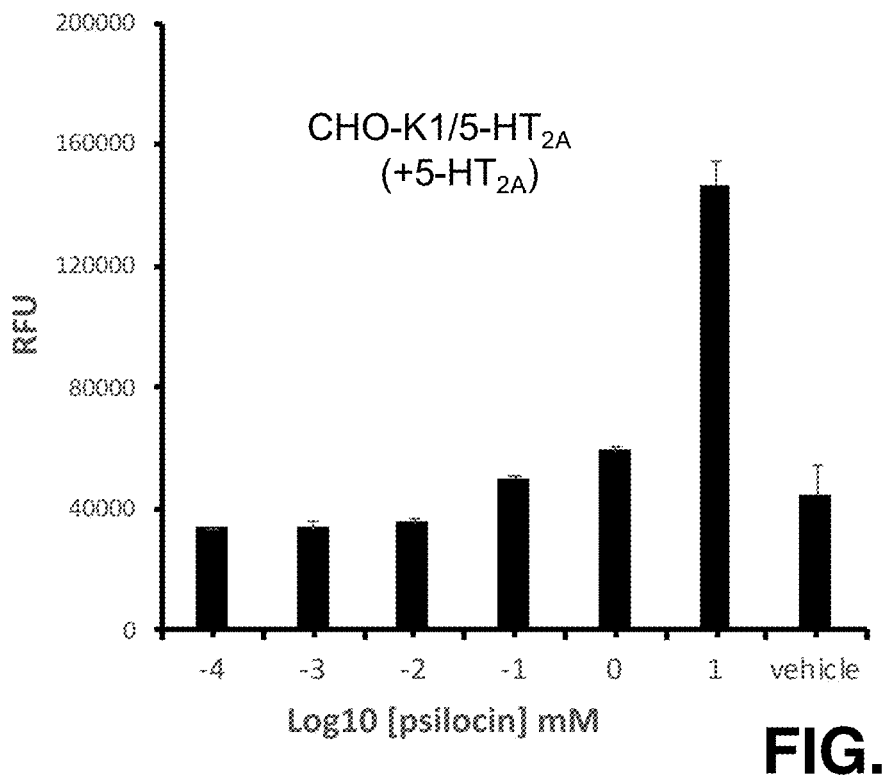
FIGS. 15A and 15B depict graphs obtained in the performance of an experimental assay to evaluate the efficacy of an example halogenated psilocybin derivative, notably a 5-$HT_{2a}$ receptor modulation assay involving +5-$HT_{2A}$ cells and an example halogenated psilocybin derivative compound having the chemical formula (XV) set forth herein (FIG. 15B) and a control (psilocin) (FIG. 15A).
Figure 15B:
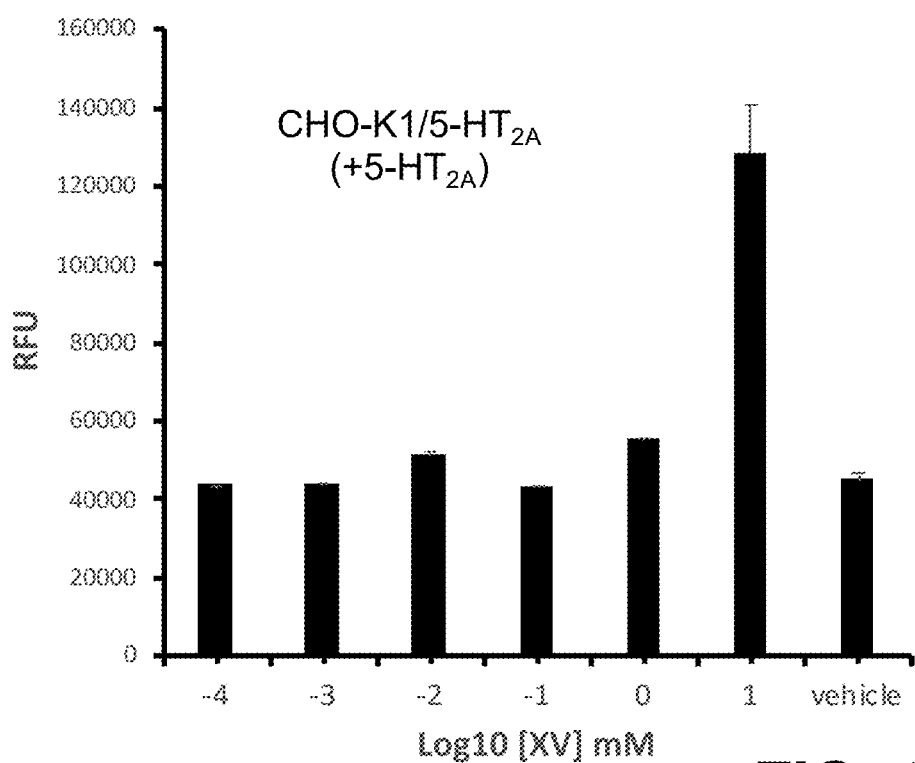
Figure 16A:
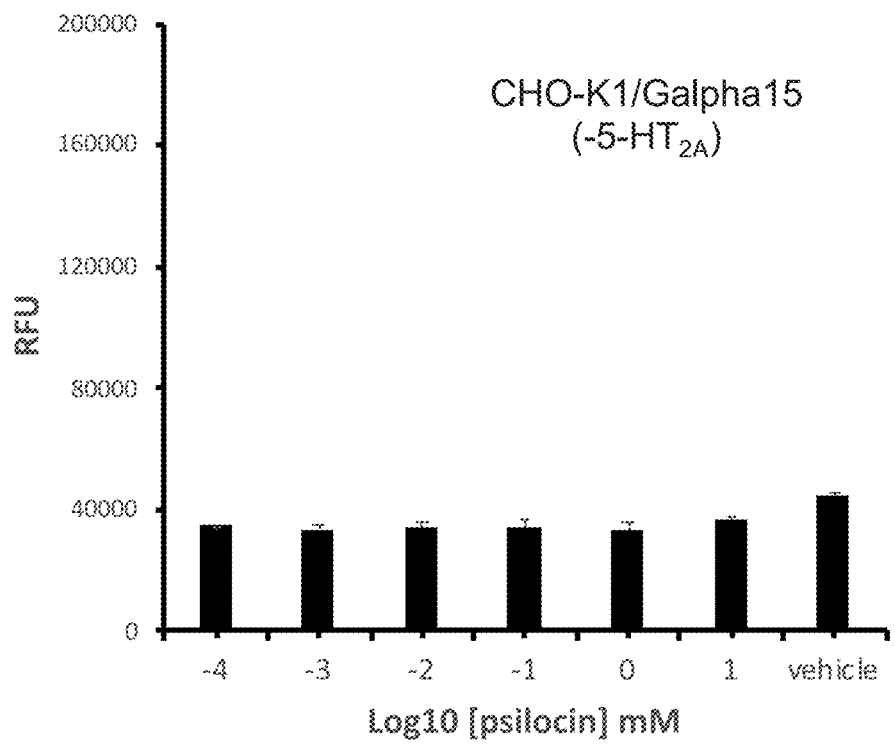
FIGS. 16A and 16B depict graphs obtained in the performance of an experimental assay to evaluate the efficacy of an example halogenated psilocybin derivative, notably a 5-$HT_{2a}$ receptor modulation assay involving −5-$HT_{2A}$ cells and an example halogenated psilocybin derivative compound having the chemical formula (XV) set forth herein (FIG. 16B) and a control (psilocin) (FIG. 16A).
Figure 16B:
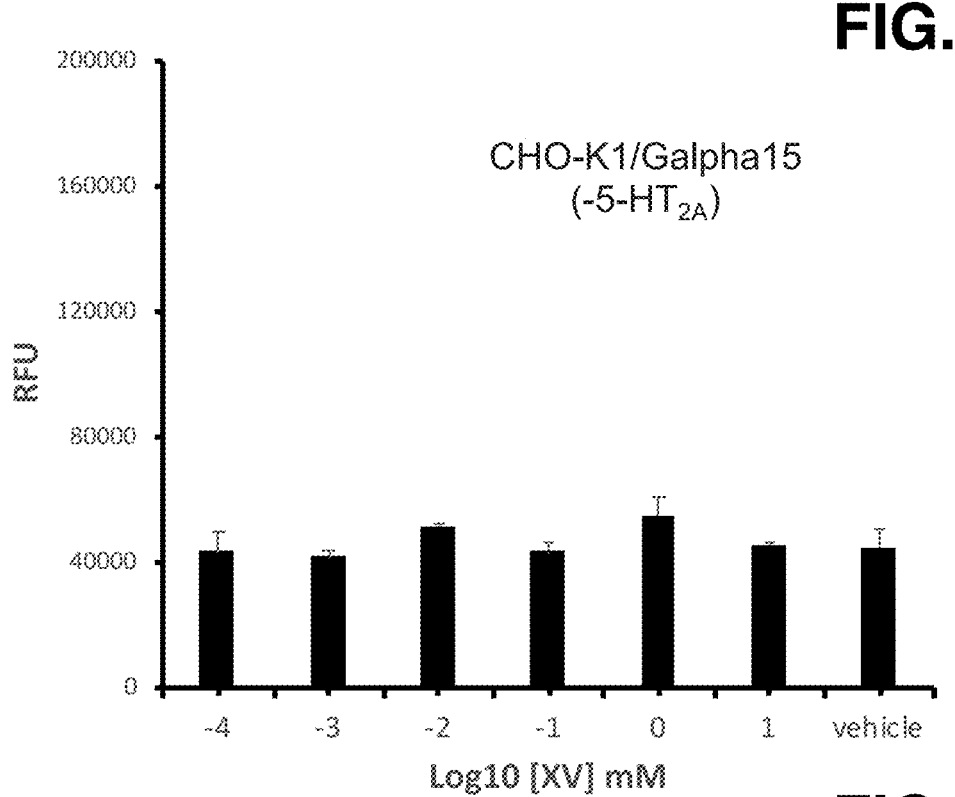

Increase in cytosolic calcium concentration by 5-HT$_{2A}$ activation. Changes in intracellular calcium concentration due to the treatment with assay compounds was measured using Fluo-8 dye (Abcam, #ab112129) according to the manufacturer's instructions. Briefly, CHO-K1 cells stably expressing 5-HT$_{2A}$ (Genscript #M00250) (+5-HT$_{2A}$) or lacking 5-HT$_{2A}$ (Genscript, M00257) (−5-HT$_{2A}$) were seeded on black walled clear bottom 96-well plates (Thermo Scientific #NUNC165305), allowing 70,000 cells/well in 100 ul media (HAM's F12, GIBCO #11765-047) with 1% FBS (Thermo Scientific #12483020). Cultures were maintained in a humidified incubator at 37° C. and 5% CO2. Fluo-8 dye was loaded into the cultures for 30 min at 37° C., followed by 30 min additional incubation at room temperature. Next, different dilutions of novel molecules and controls were prepared in serum-free culture media and added to the cells. Fluorescence (ex 490 nm/em 525 nm) obtained after the addition of molecules was expressed relative to values obtained before addition of the molecules (relative Fluo-8 fluorescence=Fmax/F0, where Fmax=maximum fluorescence and F0=baseline fluorescence). Fluorescence intensities were measured using a Spectramax ID3 plate reader (www.moleculardevices.com). Relative fluorescence (RFU) at increasing concentrations of compound was determined, illustrating concentration-dependent calcium flux. Psilocin, a known agonist with binding activity at 5-HT$_{2A}$ (Rickli A. et al., 2016, Europ. Neuropsychopharmacol., 26: 1326-1337) was used as a positive control to establish assay functionality. The Example compound (XV) was then evaluated. Results are shown in FIGS. 15A-15B and 16A-16B. The results using different concentrations of psilocin and compound with formula (XV) (indicated as "(XV)") in +5-HT$_{2A}$ cell cultures are shown in FIG. 15A and FIG. 15B, respectively. The results using different concentrations of psilocin and compound with formula (XV) (indicated as "(XV)") in −5-HT$_{2A}$ cell cultures are shown in FIG. 16A and FIG. 16B, respectively. Results for negative control treatment with vehicle containing neither psilocin nor derivative are shown in FIGS. 15A-15B and 16A-16B. Error bars show +/−SD about the mean (n=3).

Example 6—Process for Making a Sixth Halogenated Psilocybin Derivative from Halogenated Indole Feedstock

*Escherichia coli* strain Ec-1 was used to biosynthesize halogenated tryptamine derivative having chemical formula (II) from halogenated indole feedstock. The construction of Ec-1 is described in Example 5. Scaled-up culturing and material storage of engineered *E. coli* was conducted as described in Example 5, except that 4-chloroindole (Combi-Blocks, www.combi-blocks.com) was used in place of 7-fluoroindole. To assess product, high-resolution LC-HESI-LTQ-Orbitrap-XL MS analysis was conducted as described in Example 1. Singly protonated product with exact m/z and expected elemental formula matching 4-chloro-N-acetyl-tryptamine having chemical formula (II):

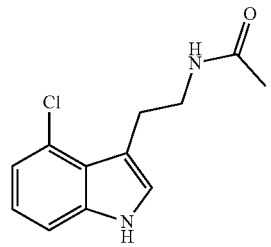

(II)

Figure 17:
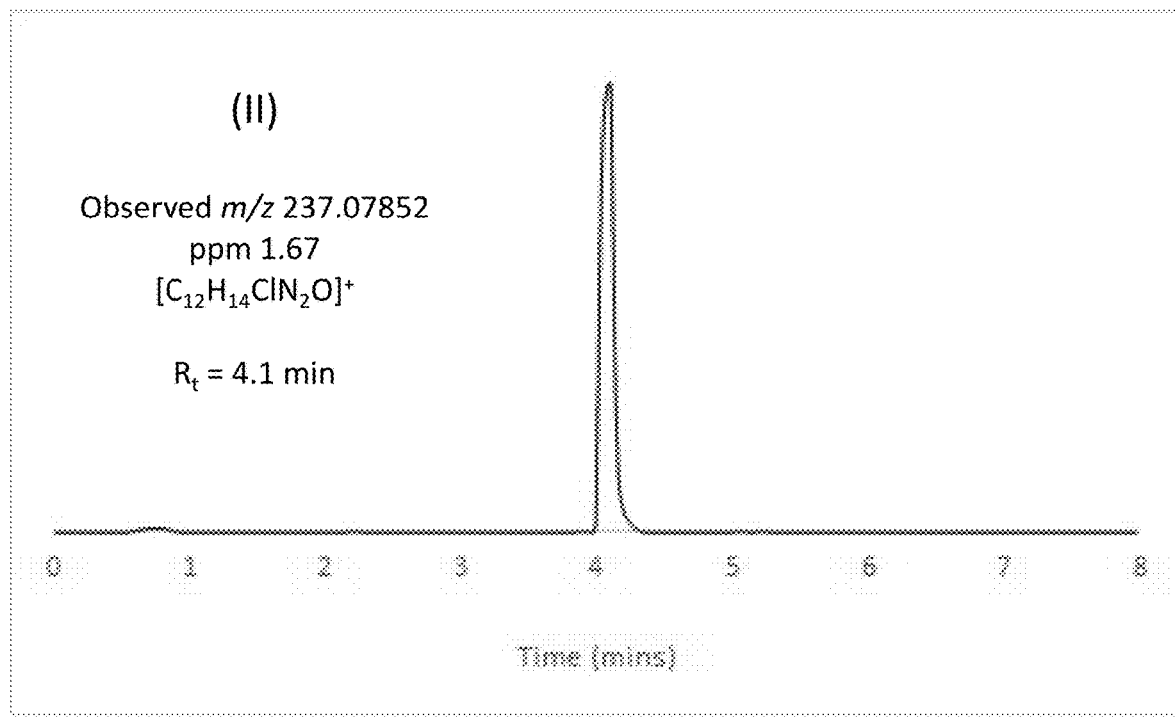
FIG. 17 depicts a representation of mass spectrometry data in the form of a chromatogram, notably a chromatogram obtained in the performance of an experiment to synthesize an example halogenated psilocybin derivative compound having the chemical formula (II) set forth herein.

Eluted at 4.1 minutes (EIC, see: FIG. 17). It is noted that the acetyl group of the compound having chemical formula (II) is included therein by virtue of the acetyl transferase having SEQ. ID NO: 63 in *Escherichia coli* strain Ec-1.

Example 7—Process for Making a Seventh Halogenated Psilocybin Derivative from Halogenated Indole Feedstock

*Escherichia coli* strain Ec-1 was used to biosynthesize halogenated tryptamine derivative having chemical formula (IX) from halogenated indole feedstock. The construction of Ec-1 is described in Example 5. Scaled-up culturing and material storage of engineered *E. coli* was conducted as described in Example 5, except that 5,6-difluoroindole (Combi-Blocks, www.combi-blocks.com) was used in place of 7-fluoroindole. N-(2-(5,6-difluoro-1H-indol-3-yl)ethyl)acetamide product having Chemical formula (IX):

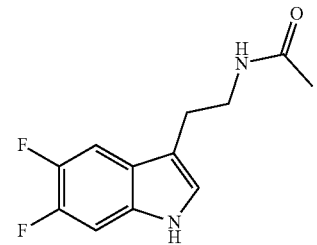

(IX)

contained in 0.55 L of *E. coli* culture was extracted by ethyl acetate (3×300 ml). The organic layer was dried over Na$_2$SO$_4$, followed by concentration under reduced pressure. The residue was purified by column chromatography on silica gel using ethyl acetate-hexane (50→80%) as eluent to give the compound as a light yellow solid (11 mg). Following purification, high-resolution MS (HRMS), $^1$H NMR, and selective $^{13}$C NMR were performed to assess purity, estimate total quantity, and confirm molecular structure. $^1$H NMR (400 MHz, CDCl$_3$): δ=1.70-1.79 (m, 1H), 1.99-2.06 (m, 1H), 2.29 (s, 6H), 2.33-2.38 (m, 1H), 2.40-2.48 (m, 1H), 3.22 (t, 1H, J=8.0 Hz), 3.28-3.36 (m, 1H), 3.68 (t, 1H, J=8.4 Hz), 3.94 (br, 1H), 6.65 (d, 1H, J=8.4 Hz), 6.74 (t, 1H, J=7.6 Hz), 7.05 (t, 1H, J=7.6 Hz), 7.11 (d, 1H, J=7.6 Hz). $^{13}$C NMR (100 MHz, CDCl$_3$): δ=23.4, 25.2, 39.7, 99.1 (d, J$_{C,F}$=21.7 Hz), 105.4 ((d, J$_{C,F}$=20.0 Hz), 123.3 (d, J$_{C,F}$=3.7 Hz), 150.6 (dd, J$_{C,F}$=237.4, 17.2 Hz), 148.9 (dd, J$_{C,F}$=238.3, 18.1 Hz), 170.1. HRMS (ESI) calcd. for C$_{12}$H$_{12}$F$_2$N$_2$O 239.0996 [M+H]$^+$, found 239.0989. The compound having chemical formula (IX) was 95% (w/w) pure. It is noted that the acetyl group of the compound having chemical formula (IX) is included therein by virtue of the acetyl transferase having SEQ. ID NO: 63 in *Escherichia coli* strain Ec-1.

Figure 18:
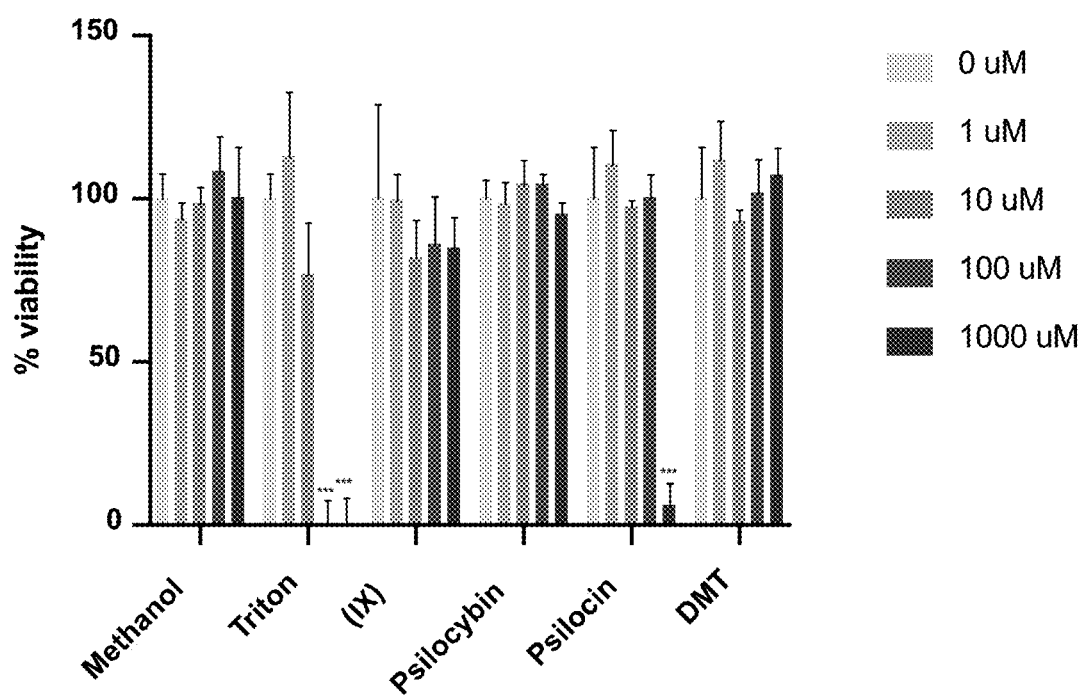
FIG. 18 depicts a graph obtained in the performance of an experimental assay to evaluate the efficacy of an example halogenated psilocybin derivative, notably a cell viability assay involving an example halogenated psilocybin derivative compound having the chemical formula (IX) set forth herein.
Figure 19A:
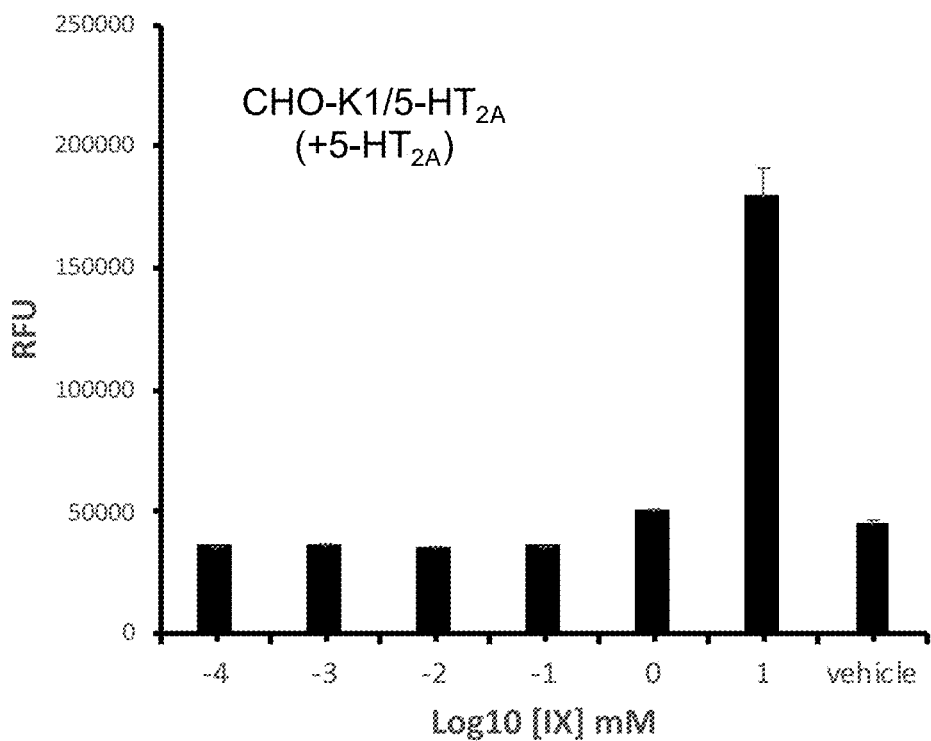
FIGS. 19A and 19B depict graphs obtained in the performance of an experimental assay to evaluate the efficacy of an example halogenated psilocybin derivative, notably a 5-$HT_{2a}$ receptor modulation assay involving +5-$HT_{2A}$ cells (FIG. 19A) and −5-$HT_{2A}$ cells (FIG. 19B) and an example halogenated psilocybin derivative compound having the chemical formula (IX) set forth herein.
Figure 19B:
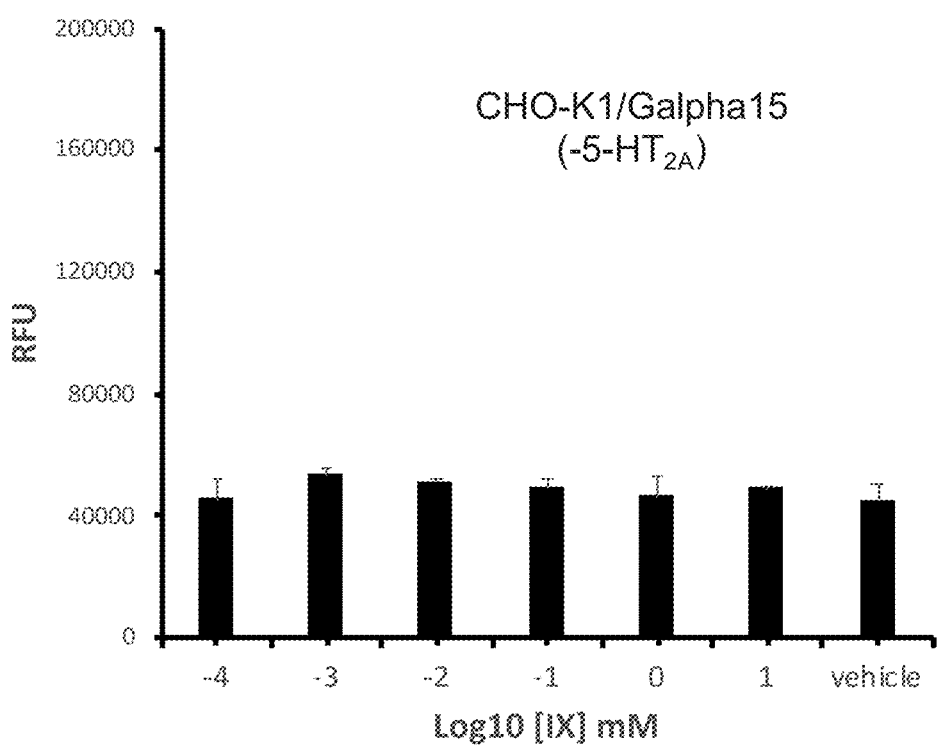

Efficacy testing was carried out as described in Example 5. MTT assay results are shown in FIG. 18, and calcium mobility assay results are shown in FIG. 19A (+5-HT$_{2A}$ cells) and FIG. 19B (−5-HT$_{2A}$ cells). In both cases, the example compound having the chemical formula (IX) is shown as "(IX)".

Example 8—Process for Making an Eighth Halogenated Psilocybin Derivative from Halogenated Indole Feedstock

*Escherichia coli* strain Ec-1 was used to biosynthesize halogenated tryptamine derivative having chemical formula (VI) from halogenated indole feedstock. The construction of Ec-1 is described in Example 5. Scaled-up culturing and material storage of engineered *E. coli* was conducted as described in Example 5, except that 4,6-difluoroindole (Combi-Blocks, www.combi-blocks.com) was used in place of 7-fluoroindole. To assess product, high-resolution LC-HESI-LTQ-Orbitrap-XL MS analysis was conducted as described in Example 1. Singly protonated product with exact m/z and expected elemental formula matching 4,6-difluoro-N-acetyltryptamine having chemical formula (VI):

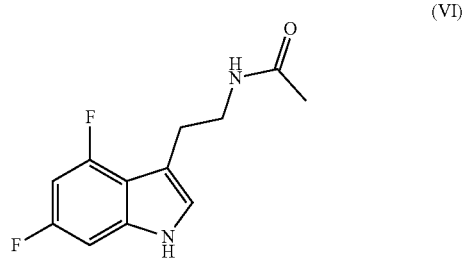 [SMILES: CC(=O)NCCc1c[nH]c2cc(F)cc(F)c12]

Figure 20:
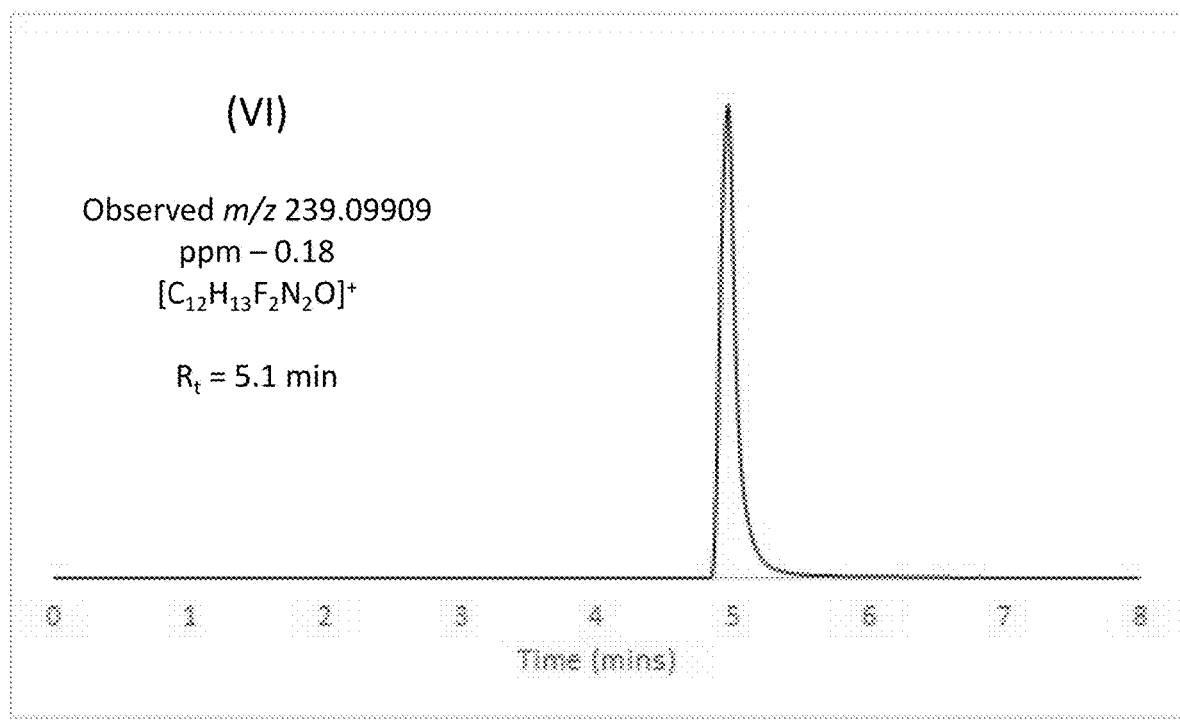
FIG. 20 depicts a representation of mass spectrometry data in the form of a chromatogram, notably a chromatogram obtained in the performance of an experiment to synthesize an example halogenated psilocybin derivative compound having the chemical formula (VI) set forth herein.

(VI)

eluted at 5.1 minutes (EIC, see: FIG. 20).

Example 9—Process for Making a Ninth Halogenated Psilocybin Derivative from Halogenated Indole Feedstock

*Escherichia coli* strain Ec-1 was used to biosynthesize halogenated tryptamine derivative having chemical formula (V) from halogenated indole feedstock. The construction of Ec-1 is described in Example 5. Scaled-up culturing and material storage of engineered *E. coli* was conducted as described in Example 5, except that 4,5-difluoroindole (Combi-Blocks, www.combi-blocks.com) was used in place of 7-fluoroindole. N-(2-(4,5-difluoro-1H-indol-3-yl)ethyl) acetamide product having chemical formula (V):

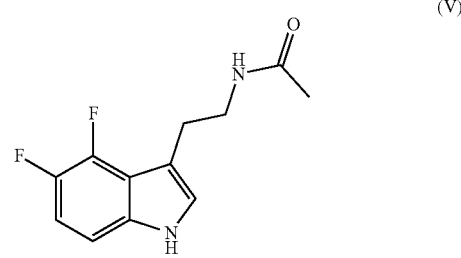 [SMILES: CC(=O)NCCc1c[nH]c2ccc(F)c(F)c12]

(V)

contained in 1 L of *E. coli* culture was extracted by ethyl acetate (3×600 ml). The organic layer was dried over Na$_2$SO$_4$, followed by concentration under reduced pressure. The residue was purified by flash chromatography on silica gel using ethyl acetate-hexane (50→80%) as eluent, followed by crystallization from EtOAc/Hexane to give the compound as a white solid (20 mg). Following purification, high-resolution MS (HRMS), $^1$H NMR, and selective $^{13}$C NMR were performed to assess purity, estimate total quantity, and confirm molecular structure. $^1$H NMR (400 MHz, CDCl$_3$): δ=1.96 (s, 3H), 3.04 (t, J=6.9 Hz, 2H,), 3.60 (dt, J=6.6, 6.4 Hz, 2H,), 5.64 (br, s, 1H), 7.01 (m, 3H), 8.41 (br, s, 1H). $^{13}$C NMR (100 MHz, CDCl$_3$): δ=23.4, 26.3, 40.5 (d, J$_{C,F}$=2.0 Hz), 106.6 (dd, J$_{C,F}$=7.7, 4.2 Hz), 111.7 (d, J$_{C,F}$=21.7 Hz), 124.0, 143.9 (dd, J$_{C,F}$=246.4, 14.5 Hz), 143.8 (dd, J$_{C,F}$=246.4, 14.5 Hz), 170.2. HRMS (ESI) m/z: calcd. for C$_{12}$H$_{12}$F$_2$N$_2$O [M+H]$^+$ 239.0996, found 239.0989. The compound having chemical formula (V) was 95% (w/w) pure. It is noted that the acetyl group of the compound having chemical formula (II) is included therein by virtue of the acetyl transferase having SEQ. ID NO: 63 in *Escherichia coli* strain Ec-1.

Figure 21:
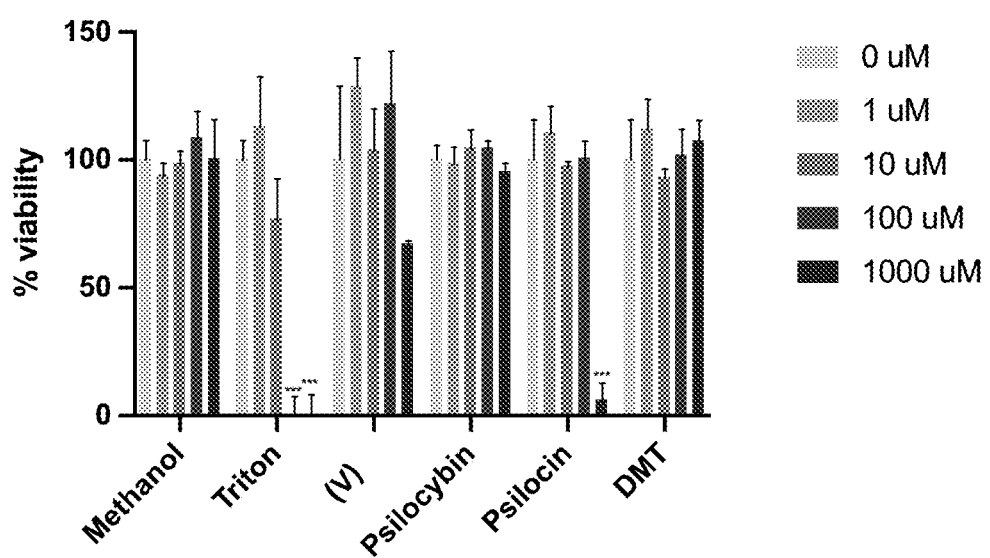
FIG. 21 depicts a graph obtained in the performance of an experimental assay to evaluate the efficacy of an example halogenated psilocybin derivative, notably a cell viability assay involving an example halogenated psilocybin derivative compound having the chemical formula (V) set forth herein.
Figure 22A:
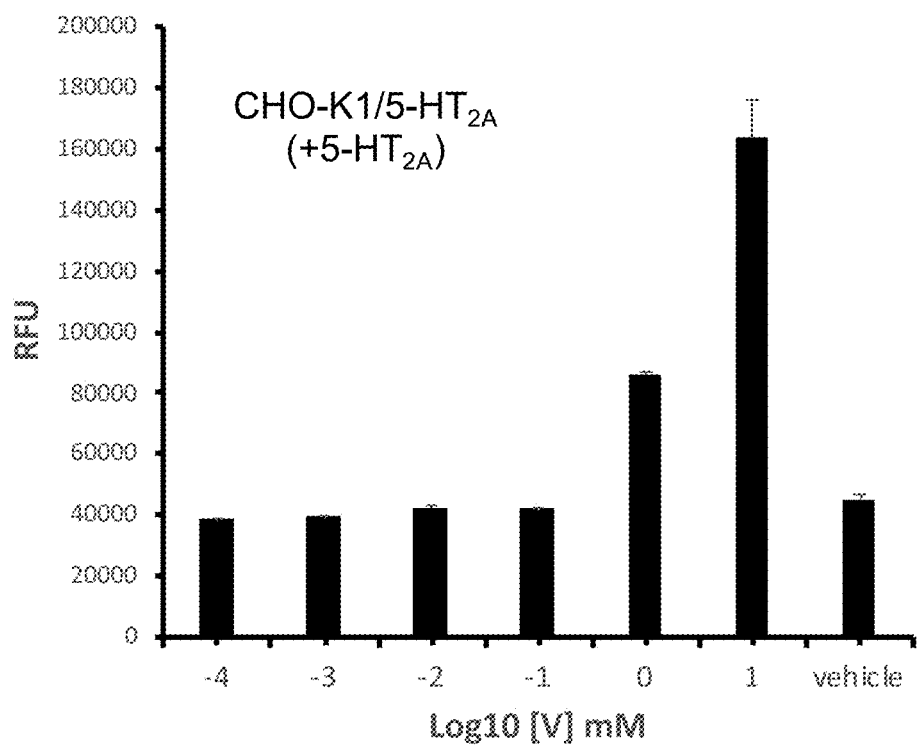
FIGS. 22A and 22B depict graphs obtained in the performance of an experimental assay to evaluate the efficacy of an example halogenated psilocybin derivative, notably a 5-$HT_{2a}$ receptor modulation assay involving +5-$HT_{2A}$ cells (FIG. 22A) and −5-$HT_{2A}$ cells (FIG. 22B), and an example halogenated psilocybin derivative compound having the chemical formula (V) set forth herein.
Figure 22B:
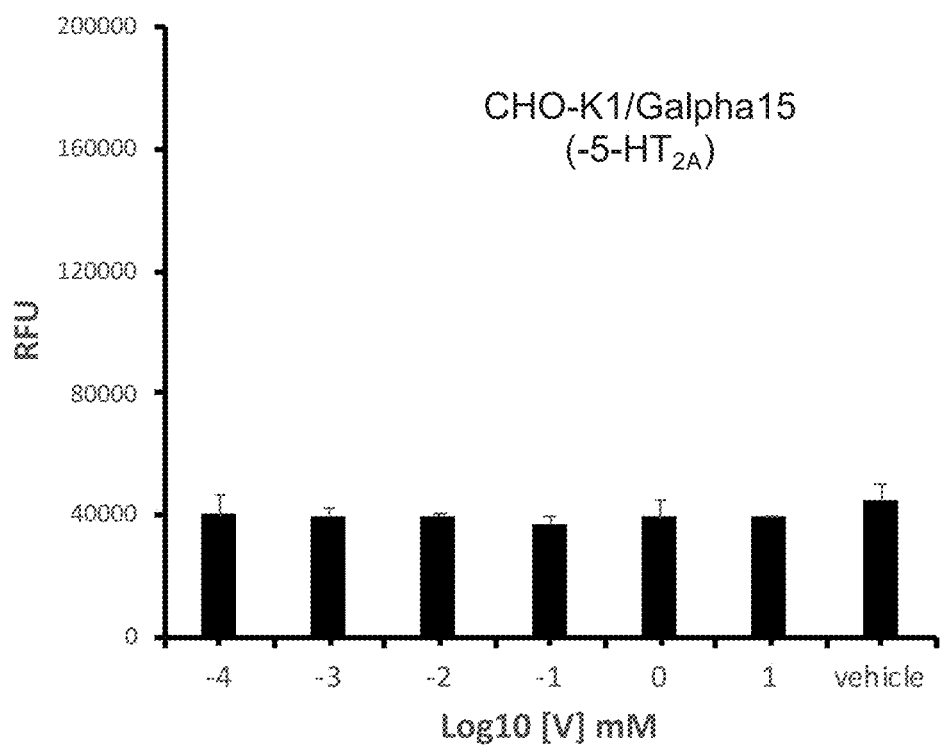

Efficacy testing was carried out as described in Example 5. MTT assay results are shown in FIG. 21, and calcium mobility assay results are shown in FIGS. 22A and 22B. In both cases, the example compound having the chemical formula (V) is shown as "(V)".

Example 10—Process for Making a Tenth Halogenated Psilocybin Derivative from Halogenated Indole Feedstock

*E. coli* strain Ec-2 was constructed as follows. For plasmid cloning, Top10 or XL1-blue strains were used depending on antibiotic markers. Standard LB media was used for culturing. For gene expression and feeding experiments, the parent host strain employed was BL21 (DE3). For this Example, heterologous expression of a non-native or engineered TrpB gene was not necessary, as endogenous tryptophan synthase activity proved sufficient. From plasmid pCDM4 (SEQ. ID NO: 92), the plasmid pCDM4-PsiD-FLAG was created by inserting an in-frame, C-terminally FLAG-tagged (SEQ. ID NO: 85) PsiD gene (SEQ. ID NO: 1) into the NdeI/XhoI site of pCDM4. The plasmid pETM6-H10-PsiK-V5-PsiM-FLAG was created by first cloning the in-frame, C-terminally V5-tagged (SEQ. ID NO: 87) PsiK (SEQ. ID NO: 5) into the NdeI/XhoI site of pETM6-H10 (SEQ. ID NO: 97) to create pETM6-H10-PsiK-V5. This intermediate plasmid was digested with SpeI and SalI, and in-frame, C-terminally FLAG tagged (SEQ. ID NO: 85) PsiM (SEQ. ID NO: 7) was cloned into the site with XbaI and SalI, nullifying the SpeI restriction site. In this setup, the T7 polymerase was able to drive the expression of the polycistronic DNA containing both PsiK and PsiM. The two target plasmids pCDM4-PsiD-FLAG and pETM6-H10-PsiK-V5-PsiM-FLAG were transformed into BL21 (DE3) cells, and antibiotics ampicillin plus streptomycin were used to select for the correct clones containing both plasmids. Scaled-up culturing of engineered *E. coli* was conducted as follows: seed cultures were inoculated in AMM (Jones et al. 2015, Sci Rep. 5: 11301) medium overnight. The overnight culture was then divided into two flasks containing 500 mL each of AMM medium additionally containing 0.5% (w/v) serine, 1M IPTG, 50 ug/L ampicillin and *Streptomyces*, and 100 mg/L 4-hydroxy-6-bromoindole (BLDPharm, www.bldpharm.com) for conversion by Ec-2. Cultures were grown for 24 h. Cultures were then centrifuged (10,000 g×5 minutes) to remove cellular content, and culture broth containing secreted derivative was stored at −80C until further processing. To assess product, high-resolution LC-HESI-LTQ-Orbitrap-XL MS analysis was conducted as described in Example 1. Singly protonated product with exact m/z and expected elemental formula matching 6-bromo-psilocybin having chemical formula (XIII):

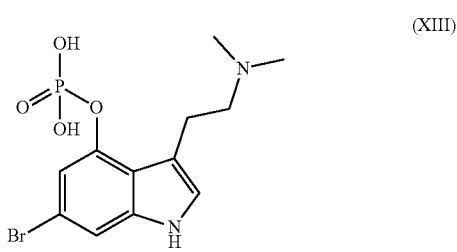 [SMILES: CN(C)CCc1c[nH]c2cc(Br)cc(OP(=O)(O)O)c12]

Figure 23:
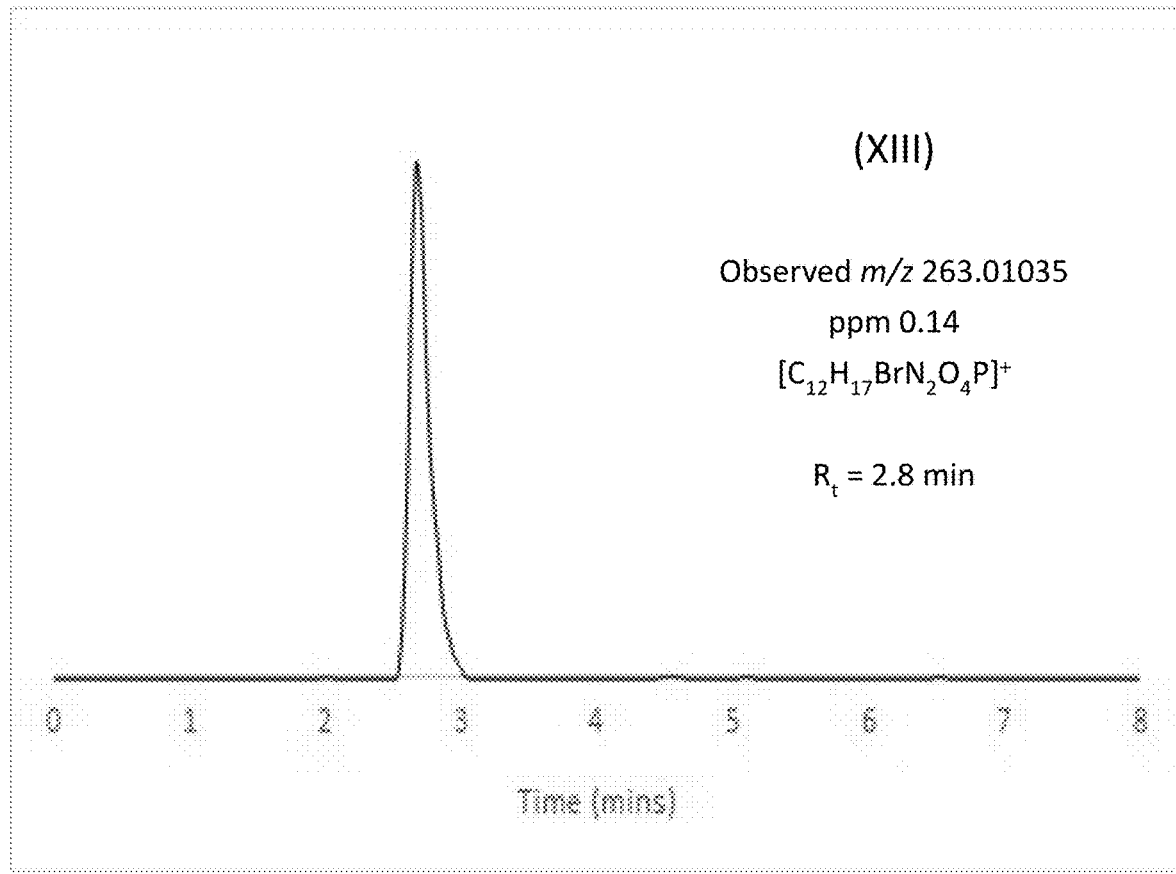
FIG. 23 depicts a representation of mass spectrometry data in the form of a chromatogram, notably a chromatogram obtained in the performance of an experiment to synthesize an example halogenated psilocybin derivative compound having the chemical formula (XIII) set forth herein.

(XIII)

eluted at 2.8 minutes (DC, see: FIG. 23).

Figure 9A:
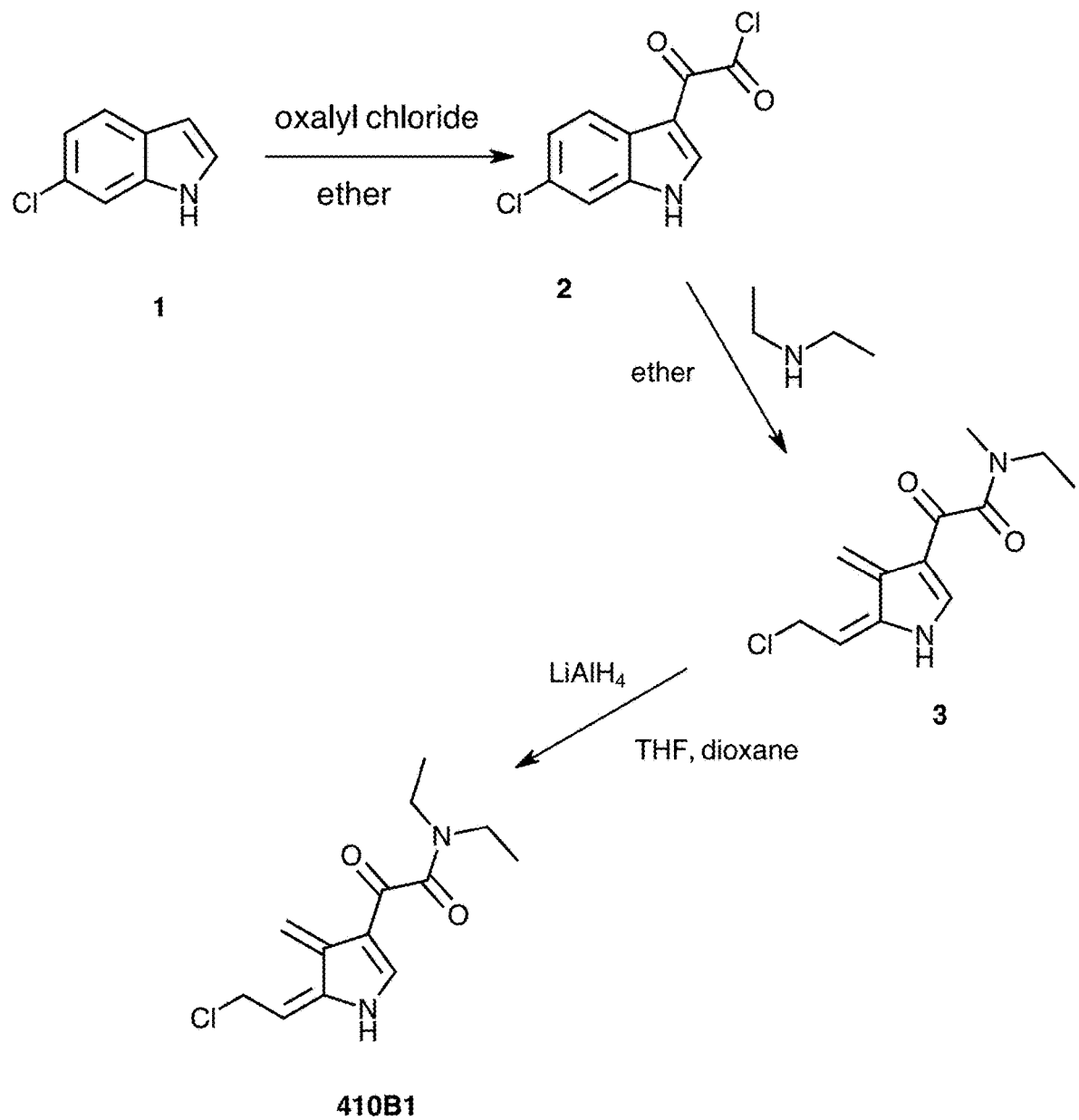
FIGS. 9A and 9B depict example chemical synthesis processes for the synthesis of certain example halogenated psilocybin derivatives, notably the compound denoted as 410B01 (FIG. 9A) and corresponding with a halogenated psilocybin derivative compound having the chemical formula (IV) set forth herein, and the compound denoted as 1 (FIG. 9B) and corresponding with a halogenated psilocybin derivative compound having the chemical formula (VIII) set forth herein.

Example 11—Process for Making an Eleventh Halogenated Psilocybin Derivative from Halogenated Indole Feedstock In a flame-dried round bottom flask under argon, 6-chloroindole (compound 1, see: FIG. 9A) (210 mg, 1.39 mmol, 1.00 eq) was dissolved in diethyl ether (4.0 mL) and cooled to 0° C. To this solution, oxalyl chloride (369 mg, 2.91 mmol, 2.10 eq) in diethyl ether (2.0 mL) was added dropwise over a period of 10 minutes. The reaction mixture was allowed to stir at room temperature for 4 hours. Additional ether (5.0 mL) was added to the reaction mixture which was then cooled to 0° C. and subsequently vacuum-filtered to yield a bright yellow solid (compound 2) (211 mg, 0.872 mmol, 63%). Compound 2 (see: FIG. 9A) was washed with cold ether (10 mL) and allowed to briefly dry before being resuspended in diethyl ether (3.0 mL) and cooled to 0° C. Diethylamine (510 mg, 6.97 mmol, 8.00 eq) was diluted with diethyl ether (3.0 mL) and added dropwise to the reaction flask, immediately precipitating out a white solid. This mixture was allowed to stir for 10 minutes at 0° C., warmed to room temperature, and stirred for an additional 1.5 hours. The visible precipitate was vacuum filtered to yield a solid which was washed with cold diethyl ether (10 mL). This solid was suspended in deionized water (50 mL), stirred for 10 minutes, vacuum-filtered, and allowed to dry overnight, yielding compound 3 (see: FIG. 9A) as a white powder (124 mg, 0.445 mmol, 51%). No further purification was required. $^1$H NMR (400 MHz, CDCl$_3$): δ (ppm)=9.56 (s, 1H), 8.24 (d, J=8.5 Hz, 1H), 7.74 (d, J=3.0 Hz, 1H), 7.36 (dd, J=1.8, 0.6 Hz, 1H), 7.28 (d, J=1.8 Hz, 1H), 3.54 (q, J=7.1 Hz, 2H), 3.36 (q, J=7.1 Hz, 2H), 1.27 (t, J=7.2 Hz, 3H), 1.19 (t, J=7.1 Hz, 3H). A THF solution of lithium aluminum hydride (2.20 mL, 2.22 mmol, 5.00 eq, 1.0 M) was added to a 3-neck, flame-dried, round-bottom flask under argon. Anhydrous dioxane (3.0 mL) was added to the reaction mixture. In a separate vial, compound 3 (124 mg, 0.445 mmol) was dissolved in a THF (2.0 mL)/dioxane (1.0 mL) solution and added dropwise to the reaction vessel. This mixture was then allowed to reflux at 95° C. for 1.5 hours. The reaction mixture was cooled to 0° C. and quenched through dropwise addition of a water (1.0 mL)/THF (2.0 mL) solution, yielding a flocculent precipitate. This precipitate was removed through vacuum-filtration and the filter-cake was washed with diethyl ether (20 mL). The filtrate was collected, dried with MgSO$_4$, and solvent removed to yield a pale-yellow oil. Purification through column chromatography on silica gel (2% MeOH/DCM+1% NEt$_3$) yielded compound 410B01 (see: FIG. 9A), corresponding to compound with formula (X):

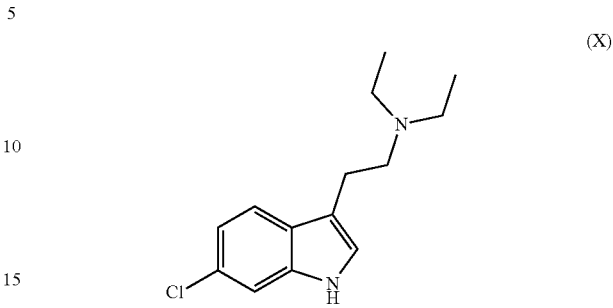

(X)

as a clear, colourless oil (34 mg, 0.136 mmol, 30%). $^1$H NMR (400 MHz, CDCl$_3$): δ (ppm)=8.37 (s, 1H), 7.49 (d, J=8.5 z, 1H), 7.30 (d, J=1.8 Hz, 1H), 7.07 (dd, J=8.5, 1.8 Hz, 1H), 6.98 (dd, J=2.5, 1.1 Hz, 1H), 2.90 (high order m, 2H), 2.79 (high order m, 2H), 2.74-2.62 (q, J=7.1 Hz, 4H), 1.15-1.04 (t, J=7.1 Hz, 6H). $^{13}$C NMR (100 MHz, CDCl$_3$): δ (ppm)=136.6, 127.8, 126.2, 122.2, 119.9, 119.7, 114.8, 111.0, 70.5, 53.5, 46.9, 22.8, 11.7. The compound having chemical formula (IX) was 95% (w/w) pure.

Figure 24:
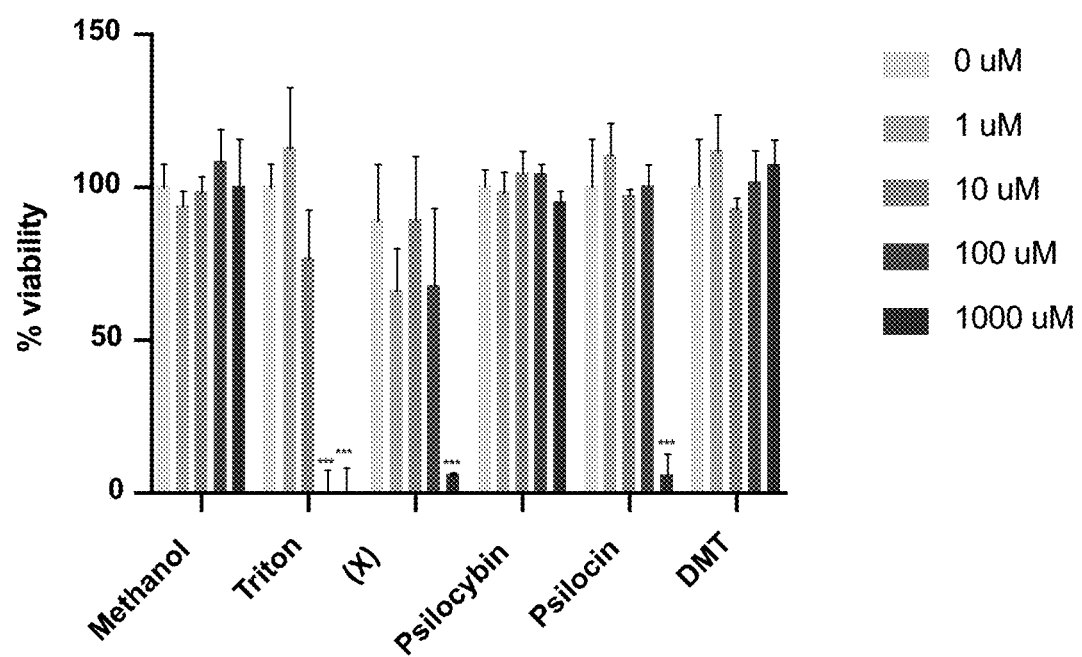
FIG. 24 depicts a graph obtained in the performance of an experimental assay to evaluate the efficacy of an example halogenated psilocybin derivative, notably a cell viability assay involving an example halogenated psilocybin derivative compound having the chemical formula (X) set forth herein.
Figure 25A:
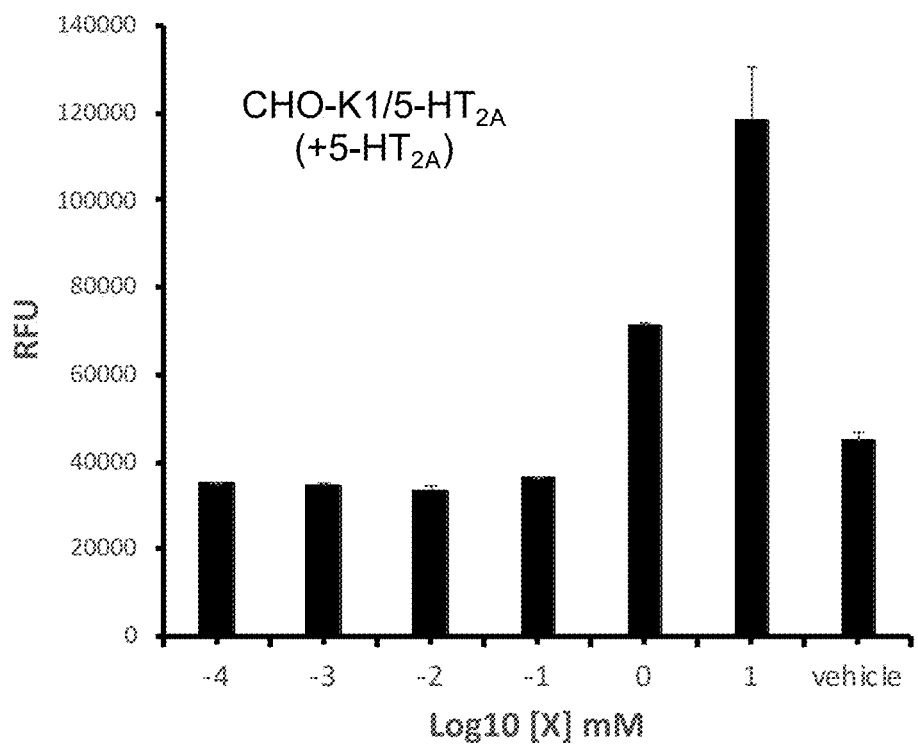
FIGS. 25A and 25B depict graphs obtained in the performance of an experimental assay to evaluate the efficacy of an example halogenated psilocybin derivative, notably a 5-$HT_{2a}$ receptor modulation assay involving +5-$HT_{2A}$ cells (FIG. 25A) and −5-$HT_{2A}$ cells (FIG. 25B), and an example halogenated psilocybin derivative compound having the chemical formula (X) set forth herein.
Figure 25B:
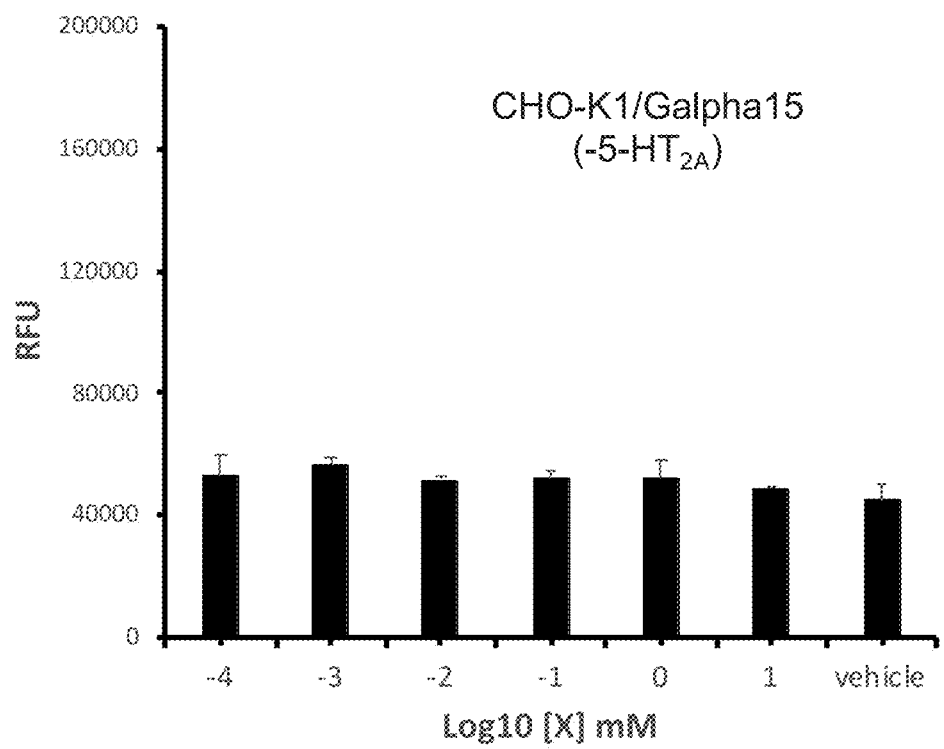

Efficacy testing was carried out as described in Example 5. MTT assay results are shown in FIG. 24, and calcium mobility assay results are shown in FIGS. 25A and 25B. In both cases, the example compound having chemical formula (X) is shown as "(X)".

Example 12—Process for Making a Twelfth Halogenated Psilocybin Derivative from Halogenated Indole Feedstock A similar process as illustrated in FIG. 9A (Example 11) was followed. In a flame-dried round bottom flask under argon, 4-fluoroindole (compound 1) (200 mg, 1.48 mmol, 1.00 eq) was dissolved in diethyl ether (4.0 mL) and cooled to 0° C. To this solution, oxalyl chloride (394 mg, 3.11 mmol, 2.10 eq) in diethyl ether (2.0 mL) was added dropwise over a period of 10 minutes. The reaction mixture was allowed to stir at room temperature for 4 hours. Additional ether (5.0 mL) was added to the reaction mixture which was then cooled to 0° C. and subsequently vacuum-filtered to yield a bright yellow solid (compound 2) (264 mg, 1.17 mmol, 79%). Compound 2 was washed with cold ether (10 mL) and allowed to briefly dry before being resuspended in diethyl ether (3.0 mL) and cooled to 0° C. N-Methylethylamine (574 mg, 9.72 mmol, 8.00 eq) was diluted with diethyl ether (3.0 mL) and added dropwise to the reaction flask. This mixture was allowed to stir for 10 minutes at 0° C., warmed to room temperature, and stirred for an additional 1.5 hours, yielding a suspension of light-pink gooey solid. The diethyl ether was decanted, and the solid dissolved in dichloromethane (10 mL) and washed with water (3×10 mL). The organic phase was dried with MgSO$_4$ and solvent removed to yield a pale-pink glassy solid (128 mg, 0.516 mmol, 43%). 1H NMR (400 MHz, CDCl$_3$): δ (ppm)= 10.72 (s, 1H), 7.72 (d, J=3.8 Hz, 1H), 7.10-7.00 (m, 2H), 6.84 (ddd, J=11.1, 7.2, 1.6 Hz, 1H), 3.55 (q, J=7.2 Hz, 1H), 3.35 (q, J=7.1 Hz, 1H), 3.05 (s, 2H), 2.98 (s, 1H), 1.23 (t, J=7.2 Hz, 2H), 1.15 (t, J=7.1 Hz, 2H). A THF solution of lithium aluminum hydride (2.58 mL, 2.58 mmol, 5.00 eq, 1.0 M) was added to a 3-neck, flame-dried, round-bottom flask under argon. Anhydrous dioxane (3.0 mL) was added to the reaction mixture. In a separate vial, compound 3 (128 mg, 0.516 mmol) was dissolved in an anhydrous THF (2.0 mL)/dioxane (1.0 mL) solution and added dropwise to the reaction vessel. This mixture was then allowed to reflux at 95° C. for 2.5 hours. The reaction mixture was cooled to 0° C. and quenched through dropwise addition of a water (1 mL)/THF (2 mL) solution, yielding a flocculent precipitate. This precipitate was removed through vacuum-filtration and the filter-cake was washed with diethyl ether (20 mL). The filtrate was collected, dried with $MgSO_4$, and solvent removed to yield a pale-orange oil. Purification through column chromatography on silica gel (1% $MeOH/CH_2Cl_2$ + 1% $NEt_3$) yielded compound 456B01, corresponding to compound having chemical formula (IV):

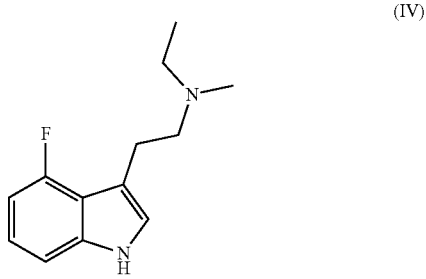 [SMILES: CCN(C)CCc1c[nH]c2cccc(F)c12]

(IV)

as clear, colourless oily crystal (86 mg, 0.390 mmol, 76%). $^1$H NMR (400 MHz, $CDCl_3$): δ (ppm)=8.68 (s, 1H), 7.12-6.99 (m, 2H), 6.91 (d, J=2.3 Hz, 1H), 6.73 (ddd, J=11.2, 6.9, 1.6 Hz, 1H), 3.04 (high order m, 2H), 2.75 (high order m, 2H), 2.57 (q, J=7.2 Hz, 2H), 2.38 (s, 3H), 1.12 (t, J=7.2 Hz, 3H). $^{13}$C NMR (100 MHz, $CDCl_3$): δ (ppm)=157.2 (d, =245.6 Hz), 139.2 (d, =11.8 Hz), 122.2 (d, $J_{C-F}$=8.2 Hz), 121.9, 107.2 (d, $J_{C-F}$=3.6 Hz), 104.2 (d, $J_{C-F}$=19.7 Hz), 58.5, 51.2, 41.5, 24.1, 12.1. The compound having chemical formula (IV) was 95% (w/w) pure.

Figure 26:
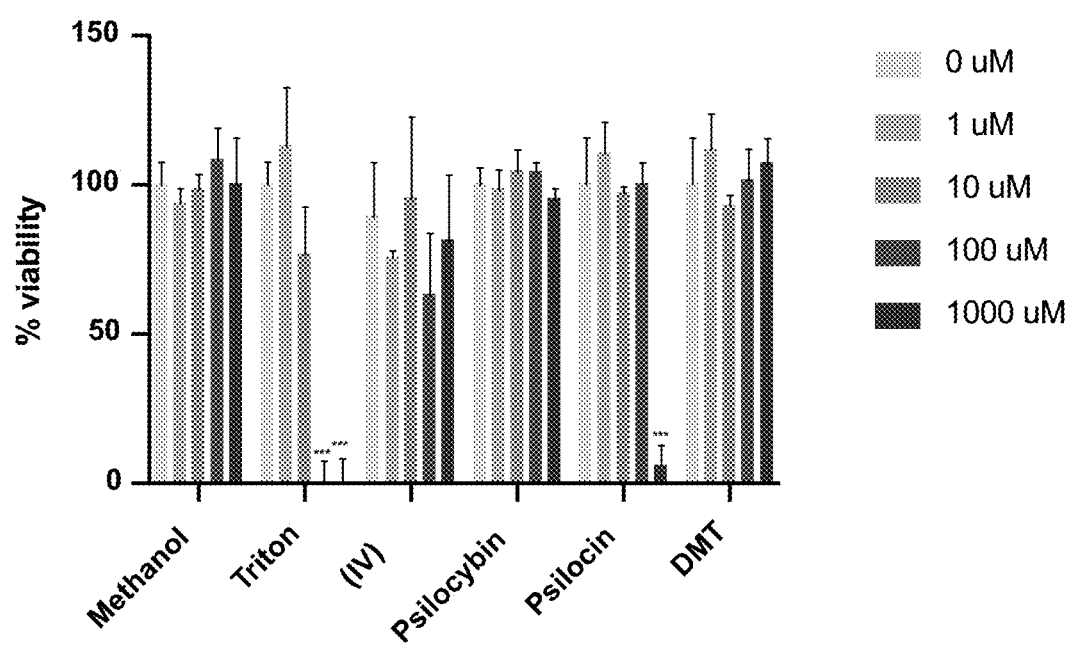
FIG. 26 depicts a graph obtained in the performance of an experimental assay to evaluate the efficacy of an example halogenated psilocybin derivative, notably a cell viability assay involving an example halogenated psilocybin derivative compound having the chemical formula (IV) set forth herein.
Figure 27A:
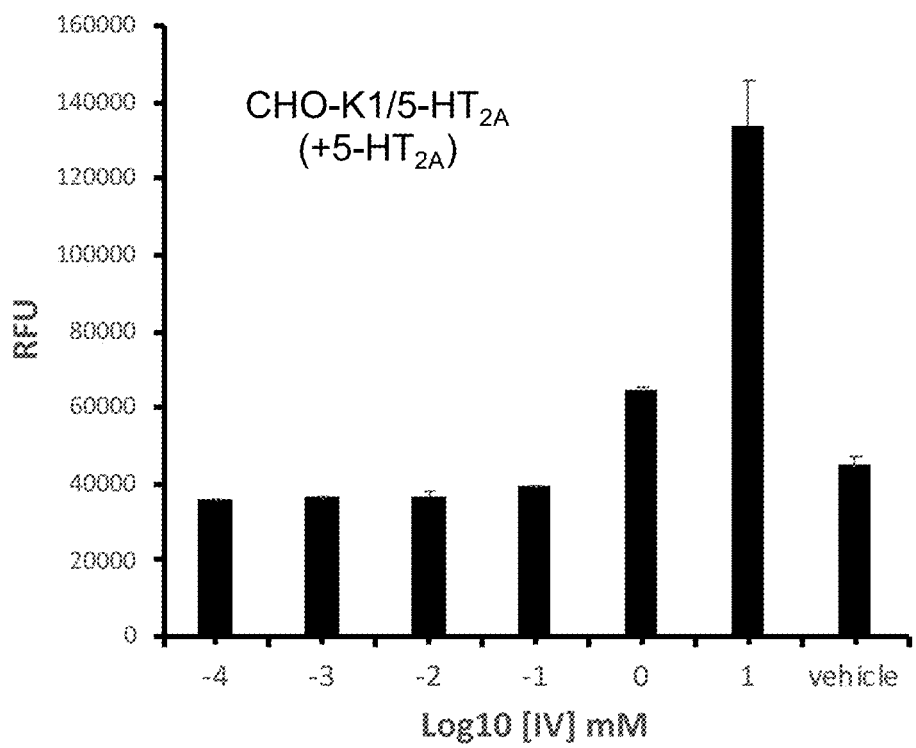
FIGS. 27A and 27B depict graphs obtained in the performance of an experimental assay to evaluate the efficacy of an example halogenated psilocybin derivative, notably a 5-$HT_{2a}$ receptor modulation assay involving +5-$HT_{2A}$ cells (FIG. 27A) and −5-$HT_{2A}$ cells (FIG. 27B), and an example halogenated psilocybin derivative compound having the chemical formula (IV) set forth herein.
Figure 27B:
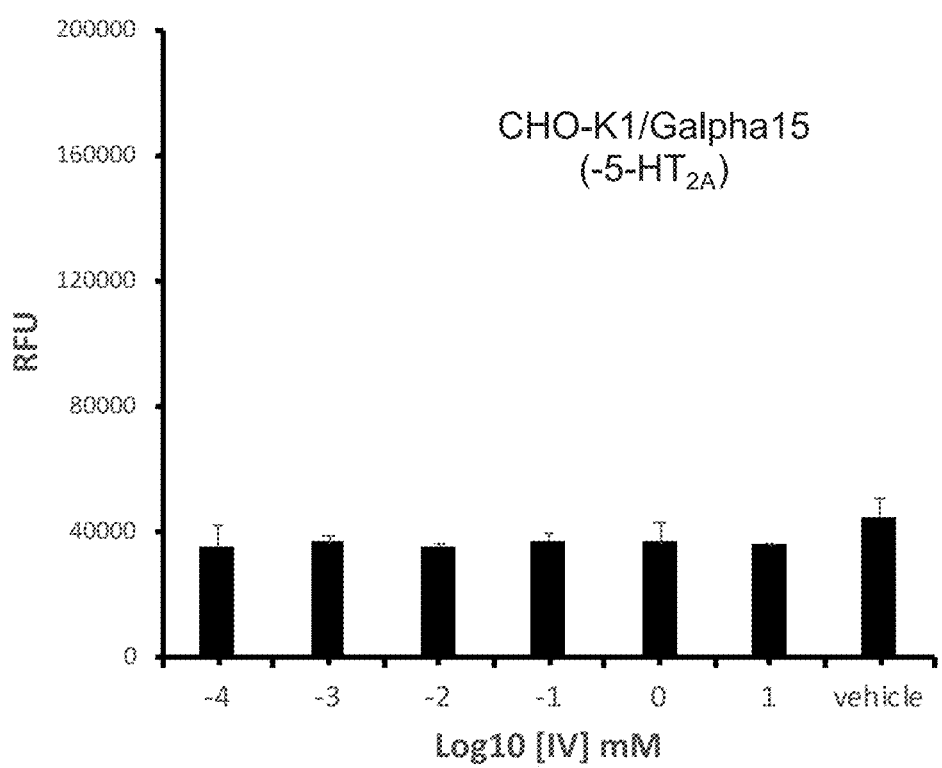

Efficacy testing was carried out as described in Example 5. MTT assay results are shown in FIG. 26, and calcium mobility assay results are shown in FIG. 27A and FIG. 27B. In both cases, the example compound having the chemical formula (IV) is shown as "(IV)".

Example 13—Process for Making a Thirteenth Halogenated Psilocybin Derivative from Halogenated Indole Feedstock A thirteenth halogenated psilocybin derivative compound was synthesized according to the method of Example 11, except using 5-fluoroindole and N-methylethylamine as starting materials. Analysis indicated the isolation of a compound having chemical formula (VII):

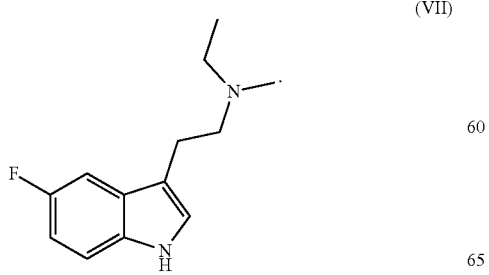

(VII)

$^1$H NMR (400 MHz, $CDCl_3$): δ (ppm)=8.09 (s, 1H), 7.29-7.20 (m, 2H), 7.06 (d, J=2.4 Hz, 1H), 6.96-6.87 (m, 1H), 2.93-2.86 (m, 2H), 2.72-2.64 (m, 2H), 2.53 (q, J=7.2 Hz, 2H), 2.35 (s, 3H), 1.11 (t, J=7.2 Hz, 3H).

Example 14—Process for Making a Fourteenth Halogenated Psilocybin Derivative from Halogenated Indole Feedstock A fourteenth halogenated psilocybin derivative was synthesized according to the method of Example 11, except using 6-fluoroindole and N-methylethylamine as starting materials. Analysis indicated the isolation of a compound having chemical formula (XII):

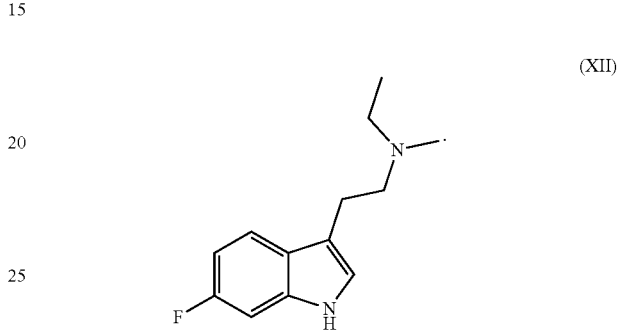

(XII)

$^1$H NMR (400 MHz, $CDCl_3$): δ (ppm)=8.05 (s, 1H), 7.50 (ddt, J=8.7, 5.3, 0.6 Hz, 1H), 7.02 (ddd, J=9.7, 2.3, 0.5 Hz, 1H), 7.00-6.97 (m, 1H), 6.88 (ddd, J=9.6, 8.6, 2.3 Hz, 1H), 2.96-2.89 (m, 2H), 2.74-2.66 (m, 2H), 2.53 (q, J=7.2 Hz, 2H), 2.35 (s, 3H), 1.11 (t, J=7.2 Hz, 3H).

Example 15—Process for Making a Fifteenth Halogenated Psilocybin Derivative from Halogenated Indole Feedstock A fifteenth halogenated psilocybin derivative was synthesized according to the method of Example 11, except using 4-chloroindole as starting material. Analysis indicated the isolation of a compound having chemical formula (III):

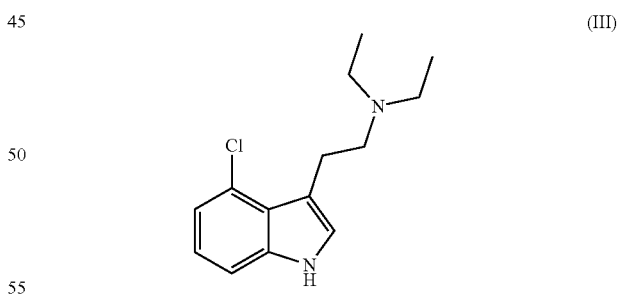

(III)

$^1$H NMR (400 MHz, $CDCl_3$): δ (ppm)=8.28 (s, 1H), 7.26-7.19 (m, 1H), 7.08-7.01 (m, 3H), 3.18-3.10 (m, 2H), 2.86-2.77 (m, 2H), 2.67 (q, J=7.1 Hz, 4H), 1.09 (t, J=7.1 Hz, 6H).

Figure 9B:
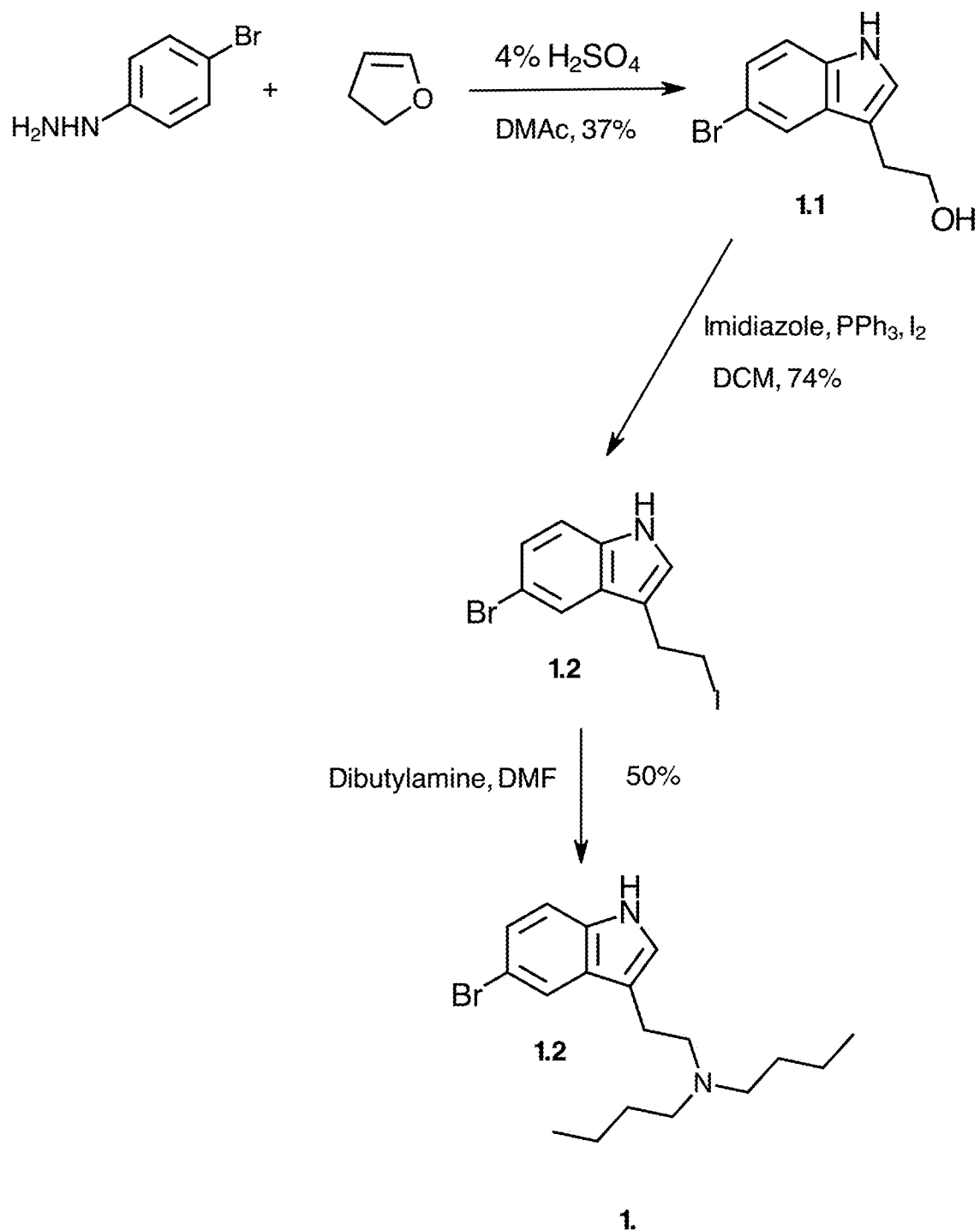

Example 16—Process for Making a Sixteenth Halogenated Psilocybin Derivative from Halogenated Indole Feedstock The initial reaction to generate compound 1.1 (see: FIG. 9B) followed a previously reported procedure with modifications (Campos et al. 2004, Org. Lett 6: 79-82). To a solution of 4-bromophenylhydrazine hydrochloride (300 mg, 1.34 mmol) in a mixture of N,N-dimethylacetamide (1.9 mL) and 4% $H_2SO_4$ (1.9 mL), was added 2,3-dihydrofuran (0.10 mL, 1.33 mmol). The reaction mixture was heated at 100° C. for 16 hours. Once the mixture was cooled to room temperature, ethyl acetate (15 mL) was added, and the organic solution was washed with water (2×6 mL), and dried over anhydrous $MgSO_4$. The organic solvent was removed in vacuo. The product (compound 1.1, (see: FIG. 9B)) was purified by flash chromatography on silica gel (eluted with a gradient of hexanes-EtOAc, 100:0 to 0:100) to afford an orange oil. Yield: 37%. The characterization of this first product agreed with previously reported procedure (Go et al. 2010, J. Med. Chem. 53: 6838-6850). $^1$H NMR (400 MHz, $CDCl_3$) δ 8.13 (bs, 1H), 7.74 (d, J=1.7 Hz, 1H), 7.28 (dd, J=8.6, 1.9 Hz, 1H), 7.23 (d, J=8.6 Hz, 1H), 7.08 (d, J=2.3 Hz, 1H), 3.89 (t, J=6.3 Hz, 2H), 2.98 (t, J=6.4 Hz, 2H). The second reaction (see: FIG. 9B) followed a previously reported procedure (Lombardo et al. 2013, Angew. Chem. Int. Ed. 52: 12910-12914). Imidazole (73 mg, 1.1 mmol), triphenyl phosphine (140 mg, 0.54 mmol), and iodine (140 mg, 0.54 mmol) were added to a solution of compound 1.1 (see: FIG. 9B) (119 mg, 0.49 mmol) in anhydrous dichloromethane (5.0 mL) cooled in an ice-water bath. The reaction was stirred at room temperature for 6 hours. The mixture was quenched with saturated sodium thiosulfate (10 mL), extracted in dichloromethane (3×10 mL), and the combined organic solution was dried over anhydrous $MgSO_4$, and concentrated under reduced pressure. The crude product was purified by flash chromatography on silica gel (eluted with a gradient of hexanes-EtOAc, 100:0 to 50:50) to afford an orange oil. Yield of compound 1.2 (see: FIG. 9B): 74%. $^1$H NMR (400 MHz, $CDCl_3$) δ 8.07 (s, 1H), 7.71-7.69 (m, 1H), 7.29 (dd, J=8.6, 1.7 Hz, 1H), 7.25 (d, J=8.6 Hz, 1H), 7.10 (d, J=2.4 Hz, 1H), 3.44-3.39 (m, 2H), 3.30 (t, J=7.0 Hz, 2H). To a solution of compound 1.2 (129 mg, 0.37 mmol) in anhydrous DMF (1.0 mL) was added di-n-butylamine (0.25 mL, 1.48 mmol). The reaction mixture was heated at 60° C. for 16 hours. The reaction was quenched with saturated sodium bicarbonate solution, extracted in ethyl acetate (3×20 mL), and the combined organic solution was washed with water (2×40 mL), brine (2×40 mL), dried over anhydrous $MgSO_4$ and concentrated under reduced pressure. The crude mixture was purified by flash column chromatography on silica gel (eluted with a gradient of hexanes-EtOAc, 100:0 to 0:100) to afford an orange oil. Yield of compound 1, with structure as indicated by compound (VIII):

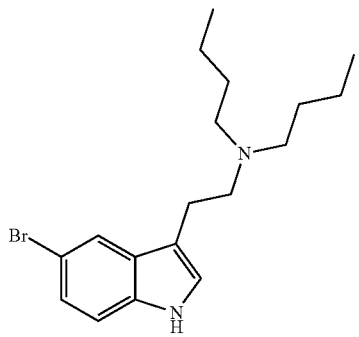

(VIII)

50%. $^1$H NMR (400 MHz, $CDCl_3$) δ 8.16 (s, 1H), 7.72 (s, 1H), 7.28-7.22 (m, 1H), 7.22-7.18 (m, 1H), 7.03-6.99 (m, 1H), 2.89-2.82 (m, 2H), 2.81-2.73 (m, 2H), 2.54 (t, J=7.6 Hz, 4H), 1.52-1.43 (m, 5H), 1.33 (h, J=7.0 Hz, 4H), 0.93 (t, J=7.4 Hz, 6H) (Figure X, NMR). $^{13}$C NMR (100 MHz, $CDCl_3$) δ 134.95, 129.58, 124.81, 122.83, 121.65, 114.83, 112.62, 112.57, 54.75, 54.01, 29.42, 22.87, 20.95, 14.27. HRMS (ESI, positive) m/z for $C_{18}H_{28}BrN_2[M+H]^+$ calcd. 351.1430, found 351.1427. The compound having chemical formula (VIII) was 95% (w/w) pure.

Figure 28:
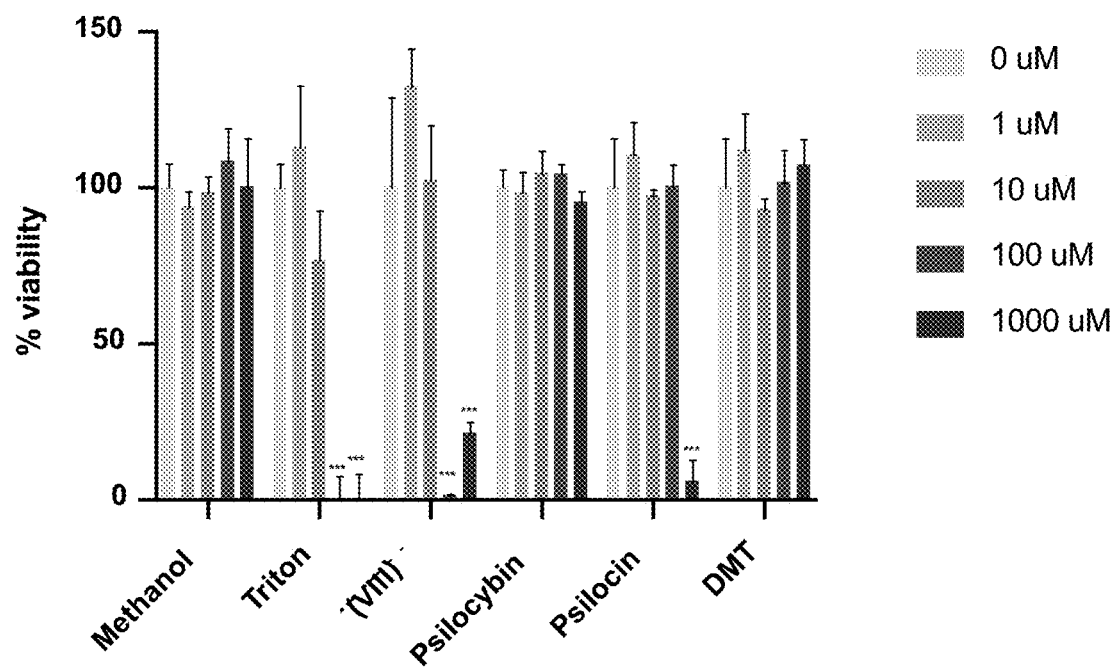
FIG. 28 depicts a graph obtained in the performance of an experimental assay to evaluate the efficacy of an example halogenated psilocybin derivative, notably a cell viability assay involving an example halogenated psilocybin derivative compound having the chemical formula (VIII) set forth herein.
Figure 29A:
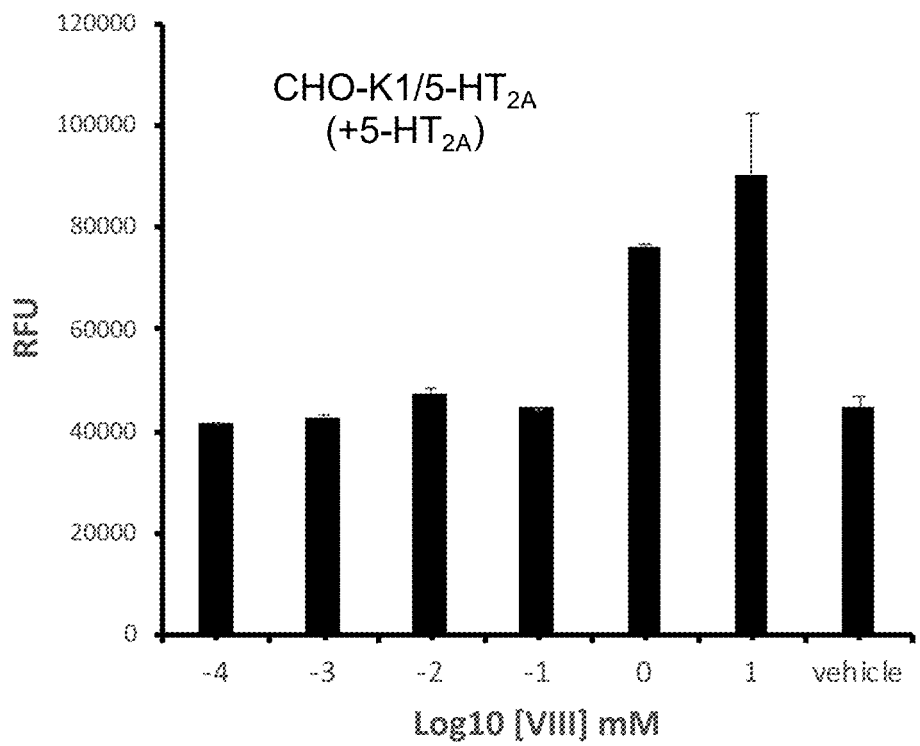
FIGS. 29A and 29B depict graphs obtained in the performance of an experimental assay to evaluate the efficacy of an example halogenated psilocybin derivative, notably a 5-$HT_{2a}$ receptor modulation assay involving +5-$HT_{2A}$ cells (FIG. 29A) and −5-$HT_{2A}$ cells (FIG. 29B), and an example halogenated psilocybin derivative compound having the chemical formula (VIII) set forth herein.
Figure 29B:
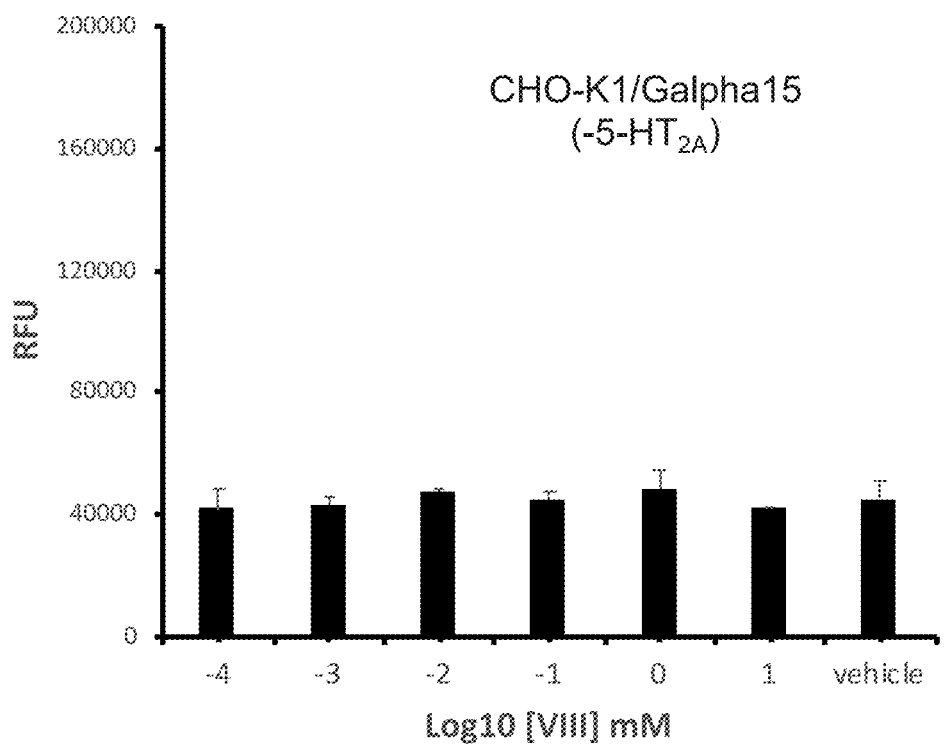

Efficacy testing was carried out as described in Example 5. MTT assay results are shown in FIG. 28, and calcium mobility assay results are shown in FIGS. 29A and 29B. In both cases, the example compound having the chemical formula (VIII) is shown as "(VIII)".

Example 17—Process for Making a Seventeenth Halogenated Psilocybin Derivative from Halogenated Indole Feedstock

*E. coli* strain Ec-3 was constructed as follows. For plasmid cloning, Top10 or XL1-blue strains were used depending on antibiotic markers. Standard LB media was used for culturing. For gene expression and feeding experiments, the parent host strain employed was BL21 (DE3). For this Example, heterologous expression of a non-native or engineered TrpB gene was not necessary, as endogenous tryptophan synthase activity proved sufficient. Plasmids pCDM4-PsiD-FLAG and pETM6-H$_{10}$-PsiK-V5-PsiM-FLAG are described in Example 10. A third plasmid, pRSM3-ThaI-HIS, was created by cloning an in-frame, C-terminally HIS-tagged (SEQ. ID NO: 89) ThaI gene (SEQ. ID NO: 19), encoding a halogenase having SEQ. ID NO: 20, into the NdeI/XhoI site of pRSM3 (SEQ. ID NO: 98). The three target plasmids pCDM4-PsiD-FLAG, pETM6-H10-PsiK-V5-PsiM-FLAG, and pRSM3-ThaI-HIS were transformed into BL21 (DE3) cells and antibiotics ampicillin plus streptomycin plus kanamycin were used to select for the correct clones containing all three plasmids. Scaled-up culturing of engineered *E. coli* was conducted as described in Example 10. To assess product, high-resolution LC-HESI-LTQ-Orbitrap-XL MS analysis was conducted as described in Example 1. Singly protonated product with exact m/z and expected elemental formula matching 6-chloro-psilocybin having chemical formula (XVIII):

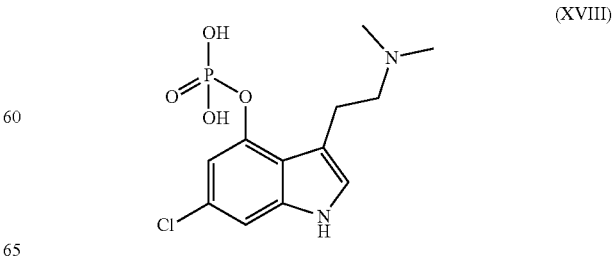

Figure 30:
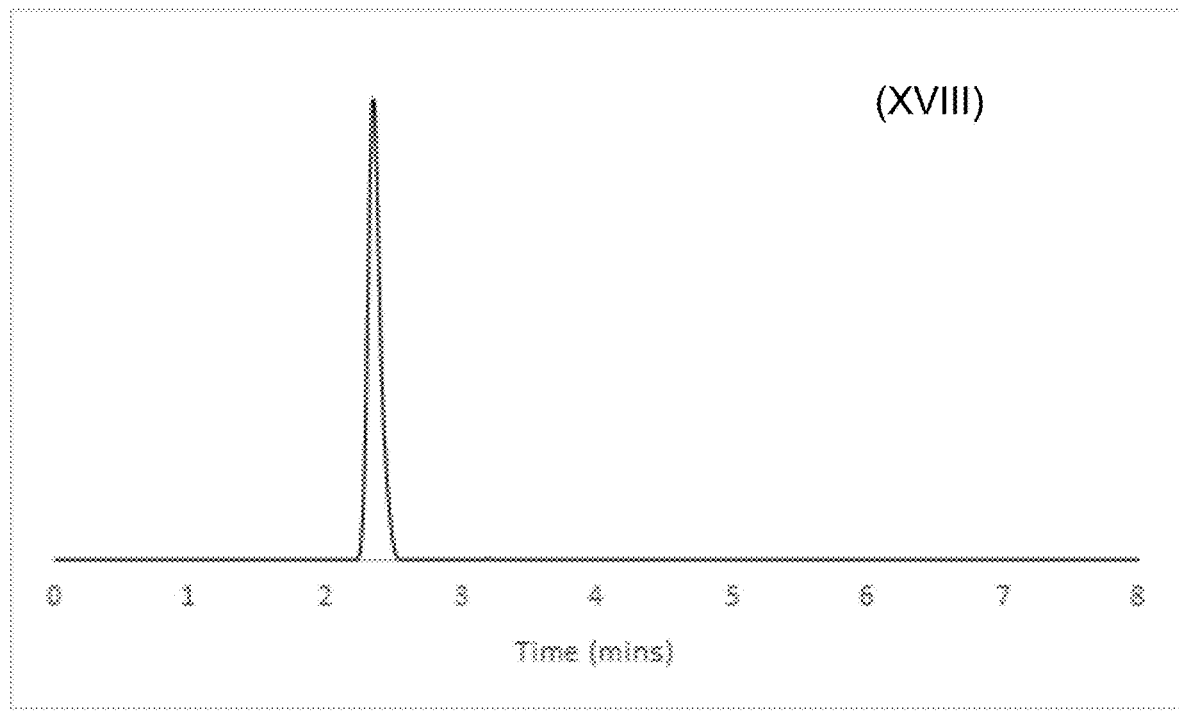
FIG. 30 depicts a representation of mass spectrometry data in the form of a chromatogram, notably a chromatogram obtained in the performance of an experiment to synthesize an example halogenated psilocybin derivative compound having the chemical formula (XVIII) set forth herein.

(XVIII)

eluted at 2.3 minutes (EIC, see: FIG. 30).

The invention claimed is:

1. A pharmaceutical drug formulation comprising an effective amount of a chemical compound or salts thereof having the formula (I):

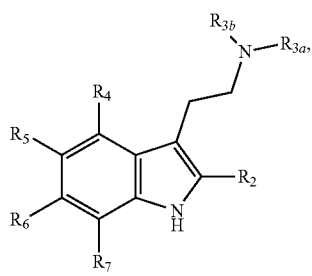

(I)

wherein, at least one of $R_2$, $R_4$, $R_5$, $R_6$, or $R_7$ is a halogen atom, wherein each non-halogenated $R_2$, $R_4$, $R_5$, $R_6$, or $R_7$ is a hydrogen atom, and wherein Ria is a hydrogen atom and $R_{3b}$ is an acyl group, together with a pharmaceutically acceptable excipient, diluent, or carrier.

2. A pharmaceutical drug formulation according to claim 1, wherein $R_7$ is a halogen atom, and $R_2$, $R_4$, $R_5$, or $R_6$ is a hydrogen atom or a halogen atom.

3. A pharmaceutical drug formulation according to claim 1, wherein $R_7$ is a first halogen atom, and one of $R_2$, $R_4$, $R_5$, or $R_6$ is a second halogen atom, wherein each non-halogenated $R_2$, $R_4$, $R_5$, or $R_6$, is a hydrogen atom.

4. A pharmaceutical drug formulation according to claim 3, wherein the first and second halogen atoms are non-identical halogen atoms.

5. A pharmaceutical drug formulation according to claim 4, wherein the first halogen atom is a fluorine (F) atom, and the second halogen atom is one of a chlorine or bromine atom.

6. A pharmaceutical drug formulation according to claim 3, wherein the first and second halogen atoms are identical halogen atoms.

7. A pharmaceutical drug formulation according to claim 1, wherein $R_7$ is a halogen atom, and each of $R_2$, $R_4$, $R_5$, and $R_6$ are a hydrogen atom.

8. A pharmaceutical drug formulation according to claim 1, wherein the halogen atom is a fluorine (F) atom.

9. A pharmaceutical drug formulation according to claim 1, wherein $R_7$ is a fluorine atom and $R_2$, $R_4$, $R_5$, or $R_6$ is a hydrogen atom or a halogen atom.

10. A pharmaceutical drug formulation according to claim 1, wherein $R_7$ is a fluorine atom, wherein additionally one of $R_2$, $R_4$, $R_5$, or $R_6$ is a halogen atom, and wherein each non-halogenated $R_2$, $R_4$, $R_5$, or $R_6$, is a hydrogen atom.

11. A pharmaceutical drug formulation according to claim 10, wherein both $R_7$ and the additionally one of $R_2$, $R_4$, $R_5$, or $R_6$ are a fluorine (F) atom.

12. A pharmaceutical drug formulation according to claim 10, wherein the additionally one of $R_2$, $R_4$, $R_5$, or $R_6$ which are a halogen atom, is a halogen atom other than a fluorine atom.

13. A pharmaceutical drug formulation according to claim 1, wherein $R_7$ is a fluorine (F) atom, and $R_2$, $R_4$, $R_5$, and $R_6$ are a hydrogen atom.

14. A pharmaceutical drug formulation according to claim 1, wherein the acyl group is a $-C(=O)C_1-C_{20}$ alkyl group.

15. A pharmaceutical drug formulation according to claim 1, wherein the acyl group is a $-C(=O)C_1-C_6$ alkyl group.

16. A pharmaceutical drug formulation according to claim 1, wherein the acyl group is $-C(=O)CH_3$ group.

17. A pharmaceutical drug formulation according to claim 1, wherein $R_{3b}$ is a $-C(=O)C_1-C_{20}$ alkyl group, and $R_{3a}$ is a hydrogen atom.

18. A pharmaceutical drug formulation according to claim 1, wherein $R_{3b}$ is a $-C(=O)C_1-C_6$ alkyl group, and $R_{3a}$ is a hydrogen atom.

19. A pharmaceutical drug formulation according to claim 1, wherein $R_{3b}$ is a $-C(=O)CH_3$ group, and $R_{3a}$ is a hydrogen atom.

20. A pharmaceutical drug formulation according to claim 1, having the chemical formula:

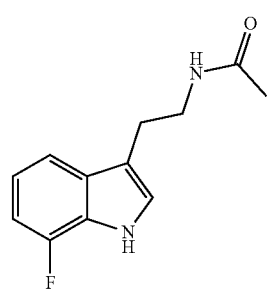

(XV)

21. A chemical compound having the formula:

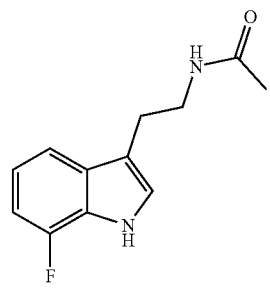

(XV)

22. A chemical compound according to claim 21, wherein the compound is at least about 95% pure.

* * * * *

UNITED STATES PATENT AND TRADEMARK OFFICE
CERTIFICATE OF CORRECTION

| | | |
|---|---|---|
| PATENT NO. | : 11,998,557 B2 | Page 1 of 1 |
| APPLICATION NO. | : 17/903080 | |
| DATED | : June 4, 2024 | |
| INVENTOR(S) | : Jillian M. Hagel and Peter J. Facchini | |

It is certified that error appears in the above-identified patent and that said Letters Patent is hereby corrected as shown below:

In the Claims

In Claim 1, at Column 221, Line 30, amend "Ria" to "$R_{3a}$"

Signed and Sealed this
Third Day of September, 2024

Katherine Kelly Vidal
Director of the United States Patent and Trademark Office

SEQUENCE LISTING

```
Sequence total quantity: 98
SEQ ID NO: 1             moltype = DNA   length = 1320
FEATURE                  Location/Qualifiers
source                   1..1320
                         mol_type = genomic DNA
                         organism = Psilocybe cubensis
SEQUENCE: 1
atgcaggtga tacccgcgtg caactcggca gcaataagat cactatgtcc tactcccgag    60
tcttttagaa acatgggatg gctctctgtc agcgatgcgg tctacagcga gttcatagga   120
gagttggcta cccgcgcttc caatcgaaat tactccaacg agttcggcct catgcaacct   180
atccaggaat tcaaggcttt cattgaaagc gacccggtgg tgcaccaaga atttattgac   240
atgttcgagg gcattcagga ctctccaagg aattatcagg aactatgtaa tatgttcaac   300
gatatctttc gcaaagctcc cgtctacgga gaccttggcc ctcccgttta tatgattatg   360
gccaaattaa tgaacacccg agcgggcttc tctgcattca cgagacaaag gttgaacctt   420
cacttcaaaa aactttttcga tacctgggga ttgttcctgt cttcgaaaga ttctcgaaat   480
gttcttgtgg ccgaccagtt cgacgacaga cattgcggct ggttgaacga gcgggccttg   540
tctgctatgg ttaaacatta caatggacgc gcatttgatg aagtcttcct ctgcgataaa   600
aatgccccat actacggctt caactcttac gacgacttct taatcgcag atttcgaaac   660
cgagatatcg accgacctgt agtcggtgga gttaacaaca ccaccctcat ttctgctgct   720
tgcgaatcac tttcctacaa cgtctcttat gacgtccagt ctctcgacac tttagttttc   780
aaaggagaga cttattcgct taagcatttg ctgaataatg accctttcac cccacaattc   840
gagcatggga gtattctaca aggattcttg aacgtcaccg cttaccaccg atggcacgca   900
cccgtcaatg ggacaatcgt caaaatcatc aacgttccga ctacctactt tgcgcaagcc   960
ccgagcacga ttggcgaccc tatcccggat aacgattacg acccacctcc ttaccttaag  1020
tctcttgtct acttctctaa tattgccgca aggcaaatta tgtttattga agccgacaac  1080
aaggaaattg gcctcatttt ccttgtgttc atcggcatga ccgaaatctc gacatgtgaa  1140
gccacgtgt ccgaaggtca acacgtcaat cgtggcgatg acttgggaat gttccatttc  1200
ggtggttctt cgttcgcgct tggtctgagg aaggattgca ggcagagat cgttgaaaag  1260
ttcaccgaac ccggaacagt gatcagaatc aacgaagtcg tcgctgctct aaaggcttag  1320

SEQ ID NO: 2             moltype = AA   length = 439
FEATURE                  Location/Qualifiers
source                   1..439
                         mol_type = protein
                         organism = Psilocybe cubensis
SEQUENCE: 2
MQVIPACNSA AIRSLCPTPE SFRNMGWLSV SDAVYSEFIG ELATRASNRN YSNEFGLMQP    60
IQEFKAPIES DPVVHQEFID MFEGIQDSPR NYQELCNMFN DIFRKAPVYG DLGPPVYMIM   120
AKLMNTRAGF SAFTRQRLNL HFKKLFDTWG LFLSSKDSRN VLVADQFDDR HCGWLNERAL   180
SAMVKHYNGR AFDEVFLCDK NAPYYGFNSY DDFFNRRFRN RDIDRPVVGG VNNTTLISAA   240
CESLSYNVSY DVQSLDTLVF KGETYSLKHL LNNDPFTPQF EHGSILQGFL NVTAYHRWHA   300
PVNGTIVKII NVPGTYFAQA PSTIGDPIPD NDYDPPPYLK SLVYFSNIAA RQIMFIEADN   360
KEIGLIFLVF IGMTEISTCE ATVSEGQHVN RGDDLGMFHF GGSSFALGLR KDCRAEIVEK   420
FTEPGTVIRI NEVVAALKA                                                439

SEQ ID NO: 3             moltype = DNA   length = 2155
FEATURE                  Location/Qualifiers
source                   1..2155
                         mol_type = genomic DNA
                         organism = Psilocybe cubensis
SEQUENCE: 3
atgatcgctg tactattctc cttcgtcatt gcaggatgca tatactacat cgtttctcgt    60
agagtgaggc ggtcgcgctt gccaccaggg ccgcctggca ttcctattcc cttcattggg   120
aacatgtttg atatgcctga gaatctccca tggttaacat ttctacaatg gggacgggat   180
tacagtctgt cttgccgcgt tgacttctaa tatatgaaca gctaatatat tgtcagacac   240
cgatattctc tacgtggatg ctggagggac agaaatggtt attcttaaca cgttggagac   300
cattaccgat ctattagaaa agcgagggtc catttattct ggccggtgag ctgatgttga   360
gtttttttgca attgaatttg tggtcacacg tttccagact tgagagtaca atggtcaacg   420
aacttatggg gtgggagttt gacttagggt tcatcacata cggcgacagg tggcgcgaag   480
aaaggcgcat gttcgccaag gagttcagtg agaagggcat caagcaattt cgccatgctc   540
aagtgaaagc tgcccatcag cttgtccaac agcttaccaa aacgccagac cgtcgggcac   600
aacatattcg ccagtaagta ctacttgagg aaaatagcgt acgcttcgct gaccggtccg   660
tacatcaaag tcagatagcg gcaatgtcac tggatattgg ttatgaatt gatcttgcag   720
aagacgaccc ttggctggaa cgacccatt tggctaatga aggcctcgcc atagcatcag   780
tgccgggcaa atttttgggtc gattcgttcc ctctcgtga gcatccttct tctatgtagg   840
aagggaagga gtcaacaag tgttagtaaa atacccttcct gcttggttcc caggtgctgt   900
cttcaagcgc aaagcgaagg tctggcgaga agccgccgac catatggttg acatgcctta   960
tgaaactatg aggaaattag cagttagtca aatgcgttct ccccgtattt tttcaatact  1020
ctaacttcag ctcacagcct caaggattga ctcgtccgtc gtatgcttca gctcgtctga  1080
aagccatgga tctcaacggt gaccttgagc atcaagaaca cgtaatcaag aacacagccg  1140
cagaggttaa tgtcggtaag tcaaaagcgt ccgtcggcaa ttcaaaattc aggcgctaaa  1200
gtgggtcttc tcaccaaggt ggaggcgata ctgtaaggat ttctcaatcg ttagagtata  1260
agtgttctaa tgcagtacat actccaccaa ccagactgta tgcgcgttcat  1320
cttggccatg gtgaagtacc ctgaggtcca gcgaaaggtt caagcggagc ttgatgctct  1380
gaccaataac ggccaaattc ctgactatga cgaagaagat gactccttgc catacctcac  1440
cgcatgtatc aaggagcttt tccggtggaa tcaaatcgca ccctcgcta taccgcacaa  1500
attaatgaag gacgacgtgt accgcgggta tctgattccc aagaacactc tagtcttcgc  1560
aaacacctgg tgaggctgtc cattcattcc tagtacatcc gttgccccac taatagcatc  1620
```

-continued

```
ttgataacag ggcagtatta aacgatccag aagtctatcc agatccctct gtgttccgcc  1680
cagaaagata tcttggtcct gacgggaagc ctgataacac tgtacgcgac ccacgtaaag  1740
cggcatttgg ctatggacga cgaaattggt aagtgcgctt tcagaacccc cccttccgtt  1800
gactagtgcc atgcgcgcat acaatatcgc tattgatctg atataacttc cctgcggcat  1860
ttattttggc attcctttag tcccggaatt catctagcgc agtcgacggt ttggattgca  1920
ggggcaaccc tcttatcagc gttcaatatc gagcgacctg tcgatcagaa tgggaagccc  1980
attgacatac cggctgattt tactacagga ttcttcaggt agctaatttc cgtctttgtg  2040
tgcataatac ccctaacgac gcacgtttac cttttttgtaa agacacccag tgcctttcca  2100
gtgcaggttt gttcctcgaa cagagcaagt ctcacagtcg gtatccggac cctga        2155

SEQ ID NO: 4         moltype = AA  length = 508
FEATURE              Location/Qualifiers
source               1..508
                     mol_type = protein
                     organism = Psilocybe cubensis
SEQUENCE: 4
MIAVLFSFVI AGCIYYIVSR RVRRSRLPPG PPGIPIPFIG NMFDMPEESP WLTFLQWGRD   60
YNTDILYVDA GGTEMVILNT LETITDLLEK RGSIYSGRLE STMVNELMGW EFDLGFITYG  120
DRWREERRMF AKEFSEKGIK QFRHAQVKAA HQLVQQLTKT PDRWAQHIRH QIAAMSLDIG  180
YGIDLAEDDP WLEATHLANE GLAIASVPGK FWVDSFPSLK YLPAWFPGAV FKRKAKVWRE  240
AADHMVDMPY ETMRKLAPQG LTRPSYASAR LQAMDLNGDL EHQEHVIKNT AAEVNVGGGD  300
TTVSAMSAFI LAMVKYPEVQ RKVQAELDAL TNNGQIPDYD EEDDSLPYLT ACIKELFRWN  360
QIAPLAIPHK LMKDDVYRGY LIPKNTLVFA NTWAVLNDPE VYPDPSVFRP ERYLGPDGKP  420
DNTVRDPRKA AFGYGRRNCP GIHLAQSTVW IAGATLLSAF NIERPVDQNG KPIDIPADFT  480
TGFFRHPVPF QCRFVPRTEQ VSQSVSGP                                     508

SEQ ID NO: 5         moltype = DNA  length = 1089
FEATURE              Location/Qualifiers
source               1..1089
                     mol_type = genomic DNA
                     organism = Psilocybe cubensis
SEQUENCE: 5
atggcgttcg atctcaagac tgaagacggc ctcatcacat atctcactaa acatctttct   60
ttggacgtcg acacgagcgg agtgaagcgc cttagcggag gctttgtcaa tgtaacctgg  120
cgcattaagc tcaatgctcc ttatcaaggt catacgagca tcatcctgaa gcatgctcag  180
ccgcacatgt ctacggatga ggattttaag ataggtgtag aacgttcggt ttacgaatac  240
caggctatca agctcatgat ggccaatcgg gaggttctgg gaggcgtgga tggcatagtt  300
tctgtgccag aaggcctgaa ctacgactta gagaataatg cattgatcat gcaagatgtc  360
gggaagatga agacccttt agattatgtc accgccaagc cgccacttgc gacggatata  420
gcccgccttg ttgggacaga aattgggggg ttcgttgcca gactccataa cataggccgc  480
gagaggcgag acgatcctga gttcaaattc ttctctggaa atattgtcgg aaggacgact  540
tcagaccagc tgtatcaaac catcatacc aacgcagcga aatatggcgt cgatgacccc  600
ttgctgccta ctgtggttaa ggaccttgtg gacgatgtca tgcacagcga aggacccctt  660
gtcatggcgg acctgtggag tggaaatatt cttctccagt tggaggaggg aaacccatcg  720
aagctgcaga agatatatat cctggattgg gaactttgca agtacggccc agcgtcgttg  780
gacctgggct atttcttggg tgactgctat ttgatatccc gctttcaaga cgagcaggtc  840
ggtacgacga tgcggcaagc ctacttgcaa agctatgcgc gtacagagca gcattcgatc  900
aactacgcca agtcactgc aggtattgct gctcatattg tgatgtggac cgactttatg  960
cagtggggga gcgaggaaga aaggataaat tttgtgaaaa agggggtagc tgcctttcac  1020
gacgccaggg gcaacaacga caatggggaa ttacgtctca ccttactgaa ggaatcatcc  1080
actgcgtaa                                                         1089

SEQ ID NO: 6         moltype = AA  length = 309
FEATURE              Location/Qualifiers
source               1..309
                     mol_type = protein
                     organism = Psilocybe cubensis
SEQUENCE: 6
MHIRNPYRTP IDYQALSEAF PPLKPFVSVN ADGTSSVDLT IPEAQRAFTA ALLHRDFGLT   60
MTIPEDRLCP TVPNRLNYVL WIEDIFNYTN KTLGLSDDRP IKGVDIGTGA SAIYPMLACA  120
RFKAWSMVGT EVERKCIDTA RLNVVANNLQ DRLSILETSI DGPILVPIFE ATEEYEYEFT  180
MCNPPFYDGA ADMQTSDAAK GFGFGVGAPH SGTVIEMSTE GGESAFVAQM VRESLKLRTR  240
CRWYTSNLGK LKSLKEIVGL LKELEISNYA INEYVQGSTR RYAVAWSFTD IQLPEELSRP  300
SNPELSSLF                                                          309

SEQ ID NO: 7         moltype = DNA  length = 930
FEATURE              Location/Qualifiers
source               1..930
                     mol_type = genomic DNA
                     organism = Psilocybe cubensis
SEQUENCE: 7
atgcatatca gaaatcctta ccgtacacca attgactatc aagcactttc agaggccttc   60
cctcccctca gccatttgt gtctgtcaat gcagatggta ccagttctgt tgacctcact  120
atcccagaag cccagagggc gttcacggcc gctcttcttc atcgtgactt cgggctcacc  180
atgaccatac cagaagaccg tctgtgccca acagtcccca ataggttgaa ctacgttctg  240
tggattgaag atatttcaa ctacacgaac aaaacccctcg gcctgtcgga tgaccgtcct  300
attaaaggcg ttgatattgg tacaggagcc tccgcaattt atcctatgct tgcctgtgct  360
cggttcaagg catggtctat ggttggaaca gaggtcgaga ggaagtgcat tgacacggcc  420
cgcctcaatg tcgtcgcgaa caatctccaa gaccgtctct cgatattaga gacatccatt  480
```

-continued

```
gatggtccta ttctcgtccc cattttcgag gcgactgaag aaatacgaata cgagtttact   540
atgtgtaacc ctccattcta cgacggtgct gccgatatgc agacttcgga tgctgccaaa   600
ggatttggat ttggcgtggg cgctccccat tctggaacag tcatcgaaat gtcgactgag   660
ggaggtgaat cggctttcgt cgctcagatg gtccgtgaga gcttgaagct tcgaacacga   720
tgcagatggt acacgagtaa cttgggaaag ctgaaatcct tgaaagaaat agtggggctg   780
ctgaaagaac ttgagataag caactatgcc attaacgaat acgttcaggg gtccacacgt   840
cgttatgccg ttgcgtggtc tttcactgat attcaactgc ctgaggagct ttctcgtccc   900
tctaaccccg agctcagctc tcttttctag                                    930

SEQ ID NO: 8           moltype = AA  length = 309
FEATURE                Location/Qualifiers
source                 1..309
                       mol_type = protein
                       organism = Psilocybe cubensis
SEQUENCE: 8
MHIRNPYRTP IDYQALSEAF PPLKPFVSVN ADGTSSVDLT IPEAQRAFTA ALLHRDFGLT    60
MTIPEDRLCP TVPNRLNYVL WIEDIFNYTN KTLGLSDDRP IKGVDIGTGA SAIYPMLACA   120
RFKAWSMVGT EVERKCIDTA RLNVVANNLQ DRLSILETSI DGPILVPIFE ATEEYEYEFT   180
MCNPPFYDGA ADMQTSDAAK GFGFGVGAPH SGTVIEMSTE GGESAFVQM VRESLKLRTR    240
CRWYTSNLGK LKSLKEIVGL LKELEISNYA INEYVQGSTR RYAVAWSFTD IQLPEELSRP   300
SNPELSSLF                                                           309

SEQ ID NO: 9           moltype = DNA  length = 3042
FEATURE                Location/Qualifiers
source                 1..3042
                       mol_type = genomic DNA
                       organism = Psilocybe cubensis
SEQUENCE: 9
atgccttcca gtcaccctca cattactcat cgctatcggg ttccttcgag tgacgaccat    60
gaacgtatat ctgctctgtt cttgggtccc aaagcagaaa atgccgcatt tctccagcaa   120
tggttgacca cggtcgtcgc acagcaaaag gctgcccgcg atgcatactt cccggatgac   180
aatgctttta ttactacaga catgcaaact tcccccgcct ttgctcagac tactaaagta   240
atcgcctcca atctcaccga attattgact gcactcggtg aaaggtcgat tcctttcttc   300
tcacctcggt acagcggcca tatgtctgtg gaccaaagtc tacctgccat tctcggattc   360
ttatcgacca cattttataa tcctaacaat gttgccttcg aggctagtcc attcactgacc  420
ctcatcgagg aagaagttgg cttgcaactc tctgaaatgc tgggttataa tcggctaaat   480
aacaccgaga aacctctcgc ctggggacat attgcatcag gtggaactgt tgcaaacttg   540
gaagcgatgt gggcggcgcg aaacctcaag tttaccctc tctcactccg tgatgcttca    600
gccgaaggcg cagagatgga attcattcgt gacacattct ccgtcaaaac ctgtgttggt   660
gacaaaaaat tattaaagga ttgcagccca tgggaactcc tcaatttgca tgtttctact   720
atcttagaca tgcccgaccg tctgcacgac gagtacaata tttcacctca gttcctcgaa   780
aaggttatgc gaaagtatat catccagtct accaacaaag acacgttgat gcagcgttgg   840
ggacttaccc aacaacctgt cgttttatcc ccgagccaga accattattc ctggccaaag   900
gctgcagctg tgctcggtat tggctcagac aaccttcgca acgtcccagt agacatccaa   960
gcccacatgg acataaacga actcgatcgt atgttaaaaa tttgcttgga cgaggagacg  1020
ccagtatatc aagtagttgc tgttatcggt accaccgaag agggcggtgt cgatcgcatt  1080
acggagatcc tgaagctgcg ccaaaagtat gaagcttttgg ggctgtcttt tgccatccat  1140
gcagatgctg cttggggagg ctattttgca accatgctac ccaaagatac attgggtcga  1200
aaccggacta ggcttcccaa agaggacact acctcgggct tgtccctca cgtcggtctg   1260
cgcgaggaga gcgcgttaca actcagccat ataaagtatg ccgattctat tactatcgac  1320
ccgcacaagg caggctatgt tccttacccc gctggggcac tctgttatcg cgacggaaga  1380
atgaggtacc tgcttacatg gtccgcgccc taccttgccc aaggcaacga gggccaaagt  1440
atcggaatat acgggatcga aggaagcaaa cctggtgcag cagcatccgc ggtattcatg  1500
gcgcacgaaa ccattggcct gactccttct ggatacggga accttcttgg ccaggcaatg  1560
tttacatgtc gccgatacgc tgctcactgg tctgcaatga caacggatac taccagtttc  1620
actgtcaccc cgttcaatcc tatccctgct gacatcgacc ccaacgctga ccccgcaaag  1680
gtcgaagagc aaaaacagtt catcagagat cgtatcttgt tcaaatcgaa cgaggaaata  1740
tacaacgatt ctgaggctat ggaactcttg caccaacttg ggtccgatct caatatcaac  1800
gttttcgcat gcaacttccg cgaccgcgat aataatctca acaccgacgt cggaggaagc  1860
aactggctca ataacgctat tttctaacgc ttttctgtta caagtcgtga ggagaaccca  1920
ttggaaacgc cattcttcct cagctcaact acattgaaac aatccgaata cggcgtctgc  1980
gcaaccgaag taaagagacg catgggactt gttggtgacc aggatgttat agtcctgagg  2040
aacgtcgtta tgtctccatt tactacaacg aacgactttg tgggaactct ggcaaacacc  2100
ttccaaaaga tcgttgagga ggagtcgag tatgcacgga tccgcaacga tatgaaaacct  2160
agcattcaca ccttccttct tcatggttca ggagagcaat actatcttgt ccacacccca  2220
acgatccata tggccagcgg ccgtcgccaa atcatccttt cagtaaatgt tgaaggccaa  2280
gttcggcagg cgatacatgc ccatgaaaga gttgaagcag tgattgtaca taacactgtg  2340
ccctccgcc ttgacgaaat cgttgacgga ggatcatttg acggcatact ccatcggga   2400
aagaggaaaa ctagtttcaa agtgaagatt tcaaacatta agtagtcaa gaagcgctca   2460
ctgatgactg aggacctgga atctgcgtac ccatcgttga tgccattcta ttttctacggg  2520
actcaaggac acgctcatct cgaccatgtc attactgtcg ttcctaacat ccatctgagt  2580
gctggcgaaa tacagtacaa attcgacgac gaggtgtcaa gcgaggacct cgccaagggc  2640
ctcattgttg ttgctgagaa cgtacacgag gcatccatgc agcccttccc gctcatgaaa  2700
gatttcaaga tcaccaacca ttcttcttc agctccggac aaatactccg cgtcaaagtg  2760
tacagagatc cataccccggc atcgacaatg gatcccatcc ctctccacga catcaagaac  2820
cagcccgtcg tgcacaagg caccatcacg ctcgtcggaa atatttacgt cgattctgat   2880
gcgctcaacg tcgcttccga gcctactgcc gacgaagacg cggcgcatgt tcctcacgct  2940
cgcaacatgt acggcgagat gaccgctgga acgatcaaag gctggcaaaa cgctgttcgt  3000
catttccaca acaaattgga gactgttgct ccgacgaagt ag                      3042
```

```
SEQ ID NO: 10            moltype = AA   length = 1013
FEATURE                  Location/Qualifiers
source                   1..1013
                         mol_type = protein
                         organism = Psilocybe cubensis
SEQUENCE: 10
MPSSHPHITH RYRVPSSDDH ERISALFLGP KAENAAFLQQ WLTTVVAQQK AARDAYFPDD    60
NAFITTDMQT SPAFAQTTKV IASNLTELLT ALGERSIPFF SPRYSGHMSV DQSLPAILGF   120
LSTTFYNPNN VAFEASPFTT LIEEEVGLQL SEMLGYNRLN NTEKPLAWGH IASGGTVANL   180
EAMWAARNLK FYPLSLRDAS AEGAEMEFIR DTFSVKTCVG DKKLLKDCSP WELLNLHVST   240
ILDMPDRLHD EYNISPQFLE KVMRKYIIQS TNKDTLMQRW GLTQQPVVLS PSTNHYSWPK   300
AAAVLGIGSD NLRNVPVDIQ AHMDINELDR MLKICLDEET PVYQVVAVIG TTEEGGVDRI   360
TEILKLRQKY EALGLSFAIH ADAAWGGYFA TMLPKDTLGR NRTRLPKEDT TSGFVPHVGL   420
REESALQLSH IKYADSITID PHKAGYVPYP AGALCYRDGR MRYLLTWSAP YLAQGNEGQS   480
IGIYGIEGSK PGAAASAVFM AHETIGLTPS GYGNLLGQAM FTCRRYAAHW SAMSTDTTSF   540
TVTPFNPIPA DIDPNADPAK VEEQKQFIRD RILFKSNEEI YNDSEAMELL HQLGSDLNIN   600
VFACNFRDRD NNLNTDVEEA NWLNNRIFQR FSVTSAEENP LETPFFLSST TLKQSEYGVC   660
ATEVKRRMGL VGDQDVIVLR NVVMSPFTTT NDFVGTLANT FQKIVEEEVE YARIRNDMKP   720
SIHTFLLHGS GEQYYLVHTP TIHMASGRRQ IILSVNVEGQ VRQAIHAHER VEAVIVHNTV   780
PLRLDEIVDG GSFDGILTIG KRKTSFKVKI SNIKVVKKRS LMTEDLESAY PSLMPFYFYG   840
TQGHAHLDHV ITVVPNIHLS AGEIQYKFDD EVSSEDLAKG LIVVAENVHE ASMQPFPLMK   900
DPFKITNQFFF SSGQILRVKV YRDPYPASTM DPIPLHDIKN QPVVTQGTIT LVGNIYVDSD   960
ALNVASEPTA DEDAAHVPHA RNMYGEMTAG TIKGWQNAVR HFHNKLETVA PTK          1013

SEQ ID NO: 11            moltype = DNA   length = 2103
FEATURE                  Location/Qualifiers
source                   1..2103
                         mol_type = genomic DNA
                         organism = Psilocybe cubensis
SEQUENCE: 11
atggaggcta tcaaaaaggt ttttgagaac aaaaaggcgg agggcattcc tgtgttggtg     60
acctttgtta ctgcaggata tcctcgtccc gaagatactg ttcccatctt gctggccatg    120
gaggccggtg gtgctgatat catcgagctt ggtatgccat tttcagaccc aattgcagat    180
ggtcctgtca tccaggaaac gaacacaatc gccgttgcaa accaggtaga ttataccact    240
gttctcggac aacttcggga agcccgcaaa caagggctca aggcaccgt tcttctgatg     300
ggatattata accccatatt ggcttacgga gaagacagat ctattcaaga tgcggctgaa    360
gctggagcca atgggtttat tatggtcgac cttccacccg aggaggctgt cgcttttcga    420
gagaaatgta tcaaatccaa cctctcatat gttcctctaa ttgcaccctc aacgactctg    480
tcgcgtataa agttcctctc aacaattgca gacacgttca tctatgtcgt gtctaaaatg    540
ggaaccaccg gatcctcaga gaaggttgcc atgaataacg cccttccac catcatcgat     600
cgtattcgcg agtacgctga agttcctta gcagtcggat ttggagtcgc cactcgggct    660
cacttcaact acgtcgccga ttccggtgct gatggtgtc ttattggcac caaactcgtt     720
aacgttatta agagtcacc gcaagggga agcaccaaaa atgttgaggc atactgccgt     780
gagatgagcc aaaagggaga aacaaatcgc gtcaaatctc caccaactgc ccgtgctgcc    840
agctccgaat caattcctgt tgttgttcct tctgttctcc ccgcacgttt cggagaattc    900
ggaggacaat acgttcccga agtccttgtc gattgtctgg ttgaactaga agaagctcac    960
aaatctgcca tggctgatcc tgaattccag aaggaactac aatcgcatgc cggatatgca    1020
aatcgtcctt cacaaatata cctcgccgaa aatctcacca aggatgctgg gggtgcaaat    1080
atttggttga acgtgaaga tttgaaccac acaggttccc acaaaatcaa taacgctttg    1140
ggacaaattc tgcttgcccg gagaatcgga agaccagaa ttatccagaa aacaggtgcg     1200
ggccagcatg tgttgcaac agcgactgtt tgcgctaagt ttggaatgga atgtgttatc    1260
tacatgggcg cagaagatgt gcgacggcaa gctctaaatg tattcaggat tgagatgcta    1320
ggagcaaaag ttgttcctgt tacttcagga tcatgcacat tgaaggacgc tgtaaacgag    1380
gccttccgtg actgggtgac aaacctttct acgacgcatt atttggttgg ctctgtaatt    1440
ggacctcatc ccttccccac cattgtccga gatttccaaa aggtcattgg tcaagagatc    1500
aaggctcaga tgttggccgc ccgcggcaaa cttcctgatg tcgtcgtcgc ttgtgttggt    1560
ggaggaagca atgctatcgg tacgttctat gatttattg gcgacaagag tgtacgtcta     1620
gttggggtgg aagcaggagg agaaggtatt gacggagacc gacatagcgc cacactttcg    1680
atggggcaac cgggagtact tcacgggtgtt agaaacatata ttctacaaga caaggccggt    1740
caaatcatcg agacgcactc aatcagcgct ggattgatt atcccggcgt tggaccagaa     1800
catgcttggc taaggactc taaaagagca gaatatgttg tcgccacaga cgaagaagca    1860
cttcgcggtt tccgtatgct aacacaaagg gagggaatta ttcctgccct tgaatcttcc    1920
catgcgatct gggaggctgt caggattgcc cgcaccatgt cgaaggacca ggatcttgtt    1980
gtgtgttgt ctggccgagg tgataaagac gttgagcaaa tttctcaact tcttcccaag    2040
tgggcggata ttctagactg gcatgttct cccatgccg ttggacacac aacaaaattc    2100
taa                                                                 2103

SEQ ID NO: 12            moltype = AA   length = 700
FEATURE                  Location/Qualifiers
source                   1..700
                         mol_type = protein
                         organism = Psilocybe cubensis
SEQUENCE: 12
MEAIKKVFEN KKAEGIPVLV TFVTAGYPRP EDTVPILLAM EAGGADIIEL GMPFSDPIAD     60
GPVIQETNTI AVANQVDYTT VLGQLREARK QGLKAPVLLM GYYNPILAYG EDRSIQDAAE    120
AGANGFIMVD LPPEEAVAFR EKCIKSNLSY VPLIAPSTTL SRIKFLSTIA DTFIYVVSKM   180
GTTGSSEKVA MNNALPTIID RIREYAEVPL AVGFGVATRA HFNYVADSGA DGVVIGTKLV   240
NVIKESPQGE APKNVEAYCR EMSQKGETNR VKSPPTARAA SSESIPVVVP SVLPARFGEF   300
```

```
GGQYVPEALV DCLVLEEEAH KSAMADPEFQ KELQSHAGYA NRPSQIYLAE NLTKDAGGAN   360
IWLKREDLNH TGSHKINNAL GQILLARRIG KTRIIAETGA GQHGVATATV CAKFGMECVI   420
YMGAEDVRRQ ALNVFRIEML GAKVVPVTSG SCTLKDAVNE AFRDWVTNLS TTHYLVGSVI   480
GPHPFPTIVR DFQKVIGQEI KAQMLAARGK LPDVVVACVG GGSNAIGTFY DFIGDKSVRL   540
VGVEAGGEGI DGDRHSATLS MGQPGVLHGV RTYILQDKAG QIIETHSISA GLDYPGVGPE   600
HAWLKDSKRA EYVVATDEEA LRGFRMLTQR EGIIPALESS HAIWEAVRIA RTMSKDQDLV   660
VCLSGRGDKD VEQISQLLPK WADILDWHVS SHAVGHTTKF                        700

SEQ ID NO: 13              moltype = DNA   length = 1599
FEATURE                    Location/Qualifiers
source                     1..1599
                           mol_type = genomic DNA
                           organism = Streptomyces rugosporus
SEQUENCE: 13
atggaaaggc ggaagcgtga gcgtcttggc tcactcggcc gaccgaccaa aaaggagctc     60
cgcatgatcc gatctgtggt gatcgtgggt ggtggcacgg cgggctggat gaccgcctcc    120
tacctcaagg ccgccttcga cgaccgcatc gacgtaacgc tcgtggagtc agggaacgtc    180
aggcggatcg gggtcggcga agcgacctttc agcacggtcc gccacttctt cgactacctg    240
ggcctcgacg agcgcgagtg gctgccccgc tgccgccggcg gctacaagct cggcatccgc    300
ttcgagaact ggagcgagcc gggcgagtac ttctaccacc cgttcgagcg cctgcgcgtc    360
gtcgacggct tcaacatggc cgagtggtgg ctcgcggtcg gcgaccgcag gacgtccttc    420
agcgaggcct gctatctcac gcaccggctg tgcgaggcca agcgggccgc ccatgctc     480
gacggctcgc tcttcgcctc ccaggtggac gagtcgctcg gccgctcgac cctggccgag    540
cagcgcgccc agttccgta cgcctaccac ttcgacgccg acgaggtcgc ccgctacctg     600
tcggagtacg ccatcgcccg cggcgtccgc cacgtggtcg acgacgtgca gcacgtcggc    660
caggacgagc gcggcgtgga tcagcggcgtc cacaccaagc agcacggcga gatcagcggc    720
gacctgttcg tcgactgcac cggcttccgc ggcctgctca tcaaccagac gctgggcggc    780
aggttccagt ccttctccga cgtgctgccc aacaaccggg cggtcgcgct gcgcgtcccg    840
cgggagaaca acgaggacat gcggccgtac acgacggcga ccgcgatgag cgccggctgg    900
atgtggacga tcccgctgtt caagcgcgac ggcaacgact acgtctactc cgacgagttc    960
atctcgccgg aggaggccga gcgcgagctg cggtccaccg tcgccccgg ccgcgacgac   1020
ctggaggcca accacatcca gatgcggatc ggcaggaacg agcgcacctg gatcaacaac   1080
tgcgtcgccg tcggcctgtc cgccgccttc gtcgagccgc tggagtcgac cggcatcttc   1140
ttcatccagc acgccatcga gcagctcgtg aagcacttcc ccggcgagcg ctgggaccgg   1200
gtgctgatca gcgcgtacaa cgagcgcatg gcgcacatgg tcgacggggt caaggagttc   1260
ctcgtcctcc actacaaggg cgcccagcgc gaggacaccc cctactgaa ggccgccaag    1320
accagggcca tgcccgacgg cctcgcccgc aagctggagc tgtccgcctc ccacctgctg   1380
gacgagcaga cgatctaccc ctactaccac ggcttcgaga cctattcgtg gatcaccatg   1440
aacctcggtc tcggcatcgt gcccgagcgg ccgcgtcccg cgctcctgca catggacccg   1500
gcgcccgcgc tggccgagtt cgaacggctc aggcgcgagg gcgacgagct gatcgccgcc   1560
ctgcccagct gctacgagta cctcgccagc atccaatga                         1599

SEQ ID NO: 14              moltype = AA   length = 532
FEATURE                    Location/Qualifiers
source                     1..532
                           mol_type = protein
                           organism = Streptomyces rugosporus
SEQUENCE: 14
MERRKRERLG SLGRPTKKEL RMIRSVVIVG GGTAGWMTAS YLKAAFDDRI DVTLVESGNV    60
RRIGVGEATF STVRHFFDYL GLDEREWLPR CAGGYKLGIR FENWSEPGEY FYHPFERLRV   120
VDGFNMAEWW LAVGDRRTSF SEACYLTHRL CEAKRAPRML DGSLFASQVD ESLGRSTLAE   180
QRAQFPAYH FDADEVARYL SEYAIARGVR HVVDDVQHVG QDERGWISGV HTKQHGEISG    240
DLFVDCTGFR GLLINQTLGG RFQSFSDVLP NNRAVALRVP RENDEDMRPY TTATAMSAGW   300
MWTIPLFKRD GNGYVYSDEF ISPEEAEREL RSTVAPGRDD LEANHIQMRI GRNERTWINN   360
CVAVGLSAAF VEPLESTGIF FIQHAIEQLV KHFPGERWDR VLISAYNERM AHMVDGVKEF   420
LVLHYKGAQR EDTPYWKAAK TRAMPDGLAR KLELSASHLL DEQTIYPYYH GFETYSWITM   480
NLGLGIVPER PRPALLHMDP APALAEFERL RREGDELIAA LPSCYEYLAS IQ          532

SEQ ID NO: 15              moltype = DNA   length = 1518
FEATURE                    Location/Qualifiers
source                     1..1518
                           mol_type = other DNA
                           note = Kutzneria sp. 744
                           organism = unidentified
SEQUENCE: 15
atgaccgccg cctacctgaa gaccgcgttc ggcgaccggc tttcgatcac cgtcgtggaa     60
tcgagcagaa tcgggaccat cggcgtcggt gaggcgacct tcagcgacat ccagcacttc    120
ttccagttcc tcaacctccg ggaacaggac tggatgccgg cctgcaacgc cacctacaag    180
ctgggcatcc gcttcgagaa ctggcggcat gtcggccatc atttctacca gccgttcgag    240
cagatccgcc cggtctacgg ctttccgctg accgactggt ggctgcacga cgcgccgacc    300
gaccgcttcg acaccgactg cttcgtcatg cccaacctgt gcgaggccgg gcgcagcccg    360
cgccacctcg acggcacgct ggccgacgag gacttcgtgg aggagggcga cgagctcgcc    420
aaccgcacca tgtccgagca ccagggcaag tcgcagttcc cgtacgccta ccacttcgag    480
gcggtcggct tggccaagtt cctcaccggg tacgacgtcg accgcacgtc    540
gtcgacgacg tcctggacgt gcggctggac cagcgcgggt ggatcgagcg cgtggtcacc    600
gccgagcacg gcgagatcca cggcgacctg ttcgtcgact gcaccggttt ccggggactg    660
ctgctgaaca aggcgctcgg tgtgccgttc gtgtcctatc aggacactct gcccaacgac    720
agcgcggtcc ccctccaggt cccgctggac atgcagcggc gcgcatcgt gccgaacacc    780
acggccaccg cgcgggaggc cggctggatc tggaccatcc cgctgttcgg tcgggtcggc    840
```

```
accgggtacg tctacgccaa ggactacctc tcgcccgagg aggccgagcg cacgctgcgc   900
gagttcgtcg gcccggcggc cgcggacgtg gaggccaacc acatccgcat gcggatcggc   960
cgcagccagg agtcctggcg gaacaactgc gtggccatcg gcctgtccag cggcttcgtc  1020
gagccgctgg agtcgaccgg gatcttcttc atccaccacg ccatcgagca gctggtgaag  1080
cacttcccgg cggccgactg gaacccgaag tcccgggaca tgtacaactc cgcggtcgcg  1140
cacgtgatgg acggcatccg cgagttcctg gtgatccact accggggcgc ggcgcgggcc  1200
gacaaccagt actggcgcga caccaagacc cgcccgctgc cggacggcct ggccgagcgc  1260
atcgagtgct ggcagacgca gctgccggac accgagacga tctacccgta ctaccacggg  1320
ctgccgccct actcctacat gtgcatcctg atgggcggcg gggccatccg cacgccggcc  1380
tcggccgcgt tggccctgac cgaccagggg gccgcgcaga aggagttcgc cgccgtccgg  1440
gaccgggccg cgcagctgcg cgacacgctg cccagccact acgagtacct cgcgcggatg  1500
cgtggtctgg atgtctga                                                1518

SEQ ID NO: 16          moltype = AA  length = 505
FEATURE                Location/Qualifiers
source                 1..505
                       mol_type = protein
                       note = Kutzneria sp. 744
                       organism = unidentified
SEQUENCE: 16
MTAAYLKTAF GDRLSITVVE SSRIGTIGVG EATFSDIQHF FQFLNLREQD WMPACNATYK   60
LGIRFENWRH VGHHFYQPFE QIRPVYGFPL TDWWLHDAPT DRFDTDCFVM PNLCEAGRSP  120
RHLDGTLADE DFVEEGDELA NRTMSEHQGK SQFPYAYHFE AALLAKFLTG YAVDRGVEHV  180
VDDVLDVRLD QRGWIEHVVT AEHGEIHGDL FVDCTGFRGL LLNKALGVPF VSYQDTLPND  240
SAVALQVPLD MQRRGIVPNT TATAREAGWI WTIPLFGRVG TGYVYAKDYL SPEEAERTLR  300
EFVGPAAADV EANHIRMRIG RSQESWRNNC VAIGLSSGFV EPLESTGIFF IHHAIEQLVK  360
HFPAADWNPK SRDMYNSAVA HVMDGIREFL VIHYRGAARA DNQYWRDTKT RPLPDGLAER  420
IECWQTQLPD TETIYPYYHG LPPYSYMCIL MGGGAIRTPA SAALALTDQG AAQKEFAAVR  480
DRAAQLRDTL PSHYEYLARM RGLDV                                        505

SEQ ID NO: 17          moltype = DNA  length = 1572
FEATURE                Location/Qualifiers
source                 1..1572
                       mol_type = genomic DNA
                       organism = Streptomyces toxytrinici
SEQUENCE: 17
atgaacacga gaaatccgga caaggtcgtc atcgtcggcg gcggcacggc gggatggatg   60
accgcctcgt acctgaagaa ggcgttcggc gagcgcgtgt ccgtgaccct cgtcgaatcg  120
ggcaccatcg gcaccgtcgg cgtcggcgag gcgaccttcc gcgacatccg gcacttcttc  180
gaattcctcg acctgcggga ggaggaatgg atgccggcct gcaacgccac gtacaagctg  240
gccgtccgct tccaggactg gcagcgcccc ggccaccact tctaccaccc gttcgagcag  300
atgcgctccg tagacgggtt cccccctgacc gactggtggc tgcagaacgg gccgaccgac  360
cggttcgaca gggactgctt cgtgatggcg tcgtctgcgg acgcggggcg cagcccgcgc  420
tatctcaacg gttccctgct gcagcaggag ttcgacgagc gcgcggagga gccggcgggg  480
ctcaccatgt ccgagcacca gggcaagacg cagttcccct acgcctacca cttcgaggcg  540
gccctgctcg ccgaattcct ttctgggtac tccaaggacc gcggcgtgaa gcacgtggtc  600
gacgaggtgc tggaggtgaa gctcgacgac gccggatgga tcagccacgt tgtcaccaag  660
gagcacggcg acatcggcgg cgacctgttc gtcgactgca ccggtttccg cggcgtactg  720
ctgaaccagg cgctgggtgt gcccttcgtc tcctaccagg acaccctgcc caatgacagc  780
gcggtcgccc tccaggtgcc gctcgacatg gaggcgcggg gcatcccgcc gtacacccgg  840
gccaccgcca aggaggccgg cgtggatctg acgatccgcg tgatcggccg gatcggcacc  900
gggtacgtgt acgccaagga ctactgctcg ccggaggagg ccgagcgcac cctgcgcgag  960
ttcgtcggtc cggaggccgc cgacgtcgag gccaaccaca tccgcatgcg gatcgggcgc 1020
agcgagcagt cctggaagaa caactgcgtc gcgatcgggc tctccagtgg cttcgtcgaa 1080
cccctcgagt cgaccggcat cttcttcatc caccacgcca tcgagcagtt ggtgaagcac 1140
ttcccggcgg gcgactggca cccgcagctg cgcgccggct acaactcggc cgtcgccaac 1200
gtcatgacg gggtccggga gttcctcgtc ctgcactacc ggcgccgc gcaacgac 1260
acccggtact ggaaggacac caagacccgg gcggttccgg atgccctggc ggagcgcatc 1320
gagcgctgga aggtgcagct gcccgactcc gagaacgtct tccccctacta ccacggcctg 1380
ccgccgtact cgtacatggc catcctgctc gggaccggcg cgatcggcct gcgaccgtcg 1440
ccggcgctcg cactggccga cccggcggcc gcggagaagg agttcaccgc gatccggac 1500
agggcgcggt tcctggtcga caccctgccg agccagtacg agtacttcgc cgcgatgggg 1560
cagcgtgtct ga                                                     1572

SEQ ID NO: 18          moltype = AA  length = 523
FEATURE                Location/Qualifiers
source                 1..523
                       mol_type = protein
                       organism = Streptomyces toxytrinici
SEQUENCE: 18
MNTRNPDKVV IVGGGTAGWM TASYLKKAFG ERVSVTLVES GTIGTVGVGE ATFSDIRHFF   60
EFLDLREEEW MPACNATYKL AVRFQDWQRP GHHFYHPFEQ MRSVDGFPLT DWWLQNGPTD  120
RFDRDCFVMA SLCDAGRSPR YLNGSLLQQE FDERAEEPAG LTMSEHQGKT QFPYAYHFEA  180
ALLAEFLSGY SKDRGVKHVV DEVLEVKLDD RGWISHVVTK EHGDIGGDLF VDCTGFRGVL  240
LNQALGVPFV SYQDTLPNDS AVALQVPLDM EARGIPPYTR ATAKEAGWIW TIPLIGRIGT  300
GYVYAKDYCS PEEAERTLRE FVGPEAADVE ANHIRMRIGR SEQSWKNNCV AIGLSSGFVE  360
PLESTGIFFI HHAIEQLVKH FPAGDWHPQL RAGYNSAVAN VMDGVREFLV LHYLGAARND  420
TRYWKDTKTR AVPDALAERI ERWKVQLPDS ENVFPYYHGL PPYSYMAILL GTGAIGLRPS  480
PALALADPAA AEKEFTAIRD RARFLVDTLP SQYEYFAAMG QRV                    523
```

```
SEQ ID NO: 19            moltype = DNA   length = 1596
FEATURE                  Location/Qualifiers
source                   1..1596
                         mol_type = genomic DNA
                         organism = Streptomyces albogriseolus
SEQUENCE: 19
atggacaatc gaatcaagac agtcgtgatc ctgggcggcg gcaccgccgg ctggatgact    60
gcggcgtatc tcggcaaggc gctgcagaac acggtgaaga tcgtggtcct ggaggcgccg   120
accatcccgc ggatcggtgt gggcgaagcc accgtcccca acctgcagcg cgccgttcttc  180
gactacctcg gcatccccga ggaggagtgg atgcgcgagt gcaacgccag ttacaagatg   240
gcggtgaagt tcatcaactg cgcacaccg ggggagggca gcccggatcc ccggacgctc    300
gacgacggtc acaccgacac cttccaccac cccttcggac tgctgccgtc cgccgaccag   360
ataccgctct cccactactg ggcggccaag cggctccagg gcgagaccga cgagaacttc   420
gacgaggcgt gtttcgccga caccgcgatc atgaacgcca agaaggcgcc ccgcttcctc   480
gacatgcggc gggcgaccaa ctacgcctgg cacttcgacg ccagcaaggt cgccgcgttc   540
ctgcgcaact tcgccgtcac caagcaggcg gtcgagcacg tcgaggacga gatgaccgag   600
gtcctcaccg acgaacgggg cttcatcacc gccctgcgca caagtcggga acggatcctg   660
cagggtgacc tcttcgtcga ctgctccggc ttccgcgggc tgctgatcaa caaggccatg   720
gaggagccgt tcatcgacat gagcgaccac ctccgtgca acagcgcggt cgccacggcc    780
gtaccgcacg acgacgagaa gaacggtgtc gagccgtaca cctcctcgat cgccatggag   840
gccggctgga cctggaagat tccatgctg ggccggttcg gcagcggtca cgtctactcg    900
gaccacttcg ccacccagga cgaggccacc ctggccttct cgaagctgtg gggcctcgac   960
ccggacaaca ccgagttcaa ccacgtccgc ttccgggtcg gccgcaaccg cagggcctgg  1020
gtgcgcaact gcgtcagcgt cggcctcgcg tcgtgcttcg tggagccgct ggagtccagc  1080
ggcatctact tcatctacgc ggccatccac atgctgaagc acttcccc cgacaagacc    1140
ttcgacaagg tgctcgtcga ccggttcaac cgggagatcg aggagatgtt cgacgacacc  1200
cgggacttcc tccaggcgca ctactacttc tcgccgcgcg tcgacacgcc gttctggcgg  1260
gcgaacaagg aactgaagct ggccgactcc atcaaggaca aggtcgagac gtaccgggcc  1320
gggctgccgg tcaacctgcc ggtcaccgac gaggggaccc actacggcaa cttcgaggcc  1380
gagttccgga acttctggac caacggcagc tactactgca tcttcgccgg cctcggcctg  1440
atgccgcgca cccgctgccc cgcgctcgcc tacaagccgc agtcgatcgc ggaggccgag  1500
ctgctgttcg ccgacgtcaa gcgcaagggg gacaccctgg tcgagtcgct gccgtcgacc  1560
tatgacctgc tgcgtcagtt gcacggtgcg tcgtga                            1596

SEQ ID NO: 20            moltype = AA    length = 531
FEATURE                  Location/Qualifiers
source                   1..531
                         mol_type = protein
                         organism = Streptomyces albogriseolus
SEQUENCE: 20
MDNRIKTVVI LGGGTAGWMT AAYLGKALQN TVKIVVLEAP TIPRIGVGEA TVPNLQRAFF    60
DYLGIPEEEW MRECNASYKM AVKFINWRTP GEGSPDPRTL DDGHTDTFHH PFGLLPSADQ   120
IPLSHYWAAK RLQGETDENF DEACFADTAI MNAKKAPRFL DMRRATNYAW HFDASKVAAF   180
LRNFAVTKQA VEHVEDEMTE VLTDERGFIT ALRTKSGRIL QGDLFVDCSG FRGLLINKAM   240
EEPFIDMSDH LLCNSAVATA VPHDDEKNGV EPYTSSIAME AGWTWKIPML GRFGSGHVYS   300
DHFATQDEAT LAFSKLWGLD PDNTEFNHVR FRVGRNRRAW VRNCVSVGLA SCFVEPLESS   360
GIYFIYAAIH MLAKHFPDKT FDKVLVDRFN REIEEMFDDT RDFLQAHYYF SPRVDTPFWR   420
ANKELKLADS IKDKVETYRA GLPVNLPVTD EGTYYGNFEA EFRNFWTNGS YYCIFAGLGL   480
MPRNPLPALA YKPQSIAEAE LLFADVKRKG DTLVESLPST YDLLRQLHGA S            531

SEQ ID NO: 21            moltype = DNA   length = 1590
FEATURE                  Location/Qualifiers
source                   1..1590
                         mol_type = genomic DNA
                         note = BorH halogenase
                         organism = unidentified
SEQUENCE: 21
atggacaaacc gcatcaaccg gatcgtcatc ctcggcggcg ggaccgcggg atggatgacc    60
gcctcctacc tggcgaaggc gctcggtgac accgtcacga tcaccctgct ggaagcaccg   120
gcgatcggcc ggatcgggt cggcgaggcc accgtgccca acctgcagcg cgtgttcttc   180
gacttcctcg gcctccgcga ggaggagtgg atgccggagt gcaacgccgc gttcaagacg   240
gccgtgaagt tcatcaactg cgtaccccc gggcccggca aggccaaggc ccgcacgatc    300
gacggccggc cggaccactt ctaccacccg ttccgggctgc tgcccgagca cggccaggtg   360
ccgctgtcgc actactgggc ctacaaccgg cgggccggca ccaccgacga ccgttcgac    420
tacgcctgtt cgccgagac cgccgccatg acgcggtcc gcgcgccaa gtggctcgac     480
gggcggcccg ccaccggta tgcctggcac ttcgacgccc acctggtcgc cgagttcctg   540
cgccggcacg ccaccgagcg gctcaacgtg agcacgtgc agggtgagat gcagcaggtg   600
ctgcgcgacg agcgggggctt catcaccgcc ctgcgcgaca tcgagggccg ggacctcgag  660
ggtgacctgt tcatcgactg ctccggcttc gcggcctgc tgatcaacaa ggccatggag   720
gagcccttca tcgacatgaa cgaccagctg ctgtgcaacc gcgcggtggc cacggcgatc   780
aagcacgacg acgacgcgca cgggtcgag ccgtacacct cggcgatcgc catgcggtcc    840
ggctggagct ggaagatccc gatgctgggc cgcttcggga ccggctacgt ctactccagc   900
cgttgcgcc agaaggacga ggccaccctg gactgccgg cgagtggga cctggaccgg     960
gagaacaccc cgctcaacca ggtgccttc cggtcggcc gcaaccgccg ggcctgggtg     1020
aagaactgcg tgagcatcgg cctggccgtcg tgctcctgg agcactgga gtccaccgcc  1080
atctacttca tcaccgcgggc catctaccag ctgactcagc acttccccgga ccgcaccttc  1140
gcgctccgcgt tgagcgacgc gttcaaccac gagatcgaag ccatgttcga cgacaccggg  1200
gacttcatcc aggcgcactt ctacgtgtcg ccgcgcaccg acacgccgtt ctggaaggcg   1260
```

```
aacaaggacc tgcacctgcc cgagcagatg cgcgagaaga tcgcgatgta caaggccggc  1320
ctgccgatca acgcgccggt caccgacgag tcgacctact acggcaggtt cgaggccgag  1380
ttccgcaact tctggaccaa cggcagctac tactgcatct tcgcgggcct cgggctgcgc  1440
ccggacaacc cgctgccgat gctgcgacac cgtccggagc aggtccgcga ggcgcaggcg  1500
ctgttcgccg gggtgaagga caagcagcgg gagttggtgg agacgctgcc gagcaacctg  1560
gagttcctgc gcagcctgca cggcaagtag                                   1590

SEQ ID NO: 22           moltype = AA  length = 529
FEATURE                 Location/Qualifiers
source                  1..529
                        mol_type = protein
                        note = BorH halogenase
                        organism = unidentified
SEQUENCE: 22
MDNRINRIVI LGGGTAGWMT ASYLAKALGD TVTITLLEAP AIGRIGVGEA TVPNLQRVFF   60
DFLGLREEEW MPECNAAFKT AVKFINWRTP GPGEAKARTI DGRPDHFYHP FGLLPEHGQV  120
PLSHYWAYNR AAGTTDEPFD YACFAETAAM DAVRAPKWLD GRPATRYAWH FDAHLVAEFL  180
RRHATERLNV EHVQGEMQQV LRDERGFITA LRTVEGRDLE GDLFIDCSGF RGLLINKAME  240
EPFIDMNDQL LCNRAVATAI KHDDDAHGVE PYTSAIAMRS GWSWKIPMLG RFGTGYVYSS  300
RFAEKDEATL DFCRMWGLDP ENTPLNQVAF RVGRNRRAWV KNCVSIGLAS CFLEPLESTG  360
IYFITAAIYQ LTQHFPDRTF ALALSDAFNH EIEAMFDDTR DFIQAHFYVS PRTDTPFWKA  420
NKDLHLPEQM REKIAMYKAG LPINAPVTDE STYYGRFEAE FRNFWTNGSY YCIFAGLGLR  480
PDNPLPMLRH RPEQVREAQA LFAGVKDKQR ELVETLPSNL EFLRSLHGK             529

SEQ ID NO: 23           moltype = DNA  length = 1602
FEATURE                 Location/Qualifiers
source                  1..1602
                        mol_type = genomic DNA
                        note = Kutzneria sp. 744
                        organism = unidentified
SEQUENCE: 23
atggatgaca atcgaattcg gagcatcctt gtccttggcg gcggcaccgg cggctggatg    60
tccgcctgct acctgagcaa ggcgctcggg ccgggcgtcg aggtcaccgt gctcgaggcg   120
ccctccatct cgcgcatccg ggtcggcgag gccaccattc ccaacctgca caaggtcttc   180
ttcgacttcc tgggcatcgc cgaggacgag tggatgcggg agtgcaacgc cagctacaag   240
gccgcggtcc ggttcgtcaa ctggcggacg ccgggcgacg gccaggccac gccgcggcgg   300
cgtccggacg gccgccccga ccacttcgac cacctgttcg gccagctgcc cgagcacgag   360
aacctgccgc tgtcgcagta ctgggcgcac cggcgcctca acggcctgac cgacgaaccc   420
ttcgaccgct cctgctacgt gcagccgcag ctgctggacc gcaagctctc gccgaggttg   480
atggacggca cgaaactggc cagctacgcc tggcacttcg acgccgacct ggtggccgac   540
ttcctctgcc ggttcgccgt gcagaagctg aacgtgaccc acgtccagga cgtgttcacg   600
catgccgacc tcgaccagcg cggccacatc acggccgtca caccgagtc cggccgcacg    660
ctggccgccg acctgttcat cgactgcagc ggcttccgca gcgtgctcat ggcgaaggtc   720
atgcaggagc cgttcctgga catgagcaag cacctgctca acgaccgcgc ggtggcgctg   780
atgctcccgc acgacgacga aaaggtgggc atcgagccgt acacctcgtc gctggccatg   840
cggtcgggct ggtcgtggaa gatcccgctg ctcggccggt tcggctccgg ctacgtctac   900
tccagccagt tcacctccca ggacgaggcg gccgaggagc tctgccgcat gtgggacgtc   960
gacccggcgg agcagacgtt caacaacgtc cggttccggg tcggccgcag ccgccgggcc  1020
tgggtgcgca actgcgtcgc catcggcgtg tccgccatgt tcgtggagcc gctggagtcg  1080
accggcctgt acttcagtta cgcctcgctc taccagctgg tgaagcactt cccggacaag  1140
cggttccggc cgatcctggc cgaccggttc aaccgcgagg tggcgaccat gtacgacgac  1200
acccgcgact tcctccaggc gcacttcagc ctgtcgccgc gtgacgactc cgagttctgg  1260
cgggcctgca aggagctgcc gttcgcggac gggttcgccg agaaggtcga gatgtacagg  1320
gccgggctgc cggtcgaact gccggtcacc atcgacgacg gcactacta cggcaatttc   1380
gaggccgagt tccgcaactt ctggaccaac tcgaactact actgcatctt cgccgggctc  1440
ggtttcctgc ccgagcatcc gctgccggtg ctcgaattcc gcccggaggc cgtcgatcgc  1500
gcggagccgg tgttcgccgc ggtgcgccgg cgcacggagg agctggtcgc caccgccccg  1560
accatgcagg cctacctgcg gcgcctgcac cagggcacgt ag                     1602

SEQ ID NO: 24           moltype = AA  length = 533
FEATURE                 Location/Qualifiers
source                  1..533
                        mol_type = protein
                        note = Kutzneria sp. 744
                        organism = unidentified
SEQUENCE: 24
MDDNRIRSIL VLGGGTAGWM SACYLSKALG PGVEVTVLEA PSISRIRVGE ATIPNLHKVF   60
FDFLGIAEDE WMRECNASYK AAVRFVNWRT PGDGQAPRR RPDGRPDHFD HLFGQLPEHE   120
NLPLSQYWAH RRLNGLTDEP FDRSCYVQPE LLDRKLSPRL MDGTKLASYA WHFDADLVAD  180
FLCRFAVQKL NVTHVQDVFT HADLDQRGHI TAVNTESGRT LAADLFIDCS GFRSVLMGKV  240
MQEPFLDMSK HLLNDRAVAL MLPHDDEKVG IEPYTSSLAM RSGWSWKIPL LGRFGSGYVY  300
SSQFTSQDEA AEELCRMWDV DPAEQTFNNV RFRVGRSRRA WVRNCVAIGV SAMFVEPLES  360
TGLYFSYASL YQLVKHFPDK RFRPILADRF NREVATMYDD TRDFLQAHFS LSPRDDSEFW  420
RACKELPFAD GFAEKVEMYR AGLPVELPVT IDDGHYYGNF EAEFRNFWTN SNYYCIFAGL  480
GFLPEHPLPV LEFRPEAVDR AEPVFAAVRR RTEELVATAP TMQAYLRRLH QGT         533

SEQ ID NO: 25           moltype = DNA  length = 1617
FEATURE                 Location/Qualifiers
source                  1..1617
```

```
                        mol_type = genomic DNA
                        organism = Pseudomonas fluorescens
SEQUENCE: 25
atgaacaagc cgatcaagaa tatcgtcatc gtgggcggcg gtactgcggg ctggatggcc    60
gcctcgtacc tcgtccgggc cctccaacag caggcgaaca ttacgctcat cgaatctgcg   120
gcgatccctc ggatcggcgt gggcgaagcg accatcccaa gtttgcagaa ggtgttcttc   180
gatttcctcg gataccgga gcgggaatgg atgcccaag tgaacggcgc gttcaaggcc    240
gcgatcaagt tcgtgaattg agaaagtct cccgacccct cgcgacga tcacttctac     300
catttgttcg gcaacgtgcc gaactgcgac ggcgtgccgc ttacccacta ctggctgcgc   360
aagcgcgaac agggcttcca gcagccgatg gagtacgcgt gctacccgca gccggggca   420
ctcgacggca agctggcacc gtgcctgtcc gacggcaccc gccagatgtc ccacgcgtgg   480
cacttcgacg cgcacctggt ggccgacttc ttgaagcgct gggccgtcga gcgcggggtg   540
aaccgcgtgg tcgatgaggt ggtggacgtt cgcctgaaca accgcggcta catctccaac   600
ctgctcacca aggaggggcg gacgctggag cggacctgt tcatcgactg ctccggcatg    660
cgggggctcc tgatcaatca ggcgctgaag gaacccttca tcgacatgtc cgactacctg   720
ctgtgcgaca gcgcggtcgc cagcgccgtg cccaacgacg acgcgcgcga tggggtcgag   780
ccgtacacct cctcgatcgc catgaactcg ggatggacct ggaagattcc gatgctgggc   840
cggttcggca gcggctacgt cttctcgagc catttcaccc tcgcgcgacca ggcaccgcc   900
gacttcctca aactctgggg cctctcggac aatcagccgc tcaaccagat caagttccgg   960
gtcgggcgca acaagcgggc gtgggtcaac aactgcgtct cgatcgggct gtcgtcgtgc 1020
tttctggagc ccctggaatc gacggggatc tacttcatct acgcggcgct ttaccagctc 1080
gtgaagcact tcccccgacac ctcgttcgac ccgcgggctga gcgacgcttt caacgccgag 1140
atcgtccaca tgttcgacga ctgccggat ttcgtccaag cgcactattt caccacgtcg  1200
cgcgatgaca cgccgttctg gctcgcgaac cggcacgacc tgcggctctc ggacgccatc 1260
aaagagaagg ttcagcgcta caaggcgggg ctgccgctga ccaccacgtc gttcgacgat 1320
tccacgtact acgagacctt cgactacgaa ttcaagaatt tctggttgaa cggcaactac 1380
tactgcatct ttgccggctt gggcatgctg cccgaccggt cgctgccgct gttgcagcac 1440
cgaccggagt cgatcgagaa agccgaggcg atgttcgcca gcatccggcg cgaggccgag 1500
cgtctgcgca ccagcctgcc gacaaactac gactacctgc ggtcgctgcg tgacggcgac 1560
gcggggctgt cgcgcggcca gcgtgggccg aagctcgcag cgcaggaaag cctgtag     1617

SEQ ID NO: 26          moltype = AA   length = 538
FEATURE                Location/Qualifiers
source                 1..538
                       mol_type = protein
                       organism = Pseudomonas fluorescens
SEQUENCE: 26
MNKPIKNIVI VGGGTAGWMA ASYLVRALQQ QANITLIESA AIPRIGVGEA TIPSLQKVFF    60
DFLGIPEREW MPQVNGAFKA AIKFVNWRKS PDPSRDDHFY HLFGNVPNCD GVPLTHYWLR   120
KREQGFQQPM EYACYPQPGA LDGKLAPCLS DGTRQMSHAW HFDAHLVADF LKRWAVERGV   180
NRVVDEVVDV RLNNRGYISN LLTKEGRTLE ADLFIDCSGM RGLLINQALK EPFIDMSDYL   240
LCDSAVASAV PNDDARDGVE PYTSSIAMNS GWTWKIPMLG RFGSGYVFSS HFTSRDQATA   300
DFLKLWGLSD NQPLNQIKFR VGRNKRAWVN NCVSIGLSSC FLEPLESTGI YFIYAALYQL   360
VKHFPDTSFD PRLSDAFNAE IVHMFDDCRD FVQAHYFTTS RDDTPFWLAN RHDLRLSDAI   420
KEKVQRYKAG LPLTTTSFDD STYYETFDYE FKNFWLNGNY YCIFAGLGML PDRSLPLLQH   480
RPESIEKAEA MFASIRREAE RLRTSLPTNY DYLRSLRDGD AGLSRGQRGP KLAAQESL     538

SEQ ID NO: 27          moltype = DNA  length = 1593
FEATURE                Location/Qualifiers
source                 1..1593
                       mol_type = genomic DNA
                       organism = Lentzea areocolonigenes
SEQUENCE: 27
atgtccggca agattgacaa gatcctcatc gtcggcggcg gcaccgccgg atggatggcc    60
gcgtcctatc tcggcaaggc cctgcagggc accgcggaca tcacactgct gcaggcaccc   120
gacatcccga cgctcggggt cggcgaggcc acgatcccca atctgcagac ggcgttcttc   180
gacttcctcg gaatcccga ggacgagtgg atgcgggagt gcaacgcgag ctacaaggtc    240
gccatcaagt tcatcaactg gcgcaccgcg ggcgagggga cgtccgaggc ccgcgagctc   300
gacggagggc ccgaccactt ctaccactcc ttcggtctgc tcaagtacca cgagcagatt   360
ccgctgtcgc actactggtt cgaccgttcg taccggggga agaccgtcga gccgttcgac   420
tacgcctgct acaaggaacc cgtcatcctc gacgccaaca ggtcaccgcg caggctcgac   480
ggttccaagg tgacgaacta cgcgtggcac ttcgacgcgc acctcgtcgc cgacttcctg   540
cgccggttcg ccaccgagaa gctcggcgtg cgccacgtcg aggaccgcgt cgagcacgtc   600
cagcgcgacg ccaacgcgca catcgagtcg gttcgcaacg caacggggcg tgtcttcgag   660
gccgacctct tcgtcgactg ctcgggcttc cgcgggctgc tgatcaacaa ggcgatggag   720
gagccccttcc tcgacatgag cgatcacctg ctcaacgaca cgccgtcgc cacccaggtg   780
ccgcacgacg acgacgcgaa cggtgtgaa ccgttcacct cggcgatcgc catgaagtcg   840
ggctggacgt ggaagatccc gatgctcggc aggttcggca ccgggtacgt ctactcgagc   900
cggttcgcca ccgaggacga ggcggtgcgc gagttcgaga agatgtggca cctcgaccccg   960
gagacccagc ccctcaacag gatccggttc cgggtcggcc gcaaccggcg cgcgtgggtc  1020
ggcaactgcg tcagcatcgg cacgtcgtcg tgcttcgtgg aaccactgga gtcgacgggc 1080
atctacttcg tctacgccgc gctgtaccag ctggtgaagc acttccccga caagagcctc 1140
aacccgtgc tgaccgccag gttcaaccgc gagatcgaga cgatgttcga cgacacgcgc 1200
gacttcatcc aggccgactt ctacttctcg ccgcgaccgc acacccgtt ctggagggcc 1260
aacaaggagc tgcgcctggc ggacggcatg caggagaaga tcgacatgta ccgcggggc  1320
atggcgatca acgcgcccgc gtccgacgac gccagctct actacggcaa cttcgaggag 1380
gagttccgca acttctggaa caacagcaac tactactgcg tgctggccgg cctcggtctg 1440
gtgcccgacg caccctcacc acgcctggcg cacatgccac aggcgacgga gtcggtggac 1500
gaggtcttcg gcgccgtcaa ggaccggcag cggaacctgc tcgagaccct gccgagcctc 1560
```

-continued

```
cacgagttcc tgaggcaaca gcacggccgc tga                            1593

SEQ ID NO: 28          moltype = AA  length = 530
FEATURE                Location/Qualifiers
source                 1..530
                       mol_type = protein
                       organism = Lentzea areocolonigenes
SEQUENCE: 28
MSGKIDKILI VGGGTAGWMA ASYLGKALQG TADITLLQAP DIPTLGVGEA TIPNLQTAFF    60
DFLGIPEDEW MRECNASYKV AIKFINWRTA GEGTSEAREL DGGPDHFYHS FGLLKYHEQI   120
PLSHYWFDRS YRGKTVEPFD YACYKEPVIL DANRSPRRLD GSKVTNYAWH FDAHLVADFL   180
RRFATEKLGV RHVEDRVEHV QRDANGNIES VRTATGRVFD ADLFVDCSGF RGLLINKAME   240
EPFLDMSDHL LNDSAVATQV PHDDDANGVE PFTSAIAMKS GWTWKIPMLG RFGTGYVYSS   300
RFATEDEAVR EFCEMWHLDP ETQPLNRIRF RVGRNRRAWV GNCVSIGTSS CFVEPLESTG   360
IYFVYAALYQ LVKHFPDKSL NPVLTARFNR EIETMFDDTR DFIQAHFYFS PRTDTPFWRA   420
NKELRLADGM QEKIDMYRAG MAINAPASDD AQLYYGNFEE EFRNFWNNSN YYCVLAGLGL   480
VPDAPSPRLA HMPQATESVD EVFGAVKDRQ RNLLETLPSL HEFLRQQHGR              530

SEQ ID NO: 29          moltype = AA  length = 516
FEATURE                Location/Qualifiers
source                 1..516
                       mol_type = protein
                       organism = Streptomyces albus
SEQUENCE: 29
MLNNVVIVGG GTAGWMTASY FKAAFGERIN ITLVESGNIG AVGVGEATFS DIRHFFDFLG    60
LKEKDWMPAC NATYKLAVRF ENWREEGHYF YHPFEQMRSV NGFPLADWWL REKPTDRFDK   120
DCFVMPSIID AGLSPRHLDG SLIDQPFVEG AEEMQGLTMS EHQGKTQFPY AYQFEAALLA   180
KYLTTYSVER GVKHIVDDVQ QVNLDERGWI RNVTTAEHGE IGGDLFIDCT GFRGLLLNKA   240
LEEPFISFQD TLPNDSAVAL QVPMDMERRG ILPCTTATAQ DAGWIWTIPL MGRVGTGYVY   300
AKDYISPEEA ERTLREFVGP AAADAEANHI KMRVGRSENS WVKNCVAIGL SSGFVEPLES   360
TGIFFIHHAI EQLAKNFPGE DWNPVQRNLY NDSVAHVMDG VREFLVLHYV AAKRSDTQYW   420
RDTKTRKIPD ALAERIEKWK TQLPDTETVF PYYHGLPPYS YHCVLLGMGG IDVKPSPALA   480
LGDSAAAERE FAEIREKTRH LTSVLPKAYD YFSRMR                            516

SEQ ID NO: 30          moltype = AA  length = 530
FEATURE                Location/Qualifiers
source                 1..530
                       mol_type = protein
                       organism = Lentzea aerocologinenes
SEQUENCE: 30
MSGKIDKILI VGGGTAGWMA ASYLGKALQG TADITLLQAP DIPTLGVGEA TIPNLQTAFF    60
DFLGIPEDEW MRECNASYKV AIKFINWRTA GEGTSEAREL DGGPDHFYHS FGLLKYHEQI   120
PLSHYWFDRS YRGKTVEPFD YACYKEPVIL DANRSPRRLD GSKVTNYAWH FDAHLVADFL   180
RRFATEKLGV RHVEDRVEHV QRDANGNIES VRTATGRVFD ADLFVDCSGF RGLLINKAME   240
EPFLDMSDHL LNDSAVATQV PHDDDANGVE PFTSAIAMKS GWTWKIPMLG RFGTGYVYSS   300
RFATEDEAVR EFCEMWHLDP ETQPLNRIRF RVGRNRRAWV GNCVSIGTSS CFVEPLESTG   360
IYFVYAALYQ LVKHFPDKSL NPVLTARFNR EIETMFDDTR DFIQAHFYFS PRTDTPFWRA   420
NKELRLADGM QEKIDMYRAG MAINAPASDD AQLYWGNFEE EFRNFWNNSN YYCVLAGLGL   480
VPDAPSPRLA HMPQATESVD EVFGAVKDRQ RNLLETLPSL HEFLRQQHGR              530

SEQ ID NO: 31          moltype = AA  length = 530
FEATURE                Location/Qualifiers
source                 1..530
                       mol_type = protein
                       organism = Lentzea aerocologinenes
SEQUENCE: 31
MSGKIDKILI VGGGTAGWMA ASYLGKALQG TADITLLQAP DIPTLGVGEA TIPNLQTAFF    60
DFLGIPEDEW MRECNASYKV AIKFINWRTA GEGTSEAREL DGGPDHFYHS FGLLKYHEQI   120
PLSHYWFDRS YRGKTVEPFD YACYKEPVIL DANRSPRRLD GSKVTNYAWH FDAHLVADFL   180
RRFATEKLGV RHVEDRVEHV QRDANGNIES VRTATGRVFD ADLFVDCSGF RGLLINKAME   240
EPFLDMSDHL LNDSAVATQV PHDDDANGVE PFTSAIAMKS GWTWKIPMLG RFGTGYVYSS   300
RFATEDEAVR EFCEMWHLDP ETQPLNRIRF RVGRNRRAWV GNCVSIGTSS CFVEPLESTG   360
IYFVYAALYQ LVKHFPDKSL NPVLTARFNR EIETMFDDTR DFIQAHFYFS PRTDTPFWRA   420
NKELRLADGM QEKIDMYRAG MAINAPASDD AQLYYGNFEE EFRNFWNNSS YYCVLAGLGL   480
VPDAPSPRLA HMPQATESVD EVFGAVKDRQ RNLLETLPSL HEFLRQQHGR              530

SEQ ID NO: 32          moltype = AA  length = 530
FEATURE                Location/Qualifiers
source                 1..530
                       mol_type = protein
                       organism = Lentzea aerocologinenes
SEQUENCE: 32
MSGKIDKILI VGGGTAGWMA ASYLGKALQG TADITLLQAP DIPTLGVGEA TMPNLQTAFF    60
DFLGIPEDEW MRECNASYKV AIKFINWRTA GEGTSEAREL DGGPDHFYHP FGLLKYHEQI   120
PLSHYWFDRL YRGKTVEPFD YACYKEPVIL DANRSPRRLD GSKVTSYAWH FDAHLVADFL   180
RRFATEKLGV RHVEDRVEHV QRDANGNIES VRTATGRVFD ADLFVDCSGF RGLLINKAME   240
EPFLDMSDHL LNDSAVATQV PHDDDANGVE PFTSAIAMKS GWTWKIPMLG RFGTGYVYSS   300
RFATEDEAVR EFCEMWHLDP ETQPLNRIRF RVGRNRRAWV GNCVSIGTSS CFVEPLESTG   360
IYFVYAALYQ LVKHFPDKSF NPVLTARFNR EIETMFDDTR DFIQAHFYFS PRTDTPFWRA   420
```

```
NKELRLADGM QEKIDMYRAG MAINAPAPDD AQLYWGNFEE EFRNLWNNSS YYCVLAGLGL    480
VPDAPSPRLA HMPRATESVD EVFGAVKDQQ RNLLETLPSL HEFLRQQHGR             530

SEQ ID NO: 33          moltype = AA  length = 530
FEATURE                Location/Qualifiers
source                 1..530
                       mol_type = protein
                       organism = Lentzea aerocologinenes
SEQUENCE: 33
MSGKIDKILI VGGGTAGWMA ASYLGKALQG TADITLLQAP DIPTLGVGEA THPNLQTAFF    60
DFLGIPEDEW MRECNASYKV AIKFINWRTA GEGTSEAREL DGGPDHFYHS FGLLKYHEQI   120
PLSHYWFDRS YRGKTVEPFD YACYKEPVIL DANRSPRRLD GSKVTNYAWH FDAHLVADFL   180
RRFATEKLGV RHVEDRVEHV QRDANGNIES VRTATGRVFD ADLFVDCSGF RGLLINKAME   240
EPFLDMSDHL LNDSAVATQV PHDDDANGVE PFTSAIAMKS GWTWKIPMLG RFGTGYVYSS   300
RFATEDEAVR EFCEMWHLDP ETQPLNRIRF RVGRNRRAWV GNCVSIGTSS CFVEPLESTG   360
IYFVYAALYQ LVKHFPDKSF NPVLTARFNR EIETMFDDTR DFIQAHFYFS PRTDTPFWRA   420
NKELRLADGM QEKIDMYRAG MAINAPASDD AQLYYGNFEE EFRNCWNNSS YYCVLAGLGL   480
VPDAPSPRLA HMPRATESVD EVFGAVKDQQ RNLLETLPSL HEFLRQQHGR             530

SEQ ID NO: 34          moltype = AA  length = 530
FEATURE                Location/Qualifiers
source                 1..530
                       mol_type = protein
                       organism = Lentzea aerocologinenes
SEQUENCE: 34
MSGKIDKILI VGGGTAGWMA ASYLGKALQG TADITLLQAP DIPTLGVGEA TIPNLQTAFF    60
DFLGIPEDEW MRECNASYKV AIKFINWRTA GEGTSEAREL DGGPDHFYHS FSLLKYHEQI   120
PLSHYWFDRS YRGKTVEPFD YACYKEPVIL DANRSPRRLD GSKVTNYAWH FDAHLVADFL   180
RRFATEKLGV RHVEDRVEHV QRDANGNIES VRTATGRVFD ADLFVDCSGF RGLLINKAME   240
EPFLDMSDHL LNDSAVATQV PHDDDANGVE PFTSAIAMKS GWTWKIPMLG RFGTGYVYSS   300
RFATEDEAVR EFCEMWHLDP ETQPLNRIRF RVGRNRRAWV GNCVSIGTSS CFVEPLESTG   360
IYFVYAALYQ LVKHFPDKSL NPVLTARFNR EIETMFDDTR DFIQAHFYFS PRTDTPFWRA   420
NKELRLADGM QEKIDMYRAG MAINAPASDD AQLYYGNFEE EFRNFWNNSS YYCVLAGLGL   480
VPDAPSPRLA HMPQATESVD EVFGAVKDRQ RNLLETLPSL HEFLRQQHGR             530

SEQ ID NO: 35          moltype = AA  length = 530
FEATURE                Location/Qualifiers
source                 1..530
                       mol_type = protein
                       organism = Lentzea aerocologinenes
SEQUENCE: 35
MSGKIDKILI VGGGTAGWMA ASYLGKALQG TADITLLQAP DIPTLGVGEA TIPNLQTAFF    60
DFLGIPEDEW MRECNASYKV AIKFINWRTA GEGTSEAREL DGGPDHFYHS FGLLKYHEQI   120
PLSHYWFDRS YRGKTVEPFD YACYKEPVIL DANRSPRRLD GSKVTNYAWH FDAHLVADFL   180
RRFATEKLGV RHVEDRVEHV QRDANGNIES VRTATGRVFD ADLFVDCSGF RGLLINKAME   240
EPFLDMSDHL LNDSAVATQV PHDDDANGVE PFTSAIAMKS GWTWKIPMLG RFGTGYVYSS   300
RFATEDEAVR EFCEMWHLDP ETQPLNRIRF RVGRNRRAWV GNCVSIGTSS CFVEPLESTG   360
IYFVYAALYQ LVKHFPDKSL NPVLTARFNR EIETMFDDTR DFIQAHFYFS PRTDTPFWRA   420
NKELRLADGM QEKIDMYRAG MVINAPASDD AQLYYGNFEE EFRNFWNNSN YYCVLAGLGL   480
VPDAPSPRLA HMPQATESVD EVFGAVKDRQ RNLLETLPSL HEFLRQQHGR             530

SEQ ID NO: 36          moltype = DNA  length = 1446
FEATURE                Location/Qualifiers
source                 1..1446
                       mol_type = genomic DNA
                       organism = Bacillus atrophaeus
SEQUENCE: 36
atgatgtctg aaaatttgca attgtcagct gaagaaatga gacaattggg ttaccaagca    60
gttgatttga tcatcgatca catgaaccat ttgaagtcta agccagtttc agaaacaatc   120
gattctgata tcttgagaaa taagttgact gaatctatcc cagaaaatgg ttcagatcca   180
aaggaattgt tgcatttctt gaacagaaac gtttttaatc aaattacaca tgttgatcat   240
ccacatttct tggcttttgt tccaggtcca ataaattacg ttggtgttgt tgcagatttc   300
ttggcttctg gttttaatgt ttttccaact gcatggattg ctggtgcagg tgctgaacaa   360
atcgaattga ctacaattaa ttggttgaaa tctatgtttg gttttccaga ttcagctgaa   420
ggttatttg tttctggtgg ttcaatggca aatttgacag ctttgactgt tgcaagacaa   480
gctaagttga caacgatat cgaaaatgct gttgtttact tctctgatca aacacatttc   540
tcagttgata gagcattgaa ggttttaggt tttaaacatc atcaaatctg tagaatcgaa   600
acagatgaac atttgagaat ctctgtttca gctttgaaga aacaaattaa agaagataa   660
actaagggta aaaagccatt ctgtgttatt gcaaatgctg tactacaaa ttgtggtgct   720
gttgattctt tgaacgaatt agcagatttg tgtaacgatg aagatgtttg ttgcatgct   780
gatggttctt atggtgctcc agctatcttg tctgaaaagg gttcagctat gttgcaaggt   840
attcatagag cagattcttt gactttagat ccacataagt ggttgttcca accatacgat   900
gttggttgtg ttttgatcag aaactctcaa tatttgtcaa agactttag aatgatgcca   960
gaatacaaga aggattcaga aactaacgtt gaaggtaaa ttaatttggt tgaatgtgat  1020
atcgaattgc caagaagatt cagagctttg aaggtttggt tgtcttttaa agttttcggt  1080
gttgctgctt ttagacaagc aatcgatcat ggtatcatgt tagcagaaca agttgaagca  1140
ttttggta aagcaaaaga ttgggaagtt gttacaccag ctcaattggg tatcgttact  1200
tttagataca ttccatctga attggcatca acagatacta ttaatgaaat taataagaaa  1260
ttggttaagg aaatcacaca tagaggtttc gctatgttat ctactacaga attgaaggaa  1320
```

-continued

```
aaggttgtta ttagattgtg ttcaattaat ccaagaacta caactgaaga aatgttgcaa    1380
atcatgatga agattaaagc attggctgaa gaagtttcta tttcataccc atgtgttgct    1440
gaataa                                                                1446

SEQ ID NO: 37            moltype = AA   length = 481
FEATURE                  Location/Qualifiers
source                   1..481
                         mol_type = protein
                         organism = Bacillus atrophaeus
SEQUENCE: 37
MMSENLQLSA EEMRQLGYQA VDLIIDHMNH LKSKPVSETI DSDILRNKLT ESIPENGSDP     60
KELLHFLNRN VFNQITHVDH PHFLAFVPGP NNYVGVVADF LASGFNVFPT AWIAGAGAEQ    120
IELTTINWLK SMLGFPDSAE GLFVSGGSMA NLTALTVARQ AKLNNDIENA VVYFSDQTHF    180
SVDRALKVLG FKHHQICRIE TDEHLRISVS ALKKQIKEDR TKGKKPFCVI ANAGTTNCGA    240
VDSLNELADL CNDEDVWLHA DGSYGAPAIL SEKGSAMLQG IHRADSLTLD PHKWLFQPYD    300
VGCVLIRNSQ YLSKTFRMMP EYIKDSETNV EGEINFGECG IELSRRFRAL KVWLSFKVFG    360
VAAFRQAIDH GIMLAEQVEA FLGKAKDWEV VTPAQLGIVT FRYIPSELAS TDTINEINKK    420
LVKEITHRGF AMLSTTELKE KVVIRLCSIN PRTTTEEMLQ IMMKIKALAE EVSISYPCVA    480
E                                                                    481

SEQ ID NO: 38            moltype = DNA   length = 1473
FEATURE                  Location/Qualifiers
source                   1..1473
                         mol_type = genomic DNA
                         organism = Ruminococcus gnayus
SEQUENCE: 38
atgtctcaag tgatcaaaaa aaagagaaac actttcatga tcggtaccga atatatattg     60
aactctaccc aattagaaga ggctattaaa tctttcgtcc atgatttctg tgccgaaaag    120
cacgaaattc acgaccaacc agttgtcgtt gaagctaagg aacaccaaga agataagatt    180
aagcaaatca aaattccaga aaagggtcgt ccagtcatga aagttgtttc tgaaatgatg    240
aacgaagtct acagatacag aggtgatgcc aaccatccaa gattcttctc tttcgttcca    300
ggtccagctt cctctgtctc ctggttgggg gacatcatga cttctgctta caacatccac    360
gctggtggtt ctaaattggc cccaatggtt aactgtatcg aacaagaagt cttgaaatgg    420
ctcgcaaagc aagttggttt caccgaaaac cctggtgtgt tttcgtttc cggtggttcc    480
atggctaaca ttactgcttt gacagccgct agagacaaca gcttaccga tattaacttg    540
cacttgggta ctgcttacat ttccgaccaa acccactctt cagttgctaa gggtttacgt    600
atcattggta tcactgactc cagaatcaga gaattccaa ctaactccca cttccaaatg    660
gacaccacta agttggaaga agctatcgaa accgacaaga agtccggtta catcccattt    720
gttgttatcg gtactgccgg taccaccaac actggttcca ttgacccatt gactgaaatt    780
tccgctttgt gtaagaagca tgacatgtgg ttccacattg atggtgccta cggtgcttca    840
gttttgttgt ctccaaagta caagtctttg ttaacaggta ccggtttggc tgactctatc    900
tcttgggatg ctcacaagtg gttatttcaa acttacggtt gtgctatggt ttggtcaag    960
gatattagaa acttgtttca ttccttccac gtcaatccag aatacttgaa ggatctggaa   1020
aacgacatcg ataacgttaa cacctgggac atcggcatgg aattgaccag accagccaga   1080
ggtttgaagt tgtggttgac tttgcaagtt ctaggttctg atcttattgg ttctgccatt   1140
gaacacggtt tccaattggc tgtctgggct gaagaagcct tgaatccaaa gaaggactgg   1200
gaaattgtct ctcctgctca aatgatgatg atcaacttca atcaacttca aaaggactgg   1260
accaaggaag aacaagatat cttgaacgaa aagatctctc accgtatttt ggaatccggt   1320
tacgctgcta tcttcactac cgtcctaaac ggtaagactg tcttgagaat ctgcgctatt   1380
cacccagaag ctactcaaga agacatgcaa cacaccattg atttgttgga ccaatacggt   1440
agagaaatct acactgaaat gaagaaggct tag                                 1473

SEQ ID NO: 39            moltype = AA   length = 490
FEATURE                  Location/Qualifiers
source                   1..490
                         mol_type = protein
                         organism = Ruminococcus gnayus
SEQUENCE: 39
MSQVIKKRN TFMIGTEYIL NSTQLEEAIK SFVHDFCAEK HEIHDQPVVV EAKEHQEDKI      60
KQIKIPEKGR PVNEVVSEMM NEVYRYRGDA NHPRFFSFVP GPASSVSWLG DIMTSAYNIH   120
AGGSKLAPMV NCIEQEVLKW LAKQVGFTEN PGGVFVSGGS MANITALTAA RDNKLTDINL   180
HLGTAYISDQ THSSVAKGLR IIGITDSRIR RIPTNSHFQM DTTKLEEAIE TDKKSGYIPF   240
VVIGTAGTTN TGSIDPLTEI SALCKKHDMW FHIDGAYGAS VLLSPKYKSL LTGTGLADSI   300
SWDAHKWLFQ TYGCAMVLVK DIRNLFHSFH VNPEYLKDLE NDIDNVNTWD IGMELTRPAR   360
GLKLWLTLQV LGSDLIGSAI EHGFQLAVWA EEALNPKKDW EIVSPAQMAM INFRYAPKDL   420
TKEEQDILNE KISHRILESG YAAIFTTVLN GKTVLRICAI HPEATQEDMQ HTIDLLDQYG   480
REIYTEMKKA                                                          490

SEQ ID NO: 40            moltype = DNA   length = 1482
FEATURE                  Location/Qualifiers
source                   1..1482
                         mol_type = genomic DNA
                         organism = Streptomyces griseofuscus
SEQUENCE: 40
atgaagccag ctgaagctaa accacctcac atgaccatg atactttcag atccttgggt      60
caccaagcta ttgactggat tgctgattac tggcaacact ggctgacag accagttgct    120
ccattggttg aaccaggtac tgttagagcc caattgccta ccactccacc agagtacggt    180
gaagacttcc cagctttgtt atctgacttg gaaagaattg tcttgccagg cttgttgcac    240
tggcaacacc caagattctt cggttacttc ccagctaacg cttccggtcc agccgtttta    300
```

```
gctgaattat tatctgctgg tctaggtgtc caaggtatga actggaacac ttctccagct   360
tgtaccgaag ttgaacaaca aatgttggac tggttcgttc atttgttagg gttgccagaa   420
cacttcagag tggtggtgt tatccaagac actgcctcct ccgccgtttt ggtcgctcta   480
ttgactgctt tgcacagagc ttctgctggt agaaccagag atcacggtac tggtgaatgt   540
ggttacaggg tttacctaac cgctgaaact cactccgctg ctagaaaggc tgccgtcatc   600
accggtttgg gtttgcgtgc tgtttgtgaa gtcgcaactg atgctgacgg tgctatggat   660
gccgctgact tggccgctcg tattcaagcc gatttggctg ccggtttgac cccattgatg   720
gttgttgcta cccgtggtac cacctctgat ttgtccttcg atccattgga agacatcggt   780
ccagtctgta gaagacatgg tgtctggtta cacgttgacg ctgcttatgc tggtgttgct   840
gcagtgtgcg atgaattgca ttgggttaat gatggtgtta gatacgctga ttcttactgt   900
actaacccac acaagtggtt gttgaccaac ttcgactgtg atttattatg ggttgccgac   960
ccagaagctt tggtcaacgc tttgtccgtt tgcctgctt acttgagaaa cccagcttct  1020
gaatcaggta gagttactga ctacagacac tggcaagttc catgggcag aagattcaga  1080
gccttgaagt tgtggtctgt cttaagatgg tacggtgccg aaggtttgag atctcacatc  1140
agaactggtg tcagacacgc cagattgttc gctgacctgg tcagagaaga tgaccgtttc  1200
accttgttgg cgccagctac tttggggttg gtcactttcc gtcacgctgg ttctgacacc  1260
gacaacagaa acttgttgca cgctatcaac gccgaaggta caactttttt aactcatagt  1320
gaaaagaacg gtacctttt cttgagattt gctaccggtg gtaccacac tgaagaccat  1380
cacgtccacg aagcttggag agctgtccaa aatgccgtcc aaaacgccgt cccaagagcc  1440
caacatgcca ccgatggtac tgccgatgct tgaacggtt aa                      1482

SEQ ID NO: 41           moltype = AA   length = 493
FEATURE                 Location/Qualifiers
source                  1..493
                        mol_type = protein
                        organism = Streptomyces griseofuscus
SEQUENCE: 41
MKPAEAKPPH MDHDTFRSLG HQAIDWIADY WQHLADRPVA PLVEPGTVRA QLPTTPPEYG   60
EDFPALLSDL ERIVLPGLLH WQHPRFFGYF PANASGPAVL AELLSAGLGV QGMNWNTSPA  120
CTEVEQQMLD WFVHLLGLPE HFRGGGVIQD TASSAVLVAL LTALHRASAG RTRDHGTGEC  180
GYRVYLTAET HSAARKAAVI TGLGLRAVCE VATDADGAMD AADLAARIQA DLAAGLTPLM  240
VVATRGTTSD LSFDPLEDIG PVCRRHGVWL HVDAAYAGVA AVCDELHWVN DGVRYADSYC  300
TNPHKWLLTN FDCDLLWVAD PEALVNALSV LPAYLRNPAS ESGRVTDYRH WQVPLGRRFR  360
ALKLWSVLRW YGAEGLRSHI RTGVRHARLF ADLVREDDRF TLLAPATLGL VTFRHAGSDT  420
DNRNLLHAIN AEGTTFLTHS EKNGTFFLRF ATGGTHTEDH HVHEAWRAVQ NAVQNAVPRA  480
QHATDGTADA LNG                                                    493

SEQ ID NO: 42           moltype = DNA   length = 1482
FEATURE                 Location/Qualifiers
source                  1..1482
                        mol_type = genomic DNA
                        organism = Ceriporiopsis subvermispora
SEQUENCE: 42
atggatattg aagcttttag aaaagcaggt taccaagcta tcgatagaat ttgtgactac    60
tactactctt tgcaaaatag accagttgtt ccatcagttc aaccaggtta tttgttagat   120
gcattaccag attctccacc agaacaaggt gaagatttca ctgttattgc tgatgattac   180
caaaagtaca tcttgccagg tttgacacat tggcaacatc catcttttctt tgcatacttt   240
ccaacagctt gtactttga aggtattttg ggtgactgt attctacatc aactgcaaat   300
ccaggttta attggttggc ttctccagca tgtactgaat agaaatggt tgttatggat   360
tggtctgcta agttgttagg tttgtcagaa catttcttgc attcttcagg taaggttggt  420
ggtgttattc aaactacagc atcagaattg ctttagttg ttgttgttgc tgcaagagaa    480
agatacttga gaattcatcc agatgctaag gcagatgaat tggttatata tactacaact  540
caaacacatt ctttgggtgt taaagctggt ttagttttg gtatggaatg tagagcattg   600
gaagttaaag ctgaagatgc ttacgcatta agagtgcaa ctttgaagtc agctttagaa   660
gaagatgaaa agagaggtaa agacccttt attttggttg caacagttgg tacaacttct   720
tcaggtgcta ttgatagatt ggatgaaatt ggtcaagttt ctgaagatta ccatcattca   780
tggattcatg ttgatgctgc atgggcaggt gttacttgg cttgtccaga atacagaggt   840
acagctcaat agaaaacat caacgcttat gcaacatctt tcggtactaa cttccataag   900
tggggttgg ttaactttga tgctgcattg ttgtgggta aggatagaaa ggatttgaca   960
gatgctttag atgttactcc agaattcttg agaacaaaac aaggtgacgc tggtgcagtt  1020
gttgatttta gaaattggca tttgggtttg gtagaagat tcagatcttt gaaggtttgg  1080
ttcgttttga gatcatacgg tgttgaaggt tagaaaact acatcagaca aggtattaaa  1140
ttgaatgaac attttacttc tttaattaga gcttcttgg atttttcatt agttacagca  1200
ccatcattcg ctttgacagt ttttagattg actccagctg gtgcatcttt gactggttca  1260
gaattgaacg aattaaacag agctttctac gcaagattat cttcaagaca tgatatcatg  1320
ttgacacaaa ctgttttgaa cggtgttttc tgtatcagat ttgcagttgg tgctgcaaga  1380
actcaacaag aacatattga tacagcttgg gatttgttac aacaagaagg tgctgttgca  1440
gttcaagaat acatgcaaaa gatttctaag gatgttcaat aa                      1482

SEQ ID NO: 43           moltype = AA   length = 493
FEATURE                 Location/Qualifiers
source                  1..493
                        mol_type = protein
                        organism = Ceriporiopsis subvermispora
SEQUENCE: 43
MDIEAFRKAG YQAIDRICDY YYSLQNRPVV PSVQPGYLLD ALPDSPPEQG EDFTVIADDY   60
QKYILPGLTH WQHPSFFAYF PTACTFEGIL GDLYSTSTAN PGFNWLASPA CTELEMVVMD  120
WSAKLLGLSE HFLHSSGKGG GVIQTTASEL ALVVVVAARE RYLRIHPDAK ADELVIYTTT  180
QTHSLGVKAG LVFGMECRAL EVKAEDAYAL RGATLKSALE EDEKRGKRPF ILVATVGTTS  240
```

```
SGAIDRLDEI GQVSEDYPSL WIHVDAAWAG VTLACPEYRG TAQLENINAY ATSFGTNFHK    300
WGLVNFDAAL LWVKDRKDLT DALDVTPEFL RTKQGDAGAV VDFRNWHLGL GRRFRSLKVW    360
FVLRSYGVEG FRNYIRQGIK LNEHFTSLIR ASLDFSLVTA PSFALTVFRL TPAGASLTGS    420
ELNELNRAFY ARLSSRHDIM LTQTVLNGVF CIRFAVGAAR TQQEHIDTAW DLLQQEGAVA    480
VQEYMQKISK DVQ                                                      493

SEQ ID NO: 44            moltype = DNA   length = 1254
FEATURE                  Location/Qualifiers
source                   1..1254
                         mol_type = genomic DNA
                         organism = Clostridium sporogenes
SEQUENCE: 44
atgaagttct ggagaaagta cacacaacaa gaaatggatg aaaagattac tgaatctttg      60
gaaaagactt tgaactacga taacactaag acaatcggta ttccaggtac taagttggat     120
gatacagttt tctatgatga tcattctttc gttaagcatt caccatactt gagaactttt     180
attcaaaacc caaccatat cggttgtcat acttatgata aggctgatat cttgttcggt      240
ggtacattcg atatcgaaag agaattaatc caattgttag caatcgatgt tttgaacggt     300
aacgatgaag aatttgatgg ttacgttact caaggtggta cagaagctaa catccaagca     360
atgtgggttt acagaaacta cttcaagaaa gaaagaaagg ctaagcatga gaaaatcgct     420
atcatcactt cagcagatac acattactct gcatacaaag ttcagatttt gttgaacatc     480
gatattatta aggttccagt tgatttttat tcaagaaaaa ttcaagaaaa tacattggat     540
tcaattgtta aagaagctaa agaaattggt aaaaagtact tcatcgttat tctctaacatg    600
ggtactacaa tgtttggttc agttgatgat ccagatttgt acgctaacat cttcgataag     660
tacaatttgg aatacaaaat tcatgttgat ggtgcatttg gtggttttat atatccaatt     720
gataataagg aatgtaaaac tgatttctct aataagaacg tttcttcaat cacattagat     780
ggtcataaca tgttgcaagc tccatacggt actggtatct tcgtttcaag aaagaatttg     840
atccataaca ctttgacaaa ggaagcaact tacatcgaaa atttggatgt tacattgtct     900
ggttcaagat ctggttcaaa tgctgttgca atttggatgg ttttagcttc ttatggtcca     960
tacggttgga tggaaaagat taataagttg agaaatagaa ctaaatggtt gtgtaagcaa    1020
ttgaacgata tgagaattaa atattacaaa gaagattcaa tgaatattgt tacaattgaa    1080
gaacaatatg ttaataagga aatcgctgaa aagtactttt tagttccaga agttcataac    1140
ccaactaaca actggtacaa gatcgttgtt atggaacatg ttgaattgga tatcttgaac    1200
tctttggttt acgatttgag aaagtttaat aaggaacatt tgaaggcaat gtaa          1254

SEQ ID NO: 45            moltype = AA    length = 417
FEATURE                  Location/Qualifiers
source                   1..417
                         mol_type = protein
                         organism = Clostridium sporogenes
SEQUENCE: 45
MKFWRKYTQQ EMDEKITESL EKTLNYDNTK TIGIPGTKLD DTVFYDDHSF VKHSPYLRTF     60
IQNPNHIGCH TYDKADILFG GTFDIERELI QLLAIDVLNG NDEEFDGYVT QGGTEANIQA    120
MWVYRNYFKK ERKAKHEEIA IITSADTHYS AYKGSDLLNI DIIKVPVDFY SRKIQENTLD    180
SIVKEAKEIG KKYFIVISNM GTTMFGSVDD PDLYANIFDK YNLEYKIHVD GAFGGFIYPI    240
DNKECKTDFS NKNVSSITLD GHKMLQAPYG TGIFVSRKNL IHNTLTKEAT YIENLDVTLS    300
GSRSGSNAVA IWMVLASYGP YGWMEKINKL RNRTKWLCKQ LNDMRIKYYK EDSMNIVTIE    360
EQYVNKEIAE KYFLVPEVHN PTNNWYKIVV MEHVELDILN SLVYDLRKFN KEHLKAM       417

SEQ ID NO: 46            moltype = DNA   length = 1443
FEATURE                  Location/Qualifiers
source                   1..1443
                         mol_type = genomic DNA
                         organism = Homo sapiens
SEQUENCE: 46
atgaatgcat ctgaattcag aagaagaggt aaagaaatgg ttgattacat ggctaactac      60
atggaaggta ttgaaggtag acaagtttat ccagatgttg aaccaggtta cttgagacca     120
ttaattccag ctgcagctcc acaagaacca gatacatttg aagatattat taacgatgtt     180
gaaaagatta tcatgccagg tgttacacat tggcattcac catatttctt tgcatacttt     240
ccaactgctt cttcatatcc agcaatgttg gctgatatgt tatgtggtgc aattggttgt     300
attggttttt cttgggcagc ttcaccagct tgtacagaat tggaaactgt tatgatggat     360
tggttaggta aaatgttgga attaccaaag gcattttttga acgaaaaggc tggtgaaggt     420
ggtggtgtta tcaaggttc tgcatcagaa gctacattag ttgctttgtt agcagctaga     480
actaaagtta ttcatagatt gcaagcagct tctccagaat taacaagca gctatcatg     540
gaaaaattgg ttgcatattc ttcagatcaa gctcattctt cagttgaaag agctggtttg     600
atcggtggtg ttaagttgaa ggcaatccca tctgatggta ttttgctat gagagcatca     660
gctttgcaag aagcattaga aagagataaa gcagctggtt tgattccatt tttcatggtt     720
gctactttag gtactacaac ttgttgttct ttcgataatt tgttagaagt tggtccaatt     780
tgtaataagg aagatatttg gttgcatgtt gatgcagctt acgcaggttc agctttttatt     840
tgtccagaat tcagacattt gttgaacggt tcgtattctt taatttcaat     900
ccacataaat ggttgttagt taacttcgat tgttcagcaa tgtgggttaa gaaaagaaca     960
gatttgactg tgctttttag attagatcca acatatttga agcattctca tcaagattca    1020
ggtttgatca ctgattacag acattggcaa attccattgg gtagaagatt cagatctttg    1080
aagatgtggt tcgtttttag aatgtacggt gttaagggtt gcaagcttta catcagaaag    1140
catgttcaat tgtctcatga attcgaatca ttagttagac aagatccaag attcgaaatc    1200
tgtgttgaag tatttttggg tttagtttgt ttcagattga agggttctaa taaggttaac    1260
gaagcattgt tgcaaagaat taattcagct aagaaaattc atttggttcc atgtcatttg    1320
cgtgataagt tcgtttttgag attcgctatt tgttcaagaa ctgttgaatc agcacatgtt    1380
caaagagctt gggaacatat caaggaattg gcagctgatg ttttgagagc tgaaagagaa    1440
taa                                                                 1443
```

```
SEQ ID NO: 47           moltype = AA   length = 480
FEATURE                 Location/Qualifiers
source                  1..480
                        mol_type = protein
                        organism = Homo sapiens
SEQUENCE: 47
MNASEFRRRG KEMVDYMANY MEGIEGRQVY PDVEPGYLRP LIPAAAPQEP DTFEDIINDV   60
EKIIMPGVTH WHSPYFFAYF PTASSYPAML ADMLCGAIGC IGFSWAASPA CTELETVMMD  120
WLGKMLELPK AFLNEKAGEG GGVIQGSASE ATLVALLAAR TKVIHRLQAA SPELTQAAIM  180
EKLVAYSSDQ AHSSVERAGL IGGVKLKAIP SDGNFAMRAS ALQEALERDK AAGLIPFFMV  240
ATLGTTTCCS FDNLLEVGPI CNKEDIWLHV DAAYAGSAFI CPEFRHLLNG VEFADSFNFN  300
PHKWLLVNFD CSAMWVKKRT DLTGAFRLDP TYLKHSHQDS GLITDYRHWQ IPLGRRFRSL  360
KMWFVFRMYG VKGLQAYIRK HVQLSHEFES LVRQDPRFEI CVEVILGLVC FRLKGSNKVN  420
EALLQRINSA KKIHLVPCHL RDKFVLRFAI CSRTVESAHV QRAWEHIKEL AADVLRAERE  480

SEQ ID NO: 48           moltype = DNA   length = 1521
FEATURE                 Location/Qualifiers
source                  1..1521
                        mol_type = genomic DNA
                        organism = Ophiorrhiza pumila
SEQUENCE: 48
atgggttcta tctcagaaaa ctgtgatgat tctatttcat tagctgcacc ttttagacca    60
ttggaaccag aagaattcag aaagcaagct catgttatgg ttgatttcat cgcagattac   120
tacaagaaca ttgaaaatta tccagttttg tcacaagttg aaccaggtta tttgaaaaat   180
agattgccag aaactgctcc acatttgcca gaatctttcg aaacaatcct gaaggatatt   240
aagaaagata tcgttcctgg tatgactaat tggttgtcac caaatttctt tgcttatttt   300
ccagcaactg tttcttcagc tgcatttgtt ggtgaaatgt tgtgtacagg ttttaattct   360
gttggttta attggttagc ttcaccagca tctacagaat tggaaatggt tgttattgat   420
tggttagcta acatgttgaa gttgccaaag tcttttagtt ttcatggtac tggtggtggt   480
gttattcaag gtactacatc tgaagctatc ttgtgtacat tgattgctgc aagagatggt   540
gctttggaaa agattggtat ggaaaacgtt ggtaaattag ttgtttacgg ttcagatcaa   600
actcattctt tctttcaaaa gacttgtaag gttgctggta tcttcccatg taacatcaag   660
ttgatcccaa ctacaagaga agataacttc tctatgtcac caatcgcatt gagagaacaa   720
attgaagcta atgttgcaga tggtttagtt ccaatttcct tgtgtactac agttggtact   780
acatcaactg ctgcaattga tccagtttct gaagttgcta aggttgcaaa cgatttcaat   840
atttgggttc atgttgatgc tgcttatgct ggttctgcat gtatttgtcc agaattcaga   900
caatacttag atggtatcga attggttgat tcttttcat tgtctccaca taagtggttg   960
tgtgtttct tggattgttg ttgtttgtgg ttgaagaaac cacatttgat ggttaaggct  1020
ttgtcaacta acccagaata tttgagaaat aagagatctg aattcgatgg tgttgttgat  1080
ttcaaggatt ggcaaatcgg tacaggtaga agattcaaag ctttgagatt atggttggtt  1140
atgagatcat acggtgttga aaatttgaag agacatatct tgtctgatgt tcaaatggct  1200
aagatgttcg aaggtttagt taaatctgat ccaagatttg aaatcatcgt tccaagagct  1260
ttcgcattag tttgtttcag attgaaccct ggtaaaggtt atgatgatga aatcgataag  1320
gaaatcttga ataaggaatt gttagatttg attaattcaa caggtagagc ttacatgact  1380
catacaaaag caggtggtat ctatatgttg agatttgctg ttggtactac attgactgaa  1440
gaacatcatg tttacgctgc atgggaattg attaaagaat gtacagatgc atctttgact  1500
aaaacaaata ttattgaata a                                            1521

SEQ ID NO: 49           moltype = AA   length = 506
FEATURE                 Location/Qualifiers
source                  1..506
                        mol_type = protein
                        organism = Ophiorrhiza pumila
SEQUENCE: 49
MGSISENCDD SISLAAPFRP LEPEEFRKQA HVMVDFIADY YKNIENYPVL SQVEPGYLKN   60
RLPETAPHLP ESFETILKDI KKDIVPGMTN WLSPNFFAYF PATVSSAAFV GEMLCTGFNS  120
VGFNWLASPA STELEMVVID WLANMLKLPK SFMFHGTGGG VIQGTTSEAI LCTLIAARDG  180
ALEKIGMENV GKLVVYGSDQ THSFFQKTCK VAGIFPCNIK LIPTTREDNF SMSPIALREQ  240
IEADVADGLV PIFLCTTVGT TSTAAIDPVS EVAKVANDFN IWVHVDAAYA GSACICPEFR  300
QYLDGIELVD SFSLSPHKWL LCFLDCCCLW LKKPHLMVKA LSTNPEYLRN KRSEFDGVVD  360
FKDWQIGTGR RFKALRLWLV MRSYGVENLK RHILSDVQMA KMFEGLVKSD PRFEIIVPRA  420
FALVCFRLNP GKGYDDEIDK EILNKELLDL INSTGRAYMT HTKAGGIYML RFAVGTTLTE  480
EHHVYAAWEL IKECTDASLT KTNIIE                                       506

SEQ ID NO: 50           moltype = DNA   length = 1545
FEATURE                 Location/Qualifiers
source                  1..1545
                        mol_type = genomic DNA
                        organism = Oryza sativa
SEQUENCE: 50
atgggttcat tagatacaaa tccaactgct ttttctgcat ttccagctgg tgaaggtgaa    60
acttttcaac cattgaacgc agatgatgtt agatcatatt tgcataaggc tgttgatttc   120
atctctgatt actacaaatc agttgaatct atgccagttt tgcaaacgt taagccaggt   180
tatttgcaag atgaattaag agcatccacca ccaacttact ctgctccatt cgatgttaca   240
atgaaggaat tgagatcttc agttgttcct ggtatgactc attgggcatc tccaaatttc   300
tttgctttct ttccatcaac aaattctgct gcagctattg ctggtgactt gattgcatca   360
gctatgaata cagttggttt tacttggcaa gcttctccag cagctactga atggaagtt   420
ttggcattag attggttggc tcaaatgttg aatttgccaa cttctttat gaacagaact   480
```

```
ggtgaaggta gaggtactgg tggtggtgtt attttgggta ctacatctga agctatgttg    540
gttacattag ttgcagctag agatgcagct tgagaagat  ctggttcaga tggtgttgca    600
ggtttgcata gattagctgt ttatgcagct gatcaaacac attcaacttt ctttaaggca    660
tgtagattgg ctggttttga tccagcaaat attagatcta ttccaacagg tgctgaaact    720
gattatggtt tagatccagc aagattgtta gaagctgatg aagcagatgc tgatgcaggt    780
ttagttccaa catacgtttg tgcaactgtt ggtactacat cttcaaatgc tgttgatcca    840
gttggtgctg ttgcagatgt tgcagctaga ttttcagctt gggttcatgt tgatgcagct    900
tacgcaggtt cagcttgtat ttgtccagaa ttcagacatc atttggatgg tgttgaaaga    960
gttgattcta tctcaatgtc tccacataag tggttgatga catgtttaga ttgtacttgt   1020
ttgtacgtta gagatacaca tagattgact ggttctttag aaactaaccc agaatacttg   1080
aaaaatcatg cttcagattc tggtgaagtt acagatttga agatatgca  agttggtgtt   1140
ggtagaagat tcagaggttt gaagttgtgg atggttatga aacttatgg  tgttgctaag   1200
ttgcaagaac atatcagatc agatgttgct atggcaaaaa ttttgaaga  tttggttaga   1260
ggtgacgata gattcgaagt tgttgttcca agaaactcg  ctttggtttg tttcagaatt   1320
agagctggtg caggtgcagc tgcagctaca gaagaagatg cagatgaagc taacagaaga   1380
ttgatggaaa gattgaataa gactggtaaa gcatacgttg ctcatacagt tgttggtggt   1440
agatttgttt tgagatttgc agttggttct tcattacaag aagaacatca tgttagatct   1500
gcttgggaat tgattaagaa aactacaact gaaatgatga actaa                   1545

SEQ ID NO: 51           moltype = AA   length = 514
FEATURE                 Location/Qualifiers
source                  1..514
                        mol_type = protein
                        organism = Oryza sativa
SEQUENCE: 51
MGSLDTNPTA FSAFPAGEGE TFQPLNADDV RSYLHKAVDF ISDYYKSVES MPVLPNVKPG     60
YLQDELRASP PTYSAPFDVT MKELRSSVVP GMTHWASPNF FAFFPSTNSA AAIAGDLIAS    120
AMNTVGFTWQ ASPAATEMEV LALDWLAQML NLPTSFMNRT GEGRGTGGGV ILGTTSEAML    180
VTLVAARDAA LRRSGSDGVA GLHRLAVYAA DQTHSTFFKA CRLAGFDPAN IRSIPTGAET    240
DYGLDPARLL EAMQADADAG LVPTYVCATV GTTSSNAVDP VGAVADVAAR FAAWVHVDAA    300
YAGSACICPE FRHHLDGVER VDSISMSPHK WLMTCLDCTC LYVRDTHRLT GSLETNPEYL    360
KNHASDSGEV TDLKDMQVGV GRRFRGLKLW MVMRTYGVAK LQEHIRSDVA MAKVFEDLVR    420
GDDRFEVVVP RNFALVCFRI RAGAGAAAAT EEDADEANRE LMERLNKTGK AYVAHTVVGG    480
RFVLRFAVGS SLQEEHHVRS AWELIKKTTT EMMN                                514

SEQ ID NO: 52           moltype = DNA   length = 1494
FEATURE                 Location/Qualifiers
source                  1..1494
                        mol_type = genomic DNA
                        organism = Oryza sativa
SEQUENCE: 52
atggaaggtg ttggtggtgg tggtggtggt gaagaatggt tgagaccaat ggatgcagaa     60
caattaagag aatgtggtca tagaatggtt gattcgttg  cagattacta caagtcaatc    120
gaagcttttc cagttttgtc tcaagttcaa ccaggttatt tgaaagaagt tttgccagat    180
tcagctccaa gacaaccaga tacttttgat tctttgttcg atgatatcca acaaaagatt    240
atcccaggtg ttacacattg gcaatcacca aactacttcg catactaccc atctaattct    300
tctactgctg gtttcttggg tgaaatgttt tctgctgctt ttaatatcgt tggttttca    360
tggatcactt ctccagctgc aacagaattg gaagttattg ttttagattg gttcgcaaag   420
atgttgcaat tgccatcaca attcttatct actgcttttg gtggtggtgt tattcaaggt    480
acagcttcag aagcagtttt ggttgcattg ttagctgcaa gagatagagc tttgaagaaa    540
catggtaaac attctttaga aaaattggtt gtttacgcat cagatcaaac tcattctgct    600
ttacaaaaag catgtcaaat cgctggtatt ttctctgaaa acgttagagt tgttattgct    660
gattgtaata gaactacgc  tgttgcacca gaagcagttt cagaagcttt gtctatcgat    720
ttgtcttcag gtttgatccc atttttcatt tgtgcaacag ttggtactac atcttcatct    780
gctgttgatc cattaccaga gttgggtcaa atcgctaagt caaacgatat gtggttccat    840
atcgatgctg cttatgctgg ttctgcatgt atttgtccag aatacagaca tcatttgaat    900
ggtgttgaag aagcagattc ttttaatatg aatgctcata agtggttctt gactaacttc    960
gattgttcat tgttgtgggt taaggataga tcatttttga tccaatcatt atctacaaat   1020
ccagaattct tgaaaaataa ggcttcacaa gcaaactctg ttgttgattt caaggattgg   1080
caaatcccat tgggtagaag attcagatca ttgaagttgt ggatggtttt gagattgtac   1140
ggtgttgata atttgcaatc ttacatcaga aagcatatcc atttggctga acatttcgaa   1200
caattgttgt tgtcagattc aagattcgaa gttgttactc caagaacatt ttcattggtt   1260
tgtttcgat  tagttccacc aacttctgat catgaaaacg gtagaaagtt gaactacgat   1320
atgatggatg gtgttaattc atctggtaaa attttcggt  cacatacagt tttgtctggt   1380
aaattcgttt tgagatttgc tgttggtgca ccattaactg aagaaagaca tgttgatgct   1440
gcatggaagt tgttgagaga tgaagctaca aaggttttag gtaaaatggt ttaa          1494

SEQ ID NO: 53           moltype = AA   length = 497
FEATURE                 Location/Qualifiers
source                  1..497
                        mol_type = protein
                        organism = Oryza sativa
SEQUENCE: 53
MEGVGGGGGG EEWLRPMDAE QLRECGHRMV DFVADYYKSI EAFPVLSQVQ PGYLKEVLPD     60
SAPRQPDTLD SLFDDIQQKI IPGVTHWQSP NYFAYYPSNS STAGFLGEML SAAFNIVGFS    120
WITSPAATEL EVIVLDWFAK MLQLPSQFLS TALGGGVIQG TASEAVLVAL LAARDRALKK    180
HGKHSLEKLV VYASDQTHSA LQKACQIAGI FSENVRVVIA DCNKNYAVAP EAVSEALSID    240
LSSGLIPFFI CATVGTTSSS AVDPLPELGQ IAKSNDMWFH IDAAYAGSAC ICPEYRHHLN    300
GVEEADSFNM NAHKWFLTNF DCSLLWVKDR SFLIQSLSTN PEFLKNKASQ ANSVVDFKDW    360
```

```
QIPLGRRFRS LKLWMVLRLY GVDNLQSYIR KHIHLAEHFE QLLLSDSRFE VVTPRTFSLV    420
CFRLVPPTSD HENGRKLNYD MMDGVNSSGK IFLSHTVLSG KFVLRFAVGA PLTEERHVDA    480
AWKLLRDEAT KVLGKMV                                                   497

SEQ ID NO: 54           moltype = DNA   length = 1944
FEATURE                 Location/Qualifiers
source                  1..1944
                        mol_type = genomic DNA
                        organism = Xenorhabdus doucetiae
SEQUENCE: 54
atgacaaagc cattccatcc aaatttgaac gttgatgcat tgttttagg tccaaagtct     60
gaaaacgctg ttttctttag agaaatgatg gattatgcag tttctgaaca catgcattgg   120
agatcaggtt ttcatccaga agattctaca ttggttactt cagttgatag atacgaacat   180
aactacagag aaacattgta cagaactgaa ggtatttga atcaattatc tgctaagttg    240
aaaaattctt caatcccatt tttctctcca agatacttag gtcatatttc ttcagatact   300
ttgatggttt ctaatttggc ttatgttatg gctatgatgt acaacccaaa caactgttct   360
tatgaagctt caccaactac aactgaattg gaattagaat ctggtttgga tttgtgtaga   420
atgttcggtt acaatccaca acaatcttgg ggtcatatta catcaggtgg tactgttgca   480
aattacgaag gtttgtgggt tgctagaaat ttgaagacat tgtcttttcg aatctctcaca  540
catccaaagg ctaaggattt gatcgaacat aagactccaa agcaattgaa aaatatgcca   600
acatctgaat tgttagattt gatcactgaa ttacaaaaga gaggtttgtt cgaagaaatc   660
agagatatga catgtagagg tactgttgtt aaggctcaaa ttttaggtaa attgttagtt   720
ccacaatcta agcattattc atggatgaaa gctgcagata tcttcggtat cggtcaagaa   780
aacatcatcc cattgccagt taatgatcat taccaaacag atgttgctca aatgagaaag   840
atcactttcg gttgattga acaaggtgaa ccaatttag caatgattgc tgttgttggt     900
acaactgaag ttggtgcaat cgatagaatc gatgaagtta ttgcttaag aaaagaatgt   960
gaagaaagat acggtgaatc tttctacatc catgttgatg ctgcttatgc tggttacgct  1020
tgttcaatgt tgttgaacga acagggtgaa ttcgttgaat acgatgaatt ggcaaactac  1080
catagatctg ctggtattat gccagaaaat atttcatggc caaaaccaga gtttaccaa   1140
tcttttaaag ctttgaaaga tgttgattca attacagttg atccacataa ggttggtttt  1200
attcaatatg ctgcaggtgc aatttgtatg aaggataaga gaattttgga attaatttct  1260
tcacatgctg catacgtttt tgaaggtcat gctgataaga catctactaa aaatagaggt  1320
attttggggtt cttcaattat ggaaggttct aaatcaggtg caacagctgc agctttgtgg  1380
gcagctctaa gattgttacc attgaacatc aacggttacg gtaaagttat tgcagctggt  1440
atcgttactg cacaatcttt gttgaataag ttggctaatt tgccaccaat cgaaatcggt   1500
aaacatagat tcgaagttca tatttttcca tcaccagatt tccacatgat caacttcact   1560
tttaagaag ttggtaacga atctttgtca accataacg ctttgaataa gagattgtat    1620
gaattatgtt cttactcagc aggtagagct tacaacgatg atttcttgac atcttcaact  1680
attttagatt acaaggaata cggtgacact ccttggcatc atgctcaaaa atgtggtttt  1740
tcaagatcag aatgggaaaa agttagaaac atctatgttt tgagagcagc tgttatgaca  1800
tactgtttga gagatgaaga acatttcgaa gaattctggg aacaattgca agctatcttc  1860
gttaagaaat tgactcaaat cgttgatgaa aagataagaa aagcaagatt gagattagaa  1920
ccagatgttc cttttattgg ttaa                                         1944

SEQ ID NO: 55           moltype = AA   length = 647
FEATURE                 Location/Qualifiers
source                  1..647
                        mol_type = protein
                        organism = Xenorhabdus doucetiae
SEQUENCE: 55
MTKPFHPNLN VDALFLGPKS ENAVFFREMM DYAVSEHMHW RSGFHPEDST LVTSVDRYEH    60
NYRETLYRTE GILNQLSAKL KNSSIPFFSP RYLGHISSDT LMVSNLAYVM AMMYNPNNCS   120
YEASPTTTEL ELESGLDLCR MFGYNPQQSW GHITSGGTVA NYEGLWVARN LKTLSFAISQ   180
HPKAKDLIEH KTPKQLKNMP TSELLDLITE LQKRGLFEEI RDMTCRGTGV KAQILGKLLV   240
PQSKHYSWMK AADIFGIGQE NIIPLPVNDH YQTDVAQMRK ITFGLIEQGE PILAMIAVVG   300
TTEVGAIDRI DEVIALRKEC EERYGESFYI HVDAAYAGYA CSMLLNEQGE FVEYDELANY   360
HRSAGIMPEN ISWPKPEVYQ SFKALKDVDS ITVDPHKVGF IQYAAGAICM KDKRILELIS   420
SHAAYVFEGH ADKTSTKNRG ILGSSIMEGS KSGATAAALW AAHRLLPLNI NGYGKVIAAG   480
IVTAQSLLNK LANLPPIEIG KHRFEVHIFP SPDFHMINFT FKEVGNESLS NHNALNKRLY   540
ELCSYSAGRA YTNDFLTSST ILDYKEYGDT PWHHAQKCGF SRSEWEKVRN IYVLRAAVMT   600
YCLRDEEHFE EFWEQLQAIF VKKLTQIVDE EDKKARLRLE PDVPFIG                 647

SEQ ID NO: 56           moltype = DNA   length = 1509
FEATURE                 Location/Qualifiers
source                  1..1509
                        mol_type = genomic DNA
                        organism = Camptotheca acuminata
SEQUENCE: 56
atgggttctt tggattcaaa ctacgatact gaatctccag cttcagttgg tcaattcaat    60
ccattagatc cagaagaatt cagaaagcaa gctcattgta tcgttgattt catcgcagat  120
tactacaaga acattgaatc ttatccagtt ttgtcacaag ttgatccagg ttacagacat  180
tcaagattgg gtaaaatgc tccatacaga tctgaaccat cgaatcaat cttgaaggat    240
gttcaaaagg atatcatccc tggtatgact cattggatgt ctccaaattt ctttgctcat  300
tttccagcaa ctgtttcttc agctgcattt gttggtaaa tgttgtac atgtttcaac     360
tctgttggtt taatttggtt agcatcacca gctgcaacga aattggaaat ggttgttatt  420
gattggttag ctaacatgtt gaagttgcca aagtcttta tgttttcagg tactggtggt   480
ggtgttttgc aaggtactac atctgaagct atccttgtgta cattgattgc tgcatccacca 540
atgcatttcg aaatcgttgg tgttaagact tctatactcat tcgttgttta tggttctgat  600
caaactcatt caacatacgc taaagcatgt aaattagcag gtatttgcc atgtaacatc   660
```

```
agatctattc caactacagc tgattcaaac ttctctgttt caccattgtt gttgagaaga    720
gctattgaag cagataaagc tgcaggtatg gttccattgt atatttgtgc tacagttggt    780
actacatcta ctacagcaat tgatccatta tcttcattgg ctgatgttgc aaatgattat    840
ggtgtttggt ttcatgttga tgctgcatac gctggttctg catgtatttg tccagaattc    900
agacattatt tggatggtat cgaaagagca gattcttttg cattgtctcc acataagtgg    960
ttgttgtctt acttagattg ttgttgtttg tgggttaagt caccatcttt attggttaag   1020
gctttatcaa ctgatccaga atatttgaaa aatcaaccat cagaatctaa gtcagttgtt   1080
gattacaagg attggcaagt tggtacaggt agaagattca aagctttgag attgtggttc   1140
gttatgagat cttatggtgt tgcaaatttg caatcacata tcagaactga tgttcaaatg   1200
gctaagatgt tcgaaggttt cgttaagtct gatccaagat tcgaaatttt ggttccaaga   1260
gttttctctt tggtttgttt cagattgaac ccaatctctg gttcagatcc aactggtaca   1320
gaagctttga acgaaagttt attggattgg ttaattctca aggtagagt ttatatgact   1380
catacaaaag ttggtggtat ctatatgttg agatttgctg ttggtgcaac tttaacagaa   1440
aagagacatg tttcttcagc ttggaagttg attaaagaag tgcagatgt tttgttgaag    1500
gaagattaa                                                            1509

SEQ ID NO: 57          moltype = AA  length = 502
FEATURE                Location/Qualifiers
source                 1..502
                       mol_type = protein
                       organism = Camptotheca acuminata
SEQUENCE: 57
MGSLDSNYDT ESPASVGQFN PLDPEEFRKQ AHCIVDFIAD YYKNIESYPV LSQVDPGYRH    60
SRLGKNAPYR SEPFESILKD VQKDIIPGMT HWMSPNFFAH FPATVSSAAF VGEMLCTCFN   120
SVGFNWLASP AATELEMVVI DWLANMLKLP KSFMFSGTGG GVLQGTTSEA ILCTLIAASP   180
MHFEIVGVKT STSFVVYGSD QTHSTYAKAC KLAGILPCNI RSIPTTADSN FSVSPLLLRR   240
AIEADKAAGM VPLYICATVG TTSTTAIDPL SSLADVANDY GVWFHVDAAY AGSACICPEF   300
RHYLDGIERA DSLSLSPHKW LLSYLDCCCL WVKSPSLLVK ALSTDPEYLK NQPSESKSVV   360
DYKDWQVGTG RRFKALRLWF VMRSYGVANL QSHIRTDVQM AKMFEGFVKS DPRFEILVPR   420
VFSLVCFRLN PISGSDPTGT EALNRKLLDW VNSTGRVYMT HTKVGGIYML RFAVGATLTE   480
KRHVSSAWKL IKEGADVLLK ED                                            502

SEQ ID NO: 58          moltype = DNA  length = 792
FEATURE                Location/Qualifiers
source                 1..792
                       mol_type = genomic DNA
                       organism = Oryctolagus cuniculus
SEQUENCE: 58
atggaaggtg gttttactgg tggtgacgaa taccaaaagc atttcttgcc aagagattac     60
ttaaacacat actactcatt ccaatctggt ccatcaccag aagctgaaat gttgaagttt    120
aatttggaat gtttgcataa gactttcggt ccaggtggtt tgcaaggtga cactttaatt    180
gatattggtt ctggtccaac aatctatcaa gttttggctg catgtgaatc ttttaaagat    240
atcactttgt cagattttac agatagaaat agagaagaat tggctaaatg gttgaagaaa    300
gaaccaggtg catacgattg gactccagct ttgaagttcg catgtgaatt agaaggcaac    360
tctggtagat ggcaagaaaa agctgaaaag ttgagagcaa cagttaagag agttttgaag    420
tgtgatgcta atttgtcaaa tccattaact ccagttgttt tgccaccagc agattgtgtt    480
ttgacattgt tagctatgga atgtgcattg tgttcttttg adcttatag agctgcattg    540
agaaatttgg catcattgtt aaaaccaggt ggtcatttgg ttactacagt tactttgcaa    600
ttatcttcat acatggttgg tgaaagagaa ttttcttgtg ttgcttttga aaaagaagaa    660
gttgaacaag ctgttttaga tgcaggtttc gatatcgaac aattgttgta ctctccacaa    720
tcttactcag cttctacagc accaaataga ggtgtttgtt tcttggttgc tagaaagaaa    780
ccaggttcat aa                                                        792

SEQ ID NO: 59          moltype = AA  length = 263
FEATURE                Location/Qualifiers
source                 1..263
                       mol_type = protein
                       organism = Oryctolagus cuniculus
SEQUENCE: 59
MEGGFTGGDE YQKHFLPRDY LNTYYSFQSG PSPEAEMLKF NLECLHKTFG PGGLQGDTLI    60
DIGSGPTIYQ VLAACESFKD ITLSDFTDRN REELAKWLKK EPGAYDWTPA LKFACELEGN   120
SGRWQEKAEK LRATVKRVLK CDANLSNPLT PVVLPPADCV LTLLAMECAC CSLDAYRAAL   180
RNLASLLKPG GHLVTTVTLQ LSSYMVGERE FSCVALEKEE VEQAVLDAGF DIEQLLYSPQ   240
SYSASTAPNR GVCFLVARKK PGS                                           263

SEQ ID NO: 60          moltype = DNA  length = 1131
FEATURE                Location/Qualifiers
source                 1..1131
                       mol_type = genomic DNA
                       organism = Hordeum vulgare
SEQUENCE: 60
atggataaga tctctgcacc attttttctct ggtacttcac cagctgcagc ttcagttgct    60
ggtgttgatg aagatgatag attgtgtttc caagctcaag aattgatgtt cgcatacaac   120
atctctatgg ttttgagagc agctattcaa ttaggtttgt tagatgcttt gtcagcagct   180
ggtggtaaag cattgactcc aaacgaatta gttgaaaacg ttgaaacatc ttcaaataag   240
gctgaagcag ctgcagctgt tgatagaatt ttgagatat tgtcttgttt caacgttgtt   300
acttgttctt cagaagcagc tggtccagat ggtacattag ttagaagata cactacaggt   360
ccattgtgta gatggttaac taagaataga ggtgacggta cattatctcc attgctgtt   420
tttgttgttg atccagatca ttttgtttcct tggcatcata ttgcagaagc tgttactgct   480
```

```
ggtggtccat cagcattcga aagaacacaa aagtggccat actacgaata catgggtaaa   540
aatcaaagat tgggtacttt gttcgataac gcaatggctc aacattctgt tattttggtt   600
acaaagatgt tagaaagatt caaaggtttt gatggtgttc aaagattagt tgatgttggt   660
ggtggtactg gttctacatt gggtatgatc acttcaaagt acaagcacat gacaggtatt   720
aattacgatt tgccacatgt tattgctcaa ggtttgccat taccaggtgt tgaacatgtt   780
gcaggtgaca tgtacgaatc tattccaact ggtgacgctg ttttgttaca atggattaca   840
ttgatgttga acgatgatga attcgttaag atctgtcaa attgtcataa tgcttttgcca   900
aaagatggta aagttattgt tgttgatggt attttaccag aaaacccaga ttcttcattg   960
actcaagag atgcttttac attagatatc atcatgttcg ttttgtttaa aggtgcaaag  1020
caaagaactg aaaaggaatt cgcaagatta gctaagcaag caggttttac tggtggtatt  1080
aagaaaactt atattttctt taattttac gctttggaat tcactaaata a            1131

SEQ ID NO: 61            moltype = AA  length = 376
FEATURE                  Location/Qualifiers
source                   1..376
                         mol_type = protein
                         organism = Hordeum vulgare
SEQUENCE: 61
MDKISAPFFS GTSPAAASVA GVDEDDRLCF QAQELMFAYN ISMVLRAAIQ LGLLDALSAA    60
GGKALTPNEL VENVETSSNK AEAAAAVDRI LRYLSCFNVV TCSSEAAGPD GTLVRRYTTG   120
PLCRWLTKDR GDGTLSPFAV FVVDPDHLFP WHHIAEAVTA GGPSAFERTQ KWPYYEYMGK   180
NQRLGTLFDN AMAQHSVILV TKMLERFKGF DGVQRLVDVG GGTGSTLGMI TSKYKHMTGI   240
NYDLPHVIAQ GLPLPGVEHV AGDMYESIPT GDAVLLQWIT LMLNDDEFVK ILSNCHNALP   300
KDGKVIVVDG ILPENPDSSL TARDAFTLDI IMFVLFKGAK QRTEKEFARL AKQAGFTGGI   360
KKTYIFFNFY ALEFTK                                                  376

SEQ ID NO: 62            moltype = DNA  length = 549
FEATURE                  Location/Qualifiers
source                   1..549
                         mol_type = genomic DNA
                         organism = Streptomyces griseofuscus
SEQUENCE: 62
atgaacacct tcagaacagc cactgccaga gacatacctg atgtagcagc aactcttacg    60
gaagccttcg caactgatcc acccacgcag tgggtgttcc ccgacggtac tgccgccgtc   120
agcaggttct ttacacatgt tgcagatagg gttcacacgg ccggtggtat tgttgagcta   180
ctaccagaca gagccgccat gattgcattg ccaccacacg tgaggctgcc aggagaagct   240
gccgacggaa ggcaggcgga aattcagaga aggctggcag acaggcaccc gctgacacct   300
cactactacc tgctgtttta cggagttaga acggcacacc agggttcggg attgggcgga   360
agaatgctgg ccagattaac tagcagagct gataggggaca gggtgggtac atatactgag   420
gcatccacct ggcgtggcgc tagactgatg ctgagacatg gattccatgc tacaaggcca   480
ctaagattgc cagatggacc cagcatgttt ccactttgga gagatccaat ccatgatcat   540
tctgattag                                                          549

SEQ ID NO: 63            moltype = AA  length = 182
FEATURE                  Location/Qualifiers
source                   1..182
                         mol_type = protein
                         organism = Streptomyces griseofuscus
SEQUENCE: 63
MNTFRTATAR DIPDVAATLT EAFATDPPTQ WVFPDGTAAV SRFFTHVADR VHTAGGIVEL    60
LPDRAMIAL PPHVRLPGEA ADGRQAEIQR RLADRHPLTP HYYLLFYGVR TAHQGSGLGG   120
RMLARLTSRA DRDRVGTYTE ASTWRGARLM LRHGFHATRP LRLPDGPSMF PLWRDPIHDH   180
SD                                                                 182

SEQ ID NO: 64            moltype = DNA  length = 1170
FEATURE                  Location/Qualifiers
source                   1..1170
                         mol_type = genomic DNA
                         organism = Thermotoga maritima
SEQUENCE: 64
atgaaaggat atttcggacc tacggtggc cagtacgtac cagaaatatt aatgggtgcc     60
ttagaggagt tagaggcagc atacgaggag attatgaagg atgagagctt ctggaaggag   120
ttcaacgatc tactgaggga ttacgcaggc agaccaacgc cattgtactt tgccaggaga   180
ttgtctgaga agtacggcgc ccgtgtttac ttgaagcgtg aggatctgct gcacactgtg   240
gcacacaaga taataacgc tatcggacag gttttattgg ccaaattaat ggggaagaca   300
cgtatccatag ccgagacggg agctgggcag catggagtcg ctactgctac cgctgctgcc   360
ctgttcggaa tggaatgtgt gatctacatg ggtgaagagg acacaatcag acagaagttg   420
aacgtggagc gtatgaaatt attaggggct aaagttgtcc ctgttaagtc tggcagtagg   480
accttgaagg atgcgataga cgaggctttg agagactgga ttactaattt acagacaaca   540
tattatgtta tcggatctgt tgttggtccc caccttacc caattatcgt aaggaatttc   600
cagaaggtta tcggtgagga gaccaagaag caaataccag aaaaggaagg tcgtttgcca   660
gactatatag ttgcctgcgt aggcggcggt agcaatgccg caggtatatt tacccattc    720
atagactctg gagtaaagct gataggtgtt gaggcaggtg gcgagggatt ggagacaggt   780
aaacacgcag cctcgttatt aaagggtaaa attggctatt tacatggcatc gaagacctt   840
gttcacaag atgactgggg tcaagtccaa gtgagccatt cggtgtcagc tggtcttgac   900
tattcaggag taggacctga gcatgcttat tggagagaga cagggaaggt tctgtacgac   960
gcagtgactg acgaagaggc tttggacgca tttatagagt tatcaagact agagggcatt  1020
ataccgctt tagagtcatc gcatgctcta gcatatttga agaagataaa tataaaaggt  1080
aaggttgtgg tggtcaacct atcagggaga ggggataaag acctggagtc agtcttaaac  1140
```

-continued

```
catccatacg tgagagaaag aattagatga                                        1170

SEQ ID NO: 65           moltype = AA  length = 389
FEATURE                 Location/Qualifiers
source                  1..389
                        mol_type = protein
                        organism = Thermotoga maritima
SEQUENCE: 65
MKGYFGPYGG QYVPEILMGA LEELEAAYEE IMKDESFWKE FNDLLRDYAG RPTPLYFARR        60
LSEKYGARVY LKREDLLHTG AHKINNAIGQ VLLAKLMGKT RIIAETGAGQ HGVATATAAA       120
LFGMECVIYM GEEDTIRQKL NVERMKLLGA KVVPVKSGSR TLKDAIDEAL RDWITNLQTT       180
YYVIGSVVGP HPYPIIVRNF QKVIGEETKK QIPEKEGRLP DYIVACVGGG SNAAGIFYPF       240
IDSGVKLIGV EAGGEGLETG KHAASLLKGK IGYLHGSKTF VLQDDWGQVQ VSHSVSAGLD       300
YSGVGPEHAY WRETGKVLYD AVTDEEALDA FIELSRLEGI IPALESSHAL AYLKKINIKG       360
KVVVVNLSGR GDKDLESVLN HPYVRERIR                                        389

SEQ ID NO: 66           moltype = DNA  length = 1167
FEATURE                 Location/Qualifiers
source                  1..1167
                        mol_type = genomic DNA
                        organism = Pyrococcus furiosus
SEQUENCE: 66
atgtggttcg gtgagtttgg tggacaatat gtgccagaga ctttagtggg tcctcttaag        60
gaattggaaa aggcatataa aaggttcaag gacgatgagg agttcaacag gcaactaaac       120
tattatttga agacatgggc cggtagacca acgcccttgt attatgctaa gaggttaact       180
gaaaagattg gcggcgcgaa agtgtatctg aaaagagaag acctagttca tggtggagca       240
cacaagacaa ataatgccat tggacaagca ctattggcaa agctaatggg taaaactaga       300
ttgatagctg agacaggagc gggtcaacat gggtcgcga cagcgatggc tggtgcacta        360
ctggggatga aggtagatat ttacatgggt gctgaggacg ttgagcgtca gaaactaaat       420
gtcttcagga tgaagctatt aggtgccaat gtttatacct taaattctgg ctcaagaaca       480
ctaaaggacg ccttcgacga ggctcttaga gactgggttg ccactttcga gtatactcat       540
tacttgatcg gttcagtggt tggaccacat ccatacccaa ccatcgttag ggactttcag       600
agcgtgattg gtagagaggc taaggcacag atcttagaag cagagggaca gctacctgac       660
gtcatagttg cctgcgtcgg cggtggctct aacgcaatgg gtatattcta tccattcgtt       720
aatgacaaga aggttaaatt agtaggagtc gaagctgacg gaaagggggtt agagtcgggt      780
aaacactcag caagcttaaa tgcaggacag gtaggggtgt cccacggcat gttgtcgtat       840
ttcttgcaag acgaggaagg tcagataaag ccaagtcatt caattgctcc aggccttgac       900
caccccggtg ttggtccaga gcacgcttac ttaaagaaga ttcaaaggggc cgagtacgtc       960
gctgtaacag acgaagaggc attgaaagct tccatgaac ataccagaac tgaggggatt      1020
ataccccgccc ttgagtctgc ccatgctgtg gcgtacgcca tgaagttagc taaagagatg     1080
tcccgtgacg aaatcatcat tgtaaatcta tcagggagag agacaaggga tttggacatt     1140
gtattgaagg caagcggaaa tgtttga                                          1167

SEQ ID NO: 67           moltype = AA  length = 388
FEATURE                 Location/Qualifiers
source                  1..388
                        mol_type = protein
                        organism = Pyrococcus furiosus
SEQUENCE: 67
MWFGEFGGQY VPETLVGPLK ELEKAYKRFK DDEEFNRQLN YYLKTWAGRP TPLYYAKRLT        60
EKIGGAKVYL KREDLVHGGA HKTNNAIGQA LLAKLMGKTR LIAETGAGQH GVATAMAGAL       120
LGMKVDIYMG AEDVERQKLN VFRMKLLGAN VIPVNSGSRT LKDAFDEALR DWVATFEYTH       180
YLIGSVVGPH PYPTIVRDFQ SVIGREAKAQ ILEAEGQLPD VIVACVGGGS NAMGIFYPFV       240
NDKKVKLVGV EAGGKGLESG KHSASLNAGQ VGVSHGMLSY FLQDEEGQIK PSHSIAPGLD       300
HPGVGPEHAY LKKIQRAEYV AVTDEEALKA FHELSRTEGI IPALESAHAV AYAMKLAKEM      360
SRDEIIIVNL SGRGDKDLDI VLKASGNV                                         388

SEQ ID NO: 68           moltype = DNA  length = 1167
FEATURE                 Location/Qualifiers
source                  1..1167
                        mol_type = genomic DNA
                        organism = Pyrococcus furiosus
SEQUENCE: 68
atgtggtttg gggaattcgg tggtcaatac gtgccagaaa ccttagtggg gcctttaaag        60
gagcttgaga aagcttacaa aagatttaag gacgacgagg agtttaatag gcaattaaac       120
tattacttga gacttgggc aggtagacca acaccacttt attacgcgaa gagacttaca       180
gagaagatcg gtgcgctaa ggtttatttg aagcgtgagg atttggttca tggtggagca        240
cataagacaa acaatgccat cgggcaagcc ttgttggcaa aattgatggg taagactagg       300
ttgatagctg gcacaggtgc cggccagcat ggcgttgcaa cagcaatggc tggtgctctt       360
ttagggatga aggtggatat ctatatgggc gccgaggacg ttgaaagaca aaagcttaac       420
gtattcagaa tgaagttatt aggtgcgaat gttattccag tgaattcagg ttccaggacg       480
ctgaaggacg caatagacga agccttgaga gactgggttg ctacttttga gtacacacat       540
tatttgattg gttccgtggt tggaccccac ccgtacccta caatagttag agattttcaa       600
tctgtaatcg gtagagaggc gaaggctcaa attccagagg ccgagggaca gctacccgat       660
gttatagtcg cctgcgttgg aggaggatca aatgcgatgg gaatcttcta cccttttgta       720
aatgataaga agttaagtt agtcggagtt gaggccggtg gtaaagggct agaaagcggc       780
aaacactcgg catctcttaa tgccggtcaa gtaggagtaa gtcacgggat gttatcttac       840
ttcttgcagg atgaggaagg tcaaattaag ccatctcatt ctatagcccc aggattagac       900
tatcccggtg ttgggcctga gcacgcttat ctgaagaaga tacagcgtgc tgagtacgtt       960
```

```
gcagtaactg atgaagaggc tttgaaggct tttcacgagt tatcaagaac tgagggaata  1020
attcctgcct tggaatcggc acatgcggtt gcctacgcca tgaagcttgc taaggaaatg  1080
tcaagagacg aaatcattat agtgaattta tcgggaaggg gcgataagga cttggacatt  1140
gttttaaaag caagtggcaa tgtataa                                     1167

SEQ ID NO: 69          moltype = AA  length = 388
FEATURE                Location/Qualifiers
source                 1..388
                       mol_type = protein
                       organism = Pyrococcus furiosus
SEQUENCE: 69
MWFGEFGGQY VPETLVGPLK ELEKAYKRFK DDEEFNRQLN YYLKTWAGRP TPLYYAKRLT   60
EKIGGAKVYL KREDLVHGGA HKTNNAIGQA LLAKLMGKTR LIAGTGAGQH GVATAMAGAL  120
LGMKVDIYMG AEDVERQKLN VFRMKLLGAN VIPVNSGSRT LKDAIDEALR DWVATFEYTH  180
YLIGSVVGPH PYPTIVRDFQ SVIGREAKAQ IPEAEGQLPD VIVACVGGGS NAMGIFYPFV  240
NDKKVKLVGV EAGGKGLESG KHSASLNAGQ VGVSHGMLSY FLQDEEGQIK PSHSIAPGLD  300
YPGVGPEHAY LKKIQRAEYV AVTDEEALKA FHELSRTEGI IPALESAHAV AYAMKLAKEM  360
SRDEIIIVNL SGRGDKDLDI VLKASGNV                                    388

SEQ ID NO: 70          moltype = DNA  length = 1173
FEATURE                Location/Qualifiers
source                 1..1173
                       mol_type = genomic DNA
                       organism = Pyrococcus furiosus
SEQUENCE: 70
atgtggtttg gtgagtttgg tggtcagtat gtgcctgaga cgctagttgg gccactgaag   60
gagttagaga aagcgtacaa gagattcaaa gatgacgagg agtttaaccg tcagttgaat  120
tattatctta agacgtgggc tggtaggccg acccctctat actacgctaa gcgtttaacc  180
gaaaagatag gtggcgccaa gatctatctg aagagagagg acctagtcca cggcggggct  240
cacaaaacta caacgcaat tggtcaggca ccattagcaa agttaatggg caaaacacgt  300
ctaattgccg aaactggtgc tggtcaacat ggagttgcta cggcaatggc gggcgcactg  360
ttaggtatga aagtggatat ctatatggga gcagaagacg tggagagaca aaagatgaac  420
gtgttccgta tgaaactatt gggagctaat gttatcccgg ttaactctgg ctcaagaact  480
gcaaaggacg ccataaacga agctttgagg gattgggaag ccacattcga gtacacacac  540
taccttatag gctcagtcgt aggcccgcat ccctacccca ccatagttcg tgacttccag  600
agtgttattg gccgtgaggc caaggcacag atcttggaag ctgaaggtca attgcctgac  660
gtaatagttg catgtgtggg tggcggttct aacgctatgg gtatattcta ccccttcgtg  720
aacgataaga agtaaagct agttggagtg gaagcaggtg gcaaagggtt ggagtcgggc  780
aagcactcag cctcattaaa cgcaggtcag gtaggcgttc tgcacggtat gttatcctat  840
ttcttacagg acgaggaagg ccaaatcaaa ccatcgcact caatcgcacc tggtttagat  900
tacccaggag tcggtcccga gcacgcatat ttaaagaaaa tccagagagc agagtacgtc  960
acggtgacga atgaggaagc ccttaaagcg tttcacgagc tgtcgaggac cgagggcata 1020
ataccgctc ttgaaagtgc ccacgcagtt gcctatgcta tgaagttggc caaggagatg 1080
agtagagacg agattatcat agtaaatctg tcaggcagag gtgacaagga tcttgacata 1140
gtccttaagg cgagcggtaa tgttttggag taa                              1173

SEQ ID NO: 71          moltype = AA  length = 390
FEATURE                Location/Qualifiers
source                 1..390
                       mol_type = protein
                       organism = Pyrococcus furiosus
SEQUENCE: 71
MWFGEFGGQY VPETLVGPLK ELEKAYKRFK DDEEFNRQLN YYLKTWAGRP TPLYYAKRLT   60
EKIGGAKIYL KREDLVHGGA HKTNNAIGQA PLAKLMGKTR LIAETGAGQH GVATAMAGAL  120
LGMKVDIYMG AEDVERQKMN VFRMKLLGAN VIPVNSGSRT AKDAINEALR DWEATFEYTH  180
YLIGSVVGPH PYPTIVRDFQ SVIGREAKAQ ILEAEGQLPD VIVACVGGGS NAMGIFYPFV  240
NDKKVKLVGV EAGGKGLESG KHSASLNAGQ VGVLHGMLSY FLQDEEGQIK PSHSIAPGLD  300
YPGVGPEHAY LKKIQRAEYV TVTDEEALKA FHELSRTEGI IPALESAHAV AYAMKLAKEM  360
SRDEIIIVNL SGRGDKDLDI VLKASGNVLE                                  390

SEQ ID NO: 72          moltype = DNA  length = 1173
FEATURE                Location/Qualifiers
source                 1..1173
                       mol_type = genomic DNA
                       organism = Pyrococcus furiosus
SEQUENCE: 72
atgtggttcg gagagttcgg cgggcagtac gtcccagaaa cgctagtcgg cccactgaag   60
gagctggaga aagcatacaa aagattcaag gatgacgagg agttcaacag gcaattaaac  120
tattacctaa agacctgggc tggtaggccc accccttat actatgcaaa acgtttaacg  180
gagaaaatcg gtggcgcaaa agtgtacttg aagagagaag acttagtcca cggtggtgct  240
cataaaacta caacgctat agggcaggca cttttagcta agttgatggg taaaacgagg  300
ttgattgcgg gtaccggtgc cggtcaacat ggcgttgcta cggcaatggc gggagcccta  360
ttgggcatga aggttgacat ttatatgggc gctgaggacg tggaacgtca gaaactgaac  420
gtctatcgta tgaaattgct tggtgccaac gttataccag tcaattccgg ctcgcgtacg  480
gttaaagacg ctttcgatga ggcactatgt gatagagttg ccactttcga atacacccac  540
tatcttattg gtactgtctg gggtccacat ccgtatccaa ctattgtaag ggacttccag  600
actgttatcg gaagagaggc aaaggcccaa atattagagg ctgagggaag gttacccgac  660
gccattgttg catgcgtagg cggtggtagt aacgcaatgg gtattttcta tcccttcgtt  720
aacgataaga aggttaagtt agtgggtgtc gaggccggtg gtaaggggct tgagtccggt  780
```

```
aaacattccg catctttgaa tgctgggcaa gtaggtgtca gtcatggaat gttatcatac  840
tttctacagg acgaggaagg acagataaaa ccttctcatt ctatagcgcc aggtcttgac  900
caccctggcg ttggaccaga gcatgcttat ttgaagaaga tccagagagc tgaatatgta  960
gctgttacga atgaggaagc tctaaaggcg ttccacgagt taagtaggac tgagggaatt 1020
ataccggcat tagagtctgc ccacgctgta gcttacgcaa tgaagctggc caaagagatg 1080
agccgtgacg agatcatcat cgtaaacttg tctggcagag gcgataagga cctagacatc 1140
gtattaaagg cctcgggaa cgtcctagag tag                                1173

SEQ ID NO: 73           moltype = AA   length = 390
FEATURE                 Location/Qualifiers
source                  1..390
                        mol_type = protein
                        organism = Pyrococcus furiosus
SEQUENCE: 73
MWFGEFGGQY VPETLVGPLK ELEKAYKRFK DDEEFNRQLN YYLKTWAGRP TPLYYAKRLT   60
EKIGGAKVYL KREDLVHGGA HKTNNAIGQA LLAKLMGKTR LIAGTGAGQH GVATAMAGAL  120
LGMKVDIYMG AEDVERQKLN VYRMKLLGAN VIPVNSGSRT VKDAFDEALC DRVATFEYTH  180
YLIGTVWGPH PYPTIVRDFQ TVIGREAKAQ ILEAEGRLPD AIVACVGGGS NAMGIFYPFV  240
NDKKVKLVGV EAGGKGLESG KHSASLNAGQ VGVSHGMLSY FLQDEEGQIK PSHSIAPGLD  300
HPGVGPEHAY LKKIQRAEYV AVTDEEALKA FHELSRTEGI IPALESAHAV AYAMKLAKEM  360
SRDEIIIVNL SGRGDKDLDI VLKASGNVLE                                   390

SEQ ID NO: 74           moltype = DNA   length = 6347
FEATURE                 Location/Qualifiers
source                  1..6347
                        mol_type = genomic DNA
                        organism = Saccharomyces cerevisiae
SEQUENCE: 74
gtatccggct gttccttcat agccctttca atgaacgttg cagccctttg aagattggcc   60
attttgtcag gactcgagcc tgacagttgg accaacgcaa ctttaatttt ttgtgaaaga  120
atcttcgaag cactcatact ggcgatcttc acgcccctcct gctattacaa aagctgtgtt  180
tttacaagaa tcaaattaag ttagcaagat attatacaac attattgata atttcaatat  240
cgtgttcgta cctgatgacg tatctgtgca ttgataaggc ccgcatggtt tcagaaagca  300
gagcggaacg attccaaatt agtggccttg tgctttgtca gtcaattgtg ttaccttcag  360
ctcgtggatt tgttttatca atacacagtc tacagtcaag aattttttt atcaaatttt  420
gcgttcgagc gtataaaata gccgctgtag ctacttaagt tcctgttcag cgatagtttt  480
tttccatcac acgtactatg gcaattaagt cctcagcgag ctcgcatgga atgcgtgcga  540
tgagcgacct catgctatac ctgagaaagc aacctgacct acaggaaaga gttactcaag  600
aataagaatt ttcgttttaa aacctaagag tcactttaaa atttgtatac acttattttt  660
tttataactt atttaataat aaaaatcata aatcataaga aattcgctta tttagaagtg  720
tcaacaacgt atctaccaac ggaatgcgtg cgattcaggc gtagtctgga acgtcgtatg  780
ggtatggacc agagacggat tgagaaactt gttcggttct tgggacgaat ctacattgga  840
atggaactgg gtgcctgaag aaaccagtgg tgaaatcgac tgggatgtca attggcttac  900
cgttttggtc aactggtctt tcaatgttga aagcagacaa caaagtagca ccggcaatcc  960
aaacagtaga ttgagctagg tgaataccctg gcagtttcct tctaccgtaa ccgaaagcag 1020
cctttcttgg gtctctaaca gtgttgtctg gtttaccatc aggacccaag tatctttctg 1080
gacggaaaac ggatggatct ggatagactt ctgggtcatt caaaactgcc caggtgttag 1140
caaaaaccaa tgtgttcttt ggaatcaaat aaccctctgta aacatcatcc ttcatcaatt 1200
tatgagggat ggctaatgga gcaatttggt tccatctgaa taattccttg atacaagcgg 1260
tcaaatatgg gagtgagtcg tcttcctcat cgtagtcagg gatttgaccg ttgttggtca 1320
aagcatccaa ttcagcttga acctttcttt gcacttctgg gtatttaacc atggccaata 1380
tgaaagcgga catagcagag acggtagtgt cgccaccacc aacgttaact tcagcagcag 1440
tgttcttgat aacatgttct tggtgttcta atcaccgtt caagtccata gcttgtaatc 1500
tagcagaagc gtaagatggt ctggttagac cttgtggagc caacttttctc atagtttcgt 1560
atggcatgtc aaccatgtgg tcagcggctt ctctccagac cttggccta cgcttgaaga 1620
cggcacctgg gaaccaagct ggcaagtact tcaaagatgg gaaggagtca acccagaact 1680
tacctggaac actagcaatg gccaaacctt cgttggctaa gtgggtagct tctaaccatg 1740
ggtcatcttc ggctagatcg ataccgtaac caatgtccaa agacatagca gcgatttgat 1800
gtctgatgtg ttgagcccac cggtccggag tcttggtcaa ttgttgaacc aattggtgag 1860
cagccttgac ttgagcgtgt ctgaattgct tgatacccctt tcagagaat tccttagcaa 1920
acattcttct ttcttctctc caacggtcac cgtaagtgat aaaacccaga tcaaattccc 1980
aacccatcaa ttcattgacc atagtggatt ccaatctacc ggagtagatg gaaccacgtt 2040
tttcaagag atccgtgata gttttccaagg tgtttaaaat gaccatttcg gtaccaccag 2100
catctacgta caagatatca gtgttgtagt cacgaccccca ttgcaagaaa gtcaaccatg 2160
gagattcttc tggcatgtcg aacatgttac caataaatgg gattggaatt cctggtggac 2220
caggtggcaa tctggatcta cgaactcttc tggagacgat gtagtaaata caaccagcaa 2280
tgacgaaaga gaacaagaca gcaatcattg ttttatattt gttgtaaaaa gtagataatt 2340
acttccttga tgatctgtaa aaaagagaaa aagaaagcat ctaagaactt gaaaaactac 2400
gaattagaaa agaccaaata tgtatttctt gcattgacca atttatgcaa gtttatatat 2460
atgtaaatgt aagtttcacg aggttctact aaactaaacc acccccttgg ttagaagaaa 2520
agagtgtgtg agaacaggct gttgttgtca cacgattcgg acaattctgt ttgaaagaga 2580
gagagtaaca gtacgatcga acgaactttg ctctggagat cacagtgggc atcatagcat 2640
gtggtactaa acccttcccc gccattccag aaccttcgat tgcttgttac aaaacctgtg 2700
agccgtgacg agaccttgt tgtgtgacga aattgaaacg tgcaatcaat aggaagacag 2760
gaagtcgagc gtgtcctggt tttttcagtt ttgttctttt tgcaaacaac agtttattcc 2820
tggcatccac taaatataat ggagcccgct ttttaagctg gcatcagaa aaaaaagaa 2880
tcccagcacc aaaatattgt tttcttcacc accatcagt tcataggtcc attctctag 2940
cgcaactaca gagaacaggg gcacaaacag gcaaaaaacg gcacaaccct caatggagtg 3000
atgcaacctg cctggagtaa atgatgacac aaggcaattg acccacgcat gtatctatct 3060
```

```
cattttctta caccttctat taccttctgc tctctctgat ttggaaaaag ctgaaaaaaa    3120
aggttgaaac cagttccctg aaattattcc cctacttgac taataagtat ataaagacgg    3180
taggtattga ttgtaattct gtaaatctat ttcttaaact tcttaaattc tactttttata  3240
gttagtcttt tttttagttt taaaacacca agaacttagt ttcgaataaa cacacataaa    3300
caaacaaaat ggcttctagt tcttccgatg tcttcgtttt gggtctaggt gttgttttgg    3360
ctgccttgta tatcttcaga gaccaattat tcgctgcttc taagccaaag gtggctccaa    3420
tttccactac gaagcctgcc aacggttccg ctaacccaag agacttcatc gccaagatga    3480
aacaaggtaa gaagagaatc gtaatcttct acggttctca aactggtacc gctgaagaat    3540
atgctattcg tttggctaag gaagctaagc aaaagttcgg tctagcctcc ttggtttgtg    3600
atccagaaga atacgatttt gaaaagttgg accaattgcc agaagattct attgcttttt    3660
tcgtcgttgc tacctatggt gaaggtgaac ctacagacaa cgctgtccaa ttgttgcaaa    3720
acttgcaaga tgaaagcttc gaattctcct ctggtgagag aaagttgtca ggtttgaagt    3780
acgttgtttt tggtctgggt aacaagacct acgaacatta caacctcatt gggagaactg    3840
ttgacgctca attggccaag atgggtgcta tcagaatcgg tgaaagaggt gaaggtgatg    3900
atgacaagtc catggaagaa gactacttgg aatggaagga tggtatgtgg gaagcgtttg    3960
ccactgctat gggtgttgaa gaaggtcaag gtggtgactc cgctgatttc gtcgtttccg    4020
aattggaatc tcacccacca gaaaaggttt accaaggtga attttctgct agagctttaa    4080
ccaaaaccaa gggtattcac gacgctaaga atccttttgc tgctccaatt gcggttgcta    4140
gagaattgtt ccaatctgtt gtcgatagaa actgtgtcca cgtcgaattc aacattgaag    4200
gctctggtat cacctatcaa cacggtgacc acgttggttt gtggccattg aatccagatg    4260
ttgaagtcga acgttgttg tgtgttttag gtttagctga aaagagagat gctgtcatct    4320
ccattgaatc cttagacccg gctttggcta aggttccatt cccagtccca actacttacg    4380
gtgctgtgtt gagacactac attgacatct ctgctgtcgc cggtagacaa atcttggta    4440
ctttgtccaa attcgctcca accccagaag ctgaagcttt cttgagaaac ttgaacacta    4500
acaaggaaga ataccacaac gtcgtcgcta acggttgttt gaaattgggt gaaattttgc    4560
aaatcgctac cggtaacgac attactgtcc caccaactac tgccaacacc accaaatgc    4620
caattccatt cgacatcatt gtttctgcca tcccaagatt gcaaccaaga tactactcta   4680
tctcttcttc cccaaaaatt catccaaaca ccatccacgc taccgttgtt gtgctcaaat    4740
acgaaaacgt tccaaccgaa ccaatcccaa gaaagtgggt ttacggtgtc ggtagtaact    4800
tcttgttgaa tttaaagtac gctgttaaca aggaaccagt tccatacatc actcaaaatg    4860
gcgaacaaag agtcggtgtc ccggaatact tgattgctgg tccacgtggt tcttacaaga    4920
ctgaatcttt ctacaaggct ccaatccatg ttagacgttc tactttccgt ttgccaacca    4980
acccaaagtc tccagtcatc atgattggtc caggtactgg tgtcgcccca ttcagaggct    5040
tcgttcaaga aagagttgcc ttggccagaa gatccatcga aaagaacgct cctgactctt    5100
tggctgactg gggtcgtatt tccttgttct acggttgtag aagatccgac gaagacttcc    5160
tgtacaagga cgaatggcca caatacgaag ctgagttgaa gggtaagttc aagttgcact    5220
gtgctttctc cagacaaaac tacaagccag acggttctaa gatttacgtc caagatttga    5280
tctgggaaga cagagaacac attgccgatg ccatcttaaa cggtaagggt tacgtctaca    5340
tctgcggtga agctaagtcc atgtctaaac aagttgaaga agttctagcc aagatcttgg    5400
gcgaagccaa aggtggttcc ggtccagttg aaggtgttgc tgaagtcaag ttactgaagg    5460
aacggtccag attgatgttg gatgtctggt ctgaacaaaa gttaatttct gaagaagatt    5520
tggaatgaat cgcgtgcatt catccgctct aaccgaaaag gaaggagtta gacaacctga    5580
agtctaggtc cctatttatt tttttatagt tatgttagta ttaagaacgt tatttatatt    5640
tcaaattttt ctttttttttc tgtacagacg cgtgtacgca tgtaacatta tactgaaaac    5700
cttgcttgag aaggttttgg gacgctcgaa gatcgcgtcc caattcgccc tatagtgagt    5760
cgtattacgc gcgctcactg gccgtcgttt tacaacgtcg tgactgggaa aaccctggcg    5820
ttacccctgc aggactagtg ctgaggcatt aatagtttac tcaattcttg aagccaattt    5880
gtacaattcc ccattagagt caaataaaag gatgcctcac ggaggtatgt tacccgcgct    5940
atttcacatg gctcattgaa ttagaggtgg aatttggtgt accctcccct cctcatctga    6000
tgaagtagtg atccgacaat tcttaaaagt tgtagacatt acttttacca ccaactaagt    6060
tgtatttata ttgctaccct tatccttttta tatctaacta gcgctcataa ggttgggca    6120
atactaaaac tgtgttctta ttcaactcat taaatacgtg gcagtacgta ccctattaga    6180
aacaatagga aacagcagag tcggaagaag ccaaatgcca gatttgaagt ccaaaacctt    6240
gtcaagccaa tctttgggag cggctattcc tccagaaatt gtgtaccaaa tacttacata    6300
ccagtttagg gatttgttaa gaaatgacca tccaggtacg gcagaaa                  6347
```

SEQ ID NO: 75        moltype = DNA   length = 4792
FEATURE                Location/Qualifiers
source                 1..4792
                        mol_type = genomic DNA
                        organism = Saccharomyces cerevisiae
SEQUENCE: 75

```
caatctggcg gcttgagttc tcaacatgtt ttattttta cttatattgc tggtagggta      60
aaaaaatata actcctagga ataggttgtc tatatgtttt tgtcttgctt ctataattgt    120
aacaaacaag gaaagggaaa atactgggtg taaaagccat tgagtcaagt taggtcatcc    180
cttttataca aaatttttca atttttttc caagattctt gtacgattaa ttattttttt    240
tttgcgtcct acagcgtgat gaaaatttcg cctgctgcaa gatgagcggg aacgggcgaa    300
atgtgcacgc gcacaactta cgaaacgcgg atgagtcact gacagccaac gcagaggttc    360
tgactcctac tgagctctat tggaggtggc agaaccggta ccggaggagg ccgctataac    420
cggtttgaat ttattgtcac agtgtcacat cagcattaag tcctcagcga gctcgcatgg    480
aatgcgtgcg atgagcgacc tcatgctata cctgagaaag caacctgacc tacaggaaag    540
agttactcaa gaataagaat tttcgtttta aaacctaaga gtcactttaa aatttgtata    600
cacttatttt ttttataact tatttaataa taaaaatcat aaatcataag aaattcgctt    660
atttagaagt gtcaacaacg tatctaccaa cggaatgcgt ggcattcagg tggagtccaa    720
acccaacaaa ggatttggaa ttggcttacc ggcagttgag gattcctta gcaacgtgga    780
agtgatttca ccgttgtcgt tgttacctct agcatcgtgg aaagcagcaa cacccttctt    840
aacaaagttg attcttcttc ttcagaacc ccattgcatg aagtcagtcc acataacaat    900
gtgagcggc ataccagcgg taaccttggc gtagttgatg gaatgcttgg aagtacgggc    960
gtaagattgc aagtaagctt gtctcatggt tgtaccaact tgttcgtctt ggaatctgct    1020
```

```
aatcaagtaa cagtcaccca agaagtaacc caaatccaat gaagctggac cgtacttaca  1080
caattcccag tctaagatgt agatcttttg caacttagat gggttacctt cttcaagttg  1140
caacaagatg ttcccagacc acaagtcagc catgaccaaa gtttcttcgg agtgcataac  1200
atcgtcaact agatccttga caacagttgg caacaatgga tcatcgacgc cgtatttagc  1260
ggcgtttggg ataatagttt ggtacaattg gtcagaggtg gttctaccga caatgttacc  1320
agagaagaac ttgaattctg ggtcgtctct tctttctcta cctatgttgt gcaatctggc  1380
gacgaaacca ccaatctcgg taccaaccaa tctagcaata tcggtagcca aaggtggctt  1440
agcagtaacg tagtctaata aggtcttcat tttaccgaca tcttgcataa tcaaagcatt  1500
gttttccaag tcatagttga gaccttctgg aacagagaca ataccatcaa caccacccaa  1560
aacttctctg ttagccatca tcaacttgat agcttggtat tcgtagacag aacgttcaac  1620
accgattttg aaatcttcat cagtagacat gtgtggttga gcgtgcttca aaatgataga  1680
agtgtgacct tggtatggag cgttcaattt aatacgccag gtgacgttaa cgaaaccacc  1740
ggataatctc ttgacaccag aagtgtcaac atctaaagac aaatgcttgg tcaaataggt  1800
gattaaaccg tcttcagtct tcaagtcaaa ggcattgtt ttatatttgt tgtaaaaagt  1860
agataattac ttccttgatg atctgtaaaa aagagaaaaa gaaagcatct aagaacttga  1920
aaaactacga attagaaaag accaaatatg tatttcttgc attgaccaat ttatgcaagt  1980
ttatatatat gtaaatgtaa gtttcacgag gttctactaa actaaaccac cccttggtt  2040
agaagaaaag agtgtgtgag aacaggctgt tgttgtcaca cgattcggac aattctgttt  2100
gaaagagaga gagtaacagt acgatcgaac gaactttgct ctggagatca cagtgggcat  2160
catagcatgt ggtactaaac cctttcccgc cattccagaa cctttcgattg cttgttacaa  2220
aacctgtgag ccgtcgctag gaccttgttg tgtgacgaaa ttggaagctg caatcaatag  2280
gaagacagga agtcgagcgt gtctgggttt tttcagttt gttcttttg caaacaacag  2340
tttattcctg gcatccacta aatataatgg agcccgcttt ttaagctggc atccagaaaa  2400
aaaaagaatc ccagcaccaa aatattgttt tcttcaccaa ccatcagttc ataggtccat  2460
tctcttagcg caactacaga gaacaggggc acaaacaggc aaaaaacggg cacaacctca  2520
atggagtgat gcaacctgcc tggagtaaat gatgacacaa ggcaattgac ccacgcatgt  2580
atctatctca ttttcttaca ccttctatta ccttctgctc tctctgattt ggaaaaagct  2640
gaaaaaaaag gttgaaacca gttccctgaa attattcccc tacttgacta ataagtatat  2700
aagacggta ggtattgatt gtaattctgt aaatctattt cttaaacttc ttaaattcta  2760
cttttatagt tagtcttttt tttagtttta aaacaccaag aacttagttt cgaataaaca  2820
cacataaaca aacaaaatgc atatcagaaa cccatataga actccaattg actaccaagc  2880
tttgtctgaa gctttcccac cattgaagcc atttgtttcc gttaacgctg atggtacctc  2940
ctcagttgac ttgaccattc cagaagccca aagagctttt accgctgccc ttttgcacag  3000
agacttcggc ttgactatga ctatcccaga agatgtttg tgtccaaccg ttccaaacag  3060
attgaactac gttttgtgga ttgaagacat tttcaactac accaacaaga ctttgggttt  3120
atctgacgac cgtccaatca agggtgttga tatcggtacc ggtgcttctg ccatttaccc  3180
aatgttggct tgcgccagat tcaaggcttg gtccatggtt ggtactgaag ttgaaagaaa  3240
gtgtatcgac actgctagat taaacgttgt tgctaacaac ttgcaagatc gtctatccat  3300
cttggaaacc tctattacg gtccaatttt agtcccaatt ttcgaagcta ccgaagaata  3360
cgaatacgaa ttcaccatgt gtaacccacc tttctacgat ggtgccgctg acatgcaaac  3420
tagcgatgct gcaaagggtt ttggtttcg tgtcggtgct ccacactctg gtacagtcat  3480
cgaaatgtct actgaaggtg gtgaatccgc tttcgtggct caaatggtta gagaatctct  3540
taagttgaga accagatgta gatggtacac ttctaactta ggtaagttga aatctttgaa  3600
ggaaattgtc ggtttgttga aggaattaga aatctctaat tacgccatca acgaatatgt  3660
ccaaggttcc actagaagat acgctgtcgc ttggagtttc actgatatcc aattgccaga  3720
agaattgtc agaccatcta atcctgaatt gtcctctttg ttcgactaca aggatgacga  3780
tgacaaatga atcgcgtgca ttcatccgct ctaaccgaaa aggaaggagt tagacaacct  3840
gaagtctagg tccctattta ttttttttata gttatgttag tattaagaac gttatttata  3900
tttcaaattt ttcttttttt tctgtacaga cgcgtgtacg catgtaacat tatactgaaa  3960
accttgcttg agaaggtttt gggacgctcg aagatcgcgt acccaattcg ccctatagtg  4020
agtcgtatta cgcgcgctca ctggccgtcg ttttacaagg tcgtgactgg gaaaacccfg  4080
gcgttacccc tgcaggacta gtgctgaggc attaatgcaa ctcagaagtt tgacagcaag  4140
caagttcatc attcgaacta gccttattgt tttagttcag tgacagcgaa ctgccgtact  4200
cgatgcttta tttctcacgg tagagcgaaa gaacagatag gggcagcgtg agaagagtta  4260
gaaagtaaat ttttatcacg tctgaagtat tcttattcat aggaaatttt gcaaggtttt  4320
ttagctcaat aacgggctaa gttatataag gtgttcacgc gattttcttg ttatgtatac  4380
ctcttctctg aggaatggta ctactgtcct gatgtaggct ccttaaattg gtgggcaaga  4440
ataacttatc gatattttgt atattggtct tggagttcac cacgtaatgc ctgtttaaga  4500
ccatcagtta actctagtat tatttggtct tggctactgg ccgtttgcta ttattcaagt  4560
cttttgtgcc ttcccgtcgg gtaagggagt tatttagggga tacagaatct aacgaaaact  4620
aaatctcaat gattaactct atttaatcct tttttgaaag gcaaaagagg tcccttgttc  4680
acttacaacg ttcttagcca aattcgctta tcacttacta cttcacgata tacagaagta  4740
aaaacatata aaaagatgtc tgtttgttta gccatcacaa aaggtatcgc ag         4792
```

| SEQ ID NO: 76 | moltype = DNA  length = 9145 |
|---|---|
| FEATURE | Location/Qualifiers |
| source | 1..9145 |
| | mol_type = genomic DNA |
| | organism = Saccharomyces cerevisiae |

SEQUENCE: 76

```
tgttttatat ttgttgtaaa aagtagataa ttacttcctt gatgatcgt aaaaaagaga   60
aaaagaaagc atctaagaac ttgaaaaact acgaattaga aagaccaaa tatgtatttc  120
ttgcattgac caatttatgc aagtttatat atatgtaaat gtaagtttca cgaggttcta  180
ctaaactaaa ccaccccctt ggttagaaga aagagtgtg tgaacagg ctgttgttga  240
cacacgattc ggacaattct gtttgaaaga gagagagta acagtacgatc gaacgaactt  300
tgctctggag atcacagtgg gcatcatagc atgtggtact aaaccctttc ccgccattcc  360
agaaccttcg attgcttgtt acaaaacctg tgagccgtcg ctaggacctt gttgtgtgac  420
gaaattggaa gctgcaatca ataggaagac aggaagtcga gcgtgtctgg gttttttcag  480
ttttgttctt tttgcaaaca acagtttatt cctggcatcc actaaatata atggagcccg  540
```

```
cttttttaagc tggcatccag aaaaaaaaag aatcccagca ccaaaatatt gttttcttca    600
ccaaccatca gttcataggt ccattctctt agcgcaacta cagagaacag ggcacaaac     660
aggcaaaaaa cgggcacaac ctcaatggag tgatgcaacc tgcctggagt aaatgatgac   720
acaaggcaat tgacccacgc atgtatctat ctcattttct tacaccttct attaccttct   780
gctctctctg atttggaaaa agctgaaaaa aaaggttgaa accagttccc tgaaattatt   840
cccctacttg actaataagt atataaagac ggtaggtatt gattgtaatt ctgtaaatct   900
atttcttaaa cttcttaaat tctacttttta tagtagtct ttttttttagt tttaaaacac  960
caagaactta gtttcgaata aacacacata aacaaacaaa ggatccatga tgaagttctg  1020
gagaaagtac acacaacaag aaatggatga aaagattact gaatctttgg aaaagacttt  1080
gaactacgat aacactaaga caatcggtat tccaggtact aagttggatg atacagtttt  1140
ctatgatgat cattctttcg ttaagcattc accatacttg agaacttttta ttcaaaaccc 1200
aaaccatatc ggttgtcata cttatgataa ggctgatatc ttgttcggtg gtacattcga  1260
tatcgaaaga gaattaatcc aattgttagc aatcgatgtt ttgaacggta acgatgaaga  1320
atttgatggt tacgttactc aaggtggtac agaagctaac atccaagcaa tgtgggttta  1380
cagaaactac ttcaagaaag aaagaaaggc taagcatgaa gaaatcgcta tcatcacttc  1440
agcagataca cattactctg catacaaagg ttcagatttg ttgaacatcg atattattaa  1500
ggttccagtt gattttttatt caagaaaaat tcaagaaaat acattggatt caattgttaa  1560
agaagctaaa gaaattggta aaaagtactt catcgttatc tctaacatgg gtactacaat  1620
gtttggttca gttgatgatc cagatttgta cgctaacatc ttcgataagt acaatttgga  1680
atacaaaatt catgttgatg gtgcatttgg tggtttttata tatccaattg ataataagga  1740
atgtaaaact gattttctcta ataagaacgt ttcttcaatc acattagatg gtcataagat  1800
gttgcaagct ccatacgtta ctggtatctt cgtttcaaga aggaatttga tccataacac  1860
tttgacaaag gaagcaactt acatcgaaaa tttggatgtt acattgtctg gttcaagatc  1920
tggttcaaat gctgttgcaa tttgatggt tttagcttct tatggtccat acggttggat   1980
ggaaaagatt aataagttga gaaatagaac taaatggttg tgtaagcaat tgaacgatat  2040
gagaattaaa tattacaaag aagattcaat gaatattgtt acaattgaag aacaatatgt  2100
taataaggaa atcgctgaaa agtacttttt agttccagaa gttcataacc caactaacaa  2160
ctggtacaag atcgttgtta tggaacatgt tgaattggat atcttgaact ctttggttta  2220
cgatttgaga aagtttaata aggaacattt gaaggcaatg catcatcatc atcatcatta  2280
accgcggcta gctaagatcc gctctaaccg aaaaggaagg agttagacaa cctgaagtct  2340
aggtccctat ttatttttttt atagttatgt tagtattaag aacgttattt atatttcaaa  2400
ttttttcttt ttttctgtac agacgcgtgt acgcatgtaa cattatactg aaaaccttgc   2460
ttgagaaggt tttgggacgc tcgaagatcc agctgcatta atgaatcggc caacgcgcgg  2520
ggagaggcgg tttgcgtatt gggcgctctt ccgcttcctc gctcactgac tcgctgcgct  2580
cggtcgttcg gctgcggcga gcggtatcag ctcactcaaa ggcggtaata cggttatcca  2640
cagaatcagg ggataacgca ggaaagaaca tgtgagcaaa aggccagcaa aaggccagga  2700
accgtaaaaa ggccgcgttg ctggcgtttt tccataggct ccgcccccct gacgagcatc  2760
acaaaaatcg acgctcaagt cagaggtggc gaaacccgac aggactataa agataccagg  2820
cgtttccccc tggaagctcc ctcgtgcgct cctcgttccc gacccctgccg cttaccggat  2880
acctgtccgc ctttctccct tcgggaagcg tggcgctttc tcatagctca cgctgtaggt  2940
atctcagttc ggtgtaggtc gttcgctcca agctgggctg tgtgcacgaa ccccccgttc  3000
agcccgaccg ctgcgcctta tccggtaact atcgtcttga gtccaacccg gtaagacacg  3060
acttatcgcc actggcagca gccactggta acaggattag cagagcgagg tatgtaggcg  3120
gtgctacaga gttcttgaag tggtggccta actacggcta cactagaaga acagtatttg  3180
gtatctgcgc tctgctgaag ccagttacct tcggaaaaag agttggtagc tcttgatccg  3240
gcaaacaaac caccgctggt agcggtggtt ttttttgtttg caagcagcag attacgcgca  3300
gaaaaaaagg atctcaagaa gatcctttga tcttttctac ggggtctgac gctcagtgga  3360
acgaaaactc acgttaaggg attttggtca tgagattatc aaaaaggatc ttcacctaga  3420
tccttttaaa ttaaaaatga agttttaaat caatctaaag tatatatgag taaacttggt  3480
ctgacagtta ccaatgctta atcagtgagg cacctatctc agcgatctgt ctatttcgtt  3540
catccatagt tgcctgactc cccgtcgtgt agataactac gatacgggag ggcttaccat  3600
ctggccccag tgctgcaatg ataccgcgag acccacgctc accggctcca gatttatcag  3660
caataaacca gccagccgga agggccgagc gcagaagtgg tcctgcaact ttatccgcct  3720
ccatccagtc tattaattgt tgccgggaag ctagagtaag tagttcgcca gttaatagtt  3780
tgcgcaacgt tgttgccatt gctacaggca tcgtggtgtc acgctcgtcg tttggtatgg  3840
cttcattcag ctccggttcc caacgatcaa ggcgagttac atgatccccc atgttgtgca  3900
aaaaagcggt tagctccttc ggtcctccga tcgttgtcag aagtaagttg gccgcagtgt  3960
tatcactcat ggttatggca gcactgcata attctcttac tgtcatgcca tccgtaagat  4020
gcttttctgt gactggtgag tactcaacca agtcattctg agaatagtgt atgcggcgac  4080
cgagttgctc ttgcccggcg tcaatacggg ataataccgc gccacatagc agaactttaa  4140
aagtgctcat cattggaaaa cgttcttcgg ggcgaaaact ctcaaggatc ttaccgctgt  4200
tgagatccag ttcgatgtaa cccactcgtg cacccaactg atcttcagca tcttttactt  4260
tcaccagcgt ttctgggtga gcaaaaacag gaaggcaaaa tgccgcaaaa aagggaataa  4320
gggcgacacg gaaatgttga atactcatac tcttcctttt tcaatattat tgaagcattt  4380
atcagggtta ttgtctcatg agcggataca tatttgaatg tatttagaaa aataaacaaa  4440
tagggggttcc gcgcacattt ccccgaaaag tgccacctga cgaagcatc tgtgcttcat  4500
tttgtagaac aaaaatgcaa cgcgagagcg ctaattttttc aaacaaagaa tctgagctgc  4560
attttttacag aacagaaatg caacgcgaaa gcgctattttc accaacgaag aatctgctgct  4620
tcattttttgt aaaacaaaaa tgcaacgcga gagcgctaat tttttcaaaca aagaatctga  4680
gctgcatttt tacagaacag aaatgcaacg cgagagcgct attttaccaa caaagaatct  4740
atacttcttt tttgttctac aaaaatgcat cccgagagcg ctattttct aacaaagcat  4800
cttagattac ttttttttctc ctttgtgcgc tctataatgc agtctcttga taacttttttg  4860
cactgtaggt ccgttaaggt tagaagaagg ctactttggt gtcattttc tcttccataa  4920
aaaaagcctg actccactttc ccgcgtttac tgattactag cgaagctgcg ggtgcatttt  4980
ttcaagataa aggcatcccc gattatattc tataccgatg tggattgcgc atactttgtg  5040
aacagaaagt gatagcgttg atgattcttc attggtcaga aaattatgaa cggtttcttc  5100
tatttttgtct ctatatacta cgtataggaa atgtttacat tttcgtattg ttttcgattc  5160
actctatgaa tagttcttac tacaattttt ttgtctaaag agtaatacta gagataaaca  5220
taaaaaatgt agaggtcgag tttagatgca agttcaagga gcgaaaggtg gatgggtagg  5280
```

```
ttatataggg atatagcaca gagatatata gcaaagagat acttttgagc aatgtttgtg    5340
gaagcggtat tcgcaatatt ttagtagctc gttacagtcc ggtgcgtttt tggttttttg    5400
aaagtgcgtc ttcagagcgc ttttggtttt caaaagcgct ctgaagttcc tatacttttct   5460
agagaatagg aacttcggaa taggaacttc aaagcgtttc cgaaaacgag cgcttccgaa    5520
aatgcaacgc gagctgcgca catacagctc actgttcacg tcgcacctat atctgcgtgt    5580
tgcctgtata tatatataca tgagaagaac ggcatagtgc gtgtttatgc ttaaatgcgt    5640
acttatatgc gtctatttat gtaggatgaa aggtagtcta gtacctcctg tgatattatc    5700
ccattccatg cgggtatcg tatgcttcct tcagcactac cctttagctg ttctatatgc    5760
tgccactcct caattggatt agtctcatcc ttcaatgcta tcatttcctt tgatattgga    5820
tcatactaag aaaccattat tatcatgaca ttaacctata aaaataggcg tatcacgagt    5880
cccttttcgtc tcgcgcgttt cggtgatgac ggtgaaaaacc tctgacacat gcagctcccg   5940
gagacggtca cagcttgtct gtaagcggat gccgggagca gacaagcccg tcagggcgcg    6000
tcagcggggtg ttggcgggtg tcgggctgg cttaactatg cggcatcaga gcagattgta    6060
ctgagagtgc accatatttc acaccgcata gatccgtcga gttcaagaga aaaaaaaaga    6120
aaaagcaaaa agaaaaaagg aaagcgcgcc tcgttcagaa tgacacgtat agaatgatgc    6180
attaccttgt catcttcagt atcatactgt tcgtatacat acttactgac attcataggt    6240
atacatatat acacatgtat atatatcgta tgctgcagct ttaaataatc ggtgtcacta    6300
cataagaaca cctttggtgg agggaacatc gttggtacca ttgggcgagg tggcttctct    6360
tatggcaacc gcaagagcct tgaacgcact ctcactacgg tgatgatcat tcttgcctcg    6420
cagacaatca acgtggaggg taattctgct agcctctgca aagctttcaa gaaaatgcgg    6480
gatcatctcg caagagagat ctcctacttt ctcccttttgc aaaccaagtt cgacaactgc    6540
gtacggcctg ttcgaaagat ctaccaccgc tctggaaagt gcctcatcca aaggcgcaaa    6600
tcctgatcca aaccttttta ctccacgcac ggccctagg gcctctttaa aagcttgacc    6660
gagagcaatc ccgcagtctt cagtggtgtg atggtcgtct atgtgtaagt caccaatgca    6720
ctcaacgatt agcgaccagc cggaatgctt ggccagagca tgtatcatat ggtccagaaa    6780
ccctatacct gtgtggacgt taatcacttg cgattgtgtg gcctgttctg ctactgcttc    6840
tgcctcttt tctgggaaga tcgagtgctc tatcgctagg ggaccaccct ttaaagagat    6900
cgcaatctga atcttggttt catttgtaat acgcttact agggcttct gctctgtcat    6960
ctttgccttc gtttatcttg cctgctcatt ttttagtata ttcttcgaag aaatcacatt    7020
actttatata atgtataatt cattatgtga taatgccaat cgctaagaaa aaaaagagt    7080
catccgctag gtggaaaaaa aaaatgaaa atcattaccg aggcataaaa aaatatagag    7140
tgtactagag gaggccaaga gtaatagaaa aagaaaattg cgggaaagga ctgtgttatg    7200
acttccctga ctaatgccgt gttcaaacga tacctggcag tgactcctag cgctcaccaa    7260
gctcttaaaa cgggaattta tggtgcactc tcagtacacg cgccagatct gtttagcttg    7320
cctcgtcccc gccgggtcac ccggccagcg acatggaggc ccagaatacc ctccttgaca    7380
gtcttgacgt gcgcagctca ggggcatgat gtgactgtcg cccgtacatt tagcccatac    7440
atccccatgt ataatcattt gcatccatac atttttgatgg ccgcacggcg cgaagcaaaa    7500
attacggctc ctcgctgcag acctgcgagc agggaaacgc tcccctcaca gacgcgttga    7560
attgtcccca cgccgcgccc ctgtagagaa atataaaagg ttaggatttg ccactgaggt    7620
tcttctttca tatacttcct ttttaaaatct tgctaggata cagttctcac atcacatccg    7680
aacataaaca accatgggta aggaaaagac tcacgtttcg aggccgcgat taaattccaa    7740
catggatgct gatttatatg ggtataaatg ggctcgcgat aatgtcgggc aatcaggtgc    7800
gacaatctat cgattgtatg ggaagcccga tgcgccaagt ttgtttctga aacatggcaa    7860
aggtagcgtt gccaatgatg ttacagatga gatggtcaga ctaaactggc tgacggaatt    7920
tatgcctctt ccgaccatca agcattttat ccgtactcct gatgatgcat ggttactcac    7980
cactgcgatc cccggcaaaa cagcattcca ggtattagaa gaatatcctg attcaggtga    8040
aaatattgtt gatgcgctgg cagtgttcct gcgccggttg cattcgattc ctgtttgtaa    8100
ttgtcctttt aacagcgatc gcgtatttcg tctcgctcag gcgcaatcac gaatgaataa    8160
cggtttggtt gatgcgagtg attttgatga cgagcgtaat ggctggcctg ttgaacaagt    8220
ctggaaagaa atgcataagc ttttgccatt ctcaccggat tcagtcgtca ctcatggtga    8280
tttctcactt gataaccttta ttttttgacga ggggaaatta ataggttgta ttgatgttgga    8340
acgagtcgga atcgcagacc gataccagga tcttgccatc ctatggaact gcctcggtga    8400
gttttctcct tcattacaga aacggctttt caaaaatat ggtattgata atcctgatat    8460
gaataaattg cagtttcatt tgatgctcga tgagttttc taatcagtac tgacaataaa    8520
aagattcttg ttttcaagaa cttgtcattt gtatagtttt tttatattgt agttgttcta    8580
ttttaatcaa atgttagcgt gatttatatt tttttttcgcc tcgacatcat ctgcccagat    8640
gcgaagttaa gtgcgcagaa agtaaatca tgcgtcaatc gtatgtgaat gctggtcgct    8700
atactgctgt cgattcgata ctaacgccgc catccagtgt cgaattcgcc attcaggctg    8760
cgcaactgtt gggaagggcg atcggtgcgg gcctcttcgc tattacgcca gctgaattgg    8820
agcgacctca tgctatacct gagaaagcaa cctgacctac aggaaagagt tactcaagaa    8880
taagaattttt cgtttaaaa cctaagagtc acttaaat ttgtatacac ttattttttt     8940
tataacttat ttaataataa aaatcataaa tcataagaaa ttcgcttatt tagaagtgtc    9000
aacaacgtat ctaccaacga tttgacccctt ttccatcttt tcgtaaattt ctggcaaggt    9060
agacaagccg acaaccttga ttggagactt gaccaaacct ctggcgaaga attgttaatt    9120
aagagctcag atcttttgcg gccgc                                           9145

SEQ ID NO: 77         moltype = DNA  length = 499
FEATURE               Location/Qualifiers
source                1..499
                      mol_type = genomic DNA
                      organism = Saccharomyces cerevisiae
SEQUENCE: 77
gtttgcaaaa agaacaaaac tgaaaaaacc cagacacgct cgacttcctg tcttcctatt     60
gattgcagct tccaatttcg tcacacaaca aggtcctagc gacggctcag aggttttgta    120
acaagcaatc gaaggttctg gaatggcggg aaagggttta gtaccacatg ctatgatgcc    180
cactgtgatc tccagagcaa agttcgttcg atcgtactgt tactctctct cttttcaaaca    240
gaattgtccg aatcgtgtga caacaacagc ctgttctcac acactctttt cttctaacca    300
aggggtggt ttagtttagt agaacctcgt gaaacttaca tttacatata tataaacttg    360
cataaattgg tcaatgcaag aaatacatat ttggtctttt ctaattcgta gttttttcaag    420
```

```
ttcttagatg ctttctttt  ctcttttta  cagatcatca aggaagtaat tatctacttt    480
ttacaacaaa tataaaaca                                                 499

SEQ ID NO: 78           moltype = DNA  length = 500
FEATURE                 Location/Qualifiers
source                  1..500
                        mol_type = genomic DNA
                        organism = Saccharomyces cerevisiae
SEQUENCE: 78
acagtttatt cctggcatcc actaaatata atggagcccg ctttttaagc tggcatccag     60
aaaaaaaaag aatcccagca ccaaaatatt gttttcttca ccaaccatca gttcataggt    120
ccattctctt agcgcaacta cagagaacag gggcacaaac aggcaaaaaa cgggcacaac    180
ctcaatggag tgatgcaacc tgcctggagt aaatgatgac acaaggcaat tgacccacgc    240
atgtatctat ctcattttct tacaccttct attacctct gctctctctg atttggaaaa     300
agctgaaaaa aaaggttgaa accagttccc tgaaattatt ccctacttg actaataagt     360
atataaagac ggtaggtatt gattgtaatt ctgtaaatct atttcttaaa cttcttaaat    420
tctacttta  tagttagtct ttttttagt  tttaaaacac caagaactta gtttcgaata    480
aacacacata aacaaacaaa                                                500

SEQ ID NO: 79           moltype = DNA  length = 500
FEATURE                 Location/Qualifiers
source                  1..500
                        mol_type = genomic DNA
                        organism = Saccharomyces cerevisiae
SEQUENCE: 79
gctggattga gctgaatggt gccaggtcga ggctgggagg gagactaact cgaaagtgac     60
gaagactcga aaattaaaaa aaagatact gcagaaggca agattgagaa tggagtaaag     120
gcagcgtggg tccctgtgg  aaaccgcagt tttcctgcgc caagtggtac cggtgcgagt    180
gcagcaatta atctctcgat attttcttag tatctctttt tatataagaa tatattttgg    240
aattggtaat gcttatcttc aatagtttct tagttgaatg cacacttaag agcaaattgg    300
ccaaggagtt cttcgttcgc tttaatttat ttcctggtta ttgtcaattt attcatccca    360
tctcccagg  atagaagaaa ttagtgtaat tttgctgaca atacatttta acgacgataa    420
caataatagc aattaaataa aatagcacta ccaccactcc actgctcgtt agctatttct    480
gtaaataaa  taaaagatc                                                 500

SEQ ID NO: 80           moltype = DNA  length = 501
FEATURE                 Location/Qualifiers
source                  1..501
                        mol_type = genomic DNA
                        organism = Saccharomyces cerevisiae
SEQUENCE: 80
attcgcgcta tctcgatttc tacctatata gttaatctct gtacaaaaac aatctttcca     60
actatccatt aatcatagta tattatcagc gtcggcgatt ttaccacgct tgacaaaagc    120
cgcgggcggg attcctgtgg gtagtggcac cggcagttaa tctaatcaaa ggcgcttgaa    180
ggaagagata gataatagaa caaagcaatc gccgctttgg acggcaaata tgtttatcca    240
ttggtgcggt gattggatat gatttgtctc cagtagtata agcaagcgcc agatctgttt    300
actgtaaaat taagtgagta atctcgcggg atgtaatgat ttaagggaat ctggttcagg    360
ttttcacata tatttgtata taaggccatt tgtaattca  atagttttag gattttccct    420
tctcccaaaa tactcactta ctgtgttaca ttacagaaag aacagacaag aaaccgtcaa    480
taagaaatat aactaagaac a                                              501

SEQ ID NO: 81           moltype = DNA  length = 27
FEATURE                 Location/Qualifiers
misc_feature            1..27
                        note = Synthetic HA epitope tag polypeptide
source                  1..27
                        mol_type = other DNA
                        organism = synthetic construct
SEQUENCE: 81
tacccatacg acgttccaga ctacgcc                                         27

SEQ ID NO: 82           moltype = AA   length = 9
FEATURE                 Location/Qualifiers
REGION                  1..9
                        note = Synthetic HA epitope tag polypeptide
source                  1..9
                        mol_type = protein
                        organism = synthetic construct
SEQUENCE: 82
YPYDVPDYA                                                              9

SEQ ID NO: 83           moltype = DNA  length = 33
FEATURE                 Location/Qualifiers
misc_feature            1..33
                        note = Synthetic c-MYC epitope tag polypeptide
source                  1..33
                        mol_type = other DNA
                        organism = synthetic construct
SEQUENCE: 83
```

```
gaacaaaagt taatttctga agaagatttg gaa                                33

SEQ ID NO: 84          moltype = AA   length = 10
FEATURE                Location/Qualifiers
REGION                 1..10
                       note = Synthetic c-MYC epitope tag polypeptide
source                 1..10
                       mol_type = protein
                       organism = synthetic construct
SEQUENCE: 84
EQKLISEEDL                                                          10

SEQ ID NO: 85          moltype = DNA   length = 24
FEATURE                Location/Qualifiers
misc_feature           1..24
                       note = Synthetic FLAG epitope tag polypeptide
source                 1..24
                       mol_type = other DNA
                       organism = synthetic construct
SEQUENCE: 85
gactacaagg atgacgatga caaa                                          24

SEQ ID NO: 86          moltype = AA   length = 8
FEATURE                Location/Qualifiers
REGION                 1..8
                       note = Synthetic FLAG epitope tag polypeptide
source                 1..8
                       mol_type = protein
                       organism = synthetic construct
SEQUENCE: 86
DYKDDDDK                                                            8

SEQ ID NO: 87          moltype = DNA   length = 42
FEATURE                Location/Qualifiers
misc_feature           1..42
                       note = Synthetic V5 epitope tag polypeptide
source                 1..42
                       mol_type = other DNA
                       organism = synthetic construct
SEQUENCE: 87
ggtaagccaa ttccaaatcc tttgttgggt ttggactcca cc                      42

SEQ ID NO: 88          moltype = AA   length = 14
FEATURE                Location/Qualifiers
REGION                 1..14
                       note = Synthetic V5 epitope tag polypeptide
source                 1..14
                       mol_type = protein
                       organism = synthetic construct
SEQUENCE: 88
GKPIPNPLLG LDST                                                     14

SEQ ID NO: 89          moltype = DNA   length = 18
FEATURE                Location/Qualifiers
misc_feature           1..18
                       note = Synthetic HIS epitope tag polypeptide
source                 1..18
                       mol_type = other DNA
                       organism = synthetic construct
SEQUENCE: 89
catcatcatc atcatcat                                                 18

SEQ ID NO: 90          moltype = AA   length = 6
FEATURE                Location/Qualifiers
REGION                 1..6
                       note = Synthetic HIS epitope tag polypeptide
source                 1..6
                       mol_type = protein
                       organism = synthetic construct
SEQUENCE: 90
HHHHHH                                                              6

SEQ ID NO: 91          moltype = DNA   length = 7882
FEATURE                Location/Qualifiers
misc_feature           1..7882
                       note = pMM1 vector
source                 1..7882
                       mol_type = other DNA
                       organism = synthetic construct
```

```
SEQUENCE: 91
caggtggcac ttttcgggga aatgtgcgcg gaaccccctat tgtttattt ttctaaatac   60
attcaaatat gtatccgctc atgagacaat aaccctgata aatgcttcaa taatattgaa  120
aaaggaagag tatgagtatt caacatttcc gtgtcgccct tattcccttt tttgcggcat  180
tttgccttcc tgttttttgct cacccagaaa cgctggtgaa agtaaaagat gctgaagatc  240
agttgggtgc acgagtgggt tacatcgaac tggatctcaa cagcggtaag atccttgaga  300
gttttcgccc cgaagaacgt tttccaatga tgagcacttt taaagttctg ctatgtggcg  360
cggtattatc ccgtattgac gccgggcaag agcaactcgg tcgccgcata cactattctc  420
agaatgactt ggttgagtac tcaccagtca cagaaaagca tcttacggat ggcatgacag  480
taagagaatt atgcagtgct gccataacca tgagtgataa cactgcggcc aacttacttc  540
tgacaacgat cggaggaccg aaggagctaa ccgcttttt gcacaacatg ggggatcatg  600
taactcgcct tgatcgttgg gaaccggagc tgaatgaagc cataccaaac gacgagcgtg  660
acaccacgat gcctgtagca atggcaacaa cgttgcgcaa actattaact ggcgaactac  720
ttactctagc ttcccggcaa caattaatag actggatgga ggcggataaa gttgcaggac  780
cacttctgcg ctcggccctt ccggctggct ggtttattgc tgataaatct ggagccggtg  840
agcgtgggtc tcgcggtatc attgcagcac tggggccaga tggtaagccc tcccgtatcg  900
tagttatcta cacgacgggg agtcaggcaa ctatggatga acgaaataga cagatcgctg  960
agataggtgc ctcactgatt aagcattggt aactgtcaga ccaagtttac tcatatatac 1020
tttagattga tttaaaacttt cattttaat ttaaaaggat ctaggtgaag atcctttttg 1080
ataatctcat gaccaaaatc ccttaacgtg agttttcgtt ccactgagcg tcagacccccg 1140
tagaaaagat caaaggatct tcttgagatc cttttttct gcgcgtaatc tgctgcttgc 1200
aaacaaaaaa accaccgcta ccagcggtgg tttgtttgcc ggatcaagag ctaccaactc 1260
tttttccgaa ggtaactggc ttcagcagag cgcagatacc aaatactgtt cttctagtgt 1320
agccgtagtt aggccaccac ttcaagaact ctgtagcacc gcctacatac ctcgctctgc 1380
taatcctgtt accagtggct gctgccagtg gcgataagtc gtgtcttacc gggttggact 1440
caagacgata gttaccggat aaggcgcagc ggtcgggctg aacgggggt tcgtgcacac 1500
agcccagctt ggagcgaacg acctacaccg aactgagata cctacagcgt gagctatgag 1560
aaagcgccac gcttcccgaa gggagaaagg cggacaggta tccggtaagc ggcagggtcg 1620
gaacaggaga gcgcacgagg gagcttccag ggggaaacgc ctggtatctt tatagtcctg 1680
tcgggtttcg ccacctctga cttgagcgtc gatttttgtg atgctcgtca gggggcgga 1740
gcctatggaa aaacgccagc aacgcggcct ttttacggtt cctggccttt tgctggcctt 1800
ttgctcacat gttctttcct gcgttatccc ctgattctgt ggataaccgt attaccgcct 1860
ttgagtgagc tgataccgct cgccgcagcc gaacgaccga gcgcagcgag tcagtgagcg 1920
aggaagcgga agagcgccca atacgcaaac cgcctctccc cgcgcgttgg ccgattcatt 1980
aatgcagctg gatcttcgag cgtcccaaaa ccttctcaag caaggttttc agtataatgt 2040
tacatgcgta cacgcgtctg tacagaaaaa aaagaaaaat ttgaaatata ataacgttc 2100
ttaatactaa cataactata aaaaaataaa tagggaccta gacttcaggt tgtctaactc 2160
cttcctttc ggttagagcg gatcttagct agccgcggta ccaagctggt ggatcctttg 2220
tttgtttatg tgtgtttatt cgaaactaag ttcttggtgt tttaaaacta aaaaaaagac 2280
taactataaa agtagaattt aagaagttta agaaatagat ttacagaatt acaatcaata 2340
cctaccgtct ttatatactt attagtcaag taggggaata atttcaggga actggtttca 2400
accttttttt tcagctttt ccaaatcaga gagagcagaa ggtaatagaa ggtgtaagaa 2460
aatgagatag atacatgcgt gggtcaattg ccttgtgtca tcatttactc caggcaggtt 2520
gcatcactcc attgaggttg tgcccgtttt ttgcctgttt gtgcccctgt tctctgtagt 2580
tgcgctaaga gaatgaccct atgaactgat ggttggtgaa gaaaacaata ttttggtgct 2640
gggattcttt ttttttctgg atgccagctt aaaaagcggg ctccattata tttagtggat 2700
gccaggaata aactgttgtt tgcaaaagaa acaaaactga aaaaacccag acacgctcga 2760
cttcctgtct tccctattgat tgcagcttcc aatttcgtca cacaacaagg tcctagcgac 2820
ggctcacagg ttttgtaaca agcaatcgaa ggttctggaa tggcgggaaa gggtttagta 2880
ccacatgcta tgatgcccac tgtgatctcc agagcaaagt tcgttcgatc gtactgttac 2940
tctctctctt tcaaacagaa ttgtccgaat cgtgtgacaa caacagcctg ttctcacaca 3000
ctcttttctt ctaaccaagg gggtggttta gtttagtaga acctcgtgaa acttacattt 3060
acatatatat aaacttgcat aaaattggtca atgcaagaaa tacatatttg gtcttttcta 3120
attcgtagtt tttcaagttc ttagatgctt tcttttttctc tttttttacag atcatcaagg 3180
aagtaattat ctactttta caacaaatat aaaacagcg ccgcaaaaga tctgagctct 3240
taattaacaa ttcttcgcca gaggtttggt caagtctcca atcaaggttg tcggcttgtc 3300
taccttgcca gaaatttacg aaaagatgga aaagggtcaa atcgttggta gatacgttgt 3360
tgacacttct aaataagcga atttcttatg atttatgatt tttattatta aataagttat 3420
aaaaaaaata agtgtataca aattttaaag tgactcttag gtttaaaac gaaaattctt 3480
attcttgagt aactctttcc tgtaggtcag gttgctttct caggtatagc atgaggtcgc 3540
tccaattcag ctggcgtaat agcgaagagg cccgcaccga tcgcccttcc caacagttgc 3600
gcagcctgaa tggcgaattc gacactggat ggcggcgtta gtatcgaatc gacagcagta 3660
tagcgaccag cattcacata cgattgacgc atgatattac ttctgcgca cttaacttcg 3720
catctgggca tgatgatgtcg aggcgaaaaa aaatataaat cacgctaaca tttgattaaa 3780
atagaacaac tacaatataa aaaaactata caaatgacaa gttcttgaaa acaagaatcc 3840
ttttattgtc agtactgatt agaaaaactc atcgagcatc aaatgaaact gcaatttatt 3900
catatcagga ttatcaatac catatttttg aaaaagccgt ttctgtaatg aaggagaaaa 3960
ctcaccgagg cagttccata ggatgcaag atctcggtat cggtctgcga ttccgactcg 4020
tccaacatca atacaaccta ttaatttccc ctcgtcaaaa ataaggttat caagtgagaa 4080
atcaccatga gtgacgactg aatccggtga gaatggcaaa agcttatgca tttctttcca 4140
gacttgttca acaggccagc cattacgctc gtcatcaaaa tcactcgcat caaccaaacc 4200
gttattcatt cgtgattgcg cctgagcgag acgaaatacg cgatcgctgt taaaaggaca 4260
attacaaaca ggaatcgaat gcaaccggcg caggaacact gccagcgcat caacaatatt 4320
ttcacctgaa tcaggatatt cttctaatac ctggaatgct gttttgccgg ggatcgcagt 4380
ggtgagtaac catgcatcat caggagtacg gataaaatgc ttgatggtcg gaagaggcat 4440
aaattccgtc agccagttta gtctgaccat ctcatctgta acatcattgg caacgctacc 4500
tttgccatgt ttcagaaaca actctggcgc atcgggcttc ccatacaatc gatagattgt 4560
cgcacctgat tgcccgacat tatcgcgagc ccatttatac ccatataaat cagcatccat 4620
gttggaattt aatcgcggcc tcgaaacgtg agtcttttcc ttacccatgg ttgtttatgt 4680
```

```
tcggatgtga tgtgagaact gtatcctagc aagattttaa aaggaagtat atgaaagaag  4740
aacctcagtg gcaaatccta acctttata tttctctaca ggggcgcggc gtggggacaa    4800
ttcaacgcgt ctgtgagggg agcgtttccc tgctcgcagg tctgcagcga ggagccgtaa   4860
ttttgcttc gcgccgtgcg gccatcaaaa tgtatggatg caaatgatta tacatgggga    4920
tgtatgggct aaatgtacgg gcgacagtca catcatgccc ctgagctgcg cacgtcaaga   4980
ctgtcaagga gggtattctg ggcctccatg tcgctggccg ggtgaccegg cggggacgaa   5040
gcaagctaaa cagatctggc gcgtgtactg agagtgcacc ataaattccc gttttaagag   5100
cttggtgagc gctaggagtc actgccaggt atcgtttgaa cacggcatta gtcagggaag   5160
tcataacaca gtcctttccc gcaatttct ttttctatta ctcttggcct cctctagtac     5220
actctatatt ttttatgcc tcggtaatga ttttcatttt ttttttcca cctagcggat      5280
gactcttttt ttttcttagc gattggcatt atcacataat gaattataca ttatataaag   5340
taatgtgatt tcttcgaaga atatactaaa aaatgagcag gcaagataaa cgaaggcaaa   5400
gatgacagag cagaaagccc tagtaaagcg tattacaaat gaaaccaaga ttcagattgc   5460
gatctcttta aagggtggtc ccctagcgat agagcactcg atcttcccag aaaaagaggc   5520
agaagcagta gcagaacagg ccacacaatc gcaagtgatt aacgtccaca caggtatagg   5580
gtttctggac catatgatac atgctctggc caagcattcc ggctggtcgc taatcgttga   5640
gtgcattggt gacttacaca tagacgacca tcacaccact gaagactgcg ggattgctct    5700
cggtcaagct tttaaagagg ccctaggggc cgtgcgtgga gtaaaaaggt ttggatcagg    5760
atttgcgcct ttggatgagg cacttttccag agcggtggta gatctttcga acaggccgta   5820
cgcagttgtc gaacttggtt tgcaaaggga gaaagtagga gatctctctt gcgagatgat    5880
cccgcatttt cttgaaagct ttgcagaggc tagcagaatt ccctccacg ttgattgtct      5940
gcgaggcaag aatgatcatc accgtagtga gagtgcgttc aaggctcttg cggttgccat    6000
aagagaagcc acctcgccca atggtaccaa cgatgttccc tccaccaaag gtgttcttat    6060
gtagtgacac cgattattta aagctgcagc atacgatata tatacatgtg tatatatgta    6120
tacctatgaa tgtcagtaag tatgtatacg aacagtatga tactgaagat gacaaggtaa    6180
tgcatcattc tatacgtgtc attctgaacg aggcgcgctt tccttttttc tttttgcttt    6240
ttctttttt ttctcttgaa ctcgacggat ctatgcggtg tgaaatatgg tgcactctca      6300
gtacaatctg ctctgatgcc gcatagttaa gccagcccg acaccegcca acaccegctg      6360
acgcgccctg acgggcttgt ctgctcccgg catccgctta cagacaagct gtgaccgtct    6420
ccgggagctg catgtgtcag aggtttttcac cgtcatcacc gaaacgcgcg agacgaaagg   6480
gcctcgtgat acgcctattt ttataggtta atgtcatgat aataatggtt tcttagtatg    6540
atccaatatc aaaggaaatg atagcattga aggatgagac taatccaatt gaggagtggc    6600
agcatataga acagctaaag ggtagtgctg aaggaagcat acgataccc gcatggaatg     6660
ggatataatc acaggaggta ctagactacc tttcatccta cataaataga cgcatataag    6720
tacgcattta agcactatgc cgttcttctc atgtatatat atatacaggc                6780
aacacgcaga tataggtgcg acgtgaacag tgagctgtat gtgcgcagct cgcgttgcat   6840
tttcggaagc gctcgttttc ggaaacgctt tgaagttcct attccgaagt tcctattctc    6900
tagaaagtat aggaacttca gagcgctttt gaaaaccaaa agcgctctga agacgcactt    6960
tcaaaaaacc aaaaacgcac cggactgtaa cgagctacta aaatattgcg aataccgctt    7020
ccacaaacat tgctcaaaag tatctctttg ctatatatct ctgtgctata tcctatata     7080
acctacccat ccacctttcg ctccttgaac ttgcatctaa actcgacctc tacatttttt    7140
atgtttatct ctagtattac tctttagaca aaaaattgt agtaagaact attcatagag     7200
tgaatcgaaa acaatacgaa aatgtaaaca tttcctatac gtagtatata gagacaaaat    7260
agaagaaacc gttcataatt ttctgaccaa tgaagaatca tcaacgctat cactttctgt    7320
tcacaaagta tgcgcaatcc acatcggtat agaatataat cggggatgcc tttatcttga    7380
aaaaatgcac ccgcagcttc gctagtaatc agtaaacgcg ggaagtggag tcaggctttt   7440
tttatggaag agaaaataga caccaaagta gccttcttc aaccttaacg gacctacagt     7500
gcaaaaagtt atcaagagac tgcattatag agcgcacaaa ggagaaaaaa agtaatcaa     7560
gatgcttgt tagaaaaata gcgctctcgg gatgcatttt tgtagaacaa aaagaagta     7620
tagattcttt gttggtaaaa tagcgctctc gcgttgcatt tctgttctgt aaaaatgcag   7680
ctcagattct ttgtttgaaa aattagcgct ctcgcgttgc attttttgttt tacaaaaatg  7740
aagcacagat tcttcgttgg taaaatagcg ctttcgcgtt gcatttctgt tctgtaaaaa   7800
tgcagctcag attctttgtt tgaaaaatta gcgctctcgc gttgcatttt tgttctacaa   7860
aatgaagcac agatgcttcg tt                                              7882

SEQ ID NO: 92       moltype = DNA   length = 3810
FEATURE             Location/Qualifiers
misc_feature        1..3810
                    note = pCDM4 vector
source              1..3810
                    mol_type = other DNA
                    organism = synthetic construct
SEQUENCE: 92
gctaacagcg cgatttgctg gtgacccaat gcgaccagat gctccacgcc cagtcgcgta    60
ccgtcttcat gggagaaaat aatactgttg atgggtgtct ggtcagagac atcaagaaat   120
aacgccggaa cattagtgca ggcagcttcc acagcaatgg catcctggtc atccagcgga   180
tagttaatga tcagcccact gacgcgttgc gcgagaagat tgtgcaccgc cgctttacag   240
gcttcgacgc cgcttcgttc taccatcgac accaccacgc tggccactcccag ttgatcggcg  300
cgagatttaa tcgccgcgac aatttcgac ggcgcgtgca gggcgacact ggaggtggca    360
acgccaatca gcaacgactg tttgcccgcc agttgttgtg ccacgcggtt gggaatgtaa   420
ttcagctccg ccatcgccgc ttccacttttt cccgcgtttt tcgcagaaac gtggctggcc  480
tggttcacca cgcgggaaac ggtctgataa agacaccgg catactctgc gacatcgtat     540
aacgttactg gtttcacatt caccaccctg aattgactct cttccgggcg ctatcatgcc   600
ataccgcgaa aggttttgcg ccattcgatg gtgtccggga tcttcgtatg ccctcctttatg  660
cgactcctgc attaggaagc agcccagtag taggttgagg ccgttgagca ccgccgccgc   720
aaggaatggt gcatgcaagg agatggcgcc caacagtccc ccggccacgg ggcctgccac   780
catcccacg ccgaaacaag cgctcatgag cccgaagtgg cgagcccgat cttcccatc     840
ggtgatgtcg gcgatatagg cgccagcaac cgcacctgtg gcgccggtga tgccggccac   900
gatgcgtccg gcgtagccta ggatcgagat cgatctcgat ccgcgaaat taatacgact   960
```

```
cactataggg gaattgtgag cggataacaa ttcccctcta gaaataattt tgtttaactt    1020
taagaaggag atatacatat ggcagatctc aattggatat cggccggcca cgcgatcgct    1080
gacgtcggta ccctcgagtc tggtaaagaa accgctgctg cgaaatttga acgccagcac    1140
atggactcgt ctactagtcg cagcttaatt aacctaaact gctgccaccg ctgagcaata    1200
actagcataa ccccttgggg cctctaaacg ggtcttgagg ggttttttgc tagcgaaagg    1260
aggagtcgac actgcttccg gtagtcaata aaccggtaaa ccagcaatag acataagcgg    1320
ctatttaacg accctgccct gaaccgacga ccgggtcatc gtggccggat cttgcggccc    1380
ctcggcttga acgaattgtt agacattatt tgccgactac cttggtgatc tcgcctttca    1440
cgtagtggac aaaattcttc aactgatctg cgcgcgaggc caagcgatct tcttcttgtc    1500
caagataagc ctgtctagct tcaagtatga cgggcgaata ctgggccggc aggcgctcca    1560
ttgcccagtc ggcagcgaca tccttcggcg cgattttgcc ggttactgcg ctgtaccaaa    1620
tgcgggacaa cgtaagcact acatttcgct catcgccagc ccagtcgggc ggcgagttcc    1680
atagcgttaa ggtttcattt agcgcctcaa atagatcctg ttcaggaacc ggatcaaaga    1740
gttcctccgc cgctggacct accaaggcaa cgctatgtc tcttgctttt gtcagcaaga    1800
tagccagatc aatgtcgatc gtggctggct cgaagatacc tgcaagaatg tcattgcgct    1860
gccattctcc aaattgcagt tcgcgcttag ctggataacg ccacgaatg atgtcgtcgt    1920
gcacaacaat ggtgacttct acagcgcgga gaatctcgct ctctcaggg gaagccgaag    1980
tttccaaaag gtcgttgatc aaagctcgcc gcgttgtttc atcaagcctt acggtcaccg    2040
taaccagcaa atcaatatca ctgtgtggct tcaggccgcc atccactgcg gagccgtaca    2100
aatgtacggc cagcaacgtc ggttcgagat ggcgctcgat gacgccaact acctctgata    2160
gttgagtcga tacttcggcg atcaccgctt ccctcatact cttcctttt caatattatt    2220
gaagcattta tcagggttat tgtctcatga gcggataaca atttcacaca ggaaacagct    2280
atgaccatga ttacgccaag cttgcatgcc tgcaggtcga ctctagagga tccccgggta    2340 
```
(note: the above is my best-effort rendering — please refer to the original)

-continued

```
gctccttcgg tcctccgatc gttgtcagaa gtaagttggc cgcagtgtta tcactcatgg   1380
ttatggcagc actgcataat tctcttactg tcatgccatc cgtaagatgc ttttctgtga   1440
ctggtgagta ctcaaccaag tcattctgag aatagtgtat gcggcgaccg agttgctctt   1500
gcccggcgtc aatacgggat aataccgcgc cacatagcag aactttaaaa gtgctcatca   1560
ttggaaaacg ttcttcgggg cgaaaactct caaggatctt accgctgttg agatccagtt   1620
cgatgtaacc cactcgtgca cccaactgat cttcagcatc ttttactttc accagcgttt   1680
ctgggtgagc aaaaacagga aggcaaaatg ccgcaaaaaa gggaataagg gcgacacgga   1740
aatgttgaat actcatactc ttcctttttc aatcatgatt gaagcattta tcagggttat   1800
tgtctcatga gcggatacat attttgaatgt atttagaaaa ataaacaaat aggtcatgac   1860
caaaatccct taacgtgagt tttcgttcca ctgagcgtca gaccccgtag aaaagatcaa   1920
aggatcttct tgagatcctt ttttttctgcg cgtaatctgc tgcttgcaaa caaaaaaacc   1980
accgctacca gcggtggttt gtttgccgga tcaagagcta ccaactcttt ttccgaaggt   2040
aactggcttc agcagagcgc agataccaaa tactgtcctt ctagtgtagc cgtagttagg   2100
ccaccacttc aagaactctg tagcaccgcc tacatacctc gctctgctaa tcctgttacc   2160
agtggctgct gccagtggcg ataagtcgtg tcttaccggg ttggactcaa gacgatagtt   2220
accggataag gcgcagcggt cgggctgaac ggggggttcg tgcacacagc ccagcttgga   2280
gcgaacgacc tacaccgaac tgagatacct acagcgtgag ctatgagaaa gcgccacgct   2340
tcccgaaggg agaaaggcgg acaggtatcc ggtaagcgga gggtcggaa caggagagcg   2400
cacgagggag cttccagggg gaaacgcctg gtatctttat agtcctgtcg ggtttcgcca   2460
cctctgactt gagcgtcgat ttttgtgatg ctcgtcaggg gggcggagcc tatgaaaaaa   2520
cgccagcaac gcggccttt tacggttcct ggccttttgc tggccttttg ctcacatgtt   2580
ctttcctgcg ttatccccctg attctgtgga taaccgtatt accgcctttg agtgagctga   2640
taccgctcgc cgcagccgaa cgaccgagcg cagcgagtca gtgagcgagg aagcggaaga   2700
gcgcctgatg cggtattttc tccttacgca tctgtgcggt atttcacacc gcatatatgg   2760
tgcactctca gtacaatctg ctctgatgcc gcatagttaa gccagtatac actccgctat   2820
cgctacgtga ctgggtcatg gctgcgcccc gacaccegct aacacccgct gacgcgccct   2880
gacgggcttg tctgctcccg gcatccgctt acagacaagc tgtgaccgtc tccgggagct   2940
gcatgtgtca gaggttttca ccgtcatcac cgaaacgcgc gaggcagctg cggtaaagct   3000
catcagcgtg gtcgtgaagc gattcacaga tgtctgcctg ttcatccgcg tccagctcgt   3060
tgagttttctc cagaagcgtt aatgtctggc ttctgataaa gcgggccata ttaagggcgg   3120
tttttttcctg tttggtcact gatgcctccg tgtaaggggg atttctgttc atggggggtaa   3180
tgataccgat gaaacgagag aggatgctca cgatacgggt tactgatgat gaacatgccc   3240
ggttactgga acgttgtgag ggtaaacaac tggcggtatg gatgcggcgg gaccagagaa   3300
aaatcactca gggtcaatgc cagcgcttcg ttaatacaga tgtaggtgtt ccacagggta   3360
gccagcagca tcctgcgatg cagatccgga acataatggt gcagggcgct gacttccgcg   3420
tttccagact ttacgaaaca cggaaaccga agaccattca tgttgttgct caggtcgcag   3480
acgttttgca gcagcagtcg cttcacgttc gctcgcgtat cggtgattca ttctgctaac   3540
cagtaaggca accccgccag cctagccggg tcctcaacga caggagcacg atcatgctag   3600
tcatgcccccg cgcccaccgg aaggagctga ctgggttgaa ggctctcaag ggcatcggtc   3660
gagatcccgg tgcctaatga gtgagctaac ttacattaat tgcgttgcgc tcactgcccg   3720
ctttccagtc gggaaacctg tcgtgccagc tgcattaatg aatcggccaa cgcgcgggga   3780
gaggcggttt gcgtattggg cgccaggtgt tttttctttt tcaccagtga cgggcaac    3840
agctgattgc ccttcaccgc ctggccctga gagagttgca gcaagcggtc cacgctgttt   3900
tgcccccagca ggcgaaaatc ctgtttgatg gtggttaacg gcgggatata acatgagctg   3960
tcttcggtat cgtcgtatcc cactaccgag atgtccgcac caacgcgcag cccggactcg   4020
gtaatggcgc gcattgcgcc cagcgccatc tgatcgttgg caaccagcat cgcagtggga   4080
acgatgccct cattcagcat ttgcatggtt tgttgaaaac cggacatggc actccagtcg   4140
ccttcccgtt ccgctatcgg ctgaatttga ttgcgagtga tatttatg ccagccagcc   4200
agacgcagac gcgccgagac agaacttaat gggcccgcta acagcgcgat ttgctggtga   4260
cccaatgcga ccagatgctc cacgcccagt cgcgtaccgt cttcatggga gaaaataata   4320
ctgttgatgg gtgtctggtc agagacatca agaaataacg ccggaacatt agtgcaggca   4380
gcttccacag caatggcatc ctggtcatcc agcggatagt taatgatcag cccactgacg   4440
cgttgcgcga agagattgtg caccgccgct ttacaggctt cgacgccgct tcgttctacc   4500
atcgacacca ccacgctggc acccagttga tcggcgcgag atttaatcgc cgcgacaatt   4560
tgcgacggcg cgtgcagggc cagactggag gtggcaacgc caatcagcaa cgactgtttg   4620
cccgccagtt gttgtgccac gcggttggga atgtaattca gctccgccat cgccgcttcc   4680
acttttttccc gcgttttcgc agaaacgtgg ctggcctggt tcaccacgcg ggaaacggtc   4740
tgataagaga caccggcata ctctgcgaca tcgtataacg ttactggttt cacattcacc   4800
accctgaatt gactctcttc cgggcgctat catgccatac cgcgaaaggt tttgcgccat   4860
tcgatggtgt ccgggatctc gacgctctcc cttatgcgac tcctgcatta ggaagcagcc   4920
cagtagtagg ttgaggccgt tgagcaccgc cgccgcaagg aatggtgcat gcaaggagat   4980
ggcgcccaac agtccccccgg ccacggggcc tgccaccata cccacgccga acaagcgct   5040
catgagcccg aagtggcgag cccgatcttc cccatccggtg atgtcggcga tataggcgcc   5100
agcaaccgca cctgtggcgc cggtgatgcc ggccacgatg cgtccggcgt agcctaggat   5160
cgagatcgat ctcgatcccg cgaaattaat acgactcact ata                   5203
```

SEQ ID NO: 94   moltype = DNA length = 5369
FEATURE    Location/Qualifiers
misc_feature  1..5369
       note = pET28a(+) vector
source     1..5369
       mol_type = other DNA
       organism = synthetic construct
SEQUENCE: 94

```
atccggatat agttcctcct ttcagcaaaa aaccccctcaa gacccgttta gaggccccaa     60
gggttatgc tagttattgc tcagcggtgg cagcagccaa ctcagcttcc tttcgggctt    120
tgttagcagc cggatctcag tggtggtggt ggtggtgctc gagtgcggcc gcaagcttgt    180
cgacggagct cgaattcgga tccgcgaccc atttgctgtc caccagtcat gctagccata    240
tggctgccgc gcggcaccag gccgctgctg tgatgatgat gatgatggct gctgcccatg    300
```

-continued

```
gtatatctcc ttcttaaagt taaacaaaat tatttctaga ggggaattgt tatccgctca   360
caattcccct atagtgagtc gtattaattt cgcgggatcg agatctcgat cctctacgcc   420
ggacgcatcg tggccggcat caccggcgcc acaggtgcgg ttgctggcgc ctatatcgcc   480
gacatcaccg atgggaaga tcgggctcgc cacttcgggc tcatgagcgc ttgtttcggc   540
gtgggtatgg tggcaggccc cgtggccggg ggactgttgg cgccatctc cttgcatgca   600
ccattccttg cggcggcggt gctcaacggc ctcaacctac tactgggctg cttcctaatg   660
caggagtcgc ataagggaga gcgtcgagat cccggacacc atcgaatggc gcaaaacctt   720
tcgcggtatg gcatgatagc gcccggaaga gagtcaattc agggtggtga atgtgaaacc   780
agtaacgtta tacgatgtcg cagagtatgc cggtgtctct tatcagaccg tttcccgcgt   840
ggtgaaccag gccagccacg tttctgcgaa aacgcgggaa aaagtggaag cggcgatggc   900
ggagctgaat tacattccca accgcgtggc acaacaactg gcgggcaaac agtcgttgct   960
gattggcgtt gccacctcca gtctggccct gcacgcgccg tcgcaaattg tcgcggcgat  1020
taaatctcgc gccgatcaac tgggtgccag cgtggtggtg tcgatggtag aacgaagcgg  1080
cgtcgaagcc tgtaaagcgg cggtgcacaa tcttctcgcg caacgcgtca gtgggctgat  1140
cattaactat ccgctggatg accaggatgc cattgctgtg gaagctgcct gcactaatgt  1200
tccggcgtta tttcttgatg tctctgacca gacacccatc aacagtatta ttttctccca  1260
tgaagacggt acgcgactgg gcgtggagca tctggtcgca ttgggtcacc agcaaatcgc  1320
gctgttagcg ggcccattaa gttctgtctc ggcgcgtctc cgtctggctg gctggcataa  1380
atatctcact cgcaatcaaa ttcagccgat agcggaacgg gaaggcgact ggagtgccat  1440
gtccggtttt caacaaacca tgcaaatgct gaatgagggc atcgttccca ctgcgatgct  1500
ggttgccaac gatcagatgg cgctgggcgc aatgcgcgcc attaccgagt ccgggctgcg  1560
cgttggtgcg gatatctcgg tagtgggata cgacgatgcc gaagacagct catgtttat   1620
cccgccgtta accaccatca acaggattt cgcctgctg gggcaaacca gcgtggaccg   1680
cttgctgcaa ctctctcagg gccaggcggt aagggcaat cagctgttgc ccgtctcact   1740
ggtgaaaaga aaaccaccc tggcgcccaa tacgcaaacc gcctctcccc gcgcgttggc   1800
cgattcatta atgcagctgc cacgacaggt ttcccgactg gaaagcgggc agtgagcgca  1860
acgcaattaa tgtaagttag ctcactcatt aggcaccggg atctcgaccg atgcccttga  1920
gagccttcaa cccagtcagc tccttccggt ggggcgcgggg catgactatc gtcgccgcac  1980
ttatgactgt cttctttatc atgcaactcg taggacaggt gccggcagcg ctctgggtca  2040
ttttcggcga ggaccgcttt cgctggagcg cgacgatgat cggcctgtcg cttgcggtat  2100
tcggaatctt gcacgccctc gctcaagcct tcgtcactgg tcccgccacc aaacgtttcg  2160
gcgagaagca ggccattatc gccggcatgg cggcccacg ggtgcgcatg atcgtgctcc  2220
tgtcgttgag gacccggcta ggctggcggg gttgccttac tggttagcag aatgaatcac  2280
cgatacgcga gcgaacgtga agcgactgct gctgcaaaac gtctgcgacc tgagcaacaa  2340
catgaatggt cttcggtttc cgtgtttcgt aaagtctgga aacgcggaag tcagcgccct  2400
gcaccattat gttccggatc tgcatcgcag gatgctgctg gctaccctgt ggaacaccta  2460
catctgtatt aacgaagcgc tggcattgac cctgagtgat ttttctctgg tcccgccgca  2520
tccataccgc cagttgttta ccctcacaac gttccagtaa ccgggcatgt tcatcatcag  2580
taacccgtat cgtgagcatc ctctctcgtt tcatcgatat cattacccc atgaacagaa  2640
atccccctta cacggaggca tcagtgacca acaggaaaa aaccgccctt aacatgcccc  2700
gctttatcag aagccagaca ttaacgcttc tggagaaact caacgagctg gacgcggatg  2760
aacaggcaga catctgtgaa tcgcttcacg accacgctga tgagctttac cgcagctgcc  2820
tcgcgccgtt tcggtgatgac ggtgaaaaacc tctgacacat gcagctcccg gagacggtca  2880
cagcttgtct gtaagcggat gccgggagca gacaagcccg tcagggcgcg tcagcggggtg  2940
ttggcgggtg tcgggcgca gccatgaccc agtcacgtag cgatagcgga gtgtatactg  3000
gcttaactat gcggcatcag agcagattgt actgagagtg caccatatat gcggtgtgaa  3060
ataccgcaca gatgcgtaag gagaaaaatac cgcatcaggc gctcttccgc ttcctcgctc  3120
actgactcgc tgcgctcggt cgttcggctg cggcgagcgg tatcagctca ctcaaaggcg  3180
gtaatacggt tatccacaga atcaggggat aacgcaggaa agaacatgtg agcaaaaggc  3240
cagcaaaagg ccaggaaccg taaaaaggcc gcgttgctgg cgtttttcca taggctccgc  3300
cccctgacg agcatcacaa aaatcgacgc tcaagtcaga ggtggcgaaa cccgacagga  3360
ctataaagat accaggcgtt tccccctgga agctccctcg tgcgctctcc tgttccgacc  3420
ctgccgctta ccggatacct gtccgccttt ctcccttcgg gaagcgtggc gctttctcat  3480
agctcacgct gtaggtatct cagttcggtg taggtcgttc gctccaagct gggctgtgtg  3540
cacgaacccc ccgttcagcc cgaccgctgc gccttatccg gtaactatcg tcttgagtcc  3600
aacccggtaa gacacgactt atcgccactg gcagcagcca ctggtaacag gattagcaga  3660
gcgaggtatg taggcggtgc tacagagttc ttgaagtggt ggcctaacta cggctacact  3720
agaaggacag tatttggtat ctgcgctctg ctgaagccag ttaccttcgg aaaaagagtt  3780
ggtagctctt gatccggcaa acaaaccacc gctggtagcg gtggtttttt tgtttgcaag  3840
cagcagatta cgcgcagaaa aaaaggatct caagaagatc ctttgatctt ttctacgggg  3900
tctgacgctc agtggaacga aaactcacgt taagggattt tggtcatgaa caataaaact  3960
gtctgcttac ataaacagta atacaaggg tgttatgagc atattcaac gggaaacgtc   4020
ttgctctagg ccgcgattaa attccaacat ggatgctgat ttatatgggt ataaatgggc  4080
tcgcgataat gtcgggcaat caggtgcgac aatctatcga ttgtatggga agcccgatgc  4140
gccagagttg tttctgaaac atggcaaagg tagcgttgcc aatgatgtta cagatgagat  4200
ggtcagacta aactggctga cggaatttat gcctcttccg accatcaagc attttatccg  4260
tactcctgat gatgcatggt tactcaccac tgcgatcccc gggaaaacag cattccaggt  4320
attagaagaa tatcctgatt caggtgaaaa tattgttgat gcgctggcag tgttcctgcg  4380
ccggttgcat tcgattcctg tttgtaattg tcctttaac agcgatcgcg tatttcgtct  4440
cgctcaggcg caatcacgaa tgaataacgg tttggttgat gcgagtgatt ttgatgacga  4500
gcgtaatggc tggcctgttg aacaagtctg gaaagaaatg cataaacttt tgccattctc  4560
accggattca gtcgtcactc atggtgattt ctcacttgat aaccttattt ttgacgaggg  4620
gaaattaata ggttgtattg atgttggacg agtcggaatc gcagaccgat accaggatct  4680
tgccatccta tggaactgcc ttcggtgagtt tctccttca acagaaac ggcttttca    4740
aaaatatggt attgataatc ctgatatgaa taaattgcag tttcatttga tgctcgatga  4800
gtttttctaa gaattaattc atgagcggat acatatttga atgtatttag aaaaataaac  4860
aaatagggg tccgcgcaca ttccccgaaa agtgccacc tgaaattgta aacgttaata   4920
ttttgttaaa attcgcgtta aatttttgtt aaatcagctc attttttaac caataggccg  4980
aaatcggcaa aatcccttat aaatcaaaag aatagaccga gatagggttg agtgttgttc  5040
```

```
cagtttggaa caagagtcca ctattaaaga acgtggactc caacgtcaaa gggcgaaaaa 5100
ccgtctatca gggcgatggc ccactacgtg aaccatcacc ctaatcaagt tttttggggt 5160
cgaggtgccg taaagcacta aatcggaacc ctaaagggag cccccgattt agagcttgac 5220
ggggaaagcc ggcgaacgtg gcgagaaagg aaggaagaa agcgaaagga gcgggcgcta 5280
gggcgctggc aagtgtagcg gtcacgctgc gcgtaaccac cacacccgcc gcgcttaatg 5340
cgccgctaca gggcgcgtcc cattcgcca                                  5369

SEQ ID NO: 95        moltype = DNA  length = 2187
FEATURE              Location/Qualifiers
source               1..2187
                     mol_type = genomic DNA
                     organism = Psilocybe cubensis
SEQUENCE: 95
atggcttcta gttcttccga tgtcttcgtt ttgggtctag gtgttgtttt ggctgccttg 60
tatatcttca gagaccaatt attcgctgct tctaagccaa aggtggctcc agtttccact 120
acgaagcctg ccaacggttc cgctaaccca agagacttca tcgccaagat gaaacaaggt 180
aagaagagaa tcgtaatctt ctacggttct caaactggta ccgctgaaga atatgctatt 240
cgtttggcta aggaagctaa gcaaaagttc ggtctagcct ccttggtttg tgatccagaa 300
gaatacgatt ttgaaaagtt ggaccaattg ccagaagatt ctattgcttt cttcgtcgtt 360
gctaccatg tgaaggtgaa acctacagac aacgctgtcc aattgttgca aaacttgcaa 420
gatgaaagct tcgaattctc ctctggtgag agaaagttgt caggtttgaa gtacgttgtt 480
tttggtctgg gtaacaagac ctacgaacat tacaacctca ttggagaac tgttgacgct 540
caattggcca gatgggtgc tatcagaatc ggtgaaagaa gtgaaggtga tgatgacaag 600
tccatggaag aagactactt ggaatggaag gatggtatgt gggaagcgtt tgccactgct 660
atgggtgttg aagaaggtca aggtggtgac tccgctgatt cgtcgtttc gaattggaa 720
tctcacccac cagaaaaggt ttaccaaggt gaattttctg ctagagcttt aaccaaaacc 780
aagggtattc acgacgctaa gaatcctttt gctgctccaa ttgcggttgc tagagaattg 840
ttccaatctg ttgtcgatag aaactgtgtc cacgtcgaat tcaacattga aggctctggt 900
atcacctatc aacacggtga ccacgttggt ttgtggccat gaatccaga tgttgaagtc 960
gaacggttgt tgtgtgtttt aggtttagct gaaaagagaa atgctgtcat ctccattgaa 1020
tccttagacc cggctttggc taaggttcca ttcccagtcc caactactta cggtgctgtg 1080
ttgagacact acattgacat ctctgctgtc gccgtagac aaatctttggg tactttgtcc 1140
aaattcgctc caaccccaga agctgaagct tccttgagaa acttgaacac taacaaggaa 1200
gaataccaca acgtcgtcgc taacgctgtt tgaaattgg gtgaaatttt gcaaatcgtt 1260
accggtaacg acattactgt cccaccaact actgccaaca ccaccaaatg gccaattcca 1320
ttcgacatca ttgtttctgc catcccaaga ttgcaaccaa gatactactc tatctcttct 1380
tccccaaaaa ttcatccaaa caccatccac gctaccgttg ttgtgctcaa atacgaaaac 1440
gttccaaccg aaccaatccc aagaaagtgg gtttacggtg tcggtagtaa cttcttgttg 1500
aatttaaagt acgtgttaa caaggaacca gttccatcaa tcactcaaaa tggcgaacaa 1560
agagtcggtg tcccggaata cttgattgct ggtccacgtg gttcttacaa gactgaatct 1620
ttctacaagg ctccaatcca tgttagacgt tctactttcc gtttgccaac caacccaaag 1680
tctccagtca tcatgattgg tccaggtact ggtgtcgccc cattcagagg cttcgttcaa 1740
gaaagagttg ccttggccag aagatccatc gaaaagaacg gtcctgactc tttggctgac 1800
tggggtcgta tttccttgtt ctacggttgt agaagatccg acgaagactt cttgtacaag 1860
gacgaatggc cacaatacga agctgagttg aagggtaagt tcaagttgca ctgtgctttc 1920
tccagacaaa actacaagcc agacggttct aagatttacg tccaagattt gatctgggaa 1980
gacagagaac acattgccga tgccatctta aacggtaagg ttacgtcta catctgcgct 2040
gaagctaagt ccatgtctaa acaagttgaa gaagttctag ccaagatctt gggcgaagcc 2100
aaaggtggtt ccggtccagt tgaaggtgtt gctgaagtca agttactgaa ggaacggtcc 2160
agattgatgt tggatgtctg gtcttga                                    2187

SEQ ID NO: 96        moltype = AA  length = 728
FEATURE              Location/Qualifiers
source               1..728
                     mol_type = protein
                     organism = Psilocybe cubensis
SEQUENCE: 96
MASSSSDVFV LGLGVVLAAL YIFRDQLFAA SKPKVAPVST TKPANGSANP RDFIAKMKQG  60
KKRIVIFYGS QTGTAEEYAI RLAKEAKQKF GLASLVCDPE EYDFEKLDQL PEDSIAFFVV 120
ATYGEGEPTD NAVQLLQNLQ DESFEFSSGE RKLSGLKYVV FGLGNKTYEH YNLIGRTVDA 180
QLAKMGAIRI GEREGDDDK SMEEDYLEWK DGMWEAFATA MGVEEGQGGD SADFVVSELE 240
SHPPEKVYQG EFSARALTKT KGIHDAKNPF AAPIAVAREL FQSVVDRNCV HVEFNIEGSG 300
ITYQHGDHVG LWPLNPDVEV ERLLCVLGLA EKRDAVISIE SLDPALAKVP FPVPTTYGAV 360
LRHYIDISAV AGRQILGTLS KFAPTPEAEA FLRNLNTNKE EYHNVVANGC LKLGEILQIA 420
TGNDITVPPT TANTTKWPIP FDIIVSAIPR LQPRYYSISS SPKIHPNTIH ATVVLKYEN 480
VPTEPIPRKW VYGVGSNFLL NLKYAVNKEP VPYITQNGEQ RVGVPEYLIA GPRGSYKTES 540
FYKAPIHVRR STFRLPTNPK SPVIMIGPGT GVAPFRGFVQ ERVALARRSI EKNGPDSLAD 600
WGRISLFYGC RRSDEDFLYK DEWPQYEAEL KGKFKLHCAF SRQNYKPDGS KIYVQDLIWE 660
DREHIADAIL NGKGYVYICG EAKSMSKQVE EVLAKILGEA KGGSGPVEGV AEVKLLKERS 720
RLMLDVWS                                                         728

SEQ ID NO: 97        moltype = DNA  length = 5203
FEATURE              Location/Qualifiers
misc_feature         1..5203
                     note = pETM6-H10 vector
source               1..5203
                     mol_type = other DNA
                     organism = synthetic construct
SEQUENCE: 97
```

```
gaagaattgt gagcggataa caattcccct ctagaaataa ttttgtttaa ctttaagaag   60
gagatataca tatggcagat ctcaattgga tatcggccgg ccacgcgatc gctgacgtcg  120
gtaccctcga gtctggtaaa gaaaccgctg ctgcgaaatt tgaacgccag cacatggact  180
cgtctactag tcgcagctta attaacctaa actgctgcca ccgctgagca ataactagca  240
taacccttg gggcctctaa acgggtcttg aggggttttt tgctagcgaa aggaggagtc   300
gactatatcc ggattggcga atgggacgcg ccctgtagcg gcgcattaag cgcggcgggt  360
gtggtggtta cgcgcagcgt gaccgctaca cttgccagcg ccctagcgcc cgtcctttc   420
gctttcttcc cttcctttct cgccacgttc gccggctttc cccgtcaagc tctaaatcgg  480
gggctccctt tagggttccg atttagtgct ttacggcacc tcgaccccaa aaaacttgat  540
tagggtgatg gttcacgtag tgggccatcg ccctgataga cggttttttcg cccttttgacg 600
ttggagtcca cgttctttaa tagtggactc ttgttccaaa ctggaacaac actcaaccct  660
atctcggtct attcttttga tttataaggg attttgccga tttcggccta ttggttaaaa  720
aatgagctga tttaacaaaa attttaaca aaatattaac gtttacaatt                780
tctggcggca cgatggcatg agattatcaa aaaggatctt cacctagatc cttttaaatt  840
aaaaatgaag ttttaaatca atctaaagta tatatgagta aacttggtct gacagttacc  900
aatgcttaat cagtgaggca cctatctcag cgatctgtct atttcgttca tccatagttg  960
cctgactccc cgtcgtgtag ataactacga tacgggaggg cttaccatct ggccccagtg 1020
ctgcaatgat accgcgagac ccacgctcac cggctccaga tttatcagca ataaaccagc 1080
cagccggaag ggccgagcgc agaagtggtc ctgcaacttt atccgcctcc atccagtcta 1140
ttaattgttg ccgggaagct agagtaagta gttcgccagt taatagtttg cgcaacgttg 1200
ttgccattgc tacaggcatc gtggtgtcac gctcgtcgtt ggtatggct tcattcagct   1260
ccggttccca acgatcaagg cgagttacat gatccccat gttgtgcaaa aaagcggtta   1320
gctccttcgg tcctccgatc gttgtcagaa gtaagttggc cgcagtgtta tcactcatgg 1380
ttatggcagc actgcataat tctcttactg tcatgccatc cgtaagatgc ttttctgtga 1440
ctggtgagta ctcaaccaag tcattctgag aatagtgtat gcggcgaccg agttgctctt 1500
gcccggcgtc aatacgggat aataccgcgc cacatagcag aactttaaaa gtgctcatca 1560
ttggaaaacg ttcttcgggg cgaaaactct caaggatctt accgctgttg agatccagtt 1620
cgatgtaacc cactcgtgca cccaactgat cttcagcatc ttttactttc accagcgttt 1680
ctgggtgagc aaaaacagga aggcaaaatg ccgcaaaaaa gggaataagg gcgacacgga 1740
aatgttgaat actcatactc ttcctttttc aatcatgatt gaagcattta tcagggttat 1800
tgtctcatga gcggatacat atttgaatgt atttagaaaa ataaacaaat aggtcatgac 1860
caaaatccct taacgtgagt tttcgttcca ctgagcgtca gaccccgtag aaaagatcaa 1920
aggatcttct tgagatcctt ttttttctgcg cgtaatctgc tgcttgcaaa caaaaaaacc 1980
accgctacca gcggtggttt gtttgccgga tcaagagcta ccaactcttt ttccgaaggt 2040
aactggcttc agcagagcgc agataccaaa tactgtcctt ctagtgtagc cgtagttagg 2100
ccaccacttc aagaactctg tagcaccgcc tacataccta gctctgctaa tcctgttacc 2160
agtggctgct gccagtggcg ataagtcgtg tcttaccggg ttggactcaa gacgatagtt 2220
accggataag gcgcagcggt cgggctgaac ggggggttcg tgcacacagc ccagcttgga 2280
gcgaacgacc tacaccgaac tgagatacct acagcgtgag ctatgagaaa gcgccacgct 2340
tcccgaaggg agaaaggcgg acaggtatcc ggtaagcggc agggtcggaa caggagagcg 2400
cacgagggag cttccagggg gaaacgcctg gtatctttat agtcctgtcg ggtttcgcca 2460
cctctgactt gagcgtcgat ttttgtgatg ctcgtcaggg gggcggagcc tatggaaaaa 2520
cgccagcaac gcggcctttt tacggttcct ggccttttgc tggccttttg ctcacatgtt 2580
ctttcctgcg ttatcccctg attctgtgga taaccgtatt accgcctttg agtgagctga 2640
taccgctcgc cgcagccgaa cgaccgagcg cagcgagtca gtgagcgagg aagcggaaga 2700
gcgcctgatg cggtattttc tccttacgca tctgtgcggt atttcacacc gcatatatgg 2760
tgcactctca gtacaatctg ctctgatgcc gcatagttaa gccagtatac actccgctat 2820
cgctacgtga ctgggtcatg gctgcgcccc gacacccgcc aacacccgct gacgcgccct 2880
gacgggcttg tctgctcccg gcatccgctt acagacaagc tgtgaccgtc tccgggagct 2940
gcatgtgtca gaggttttca ccgtcatcac cgaaacgcgc gaggcagctg cggtaaagct 3000
catcaggcgg gtcgtgaagc gattcacaga tgtctgcctg ttcatccgcg tccagctcgt 3060
tgagtttctc cagaagcgtt aatgtctggc ttctgataaa gcgggccatg ttaagggcgg 3120
ttttttcctg tttggtcact gatgcctccg tgtaagggggg atttctgttc atgggggtaa 3180
tgataccgat gaaacgagag aggatgctca cgatacgggt tactgatgat gaacatgccc 3240
ggttactgga acgttgtgag ggtaaacaac tggcggtatg gatgcggcgg gaccagagaa 3300
aaatcactca gggtcaatgc cagcgcttcg ttaatacaga tgtaggtgtt ccacaggta  3360
gccagcagca tcctgcgatg cagatccgga acataatggt gcagggcgct gacttccgcg 3420
tttcagact ttacgaaaca cggaaaccga agaccattca tgttgttgct caggtcgcag   3480
acgttttgca gcagcagtcg cttcacgttc gctcgcgtat cggtgattca ttctgctaac 3540
cagtaaggca accccgccag cctagccggg tcctcaacga caggagcacg atcatgctag 3600
tcatgccccg cgcccaccgg aaggagctga ctggggttgaa ggctctcaag gcatcggtc  3660
gagatcccgt gcctaatga gtgagctaac ttacattaat tgcgttgcgc tcactgcccg 3720
ctttccagtc gggaaacctg tcgtgccagc tgcattaatg aatcggccaa cgcgcgggga 3780
gaggcggttt gcgtattggg cgccagggtg gtttttcttt tcaccagtga gacggcaaca 3840
agctggattgc ccttcaccgc ctggccctga gagagttgca gcaagcggtc cacgctggtt 3900
tgccccagca ggcgaaaatc ctgtttgatg gtggttaacg gcgggatata acatgagctg 3960
tcttcggtat cgtcgtatcc cactaccgag atgtccgcac caacgcgcag cccggactcg 4020
gtaatggcgc gcattgcgcc cagcgccatc tgatcgttgg caaccagcat cgcagtggga 4080
acgatgccct cattcagcat ttgcatggtt tgttgaaaac cggacatggc actccagtcg 4140
ccttcccgtt ccgctatcgg ctgaatttga ttgcgagtga gatatttatg ccagccagcc 4200
agacgcagac gcgccgagac agaacttaat gggcccgcta acagcgcgat ttgctggtga 4260
cccaatgcga ccagatgctc cacgcccagt cgcgtaccgt cttcatggga gaaaataata 4320
ctgttgatgg gtgtctggtc agagacatca agaaataacg ccggaacatt agtgcaggca 4380
gcttcacag caatggcatc ctggtcatcc agcggatagt taatgatcag cccactgacg  4440
cgttgcgcga agattgtg caccgccgct ttacaggctt cgacgccgct tcgttctacc    4500
atcgacacca ccacgctggc acccagttga tcggcgcgag atttaatcgc cgcgacaatt 4560
tgcgacggcg cgtgcagggc cagactggag gtggcaacgc caatcagcaa cgactgtttg 4620
cccgccagtt gttgtgccac gcggttggga atgtaattca gctccgccat cgccgcttcc 4680
acttttttccc gcgttttcgc agaaacgtgg ctggcctggt tcaccacgcg ggaaacggtc 4740
```

```
tgataagaga caccggcata ctctgcgaca tcgtataacg ttactggttt cacattcacc   4800
accctgaatt gactctcttc cgggcgctat catgccatac cgcgaaaggt tttgcgccat   4860
tcgatggtgt ccgggatctc gacgctctcc cttatgcgac tcctgcatta ggaagcagcc   4920
cagtagtagg ttgaggccgt tgagcaccgc cgccgcaagg aatggtgcat gcaaggagat   4980
ggcgcccaac agtcccccgg ccacggggcc tgccaccata cccacgccga aacaagcgct   5040
catgagcccg aagtggcgag cccgatcttc cccatcggtg atgtcggcga tataggcgcc   5100
agcaaccgca cctgtggcgc cggtgatgcc ggcacgatg cgtccggcgt agcctaggat   5160
cgagatcgat ctcgatcccg cgaaattaat acgactcact acg                    5203

SEQ ID NO: 98           moltype = DNA   length = 3777
FEATURE                 Location/Qualifiers
misc_feature            1..3777
                        note = pRSM3 vector
source                  1..3777
                        mol_type = other DNA
                        organism = synthetic construct
SEQUENCE: 98
cgctaacagc gcgatttgct ggtgacccaa tgcgaccaga tgctccacgc ccagtcgcgt     60
accgtcttca tgggagaaaa taatactgtt gatgggtgtc tggtcagaga catcaagaaa    120
taacgccgga acattagtgc aggcagcttc cacagcaatg gcatcctggt catccagcgg    180
atagttaatg atcagcccac tgacgcgttg cgcgagaaga ttgtgcaccg ccgctttaca    240
ggcttcgacg ccgcttcgtt ctaccatcga caccaccacg ctggcaccca gttgatcggc    300
gcgagattta atcgccgcga caatttgcga cggcgcgtgc agggccagac tggaggtggc    360
aacgccaatc agcaacgact gtttgcccgc cagttgttgt gccacgcggt tgggaatgta    420
attcagctcc gccatcgccg cttccacttt ttcccgcgtt ttcgcagaaa cgtggctggc    480
ctggttcacc acgcgggaaa cggtctgata agagacaccg gcatactctg cgacatcgta    540
taacgttact ggtttcacat tcaccaccct gaattgactc tcttccggcc gctatcatgc    600
cataccgcga aaggttttgc gccattcgat ggtgtccggg atctcgacgc tctcccttat    660
gcgactcctg cattaggaag cagcccagta gtaggttgag gccgttgagc accgccgccg    720
caaggaatgg tgcatgcaag gagatggcgc ccaacagtcc cccggccacg gggcctgcca    780
ccataccccac gccgaaacaa gcgctcatga gcccgaagtg gcgagcccga tcttccccat    840
cggtgatgtc ggcgatatag gcgccagcaa ccgcacctgt ggcgccggtg atgccggcca    900
cgatgcgtc ggcgtagcct aggatcgaga tcgatctcga tcccgcgaaa ttaatacgac    960
tcactatagg ggaattgtga gcggataaca attcccctct agaaataatt ttgtttaact   1020
ttaagaagga gatatacata tggcagatct caattggata tcggccggcc acgcgatcgc   1080
tgacgtcggt accctcgagt ctggtaaaga accgctgct gcgaaattg aacgccagca     1140
catggactcg tctactagtc gcagcttaat taacctaaac tgctgccacc gctgagcaat   1200
aactagcata accccctggg gcctctaaac gggtcttgag gggttttttg ctagcgaaag   1260
gaggagtcga caagctgacg accgggtctc cgcaagtggc actttttcggg gaaatgtgcg   1320
cggaaccct atttgtttat ttttctaaat acattcaaat atgtatccgc tcatgaatta    1380
attcttagaa aaactcatcg agcatcaaat gaaactgcaa tttattcata tcaggattat   1440
caataccata ttttttgaaaa agccgtttct gtaatgaagg agaaaactca ccgaggcagt   1500
tccataggat ggcaagatcc tggtatcggt ctgcgattcc gactcgtcca acatcaatac   1560
aacctattaa tttcccctcg tcaaaaataa ggttatcaag tgagaaatca ccatgagtga   1620
cgactgaatc cggtgagaat ggcaaaagtt tatgcatttc tttccagact tgttcaacag   1680
gccagccatt acgctcgtca tcaaaatcac tcgcatcaac caaaccgtta ttcattcgtg   1740
attgcgcctg agcgagacga atacgcggt cgctgttaaa aggacaatta caaacaggaa    1800
tcgaatgcaa ccggcgcagg aacactgcca gcgcatcaac aatatttca cctgaatcag   1860
gatattcttc taatacctgg aatgctgttt tcccggggat cgcagtggtg agtaaccatg   1920
catcatcagg agtacggata aaatgcttga tggtcggaag aggcataaat tccgtcagcc   1980
agtttagtct gaccatctca tctgtaacat cattggcaac gctacctttg ccatgtttca   2040
gaaacaactc tggcgcatcg ggcttcccat acaatcgata gattgtcgca cctgattgcc   2100
cgacattatc gcgagcccat ttatacccat ataaatcagc atccatgttg gaatttaatc   2160
gcggcctaga gcaagacgtt tcccgttgaa tatggctcat actcttcctt tttcaatatt   2220
attgaagcat ttatcagggt tattgtctca tgagcggata catatttgaa tgtatttaga   2280
aaaataaaca aataggcatg cagcgctctt ccgcttcctc gctcactgac tcgctacgct   2340
cggtcgttcg actgcggcga gcggtgtcag ctcactcaaa gcggtaata cggttatcca    2400
cagaatcagg ggataaagcc ggaaagaaca tgtgagcaaa aagcaaagca ccggaagaag   2460
ccaacgccgc aggcgttttt ccataggctc cgcccccctg acgagcatca caaaatcga   2520
cgctcaagcc agaggtggcg aaacccgaca ggactataaa gataccaggc gtttccccct   2580
ggaagctccc tcgtgcgctc tcctgttccg accctgccgc ttaccggata cctgtccgcc   2640
tttctccctt cgggaagcgt ggcgctttct catagctcac gctgttggta tctcagttcg   2700
gtgtaggtcg ttcgctccaa gctgggctgt gtgcacgaac cccccgttca gcccgaccgc   2760
tgcgccttat ccggtaacta tcgtcttgag tccaacccgg taagacacga cttatcgcca   2820
ctggcagcag ccattggtaa ctgatttaga gacttgtc ttgaagttat gcacctgtta     2880
aggctaaact gaaagaacag attttggtga gtgcggtcct caacccact tacccttggtt   2940
caaagagttg gtagctcagc gaaccttgag aaaaccaccg ttggtagcgg tggtttttct   3000
ttatttatga gatgatgaat caatcggtct atcaagtcaa cgaacagcta ttccgttact   3060
ctagatttca gtgcaattta tctcttcaaa tgtagcacct gaagtcagcc ccatacgata   3120
taagttgtaa ttctcatgtt agtcatgccc gcgcccacc ggaaggagct gactgggttg    3180
aaggctctca agggcatcgg tcgagatccc ggtgcctaat gagtgagcta acttacatta   3240
attgcgttgc gctcactgcc cgctttccag tcgggaaacc tgtcgtgcca gctgcattaa   3300
tgaatcggcc aacgcgcggg gagaggcggt ttgcgtattg ggcgcagggt ggtttttct    3360
tttcaccagt gagacgggca acagctgatt gcccttcacc gcctggccct gagagagttg   3420
cagcaagcgg tccacgctgg tttgccccag caggcgaaaa tcctgtttga tggtggttaa   3480
```

```
cggcgggata taacatgagc tgtcttcggt atcgtcgtat cccactaccg agatgtccgc  3540
accaacgcgc agcccggact cggtaatggc gcgcattgcg cccagcgcca tctgatcgtt  3600
ggcaaccagc atcgcagtgg gaacgatgcc ctcattcagc atttgcatgg tttgttgaaa  3660
accggacatg gcactccagt cgccttcccg ttccgctatc ggctgaattt gattgcgagt  3720
gagatattta tgccagccag ccagacgcag acgcgccgag acagaactta atgggcc     3777
```